US009243298B2

(12) United States Patent
Barry et al.

(10) Patent No.: US 9,243,298 B2
(45) Date of Patent: Jan. 26, 2016

(54) ***LEPA*/GUF1 GENE SEQUENCES AS A DIAGNOSTIC TARGET FOR THE IDENTIFICATION OF BACTERIAL SPECIES**

(75) Inventors: Thomas Gerard Barry, Kinarva (IE); Majella Maher, Moycullen (IE); Terence James Smith, Galway (IE); Justin O'Grady, Galway (IE)

(73) Assignee: National University of Ireland, Galway, Galway (IE)

( * ) Notice: Subject to any disclaimer, the term of this patent is extended or adjusted under 35 U.S.C. 154(b) by 1411 days.

(21) Appl. No.: 12/999,052

(22) PCT Filed: Jun. 15, 2009

(86) PCT No.: PCT/EP2009/057389

§ 371 (c)(1), (2), (4) Date: Mar. 30, 2011

(87) PCT Pub. No.: WO2010/003765

PCT Pub. Date: Jan. 14, 2010

(65) Prior Publication Data

US 2011/0217704 A1 Sep. 8, 2011

(30) Foreign Application Priority Data

Jun. 16, 2008 (IE) .................................... 2008/0494

(51) Int. Cl.
*C12Q 1/68* (2006.01)

(52) U.S. Cl.
CPC .............. *C12Q 1/6895* (2013.01); *C12Q 1/689* (2013.01)

(58) Field of Classification Search
None
See application file for complete search history.

(56) References Cited

U.S. PATENT DOCUMENTS

| | | | |
|---|---|---|---|
| 6,617,156 B1 | 9/2003 | Doucette-Stamm et al. | |
| 2005/0136404 A1 | 6/2005 | Doucette-Stamm et al. | |
| 2006/0172330 A1 | 8/2006 | Osborn et al. | |
| 2007/0027309 A1 | 2/2007 | Weinstock et al. | |
| 2007/0059802 A1 | 3/2007 | Doucette-Stamm et al. | |
| 2010/0150943 A1 * | 6/2010 | Grandi et al. | 424/165.1 |

FOREIGN PATENT DOCUMENTS

WO WO 2005/014857 A2 2/2005

OTHER PUBLICATIONS

Database Geneseq, "C. Albicans Pathological Condition Related DNA SEQ ID No. 5753," May 17, 2007, retrieved from EBI accession No. GSN:AET06776.

Database Geneseq, "Enterococcus Faecalis Polynucleotide #2365," Apr. 22, 2004, retrieved from EBI accession No. GSN:ADH84480.

Database Geneseq, "*Streptococcus pneumoniae* ORF Nucleic Acid Sequence SEQ ID No. 208," Aug. 25, 2005, retrieved from EBI accession No. GSN:AEA55443.

Database Geneseq, "*Streptococcus pneumoniae* Strain 14453 ORF SPX1950 DNA, SEQ:1950," Nov. 15, 2007, retrieved from EBI accession No. GSN:AJG98642.

Kiser, G.L. et al. (1995) "GUF1, a Gene Encoding a Novel Evolutionarily Conserved GTPase in Budding Yeast," Yeast 11(13):1311-1316.

Meena, L.S. et al. (2008) "Cloning and Characterization of GTP-binding Proteins of *Mycobacterium tuberculosis* H37Rv", Enzyme and Microbial Technology 42(2):138-144.

Santos, S.R. et al. (2004) "Identification and Phylogenetic Sorting of Bacterial Lineages with Universally Conserved Genes and Proteins," Environmental Microbiology 6(7):754-759.

International Search Report and Written Opinion for International Patent Application No. PCT/EP2009/057389, dated Jan. 7, 2010, 21 pages.

* cited by examiner

*Primary Examiner* — Kenneth R. Horlick
*Assistant Examiner* — David Thomas
(74) *Attorney, Agent, or Firm* — Foley & Lardner LLP; Antoinette F. Konski

(57) ABSTRACT

The current invention relates to a diagnostic kit for a bacterial species and/or fungal and/or yeast species comprising at least one oligonucleotide probe capable of binding to at least a portion of the LepA and/or Guf1 genes or its corresponding mRNA.

2 Claims, 4 Drawing Sheets

SEQUENCE LISTING

```
<160> NUMBER OF SEQ ID NOS: 178

<210> SEQ ID NO 1
<211> LENGTH: 17
<212> TYPE: DNA
<213> ORGANISM: Artificial Sequence
<220> FEATURE:
<223> OTHER INFORMATION: BR1F PRIMER

<400> SEQUENCE: 1

agcgccttga cgttctc                                              17


<210> SEQ ID NO 2
<211> LENGTH: 18
<212> TYPE: DNA
<213> ORGANISM: Artificial Sequence
<220> FEATURE:
<223> OTHER INFORMATION: BR1R PRIMER
<220> FEATURE:
<221> NAME/KEY: y
<222> LOCATION: (6)..(6)
<223> OTHER INFORMATION: y = c/t
<220> FEATURE:
<221> NAME/KEY: h
<222> LOCATION: (12)..(12)
<223> OTHER INFORMATION: h = a/c/t

<400> SEQUENCE: 2

aagatygccg ahatccgc                                             18


<210> SEQ ID NO 3
<211> LENGTH: 18
<212> TYPE: DNA
<213> ORGANISM: Artificial Sequence
<220> FEATURE:
<223> OTHER INFORMATION: BR2F PRIMER
<220> FEATURE:
<221> NAME/KEY: s
<222> LOCATION: (10)..(10)
<223> OTHER INFORMATION: s = c/g

<400> SEQUENCE: 3

rtaytcctgs ggcatgaa                                             18


<210> SEQ ID NO 4
<211> LENGTH: 17
<212> TYPE: DNA
<213> ORGANISM: Artificial Sequence
<220> FEATURE:
<223> OTHER INFORMATION: BR2R PRIMER
<220> FEATURE:
<221> NAME/KEY: r
<222> LOCATION: (16)..(16)
```

<223> OTHER INFORMATION: r = a/g

<400> SEQUENCE: 4
cgtgttcacg cccaart 17

<210> SEQ ID NO 5
<211> LENGTH: 16
<212> TYPE: DNA
<213> ORGANISM: Artificial Sequence
<220> FEATURE:
<223> OTHER INFORMATION: BR3F PRIMER
<220> FEATURE:
<221> NAME/KEY: r
<222> LOCATION: (12)..(12)
<223> OTHER INFORMATION: r = a/g

<400> SEQUENCE: 5
ttgatgccsg cratga 16

<210> SEQ ID NO 6
<211> LENGTH: 17
<212> TYPE: DNA
<213> ORGANISM: Artificial Sequence
<220> FEATURE:
<223> OTHER INFORMATION: BR3R PRIMER
<220> FEATURE:
<221> NAME/KEY: s
<222> LOCATION: (12)..(12)
<223> OTHER INFORMATION: s = c/g

<400> SEQUENCE: 6
acsatcaagg cscagac 17

<210> SEQ ID NO 7
<211> LENGTH: 21
<212> TYPE: DNA
<213> ORGANISM: Artificial Sequence
<220> FEATURE:
<223> OTHER INFORMATION: BPF1A PRIMER

<400> SEQUENCE: 7
acgaactcgt agtccatcga c 21

<210> SEQ ID NO 8
<211> LENGTH: 19
<212> TYPE: DNA
<213> ORGANISM: Artificial Sequence
<220> FEATURE:
<223> OTHER INFORMATION: BPR1A PRIMER

<400> SEQUENCE: 8
gcgcttgttg ttgcacagt 19

<210> SEQ ID NO 9
<211> LENGTH: 18
<212> TYPE: DNA
<213> ORGANISM: Artificial Sequence
<220> FEATURE:
<223> OTHER INFORMATION: BPF1B PRIMER

<400> SEQUENCE: 9
gtcgaagaaa tcgagcac 18

<210> SEQ ID NO 10
<211> LENGTH: 18
<212> TYPE: DNA
<213> ORGANISM: Artificial Sequence

<220> FEATURE:
<223> OTHER INFORMATION: BPR1A PRIMER

<400> SEQUENCE: 10
gtattcctgg ggcatgaa 18

<210> SEQ ID NO 11
<211> LENGTH: 19
<212> TYPE: DNA
<213> ORGANISM: Artificial Sequence
<220> FEATURE:
<223> OTHER INFORMATION: BP1PA PROBE

<400> SEQUENCE: 11
ctggcgcccg tggtagctc 19

<210> SEQ ID NO 12
<211> LENGTH: 22
<212> TYPE: DNA
<213> ORGANISM: Artificial Sequence
<220> FEATURE:
<223> OTHER INFORMATION: BP1PB PROBE

<400> SEQUENCE: 12
ttgttgcaca gtgtcatcac cg 22

<210> SEQ ID NO 13
<211> LENGTH: 18
<212> TYPE: DNA
<213> ORGANISM: Artificial Sequence
<220> FEATURE:
<223> OTHER INFORMATION: BP2F1 PRIMER

<400> SEQUENCE: 13
cgctgttcga cctcatag 18

<210> SEQ ID NO 14
<211> LENGTH: 18
<212> TYPE: DNA
<213> ORGANISM: Artificial Sequence
<220> FEATURE:
<223> OTHER INFORMATION: BP2R1 PRIMER

<400> SEQUENCE: 14
cagctggtcg tattcgga 18

<210> SEQ ID NO 15
<211> LENGTH: 22
<212> TYPE: DNA
<213> ORGANISM: Artificial Sequence
<220> FEATURE:
<223> OTHER INFORMATION: BP2P PROBE

<400> SEQUENCE: 15
gacacttcgg gctcgaacat ca 22

<210> SEQ ID NO 16
<211> LENGTH: 17
<212> TYPE: DNA
<213> ORGANISM: Artificial Sequence
<220> FEATURE:
<223> OTHER INFORMATION: BP3FI PRIMER

<400> SEQUENCE: 16
tccatcttgt tgagcac 17

-continued

<210> SEQ ID NO 17
<211> LENGTH: 17
<212> TYPE: DNA
<213> ORGANISM: Artificial Sequence
<220> FEATURE:
<223> OTHER INFORMATION: BP3R1 PRIMER

<400> SEQUENCE: 17
aacgactgac ttcgtac 17

<210> SEQ ID NO 18
<211> LENGTH: 15
<212> TYPE: DNA
<213> ORGANISM: Artificial Sequence
<220> FEATURE:
<223> OTHER INFORMATION: BP3F2 PRIMER

<400> SEQUENCE: 18
tgccgatcac gtctt 15

<210> SEQ ID NO 19
<211> LENGTH: 16
<212> TYPE: DNA
<213> ORGANISM: Artificial Sequence
<220> FEATURE:
<223> OTHER INFORMATION: BP3R2 PRIMER

<400> SEQUENCE: 19
ggtggttcga cgcttc 16

<210> SEQ ID NO 20
<211> LENGTH: 18
<212> TYPE: DNA
<213> ORGANISM: Artificial Sequence
<220> FEATURE:
<223> OTHER INFORMATION: BP3P1 PROBE

<400> SEQUENCE: 20
acttccatgc ccagttcg 18

<210> SEQ ID NO 21
<211> LENGTH: 17
<212> TYPE: DNA
<213> ORGANISM: Artificial Sequence
<220> FEATURE:
<223> OTHER INFORMATION: BP3P2 PROBE

<400> SEQUENCE: 21
cgaactgggc atggaag 17

<210> SEQ ID NO 22
<211> LENGTH: 18
<212> TYPE: DNA
<213> ORGANISM: Artificial Sequence
<220> FEATURE:
<223> OTHER INFORMATION: SAF1 PRIMER

<400> SEQUENCE: 22
taccaactgc tttcatct 18

<210> SEQ ID NO 23
<211> LENGTH: 20
<212> TYPE: DNA
<213> ORGANISM: Artificial Sequence
<220> FEATURE:
<223> OTHER INFORMATION: SAR1 PRIMER

<400> SEQUENCE: 23
caatttgaag tacctgtaca 20

<210> SEQ ID NO 24
<211> LENGTH: 20
<212> TYPE: DNA
<213> ORGANISM: Artificial Sequence
<220> FEATURE:
<223> OTHER INFORMATION: SAF2 PRIMER

<400> SEQUENCE: 24
tttacgttga cataattcca 20

<210> SEQ ID NO 25
<211> LENGTH: 18
<212> TYPE: DNA
<213> ORGANISM: Artificial Sequence
<220> FEATURE:
<223> OTHER INFORMATION: SAR2 PRIMER

<400> SEQUENCE: 25
cagaagtgac ggttgata 18

<210> SEQ ID NO 26
<211> LENGTH: 23
<212> TYPE: DNA
<213> ORGANISM: Artificial Sequence
<220> FEATURE:
<223> OTHER INFORMATION: SAP1 PROBE

<400> SEQUENCE: 26
tttacggctt atgtcaccgc cat 23

<210> SEQ ID NO 27
<211> LENGTH: 22
<212> TYPE: DNA
<213> ORGANISM: Artificial Sequence
<220> FEATURE:
<223> OTHER INFORMATION: SAP2 PROBE

<400> SEQUENCE: 27
tagttgcacg aacatatggc tc 22

<210> SEQ ID NO 28
<211> LENGTH: 16
<212> TYPE: DNA
<213> ORGANISM: Artificial Sequence
<220> FEATURE:
<223> OTHER INFORMATION: GBSF1 PRIMER

<400> SEQUENCE: 28
aaccaattgc tttcat 16

<210> SEQ ID NO 29
<211> LENGTH: 16
<212> TYPE: DNA
<213> ORGANISM: Artificial Sequence
<220> FEATURE:
<223> OTHER INFORMATION: GBSR1 PRIMER

<400> SEQUENCE: 29
cagctattgg acaaaa 16

<210> SEQ ID NO 30

```
<211> LENGTH: 23
<212> TYPE: DNA
<213> ORGANISM: Artificial Sequence
<220> FEATURE:
<223> OTHER INFORMATION: GBSP1 PROBE

<400> SEQUENCE: 30

cgtagtgctt ttatatcaga acg                                              23


<210> SEQ ID NO 31
<211> LENGTH: 18
<212> TYPE: DNA
<213> ORGANISM: Artificial Sequence
<220> FEATURE:
<223> OTHER INFORMATION: MycobSF3 PRIMER

<400> SEQUENCE: 31

cactccgcgg tagatgtc                                                    18


<210> SEQ ID NO 32
<211> LENGTH: 19
<212> TYPE: DNA
<213> ORGANISM: Artificial Sequence
<220> FEATURE:
<223> OTHER INFORMATION: MycobSR2 PRIMER

<400> SEQUENCE: 32

aagttcctaa tctgcgccg                                                   19


<210> SEQ ID NO 33
<211> LENGTH: 17
<212> TYPE: DNA
<213> ORGANISM: Artificial Sequence
<220> FEATURE:
<223> OTHER INFORMATION: MTCF1 PRIMER

<400> SEQUENCE: 33

agaccgtgcg gatcttg                                                     17


<210> SEQ ID NO 34
<211> LENGTH: 18
<212> TYPE: DNA
<213> ORGANISM: Artificial Sequence
<220> FEATURE:
<223> OTHER INFORMATION: MTCR1 PRIMER

<400> SEQUENCE: 34

catggagatc acccgtga                                                    18


<210> SEQ ID NO 35
<211> LENGTH: 21
<212> TYPE: DNA
<213> ORGANISM: Artificial Sequence
<220> FEATURE:
<223> OTHER INFORMATION: MTCP PROBE

<400> SEQUENCE: 35

tcgtctttgt gcacccgata c                                                21


<210> SEQ ID NO 36
<211> LENGTH: 19
<212> TYPE: DNA
<213> ORGANISM: Artificial Sequence
<220> FEATURE:
<223> OTHER INFORMATION: MSP PROBE

<400> SEQUENCE: 36
```

acgaccttct cggaaccgt 19

<210> SEQ ID NO 37
<211> LENGTH: 31
<212> TYPE: DNA
<213> ORGANISM: Artificial Sequence
<220> FEATURE:
<223> OTHER INFORMATION: Guf1 Region 1 Probe P1-CalbiGuf1

<400> SEQUENCE: 37
cgagagggaa agaggaatta cagtgaaagc c 31

<210> SEQ ID NO 38
<211> LENGTH: 23
<212> TYPE: DNA
<213> ORGANISM: Artificial Sequence
<220> FEATURE:
<223> OTHER INFORMATION: Guf1 Region 1 CanGuf1-1f Forward primer

<400> SEQUENCE: 38
attgtggcac acgttgacca tgg 23

<210> SEQ ID NO 39
<211> LENGTH: 26
<212> TYPE: DNA
<213> ORGANISM: Artificial Sequence
<220> FEATURE:
<223> OTHER INFORMATION: Guf1 Region 1 CanGuf1-1r Reverse primer

<400> SEQUENCE: 39
tgtgcttgaa ctccttgaga tgcatc 26

<210> SEQ ID NO 40
<211> LENGTH: 31
<212> TYPE: DNA
<213> ORGANISM: Artificial Sequence
<220> FEATURE:
<223> OTHER INFORMATION: Guf1 Region 2 Probe P2-CalbiGuf1

<400> SEQUENCE: 40
ctacttggca tacagcatgg gattgaaatt g 31

<210> SEQ ID NO 41
<211> LENGTH: 23
<212> TYPE: DNA
<213> ORGANISM: Artificial Sequence
<220> FEATURE:
<223> OTHER INFORMATION: Guf1 Region 1 CanGuf1-2f Forward primer

<400> SEQUENCE: 41
gatgcatctc aaggagttca agc 23

<210> SEQ ID NO 42
<211> LENGTH: 23
<212> TYPE: DNA
<213> ORGANISM: Artificial Sequence
<220> FEATURE:
<223> OTHER INFORMATION: Guf1 Region 2 CanGuf1-2r Reverse primer

<400> SEQUENCE: 42
atcatgccaa gaatccacca ata 23

<210> SEQ ID NO 43
<211> LENGTH: 31
<212> TYPE: DNA

<213> ORGANISM: Artificial Sequence
<220> FEATURE:
<223> OTHER INFORMATION: Guf1 Region 3 Probe P3-CalbiGuf1

<400> SEQUENCE: 43
cttgtcagcg cacacaaata ggacatacga c 31

<210> SEQ ID NO 44
<211> LENGTH: 23
<212> TYPE: DNA
<213> ORGANISM: Artificial Sequence
<220> FEATURE:
<223> OTHER INFORMATION: Guf1 Region 3 CanGuf1-3f, Forward primer

<400> SEQUENCE: 44
tattggtgga ttcttggcat gat 23

<210> SEQ ID NO 45
<211> LENGTH: 22
<212> TYPE: DNA
<213> ORGANISM: Artificial Sequence
<220> FEATURE:
<223> OTHER INFORMATION: Guf1 Region 3 CanGuf1-3r, Reverse primer

<400> SEQUENCE: 45
gggaatgccc caacaaatac ca 22

<210> SEQ ID NO 46
<211> LENGTH: 29
<212> TYPE: DNA
<213> ORGANISM: Artificial Sequence
<220> FEATURE:
<223> OTHER INFORMATION: Guf1 Region 1 probe P1-AfumiGuf1

<400> SEQUENCE: 46
cgcaaacctg ctcgatgata tacaatcac 29

<210> SEQ ID NO 47
<211> LENGTH: 23
<212> TYPE: DNA
<213> ORGANISM: Artificial Sequence
<220> FEATURE:
<223> OTHER INFORMATION: Guf1 Region 1 AspGuf1-1f, Forward primer

<400> SEQUENCE: 47
gcccatgtcg atcatggcaa aag 23

<210> SEQ ID NO 48
<211> LENGTH: 20
<212> TYPE: DNA
<213> ORGANISM: Artificial Sequence
<220> FEATURE:
<223> OTHER INFORMATION: Guf1 Region 1 AspGuf1-1r Revere primer

<400> SEQUENCE: 48
acctctgcac ggaagtccac 20

<210> SEQ ID NO 49
<211> LENGTH: 26
<212> TYPE: DNA
<213> ORGANISM: Artificial Sequence
<220> FEATURE:
<223> OTHER INFORMATION: Guf1 Region 2 probe P2-AfumiGuf1

<400> SEQUENCE: 49
caccacagag cgtgctccgt gccggc 26

<210> SEQ ID NO 50
<211> LENGTH: 20
<212> TYPE: DNA
<213> ORGANISM: Artificial Sequence
<220> FEATURE:
<223> OTHER INFORMATION: Guf1 Region 2 AspGuf1-2f, Forward primer

<400> SEQUENCE: 50
gaggttggca tcatgtatcc 20

<210> SEQ ID NO 51
<211> LENGTH: 20
<212> TYPE: DNA
<213> ORGANISM: Artificial Sequence
<220> FEATURE:
<223> OTHER INFORMATION: Guf1 Region 2 AspGuf1-2r Reverse primer

<400> SEQUENCE: 51
agctggttga tactgtcttc 20

<210> SEQ ID NO 52
<211> LENGTH: 29
<212> TYPE: DNA
<213> ORGANISM: Artificial Sequence
<220> FEATURE:
<223> OTHER INFORMATION: Guf1 Region 3 probe P3-AfumiGuf1

<400> SEQUENCE: 52
ccactcaagt caagtggaaa ggctcggac 29

<210> SEQ ID NO 53
<211> LENGTH: 23
<212> TYPE: DNA
<213> ORGANISM: Artificial Sequence
<220> FEATURE:
<223> OTHER INFORMATION: Guf1 Region 3 AspGuf1-3f Forward primer

<400> SEQUENCE: 53
gagtatttca caccaacgca ggt 23

<210> SEQ ID NO 54
<211> LENGTH: 22
<212> TYPE: DNA
<213> ORGANISM: Artificial Sequence
<220> FEATURE:
<223> OTHER INFORMATION: Guf1 Region 2 AspGuf1-3r Reverse primer

<400> SEQUENCE: 54
ttgaattttg tcacccattg tc 22

<210> SEQ ID NO 55
<211> LENGTH: 2442
<212> TYPE: DNA
<213> ORGANISM: Aspergillus fumigatus

<400> SEQUENCE: 55
atgagtatgc gttgcaccca tcctccagcg cacatcaaca tacaggatgg agtttatcga 60
gtattcaaac taagtcttgt caaccggtgt tctccgtcca gatcgatgga attgactcac 120
gaattctgcc acgagcttcg ccgagcctgt catagatgga tgggatgctt tctcgttcgt 180
gaggtctctt ggctggtcag aaacgaggca gcttttgttt acctcgatag tcacctcagc 240
aatccgttgt tccaccgccc ggagctaagc actttttctc cgcagcaagt gatccgttgc 300

-continued

```
cgcagttttt cttttctcgg aatcggcagt ggaaaactcg aatcctcatc ccaaaaggca    360
ttttattccc atgccattgc agtactccag atgcgaggat gcttgcagtt agccagatgg    420
ctgagcgctg caccgaaagg cacagctgca agcctgacga gggcgccgtt cgtccttgct    480
aacgctcccc ggtatttcac cagctccgct tctcgtgctg gatcgagatc gaccgctacc    540
aagccgttat ccgacctcga gaagagaata tctgcgattc caatcgagcg ataccggaac    600
ttttgcatcg ttgcccatgt cgatcatggc aaaagcacac tttcggaccg cctgctcgaa    660
ctcacgggga cgattgagcc cggctcgaac aaacaagtgt tggacaagct cgacgtggag    720
cgtgaacgtg gcatcaccgt gaaggcgcaa acctgctcga tgatatacaa tcacaatggt    780
gaagactatt tattgcacct ggttgatact ccaggccatg tggacttccg tgcagaggta    840
tcccgtagtt atgctagttg cggaggagca ttgctcctgg tcgatgccag tcaaggaatc    900
caggcacaga ccgttgcgaa cttctacctc gcttttgcgc agggcttgga attgattcca    960
gtcatcaaca aggtagattt gccctcggct gaaccagagc gagctcttga gcagatgaag   1020
aattccttcg agctcgacac cgagaacgca gtgatggttt cagctaagac aggcctcaat   1080
gttgagaaat tacttccgac agttattgag aagatcccag cgtatggcca tttccccgtc   1140
gattctcatg agctgcttcc gttactgact cttagcagcc ccatcggcga ttgcaagaag   1200
cccctgcgaa tgttactcgt tgactcgtgg tacgattcct acaaaggcgt aatctgtctg   1260
gtccgcatct tcgacggtga aattcgagca ggccagcagg tcgtgtcgtt tgcgacgggt   1320
cttaaatact acgttggcga ggttggcatc atgtatccaa atgaaacacc acagagcgtg   1380
ctccgtgccg gccaagttgg atacatctac ttcaacccag gtatgaaacg aagcaaagaa   1440
gcgaagattg gtgacacatt tacaagggtc ggatttgaga aagccgttga accacttcct   1500
ggctttgagg agcccaaagc gatggttttt gtggcggctt acccggtgga tgcagaccat   1560
tttgagcact tggaagacag tatcaaccag ctcgtgctta acgacaggag tatcaccgtg   1620
cagaaggagt cctcagaggc tcttggcgcc ggcttcagat tgggatttct aggcacactg   1680
cactgttctg tgtttgagga tcgtttgcgt caggagcatg gtgctagcat catcatcaca   1740
cctccatcag tgcctgtcaa gatcatttgg aaggacggaa aagaggagat cattaccagc   1800
cctgccaaat ttcctgaaga cgaagaactg cgctccaagg tggctgagat tcaagagccc   1860
tacgtcctgg ctacactgac cttccccgag gagtaccttg gcaaggtcat tgagctttgc   1920
gaggcaaaca gaggcgagca gaagagttta gagtatttca caccaacgca ggtcattctt   1980
aagtatgaac tgcctcttgc tcaactcgtt gatgacttct tcggcaagct caaggggtct   2040
accaaaggct acgccagcct ggactatgag gagtccgctt ggcaaacagg gaacatcgtc   2100
aagctgcaac ttttggtaaa taaggcgcct gtcgatgctg ttgctcgcat cgtccactca   2160
agtcaagtgg aaaggctcgg acgacaatgg gtgacaaaat tcaaggagca tgtcgatcga   2220
caactgttcg aggttgtgat ccaggctgct gttggtaaaa agatcatcgc ccgagagaca   2280
gtcaaaccct accgaaaaga tgtcttggcc aagctccatg ctagcgatgt cagtcggcgc   2340
cggaaactgc tggagaagca gaaagaagga cgaaagagac tgagagctgt tggaaacgtg   2400
gtgattgagc acaaggcatt ccaggccttc ctcgccaaat aa                      2442
```

<210> SEQ ID NO 56
<211> LENGTH: 1998
<212> TYPE: DNA
<213> ORGANISM: Aspergillus terreus

<400> SEQUENCE: 56

```
atgcgaggat gcctgcagtt agccagatgg ctgagcgcag cgccaacccg ccctgctgct     60
agccattggc ctggcctttg cgccgctccg cggtttttct cccattcagc gatcctccga    120
gcctccgcaa ggacagcccg cgcggcggcg agcaaacctc cctccgacct tgaatcgcga    180
atcgcggcga tcccaatcga gcggtaccgg aatttctgca tcgtcgcgca cgtcgaccat    240
ggcaaaagca ccctctctga ccgactgctg gaactgacgg ggacgattga gccggggaca    300
aacaagcagg ttctggacaa actcgatgtg gagcgtgaac ggggtatcac agtcaaggcg    360
cagacatgta cgatgatcta caatcacaac ggcgaggact atctgctgca tctggtcgat    420
accccgggac atgtggattt ccgtgcggag gtctcgcgca gttacgccag ctgcggcggt    480
gcgttgcttc ttgttgatgc gagccagggt gtccaggcgc agaccgtggc gaacttctac    540
ctcgcctttg cccagggtct ggagcttatc cctgtcatta acaaagtaga tttgccgtcg    600
gcggagcccg agcgcgccct cgagcagatg aaacagtctt tcgaactcga cacggaaaat    660
gctgtgatgg tttcggcgaa gtcgggactg aatgtggaga aacttcttcc tacggtggtg    720
gataagattc cagcaccgat tggcgactgc aaaaagcccc tgcgaatgct ccttgtcgac    780
tcgtggtacg actcctacaa aggcgtgata tgcttggtcc gcgtattcga cggcgaaatc    840
cgcgcggggg accaattggt gtcgttcgcc acgggcatca agtactacgt gggcgaggtc    900
ggcatcatgt atcccaacga gactcctcag acggtcattc gtgcgggaca agtcggatac    960
atcttcttca acccgggtat gaagcgcagt aaggaagcca agattgggga cacctacacg   1020
aaagtcggct ccgagaaggc tgttgagccg cttccgggct tcgaagaacc aaaggcgatg   1080
gtctttgtgg cggcataccc cgtggacgcc gaccatttcg agcatctcga agacagcatc   1140
aaccagctta tgctgaacga ccggagcatc acggtgcaga aggagtcttc cgaggctctg   1200
ggcgcgggct tccggctcgg atttctggga acactgcatt gctccgtatt cgaggaccgt   1260
ctgcgccagg agcacggcgc cagcatcatt atcaccccgc cttcagtgcc cgtgaaggtt   1320
ctgtggaaag acgggcggga ggagatcgtc accagccctg caaagttccc agatgaagat   1380
gaactgcggt ctaaggtcgc ggagatcaag gaaccctacg tgctggctac cttgacgttc   1440
ccagatgaat acctcggaaa agtcattgaa ctgtgcgaat ccaaccgtgg tgtccagcag   1500
agcctcgagt acttcacgtc aacgcaggtc atcctcaaat acgaactgcc aatggctcag   1560
cttgtggacg atttcttcgg aaagctgaag ggatcgacga agggctacgc gtctttagac   1620
tacgaggaat ccgcttggca gacgagcaac attgtgaagc tgcagctcct cgtcaataaa   1680
gctcctgtgg atgctgtggc gagaattgtg cactatagtc aaattgagag acttggcagg   1740
aaatgggtga ccaagttcaa ggaacatgtt gatcggcagc tcttcgaggt cgtgatccaa   1800
gccgctgtcg gacggaaggt cattgcgcgt gaaacggtca aaccgtaccg caaagacgtc   1860
ctcgccaaac tccatgccag cgatgtcagt cgacggagaa aactgttgga gaagcagaag   1920
gagggacgga agagactgag agcagtcggc aatgtcgtga tagaacataa ggcgttccag   1980
gctttcttgt ccaagtga                                                 1998
```

<210> SEQ ID NO 57
<211> LENGTH: 1995
<212> TYPE: DNA
<213> ORGANISM: Aspergillus clavatus

<400> SEQUENCE: 57

```
atgcgaggat gcctgcagtt agccagatgg ctgagcgcag caccgaaagg caccgctgca     60
```

```
agcctgacca gggcgccatt tggccttgct aacgcaactc ggtttttcac caattccgct    120

gcgcgcgccg gctcaagagc cactgccagc aaaccggtaa ccgatctcga gaacagaata    180

tccgcgattc cgatcgagcg ctaccgcaat ttctgcatcg tcgcccacgt tgatcatggc    240

aaaagcaccc tttccgaccg gctgctcgaa ctgacgggca ccatccagcc cggttcgaac    300

aagcaagtcc tggacaaact cgatgtcgaa cgagaacgcg gcatcactgt gaaggcacag    360

acgtgtacta tgatatataa ccacaacggc gaagactact tgttgcatct ggttgatacc    420

ccgggacatg tggacttccg cgcggaggtc tcgcgcagtt atgccagctg cggaggagca    480

ctgctcttgg tcgacgccag tcagggagtc caggcacaga cggttgcgaa cttttatctt    540

gcttttgcac agggattaga attgatcccc gtcatcaaca aggtggatct accgtcggct    600

gagccacagc gggctttaga ccagatgaag catacctttg agcttgatac agaaaacgca    660

gtcatggttt cggccaagac aggactcaat gtcgagcagt tgcttccgac agttgttgac    720

aagattcctg cgccgatcgg cgattgcaag aaacccctcc gaatgttact cgttgattcc    780

tggtatgatt cctacaaggg tgttatctgt ttggttcgta tcttcgacgg cgaactgcgg    840

gctggccagc aagttgtgtc atttgccacg ggtctcaaat actatgtggg agaagtagga    900

attatgtatc cgaacgagac agcgcagagc gtgatccgtg ctggtcaagt cggttatatc    960

tatttcaacc ccggcatgaa acggagccag gaagcgaaaa ttggcgacac atttacaaag   1020

gtcggctcgg agaaagctgt gcagcccctt ccaggcttcg aagagccgaa ggcaatggtc   1080

tttgtcgccg cttatcctgt ggatgcggac catttcgagc atctggaaga cagtatcaac   1140

cagcttgtgc tcaatgatag aagtatcacg gttcagaagg agtcctcgga ggcccttggt   1200

gcaggcttca gactcggatt ccttgggacc ttgcattgtt cggtcttcga ggatcgtctg   1260

cgtcaggaac acggcgccag tatcatcatc actcccccct cagtgcctgt gaaggtcatt   1320

tggacggacg gcaaagagga aatcatcacg agcccagtcc gtttcccaga tgatgaggaa   1380

gtgcgtaaca agatcgcaga gattcaagag ccgtatgtcc tggccacatt gacattccca   1440

gaagaatatc ttggcaaagt gatcgaactt tgcgaggcca atcggggtga gcagaagact   1500

ctcgagtatt tcacagcaac ccaggtcatt ctcaagtatg agctgcctct tgcgcaattg   1560

gttgacgact tctttggaaa gctgaaaggg tctaccaaag gatatgccag cttggactat   1620

gaagaatccg cgtggcaacc gggacatatc gtcaagctgc aactcttggt caacaaggca   1680

ccggtcgatg ctgttgcgcg catcatgcat tcgagccaag tcgataggct cgcaagacaa   1740

tgggtaacca agttcaaaca acacgtcgat cgacagctgt tcgaagtcgt gatccaggct   1800

gctgtcggtc gcaaggtcat cgcacgagag acggtcaagc cgtaccggaa ggatgtcttg   1860

gcgaagctac atgctagtga tgtgagtcgg cgccggaaac tgctcgagaa gcagaaagaa   1920

ggacgaaaga ggctccgggc agttgggaac gtggtgattg agcacaaggc attccaggct   1980

tttctcgcga aatag                                                    1995
```

<210> SEQ ID NO 58
<211> LENGTH: 2001
<212> TYPE: DNA
<213> ORGANISM: Aspergillus niger

<400> SEQUENCE: 58

```
atgcgaggat gcctgcagtt agccaggtgg ctgcgcgcag caccgaaatg tcctgctgca     60

agccttctca agccgccatc cggccttgct aatccagccc ggtttttcac gacttccacc    120

gcatgctggg catcgcgctc cagggctccg gccagccagc catcctccga ccttgaatca    180
```

```
agaatcgcag ctatcccgat tgatcgatac cgtaacttct gcattgtcgc ccacgtcgat    240
catggcaaaa gtaccctctc cgatcggctg ttggaactca caggaacgat ccagcccggt    300
atgaacaagc aggttttgga caagcttgac gtcgagcgtg aacggggtat tacggtgaag    360
gcacagacat gtacaatgat ttacaaccat aatggcgagg actatctgtt gcatctggtt    420
gatacaccgg gacatgtgga cttccgtgcg gaggtttcgc gcagttatgc cagttgcgga    480
ggagcgttgc tcttagttga cgccagtcaa ggtatccagg ctcagacagt cgccaacttc    540
tatctcgcat tctctcaggg cctggagttg atccccgtca tcaacaaggt ggacctgccg    600
tccgctgatc cggagcgtgc tcttgaccag atggaacagt cttttgagct tgacacggaa    660
agtgcagtgt tggtatcagc caagacggga cttaatgtgc agcaattgct tcctactgta    720
gtcgagaaga ttccggcacc ggtgggagat gttaacaatc ccctacggat gcttctcgtc    780
gattcctggt atgattcgta ccgaggtgtc atctgcttgg tccgcgtttt cgacggcgaa    840
atccgggcag gagaccagct tgtgtcgttc gcgactggaa tcaaatactt cgtgggcgag    900
gtcggaatta tgtatcccaa cgagacggcc cagtcggtcc ttcgggctgg ccaggtcggc    960
tacatcttct tcaaccctgg tatgaagcga agcaaggaag ctaaaatcgg tgatacctac   1020
accaaggttg ggtttgagaa agtcgtcgag ccgcttccgg gcttcgaaga acccaaggca   1080
atggttttcg tggccgccta tcccgtggac gccgatcact tcgagcactt ggaagatagt   1140
atcaaccagc tttgtctgaa cgaccggagt attactgtgc aaaaagagtc atctcatgct   1200
cttggagcag gtttccggtt gggctttttg ggaacactgc attgctctgt ctttgaggat   1260
cgtctgcgcc aggagcacgg tgccagtatc atcatcactc ctccttccgt tcccgtgaaa   1320
ctcatctgga aagacggcaa ggaagagatc atctccaatc ccgccaagtt cccggaggat   1380
gaagagcttc gtggcaagat ctccgagatt caggagcctt atgttgtcgc tactttgacc   1440
ctccccgatg agtatcttgg aaaggtcatc gagctctgcg agtccaaccg aggcgtgcaa   1500
aagagcctcg agtatttcac atccactcag gttattctca agtatgaact gccccttgcg   1560
cagctggttg atgacttctt cggaaagctg aagggctcta ctaagggcta cgccaccctt   1620
gattacgagg aatctgcgtg gcaaacaagc aacatcgtca agttacaact tctggtcaac   1680
aaggctccgg tggatgcggt cgcacggctc gttcattaca gccaagtaga gcgattgggc   1740
agacaatggg tgactaagtt caaagagcac gttgaccggc aactgttcga gatcgtcatc   1800
caagcagctg ttggccgtaa ggttgtggcg cgtgagaccg ttaagccgta ccggaaggat   1860
gtcctcgcga agctgcatgc cagtgatgtc agtcggcgca ggaagctctt ggaaaagcag   1920
aaggagggac gcaagaagct gcgggctgtt ggaaacgtgg tgattgaaca aaaggcattc   1980
caggcattct tggctaaata a                                             2001
```

<210> SEQ ID NO 59
<211> LENGTH: 1965
<212> TYPE: DNA
<213> ORGANISM: Candida albicans

<400> SEQUENCE: 59

```
atgctactaa ggccgaattc tgggaatact ttaaagtatg gttgtcttct aacgaaaaga     60
tggttaacaa ctctgaaact actatactct gtggaagata tgaagatcaa gattggtcag    120
gaacaatatc gaaaggcact tgaagaaagg atagataaaa taccaattga aaactaccgg    180
aacttcagta ttgtggcaca cgttgaccat ggcaagtcca cattatcaga tcgattatta    240
```

-continued

```
gaaatgacag gggtgatcaa accaggatcc aagtctcagg ttttggataa attagatgtc    300
gagagggaaa gaggaattac agtgaaagcc cagactgtgt ctatgtttta taacgatggg    360
aaacaagatt atttgttaca tttggttgac acaccagggc atgtggattt cagagcagaa    420
gtgtcaaggt catatgcatc ttgtggagga gcattgttgt tagtcgatgc atctcaagga    480
gttcaagcac agacagtagc aaatttctac ttggcataca gcatgggatt gaaattgatt    540
cccataataa acaaaattga tttggatctg gctaacattc ctggagcgag ggagcaaatt    600
gaaacgacat ttgagttaga ccccaatgaa tgcatcccag tgagcgccaa aaccggttta    660
aatgtcgaac aaataatacc gtctgtaatt aaaaatatcc catctcctgt atgtgatgtg    720
aacaagcctt tgcgagcttt attggtggat tcttggcatg atccctacgt tggtgtggta    780
atgcttgttc atattgtgga tggtagaatg aaaaaaggta tgaaaatctt gtcagcgcac    840
acaaatagga catacgacgt taaggaagtt gggataatgt atccagatag aacaccgacc    900
agtttcatta aagctggaca agtcgcctat attataccgg ggatgaagaa ccctcgggaa    960
gcgcttgtgg gtgacacgtt ttatcaaatg ggcaaacatg aaggtcttga acctttacca   1020
ggatttgaag aacctaagcc aatggtattt gttggggcat tccctgcaga tgggaaagag   1080
tttaatgcta tggatgatca aatgcagaat ttagttttga atgataggtc ggtaacctta   1140
gagcaggaaa catcaaatgc attggggtta ggttggagat tgggattctt aggctcatta   1200
catgcgtcag tgtttaaaga aagattagaa aaagaatatg gggcgaaaat tattttgaca   1260
gcccccaccg tgccctacaa gattatctat aaaaatggcg aagaaaaaat tgttactaat   1320
cctgatgatt ttccagacaa ccagaaacat cacgatgttg aaagctatat ggaaccatat   1380
gttgaggcga taatgaccgt tccaaatgaa tatgttggaa atgttatgac tttgtgttta   1440
aataatcgag gagaacagaa agagatcgaa tacttgacaa caggacaggt attgctaaag   1500
tatgagatcc caacctcaca actagtggag gatttttttg ggaaactaaa aggatgcacc   1560
aaaggatatg cttcgcttga ctatgaagaa gcaggatata gaaaatcaga tatagttaag   1620
atgcagcttt gtgtgaatgg tgagccacaa gatgcgttaa ctacagttat acacagatca   1680
caagcgcaag caaggggtaa ggagtacgtt acgaggttta agaaattttt gagctaccag   1740
ctatttgaag ttgccattca agcaaaaatt aataacaaag tggtggcaag agaaaccatc   1800
aaagcaaaaa gaaaagacgt aacacaaaga ttacatgcag cagacatatc aagatataag   1860
aaattgttgg aaagacaaaa ggagggtaag aaacagatga aattaagcgg cagagtgaca   1920
atcaagaacg acgcttatca agccttctta cgtagagaag actaa                  1965
```

<210> SEQ ID NO 60
<211> LENGTH: 1974
<212> TYPE: DNA
<213> ORGANISM: Candida glabrata

<400> SEQUENCE: 60

```
atgctgaaga ccttaggttt aagaagtttg tgcccttcac ttggtggtcg aggctttcga     60
aggcatccca atattaataa atacacattg tcgttggtca gagtacgatg gaatcaccat    120
ttaagtaatg ctgagataca ggcacgaatt gagaacatac cacaggagaa ctatagaaac    180
ttttcgattg tcgcccatgt tgatcatggg aaatcgactt tgagtgatcg attgttagag    240
ataacgggag tcatagacaa gaactcttca aacaaacaag tgcttgataa attagaagta    300
gaaagagaaa gaggtattac aatcaaagct cagacttgta caatgttcta ccatgacaag    360
cgtaatggag aagattattt gctacattta gtcgatacgc caggtcatgt tgattttcga    420
```

-continued

```
ggagaagtct cgaggtctta tgcttcttgt ggtggagctc tattgcttgt tgatgcatct    480

caaggagttc aagctcaaac agttgctaat ttttatcttg cttatagtat gggcttaaaa    540

cttatacctg tggtcaacaa aattgattta aatgttgcag atgtcgaaag agctaaagct    600

gaaatcgagg acaattttga gctaccgaga gatgaaataa ttggtgtgag tgctaaaaca    660

ggtcttaatg tcaaagagat gcttctgcct accatcgttg atagaatccc tcctcctact    720

ggtaataaga agaaaccatt ccgcgcacta ttggtggatt cttggtatga ttcatactta    780

ggagtaatac ttctagtaaa tattgttgac ggaaaattaa aaaagggtga aaaggtacta    840

tgtgcacata ctaacaaaaa gtatgaggtg aaagaacttg gcattatgta tcctgataga    900

gttccaaccg gttcattggt tgtgggtcaa gtagggtatg tcgttttggg aatgaaagac    960

tcttcagatg cccatgtagg tgatacatta atgcatgtag gaaaagagag tgtgacagat   1020

attctacctg gattcgagga acaaaaacca atggtctatg ttggagcttt cccctctact   1080

ggaactgaat ttaaggcaat ggacgatgat attaaccggt tggttctgaa tgataggtcg   1140

gtaacactgg aaagagaaac atctaatgct ttagggcaag gatggagatt agggtttttg   1200

ggctccttgc atgcatctgt atttagagaa agactagaaa aggaatacgg ctcaaagcta   1260

attatcacac aacccacggt cccatatatg gtaagaatga cagatggtac agagtctatt   1320

attacaaatc ctgatgactt tccagatagc gctacaaggc gaatgaaggt tgaagaactt   1380

ctggaaccct ttgtagaagc caccataaca ttgcctcaag aatttctggg aaatgtcatt   1440

aaactctgtg atgccaatag aggtcaacag aaggaaataa cttatttgaa tacaagaggc   1500

caagttgtct tgaaatacca tttgccattg gctcatctag tagatgactt ctttggaaaa   1560

ttgaaagcgg cgtctaaggg atatgcctct ttagattatg aagatattgg ctacagagaa   1620

tctgatgtag tcaaactaga gcttttggtt aatggtcaaa gtattgatgc tttagcaagg   1680

gtgcttcatc gaactgaagt tgaaaaagtg ggtagagaat gggtgcaaaa gttcaaggag   1740

tatgttaagt ctcaattatt tgaagttgta atccaggcta gggcaggcac caagattgta   1800

gctagacaaa caataaaggc tagaagaaag gatgttcttg caaggttgca tgcttcagat   1860

gtatccagaa gaaagaagtt gcttgaaaag caaaaggaag gtaaaaaaca aatgagatcg   1920

gttggtagag tacaaataaa ccaagaggca tatcaagcct tttgaaacg ttga          1974
```

<210> SEQ ID NO 61
<211> LENGTH: 1821
<212> TYPE: DNA
<213> ORGANISM: Bacillus anthracis

<400> SEQUENCE: 61

```
atgaacaaag aagaaagagc aaaaagacag tccaaaattc gtaatttctc tatcattgct     60

catattgacc acggaaagtc aacgttagca gaccgtattt tagagaaaac aaacgcgtta    120

acacaacgtg aaatgaaagc tcagttgctt gactctatgg atttagagcg tgagcgtggt    180

attacaatta aattaaacgc aatacaatta aactataaag caaaagacgg cgaagaatat    240

attcttcact taattgatac accaggacac gtcgacttta cgtacgaagt atctcgtagt    300

ttagcggctt gtgaaggtgc gattcttgta gtagatgcag cgcaaggtat tgaagcgcaa    360

acgttagcaa acgtatactt agcgcttgat aacaatttag aaattttacc ggttattaat    420

aaaatcgact taccaagtgc agacccagag cgtgtacgcc aagaagtaga agatgtaatt    480

ggattagatg catcagaagc tgtacttgct tctgcaaaag ctgggattgg tattgaagag    540
```

```
attttagaac aaatcgttga aaaagtacca gcaccaacag gtgattcaga agaaccgtta    600
caatgtatga tctttgactc tttatatgat ccataccgcg gtgtaattgc gtatatccgt    660
gttgtaaatg gaacggtaaa agttggcgat aaagtacgta tgatggcaac tggaaaagaa    720
tttgaagtaa cagaagtagg tgtatttaca ccgaaaacta cgcaacgtga cgagttaaca    780
gtaggtgatg taggtttctt agcggcatcg attaaaaatg ttggtgatac acgcgttggt    840
gatacgatta cacacgcgaa acgtccggca gctgagccgt tagcaggtta tcgtaaatta    900
aatccaatgg tattctgtgg tttatatccg attgattctg cacgttataa cgacttacgt    960
gatgcgttag aaaaattaga attaaacgat tctgcacttg agtttgaacc agaaacatct   1020
caagcgctag gatttggttt ccgttgtgga ttcttaggac ttcttcatat ggaaatcctt   1080
caagaacgta ttgaacgtga atttaagatt gatttaatta caacagcgcc aagcgttatt   1140
tataaagtat tcttaacaaa tggtgaagac atgattgtcg ataacccgtc taatatgccg   1200
gatccacaaa caattgatcg tgttgaagag ccatttgtta aagctgcaat tatggttccg   1260
aacgactatg ttggagctgt aatggaaatt tgccaaggta aacgcggaac atttattgat   1320
atgcaatatt tagatgaaac gcgtgttaca ttgacatatg aaatcccgtt atcagaaatc   1380
gtatatgact tcttcgatca gttgaaatca aatacgaaag gatatgcatc atttgattat   1440
gagttaattg gttacaaacc atctaaactt gtaaaaatgg atattctttt aaattctgag   1500
caagtcgatg ctctatcatt tatcgtacac cgtgattcag cgtatgaccg tggtaaagta   1560
atcgtagaaa aattaaaaga attaattcca agacagcagt tcgaagtgcc aattcaagcg   1620
actatcggaa acaaagttgt agcgcgttct acaattaagg cgatgcgtaa aaacgtactt   1680
gcgaaatgtt acggtggtga catttctcgt aagcgtaaac ttcttgacaa gcaaaaagaa   1740
ggtaaaaaac gtatgaagtc tgttggttct gtagaagtac cgcaagaagc attcatggct   1800
gtactgaaaa tggatgacaa c                                             1821
```

<210> SEQ ID NO 62
<211> LENGTH: 1821
<212> TYPE: DNA
<213> ORGANISM: Bacillus cereus

<400> SEQUENCE: 62

```
atgaacaaag aagaaagagc aaaaagacag tccaaaattc gtaatttctc tatcattgct     60
catattgacc acggaaagtc aacgttagca gaccgtattt tagagaaaac aaacgcgtta    120
acacaacgtg aaatgaaagc tcagttgctt gactctatgg atttagagcg tgagcgtggt    180
attacaatta aattaaacgc agtacaatta aactataaag caaaagacgg tgaagaatat    240
attcttcact taattgatac accaggacac gtcgacttta cgtacgaagt atctcgtagt    300
ttagcggctt gtgaaggtgc aattcttgta gtagatgcag cgcaaggtat tgaagcgcaa    360
acgttagcga acgtatactt agcgcttgat aacaatttag aaattttacc ggttattaat    420
aaaatcgact taccaagtgc agacccagag cgtgtacgcc aagaggtgga agatgtaatt    480
gggttagatg catcagaagc tgtacttgct tcggcaaaag ctgggattgg tatcgaagag    540
attctagaac aaatcgttga aaaagtgcca gcaccaacag gtgattcaga agaaccgtta    600
caatgtatga tctttgactc tttatatgat ccataccgcg gtgtaattgc gtatatccgt    660
gttgtaaatg gaacggtaaa agttggcgat aaagtacgta tgatggcaac tggaaaagaa    720
tttgaagtaa cagaagtagg tgtgtttaca ccgaaaacta cgcaacgtga tgagttaaca    780
gtaggtgatg taggtttctt agcggcatcg attaaaaatg ttggtgacac acgcgttggt    840
```

```
gatacgatta cacatgcgaa acgtccagca gctgagccat tacctggtta ccgtaaatta    900
aatccaatgg tattctgtgg tctgtacccg attgactctg cacgttacaa cgacttacgt    960
gatgcgctag agaaattaga attaaacgat tctgctcttg agtttgagcc agaaacatct   1020
caagcgctag gatttggttt ccgttgtgga ttcttaggac ttcttcatat ggaaatcatt   1080
caagagcgta ttgaacgtga atttaaaatt gatttaatta caacagcgcc aagtgttatt   1140
tataaagtat tcttaacgaa tggtgaagac atgattgtcg ataacccgtc taatatgccg   1200
gatccacaga caattgatcg tgttgaagag ccatttgtta aagcggcaat tatggttccg   1260
aatgactatg ttggagctgt aatggaaatt tgccaaggta aacgcggaac gtttattgat   1320
atgcaatatt tagatgaaac gcgtgttaca ttgacatatg aaatcccatt atcagaaatc   1380
gtatatgact tcttcgatca gttgaaatca aatacgaaag gatatgcatc atttgattat   1440
gagttaattg gttataaacc atctaaactt gtgaaaatgg atattctttt aaattctgag   1500
caagtcgatg ctctatcatt tatcgtacac cgtgattcag cgtatgaccg tggtaaagta   1560
atcgtagaaa aattaaaaga attaattcca agacagcagt tcgaagtgcc aattcaagcg   1620
acgatcggaa acaaagttgt agcgcgttct acaattaagg cgatgcgtaa aaacgtactt   1680
gcgaaatgtt acggtggtga catttctcgt aagcgtaaac ttcttgataa gcaaaaagaa   1740
ggtaaaaaac gtatgaagtc tgttggttct gtagaagtac cgcaagaagc attcatggct   1800
gtactgaaaa tggatgacaa c                                             1821
```

```
<210> SEQ ID NO 63
<211> LENGTH: 1827
<212> TYPE: DNA
<213> ORGANISM: Bacillus halodurans

<400> SEQUENCE: 63
```

```
atgaacagag aggaacgtct cgctcgtcag tcgcgaattc ggaatttctc gattatcgcc     60
cacattgacc atgggaagtc aacgttggcg gaccgaattc ttgagaagac gagtgccctc    120
acgcaacgag aaatgaaaga ccagatgttg gatgctatgg atcttgagcg tgaacggggc    180
ataaccatta agctgaatgc agttcagctt gtttataaag cgaacgatgg aaatgagtac    240
atttttcatt taattgatac accaggtcac gtggatttct catatgaagt ttcccggagt    300
ttagctgcct gtgaaggggc actgcttatt gttgatgcgg cgcaagggat tgaggcgcaa    360
acgttggcca atgtttattt agccctcgat aatgatcttg aaatcctacc ggttattaat    420
aaaattgatt tgccgagtgc tgagcctgag cgtgttcgcc aagaagtgga ggatgtgatc    480
ggtcttgatg cgtcggaagc tgtccttgct tcagctaaaa atggaattgg gattgaagaa    540
attttagaac aaattgttga aaaagttcca gcgccgagtg gagatccaga aggtccgcta    600
aaagcattga ttttcgattc attgtacgat tcttatcgag gcgttgttgc ctatattcga    660
attgtagaag gatctgtgaa acctggacaa aaaattaaaa tgatggcaac tggaaaagag    720
tttgaagtta ccgaagtggg cgtcttcaca ccaaagcctg agaagcggga agagcttact    780
gtaggtgatg ttggctttct aaccgcttct ataaaaaatg tcggtgatac tcgggtcggt    840
gatacgatca cgagcgcgaa caacccggcg gacgagcccc ttcctggtta tcgacgaatg    900
aatccgatgg tttactgcgg cttataccca gtcgatacga atgattacaa cgacttgcgc    960
gaggcgttag agcgtcttga attgaacgat gcgtcattgc aatatgaacc tgaaacgtca   1020
caagctctcg gttttggttt tcgctgcggc ttcttaggac ttctccatat ggaaatcatt   1080
```

-continued caagagcgga tcgagcgaga atttggtatt gatttaatta cgacggcacc aagcgttgta 1140
tatagcgttc aactgacgaa cggggaagta cagcaaattg ataatccgtc taacatgcct 1200
gataggcaaa agattgagga agtagaagag ccgtatgtca aagcgacgat catggttcca 1260
aacgattttg tcggagctgt catggagctt tgtcaaggga agcgcgggat tttcatcgac 1320
atgcaatacc ttgatgaaaa cagagtgcaa atcatttatg aaattcccct atcagaaatc 1380
gtctatgatt tctttgatca attaaaatca aacacgaaag gatacgcctc ctttgactat 1440
gaattgatcg gttataagcc atctaactta gtgaaaatgg acattttgct gaatggtgaa 1500
gtcgttgatg ccctttctgt cattgtccac cgtgactctg catatgaacg aggaaaacaa 1560
attgttgaaa agctaaaaga actcatccca cgccagcaat ttgaggtgcc agttcaagcg 1620
agtattggca cgaaaattat tgcccgttca acgatcaaag cgatgcgtaa aaacgtatta 1680
gcgaaatgtt acggcggtga catctcacgt aaacggaagc ttctagaaaa gcaaaaagaa 1740
ggaaagaagc gaatgaaagc tgtggggaat gtggaggttc cacaggaagc atttatggcc 1800
gtattgcgta tggatgaacc gaaaaag 1827

<210> SEQ ID NO 64
<211> LENGTH: 1836
<212> TYPE: DNA
<213> ORGANISM: Bacillus subtilis

<400> SEQUENCE: 64
atgacagata aagaaaagcg tttagagagg caatcgagaa tacggaattt ctctatcatt 60
gcccatattg accacggaaa atcgacctta gcggatcgta ttttagaaaa aacgtcggca 120
atcactcaac gagaaatgaa agaacaattg ctcgattcta tggatcttga acgtgagcgg 180
ggcataacca ttaaattaaa ctctgttcag cttaaatata aagcaaaaga cggagaagaa 240
tatatctttc atctaatcga tacgccggga cacgtcgact tcacgtatga agtatcccga 300
agccttgctg cctgcgaggg agcgattctt gtcgtggatg cagcccaggg gattgaagcg 360
cagacgctcg ccaatgtcta cttagcgctt gacaacgatc ttgaaatcct tccggtcatc 420
aataaaatcg accttccgag cgccgagccc gaacgtgtgc gccaagaggt agaagacgtt 480
atcggccttg acgcatcaga agccgtgctt gcttcagcaa aagccggtat cgggattgag 540
gagattttag aacaaatcgt agaaaaggtg ccagctccga ccggagatcc ggaggcgccg 600
ctcaaagcgc tgatcttcga ctcgctttat gacgcctacc gcggtgtcgt ggcttatatc 660
agagtcgttg aaggaacggt aaagccggga caaaaaatca aaatgatggc aaccggcaaa 720
gaattcgaag taacagaggt gggcgtgttc acgccgaaag caactccgac aaatgaactg 780
acggtcggtg atgtaggctt cctgactgcc tcaatcaaaa atgttggtga cacacgtgtc 840
ggtgatacaa taacgagcgc tgccaatcct gcagaagaag cgctgccggg ataccgcaag 900
ctaaacccga tggtgtactg tggtttgtat ccgattgata cagcgaagta taatgattta 960
agggaagctc ttgaaaagct tgagctgaat gattcctccc ttcaatatga agcggaaact 1020
tcgcaagcgc ttggattcgg gttccgctgc ggatttttag gcatgcttca catggagatc 1080
attcaggagc gaattgagcg tgagttcaac atcgacctga ttacgacagc gccaagcgtt 1140
atctatgacg tgtatatgac agacggcgaa aaggtcgttg tcgacaaccc gtccaacatg 1200
ccggatcctc aaaagatcga aagggttgag gagccatacg taaaagcgac gatgatggtg 1260
ccgaatgact atgtcggcgc tgtaatggag ctttgccaag gaaaacgcgg caatttcatt 1320
gatatgcagt atttagacgc aaaccgtgtc agcatcattt atgatatgcc attagcggaa 1380

-continued atcgtatatg agttttttga tcagctgaaa tcaagcacta aaggctatgc gtcctttgat 1440
tatgaactga tcggctacaa accgtccaag cttgtgaaaa tggacattat gctgaatggt 1500
gaaaaaatcg atgccctttc ctttatcgtg catcgtgatt acgcatatga acggggaaaa 1560
gtgatcgttg aaaaactgaa agaactcatt ccgcgccagc agtttgaagt tccggtacaa 1620
gccgcaatcg gccagaaaat cgtggcccgc tccaccataa aagcaatgcg taaaaacgta 1680
ttggctaaat gttacggagg ggacatctcg cgtaaacgga aacttcttga aaaacaaaaa 1740
gaaggaaagc gccgtatgaa gcaggtcggc tcagttgaag tgccgcaaga agcatttatg 1800
gcagttctga aaatggacga cagtccgaaa aaacaa 1836

<210> SEQ ID NO 65
<211> LENGTH: 1839
<212> TYPE: DNA
<213> ORGANISM: Bacillus licheniformis

<400> SEQUENCE: 65
gtgacagata aagaaaaacg attacaaagg cagtcgagaa tccgaaattt ctctattatc 60
gcccatatcg accacggcaa gtcaacgctt gcggatcgaa tcttggaaaa aacggcggca 120
atcactcaaa gggaaatgaa agaacagctc ctcgactcaa tggatttgga acgtgaaaga 180
ggaatcacca ttaaactgaa ctccgtacag ctgaaatatc aggcgaagga cggagaggaa 240
tatatttttc atctgatcga taccccggga cacgtcgatt ttacgtatga ggtttcgaga 300
agccttgccg catgcgaagg cgcgattctc gtcgtagacg ccgcccaggg aatcgaggcg 360
caaacgctgg caaacgttta ccttgcgctt gacaacgacc ttgaaatcct gccggtcatt 420
aataaaatcg accttccgag cgcagaaccc gaacgcgtcc gccaggaagt cgaggatgtt 480
atcggtcttg acgcttcaga agccgtcctt gcttcagcaa aagcaggcat cggaattgag 540
gaaatattgg agcagatcgt tgaaaaggtt cccgcaccaa gcggagatcc ggaagcgccg 600
cttcaggcgc tgatctttga ctccctgtat gatgcttacc gcggggtcgt cgcctatatc 660
agagtcgtgc aaggtaccgt aaaagccggt caaaaaaatca agatgatggc gaccggaaag 720
gaatttgaag tcactgaagt cggcgttttc acaccgaagg ccgttccggc tgacgaactg 780
actgtcggcg acgtcggatt cctgacggcc gcaatcaaaa acgtcggaga cactcgtgta 840
ggggatacga ttacgagcgc ggaaaaccct gcacccgaag ccctgccagg ctacagaaag 900
ctgaatccga tggtttattg cggcctgtat ccgattgata cagcgaaata caacgacttg 960
cgggaagcgc ttgaaaaact tgagctgaac gattcagccc tgcagtacga agcggaaacg 1020
tcccaagctc tcggattcgg cttccgctgc ggtttcttag ggatgctcca catggaaatc 1080
atccaggagc ggattgaacg cgaattcaac atcgatttga ttacgacggc tccgagcgta 1140
atctacgacg tgtacatgac agacggtgaa aaaatcgtcg tcgataaccc gtcaaacatg 1200
cctgatccgc agaagatcga ccgggtggaa gaaccgttcg tcaaagcgac gatgatggtg 1260
ccgaacgact ttgtcggagc ggtcatggaa ctgtgccagg gcaagcgcgg ccagtttatt 1320
gatatgcagt accttgatgc gaaccgcgtc agcattgtct acgaaattcc gcttgcggaa 1380
atcgtctacg agtttttcga tcagcttaaa tcaaatacga aaggctatgc gtcatttgat 1440
tacgaactca tcggatataa accgtccaag ctcgtgaaaa tggatattat gctgaacggc 1500
gaaaaaatcg atgccctttc ctttatcgtt caccgcgatt atgcttatga acgaggaaaa 1560
gttatcgtcg aaaagctgaa agagctcatt ccgcgccagc agtttgaagt gcctgtccag 1620

-continued

```
gcagccatcg gtacaaaaat tgtcgcccgt tcaaccatca aagcaatgcg caaaaacgtt   1680

ttggcgaagt gctacggcgg ggatatttcc agaaagcgca aactgcttga aaagcaaaag   1740

gaaggaaagc gaagaatgaa acaggtcggc tctgtcgaag ttccgcagga agcctttatg   1800

gcagtcctga aaatggacga cagcggcccg aaatcataa                          1839
```

<210> SEQ ID NO 66
<211> LENGTH: 1821
<212> TYPE: DNA
<213> ORGANISM: Bacillus cereus

<400> SEQUENCE: 66

```
atgaacaaag aagaaagagc aaaaagacag tccaaaattc gtaatttctc tatcattgct     60

catattgacc acggaaagtc aacgttagca gaccgtattt tagagaaaac aaacgcgtta    120

acacaacgtg aaatgaaagc tcagttgctt gactctatgg atttagagcg tgagcgtggt    180

attacaatta aattaaacgc agtacaatta aactataaag caaaagacgg tgaagaatat    240

attcttcact taattgatac accaggacac gtcgacttta cgtacgaagt atctcgtagt    300

ttagcggctt gtgaaggtgc aattcttgta gtagatgcag cgcaaggtat tgaagcgcaa    360

acgttagcga acgtatactt agcgcttgat aacaatttag aaattttacc ggttattaat    420

aaaatcgact taccaagtgc agacccagag cgtgtacgcc aagaggtgga agatgtaatt    480

gggttagatg catcagaagc tgtacttgct tcggcaaaag ctgggattgg tatcgaagag    540

attctagaac aaatcgttga aaaagtgcca gcaccaacag gtgattcaga agaaccgtta    600

caatgtatga tctttgactc tttatatgat ccataccgcg gtgtaattgc gtatatccgt    660

gttgtaaatg gaacggtaaa agttggcgat aaagtacgta tgatggcaac tggaaaagaa    720

tttgaagtaa cagaagtagg tgtgtttaca ccgaaaacta cgcaacgtga tgagttaaca    780

gtaggtgatg taggtttctt agcggcatcg attaaaaatg ttggtgacac acgcgttggt    840

gatacgatta cacatgcgaa acgtccagca gctgagccat tacctggtta ccgtaaatta    900

aatccaatgg tattctgtgg tctgtacccg attgactctg cacgttacaa cgacttacgt    960

gatgcgctag agaaattaga attaaacgat tctgctcttg agtttgagcc agaaacatct   1020

caagcgctag gatttggttt ccgttgtgga ttcttaggac ttcttcatat ggaaatcatt   1080

caagagcgta ttgaacgtga atttaaaatt gatttaatta caacagcgcc aagtgttatt   1140

tataaagtat tcttaacgaa tggtgaagac atgattgtcg ataacccgtc taatatgccg   1200

gatccacaga caattgatcg tgttgaagag ccatttgtta aagcggcaat tatggttccg   1260

aatgactatg ttggagctgt aatggaaatt tgccaaggta aacgcggaac gtttattgat   1320

atgcaatatt tagatgaaac gcgtgttaca ttgacatatg aaatcccatt atcagaaatc   1380

gtatatgact tcttcgatca gttgaaatca aatacgaaag gatatgcatc atttgattat   1440

gagttaattg gttataaacc atctaaactt gtgaaaatgg atattctttt aaattctgag   1500

caagtcgatg ctctatcatt tatcgtacac cgtgattcag cgtatgaccg tggtaaagta   1560

atcgtagaaa aattaaaaga attaattcca agacagcagt tcgaagtgcc aattcaagcg   1620

acgatcggaa acaaagttgt agcgcgttct acaattaagg cgatgcgtaa aaacgtactt   1680

gcgaaatgtt acggtggtga catttctcgt aagcgtaaac ttcttgataa gcaaaaagaa   1740

ggtaaaaaac gtatgaagtc tgttggttct gtagaagtac cgcaagaagc attcatggct   1800

gtactgaaaa tggatgacaa c                                             1821
```

<210> SEQ ID NO 67
<211> LENGTH: 1820
<212> TYPE: DNA
<213> ORGANISM: Bacillus cereus

<400> SEQUENCE: 67

```
atgaataaag aagaaagagc aaaaagacag tccaaaatcc gtaatttctc tattattgct     60
catattgacc acggaaaatc aacgttagca gaccgtattt tagagaaaac aaacgcgtta    120
acacaacgtg aaatgaaagc tcagttgctt gactctatgg atttagagcg tgagcgtggt    180
attacaatca aattaaacgc agtacaatta aactataaag caaaagatgg tgaagagtat    240
attcttcatt taattgatac accaggacac gtcgacttta cgtacgaagt atctcgtagt    300
ttagcggctt gtgaaggcgc gattcttgta gtagatgcag cgcaaggtat tgaagcgcaa    360
acgttagcaa acgtatactt agcgcttgat aataatttag aaattttacc agttattaat    420
aaaatcgact taccgagtgc ggatccagaa cgtgtacgtc aagaggtaga agatgtaatt    480
ggtttagatg catcagaagc ggtacttgct tctgcgaaag ctggaattgg tttgaagaaa    540
ttttagaaca aattgttgaa aaagtaccag ctccggcggg tgattcagaa gagccgttac    600
aatgtatgat tttcgactct ttatatgatc cataccgcgg tgtaattgct tatatccgtg    660
ttgtaaatgg aacagtaaaa gttggcgata aagtacgtat gatggcaacg ggtaaagaat    720
ttgaagtaac agaagtaggt gtatttacac cgaaaactac gcaacgtgac gagttaacgg    780
taggtgatgt aggtttctta gcagcatcga ttaaaaatgt tggtgacaca cgcgttggtg    840
atacgattac acatgcgaaa cgtccagctg cagagccgtt agcaggttac cgtaagttaa    900
acccgatggt attctgtggt ctgtatccaa ttgactctgc tcgttataac gatttacgtg    960
atgcattaga aaaattagag ttaaacgatt ctgcccttga gtttgaacca gaaacatctc   1020
aagcgctagg atttggtttc cgttgtggtt tcttaggact tcttcacatg gaaatcattc   1080
aagaacgtat tgaacgtgaa tttaagattg acttaattac aacagcgcca agcgttattt   1140
ataaagttta tttaactaac ggtgaagatg ttattgttga taacccatct aatatgccag   1200
atccacagtc tatcgatcgt gtagaagagc cgtttgtgaa ggcttcaatt atggttccga   1260
atgactatgt tggagctgta atggagattt gccaaggtaa acgtggaacg tttattgata   1320
tgcaatattt agatgaaacg cgtgttacat taacatatga aatcccgtta tcagaaatcg   1380
tatatgactt ctttgatcaa ttgaaatcaa atacgaaagg gtatgcatca tttgactacg   1440
agttaattgg ctataaacca tctaaacttg tgaaaatgga tattctttta aataatgaac   1500
aagtggatgc tttatcattt atcgtacacc gtgattcagc gtatgaccgt ggtaaagtaa   1560
tcgtagagaa attaaaagaa ttaattccga gacaacagtt cgaagtgcca attcaggcga   1620
ctatcggaaa taaagttgta gcacgttcta caattaaagc gatgcgtaaa aacgtacttg   1680
caaaatgtta cggcggtgac atttctcgta agcgtaaact tcttgataag caaaaagaaa   1740
gtaaaaaacg tatgaagtcc gttggctctg tagaagtacc gcaagaagca ttcatggctg   1800
tactgaaaat ggatgacaac                                               1820
```

<210> SEQ ID NO 68
<211> LENGTH: 1797
<212> TYPE: DNA
<213> ORGANISM: Escherichia coli

<400> SEQUENCE: 68

```
atgaagaata tacgtaactt ttcgatcata gctcacattg accacggtaa atcgacgctg     60
```

```
tctgaccgta ttatccagat ctgcggtggc ctgtctgacc gtgaaatgga ggcgcaggtt    120
ctcgattcca tggatcttga gcgtgagcgt ggcattacca tcaaagcgca aagcgtgacg    180
ctggactaca aagcgtctga cggcgaaacc tatcagctta actttatcga caccccgggc    240
cacgtagact tctcctatga agtttcccgt tcgctggctg cctgtgaagg tgcattgctg    300
gtggtcgacg ccgggcaggg cgtagaagcg caaaccctgg caaactgcta caccgccatg    360
gaaatggatc tcgaagttgt gccggtactg aacaagattg acctgccggc agccgatcct    420
gaacgcgtgg cggaagaaat tgaagatatc gtcggcatcg acgccaccga cgcggtgcgc    480
tgttcagcga aaaccggcgt tggtgtgcag gacgttctcg aacgtctggt gcgcgacatt    540
ccgccgccgg aaggcgatcc ggaaggcccg ttgcaggcac taattatcga ctcatggttc    600
gacaactacc tgggcgttgt ttcacttatc cgtattaaaa acggcaccct gcgtaagggc    660
gacaaagtga aagtcatgag taccgggcag acctataacg ccgaccgtct gggcatcttc    720
acgccgaaac aggttgaccg cactgaactg aaatgtggcg aagtaggctg gctcgtatgt    780
gcgattaaag atatccacgg cgctccagtc ggcgatacct taacgctggc gcgtaatccg    840
gcagaaaagg cgctgcctgg ctttaagaaa gtcaaaccgc aggtatacgc cggtctgttc    900
ccggtaagtt ccgacgacta tgaagccttc cgtgacgcgc tgggtaaact cagcctgaac    960
gatgcctcac tgttctatga gccggaaagc tccagcgcgc tgggctttgg tttccgctgc   1020
ggcttcctcg gcctgctgca catggagatc atccaggaac gtctggaacg tgaatacgat   1080
ctggatctga tcaccactgc gccgaccgta gtgtatgaag ttgaaaccac gtcaagagaa   1140
gttatctacg tcgacagccc atccaagctg cctgcggtaa ataacatcta cgaactgcgc   1200
gagccgattg cagagtgtca catgctgctg ccgcaggcat atctcggcaa cgttattacg   1260
ttgtgcgtag aaaaacgcgg cgtgcagacc aatatggttt accacggtaa tcaggtggcg   1320
ctgacgtacg agatcccgat ggcggaagtg gtgctcgact tcttcgatcg cctgaaatct   1380
acctcgcgtg gttatgcgtc tctggattac aacttcaagc gcttccaggc gtccgacatg   1440
gtacgtgtag acgtattaat caacggtgaa cgtgttgatg cgctggcgtt gatcacccac   1500
cgtgataatt cgcaaaaccg cggtcgcgag ttggtggaga agatgaaaga tctgatccca   1560
cgccagcagt ttgatatcgc cattcaggca gcgattggta cgcacatcat tgcgcgatcc   1620
accgtgaaac agctgcgtaa aaacgtactg gctaaatgtt atggcggcga tatcagccgt   1680
aagaaaaagc tgctgcagaa gcagaaagaa ggtaagaaac gcatgaagca gatcggtaac   1740
gtcgagctgc cgcaggaagc gttcctcgcc attctgcacg tcggcaaaga caacaaa      1797
```

<210> SEQ ID NO 69
<211> LENGTH: 1797
<212> TYPE: DNA
<213> ORGANISM: Escherichia coli

<400> SEQUENCE: 69

```
atgaagaata tacgtaactt ttcgatcata gctcacattg accacggtaa atcgacgctg     60
tctgaccgta ttatccagat ctgcggtggc ctgtctgacc gtgaaatgga ggcgcaggtt    120
ctcgattcca tggatcttga gcgtgagcgt ggcattacca tcaaagcgca aagcgtgacg    180
ctggactaca aagcgtctga cggcgaaacc tatcagctta actttatcga caccccgggc    240
cacgtagact tctcctatga agtttcccgt tcgctggctg cctgtgaagg tgcattgctg    300
gtggtcgacg ccgggcaggg cgtggaagcg caaaccctgg caaactgcta caccgccatg    360
gaaatggatc tcgaagtggt gccggtactg aacaagattg acctgccggc agccgatcct    420
```

-continued

```
gaacgcgtgg cggaagaaat tgaagatatc gtcggcatcg acgccactga cgcggtgcgc    480
tgttcagcga aaaccggcgt tggcgtgcag gacgttctcg aacgtctggt gcgcgacatt    540
ccgccgccgg aaggcgatcc ggaaggcccg ttgcaggcac taattatcga ctcatggttc    600
gacaactacc tgggcgttgt ttcacttatc cgtattaaaa acggcaccct gcgtaagggc    660
gacaaagtga aagtcatgag taccgggcag acctataacg ccgaccgtct gggcatcttc    720
acgccgaaac aggttgaccg cactgaactg aaatgtggcg aagtaggctg gctcgtatgt    780
gcgattaaag atatccacgg cgctccagtc ggcgatacct taacgctggc gcgtaatccg    840
gcagaaaagg cgctgcctgg ctttaagaaa gtcaaaccgc aggtatacgc cggtctgttc    900
ccggtaagtt ccgacgacta tgaagccttc cgtgacgcgc tgggtaaact cagcctgaac    960
gatgcctcac tgttctatga gccggaaagc tccagcgcgc tgggctttgg tttccgctgc   1020
ggcttccttg gcctgctgca catggagatc atccaggagc gtctggaacg tgaatacgat   1080
ctggatctga tcaccactgc gccgaccgta gtgtatgaag ttgaaaccac gtcaagggaa   1140
gttatctacg tcgacagccc atccaagctg cctgcggtaa ataacattta cgaactgcgc   1200
gagccgattg cagagtgtca catgctgctg ccgcaggcat atctcggcaa cgttattacg   1260
ctgtgcgtag aaaaacgcgg cgtgcagacc aatatggttt accacggtaa tcaggtggcg   1320
ctgacgtacg agatcccgat ggcggaagtg gtgctcgact tcttcgatcg cctgaaatct   1380
acctcgcgtg gttatgcgtc tctggattac aacttcaaac gcttccaggc gtccgacatg   1440
gtacgtgtag acgtattaat caacggtgaa cgtgttgatg cgctggcgtt gatcacccac   1500
cgtgataatt cgcaaaaccg cggtcgcgag ttggtggaga agatgaaaga tctgatccca   1560
cgccagcagt ttgatatcgc cattcaggca gcgattggta cgcacattat tgcgcgatcc   1620
accgtgaaac agctgcgtaa aaacgtactg gctaaatgtt atggcggcga tatcagccgt   1680
aagaaaaagc tgctgcagaa gcagaaagaa ggtaagaaac gcatgaagca gatcggtaac   1740
gtcgagctgc cgcaggaagc gttcctcgcc attctgcacg tcggcaaaga caacaaa      1797
```

<210> SEQ ID NO 70
<211> LENGTH: 1797
<212> TYPE: DNA
<213> ORGANISM: Escherichia coli

<400> SEQUENCE: 70

```
atgaagaata tacgtaactt ttcgatcata gctcacattg accacggtaa atcgacgctg     60
tctgaccgta ttatccagat ctgcggtggc ctgtctgacc gtgaaatgga ggcgcaggtt    120
ctcgattcca tggatcttga gcgtgagcgt ggcattacca tcaaagcgca aagcgtgacg    180
ctggactaca aagcgtctga cggcgaaacc tatcagctta actttatcga caccccgggc    240
cacgtagact tctcctatga agtttcccgt tcgctggctg cctgtgaagg tgcattgctg    300
gtggtcgacg ccgggcaggg cgtggaagcg caaaccctgg caaactgcta caccgccatg    360
gaaatggatc tcgaagtggt gccggtactg aacaagattg acctgccggc agccgatcct    420
gaacgcgtgg cggaagaaat tgaagatatc gtcggcatcg acgccactga cgcggtgcgc    480
tgttcagcga aaaccggcgt tggcgtgcag gacgttctcg aacgtctggt gcgcgacatt    540
ccgccgccgg aaggcgatcc ggaaggcccg ttgcaggcac taattatcga ctcatggttc    600
gacaactacc tgggcgttgt ttcacttatc cgtattaaaa acggcaccct gcgtaagggc    660
gacaaagtga aagtcatgag taccgggcag acctataacg ccgaccgtct gggcatcttc    720
```

-continued

```
acgccgaaac aggttgaccg cactgaactg aaatgtggcg aagtaggctg gctcgtatgt    780

gcgattaaag atatccacgg cgctccagtc ggcgatacct taacgctggc gcgtaatccg    840

gcagaaaagg cgctgcctgg ctttaagaaa gtcaaaccgc aggtatacgc cggtctgttc    900

ccggtaagtt ccgacgacta tgaagccttc cgtgacgcgc tgggtaaact cagcctgaac    960

gatgcctcac tgttctatga gccggaaagc tccagcgcgc tgggctttgg tttccgctgc   1020

ggcttccttg gcctgctgca catggagatc atccaggagc gtctggaacg tgaatacgat   1080

ctggatctga tcaccactgc gccgaccgta gtgtatgaag ttgaaaccac gtcaagggaa   1140

gttatctacg tcgacagccc atccaagctg cctgcggtaa ataacattta cgaactgcgc   1200

gagccgattg cagagtgtca catgctgctg ccgcaggcat atctcggcaa cgttattacg   1260

ctgtgcgtag aaaaacgcgg cgtgcagacc aatatggttt accacggtaa tcaggtggcg   1320

ctgacgtacg agatcccgat ggcggaagtg gtgctcgact tcttcgatcg cctgaaatct   1380

acctcgcgtg gttatgcgtc tctggattac aacttcaaac gcttccaggc gtccgacatg   1440

gtacgtgtag acgtattaat caacggtgaa cgtgttgatg cgctggcgtt gatcacccac   1500

cgtgataatt cgcaaaaccg cggtcgcgag ttggtggaga agatgaaaga tctgatccca   1560

cgccagcagt ttgatatcgc cattcaggca gcgattggta cgcacattat tgcgcgatcc   1620

accgtgaaac agctgcgtaa aaacgtactg gctaaatgtt atggcggcga tatcagccgt   1680

aagaaaaagc tgctgcagaa gcagaaagaa ggtaagaaac gcatgaagca gatcggtaac   1740

gtcgagctgc cgcaggaagc gttcctcgcc attctgcacg tcggcaaaga caacaaa      1797
```

```
<210> SEQ ID NO 71
<211> LENGTH: 1833
<212> TYPE: DNA
<213> ORGANISM: Enterococcus faecalis

<400> SEQUENCE: 71

atgaacaata aagaaatgaa agcaagacaa gagaaaattc gtaatttctc gatcattgcc     60

cacattgacc atgggaagtc aactttagcc gaccggattt tggaaaaaac aaatacagtt    120

agcagtcgag aaatgcaaga tcaattactt gattcaatgg atttagagag agaacgcggc    180

attactatca aattaaacgc aattgaatta aactatacag ccaaagatgg tgaaatctat    240

actttccatt tgattgacac accagggcac gtcgatttca cctacgaagt ttctcgtagc    300

ttggcagctt gtgaaggggc tgttctagtt gttgatgcgg cgcaaggaat tgaagcgcaa    360

acgctagcaa atgtctattt ggcattggat aatgacttag aaattttacc tgttattaat    420

aaaattgatt tacccgccgc tgatccagag cgtgttcgga cagagattga agacgtaatt    480

ggaattgatg catcggaagc tgttttagca agtgcaaaag cagggattgg gattgaagat    540

attttagaac aagtggtgga gtatgtacca gctccatcag gcgatattga ggctccttta    600

aaggctttga tttttgactc tatttacgat agttatcggg gggtcgtttt aaacatccgt    660

gtaattgacg gtgtcgttcg tcctggggat aaaatccaaa tgatgagtaa cggtaaaacg    720

tttgatgtaa cagaagtcgg cgttttttca ccgaaaccga ttgctcgtga ttatttaatg    780

gttggtgatg tgggctatat caccgctagc attaaaacgg ttcaagatac acgggtcggg    840

gatacagtga ctttggccga caatccagca gcagaagcac taccaggcta ccgcaaaatg    900

aatccaatgg tttattgtgg tttatatcca attgatacgt cgcgctacaa cgatttacgg    960

gaagcattag aaaaattaca attaaatgat gcggcgttac aatttgaacc ggaaacatcg   1020

caagctttag ggtttggttt ccgttgtggt ttcttaggtt tgctgcacat ggatgttgtt   1080
```

caggaacgtt tggaacgaga atttaattta gagttaatta caacagcacc gtctgtaatc 1140
tatcacgtta ataaaactga cggaacaacc gttgttgttg acaacccagc tgaatttcca 1200
gaaccagtaa cgattgaatc tgtggaagaa ccttatgtta aagcgcaaat catggtgcca 1260
aacgattatg taggagcagt aatggaatta tcacaacgta aacgtggcga attcattaca 1320
atggattact tagacgatta tcgtgtaaac gtagtttatg aaattccgtt atctgaaatc 1380
gtgtttgact tttcgataa attgaaatca agtacaaaag gctatgcatc cttagattac 1440
gaaatggctg gctatcgtac cagccgccta gtgaaaatgg atattctatt aaatgctgaa 1500
aaagtggatg ctttaagctt tattgttcac cgagatttcg catttgagcg tggtaaagcg 1560
attgttgaga aactgaaaaa actaattcca cgtcaacagt ttgaagtccc agttcaagcg 1620
gcgattggtc aaaaaattgt ggctcgttca gatattaaag ccttacgcaa aaacgtactg 1680
gctaaatgct atggtggcga tgtttctcgt aaacgtaaat tgttagagaa acaaaaagaa 1740
gggaagaaac ggatgaaaca aattggatcc gtggaagttc ctcaagaagc ctttatggcg 1800
gttctgaaaa tggacgacca agataacgcg aaa 1833

<210> SEQ ID NO 72
<211> LENGTH: 1797
<212> TYPE: DNA
<213> ORGANISM: Erwinia carotovora

<400> SEQUENCE: 72
atgaagcata tacgaaattt ctccattatt gcccatatcg accacggtaa atcgacatta 60
tctgaccgta ttatccagat ctgcggcgga ttaaccgaac gtgaaatggc tgcgcaggtt 120
ctggattcca tggatctgga acgtgaacgc ggaataacga ttaaagcgca aagcgtgacg 180
ctggattata aatcgcagga cggccaaacc taccagttaa acttcattga tacgcctggg 240
cacgtagact tctcttatga ggtttcccgc tcgcttgccg cctgtgaagg tgcgctgctt 300
gttgttgatg ccgggcaggg tgttgaagct caaacgttgg ctaactgtta taccgcgttg 360
gatatgaatc tggaagtggt gcctgtccta aacaagattg acctgcctgc tgctgacccg 420
gatcgtgttg ctcaagaaat tgaagatatc gttggtatcg atgccactga tgctgtgcgc 480
tgctccgcga aaacaggggt tggtgtgccg gatattctgg atcgtttggt gcgtgatatt 540
ccgccgccgg aaggcagccc tgatgcgccg ttgcaagcgc tgattatcga ctcctggttt 600
gataactacc ttggcgttgt gtcgctggtt cgtatcaaaa acggcacgat gcgcaaaggc 660
gacaaaatta aggtgatgag tacgggtcag gtgtataacg ccgaccgtct cggtattttt 720
acaccgaagc agattgaccg cgatgtattg aattgcggtg aagtaggctg gctggtgtgc 780
gccatcaaag atattttggg tgcgccagtc ggggataccc tgacgctggc acgtcagcca 840
gctgaaaaag cgctgccggg cttcaaaaaa gtcaaacctc aggtctatgc cggtttgttc 900
ccgatcagtt ccgacgacta tgaagcattc cgtgacgcgt taggtaagct gagtctcaat 960
gatgcctctc tgttctatga accggaaagc tctaccgcgc tgggctttgg tttccgctgc 1020
ggcttcctag gtctgctgca catggagatc attcaggaac gtctggagcg tgaatacgat 1080
ctggaactga tcaccacggc gccgacggta gtgtatgaag tagaaacgac ggctaaagaa 1140
accatttatg tcgatagtcc gtctaaactg ccgccgctga ataatattca ggaactgcgc 1200
gaaccgattg ccgagtgtca catgctgatg cctcaggaat atctgggtaa cgtgattacg 1260
ctctgtattg agaagcgcgg tgtgcagacg aatatggtgt atcacggtaa tcaggttgca 1320

-continued

```
ttgacctatg agatcccgat ggccgaggtg gtgctcgatt tctttgaccg tctgaaatca   1380

acctctcggg gttatgcatc gctggattac ggcttcaaac gtttccagac atcggacatg   1440

gtgcgcgttg atgtattaat caacaacgag cgtgtcgatg cgttggccct gattactcac   1500

cgtgataact cacaatatcg tggccgtgag tttgtcgaaa aaatgaaaga actcattccg   1560

cgtcagcagt ttgatattgc gattcaggct gcgattggta accacattat tgcgcgtgcg   1620

acggttaagc aattgcgtaa aaacgtactg gccaagtgtt atggtggtga cgtcagccgt   1680

aagaagaaac tgttgcagaa acagaaagac ggtaagaagc gtatgaagca ggtcggtaac   1740

gtcgagctgc cgcaagaagc gtttctggca attctgcacg tcggcaaaga cagtaaa      1797
```

<210> SEQ ID NO 73
<211> LENGTH: 1797
<212> TYPE: DNA
<213> ORGANISM: Salmonella typhi

<400> SEQUENCE: 73

```
atgaagaaca tacgtaactt ttcgatcatt gctcacattg accacggtaa atcgacgctg     60

tctgaccgta ttatccaaat ctgcggtggc ctgtctgacc gtgaaatgga agctcaggta    120

cttgattcga tggatcttga gcgtgagcgc ggtattacta ttaaagccca gagtgtgacg    180

ctggatttta aagcgtctga tggtgaaact tatcaactga actttatcga cacgccggga    240

cacgttgact tttcctatga agtttcccgt tcgttagccg cctgcgaggg cgcgctgctg    300

gtggtggatg ccggccaggg cgtagaagcg caaacgttgg cgaactgcta caccgcgatg    360

gaaatggatc ttgaagtggt gccggtgctt aacaagattg acctgccggc cgccgatccg    420

gagcgtgtgg cggaagaaat cgaagacatt gtcggcatcg atgcgacgga cgcggtacgc    480

tgctccgcca aaacgggtgt cggcgtgacg gacgttctgg aacgcctggt gcgcgatatc    540

ccgccgccgc aaggcgatcc ggacggcccg ctgcaggcgc tgattattga ctcctggttc    600

gataactacc tgggcgtggt atccctggtg cgtattaaaa acggcaccat gcgtaaaggc    660

gacaaaatta aagtgatgag caccgggcag acctacaacg ctgaccgcct ggggatcttc    720

acgccgaaac aggttgatcg taccgagctg aagtgcggcg aagtaggctg gctggtctgc    780

gccattaaag atatcctcgg cgcgccggtt ggcgatacct taacctcagc gcgtaaccca    840

gctgaaaaag cgttgccggg ctttaagaag gtgaaaccgc aggtctatgc aggtctgttc    900

ccggtcagct ccgacgatta tgaaagtttc cgcgacgcgc tcggcaagct gagcctgaac    960

gatgcctcac tgttttatga accggaaagc tcctcggcgc tgggctttgg tttccgctgc   1020

ggcttcctcg gcctgttgca catggagatc attcaggagc gtctggaacg cgaatacgat   1080

ctggatctga tcaccactgc gccgaccgtg gtttatgaag tagaaacaac ggcgaaagag   1140

actatctatg ttgatagccc ctccaagctg ccgccgttga ataacattta tgaactgcgc   1200

gagcctatcg ccgaatgtca tatgctgtta ccacaagcct atttaggtaa cgttattacg   1260

ctgtgtattg agaaacgcgg cgtacaaact aacatggtgt atcacggtaa ccaggttgcg   1320

ttgacctatg aaatcccgat ggcggaagtg gtgctcgact tctttgaccg tctgaaatca   1380

acgtcgcgcg gctatgcgtc tctggattat aacttcaagc gcttccaggc ttccgatatg   1440

gtgcgtgttg atgtgttaat caacaacgag cgtgtcgatg cgctggcgct gatcacgcac   1500

cgtgataact cgcaaagccg tggtcgcgag ctggtggaga aaatgaaaga tttgattcca   1560

cgccagcagt ttgatatcgc gattcaggcg gcgattggta cgcatattat tgcccgttcg   1620

acggtaaaac agttacgtaa aaacgtgctg gcgaagtgct acggcggcga tatcagtcgt   1680
```

aagaaaaaac tgctgcagaa acagaaagaa ggtaagaaac gcatgaagca gatcggtaac 1740
gtcgagctgc ctcaggaggc gttcctcgcc attctgcatg tcggtaaaga caataaa 1797

<210> SEQ ID NO 74
<211> LENGTH: 1797
<212> TYPE: DNA
<213> ORGANISM: Salmonella typhimurium

<400> SEQUENCE: 74
atgaagaaca taagaaattt ctccatcatt gctcacattg accacggtaa atcgacgctg 60
tctgaccgta ttatccaaat ctgcggtggc ctgtctgacc gtgaaatgga agctcaggta 120
cttgattcga tggatcttga gcgtgagcgc ggtattacta ttaaagccca gagtgtgacg 180
ctggatttta aagcgtctga tggtgaaact tatcaactga actttatcga cacgccggga 240
cacgttgact tttcctatga agtttcccgt tcgttagccg cctgcgaggg cgcgctgctg 300
gtggtggatg ccggccaggg cgtagaagcg caaacgttgg cgaactgcta caccgcgatg 360
gaaatggatc ttgaagtggt gccggtgctt aacaagattg acctgccggc cgccgatccg 420
gagcgtgtgg cggaagaaat cgaagacatt gtcggtatcg atgcgacgga cgcggtacgc 480
tgctccgcca aaacgggtgt cggcgtgacg gatgttctgg aacgcctggt gcgcgatatc 540
ccgccgccgc aaggcgatcc ggacggcccg ctgcaggcgc tgattattga ctcctggttc 600
gataactacc tgggcgtggt atcgctggtg cgtattaaaa acggcaccat gcgtaaaggc 660
gacaaaatta aagtgatgag caccgggcag acctacaacg ctgaccgcct ggggatcttc 720
acgccaaaac aggttgatcg taccgagctg aagtgcggcg aagtaggctg gctggtctgc 780
gccattaaag atatcctcgg cgcgccggtt ggcgatacct taacctcagc gcgtaaccca 840
gcggaaaaag cgttgccggg ctttaagaag gtgaaaccgc aggtctatgc aggtctgttc 900
ccggtcagct ccgacgatta tgaaagtttc cgcgacgcgc tcggcaagct gagcctgaac 960
gatgcctcac tgttttatga accggaaagc tcctcggcgc tgggctttgg tttccgctgc 1020
ggcttcctcg gcctgttgca catggagatc attcaggagc gtctggaacg cgaatacgat 1080
ctggatctga tcaccactgc gccgaccgtg gtgtatgaag tagaaacaac ggcgaaagag 1140
actatctatg ttgatagccc ctccaagctg ccgccgttga ataacattta tgaactgcgc 1200
gagcctatcg ccgaatgtca tatgctgtta ccacaagcct atttaggtaa cgttattacg 1260
ctgtgtattg agaaacgcgg cgtacaaact aacatggtgt atcacggtaa ccaggtcgcg 1320
ttgacctatg aaatcccgat ggcggaagtg gtgctcgact tctttgaccg tctgaaatca 1380
acgtcgcgcg gctatgcgtc tctggattat aacttcaagc gcttccaggc ttccgatatg 1440
gtgcgtgttg atgtgttaat caacaacgag cgtgtcgatg cgctggcgct gatcacgcac 1500
cgtgataact cgcaaagccg tggtcgcgag ctggtggaga agatgaaaga tttgatccca 1560
cgccagcagt ttgatatcgc gattcaggcg gcgattggta cgcatattat tgcccgttcg 1620
acggtaaaac agttacgtaa aaacgtgctg gcgaagtgct acggcggcga tatcagtcgt 1680
aagaaaaaac tgctgcagaa acagaaagaa ggtaagaaac gcatgaagca gatcggtaac 1740
gtcgagctgc ctcaggaagc gttcctcgcc attctgcatg tcggtaaaga caataaa 1797

<210> SEQ ID NO 75
<211> LENGTH: 1800
<212> TYPE: DNA
<213> ORGANISM: Shigella flexneri

<400> SEQUENCE: 75
atgaagaata tacgtaactt ttcgatcata gctcacattg accacggtaa atcgacgctg 60
tctgaccgta ttatccagat ctgcggtggc ctgtctgacc gtgaaatgga ggcgcaggtt 120
ctcgattcca tggatcttga gcgtgagcgt ggcattacca tcaaagcgca aagcgtgacg 180
ctggactaca aagcgtctga cggcgaaacc tatcagctta actttatcga caccccgggc 240
cacgtagact tctcctatga agtttcccgt tcgctggctg cctgtgaagg tgcattgctg 300
gtggtcgacg ccgggcaggg cgtagaagcg caaaccctgg caaactgcta caccgccatg 360
gaaatggatc tcgaagtggt gccggtactg aacaagattg acctgccggc agccgatcct 420
gaacgcgtgg cggaagaaat tgaagatatc gtcggcatcg acgccaccga tgcagtgcgc 480
tgttcagcga aaaccggcgt tggcgtgcag gacgttctcg aacgtctggt gcgcgacatt 540
ccgccgccgg aaggcgatcc ggaaggcccg ttgcaggcac taattatcga ctcctggttc 600
gacaactacc tgggcgttgt ttcacttatc cgtattaaaa acggcaccct gcgtaagggc 660
gacaaagtga aagtcatgag taccgggcag acctataacg ccgaccgtct gggcatcttc 720
acgccgaaac aggttgaccg cactgaactg aaatgtggcg aagtaggctg gctcgtatgt 780
gcgattaaag atatccacgg cgctccagtc ggcgatacct taacgctggc gcgtaatccg 840
gcagaaaagg cgctgcctgg ctttaagaaa gtcaaaccgc aggtatacgc cggtctgttc 900
ccggtaagtt ccgacgacta tgaagccttc cgtgacgcgc tgggtaaact cagcctgaac 960
gatgcctcac tgttctatga gccggaaagc tccagcgcgc tgggctttgg tttccgctgc 1020
ggcttccttg gcctgctgca catggagatc atccaggagc gtctggaacg tgaatacgat 1080
ctggatctga tcaccactgc gccgaccgta gtgtatgaag ttgaaaccac gtcaagggaa 1140
gttatctacg tcgacagccc atccaagctg cctgcggtaa ataacattta cgaactgcgc 1200
gagccgattg cagagtgtca catgctgctg ccgcaggcat atctcggcaa cgttattacg 1260
ctgtgcgtag aaaaacgcgg cgtgcagacc aatatggttt accacggtaa tcaggtggcg 1320
ctgacgtacg agatcccgat ggcggaagtg gtgctcgact tcttcgatcg cctgaaatct 1380
acctcgcgtg gttatgcgtc tctggattac aacttcaaac gcttccaggc gtccgacatg 1440
gtacgtgtag acgtattaat caacggtgaa cgtgttgatg cgctggcgtt gatcacccac 1500
cgtgataatt cgcaaaaccg cggtcgcgag ttggtggaga agatgaaaga tctgatccca 1560
cgccagcagt ttgatatcgc cattcaggca gcgattggta cgcacattat tgcgcgatcc 1620
accgtgaaac agctgcgtaa aaacgtactg gctaaatgtt atggcggcga tatcagccgt 1680
aagaaaaagc tgctgcagaa gcagaaagaa ggtaagaaac gcatgaagca gatcggtaac 1740
gttgagctgc cgcaggaagc gttcctcgcc attctgcacg tcggcaaaga caacaaataa 1800

<210> SEQ ID NO 76
<211> LENGTH: 1797
<212> TYPE: DNA
<213> ORGANISM: Yersinia pestis

<400> SEQUENCE: 76
atgaagcaca taagaaactt ttctattatt gcccatattg accacggtaa gtcgacgctg 60
tctgatcgga ttattcagat ctgtggcggt ttatctgagc gtgaaatggc cgcacaggta 120
ctggattcca tggatctaga acgtgagcgt ggtattacca tcaaggcaca gagtgtgacg 180
cttgattacc attcgaagga tggtcaaacc tatcaactta actttatcga tacccccggc 240
catgttgact tctcttatga agtttcacgc tctttagccg cgtgtgaagg ggctctattg 300
gttgtggatg cagggcaagg cgttgaggct cagacgctag caaactgcta caccgcgatg 360
gagatggacc tggaagttgt tccggttctg aacaaaattg atttgcctgc tgccgatcct 420
gagcgggttg ctgaagaaat cgaagacatt gtggggattg atgccactga tgcgattcgt 480
tgctcggcaa aaaccggtgt gggcgtgcct gatgttcttg agcggttggt ccgcgatatt 540
ccagcccctg agggggatcc aaatgggcca ttgcaggcat tgattatcga ttcctggttt 600
gataactacc tgggtgttgt gtcattaata cgtatcaaga atggttcgtt gcgtaaaggc 660
gataaagtta aggttatgag taccggccag agctataacg cggatcgttt agggatattt 720
acaccaaaac gtgttgatcg tgatgttctg aactgcggcg aagtaggctg gttggtttgt 780
gcaataaaag acattcttgg cgcacctgtt ggcgatacat tgacattaac gcgtaacccg 840
gcagaaaaat cattgcctgg ctttaagaaa gtaaaaccac aagtttatgc gggcctgttc 900
ccgataagct ctgatgatta tgaatctttc cgggatgcgt taggtaagtt aagtcttaac 960
gatgcctctt tgttctatga accagaaagc tctacagcat taggctttgg tttccgatgc 1020
ggcttccttg gcttgttaca tatggagatc atccaggagc gtctggagcg tgaatatgat 1080
ctggaactga ttactacggc accaacagtg gtgtacgagg tgattacgac taatcaggaa 1140
acggtctatg tcgatagccc ttctaaactg cctgcgttga acaatattga agaactgcgc 1200
gaaccgatcg ctgaatgcca tatgttgttg ccacaggaat acctcggtaa cgtcattaca 1260
ttgtgtatcg aaaaacgtgg tacacagacc aatatggttt atcacggtaa gcaagtcgcg 1320
ctgacatatg aaattccaat ggcggaagtc gtgcttgatt tctttgatcg tttgaaatca 1380
acgtcacggg gttatgcttc actggattat aatttcaaac gcttccagac gtctgacatg 1440
gtacgtgttg atgtattaat caataacgaa cgtgtggatg cgctggcact gatcacgcat 1500
cgtgataatg cacaatatcg tggccgtgat ttggttgaga aaatgaaaga actgatccca 1560
cgtcaacaat ttgatattgc gatccaggct gcgattggta accacatcat tgctcgctca 1620
acggtaaaac agctacgtaa aaacgtattg gcgaagtgtt atggtgggga tgttagccgt 1680
aagaaaaaac ttctgcagaa acaaaaagac ggtaagaaac gtatgaagca agtcggtaac 1740
gttgaattac cacaagaggc cttcctggct attctgcatg ttggaaaaga cagtaaa 1797

<210> SEQ ID NO 77
<211> LENGTH: 1833
<212> TYPE: DNA
<213> ORGANISM: Streptococcus agalactiae

<400> SEQUENCE: 77
ttattttttg tcatcatcgt ccattgataa aacacttaag aaagcttcct gaggaacttc 60
gacggaacca attgctttca tgcgcttttt accagctttt tgtttttcaa gcaacttacg 120
tttacgtgaa acgtcaccac cataacattt tgctaagaca tttttgcgta gtgcttttat 180
atcagaacga gccacaattt tttgtccaat agctgcttgg ataggaactt caaactgctg 240
acgaggaatg atttttttca acttatcaac gatcaattta ccacgttcat aagcaaattc 300
tttgtgaaca ataaagctta aagcatcaac tttatcacca tttaaaagaa tatccatttt 360
aactaactgt gagcgacgat attcggaaat ttcataatca aaactagcat agcctcgtgt 420
tgatgattta agcttatcaa agaagtcaaa cacaatttca gctaaaggaa tttggtaaat 480
aacattaaca cgattatcat caatataatc cattgttaca aagtcaccac gtttacgttg 540
tgctaactcc attacagcac cgacaaattc ttgaggaacc ataatttgcg ccttaacata 600

-continued

```
tggttcttca atgctgtcaa cacgagtagg atcaggaaat tcagatggat tcgaaacttc    660
aagcatttca ccgtcagttg tattaacatg ataaactact gatggtgcag tcataataag    720
atcaatattg aactctcgtt ccaagcgctc ttggataacg tccatatgta aaagtcctaa    780
gaaaccacaa cggaaaccaa accctaatgc ttgtgatgtt tccggttcaa actgtagact    840
agcatcattc aattgtaatt tttcaagggc ttcacgcaga tcgttatact tatttgattc    900
aattggataa agaccggcaa aaaccatcgg gttcatttgc ttatagccat gcaaaggttc    960
tattgctggg ttattagcaa gggtaatggt atcaccaaca cgtgtatcag caaccgtttt   1020
aattgaggca gcaatatacc ctacatctcc agttgctaaa aaatcacgtc caactgcttt   1080
gggagtgaaa ataccaacct cagtaacgtc gaaggtttta ccattagaca tcatttgaat   1140
tttatctcct ggcttaacca taccatttac aatccttact tgcagaatta ccccacgata   1200
agcatcgtaa acagaatcaa aaattaaagc ttgcagagga gcatctactt ccccagtcgg   1260
agcaggaact tttcaacga tctgctctaa aatttcttca ataccaatcc ctgccttagc   1320
tgaggcaagc acagcttctg aagcatctag accaataaca tcctctactt ctgcacgtac   1380
acgttctgga tctgctgctg gtaaatcaat tttattaata actggtagta tctctaaatc   1440
attgtctaga gccaaataaa catttgccag agtttgagct tcaattcctt gagctgcgtc   1500
aacaaccagt atagcaccct cacaagctgc taatgaacgt gatacttcat atgtgaagtc   1560
aacatgccct ggcgtgtcaa tcaagtgaaa aatgtaagtt tcaccatctt tagcagtata   1620
attaagctca atagcattta actttatagt aatcccacgc tcacgttcta gatccataga   1680
gtccaacagc tgcgcctgca tttcacgact agaaaccgtt tctgttttct ctaaaatacg   1740
gtctgctaag gttgattttc catggtcaat atgagcgata atcgaaaagt ttctaatctt   1800
ttcttgacgt ttcttcaaat cttcaatatt cat                                1833
```

<210> SEQ ID NO 78
<211> LENGTH: 1833
<212> TYPE: DNA
<213> ORGANISM: Streptococcus agalactiae

<400> SEQUENCE: 78

```
ttattttttg tcatcatcgt ccattgataa aacacttaag aaagcttcct gaggaacttc     60
gacggaacca attgctttca tgcgcttttt accagctttt tgtttttcaa gcaacttacg    120
tttacgtgaa acgtcaccac cataacattt tgctaagaca tttttacgta gtgcttttat    180
atcagaacgg gccacaattt tttgtccaat agctgcttgg ataggaactt caaactgctg    240
acgaggaatg attttttca acttatcaac gatcaattta ccacgttcat aggcaaattc    300
tttgtgaaca ataaagctta aagcatccac tttatcacca tttaaaagaa tatccatttt    360
aactaattgt gagcgacgat attcggaaat ttcataatca aaactagcat agccacgtgt    420
tgatgattta agcttatcaa agaagtcaaa cacaatttca gctaaaggaa tttggtaaat    480
aacattaaca cgattatcat caatataatc cattgttaca aagtcaccac gtttacgttg    540
tgctaactcc attacagcac cgacaaattc ttgaggaacc ataatttgcg ccttaacata    600
tggttcttca atgctgtcaa cacgagtagg atcaggaaat tcagatggat tcgaaacttc    660
aagcatttca ccgtcagttg tattaacatg ataaactact gatggtgcag tcataataag    720
atcaatattg aactctcgtt ccaagcgctc ttggataacg tccatatgta aaagtcctaa    780
gaaaccacaa cggaaaccaa accctaatgc ttgtgatgtt tccggttcaa actgtagact    840
agcatcattc aattgtaatt tttcaagggc ttcacgcaga tcgttatact tatttgattc    900
```

```
aattggataa agaccggcaa aaaccattgg gttcatttgc ttatagccat gcaagggttc    960
tattgctggg ttattagcaa gggtaatggt atcaccaaca cgtgtatcag caaccgtttt   1020
aattgaggca gcaatatacc ctacatctcc agttgctaaa aaatcacgtc caactgcttt   1080
gggagtgaaa ataccaacct cagtaacgtc gaaggtttta ccattagaca tcatttgaat   1140
cttatctcct ggcttaacca taccatttac aatccttact tgaagaatta ctccacgata   1200
agcatcataa acagaatcaa aaattagagc ttgaagagga gcatctactt ccccagtcgg   1260
tgcaggaact ttttcaacga tctgctctaa aatttcttca ataccaatcc ctgccttagc   1320
tgaggcaagc acagcttctg aagcatctag accaataaca tcctctactt ctgcacgtac   1380
acgttctgga tctgctgctg gtaaatcaat tttattaata actggtagta tctctaaatc   1440
attgtctaga gccaaataaa catttgccag agtttgagct tcaattcctt gggctgcatc   1500
aacaaccagt atagcaccct cacaagctgc caatgaacgt gatacttcat atgtgaagtc   1560
aacatgccct ggcgtgtcaa tcaagtgaaa aatgtaagtt tcaccatctt tagcagtata   1620
attaagctca atagcattta actttatagt aattccacgc tcacgttcta gatccataga   1680
gtccaacagt tgcgcctgca tttcacgact agaaaccgtt tctgttttct ctaaaatacg   1740
gtctgctaag gttgattttc catggtcaat atgagcgata atcgaaaagt ttctaatctt   1800
ttcttgacgt ttcttcaaat cttcaatatt cat                                1833
```

<210> SEQ ID NO 79
<211> LENGTH: 1833
<212> TYPE: DNA
<213> ORGANISM: Streptococcus agalactiae

<400> SEQUENCE: 79

```
ttattttttg tcatcatcgt ccattgataa aacacttaag aaagcttcct gaggaacttc     60
gacggaacca attgctttca tgcgcttttt accagctttt tgtttttcaa gcaacttacg    120
tttacgtgaa acgtcaccac cataacattt tgctaagaca tttttacgta gtgcttttat    180
atcagaacgg gccacaattt tttgtccaat agctgcttgg ataggaactt caaactgctg    240
acgaggaatg atttttttca acttatcaac gatcaattta ccacgttcat aggcaaattc    300
tttgtgaaca ataaagctta aagcatccac tttatcacca tttaaaagaa tatccatttt    360
aactaattgt gagcgacgat attcggaaat ttcataatca aaactagcat agccacgtgt    420
tgatgattta agcttatcaa agaagtcaaa cacaatttca gctaaaggaa tttggtaaat    480
aacattaaca cgattatcat caatataatc cattgttaca aagtcaccac gtttacgttg    540
tgctaactcc attacagcac cgacaaattc ttgaggaacc ataatttgcg ccttaacata    600
tggttcttca atgctgtcaa cacgagtagg atcaggaaat tcagatggat tcgaaacttc    660
aagcatttca ccgtcagttg tattaacatg ataaactact gatggtgcag tcataataag    720
atcaatattg aactctcgtt ccaagcgctc ttggataacg tccatatgta aaagtcctaa    780
gaaaccacaa cggaaaccaa accctaatgc ttgtgatgtt tccggttcaa actgtagact    840
agcatcattc aattgtaatt tttcaagggc ttcacgcaga tcgttatact tatttgattc    900
aattggataa agaccggcaa aaaccattgg gttcatttgc ttatagccat gcaagggttc    960
tattgctggg ttattagcaa gggtaatggt atcaccaaca cgtgtatcag caaccgtttt   1020
aattgaggca gcaatatacc ctacatctcc agttgctaaa aaatcacgtc caactgcttt   1080
gggagtgaaa ataccaacct cagtaacgtc gaaggtttta ccattagaca tcatttgaat   1140
```

```
cttatctcct ggcttaacca taccatttac aatccttact tgaagaatta ctccacgata   1200
agcatcataa acagaatcaa aaattagagc ttgaagagga gcatctactt ccccagtcgg   1260
tgcaggaact ttttcaacga tctgctctaa aatttcttca ataccaatcc ctgccttagc   1320
tgaggcaagc acagcttctg aagcatctag accaataaca tcctctactt ctgcacgtac   1380
acgttctgga tctgctgctg gtaaatcaat tttattaata actggtagta tctctaaatc   1440
attgtctaga gccaaataaa catttgccag agtttgagct tcaattcctt gggctgcatc   1500
aacaaccagt atagcaccct cacaagctgc caatgaacgt gatacttcat atgtgaagtc   1560
aacatgccct ggcgtgtcaa tcaagtgaaa aatgtaagtt tcaccatctt tagcagtata   1620
attaagctca atagcattta actttatagt aattccacgc tcacgttcta gatccataga   1680
gtccaacagt tgcgcctgca tttcacgact agaaaccgtt tctgttttct ctaaaatacg   1740
gtctgctaag gttgattttc catggtcaat atgagcgata atcgaaaagt ttctaatctt   1800
ttcttgacgt ttcttcaaat cttcaatatt cat                                1833
```

<210> SEQ ID NO 80
<211> LENGTH: 1833
<212> TYPE: DNA
<213> ORGANISM: Streptococcus agalactiae

<400> SEQUENCE: 80

```
ttattttttg tcatcatcgt ccattgataa aacacttaag aaagcttcct gaggaacttc     60
gacggaacca attgctttca tacgcttttt accagctttt tgtttttcaa gcaacttacg    120
tttacgtgaa acgtcaccac cataacattt tgctaagaca tttttgcgta gtgcttttat    180
atcagaacga gccacaattt tttgtccaat agctgcttgg ataggaactt caaactgctg    240
acgaggaatg atttttttca acttatcaac gatcaattta ccacgttcat aggcaaattc    300
tttgtgaaca ataaagctta aagcatccac tttatcacca tttaaaagaa tatccatttt    360
aactaactgt gagcgacgat attcggaaat ttcataatca aaactagcat agccacgtgt    420
tgatgattta agcttatcaa agaagtcaaa cacaatttca gctaaaggaa tttggtaaat    480
aacattaaca cgattatcat caatataatc cattgttaca aagtcaccac gtttacgttg    540
tgctaactcc attacagcac cgacaaattc ttgaggaacc ataatttgcg ccttaacata    600
tggttcttca atgctgtcaa cacgagtagg atcaggaaat tcagatggat tcgaaacttc    660
aagcatttca ccatcagttg tattaacatg ataaactact gatggtgcag tcataataag    720
atcaatattg aactctcgtt ccaagcgctc ttggataacg tccatatgta aaagtcctaa    780
gaaaccacaa cggaaaccaa accctaatgc ttgtgatgtt tccggttcaa actgtagact    840
agcatcattc aattgtaatt tttcaagggc ttcacgcaga tcgttatact tatttgattc    900
aattggataa agaccggcaa aaaccattgg gttcatttgc ttatagccat gcaaggggtc    960
tatagctggg ttattagcaa gggtaatggt atcaccaaca cgtgtatcag caactgtttt   1020
aattgaggca gcaatatacc ctacatctcc agttgctaaa aaatcacgtc caactgcttt   1080
gggagtgaaa ataccaacct cagtaacgtc gaaggtttta ccattagaca tcatttgaat   1140
cttatctcct ggcttaacca taccatttac aatccttact tgcagaatta ctccacgata   1200
agcatcgtaa acagaatcaa aaattagagc ttgaagagga gcatctactt ccccagtcgg   1260
agcaggaact ttttcaacga tctgctctaa aatttcttca ataccaatcc ctgccttagc   1320
tgaggcaagt acagcttctg aagcatctag accaataaca tcctctactt ctgcacgtac   1380
acgttctgga tctgctgctg gtaaatcaat tttattaata actggtagta tctctaaatc   1440
```

```
attgtctaga gccaaataaa catttgccag agtttgagct tcaattcctt gggctgcatc   1500
aacaaccagt atagcaccct cacaagctgc caatgaacgt gatacttcat atgtaaagtc   1560
aacatgccct ggcgtgtcaa tcaagtgaaa aatgtaagtt tcaccatctt tagcagtata   1620
attaagctca atagcattta actttatagt aatcccacgc tcacgttcta ggtccataga   1680
gtccaacagt tgcgcctgca tttcacgact agaaaccgtt tctgttttct ctaaaatacg   1740
gtctgctaag gttgattttc catggtcaat atgagcgata atcgaaaagt ttctaatctt   1800
ttcttgacgt ttcttcaaat cttcaatatt cat                                1833
```

<210> SEQ ID NO 81
<211> LENGTH: 1833
<212> TYPE: DNA
<213> ORGANISM: Streptococcus agalactiae

<400> SEQUENCE: 81

```
ttattttttg tcatcatcgt ccattgataa aacacttaag aaagcttcct gaggaacttc     60
gacggaacca attgctttca tgcgcttttt accagctttt tgtttttcaa gcaacttacg    120
tttacgtgaa acgtcaccac cataacattt tgctaagaca tttttacgta gtgcttttat    180
atcagaacgg gccacaattt tttgtccaat agctgcttgg ataggaactt caaactgctg    240
acgaggaatg atttttttca acttatcaac gatcaattta ccacgttcat aggcaaattc    300
tttgtgaaca ataaagctta aagcatccac tttatcacca tttaaaagaa tatccatttt    360
aactaattgt gagcgacgat attcggaaat ttcataatca aaactagcat agccacgtgt    420
tgatgattta agcttatcaa agaagtcaaa cacaatttca gctaaaggaa tttggtaaat    480
aacattaaca cgattatcat caatataatc cattgttaca aagtcaccac gtttacgttg    540
tgctaactcc attacagcac cgacaaattc ttgaggaacc ataatttgcg ccttaacata    600
tggttcttca atgctgtcaa cacgagtagg atcaggaaat tcagatggat tcgaaacttc    660
aagcatttca ccgtcagttg tattaacatg ataaactact gatggtgcag tcataataag    720
atcaatattg aactctcgtt ccaagcgctc ttggataacg tccatatgta aaagtcctaa    780
gaaaccacaa cggaaaccaa accctaatgc ttgtgatgtt tccggttcaa actgtagact    840
agcatcattc aattgtaatt tttcaagggc ttcacgcaga tcgttatact tatttgattc    900
aattggataa agaccggcaa aaaccattgg gttcatttgc ttatagccat gcaagggttc    960
tattgctggg ttattagcaa gggtaatggt atcaccaaca cgtgtatcag caaccgtttt   1020
aattgaggca gcaatatacc ctacatctcc agttgctaaa aaatcacgtc caactgcttt   1080
gggagtgaaa ataccaacct cagtaacgtc gaaggtttta ccattagaca tcatttgaat   1140
cttatctcct ggcttaacca taccatttac aatccttact tgaagaatta ctccacgata   1200
agcatcataa acagaatcaa aaattagagc ttgaagagga gcatctactt ccccagtcgg   1260
tgcaggaact ttttcaacga tctgctctaa aatttcttca ataccaatcc ctgccttagc   1320
tgaggcaagc acagcttctg aagcatctag accaataaca tcctctactt ctgcacgtac   1380
acgttctgga tctgctgctg gtaaatcaat tttattaata actggtagta tctctaaatc   1440
attgtctaga gccaaataaa catttgccag agtttgagct tcaattcctt gggctgcatc   1500
aacaaccagt atagcaccct cacaagctgc caatgaacgt gatacttcat atgtgaagtc   1560
aacatgccct ggcgtgtcaa tcaagtgaaa aatgtaagtt tcaccatctt tagcagtata   1620
attaagctca atagcattta actttatagt aattccacgc tcacgttcta gatccataga   1680
```

gtccaacagt tgcgcctgca tttcacgact agaaaccgtt tctgttttct ctaaaatacg 1740
gtctgctaag gttgattttc catggtcaat atgagcgata atcgaaaagt ttctaatctt 1800
ttcttgacgt ttcttcaaat cttcaatatt cat 1833

<210> SEQ ID NO 82
<211> LENGTH: 1833
<212> TYPE: DNA
<213> ORGANISM: Streptococcus agalactiae

<400> SEQUENCE: 82
ttattttttg tcatcatcgt ccattgataa aacacttaag aaagcttcct gaggaacttc 60
gacggaacca attgctttca tgcgcttttt accagctttt tgtttttcaa gcaacttacg 120
tttacgtgaa acgtcaccac cataacattt tgctaagaca tttttacgta gtgcttttat 180
atcagaacgg gccacaattt tttgtccaat agctgcttgg ataggaactt caaactgctg 240
acgaggaatg atttttttca acttatcaac gatcaattta ccacgttcat aggcaaattc 300
tttgtgaaca ataaagctta aagcatccac tttatcacca tttaaaagaa tatccatttt 360
aactaattgt gagcgacgat attcggaaat ttcataatca aaactagcat agccacgtgt 420
tgatgattta agcttatcaa agaagtcaaa cacaatttca gctaaaggaa tttggtaaat 480
aacattaaca cgattatcat caatataatc cattgttaca aagtcaccac gtttacgttg 540
tgctaactcc attacagcac cgacaaattc ttgaggaacc ataatttgcg ccttaacata 600
tggttcttca atgctgtcaa cacgagtagg atcaggaaat tcagatggat tcgaaacttc 660
aagcatttca ccgtcagttg tattaacatg ataaactact gatggtgcag tcataataag 720
atcaatattg aactctcgtt ccaagcgctc ttggataacg tccatatgta aaagtcctaa 780
gaaaccacaa cggaaaccaa accctaatgc ttgtgatgtt tccggttcaa actgtagact 840
agcatcattc aattgtaatt tttcaagggc ttcacgcaga tcgttatact tatttgattc 900
aattggataa agaccggcaa aaaccattgg gttcatttgc ttatagccat gcaagggttc 960
tattgctggg ttattagcaa gggtaatggt atcaccaaca cgtgtatcag caaccgtttt 1020
aattgaggca gcaatatacc ctacatctcc agttgctaaa aaatcacgtc caactgcttt 1080
gggagtgaaa ataccaacct cagtaacgtc gaaggtttta ccattagaca tcatttgaat 1140
cttatctcct ggcttaacca taccatttac aatccttact tgaagaatta ctccacgata 1200
agcatcataa acagaatcaa aaattagagc ttgaagagga gcatctactt ccccagtcgg 1260
tgcaggaact ttttcaacga tctgctctaa aatttcttca ataccaatcc ctgccttagc 1320
tgaggcaagc acagcttctg aagcatctag accaataaca tcctctactt ctgcacgtac 1380
acgttctgga tctgctgctg gtaaatcaat tttattaata actggtagta tctctaaatc 1440
attgtctaga gccaaataaa catttgccag agtttgagct tcaattcctt gggctgcatc 1500
aacaaccagt atagcaccct cacaagctgc caatgaacgt gatacttcat atgtgaagtc 1560
aacatgccct ggcgtgtcaa tcaagtgaaa aatgtaagtt tcaccatctt tagcagtata 1620
attaagctca atagcattta actttatagt aattccacgc tcacgttcta gatccataga 1680
gtccaacagt tgcgcctgca tttcacgact agaaaccgtt tctgttttct ctaaaatacg 1740
gtctgctaag gttgattttc catggtcaat atgagcgata atcgaaaagt ttctaatctt 1800
ttcttgacgt ttcttcaaat cttcaatatt cat 1833

<210> SEQ ID NO 83
<211> LENGTH: 1833

<212> TYPE: DNA
<213> ORGANISM: Streptococcus agalactiae

<400> SEQUENCE: 83

```
ttattttttg tcatcatcgt ccattgataa aacacttaag aaagcttcct gaggaacttc      60
gacggaacca attgctttca tgcgcttttt accagctttt tgtttttcaa gcaacttacg     120
tttacgtgaa acgtcaccac cataacattt tgctaagaca tttttacgta gtgcttttat     180
atcagaacgg gccacaattt tttgtccaat agctgcttgg ataggaactt caaactgctg     240
acgaggaatg atttttttca acttatcaac gatcaattta ccacgttcat aggcaaattc     300
tttgtgaaca ataaagctta aagcatccac tttatcacca tttaaaagaa tatccatttt     360
aactaattgt gagcgacgat attcggaaat ttcataatca aaactagcat agccacgtgt     420
tgatgattta agcttatcaa agaagtcaaa cacaatttca gctaaaggaa tttggtaaat     480
aacattaaca cgattatcat caatataatc cattgttaca aagtcaccac gtttacgttg     540
tgctaactcc attacagcac cgacaaattc ttgaggaacc ataatttgcg ccttaacata     600
tggttcttca atgctgtcaa cacgagtagg atcaggaaat tcagatggat tcgaaacttc     660
aagcatttca ccgtcagttg tattaacatg ataaactact gatggtgcag tcataataag     720
atcaatattg aactctcgtt ccaagcgctc ttggataacg tccatatgta aaagtcctaa     780
gaaaccacaa cggaaaccaa accctaatgc ttgtgatgtt tccggttcaa actgtagact     840
agcatcattc aattgtaatt tttcaagggc ttcacgcaga tcgttatact tatttgattc     900
aattggataa agaccggcaa aaaccattgg gttcatttgc ttatagccat gcaagggttc     960
tattgctggg ttattagcaa gggtaatggt atcaccaaca cgtgtatcag caaccgtttt    1020
aattgaggca gcaatatacc ctacatctcc agttgctaaa aaatcacgtc caactgcttt    1080
gggagtgaaa ataccaacct cagtaacgtc gaaggtttta ccattagaca tcatttgaat    1140
cttatctcct ggcttaacca taccatttac aatccttact tgaagaatta ctccacgata    1200
agcatcataa acagaatcaa aaattagagc ttgaagagga gcatctactt ccccagtcgg    1260
tgcaggaact ttttcaacga tctgctctaa aatttcttca ataccaatcc ctgccttagc    1320
tgaggcaagc acagcttctg aagcatctag accaataaca tcctctactt ctgcacgtac    1380
acgttctgga tctgctgctg gtaaatcaat tttattaata actggtagta tctctaaatc    1440
attgtctaga gccaaataaa catttgccag agtttgagct tcaattcctt gggctgcatc    1500
aacaaccagt atagcaccct cacaagctgc caatgaacgt gatacttcat atgtgaagtc    1560
aacatgccct ggcgtgtcaa tcaagtgaaa aatgtaagtt tcaccatctt tagcagtata    1620
attaagctca atagcattta actttatagt aattccacgc tcacgttcta gatccataga    1680
gtccaacagt tgcgcctgca tttcacgact agaaaccgtt tctgttttct ctaaaatacg    1740
gtctgctaag gttgattttc catggtcaat atgagcgata atcgaaaagt ttctaatctt    1800
ttcttgacgt ttcttcaaat cttcaatatt cat                                 1833
```

<210> SEQ ID NO 84
<211> LENGTH: 1833
<212> TYPE: DNA
<213> ORGANISM: Streptococcus agalactiae

<400> SEQUENCE: 84

```
ttattttttg tcatcatcgt ccattgataa aacacttaag aaagcttcct gaggaacttc      60
gacggaacca attgctttca tgcgcttttt accagctttt tgtttttcaa gcaacttacg     120
```

-continued

```
tttacgtgaa acgtcaccac cataacattt tgctaagaca tttttgcgta gtgcttttat    180

atcagaacga gccacaattt tttgtccaat agctgcttgg ataggaactt caaactgctg    240

acgaggaatg atttttttca acttatcaac gatcaattta ccacgttcat aagcaaattc    300

tttgtgaaca ataaagctta aagcatcaac tttatcacca tttaaaagaa tatccatttt    360

aactaactgt gagcgacgat attcggaaat ttcataatca aaactagcat agcctcgtgt    420

tgatgattta agcttatcaa agaagtcaaa cacaatttca gctaaaggaa tttggtaaat    480

aacattaaca cgattatcat caatataatc cattgttaca aagtcaccac gtttacgttg    540

tgctaactcc attacagcac cgacaaattc ttgaggaacc ataatttgcg ccttaacata    600

tggttcttca atgctgtcaa cacgagtagg atcaggaaat tcagatggat tcgaaacttc    660

aagcatttca ccgtcagttg tattaacatg ataaactact gatggtgcag tcataataag    720

atcaatattg aactctcgtt ccaagcgctc ttggataacg tccatatgta aaagtcctaa    780

gaaaccacaa cggaaaccaa accctaatgc ttgtgatgtt tccggttcaa actgtagact    840

agcatcattc aattgtaatt tttcaagggc ttcacgcaga tcgttatact tatttgattc    900

aattggataa agaccggcaa aaaccatcgg gttcatttgc ttatagccat gcaaaggttc    960

tattgctggg ttattagcaa gggtaatggt atcaccaaca cgtgtatcag caaccgtttt   1020

aattgaggca gcaatatacc ctacatctcc agttgctaaa aaatcacgtc caactgcttt   1080

gggagtgaaa ataccaacct cagtaacgtc gaaggtttta ccattagaca tcatttgaat   1140

tttatctcct ggcttaacca taccatttac aatccttact tgcagaatta ccccacgata   1200

agcatcgtaa acagaatcaa aaattaaagc ttgcagagga gcatctactt ccccagtcgg   1260

agcaggaact ttttcaacga tctgctctaa aatttcttca ataccaatcc ctgccttagc   1320

tgaggcaagc acagcttctg aagcatctag accaataaca tcctctactt ctgcacgtac   1380

acgttctgga tctgctgctg gtaaatcaat tttattaata actggtagta tctctaaatc   1440

attgtctaga gccaaataaa catttgccag agtttgagct tcaattcctt gagctgcgtc   1500

aacaaccagt atagcaccct cacaagctgc taatgaacgt gatacttcat atgtgaagtc   1560

aacatgccct ggcgtgtcaa tcaagtgaaa aatgtaagtt tcaccatctt tagcagtata   1620

attaagctca atagcattta actttatagt aatcccacgc tcacgttcta gatccataga   1680

gtccaacagc tgcgcctgca tttcacgact agaaaccgtt tctgttttct ctaaaatacg   1740

gtctgctaag gttgattttc catggtcaat atgagcgata atcgaaaagt ttctaatctt   1800

ttcttgacgt ttcttcaaat cttcaatatt cat                                1833
```

<210> SEQ ID NO 85
<211> LENGTH: 1833
<212> TYPE: DNA
<213> ORGANISM: Streptococcus pyogenes

<400> SEQUENCE: 85

```
ttatttcttg gcatcgtcat ccattgaaag aacactcaag aaggcttctt gagggacttc     60

gacagaacca atagccttca tccgtttttt accagccttt tgtttttcga gcaatttacg    120

tttacgagac acgtcaccac cataacactt cgccaaaacg tttttacgaa gggccttgat    180

gtctgaacgc gcaacaattt tttgaccaat agcggcttgg atcggcactt caaactgttg    240

acgtggaatg atttttttca atttctcaac aataattttc ccacgttcat aagcaaattc    300

tttatgaaca ataaagctga gcgcatcgac cttatcaccg ttcaaaagaa tgtccatttt    360

caccaattgt gacctgcggt attctgacat gtcataatca aaactcgcat agcctcgcgt    420
```

```
tgaggatttc aatttatcaa agaaatcaaa gacaatttca gccagcggga tttggtaaat    480
cacattgaca cggttatcat caatgtaatc catggtcaca aaatcaccac gcttgcgctg    540
cgataattcc ataacagccc ctacgaactc ttgtggcacc atgatttgcg ctttaacata    600
aggctcttca ataaaagcca cccgtgttgg gtctggaaat tctgaagggt tagacacttc    660
aatcatgtcc tcatctgttg tgtgaacatg gtagactaca gatggtgctg tcatgatcaa    720
atcaatgtta aattcacgtt ccaaacgttc ttgaatcaca tccatgtgaa gcaagcctaa    780
aaaaccgcat cgaaaaccaa agccaagcgc ttgtgacgtt tcgggttcaa actgtaaact    840
ggcatcgtta agctgtaatt tttcaagcgc ttcacgcaag tcattgtatt tatttgattc    900
aatcggataa atccctgcaa agaccatcgg gttcatctgc ttgtagccat gcaaggcttc    960
cttagcaggg ttattagcta aagtcaccgt atcccccaca cgggtatctg ctaccgtttt   1020
gatagaggcc gcaacataac caacatctcc cgtcgcaagg aaatctcgtc caactgcctt   1080
aggagtgaaa atgccaactt ctgtaacatc aaaagttttt ccattcgaca tcatctggat   1140
tttatcgcca gacttgacaa taccgttcac aatccgaact tgcaggataa cgcctcgata   1200
agcatcgtaa acagagtcaa aaatcaaggc ctgtaaaggc gcatccacat cacccgtagg   1260
agcaggaacc ttctcaacaa tttgctcaag aatctcttcg atcccaatac cagccttggc   1320
tgacgccaga acagcctcag aagcatcaag tccaatgaca tcttctactt catggcggac   1380
cctctcaggg tctgcagctg gcaaatcaat tttattgata accggtaaaa tttccaaatc   1440
attatcgagg gctaggtaaa cattggccag ggtctgtgct tcaatgccct gcgctgcatc   1500
cacaactaga atcgctccct cacaggctgc caacgaacgc gatacttcat aagtaaagtc   1560
cacatgccct ggggtatcaa taaggtggaa aatgtaggtt tccccatctt tagccgtgta   1620
attaagctca atggcgttta acttgatggt aatcccacgc tcacgctcca aatccatgga   1680
gtccaataac tgagcctgca tttcacgaga cgaaaccgtc tctgtctttt ccaaaatgcg   1740
gtcagcgaga gtagattttc catggtcaat atgtgcaata atggagaaat tacgaatctt   1800
ctcctgacgt ttttttaaat cttgactgtt cat                                1833
```

<210> SEQ ID NO 86
<211> LENGTH: 1817
<212> TYPE: DNA
<213> ORGANISM: Streptococcus pyogenes

<400> SEQUENCE: 86

```
catccattga aagaacactc aagaaggctt cttgagggac ttcgacagaa ccaatagcct     60
tcattccgtt ttttaccagc cttttgtttt tcgagcaatt tacgtttacg agacacgtca    120
ccgccataac acttcgctaa aacgtttttta cgaagggcct tgatgtctga acgcgcaaca   180
attttttgac caatagcggc ttggatcggc acttcaaact gttgacgtgg aatgattttt    240
ttcaatttct caacaataat tttcccgcgt tcataagcaa attctttatg aacaataaag    300
ctgagcgcat cgaccttatc accgttcaaa agaatgtcca ttttcaccaa ttgtgacctg    360
cggtattctg acatgtcata atcaaaactc gcatagcctc gcgttgagga tttcaattta    420
tcaaagaaat caaagacaat ttcagccagc gggatttggt aaatcacatt gacacggtta    480
tcatcaatgt aatccatggt cacaaaatca ccacgcttgc gctgcgataa ttccataaca    540
gcccctacga actcttgtgg caccatgatt tgcgctttaa cataaggctc ttcaataaaa    600
gccacacggg ttgggtctgg aaattctgaa gggttagaca cttcaatcat atcctcatct    660
```

-continued gttgtgtgaa cgtgatacac cacggacggt gctgtcatga tcaaatcaat gttaaattca 720
cgctctaaac gttcttgaat cacgtccatg tgaagcaaac ctaaaaagcc gcatcgaaaa 780
ccaaagccaa gcgcttgtga cgtttcgggt tcaaactgta aactggcatc gttcagttgt 840
aatttttcaa gcgcttcacg caagtcattg tatttatttg attcaatcgg ataaatccct 900
gcaaagacca tcgggttcat ctgcttgtag ccatgcaagg cttccttagc agggttatta 960
gctaaagtca ccgtatcccc cacacgggta tctgctaccg ttttgataga agccgcaaca 1020
taaccaacat ctcccgtcgc aaggaaatct cgtccaactg ccttaggagt gaaaatccca 1080
acttctgtaa catcaaaggt ttttccattc gacatcatct ggattttatc gccaggcttg 1140
acaataccgt tcacaatccg aacctgcaaa attacccctc ggtaagcatc atacacagag 1200
tcaaaaatca aggcctgtaa aggcgcatcc acatcacccg taggagcagg aaccttctca 1260
acaatttgct caagaatctc ttcgatccca ataccagcct tggctgacgc cagaacagcc 1320
tcagaagcat caagtccaat gacatcttct acttcatggc ggactctctc agggtcagca 1380
gcaggcaaat caattttatt gataaccggt aaaatttcca aatcattatc aagagctagg 1440
taaacattgg caagggtctg cgcttcaatg ccctgcgctg catccacaac taaaatcgct 1500
ccctcacagg ctgccaacga acgcgatact tcataagtaa agtccacatg ccctggggta 1560
tcaataaggt ggaaaatgta ggtttcccca tctttagccg tgtaattaag ctcaatggcg 1620
tttaacttaa tggtaatccc acgctcacgc tccaaatcca tggagtccaa taactgagcc 1680
tgcatttcac gagacgaaac cgtctctgtc ttttccaaaa tgcggtcagc gagagtagat 1740
ttgccatggt caatatgtgc aataatggag aaattacgaa tcttctcctg acgttttttt 1800
aaatcttgac tgttcat 1817

<210> SEQ ID NO 87
<211> LENGTH: 1824
<212> TYPE: DNA
<213> ORGANISM: Streptococcus pneumoniae

<400> SEQUENCE: 87
ttattcttca tccatactca agacgctgag gaaggcttct tgcggaactt caactgatcc 60
gatggatttc atgcgtttct taccagcttt ttgtttttca aggagtttac gcttacgaga 120
aacgtcacca ccataacatt tagcaagtac gttcttacga agggccttga tatcagtacg 180
agcgacaatc ttgtgtccaa tagccgcttg gattggaact tcaaattgtt ggcgagggat 240
gattttcttg agtttatcaa cgatgagttt cccacgttcg taggcaaagt ccttgtgaac 300
gataaagctg agggcatcca ccttatctcc attgagaaga atatccattt tcaccagctt 360
agatgggcga tattctgaca attcgtagtc aaagcttgca taaccacgtg tcgaagactt 420
aagtttatca aagaagtcaa agacaatttc agcaagagga atttgataga taacattgac 480
acggttatca tcaatatagt ccatagtcac aaagtcccca cgcttacgct gagctagctc 540
cattactgct ccgacgaact cctgtggtac catgatttgc gccttgacat aaggctcttc 600
aatggtcgca atcttagttg ggtctggaaa ctcagatggg ttagacacat ccatagactc 660
accgtcggtc aaattaactt tgtaaataac agacggagct gtcatgatga ggtcaatatt 720
gaactcacgc tctaaacgtt cctggataac atccatatgg agaagtccaa gaaatccaca 780
acggaaacca aatccaagtg cctgagatgt ttctggttca aactgaagac tagcatcatt 840
cagttgcaat ttttcaagcg cttcacgcag gtcattgtac ttgtttgatt cgattgggta 900
gagacccgca aagaccatag gattcatctg cttataacca tgtaatggtt ctgccgcagg 960
attggttgcc aaggtaacgg tatcacccac acgagtatcc tgaaccgtct tgatagacgc 1020
cgcaatgtaa ccaacatcac cagtcgcaag gaaatcacga ccaaccgctt ttggtgtaaa 1080
aataccgact tcggccacat caaaggtctt actattgctc atgagctgaa tcttatcacc 1140
aggtttgacc actccgtcca tgacacgcac ttggaggata accccacggt aagcatcgta 1200
aacagagtcg aaaatcaagg ccttaagtgg cgccgtcaca tcacccgttg gtgctggtac 1260
tttttctaca atttgctcga ggatttcttc aatcccaata ccagccttgg cagaagccaa 1320
aactgcttca ctggcatcca aaccaatcac atcttcaatc tctgtacgca cgcgctccgg 1380
atctgcagcc ggcaggtcaa ttttattaat gataggcatg atttccaaat cattatccaa 1440
agccagataa acgttggcaa gagtttgagc ctcaattcct tgagccgcat cgaccaccaa 1500
aatagcaccc tcacaggcag ctagcgaacg tgaaacttca taggtaaagt caacgtgccc 1560
tggtgtgtca atcaagtgga aaatataagt ttccccatct tttgcagtgt aattcaactc 1620
gatggcattc aacttaatag taattccacg ttcccgctct agctccatgc tatccaaaag 1680
ctgggcctgc atttcacgac ttgaaaccgt ctctgttttt tccaaaatgc ggtctgctag 1740
agttgatttt ccgtggtcaa tatgggcgat aatagagaag ttacggatct tctcctgtcg 1800
ttttttcaat tcttctaagt tcat 1824

<210> SEQ ID NO 88
<211> LENGTH: 1836
<212> TYPE: DNA
<213> ORGANISM: Streptococcus mutans

<400> SEQUENCE: 88
ctattttttc ttatcgtcat catccatgga cagaacgctg agaaaggctt cctgagggac 60
ctcaactgaa ccaattgatt tcatccgctt tttaccagcc ttttgttttt ccaaaagttt 120
acgctttctg gaaacatctc cgccataaca tttagcaaga acatttttcc gcaaggcctt 180
aatatcagaa cgcgccacaa ttttttgacc gatcgctgct tgaatgggaa cttcgaattg 240
ttgccgcgga atgatcttct tcaacttttc aacaattaat ttccccccttt cataggcaaa 300 ctctttatgg acaatgaagc taagcgcatc aactttatca ccattgagca aaatatccat 360
ttttaccagc ttagacttgc gatactcaga aatatcataa tcaaaactag cataaccacg 420
ggtagaggat tttagtttat caaaaaaatc aaaaacaatt tcagccaaag ggatctggta 480
aataacattg actcggttat tatcaatgta atccatagtc acaaagtcgc cgcgcttacg 540
ttgtgataat tccatgacag ctcccacata ctcttgcggc accataatct gggctttaac 600
gtaaggttcc tcaatactat caaccttagt tggatcagga aattcagatg gattagaaac 660
ctcaagcctc tccccatctg tggtataaac atggtaaact acagatggcg ctgtcataat 720
gagatcaata ttaaactcac gctccaatcg ctcttgaatg acatccatat gcaaaagacc 780
taagaagcca caacgaaaac caaagccaag ggcttgagaa gtctcaggtt caaagtgaag 840
actggcatca ttaagctgta atttctctag ggcttcacgc atgtcattat atttgctgga 900
atcaatagga taaattcctg caaaaaccat gggattcaac tgcttataac catgcaaagg 960
tgcttcggca gggcagtccg ccagagtcac tgtatcacca acacgagtgt ctgccactgt 1020
cttgattgaa gcagctaaat aacctacatc acccgttgcc aaaaagtcac gattaacagc 1080
cttaggagtg aaaattccta cttctgtcac gtcaaaagtc ttgccattgc tcatgagttc 1140
aattttatct ccgggtttga ccataccatc catgacccga atttgcagaa taacgccgcg 1200

-continued

```
ataagcatca tagacagaat caaaaataag agctttgagt ggggcttcaa catccccctt   1260

tggagctggt actttttcca caatttgctc caaaatctct tcaatcccga tgcctgcttt   1320

ggcggaagcc aaaacagctt cactagcatc cagtccaatg acatcttcaa tctcagtgcg   1380

cacacgttca ggatcagctg ctggcaagtc aattttattg ataacaggta aaatttccag   1440

atcattatct aaagccaaat aaacattggc taaggtctgc gcttcaatac cttgtgcagc   1500

atctaccacc aaaatggcac cttcacaggc tgccaaagaa cgtgacactt cataagtaaa   1560

gtcaacatgt cctggcgtgt caatcaagtg aaaaatataa gtttcaccat ttttagcctt   1620

ataattaagc tcaatcgcat ttaatttaat ggtaatacca cgctcacgtt ctaagtccat   1680

gctgtccaaa agctgagctt gcatttctct gctagaaaca gtttctgtct gttccaaaat   1740

acgatctgcc agcgttgact tcccatggtc tatatgggca ataatagaga aattacgaat   1800

tttctcctga cgatttttaa gttgttctat agtcat                             1836
```

<210> SEQ ID NO 89
<211> LENGTH: 1833
<212> TYPE: DNA
<213> ORGANISM: Streptococcus thermophilus

<400> SEQUENCE: 89

```
ttatttctca tcttcgtcca ttgaaagcac agacaagaag gcttcttgtg gtacctccac     60

cgaaccgatg gctttcatac gtttcttacc ggcttttttgt ttttcgagga gtttacgttt    120

acgtgaaacg tcaccaccgt aacatttagc caagacgttt ttacgaagag ctttgatatc    180

tgtacgggca acaatttttt gaccaatagc cgcttggata ggaacttcaa attgttgacg    240

tggaataatt ttcttaagtt tatcaacgat aagttttcca cgttcgtagg caaattctct    300

atggacaata aagctaaggg catcgacctt atcaccatta aggagaatat ccattttcac    360

caattgtgaa cgacggtact ctgacaattc atagtcaaaa cttgcataac cacgagttga    420

tgacttcaat ttatcaaaga agtcaaagac gatttcagca agtggaattt gatagataac    480

gttaacacga ttatcatcaa tatattccat ggtttcaaaa tcaccacgtt tacgttgcgc    540

caactccata acagcaccaa catactcttg aggaaccata atttgagctt tgacataagg    600

ctcttcaatg gtatcaatac gtgtaggatc tggaaattca gatgggttgg acacttcaag    660

catttcaccg tcagtagtgt taacatggta aactactgat ggtgcagtca tgatgagatc    720

gatgttaaac tcacgttcca aacgctcttg gataacatcc atgtgaagaa ggcccaagaa    780

accacaacgg aaaccaaaac caagagcttg agacgtttca ggctcaaatt gaagactggc    840

atcattcaat tggagctttt caagagcctc acgcaagtcg ttatatttat ttgactcaat    900

tggataaaga ccagcaaaga ccattgggtt catttgctta taaccatgaa gtggttctgc    960

ggctggatta tccgcaagtg tcactgtatc accgacacga gtatccgcaa ctgtcttaat   1020

tgaagctgct acataaccaa catctccagt cgcaaggtag tcacggccaa cagctttagg   1080

agtgaaaata ccaacctcag taacgtcaaa ggtcttgcca ttagacatca tttgaatctt   1140

atcacccgtt ttaaccattc cgttaaccac acgcacttgg agtatgacgc cacgatacgc   1200

atcataaaca gagtcaaaga taagggcttg gagaggtgct tccacatcac cttggggcgc   1260

aggaactttc tcaacaattt gttcgagaat ctcttcgata ccaatgccag ccttagctga   1320

tgcaagcaca gcttccgagg catctaatcc gataacatct tcaatctctg tacgtacacg   1380

ctcaggatct gccgctggaa ggtcgatttt attgataact ggtaagattt ccaagtcatt   1440

atcaagtgcc aagtaaacat tggcaagtgt ttgtgcttca atcccttgag ctgcatctac   1500
```

-continued caccaagata gcaccctcac aggcggcaag ggaacgtgac acctcataag taaagtccac 1560
atgtcccggt gtgtcgataa ggtggaaaat ataagtctcg ccgtctttag ctttgtagtt 1620
aagctcaatg gcattcagtt tgatagtgat accacgttcg cgctcaagat ccatactatc 1680
aaggagttgt gcctgcatct cacgacttga tacagtctca gtcttttcca agatacggtc 1740
agcaagcgtt gatttaccat ggtcaatatg agcaataatc gagaagttgc gaatcttctc 1800
ctgtctttgt tttaattctt caatatttgg cat 1833

<210> SEQ ID NO 90
<211> LENGTH: 1836
<212> TYPE: DNA
<213> ORGANISM: Enterococcus faecalis

<400> SEQUENCE: 90
ctatttcgcg ttatcttggt cgtccatttt cagaaccgcc ataaaggctt cttgaggaac 60
ttccacggat ccaatttgtt tcatccgttt cttcccttct ttttgtttct ctaacaattt 120
acgtttacga gaaacatcgc caccatagca tttagccagt acgtttttgc gtaaggcttt 180
aatatctgaa cgagccacaa ttttttgacc aatcgccgct tgaactggga cttcaaactg 240
ttgacgtgga attagttttt tcagtttctc aacaatcgct ttaccacgct caaatgcgaa 300
atctcggtga acaataaagc ttaaagcatc cactttttca gcatttaata gaatatccat 360
tttcactagg cggctggtac gatagccagc catttcgtaa tctaaggatg catagccttt 420
tgtacttgat ttcaatttat cgaaaaagtc aaacacgatt tcagataacg gaatttcata 480
aactacgttt acacgataat cgtctaagta atccattgta atgaattcgc cacgtttacg 540
ttgtgataat tccattactg ctcctacata atcgtttggc accatgattt gcgctttaac 600
ataaggttct tccacagatt caatcgttac tggttctgga aattcagctg ggttgtcaac 660
aacaacggtt gttccgtcag ttttattaac gtgatagatt acagacggtg ctgttgtaat 720
taactctaaa ttaaattctc gttccaaacg ttcctgaaca acatccatgt gcagcaaacc 780
taagaaacca caacggaaac caaaccctaa agcttgcgat gtttccggtt caaattgtaa 840
cgccgcatca tttaattgta atttttctaa tgcttcccgt aaatcgttgt agcgcgacgt 900
atcaattgga tataaaccac aataaaccat tggattcatt ttgcggtagc ctggtagtgc 960
ttctgctgct ggattgtcgg ccaaagtcac tgtatccccg acccgtgtat cttgaaccgt 1020
tttaatgcta gcggtgatat agcccacatc accaaccatt aaataatcac gagcaatcgg 1080
tttcggtgaa aaaacgccga cttctgttac atcaaacgtt ttaccgttac tcatcatttg 1140
gattttatcc ccaggacgaa cgacaccgtc aattacacgg atgtttaaaa cgaccccccg 1200
ataactatcg taaatagagt caaaaatcaa agcctttaaa ggagcctcaa tatcgcctga 1260
tggagctggt acatactcca ccacttgttc taaaatatct tcaatcccaa tccctgcttt 1320
tgcacttgct aaaacagctt ccgatgcatc aattccaatt acgtcttcaa tctctgtccg 1380
aacacgctct ggatcagcgg cgggtaaatc aattttatta ataacaggta aaatttctaa 1440
gtcattatcc aatgccaaat agacatttgc tagcgtttgc gcttcaattc cttgcgccgc 1500
atcaacaact agaacagccc cttcacaagc tgccaagcta cgagaaactt cgtaggtgaa 1560
atcgacgtgc cctggtgtgt caatcaaatg gaaagtatag atttcaccat ctttggctgt 1620
atagtttaat tcaattgcgt ttaatttgat agtaatgccg cgttctctct ctaaatccat 1680
tgaatcaagt aattgatctt gcatttctcg actgctaact gtatttgttt tttccaaaat 1740
ccggtcggct aaagttgact tcccatggtc aatgtgggca atgatcgaga aattacgaat 1800
tttctcttgt cttgctttca tttctttatt gttcat 1836

<210> SEQ ID NO 91
<211> LENGTH: 1836
<212> TYPE: DNA
<213> ORGANISM: Enterococcus faecium

<400> SEQUENCE: 91
ctatttcttc ggttcgtcct cgtccatttt cagaacggcc atgaaggctt cttgcggaac 60
ttcgacggag ccgatttgtt tcatccgctt cttcccttct ttttgtttct ctaagagttt 120
acgtttacga gaaacatctc caccataaca tttagccaag acgtttttac gcaaggcttt 180
gatgtctgaa cgggcaacga ttttttgtcc aatagctgct tggattggca cctcaaattg 240
ttggcgtggg attagttttt tcagtttttc aacgattgct tttccacgtt cataggcaaa 300
gtctcggtga acgataaagc ttaatgcatc gacttttttct ccattcagca agatgtccat 360
cttcactaac ttgctttttt gataaccaga catttcataa tccaatgagg catagccttt 420
cgtgcttgat ttcaatttgt cgaaaaagtc aaagacaatt tcagaaagcg gaatattata 480
gacgacattt actcggtaat catctaaata atccatcgta atgaattctc cccgttttcg 540
ttgagaaagt tccattactg caccgacaaa atcatttggg accatgatct gtgctttgac 600
gaatggttct tctacatcct gaatcgttac aggttcagga aaatctgccg ggttatctac 660
tgtagcagtc gtaccatccg ttttattaac atggtaaata acggatggtg cagtcgtgat 720
caattctaga ttgaattccc gttccaagcg ttcttggacg acatccatat gaagaagtcc 780
gaggaatcca cagcggaacc caaaacctaa tgcttgagag gtttctggtt cgaattgtaa 840
agcagcatca ttcaattgca gtttttctaa agcttcccgc aaatcgttgt aacgagaagt 900
atcaattgga taaagaccac aataaaccat cggattcatt tttcggtaac ctggtaaagc 960
ttcagcggca ggattgtctg ctaacgttac tgtatcccct actcgtgtat cttggacagt 1020
tttgatactt gctgtgatat aaccgacatc accgaccatc aaaaagtctc tagcaactgc 1080
ttttggcgag aagaccccga cctctgtaac atcaaatgtt ttgccattac tcatcagttt 1140
gattttgtct ccgggtttga ccataccgtc cgtgatccgg acatttagaa caacaccgcg 1200
gtaactatca taaatagagt caaagatcaa agcttttagc ggtgcatcta agtctccact 1260
tggtgcagga acatattcca cgatctgctc gagaatatct tcaatcccaa tccctgattt 1320
ggcactggct aatacagctt cactagcatc gattccgatt acgtcttcga tttcttgacg 1380
gacacgttcg ggatctgctg cgggtaggtc gattttattg atgactggca ggatctccaa 1440
atcattgtct aacgctaaat aaacattggc caatgtttgt gcttcgattc cttgtgctgc 1500
atcgaccact aaaacggcac cctcacaggc agcaaggctt cgagagactt cataggtgaa 1560
gtcgacgtgc cctggggtgt caatcaagtg aaagatatat gtttctccat ttttcgctgt 1620
gtaattgagt tctacagcat ttaatttaat cgtgattcca cgttcacgtt ccaaatccat 1680
cgagtctaac agctgatctt gcatttcgcg agacgtcaca gtgtgcgtca tttctaaaat 1740
acgatcggcc aatgtagatt tcccatggtc gatatgagcg atgatcgaaa aattacgaat 1800
ctgctcttgg cgttctttca ttttctttat atccat 1836

<210> SEQ ID NO 92
<211> LENGTH: 1833
<212> TYPE: DNA
<213> ORGANISM: Streptococcus sanguinis

<400> SEQUENCE: 92

```
ttattcctca tccatactca ggacgctgag gaaggcttct tgtggaactt cgacagatcc     60
gatagctttc atccgttttt taccggcttt ttgtttttct aggagtttgc gcttccgaga    120
aacgtcacca ccataacact tggccaagac attcttacgc agagccttga tgtctgtccg    180
agccacgatt ttctgaccaa tagcagcctg aatgggtact tcaaattgct gacgaggaat    240
gattttcttg agcttgtcta caatcagctt accacgctca taggcaaatt ccttgtgaac    300
gataaagctg agagcatcga ccttgtcgcc attaaggaga atatccatct tcaccagctt    360
ggacgagcga tactcggaga tttcgtagtc aaagctcgca tagccacgag tagaggactt    420
gagcttgtca aagaagtcaa agacgatttc agcaagtggg atttgataga tgacattgac    480
ccgattatca tcgatatagt ccatggtcac aaagtcaccg cgcttgcgtt gagccaactc    540
catcaccgct ccgacaaatt cctggggaac cataatctgc gccttgacat agggctcctc    600
gatggaatca atcttggtcg ggtccggaaa ctcgctcgga ttggacacat caagagaagt    660
cccatccgtc atattgacct tatagataac agacggagcc gtcataatca gatcaatatt    720
aaactcgcgc tccaaacgct cctgaatgac gtccatgtgc agtaagccca ggaatccaca    780
acggaaccca aatcctaatg cctgtgatgt ttctggctca aactgcagac tggcatcgtt    840
tagctggagc ttttcaaggg cctcacgcag gtcgttgtat ttattggact cgataggata    900
gagaccagcg aagaccatag gattcatctg cttgtagcca gctaatggct cagcagctgg    960
attgtccgcc aaggtcactg tatctccgac ccgagtgtcc tgtaccgtct tgatagaggc   1020
tgcgatatag ccaacatccc cagtagccaa gaaatcacga ccaatggctt tgggagtaaa   1080
gatgccgacc tcagtcacgt caaaggtctt accattgctc atgagctgaa tgatatctcc   1140
tggcttgacc acaccgtcca tcacccgcac ttgcaggatt accccacgat aggcgtcata   1200
gaccgagtca aagattaagg ccttgagcgg tgcttcaaca tttccagtcg gagctggaac   1260
tttctccaca atctgctcta aaatttcctc aattccgata ccagccttgg cagaagccaa   1320
tacggcttcg ctagcatcca gtccaatcac gtcttcaatt tctgcccgca cccgctctgg   1380
atccgcagct ggcaggtcaa ttttattgat gactggcagg atttccaagt cattatccag   1440
cgctagataa acattagcca aggtctgagc ctcaatcccc tgagccgcat ccacaaccaa   1500
aatagcccct tcgcaggccg ctaacgaccg cgatacctca taggtaaagt ccacgtgtcc   1560
cggcgtgtca atcaagtgga agatataggt ttcaccgtcc ttggcggtat aattgagctc   1620
gatagcattg agcttaatgg tgatgccgcg ctcccgctcc aagtccatgc tgtccaagag   1680
ttgggcctgc atttcccgac tggaaaccgt ctcagtcgcc tccaaaatcc ggtcagccaa   1740
ggttgatttc ccgtggtcaa tgtgagcaat gatggagaaa ttgcggatct tctcctgacg   1800
ttttttcaaa tcttctaaat tcatttttct cat                                1833
```

<210> SEQ ID NO 93
<211> LENGTH: 1824
<212> TYPE: DNA
<213> ORGANISM: Streptococcus gordonii

<400> SEQUENCE: 93

```
ttattcctca tccatactca agacactgag gaaagcttct tgtggaactt cgactgagcc     60
gatagctttc atccgttttt taccagcttt ttgtttttca aggagtttgc gcttccgaga    120
aacgtcacca ccataacact tggccaagac attcttacgc aaggctttga tgtctgtccg    180
```

agccacaatt ttctgaccga tagcagcctg aatgggtact tcaaactgct gacgaggaat 240
gattttcttg agcttgtcta caatcagctt accacgctca taagcaaatt ccttgtgaac 300
gataaagcta agggcatcaa ccttgtcgcc attgaggaga atatccatct tcaccagctt 360
ggacgagcgg tactcagaaa tctcatagtc aaagctcgca tagccacgag tagaggactt 420
gagcttgtca aaaaagtcaa agacaatttc agcaagcgga atttgataga tgacattgac 480
ccgattatcg tcgatatagt ccatagtcac aaagtcaccg cgcttgcgtt gagccaactc 540
catcactgct ccgacaaatt cctgtggcac cataatctgc gccttaacat aaggctcctc 600
gatagaatca atcttggtcg gatccggaaa ctcactcgga ttagagacat caatggcttc 660
accatctgtc agattaacct tatagataac ggacggagcc gtcataatca gatcaatatt 720
aaactcacgc tccaagcgct cctgaataac atccatgtgt agcaagccca agaagccaca 780
acggaatcca aatcctagcg cttgtgatgt ttctggctca aactgcaagc tggcatcgtt 840
tagctggagc ttttcaagag cctcacgtaa gtcattgtat ttattggact cgataggata 900
gagaccagca aaaaccatcg ggttcatctg cttgtagcca tgcagaggtt ctgtagctgg 960
attatcagcc aaggttacag tatctccgac tcgggtatcc tgtaccgtct tgatagaggc 1020
tgcaatatag ccaacatccc ctgtcgctaa gaaatcacgc ccaatagcct taggtgtaaa 1080
gatgccaacc tcagttacgt caaaggtctt gccattgctc atgagctgaa tggtatctcc 1140
tggcttgacc acaccatcca tcaccctcac ttgtagaatt accccacgat aggcgtcata 1200
gactgagtca aaaatcaagg ccttgagtgg cgcttcaaca tttccagtcg gagctggaac 1260
tttctccaca atctgctcta gaatatcttc aatcccgata ccagccttgg cagaagctaa 1320
tacggcttcg ctagcatcta gtccaatcac atcttcaatc tcagctcgca cccgttctgg 1380
atccgcagct ggcaggtcaa tcttattgat aaccggcaga atttccaaat cattgtccag 1440
cgctagatag acatttgcca aggtctgagc ttcaatcccc tgagctgcat caacgaccaa 1500
aatagctcct tcacaggctg ctaacgaccg cgatacttca taggtaaagt ccacgtgtcc 1560
aggcgtgtca atgaggtgga agatataggt ttcaccatct ttagctgtgt aattaagctc 1620
gatagcattt agtttgatgg tgataccgcg ctcccgctcc aagtccatgc tgtccaagag 1680
ttgggcctgc atttcccggc tggaaaccgt ctcagtcgcc tccaaaatcc ggtcagccaa 1740
ggttgatttc ccgtggtcga tatgggcaat gatggagaaa ttacggatct tctcctgacg 1800
ttttttcaaa tcttctaaat tcat 1824

<210> SEQ ID NO 94
<211> LENGTH: 1833
<212> TYPE: DNA
<213> ORGANISM: Streptococcus suis

<400> SEQUENCE: 94
ttatttctta tcgtcttcat ccatgctgag aacactgagg aaggcttctt gtggaacttc 60
gacagagccg atggctttca tccgtttttt accagctttt tgcttttcta ggagtttgcg 120
tttacgggaa acgtcaccac cataacactt ggccaaaacg ttcttccgaa gagccttgat 180
gtcgctacgg gcaacaattt tctgaccgat agctgcttgt attggtactt caaactgttg 240
acggggaatg attttcttga gtttgtccac gataattttc ccacgttcgt aggcaaattc 300
cttgtggacg ataaagctga gggcatcgac cttgtcacca ttgaggagaa tatccatttt 360
caccaacttg gatgaacggt attcagaaat ctcatagtcg aagctggcat aaccacgagt 420
ggacgactta agcttatcaa agaagtcaaa aacaatctcc gcaagtggaa tttggtagat 480

```
gacattgaca cgattatcat cgatgtaatc catagtcaca aagtcaccgc gtttgcgttg    540

ggccaattcc atgactgcac cgacgtattc ctgtggtacc atgatttgtg ccttaacgta    600

aggctcttcg atagtggcaa tctttgttgg gtctgggaat tcggatgggt tggctacatc    660

aatcatttca ccgtccgtca tgttgacatg gtaaaccacc gacggtgctg tcatgatgag    720

gtcaatgtta aactcacgct caatccgttc ttggataaca tccatgtgca agaggcccaa    780

gaatccacaa cggaaaccaa atccgagtgc ctgcgatgtt tctggctcaa actgcaagct    840

ggcatcgttg agttggagtt tttccaaggc ttcacggagg tcattgtact tgttggaatc    900

gattggatag atacctgcaa agaccattgg attcatctgc ttgtagcccg ctagtggctc    960

gctggcagga ttttctgcca aggttaccgt atcaccgaca cgggtatctg caacggtctt   1020

gatagaggct gcaatgtaac caacatcacc agtcgccaaa taatcacgac cgattgcttt   1080

gggtgtgaaa atccccactt ccgtcacatc gaaagtctta ccattgctca tcatctgaat   1140

ggtgtcacca ggttttacca caccattgac gatacgaact tggaggataa cgcctcgata   1200

cggatcgtaa accgagtcaa aaatcaaggc ttgcaatgga gcttcgacat caccagtcgg   1260

tgctggaacc ttctcgacaa tctgctccaa gatttcctcg ataccaatac ctgccttggc   1320

tgatgttggc actgcttcag aagcatccaa accaatcaca tcttcgattt cctgacgaac   1380

acgttctggg tctgctgctg gcaggtcaat cttgttaatg attggcaaga tttccaaatc   1440

attgtccaag gctagataaa cgttggccaa ggtctgtgct tcaatccctt gagcagcatc   1500

caccactaaa atcgctcctt cacaggcagc caacgaacgc gatacctcat aggtaaaatc   1560

cacgtgtcct ggtgtgtcaa tcaagtggaa aatgtatgtc tctccatctt tagctgtata   1620

gttgagttcg attgcgttga gtttaattgt gataccacgc tcgcgttcca agtccatact   1680

atccagcaac tgggcttgca tttcacggct ggaaactgtt tccgtcttct caagaatacg   1740

gtcagccaag gttgatttac catggtcgat gtgggcaata atggagaaat tacgaatttt   1800

ctcctgtcgt tttttcaaat cttctaaatt cat                                1833
```

<210> SEQ ID NO 95
<211> LENGTH: 1824
<212> TYPE: DNA
<213> ORGANISM: Listeria monocytogenes

<400> SEQUENCE: 95

```
atgaacaaag aagaaatgaa tgcaagacaa aagaaaatta gaaacttttc gattatcgcg     60

cacatagatc atggtaaatc tacactcgct gatcggattt tagaacaaac gggtgctttg    120

acgcatcgtg aaatgaaaaa tcagctacta gattcgatgg atttagaacg tgaacgcggg    180

ataaccataa aattaaatgc tgtacaatta aaatataaag caaaagatgg agaaacatat    240

atcttccatc tgattgatac gcctgggcat gtcgatttca cctatgaagt atcaagaagt    300

ttagctgcat gtgagggagc aatccttgtt gtagatgctg cgcaaggaat tgaagcacaa    360

acccttgcta atgtttattt agcactagac aacgatttag aaattttacc agtcattaac    420

aaaatcgatt taccagcggc cgatccggaa agagtccgcg aagaaattga agatgtaatt    480

ggtttagatg cttctgacgc tgtacttgct tctgcgaaat ctggtattgg tattgaagac    540

attctagaac aaattgtcga aaaagttcct gagccatctg gtgatgtaaa taaaccacta    600

aaagcgctca tttttgactc tgtttttgat gcatatcgtg gtgttattgc taatatccgt    660

atcatggatg gtgttgtaaa agcaggcgac cgaattaaaa tgatgtccaa tggcaaagaa    720
```

-continued

```
ttcgaagtaa cggaggttgg tgtattctca ccaaaggcaa caccacgtga cgaattactt    780

gttggtgacg ttggttactt aacagcagct ataaaaaatg ttggagatac gcgcgtaggt    840

gatacaatca cacttgcgaa taatccagct gaagaagcgc tggatggtta ccgtaaatta    900

aatccaatgg tttattgtgg tctatatcca atcgactcct ctaaatataa tgatcttcgt    960

gatgctttag aaaaactaga attaaatgac tctgctttgc aatttgaagc ggaaacttct   1020

caagcattag gttttggttt ccgttgtggt ttcttaggat tactacatat ggaaattatt   1080

caagagcgaa tcgaacgtga atttaacatt gatttaatta ccactgctcc aagtgttatc   1140

tatcatgtca acttgacaga tggttctaac attgtggttg ataatcctgc tgaaatgcca   1200

gaacctggtg ttattgaaag cgtggaagag ccatatgtaa aagcaactgt gatggttcca   1260

aatgattatg ttggtgcagt gatggaactg gcacaaaaca aacgtggaaa cttcattacg   1320

atggagtact tagatgatat tcgcgtaagt attgtgtacg aaattccatt atccgaaatc   1380

gtatatgact tttttgacca attaaaatca tctacaaaag gttatgcgtc ctttgattat   1440

gaattaattg gctataaagc ttctaaactt gtgaaaatgg atattctttt aaatgcagaa   1500

aaagttgatg cacttagctt tatcgttcac cgtgattttg cttatgagcg tggaaaaatc   1560

atcgtggaga aattaaaaga acttattcca agacaacaat ttgaagtacc tattcaagca   1620

gcaattgcca caaaaattgt ttctcgttct actattaaag cgttgcgaaa aaacgtactt   1680

gctaaatgtt acggtgggga cgtatctcgt aaacgaaaac ttttagagaa acaaaaagaa   1740

ggtaaaaaac gaatgaaaca aatcggttca gttgaagtcc cgcaagaagc atttatggca   1800

atcttgaaaa tggacgaatc caaa                                          1824
```

<210> SEQ ID NO 96
<211> LENGTH: 1827
<212> TYPE: DNA
<213> ORGANISM: Listeria welshimeri

<400> SEQUENCE: 96

```
atgaacaaag aagaaatgaa tgcaagacaa aagaaaatta gaaacttttc gattatcgcg     60

cacatagatc atggtaaatc tacactcgct gatcggattt tagaacaaac tggtgcttta    120

acgcatcgtg aaatgaaaaa tcagctacta gattcgatgg atttagaacg tgaacgcggg    180

ataaccataa aattaaatgc tgtacaatta aaatataaag caaaagacgg ggaaacttat    240

atctttcatt taattgatac gcctgggcat gtcgatttta cctatgaagt atcaagaagt    300

ttagctgcat gtgagggagc aatccttgtt gtagatgctg cgcaaggaat tgaagcacaa    360

acccttgcca atgtttattt agcactagac aatgatttag aaatcttacc agtaataaat    420

aaaattgatt tgccagcagc tgacccagaa cgcgttcgtg cagaaattga agatgtcatt    480

ggtttagatg cttctgacgc tgtacttgct tctgcaaaat ctggtattgg tattgaagac    540

attctagaac aaattgttga aaaagttcct gagccatctg gtgatgtaaa taaaccacta    600

aaagcgctca ttttcgactc tgtttttgat gcgtatcgcg gtgttattgc caatattcgt    660

atcatggacg gcgttgtaaa ggctggcgac agaataaaaa tgatgtcgaa tggcaaagaa    720

tttgaagtga ccgaagtagg tgtttttca ccaaaggcaa caccgcgaga tgagctactt    780

gttggtgatg tagggtattt aacagcagcc atcaaaaatg ttggagatac tcgagttggt    840

gatactatca cacttgcgaa taatccagcg gaagaagcac tagatggtta tcgtaaatta    900

aatccaatgg tatattgtgg tctttatcca attgattctt ctaagtataa tgatttgcgt    960

gatgcacttg aaaagcttga actaaatgat tcggctttac aatttgaagc agaaacttct   1020
```

```
caagcattag gttttggatt ccgttgtggg ttcttagggt tgttacacat ggaaattatt   1080

caagaaagaa tcgagcgcga atttaatata gacttaatta ctactgcacc aagcgtaatc   1140

tatcatgtga atttgacaga tggatctaat attgtggttg ataatccagc agacatgcct   1200

gaacctggtg tcattgaaag tgtagaagag ccttatgtaa aagcaactgt tatggtgcca   1260

aatgattatg ttggtgcggt aatggaactt gcacaaaaca aacggggtaa cttcattacg   1320

atggagtacc tggatgatat tcgagtaagt attgtgtacg aaattccact atctgaaata   1380

gtatacgact tcttcgacca attaaaatca tctacaaaag gctatgcttc ttttgattat   1440

gaattaattg gctataaagc ttctaaactt gtgaaaatgg atattctatt gaacgcagaa   1500

aaagtcgatg ctttaagctt tattgttcat cgtgattttg cttacgagcg tggaaaaatt   1560

atcgtagaaa aactaaaaga acttattcct agacaacaat ttgaagtccc aattcaagca   1620

gcaattgcaa caaaaattgt ttctcgttcc actattaaag cacttcgtaa aaacgtactt   1680

gcaaaatgct atggtgggga tgtatcgcgt aaaagaaaac ttttagagaa acaaaaagaa   1740

ggtaaaaaac gaatgaaaca aattgggtca gttgaagttc ctcaagaagc cttcatggca   1800

atcttaaaaa tggatgaatc aaaataa                                        1827
```

<210> SEQ ID NO 97
<211> LENGTH: 1827
<212> TYPE: DNA
<213> ORGANISM: Listeria innocua

<400> SEQUENCE: 97

```
atgaacaaag aagaaatgaa tgcaagacaa aagaaaatta gaaacttttc gattatcgcg     60

cacatagatc atggtaaatc tacactcgct gatcggattt tagaacaaac aggtgctttg    120

acgcatcgtg aaatgaaaaa tcagctacta gattcgatgg atttagaacg tgaacgcggg    180

ataaccataa aattaaatgc tgtacaatta aaatataaag caaaagacgg agaaacgtat    240

atctttcatt taatcgatac accgggacac gtcgatttca cttatgaagt atctagaagt    300

ttagccgcat gtgaaggtgc tattttagta gtagacgctg cacaaggtat cgaagcgcaa    360

acactggcaa acgtttattt agctctagat aatgatttag aaattttacc tgtaattaat    420

aagattgatt tgccagcagc agatccagaa agagttcgtg ctgaaattga agatgttatt    480

ggcttggatg catcagatac tgtccttgct tctgcaaaat caggcatcgg gattgaagac    540

atccttgaac aaatagttga aaaagtacca gaaccatctg gtgacgttga taaaccactt    600

aaagcactta tttttgattc tgtttttgat gcgtatcgtg gcgtaatagc taatatccgt    660

attatggatg gtgttgtaaa agctggcgac agaattaaga tgatgtcaaa cggcaaagag    720

tttgaagtta cagaagttgg tgttttctct ccaaaagcaa caccacgtga tgagcttctt    780

gttggtgacg ttggttactt aacagctgca atcaaaaatg ttggagatac tcgagtgggt    840

gatacaatca cacttgcgaa caatcctgct gaagaagctc ttgacggata ccgcaaatta    900

aatccaatgg tttattgcgg actttatcca attgactctt ccaaatataa cgatttacgt    960

gatgcacttg aaaaattaga actcaatgat tcagctttac aatttgaagc agagacttct   1020

caagcattag gttttggatt ccgttgtgga tttttaggtc tactacacat ggaaattatt   1080

caagaaagaa ttgagcgcga atttaatatc gatttaatta ctacggcccc aagtgttatt   1140

taccacgtga atttaacaga tggatctaat attgtggtcg ataacccagc tgatatgcct   1200

gaacctggcg taattgaaag cgtggaagaa ccatacgtta aagcaactgt catggttcca   1260
```

aatgattatg ttggtgcggt aatggaactt gcacaaaaca aacgggggaa cttcattaca 1320
atggagtact tggatgatat tcgcgttagt attgtgtacg aaattccact atctgaaata 1380
gtttacgact tcttcgacca attaaaatct tctacaaaag gctatgcgtc ctttgattat 1440
gaattaattg gctataaagc ttctaaactt gtgaaaatgg atattctttt aaatgcagaa 1500
aaagtggatg cacttagctt tatcgttcac cgtgattttg cctacgagcg tggaaaaatc 1560
attgtcgaga aattaaaaga acttattcca agacaacaat ttgaagtacc tattcaagca 1620
gcaattgcaa caaaaattgt ttctcgttcc actattaaag ctctacgtaa aaacgtactt 1680
gctaaatgtt atggtgggga cgtatcgcgt aaacgaaaac tcttagagaa acaaaaagaa 1740
ggtaaaaaac gaatgaaaca aatcggttct gtggaagtgc cgcaagaagc tttcatggca 1800
atcttgaaaa tggacgaatc gaaataa 1827

<210> SEQ ID NO 98
<211> LENGTH: 1962
<212> TYPE: DNA
<213> ORGANISM: Mycobacterium bovis

<400> SEQUENCE: 98
tcacttcttg cctttgtccc cggcggcatc ggtggacaat gccgcgacga aagcctcctg 60
tggcacctcg acgcgcccga tggtcttcat ccgcttcttg ccttccttct gcttctccag 120
cagcttgcgt ttgcgcgtga tgtcgccgcc gtagcacttg gacaacacgt ccttgcggat 180
cgcgcggatg ttttcgcggg caatgatttt cgatccgatg gcggcctgca ccggcacctc 240
gaactgctgg cgcgggatca gctccttgag tttggtggtc atcttgttgc cgtaggcata 300
cgccgtgtcc ttgtgcacga tcgcgctgaa cgcatccacc gcctcgccct gcagcaggat 360
gtcgaccttg accagcgcgg cctcctgttc gccggcctcc tcgtagtcga ggctggcata 420
gccgcgggtg cgcgatttca gtgcgtcgaa gaagtcgaag atgatctcgc cgagcggcat 480
ggtgtagcgc agttccaccc gctcggggga gagatagtcc atgccgccca actcgccgcg 540
gcgcgactgg cacagctcca tgatggtgcc gatgaactcg ctgggcgcga tgatggtggt 600
cttgacgacg ggctcgtaga ccgtgcggat cttgccctcc ggccagtccg acggattggt 660
cacccggatt tcggtgccgt cgtctttgtg cacccgatac accacattgg gtgaggtcga 720
gatcaggtcc aggccgaact cgcgctcaag gcgctcacgg gtgatctcca tgtgcagcag 780
gcccaagaaa ccgcaccgga acccaaaacc cagcgccacc gaggtttccg gctcataggt 840
caaggccgcg tcgttgagct gcagcttgtc cagggcgtcg cgcaggttcg ggtagtccga 900
accgtcgacc ggatacaacc ccgagtagac catcggtttg ggctcacggt agccggtcaa 960
cgcttcggcg gcagccccgc gggcccggga gaggctggtc acggtgtcgc ccaccttgga 1020
ctggcggacg tccttgacgc cggtgatcag gtaacccacc tcgccgacac cgaggccctc 1080
acacggtttc ggctcgggtg agacgatgcc gacctcaagc agctcgtggg tggcgccggt 1140
ggacatcatc atgatgcgct cacgggggct gatcttgccg tcgacgacgc ggacgtaggt 1200
caccactccg cggtagatgt cgtaaacgga gtcgaaaatc attgcgcggg taggtgcctc 1260
ggcgtcgccc tgagggggcg gcacctgtcg gaccacctcg tcgagcaggt cggacacgcc 1320
ttcgccggtt ttgccggaca cccgcaacac ctcggccggc tcgcagccga tgatgtgtgc 1380
catctcggcg gcgtaacggt ccgggtcggc cgcgggcagg tcgatcttgt tgagcaccgg 1440
gatgatgtgc aggtcgcggt ccaacgccag gtagaggttc gccagcgtct gcgcctcgat 1500
gccttgcgcg gcatcgacca acagcaccgc accctcgcaa gcctccagcg cacgcgagac 1560

-continued

```
ttcgtaggtg aagtcgacat ggcccggggt gtcgatcaga tgcagcacgt agtcggtctt   1620

gtcgacccgc cagggtagcc gcacattctg ggccttgatg gtgatgccgc gttcccgctc   1680

gatgtccatc cgatccaagt actgggcccg catagagcgt tcgtcgacca ctccggtgag   1740

ctgcagcatc cggtcggcca acgttgactt gccgtggtcg atgtgggcga tgatgcaaaa   1800

gttcctaatc tgcgccggcg cagtgaaggt tttgtcggcg aaactgctga tgggaatctc   1860

ctggagcggg ggttgacggg tatccagggt atccgcgtcg ggcagctgcg acccaatcgc   1920

gctcggtcga tcgcgtctat gctgcgagca tggcgtccgc ac                      1962
```

<210> SEQ ID NO 99
<211> LENGTH: 1962
<212> TYPE: DNA
<213> ORGANISM: Mycobacterium bovis

<400> SEQUENCE: 99

```
tcacttcttg cctttgtccc cggcggcatc ggtggacaat gccgcgacga aagcctcctg     60

tggcacctcg acgcgcccga tggtcttcat ccgcttcttg ccttccttct gcttctccag    120

cagcttgcgt ttgcgcgtga tgtcgccgcc gtagcacttg gacaacacgt ccttgcggat    180

cgcgcggatg ttttcgcggg caatgatttt cgatccgatg gcggcctgca ccggcacctc    240

gaactgctgg cgcgggatca gctccttgag tttggtggtc atcttgttgc cgtaggcata    300

cgccgtgtcc ttgtgcacga tcgcgctgaa cgcatccacc gcctcgccct gcagcaggat    360

gtcgaccttg accagcgcgg cctcctgttc gccggcctcc tcgtagtcga ggctggcata    420

gccgcgggtg cgcgatttca gtgcgtcgaa gaagtcgaag atgatctcgc cgagcggcat    480

ggtgtagcgc agttccaccc gctcggggga gagatagtcc atgccgccca actcgccgcg    540

gcgcgactgg cacagctcca tgatggtgcc gatgaactcg ctgggcgcga tgatggtggt    600

cttgacgacg ggctcgtaga ccgtgcggat cttgccctcc ggccagtccg acggattggt    660

cacccggatt tcggtgccgt cgtctttgtg cacccgatac accacattgg gtgaggtcga    720

gatcaggtcc aggccgaact cgcgctcaag gcgctcacgg gtgatctcca tgtgcagcag    780

gcccaagaaa ccgcaccgga acccaaaacc cagcgccacc gaggtttccg gctcataggt    840

caaggccgcg tcgttgagct gcagcttgtc cagggcgtcg cgcaggttcg ggtagtccga    900

accgtcgacc ggatacaacc ccgagtagac catcggtttg ggctcacggt agccggtcaa    960

cgcttcggcg gcagccccgc gggcccggga gaggctggtc acggtgtcgc ccaccttgga   1020

ctggcggacg tccttgacgc cggtgatcag gtaacccacc tcgccgacac cgaggccctc   1080

acacggtttc ggctcgggtg agacgatgcc gacctcaagc agctcgtggg tggcgccggt   1140

ggacatcatc atgatgcgct cacgggggct gatcttgccg tcgacgacgc ggacgtaggt   1200

caccactccg cggtagatgt cgtaaacgga gtcgaaaatc attgcgcggg taggtgcctc   1260

ggcgtcgccc tgagggggcg gcacctgtcg gaccacctcg tcgagcaggt cggacacgcc   1320

ttcgccggtt ttgccggaca cccgcaacac ctcggccggc tcgcagccga tgatgtgtgc   1380

catctcggcg gcgtaacggt ccgggtcggc cgcgggcagg tcgatcttgt tgagcaccgg   1440

gatgatgtgc aggtcgcggt ccaacgccag gtagaggttc gccagcgtct gcgcctcgat   1500

gccttgcgcg gcatcgacca acagcaccgc accctcgcaa gcctccagcg cacgcgagac   1560

ttcgtaggtg aagtcgacat ggcccggggt gtcgatcaga tgcagcacgt agtcggtctt   1620

gtcgacccgc cagggtagcc gcacattctg ggccttgatg gtgatgccgc gttcccgctc   1680
```

```
gatgtccatc cgatccaagt actgggcccg catagagcgt tcgtcgacca ctccggtgag   1740

ctgcagcatc cggtcggcca acgttgactt gccgtggtcg atgtgggcga tgatgcaaaa   1800

gttcctaatc tgcgccggcg cagtgaaggt tttgtcggcg aaactgctga tgggaatctc   1860

ctggagcggg ggttgacggg tatccagggt atccgcgtcg ggcagctgcg acccaatcgc   1920

gctcggtcga tcgcgtctat gctgcgagca tggcgtccgc ac                      1962


<210> SEQ ID NO 100
<211> LENGTH: 1962
<212> TYPE: DNA
<213> ORGANISM: Mycobacterium tuberculosis

<400> SEQUENCE: 100

tcacttcttg cctttgtccc cggcggcatc ggtggacaat gccgcgacga aagcctcctg     60

tggcacctcg acgcgcccga tggtcttcat ccgcttcttg ccttccttct gcttctccag    120

cagcttgcgt ttgcgcgtga tgtcgccgcc gtagcacttg gacaacacgt ccttgcggat    180

cgcgcggatg ttttcgcggg caatgatttt cgatccgatg gcggcctgca ccggcacctc    240

gaactgctgg cgcgggatca gctccttgag tttggtggtc atcttgttgc cgtaggcata    300

cgccgtgtcc ttgtgcacga tcgcgctgaa cgcatccacc gcctcgccct gcagcaggat    360

gtcgaccttg accagcgcgg cctcctgttc gccggcctcc tcgtagtcga ggctggcata    420

gccgcgggtg cgcgatttca gtgcgtcgaa gaagtcgaag atgatctcgc cgagcggcat    480

ggtgtagcgc agttccaccc gctcggggga gagatagtcc atgccgccca actcgccgcg    540

gcgcgactgg cacagctcca tgatggtgcc gatgaactcg ctgggcgcga tgatggtggt    600

cttgacgacg ggctcgtaga ccgtgcggat cttgccctcc ggccagtccg acggattggt    660

cacccggatt tcggtgccgt cgtctttgtg cacccgatac accacattgg gtgaggtcga    720

gatcaggtcc aggccgaact cgcgctcaag gcgctcacgg gtgatctcca tgtgcagcag    780

gcccaagaaa ccgcaccgga acccaaaacc cagcgccacc gaggtttccg gctcataggt    840

caaggccgcg tcgttgagct gcagcttgtc cagggcgtcg cgcaggttcg ggtagtccga    900

accgtcgacc ggatacaacc ccgagtagac catcggtttg ggctcacggt agccggtcaa    960

cgcttcggcg gcagccccgc gggcccggga gaggctggtc acggtgtcgc ccaccttgga   1020

ctggcggacg tccttgacgc cggtgatcag gtaacccacc tcgccgacac cgaggccctc   1080

acacggtttc ggctcgggtg agacgatgcc gacctcaagc agctcgtggg tggcgccggt   1140

ggacatcatc atgatgcgct cacgggggct gatcttgccg tcgacgacgc ggacgtaggt   1200

caccactccg cggtagatgt cgtaaacgga gtcgaaaatc attgcgcggg taggtgcctc   1260

ggcgtcgccc tgagggggcg gcacctgtcg gaccacctcg tcgagcaggt cggacacgcc   1320

ttcgccggtt ttgccggaca cccgcaacac ctcggccggc tcgcagccga tgatgtgtgc   1380

catctcggcg gcgtaacggt ccgggtcggc cgcgggcagg tcgatcttgt tgagcaccgg   1440

gatgatgtgc aggtcgcggt ccaacgccag gtagaggttc gccagcgtct gcgcctcgat   1500

gccttgcgcg gcatcgacca acagcaccgc accctcgcaa gcctccagcg cacgcgagac   1560

ttcgtaggtg aagtcgacat ggcccggggt gtcgatcaga tgcagcacgt agtcggtctt   1620

gtcgacccgc cagggtagcc gcacattctg ggccttgatg gtgatgccgc gttcccgctc   1680

gatgtccatc cgatccaagt actgggcccg catagagcgt tcgtcgacca cgccggtgag   1740

ctgcagcatc cggtcggcca acgttgactt gccgtggtcg atgtgggcga tgatgcaaaa   1800

gttcctaatc tgcgccggcg cagtgaaggt tttgtcggcg aaactgctga tgggaatctc   1860
```

-continued

```
ctggagcggg ggttgacggg tatccagggt atccgcgtcg ggcagctgcg acccaatcgc   1920

gctcggtcga tcgcgtctat gctgcgagca tggcgtccgc ac                      1962


<210> SEQ ID NO 101
<211> LENGTH: 1971
<212> TYPE: DNA
<213> ORGANISM: Mycobacterium tuberculosis

<400> SEQUENCE: 101

tcacttcttg cctttgtccc cggcggcatc ggtggacaat gccgcgacga aagcctcctg     60

tggcacctcg acgcgcccga tggtcttcat ccgcttcttg ccttccttct gcttctccag    120

cagcttgcgt ttgcgcgtga tgtcgccgcc gtagcacttg gacaacacgt ccttgcggat    180

cgcgcggatg ttttcgcggg caatgatttt cgatccgatg gcggcctgca ccggcacctc    240

gaactgctgg cgcgggatca gctccttgag tttggtggtc atcttgttgc cgtaggcata    300

cgccgtgtcc ttgtgcacga tcgcgctgaa cgcatccacc gcctcgccct gcagcaggat    360

gtcgaccttg accagcgcgg cctcctgttc gccggcctcc tcgtagtcga ggctggcata    420

gccgcgggtg cgcgatttca gtgcgtcgaa gaagtcgaag atgatctcgc cgagcggcat    480

ggtgtagcgc agttccaccc gctcggggga gagatagtcc atgccgccca actcgccgcg    540

gcgcgactgg cacagctcca tgatggtgcc gatgaactcg ctgggcgcga tgatggtggt    600

cttgacgacg ggctcgtaga ccgtgcggat cttgccctcc ggccagtccg acggattggt    660

cacccggatt tcggtgccgt cgtctttgtg cacccgatac accacattgg gtgaggtcga    720

gatcaggtcc aggccgaact cgcgctcaag gcgctcacgg gtgatctcca tgtgcagcag    780

gcccaagaaa ccgcaccgga acccaaaacc cagcgccacc gaggtttccg gctcataggt    840

caaggccgcg tcgttgagct gcagcttgtc cagggcgtcg cgcaggttcg ggtagtccga    900

accgtcgacc ggatacaacc ccgagtagac catcggtttg ggctcacggt agccggtcaa    960

cgcttcggcg gcagccccgc gggcccggga gaggctggtc acggtgtcgc ccaccttgga   1020

ctggcggacg tccttgacgc cggtgatcag gtaacccacc tcgccgacac cgaggccctc   1080

acacggtttc ggctcgggtg agacgatgcc gacctcaagc agctcgtggg tggcgccggt   1140

ggacatcatc atgatgcgct cacgggggct gatcttgccg tcgacgacgc ggacgtaggt   1200

caccactccg cggtagatgt cgtaaacgga gtcgaaaatc attgcgcggg taggtgcctc   1260

ggcgtcgccc tgagggggcg gcacctgtcg gaccacctcg tcgagcaggt cggacacgcc   1320

ttcgccggtt ttgccggaca cccgcaacac ctcggccggc tcgcagccga tgatgtgtgc   1380

catctcggcg gcgtaacggt ccgggtcggc cgcgggcagg tcgatcttgt tgagcaccgg   1440

gatgatgtgc aggtcgcggt ccaacgccag gtagaggttc gccagcgtct gcgcctcgat   1500

gccttgcgcg gcatcgacca acagcaccgc accctcgcaa gcctccagcg cacgcgagac   1560

ttcgtaggtg aagtcgacat ggcccggggt gtcgatcaga tgcagcacgt agtcggtctt   1620

gtcgacccgc cagggtagcc gcacattctg ggccttgatg gtgatgccgc gttcccgctc   1680

gatgtccatc cgatccaagt actgggcccg catagagcgt tcgtcgacca cgccggtgag   1740

ctgcagcatc cggtcggcca acgttgactt gccgtggtcg atgtgggcga tgatgcaaaa   1800

gttcctaatc tgcgccggcg cagtgaaggt tttgtcggcg aaactgctga tgggaatctc   1860

ctggagcggg ggttgacggg tatccagggt atccgcgtcg ggcagctgcg acccaatcgc   1920

gctcggtcga tcgcgtctat gctgcgagca tggcgtccgc acggaagtca c            1971
```

<210> SEQ ID NO 102
<211> LENGTH: 1962
<212> TYPE: DNA
<213> ORGANISM: Mycobacterium tuberculosis

<400> SEQUENCE: 102
tcacttcttg cctttgtccc cggcggcatc ggtggacaat gccgcgacga aagcctcctg 60
tggcacctcg acgcgcccga tggtcttcat ccgcttcttg ccttccttct gcttctccag 120
cagcttgcgt ttgcgcgtga tgtcgccgcc gtagcacttg gacaacacgt ccttgcggat 180
cgcgcggatg ttttcgcggg caatgatttt cgatccgatg gcggcctgca ccggcacctc 240
gaactgctgg cgcgggatca gctccttgag tttggtggtc atcttgttgc cgtaggcata 300
cgccgtgtcc ttgtgcacga tcgcgctgaa cgcatccacc gcctcgccct gcagcaggat 360
gtcgaccttg accagcgcgg cctcctgttc gccggcctcc tcgtagtcga ggctggcata 420
gccgcgggtg cgcgatttca gtgcgtcgaa gaagtcgaag atgatctcgc cgagcggcat 480
ggtgtagcgc agttccaccc gctcggggga gagatagtcc atgccgccca actcgccgcg 540
gcgcgactgg cacagctcca tgatggtgcc gatgaactcg ctgggcgcga tgatggtggt 600
cttgacgacg ggctcgtaga ccgtgcggat cttgccctcc ggccagtccg acggattggt 660
cacccggatt tcggtgccgt cgtctttgtg cacccgatac accacattgg gtgaggtcga 720
gatcaggtcc aggccgaact cgcgctcaag gcgctcacgg gtgatctcca tgtgcagcag 780
gcccaagaaa ccgcaccgga acccaaaacc cagcgccacc gaggtttccg gctcataggt 840
caaggccgcg tcgttgagct gcagcttgtc cagggcgtcg cgcaggttcg ggtagtccga 900
accgtcgacc ggatacaacc ccgagtagac catcggtttg ggctcacggt agccggtcaa 960
cgcttcggcg gcagccccgc gggcccggga gaggctggtc acggtgtcgc ccaccttgga 1020
ctggcggacg tccttgacgc cggtgatcag gtaacccacc tcgccgacac cgaggccctc 1080
acacggtttc ggctcgggtg agacgatgcc gacctcaagc agctcgtggg tggcgccggt 1140
ggacatcatc atgatgcgct cacgggggct gatcttgccg tcgacgacgc ggacgtaggt 1200
caccactccg cggtagatgt cgtaaacgga gtcgaaaatc attgcgcggg taggtgcctc 1260
ggcgtcgccc tgagggggcg gcacctgtcg gaccacctcg tcgagcaggt cggacacgcc 1320
ttcgccggtt ttgccggaca cccgcaacac ctcggccggc tcgcagccga tgatgtgtgc 1380
catctcggcg gcgtaacggt ccgggtcggc cgcgggcagg tcgatcttgt tgagcaccgg 1440
gatgatgtgc aggtcgcggt ccaacgccag gtagaggttc gccagcgtct gcgcctcgat 1500
gccttgcgcg gcatcgacca acagcaccgc accctcgcaa gcctccagcg cacgcgagac 1560
ttcgtaggtg aagtcgacat ggcccggggt gtcgatcaga tgcagcacgt agtcggtctt 1620
gtcgacccgc cagggtagcc gcacattctg ggccttgatg gtgatgccgc gttcccgctc 1680
gatgtccatc cgatccaagt actgggcccg catagagcgt tcgtcgacca cgccggtgag 1740
ctgcagcatc cggtcggcca acgttgactt gccgtggtcg atgtgggcga tgatgcaaaa 1800
gttcctaatc tgcgccggcg cagtgaaggt tttgtcggcg aaactgctga tgggaatctc 1860
ctggagcggg ggttgacggg tatccagggt atccgcgtcg ggcagctgcg acccaatcgc 1920
gctcggtcga tcgcgtctat gctgcgagca tggcgtccgc ac 1962

<210> SEQ ID NO 103
<211> LENGTH: 1962
<212> TYPE: DNA
<213> ORGANISM: Mycobacterium tuberculosis

<400> SEQUENCE: 103

```
tcacttcttg cctttgtccc cggcggcatc ggtggacaat gccgcgacga aagcctcctg      60
tggcacctcg acgcgcccga tggtcttcat ccgcttcttg ccttccttct gcttctccag     120
cagcttgcgt ttgcgcgtga tgtcgccgcc gtagcacttg gacaacacgt ccttgcggat     180
cgcgcggatg ttttcgcggg caatgatttt cgatccgatg gcggcctgca ccggcacctc     240
gaactgctgg cgcgggatca gctccttgag tttggtggtc atcttgttgc cgtaggcata     300
cgccgtgtcc ttgtgcacga tcgcgctgaa cgcatccacc gcctcgccct gcagcaggat     360
gtcgaccttg accagcgcgg cctcctgttc gccggcctcc tcgtagtcga ggctggcata     420
gccgcgggtg cgcgatttca gtgcgtcgaa gaagtcgaag atgatctcgc cgagcggcat     480
ggtgtagcgc agttccaccc gctcggggga gagatagtcc atgccgccca actcgccgcg     540
gcgcgactgg cacagctcca tgatggtgcc gatgaactcg ctgggcgcga tgatggtggt     600
cttgacgacg ggctcgtaga ccgtgcggat cttgccctcc ggccagtccg acggattggt     660
cacccggatt tcggtgccgt cgtctttgtg cacccgatac accacattgg gtgaggtcga     720
gatcaggtcc aggccgaact cgcgctcaag gcgctcacgg gtgatctcca tgtgcagcag     780
gcccaagaaa ccgcaccgga acccaaaacc cagcgccacc gaggtttccg gctcataggt     840
caaggccgcg tcgttgagct gcagcttgtc cagggcgtcg cgcaggttcg ggtagtccga     900
accgtcgacc ggatacaacc ccgagtagac catcggtttg ggctcacggt agccggtcaa     960
cgcttcggcg gcagccccgc gggcccggga gaggctggtc acggtgtcgc ccaccttgga    1020
ctggcggacg tccttgacgc cggtgatcag gtaacccacc tcgccgacac cgaggccctc    1080
acacggtttc ggctcgggtg agacgatgcc gacctcaagc agctcgtggg tggcgccggt    1140
ggacatcatc atgatgcgct cacgggggct gatcttgccg tcgacgacgc ggacgtaggt    1200
caccactccg cggtagatgt cgtaaacgga gtcgaaaatc attgcgcggg taggtgcctc    1260
ggcgtcgccc tgagggggcg gcacctgtcg gaccacctcg tcgagcaggt cggacacgcc    1320
ttcgccggtt ttgccggaca cccgcaacac ctcggccggc tcgcagccga tgatgtgtgc    1380
catctcggcg gcgtaacggt ccgggtcggc cgcgggcagg tcgatcttgt tgagcaccgg    1440
gatgatgtgc aggtcgcggt ccaacgccag gtagaggttc gccagcgtct gcgcctcgat    1500
gccttgcgcg gcatcgacca acagcaccgc accctcgcaa gcctccagcg cacgcgagac    1560
ttcgtaggtg aagtcgacat ggcccggggt gtcgatcaga tgcagcacgt agtcggtctt    1620
gtcgacccgc cagggtagcc gcacattctg ggccttgatg gtgatgccgc gttcccgctc    1680
gatgtccatc cgatccaagt actgggcccg catagagcgt tcgtcgacca cgccggtgag    1740
ctgcagcatc cggtcggcca acgttgactt gccgtggtcg atgtgggcga tgatgcaaaa    1800
gttcctaatc tgcgccggcg cagtgaaggt tttgtcggcg aaactgctga tgggaatctc    1860
ctggagcggg ggttgacggg tatccagggt atccgcgtcg ggcagctgcg acccaatcgc    1920
gctcggtcga tcgcgtctat gctgcgagca tggcgtccgc ac                       1962
```

<210> SEQ ID NO 104
<211> LENGTH: 1962
<212> TYPE: DNA
<213> ORGANISM: Mycobacterium tuberculosis

<400> SEQUENCE: 104

```
tcacttcttg cctttgtccc cggcggcatc ggtggacaat gccgcgacga aagcctcctg      60
```

```
tggcacctcg acgcgcccga tggtcttcat ccgcttcttg ccttccttct gcttctccag    120
cagcttgcgt ttgcgcgtga tgtcgccgcc gtagcacttg gacaacacgt ccttgcggat    180
cgcgcggatg ttttcgcggg caatgatttt cgatccgatg gcggcctgca ccggcacctc    240
gaactgctgg cgcgggatca gctccttgag tttggtggtc atcttgttgc cgtaggcata    300
cgccgtgtcc ttgtgcacga tcgcgctgaa cgcatccacc gcctcgccct gcagcaggat    360
gtcgaccttg accagcgcgg cctcctgttc gccggcctcc tcgtagtcga ggctggcata    420
gccgcgggtg cgcgatttca gtgcgtcgaa gaagtcgaag atgatctcgc cgagcggcat    480
ggtgtagcgc agttccaccc gctcggggga gagatagtcc atgccgccca actcgccgcg    540
gcgcgactgg cacagctcca tgatggtgcc gatgaactcg ctgggcgcga tgatggtggt    600
cttgacgacg ggctcgtaga ccgtgcggat cttgccctcc ggccagtccg acggattggt    660
cacccggatt tcggtgccgt cgtctttgtg cacccgatac accacattgg gtgaggtcga    720
gatcaggtcc aggccgaact cgcgctcaag gcgctcacgg gtgatctcca tgtgcagcag    780
gcccaagaaa ccgcaccgga acccaaaacc cagcgccacc gaggtttccg gctcataggt    840
caaggccgcg tcgttgagct gcagcttgtc cagggcgtcg cgcaggttcg ggtagtccga    900
accgtcgacc ggatacaacc ccgagtagac catcggtttg ggctcacggt agccggtcaa    960
cgcttcggcg gcagccccgc gggcccggga gaggctggtc acggtgtcgc ccaccttgga   1020
ctggcggacg tccttgacgc cggtgatcag gtaacccacc tcgccgacac cgaggccctc   1080
acacggtttc ggctcgggtg agacgatgcc gacctcaagc agctcgtggg tggcgccggt   1140
ggacatcatc atgatgcgct cacgggggct gatcttgccg tcgacgacgc ggacgtaggt   1200
caccactccg cggtagatgt cgtaaacgga gtcgaaaatc attgcgcggg taggtgcctc   1260
ggcgtcgccc tgagggggcg gcacctgtcg gaccacctcg tcgagcaggt cggacacgcc   1320
ttcgccggtt ttgccggaca cccgcaacac ctcggccggc tcgcagccga tgatgtgtgc   1380
catctcggcg gcgtaacggt ccgggtcggc cgcgggcagg tcgatcttgt tgagcaccgg   1440
gatgatgtgc aggtcgcggt ccaacgccag gtagaggttc gccagcgtct gcgcctcgat   1500
gccttgcgcg gcatcgacca acagcaccgc accctcgcaa gcctccagcg cacgcgagac   1560
ttcgtaggtg aagtcgacat ggcccggggt gtcgatcaga tgcagcacgt agtcggtctt   1620
gtcgacccgc cagggtagcc gcacattctg ggccttgatg gtgatgccgc gttcccgctc   1680
gatgtccatc cgatccaagt actgggcccg catagagcgt tcgtcgacca cgccggtgag   1740
ctgcagcatc cggtcggcca acgttgactt gccgtggtcg atgtgggcga tgatgcaaaa   1800
gttcctaatc tgcgccggcg cagtgaaggt tttgtcggcg aaactgctga tgggaatctc   1860
ctggagcggg ggttgacggg tatccagggt atccgcgtcg ggcagctgcg acccaatcgc   1920
gctcggtcga tcgcgtctat gctgcgagca tggcgtccgc ac                      1962
```

<210> SEQ ID NO 105
<211> LENGTH: 1962
<212> TYPE: DNA
<213> ORGANISM: Mycobacterium tuberculosis

<400> SEQUENCE: 105

```
tcacttcttg cctttgtccc cggcggcatc ggtggacaat gccgcgacga aagcctcctg     60
tggcacctcg acgcgcccga tggtcttcat ccgcttcttg ccttccttct gcttctccag    120
cagcttgcgt ttgcgcgtga tgtcgccgcc gtagcacttg gacaacacgt ccttgcggat    180
cgcgcggatg ttttcgcggg caatgatttt cgatccgatg gcggcctgca ccggcacctc    240
```

```
gaactgctgg cgcgggatca gctccttgag tttggtggtc atcttgttgc cgtaggcata    300
cgccgtgtcc ttgtgcacga tcgcgctgaa cgcatccacc gcctcgccct gcagcaggat    360
gtcgaccttg accagcgcgg cctcctgttc gccggcctcc tcgtagtcga ggctggcata    420
gccgcgggtg cgcgatttca gtgcgtcgaa gaagtcgaag atgatctcgc cgagcggcat    480
ggtgtagcgc agttccaccc gctcggggga gagatagtcc atgccgccca actcgccgcg    540
gcgcgactgg cacagctcca tgatggtgcc gatgaactcg ctgggcgcga tgatggtggt    600
cttgacgacg ggctcgtaga ccgtgcggat cttgccctcc ggccagtccg acggattggt    660
cacccggatt tcggtgccgt cgtctttgtg cacccgatac accacattgg gtgaggtcga    720
gatcaggtcc aggccgaact cgcgctcaag gcgctcacgg gtgatctcca tgtgcagcag    780
gcccaagaaa ccgcaccgga acccaaaacc cagcgccacc gaggtttccg gctcataggt    840
caaggccgcg tcgttgagct gcagcttgtc cagggcgtcg cgcaggttcg ggtagtccga    900
accgtcgacc ggatacaacc ccgagtagac catcggtttg ggctcacggt agccggtcaa    960
cgcttcggcg gcagccccgc gggcccggga gaggctggtc acggtgtcgc ccaccttgga   1020
ctggcggacg tccttgacgc cggtgatcag gtaacccacc tcgccgacac cgaggccctc   1080
acacggtttc ggctcgggtg agacgatgcc gacctcaagc agctcgtggg tggcgccggt   1140
ggacatcatc atgatgcgct cacgggggct gatcttgccg tcgacgacgc ggacgtaggt   1200
caccactccg cggtagatgt cgtaaacgga gtcgaaaatc attgcgcggg taggtgcctc   1260
ggcgtcgccc tgagggggcg gcacctgtcg gaccacctcg tcgagcaggt cggacacgcc   1320
ttcgccggtt ttgccggaca cccgcaacac ctcggccggc tcgcagccga tgatgtgtgc   1380
catctcggcg gcgtaacggt ccgggtcggc cgcgggcagg tcgatcttgt tgagcaccgg   1440
gatgatgtgc aggtcgcggt ccaacgccag gtagaggttc gccagcgtct gcgcctcgat   1500
gccttgcgcg gcatcgacca acagcaccgc accctcgcaa gcctccagcg cacgcgagac   1560
ttcgtaggtg aagtcgacat ggcccggggt gtcgatcaga tgcagcacgt agtcggtctt   1620
gtcgacccgc cagggtagcc gcacattctg ggccttgatg gtgatgccgc gttcccgctc   1680
gatgtccatc cgatccaagt actgggcccg catagagcgt tcgtcgacca cgccggtgag   1740
ctgcagcatc cggtcggcca acgttgactt gccgtggtcg atgtgggcga tgatgcaaaa   1800
gttcctaatc tgcgccggcg cagtgaaggt tttgtcggcg aaactgctga tgggaatctc   1860
ctggagcggg ggttgacggg tatccagggt atccgcgtcg ggcagctgcg acccaatcgc   1920
gctcggtcga tcgcgtctat gctgcgagca tggcgtccgc ac                      1962
```

<210> SEQ ID NO 106
<211> LENGTH: 1983
<212> TYPE: DNA
<213> ORGANISM: Mycobacterium avium

<400> SEQUENCE: 106

```
ttacttcttg gatttgtcgc ccgcggcgtc ggcggacagc gcggcgacga acgcctcctg     60
cggcacgtcg acccggccga tggtcttcat ccgcttcttg ccctccttct gcttttccag    120
aagtttgcgc ttgcgggtga tgtcaccgcc gtaacacttg gacagcacgt ccttgcggat    180
ggcccgaatg ttctcgcggg caatgatttt cgagccgatc gcggcctgga cgggcacctc    240
gaactgctgg cgcgggatca gctccttgag cttggtggtc atcttgttgc cgtacgcgaa    300
cgccgcatcc ttgtgcacga tcgcgctgaa cgcgtcgacg gcctccccct gcaacaggat    360
```

gtccaccttg accagctggg cctcctgctc gccggcctcc tcgtagtcca ggctggcgta 420
gccgcgggtc cgcgacttca gcgagtcgaa gaagtcgaag atgatctcgc ccaacggcat 480
ggtgtagcgc agctcaaccc gttccggcga caggtaatcc atgccgccca gctcgccgcg 540
gcgggactgg cacagctcca tgatggtgcc gatgaattcg ctgggcgcga tgatggtggt 600
cttgaccacc ggctcgtaca ccgtgcgcac cttgccctcg ggccagtccg acgggttggt 660
caccacgatc tcggtgccgt cctctttgat cacccggtac accacgttgg gcgacgtcga 720
gatcaggtcg aggtcgaact cgcgctccag gcgctcgcgg gtgatctcca tgtgcagcaa 780
acccaaaaag ccacaacgga atccgcagcc cagcgccacc gatgtctccg gttcgtaggt 840
gagcgcggcg tcgttgagcc gcagccggtc cagcgcgtcg cgcagatccg gatagtccga 900
gccgtccacc ggatacagac ccgaatagac catcggcttg ggttcgcggt atccggtcag 960
cgcctcttgc gcgccgtggc gcgcgctggt gacggtgtcg cccactttgg actggcggac 1020
gtccttcacc ccggtgatca ggtagcccac ctcgccgacg ccaaggccgt cgctggcctt 1080
cggctcgggt gagacgatgc cgacctcgag cagttcgtgg gtggcgccgg tggacatcat 1140
cgcgatgcgt tcgcgcgggg tgatcttgcc gtcgaccacc cgcacgtagg tcaccacgcc 1200
gcggtagatg tcgtagaccg agtcgaagat catcgcgcgc agcggcgcat cggcctgccc 1260
ctgcggcggc ggcacctggc gcaccacctc gtcgagcagc cgcgccacgc cctccccggt 1320
tttgccggac acccacagca cgtcgtcggg ttcgcacccg atgatgtggg cgagctcgcc 1380
ggcgtagcga tccgggtcgg cggccggcag gtcgatcttg ttgaggaccg ggatgatggt 1440
cagatcgcgg tccagcgcca ggtagaggtt ggccagcgtc tgggcctcga tgccctgcgc 1500
ggcgtcgacc agcagcacgg caccttcgca ggcctccagt gcgcgcgaca cctcgtaggt 1560
gaagtcgacg tggcccgggg tgtcgatcag gtgcaggaca aattctttgc cggcgtcctc 1620
gccgccggag acctgccagg gcagccgcac gttctgcgcc ttgatggtga tgccgcgctc 1680
ccgctcgatg tccatccggt ccaggtactg ggcgcgcatc gaccgctcgt cgacgacgcc 1740
ggtgagctgc agcatccggt cggccagcgt cgacttgccg tgatcgatgt gggcgatgat 1800
gcagaagttg cgaatctgcg ccggcgcggt gaaggtcttg tcggcgaaac tgctgatggg 1860
tatctcctgg tccgggcctg ctagacggcg gttcgcaagt gtgtccagcg tatcggcgcg 1920
gccggactgc ggcacaatcg gcgcgtctat gctgcgaata tggcgtccgg ccggaagtcg 1980
cag 1983

<210> SEQ ID NO 107
<211> LENGTH: 1941
<212> TYPE: DNA
<213> ORGANISM: Mycobacterium leprae

<400> SEQUENCE: 107
ttatttcttg tccttgtctc ctgcggcatc ggcggacaac gcggcgacaa acgcttcctg 60
cggcacctcg acccgcccaa tggtcttcat ccgtttcttg ccttccttct gcttttccag 120
aagcttacgt ttgcgggtga tatcgccgcc ataacatttc gacagcacat ccttgcgtat 180
cgccctaata ttttcgcgcg caatgacttt cgatccaata gccgcctgta ctggcacctc 240
aaactgctga cgtgggatca gttctttgag cttgttggtc atcttgttgc cataggcaga 300
ggctgaatcc ttgtgcacaa tcgcgctgaa tgcgtcgacg gcctcgcctt gcagcaggat 360
gtcaaccttg accagttggg cctcctgctc gccagcctcc tcatagtcga ggctagcgta 420
gccccgggtg cgtgacttca gcgaatcgaa gaaatcgaag atgatttccc cgagcggcat 480
aatgtagcgt aactcgactc gctcaggtga aagatagtcc atgccaccta attcgccacg 540
gcgcgactgg cacagctcca tgatcgttcc gatgaactcg ctgggcgcaa tgatggtgat 600
cttcaccact ggctcgtaca ccgttcggat cttgccctcc ggccagtctg acgggttggt 660
caccacaatc tcggtgttat cttctgtcac cacacggtat acgacgttgg gcgacgtgga 720
gatcaggtcc aggtcgaact cgcgctctaa gcgttcgcgg gttatatcta tgtgcagcaa 780
accgaggaag ccgcaccggt acccaacgcc cagcgccacc gatgtttccg gctcgtaggt 840
cagcgccgcg tcgttgagct gtaacttacc tagagcgtca cgcaaactcg ggtagtccga 900
actgtcgacg ggatacagcc cggagtacac catgggcttg ggttctcggt agccagttaa 960
cggttcagtg gcaccataac gaaccgtcgt tacagtgtcg ccgactttgg attggcggac 1020
gtctttaacc ccagtaatca ggtagcccac ctcccccacg cccaggcccg cgctggcctt 1080
cggttcaggc gacacgatgc cgacctcgag cagttcgtac gtcgcaccgg tggacatcat 1140
cgcgatgcgc tcacgcgggc tgatcttgcc gtcgaccaca cggacgtagg tgaccacgcc 1200
tcggtagatg tcgtagacgg agtcgaagat catcgcgcgg gtaggcgcat cagggtcacc 1260
ttgcggatgc ggcacccgac ggaccacctc gtcaagaagg tcagaaaccc cctcgccggt 1320
tttgccggac acccgaagca catcgcctga ctcataacca atgatgtggg cgatctcagc 1380
ggcgtaacgg tccggatcgg cagccggcag gtcgattttg tttagcaccg gaataatcgt 1440
caagtcacgc tccagagcga gatagagatt ggccaaggtc tgagcttcga tgccctggac 1500
ggcgtctacc agcagcaccg caccctcaca ggcttccaat gctcgcgata cctcgtaggt 1560
gaagtccaca tggccggggg tgtcgatcaa gtgcaacaca taattctcag tcgtcccacc 1620
agctgtgaca ctccaagaca gccgcacgtt ctgcgcttta atcgtgattc cgcgctcacg 1680
ttcgatgtcc atccggtcca ggtactgggc acgcatcgac cgctcatcga cgacaccagt 1740
cagctgaagc atccggtccg ccagcgtgga tttgccgtga tcaatatgag cgattatgca 1800
gaagttccta atctgcgccg gcgcggtaaa ggtcttgtca gcgaaactgc tgatgggaat 1860
ctcctgggct ccagttacta gagaatgttt gaacggcgat tcgccggtgt ccggcttatc 1920
cacgcgaagt gaccaagaca c 1941

<210> SEQ ID NO 108
<211> LENGTH: 1896
<212> TYPE: DNA
<213> ORGANISM: Mycobacterium smegmatis

<400> SEQUENCE: 108
ctacttcttg ggcttgtcgc ccgccgcgtc ggtggacagc gccgcgacga atgcctcctg 60
cggcacgtcg acccggccga tcgtcttcat gcgcttcttg ccctctttct gcttctcgag 120
cagcttgcgc ttacgggtga tgtcaccgcc gtagcacttc gagagcacgt ccttgcggat 180
ggcccggatg ttttcgcgcg caatgattct cgagccgatc gcggcctgca ccgggacctc 240
gaactgctgt cgcgggatca gttctttgag cttggaggtc atcttgttgc cgtaggccga 300
cgcaccgtcc ttgtggacga tagccgagaa cgcgtcgacg gcctcgccct gcagcaggat 360
gtcgaccttg accagatcgg cctcctgctc accggcctcc tcgtagtcga ggctcgcgta 420
gccgcgggtg cgggacttca gcgagtcgaa gaagtcgaag atgatctcgc ccaacggcat 480
gatgtagcgc agttcgacac gctcgggcga caggtagtcc atgccctgca gttcgccgcg 540
acgggactgg cacagctcca tgatggtgcc gatgaactcg ctgggcgcga tgatcgtggt 600
cttcacgacg ggctcgaaca ccgtgcggat cttgccttcc ggccagtccg acgggttcgt 660
cacgaccttc tcggaaccgt cgtcctgcac gacgcggtac accacgttgg gtgaggtgga 720
gatcaggtcc aggccgaact cgcgctccag gcgttcacgg gtgatctcca tgtgcagcag 780
tccgaggaag ccgcagcgga acccgaagcc cagggccacc gaggtctccg gctcatacgt 840
cagtgcggcg tcgttgagtt gcagcttgtc cagcgcgtca cgcagatccg ggtagtccga 900
accgtcgacg ggatacaggc ccgagtacac catcggcttg ggctcgcgat aacccgtgag 960
cgcctcggtc gcgcccttgc gcgccgtggt caccgtgtca ccgaccttcg actggcggac 1020
gtccttcaca cccgtgatca ggtaaccgac ctcaccgacg cccaggcccg cactggcctt 1080
cggttccggt gagacgatgc cgacctcgag cagttcatgg gtggcgccgg tggacatcat 1140
cgcgatgcgt tcgcgcggca cgatcttgcc gtcgaccaca cggacgtagg tcaccacgcc 1200
gcggtagatg tcgtacacgg agtcgaagat catcgcgcgc gtcggggcgt cggggtcacc 1260
gaccggcggc ggcaccttac gcaccacctc gtcgagcagc tcggccacgc cttcgccggt 1320
cttgcccgag acacgcagca cgtccgacgg ctcacacccg atgatgtggg cgagctcgtc 1380
ggcatagcgg tccgggtcag cggcgggcag gtcgatcttg ttgagcaccg ggatgatcgc 1440
caggtcgcgg tccagcgcca ggtacaggtt ggccagcgtc tgcgcctcga tgccctgcgc 1500
cgcgtcgacc agcagcaccg cgccctcgca ggcctccagc gcgcgcgaca cctcgtaggt 1560
gaagtcgacg tggcccgggg tgtcgatcag gtgcagcacg taatcacccg cgtccgcgcc 1620
gtcttggccg tccttcagcg tccacggaag ccggacgttc tgagccttga tggtgatccc 1680
gcgctcacgt tcgatgtcca tgcggtcgag gtactgggcc cgcatcgacc gctcatcgac 1740
aacaccggtg agctgcagca tccggtcggc cagcgtcgac ttgccgtggt cgatgtgggc 1800
gatgatgcag aagttccgaa tctgcgccgg cgcagtgaac gtcttgtcgg cgaagctgct 1860
gatgggaatc tcctggtgag cgtgggtcaa gcgcac 1896

<210> SEQ ID NO 109
<211> LENGTH: 1740
<212> TYPE: DNA
<213> ORGANISM: Mycobacterium ulcerans

<400> SEQUENCE: 109
ctacttcttg cccttatccc ccgcggcgtc ggtggacagt gccgcgacaa acgcctcctg 60
cggcacctcg acccggccga tggacttcat ccgcttcttg ccctctttct gcttttccag 120
cagcttgcgt ttgcgggtga tgtcaccgcc gtagcacttc gacaacacat ccttgaggat 180
cgcgcggatg ttctcgcgcg cgatgatctt ggaaccgatg gccgcctgca ccggcacctc 240
gaactgctga cgcggaatca gctccttgag cttggtggtc atcttgttgc cgtaggcgaa 300
cgccgaatcc ttgtggacga tagcgctgaa cgcatcgacg gcctcgcctt gcagcaggat 360
gtcgaccttg accagttggg cttcctgctc gccggactcc tcgtaatcga gactggcgta 420
gccacgggtc cgcgatatga gcgagtcgaa gaagtcaaag atgatctccc ccaacggcat 480
tgtgtatcgc agttccaccc gttcgggcga caaatagtcc atgcccccca gctcgccgcg 540
ccgcgactgg cacagctcca tgatggtgcc gatgaattcg ctgggcgcga tgatggtggt 600
cttcaccacc ggctcgtaga cggtgcggat cttgccctcg ggccagtccg acgggttggt 660
cacctgcatt tcggtgccgt cgtccttgat gacgcggtac acgacgttgg gcgaggtcga 720
gatcaggtcg aggtcgaact cgcgctccag acgttcccga ctgatctcca tgtgcagcag 780
gcccaggaag ccgcaccgga atccgaaacc cagcgccacc gacgtttcgg gctcataggt 840
cagggccgcg tcgttgagct gcagcttgtc cagggcgtcc cgcaggttcg gatagtccga 900
tccgtcaacg ggatacagtc ccgaatacac catcggcttg ggttcgcggt agccggtcag 960
tgcctcggtg gcaccttttc gggcggtcgt gacggtgtcg ccgaccttgg actgccacac 1020
gtccttgacc ccggtgataa gataacccac ctcgccgaca ccaaggccgt cgctggcctt 1080
gggttcgggt gagacgatgc cgacctcgag cagttcgtgg gtggcgccgg tggacatcat 1140
ggcgatgcgc tcgcgggggg tgatcttgcc gtcgacgacg cggacgtagg tgaccacacc 1200
gcggtagatg tcatagacgg agtcgaagat cattgcgcga gtgggtgcgt cggcatcgcc 1260
ctgcggtggc ggcacctcgc gcaccacgtg gtcgagcagg tctgcgacgc cttccccggt 1320
tttgccggaa acccgcagca cgtcgccggg ctcgcagccg atgatgtgag caatctcgcc 1380
cgcgtagcgg tccgggtcgg cggccggcag gtcgatcttg ttcagcaccg gaatgatgtg 1440
caggtcgcgg tccagtgcca ggtagaggtt ggccagcgtc tgggcctcga tgccctgggc 1500
ggcgtcaacc agcagcaccg cgccctcgca ggcctccagc gcacgtgaca cctcgtaggt 1560
gaagtcgacg tgtcctggcg tgtcgatgag atgcaggacg tactcggttc catcgagctg 1620
ccagggcagc cgcacattct gcgccttgat ggtgatcccg cgttcgcgtt cgatatccat 1680
ccggtccagg tactgggccc gcatcgagcg ctcgtcaacg accccggtca actgcagcat 1740

<210> SEQ ID NO 110
<211> LENGTH: 1935
<212> TYPE: DNA
<213> ORGANISM: Mycobacterium avium

<400> SEQUENCE: 110
ttacttcttg gatttgtcgc ccgcggcgtc ggcggacagc gccgcgacga acgcctcctg 60
cggcacgtcg acccggccga tggtcttcat ccgcttcttg ccctccttct gcttttccag 120
aagtttgcgc ttacgggtga tgtcaccgcc gtaacacttg gacagcacgt ccttgcggat 180
ggcccgaatg ttctcgcggg caatgatttt cgagccgatc gcggcctgga cgggcacctc 240
gaactgctga cgggggatca gctccttgag cttggtggtc atcttgttgc cgtaggcgaa 300
cgccgcatcc ttgtgcacga tcgcgctgaa cgcgtcgacg gcctccccct gcaacaggat 360
gtccaccttg accagctggg cctcctgctc gccggcctcc tcgtagtcca ggctggcgta 420
gccgcgggtc cgcgacttca gcgagtcgaa gaagtcgaag atgatctcgc ccaacggcat 480
ggtgtagcgc agctcgaccc gttccggcga caggtaatcc atgccgccca gctcgccgcg 540
gcgggactgg cacagctcca tgatggtgcc gatgaattcg ctgggcgcga tgatggtggt 600
cttgaccacc ggctcgtaca ccgtgcgcac cttgccctcg ggccagtccg acgggttggt 660
caccacgatc tcggtgccgt cctctttgat cacccggtac accacgttgg gcgacgtcga 720
gatcaggtcg aggtcgaact cgcgctccag gcgctcgcgg gtgatctcca tgtgcagcaa 780
acccaaaaag ccgcaacgga atccgaagcc cagcgccacc gacgtctccg gttcgtaggt 840
gagcgcggcg tcgttgagcc gcagccggtc cagcgcgtcg cgcagatccg gatagtccga 900
gccgtccacc ggatacagac ccgaatagac catcggcttg ggttcgcgat atccggtcag 960
cgcctcttgc gcgccgtggc gcgcgctggt cacggtgtcg cccactttgg actggcggac 1020
gtccttcacc ccggtgatca ggtagcccac ctcgccgacg cccaggccgt cgctggcctt 1080
cggctcgggt gagacgatgc cgacttcgag cagttcgtgg gtggcgccgg tggacatcat 1140
cgcgatgcgt tcgcgcgggg tgatcttgcc gtcgaccacc cgcacgtagg tcaccacgcc 1200

```
gcggtagatg tcgtagaccg agtcgaagat catcgcgcgc agcggcgcat cggcctgccc   1260
ctgcggcggc ggcacctggc gcaccacctc gtcgagcagc cgcgccacgc cctccccggt   1320
tttgccggac acccgcagca cgtcgtcggg ttcgcacccg atgatgtggg cgagctcgcc   1380
ggcgtaccgg tccgggtcgg cggccggcag gtcgatcttg ttgaggaccg ggatgatggt   1440
cagatcgcgg tccagcgcca ggtagaggtt ggccagcgtc tgggcctcga tgccctgcgc   1500
ggcgtcgacc agcagcacgg caccttcgca ggcctccagt gcgcgcgaca cctcgtaggt   1560
gaagtcgacg tggcccgggg tgtcgatcag gtgcaggaca aattctttgc cggcgtcctc   1620
gccgccggag acctgccagg gcagccgcac gttctgcgcc ttgatggtga tgccgcgctc   1680
ccgctcgatg tccatccggt ccaggtactg ggcgcgcatc gaccgctcgt cgacgacgcc   1740
ggtgagctgc agcatccggt cggccagcgt cgacttgccg tgatcgatgt gggcgatgat   1800
gcagaagttg cgaatctgcg ccggcgcggt gaaggtcttg tcggcgaaac tgctgatggg   1860
tatctcctgg tccgggcctg ctagacggcg gttcgcaagt gtgtccagcg tatcggcgcg   1920
gccggactgc ggcac                                                    1935
```

```
<210> SEQ ID NO 111
<211> LENGTH: 1959
<212> TYPE: DNA
<213> ORGANISM: Mycobacterium vanbaalenii

<400> SEQUENCE: 111

tcatttcttc ggcttgtccg cggtggattc ggtggacagc gcggcgacga aggcctcctg     60
cgggacgtcg acccggccga tggtcttcat ccgcttcttg ccttccttct gcttttccag    120
cagcttgcgc ttacgggtga tgtcaccgcc gtagcacttg gacagcacat ccttgcggat    180
cgcccgaatg ttctcgcggg caatgattct cgagccgacg gcggcctgca cgggcacctc    240
gaactgctgg cgcgggatga gctccttgag cttggtggtc atcttgttgc cgtaggccga    300
ggccccgtcc ttgtgcacga tcgccgagaa cgcgtcgacg gcctcgccct gcagcaggat    360
gtcgaccttg accaggtcgg cctcctgctc gcctgcctcc tcgtagtcca ggctggcgta    420
gccgcgggtg cgcgatttca gcgagtcgaa gaagtcgaag atgatctcgc ccagcggcat    480
ggtgtagcgc agctcgacgc gctcgggcga caggtagtcc attccgccga gttcaccgcg    540
ccgcgactgg cacagctcca tgatcgtgcc gatgaactcg ctgggcgcga tcaccgtcgt    600
cttgaccacc ggctcgaaca ccgatcgcac cttgccctcg ggccagtccg aggggttggt    660
gacgatgatc tcggacccgt cgtccttgac gacgcggtag accacgttgg gcgcggtcga    720
gatcaggtcc aggttgaact cgcgctccag gcgttcccgg gtgatctcca tgtgcagcag    780
cccgaggaac ccgcagcgga acccgaaccc gagcgccacc gacgtctcgg gttcgtacgt    840
cagcgccgcg tcgttgagtt gcagcttgtc cagcgcctcg cgcagcaccg ggtagtccga    900
gccgtcgacc ggatacaggc ccgagtagac catcggcctg ggctcccggt agccggtcaa    960
cgcttccttg gcaccgttac gcgccgtcgt caccgtgtcg ccgaccttgg actggcgcac   1020
gtccttcaca ccggtgatga ggtagccgac ctcgccgacg ccgaggccgt cggagggctt   1080
gggctcgggt gagacgattc ccacctcgag cagttcgtgg gtggcgccgg tcgacatcat   1140
cgcgatgcgc tcgcgcgggg tgatcttccc gtccaccacc cgcacgtagg tcaccacgcc   1200
gcggtagatg tcgtagaccg agtcgaagat catcgcgcgg gcaggcgcgt ccgggtcgcc   1260
ctgcggcgcc gggatctccc gcaccacgtg gtcgagcagc tcggccacac cctcacccgt   1320
cttgcccgac acccgcaaca cgtcctcggg ctcgcagccg atgatgtggg cgatctcggc   1380
```

ggcgtaccgg tccgggtctg cggcgggcag atcgatcttg ttcagcaccg ggatgatcgt 1440
caggtcgcgg tccagcgcca gatacaggtt cgccagcgtc tgcgcttcga tgccctgggc 1500
ggcgtcgacc agcagcaccg cgccctcgca cgcctccagc gcgcgggaca cctcataggt 1560
gaaatcaaca tggccgggcg tgtcaatcaa atgcagcacg aactcctcac cgttgaccac 1620
ccacggcagc cgcacgttct gcgccttgat cgtgatcccg cgctcacgct cgatgtccat 1680
ccggtccagg tactgcgccc gcatcgagcg ctcgtcgacc acaccggtga gctgcagcat 1740
ccggtcggcc agggtggact ttccgtggtc gatgtgggcg atgatgcaga agttccgaat 1800
ctgcgccggc gcagtgaacg tcttgtcggc gaagctgctg atgggaatct cctggtgagc 1860
gggtcgtggc ggcctgaaca ggcctgtcca gagtatcgag cgcacacccc cgcgacacaa 1920
tcgagccgtg atcgaggcgg cttcggggca ccggggcac 1959

<210> SEQ ID NO 112
<211> LENGTH: 1905
<212> TYPE: DNA
<213> ORGANISM: Mycobacterium gilvum

<400> SEQUENCE: 112
ctacttcttc ggcttgtccg cggcggactc ggtcgacagt gccgcgacga aggcctcctg 60
cggcacctcg acccggccga tcgtcttcat ccgcttcttg ccttccttct gcttctccag 120
cagcttgcgc ttacgagtga tgtcaccgcc gtagcacttc gacagcacgt ccttgcggat 180
cgcccggatg ttctctcgcg caatgattct cgagccgatc gcggcctgca cgggcacctc 240
gaactgctgg cgtgggatca gttccttcag cttggtcgtc atcttgttgc cgtacgccgc 300
ggcaccgtcc ttgtggacga tggcgctgaa cgcgtcgacg gcttcgccct gcagcaggat 360
gtcgaccttg accaggtcgg cctcctgctc gcccgcctcc tcgtagtcga ggctcgcgta 420
gccgcgggtg cgggacttca gcgagtcgaa gaagtcgaag atgatctcgc ccagcggcat 480
cgtgtagcgc agctcgaccc gctcgggtga caggtagtcc atgccgccga gctcgccacg 540
gcgcgactgg cacagctcca tgatcgttcc gatgaactca ctcggcgcga tcaccgtcgt 600
cttgacgacc ggctcgaaca ccgaacggac cttgccctcg ggccagtccg acgggttggt 660
gaccgtgagc tcgctgttgt cctctttgat gacgcggtag acgacgttgg gcgcggtcga 720
gatcaggtcg aggttgaact cgcgttcgag ccgctcgcgc gtgatctcca tgtgcagcaa 780
gcccaggaag ccgcagcgga agccgaaccc gagcgcgacc gacgtctccg gctcgtaagt 840
cagtgccgcg tcgttcagct gcagtttgtc gagcgcctcg cgcaacaccg ggtagtcgga 900
accgtccacg ggatacaggc ccgagtagac catcggcttg ggctcgcggt agccggtcag 960
cgcttcggtg gcacccttgc gtgccgtcgt caccgtgtcg ccgaccttgg actgacgcac 1020
gtccttcacg ccggtgatca ggtagccgac ctcgccgaca ccgagaccga ccgaaggctt 1080
ggggtccggc gagacgatgc ccacttcgag gagttcgtgc gtcgcgccgg tcgacatcat 1140
cgcgatgcgc tcacgcgggg tgatcctgcc gtcgacgacg cgcacatagg tgacgacgcc 1200
gcggtagatg tcgtacaccg agtcgaagat catcgcgcgc gccggagcgt ccgggtcgcc 1260
ctgcggcggc gggatctccc ggacgacgtg gtcgagcagg tcgccgacgc cggcgccggt 1320
cttgcccgac acccgcagca catcctccgg ttcgcagccg atgatgtgcg cgatctcacc 1380
ggcgtagcgg tcggggtcgg cggcgggcag gtcgatcttg ttgagcaccg ggatgattgt 1440
caggtcgcga tccagcgcca ggtacaggtt cgccagggtc tgcgcctcga tgccctgggc 1500

-continued

```
ggcgtcgacc agcagcaccg caccctcgca ggcctccagc gcgcgcgaca cctcgtaggt   1560

gaaatcgacg tggccagggg tgtcgatcag atgcaggacg aactcttcgc cgttgacgac   1620

ccacggcagg cgcacgttct gcgccttgat cgtgatgccg cgttcccgct cgatgtccat   1680

ccggtccagg tactgcgccc gcatgtccct gtccgcgacc acaccggtga gctgcagcat   1740

ccgatcggcc agggtggact tgccgtggtc gatgtgggcg atgatgcaga agttcctgat   1800

ctgcgccggc gcagtgaacg tcttgtcggc gaagctggcg atgggaatct cctggtgagc   1860

ggggtctgtc ggcctgagca ggccagtcca gagtatcgag cgcat                   1905
```

```
<210> SEQ ID NO 113
<211> LENGTH: 1824
<212> TYPE: DNA
<213> ORGANISM: Staphylococcus aureus

<400> SEQUENCE: 113

ttattcgtca tccattttca atacagccaa gaaagcatcc tgtggaattt caacattacc     60

aactgctttc atcttagctt tacctgcttt ttgtttttca agtaatttac gtttacggct    120

tatgtcaccg ccataacatt tagctaaaac gtttttaccc attgatttaa tatttgtacg    180

cgctacaatt ttttgtccta ttgcagcctg tacaggtact tcaaattgct gtcttggaat    240

taacgtttta agtttttcaa ctaatgcttt accacgttca tatgcaaaat ctctatgaac    300

tatgaagctc agcgcatcca ctttatcacc gtttaataaa atatccatct taactaaatt    360

actttcttta ttttcgatga attcataatc aaatgatgca tatcctttag tattagattt    420

aagttgatcg aagaaatcaa atacaacttc agctaaaggt aattcataaa caatatttac    480

acgaatatca tctaaatagt ccatatttat aaattgtcca cgtttacgtt gacataattc    540

cattactgca cctacatagt catttggaac catcatagtt gcacgaacat atggctcaaa    600

tattttatca attttatcac gatctggcat ttgtgctggg ttatcaaccg tcacttctga    660

accgtccctt aaaatacatt gataaattac agatggtgct gttgcaatta attcaatgcc    720

aaattctctt tcaattcttt cttgaattat ttccatgtgt aacataccta agaaaccagt    780

tctataacca aaacctaatg cttgtgacga ttcaggctca aattctaatg atgcatcatt    840

caattgtaat ttttctaatg cttctcttaa atcattataa tttttgttat ctattgggaa    900

cagtccgcaa tataccattg gattcatttt cttataacct tgcaatggtt ctgatgcagg    960

tctactagct aatgtgatgg tgtcaccaac cctagaatca tcaacatttt taatacttgc   1020

aataatataa ccaacatcac caactgttaa ttcatcaact ggaagctgct taggtgtatt   1080

aattccaact tctgttactt cgaactcttt accagtggcc atcattcgaa ttttatctcc   1140

agctttaaca acaccgtcta caattcttat cgatgaaatt acccctctat atggatcata   1200

ctcagaatca aatattaatg cttttagtgg tgcttctggg tcaccatctg gagctggcac   1260

aacttcaact attttctcta gtatctcttc aattccaatg ttagatttag cacttgctaa   1320

aacaacatcg tcttggtcta aacctatcat atcttcaatt tcttgtttca cgcgttcagg   1380

ttctgcagca ggtaaatcaa ttttgttaat aacaggcaat aactctaact cattatctaa   1440

tgccaaataa acatttgcta atgtttgtgc ttcgatacct tgagccgcat ctactactaa   1500

aatcgcaccc tcacaagctg ccaaagaacg tgacacttca tatgtaaaat cgacgtgtcc   1560

aggcgtatcg attaaatgga atgtataagt atttccatct ttagcttcgt actttaaacg   1620

aactgcgttt aatttgattg taataccacg ttctctttct aaatccattg aatctagtaa   1680

ctgatcttgc atatctcttg tttcaactga tttggtattt tctaaaattc tatcagccaa   1740
```

tgtagatttt ccgtggtcaa tatgtgctat aatcgagaaa ttccttatat tctctcttct 1800
ttttaagcgt tgctcattat ccat 1824

<210> SEQ ID NO 114
<211> LENGTH: 1824
<212> TYPE: DNA
<213> ORGANISM: Staphylococcus aureus

<400> SEQUENCE: 114
ttattcatca tccattttca atacagccaa gaaagcatct tgtggaattt caacattacc 60
aactgctttc atcttagctt tacctgcttt ttgtttttca agtaatttac gtttacggct 120
tatgtcaccg ccataacatt tagctaaaac gtttttaccc attgatttaa tatttgtacg 180
cgctacaatt ttttgtccta ttgcagcctg tacaggtact tcaaattgct gtcttggaat 240
taacgtttta agtttttcaa ctaatgcttt accacgttca tatgcaaaat ctctatgaac 300
tatgaagctt agcgcatcca ctttatcacc atttaataaa atatccatct tgactaaatt 360
actttcttta ttttcgatga attcataatc aaatgatgca tatcctttag tattagattt 420
aagttgatcg aagaaatcaa atacaacttc agctaaaggt aattcataaa caatatttac 480
acgaatatca tctaaatagt ccatatttat aaattgtcca cgtttacgtt gacataattc 540
cattactgca ccgacatagt catttggaac catcatagtt gcacgaacat atggctcaaa 600
tattttatca attttatcac gatctggcat ttgtgctggg ttatcaaccg tcacttctga 660
accgtccctt aaaacacatt gataaattac agatggtgca gttgcaatta attcaatacc 720
aaattctctt tcaattcttt cttgaattat ttccatgtgt aacataccta agaaaccagt 780
tctataacca aaacctaatg cttgtgacga ttcaggctca aattctaatg atgcatcatt 840
caattgtaat ttttctaatg cttctcttaa atcattataa tttttgttat ctattgggaa 900
cagtccgcaa tataccattg gattcatttt cttataacct tgcaatggtt ctgatgcagg 960
tctactagct aatgtgatgg tgtcaccaac cctagaatca tcaacatttt taatacttgc 1020
aataatataa ccaacatcac caactgttaa ttcatcaact ggaagctgct taggtgtatt 1080
aattccaact tctgttactt cgaactcttt accagtggcc atcattcgaa ttttatctcc 1140
ggctttaaca acaccgtcca caattcttat cgatgaaatt acccctctat atggatcata 1200
ctcagaatca aatattaacg cttttagtgg tgcttctggg tcaccatctg gagctggcac 1260
aacttcaact attttctcta gtatctcttc aattccaatg ttagatttag cacttgctaa 1320
aacaacatcg tcttggtcta aacctatcat atcttcaatt tcttgtttca cgcgttcagg 1380
ttctgcagca ggtaaatcaa ttttgttaat aacaggcaat aactctaact cattatctaa 1440
tgctaaataa acatttgcta atgtttgtgc ttcgatacct tgagccgcat ctactactaa 1500
aatcgcgccc tcacaagctg ccaaagaacg tgacacttca tatgtaaaat cgacgtgtcc 1560
aggcgtatcg attaaatgga atgtataagt atttccatct ttagcttcgt actttaaacg 1620
tactgcgttt aatttgattg taataccacg ttctctttct aaatccattg aatctagtaa 1680
ctgatcttgc atatctcttg tttcaactga tttggtattt tctaaaattc tatcagccaa 1740
tgtagatttt ccgtggtcaa tatgtgctat aatcgagaaa ttccttatat tctctcttct 1800
ttttaagcgt tgctcattat ccat 1824

<210> SEQ ID NO 115
<211> LENGTH: 1824
<212> TYPE: DNA

<213> ORGANISM: Staphylococcus aureus

<400> SEQUENCE: 115
ttattcgtca tccattttca atacagccaa gaaagcatcc tgtggaattt caacattacc 60
aactgctttc atcttagctt tacctgcttt ttgtttttca agtaatttac gtttacggct 120
tatgtcaccg ccataacatt tagctaaaac gtttttaccc attgatttaa tatttgtacg 180
cgctacaatt ttttgtccta ttgcagcctg tacaggtact tcaaattgct gtcttggaat 240
taacgtttta agtttttcaa ctaatgcttt accacgttca tatgcaaaat ctctatgaac 300
tatgaagctc agcgcatcca ctttatcacc gtttaataaa atatccatct taactaaatt 360
actttcttta ttttcgatga attcataatc aaatgatgca tatcctttag tattagattt 420
aagttgatcg aagaaatcaa atacaacttc agctaaaggt aattcataaa caatatttac 480
acgaatatca tctaaatagt ccatatttat aaattgtcca cgtttacgtt gacataattc 540
cattactgca cctacatagt catttggaac catcatagtt gcacgaacat atggctcaaa 600
tattttatca attttatcac gatctggcat ttgtgctggg ttatcaaccg tcacttctga 660
accgtccctt aaaatacatt gataaattac agatggtgct gttgcaatta attcaatgcc 720
aaattctctt tcaattcttt cttgaattat ttccatgtgt aacataccta agaaaccagt 780
tctataacca aaacctaatg cttgtgacga ttcaggctca aattctaatg atgcatcatt 840
caattgtaat ttttctaatg cttctcttaa atcattataa tttttgttat ctattgggaa 900
cagtccgcaa tataccattg gattcatttt cttataacct tgcaatggtt ctgatgcagg 960
tctactagct aatgtgatgg tgtcaccaac cctagaatca tcaacatttt taatacttgc 1020
aataatataa ccaacatcac caactgttaa ttcatcaact ggaagctgct taggtgtatt 1080
aattccaact tctgttactt cgaactcttt accagtggcc atcattcgaa ttttatctcc 1140
agctttaaca acaccgtcta caattcttat cgatgaaatt acccctctat atggatcata 1200
ctcagaatca aatattaatg cttttagtgg tgcttctggg tcaccatctg gagctggcac 1260
aacttcaact attttctcta gtatctcttc aattccaatg ttagatttag cacttgctaa 1320
aacaacatcg tcttggtcta aacctatcat atcttcaatt tcttgtttca cgcgttcagg 1380
ttctgcagca ggtaaatcaa ttttgttaat aacaggcaat aactctaact cattatctaa 1440
tgccaaataa acatttgcta atgtttgtgc ttcgatacct tgagccgcat ctactactaa 1500
aatcgcaccc tcacaagctg ccaaagaacg tgacacttca tatgtaaaat cgacgtgtcc 1560
aggcgtatcg attaaatgga atgtataagt atttccatct ttagcttcgt actttaaacg 1620
aactgcgttt aatttgattg taataccacg ttctcttttct aaatccattg aatctagtaa 1680
ctgatcttgc atatctcttg tttcaactga tttggtattt tctaaaattc tatcagccaa 1740
tgtagatttt ccgtggtcaa tatgtgctat aatcgagaaa ttccttatat tctctcttct 1800
ttttaagcgt tgctcattat ccat 1824

<210> SEQ ID NO 116
<211> LENGTH: 1824
<212> TYPE: DNA
<213> ORGANISM: Staphylococcus aureus

<400> SEQUENCE: 116
ttattcgtca tccattttca atacagccaa aaaagcatcc tgtggaattt caacattacc 60
aactgctttc atcttagctt tacctgcttt ttgtttttca agtaatttac gtttacggct 120
tatgtcaccg ccataacatt tagctaaaac gtttttaccc attgatttaa tatttgtacg 180

```
tgctacaatt ttttgtccta ttgcagcttg tacaggtact tcaaattgct gtcttggaat    240

taacgtttta agtttttcaa ctaatgcttt accacgttca tatgcaaaat ctctatggac    300

tatgaagctt agagcatcca ctttatcacc gtttaataaa atatccatct tcactaaatt    360

actttcttta ttttcgatga actcataatc aaatgatgca tatcctttag tattagattt    420

aagttgatcg aagaaatcaa atacaacttc agctaaaggt aattcataaa caatatttac    480

acgaatatca tctaaatagt ccatatttat aaattgtcca cgtttacgtt gacataattc    540

cattactgca cctacatagt catttggaac catcatagtt gcacgaacat atggctcgaa    600

tattttatca attttatcac ggtctggcat ttgtgctgga ttatcaaccg tcacttctga    660

accgtccctt aaaatacatt gataaattac agatggtgcg gttgcaatta attcaatgcc    720

aaattctctt tcaattcttt cttgaattat ttccatgtgt aacataccta agaaaccagt    780

tctataacca aaacctaatg cttgtgatga ttcaggctca aattctaatg atgcatcatt    840

caattgtaat ttttctaatg cttctcttaa atcattataa tttttgttat ctattgggaa    900

cagtccgcaa tataccattg gattcatttt cttataacct tgcaatggtt ctgatgcagg    960

tctactagct aatgtgattg tgtcaccaac cctagaatca tcaacatttt taatacttgc   1020

aataatgtaa ccaacatcac caactgttaa ttcatcaact ggaagttgct taggtgtatt   1080

aattccaact tctgttactt cgaactcttt accagtggcc atcattcgaa ttttatctcc   1140

ggctttaaca acaccgtcta caattcttat cgatgaaatt acccctctat atggatcata   1200

ctcagaatca aatattaacg cttttagtgg tgcttctggg tcaccatctg gagctggcac   1260

aacttcaact attttctcaa gtatctcttc aattccaatg ttagatttag cacttgctaa   1320

aacaacatcg tcttggtcta aacctatcat atcttcaatt tcttgtttca cgcgttcagg   1380

ttctgcagca ggtaaatcaa ttttgttaat aacaggcaat aactctaact cattatctaa   1440

tgccaaataa acatttgcta atgtttgtgc ttcgatacct tgagccgcat ctactactaa   1500

aatcgcgccc tcacaagctg ccaaagaacg tgacacttca tatgtaaaat cgacgtgtcc   1560

aggcgtatcg attaaatgga atgtataagt atttccatct ttagcttcgt actttaaacg   1620

tactgcgttt aatttgattg taataccacg ttctctttct aaatccattg aatctagtaa   1680

ctgatcttgc atatctcttg tttcaactga tttggtattt tctaaaattc tatcagccaa   1740

tgtagatttt ccgtggtcaa tatgtgctat aatcgagaaa ttccttatat tctctcttct   1800

ttttaagcgt tgctcattat ccat                                          1824


<210> SEQ ID NO 117
<211> LENGTH: 1824
<212> TYPE: DNA
<213> ORGANISM: Staphylococcus aureus

<400> SEQUENCE: 117

ttattcatca tccattttca atacagccaa gaaagcatct tgtggaattt caacattacc     60

aactgctttc atcttagctt tacctgcttt ttgtttttca agtaatttac gtttacggct    120

tatgtcaccg ccataacatt tagctaaaac gtttttaccc attgatttaa tatttgtacg    180

cgctacaatt ttttgtccta ttgcagcctg tacaggtact tcaaattgct gtcttggaat    240

taacgtttta agtttttcaa ctaatgcttt accacgttca tatgcaaaat ctctatgaac    300

tatgaagctt agcgcatcca ctttatcacc atttaataaa atatccatct tgactaaatt    360

actttcttta ttttcgatga attcataatc aaatgatgca tatcctttag tattagattt    420
```

```
aagttgatcg aagaaatcaa atacaacttc agctaaaggt aattcataaa caatatttac    480
acgaatatca tctaaatagt ccatatttat aaattgtcca cgtttacgtt gacataattc    540
cattactgca ccgacatagt catttggaac catcatagtt gcacgaacat atggctcaaa    600
tattttatca attttatcac gatctggcat ttgtgctggg ttatcaaccg tcacttctga    660
accgtccctt aaaacacatt gataaattac agatggtgca gttgcaatta attcaatacc    720
aaattctctt tcaattcttt cttgaattat ttccatgtgt aacataccta agaaaccagt    780
tctataacca aaacctaatg cttgtgacga ttcaggctca aattctaatg atgcatcatt    840
caattgtaat ttttctaatg cttctcttaa atcattataa tttttgttat ctattgggaa    900
cagtccgcaa tataccattg gattcatttt cttataacct tgcaatggtt ctgatgcagg    960
tctactagct aatgtgatgg tgtcaccaac cctagaatca tcaacatttt taatacttgc   1020
aataatataa ccaacatcac caactgttaa ttcatcaact ggaagctgct taggtgtatt   1080
aattccaact tctgttactt cgaactcttt accagtggcc atcattcgaa ttttatctcc   1140
ggctttaaca acaccgtcca caattcttat cgatgaaatt acccctctat atggatcata   1200
ctcagaatca aatattaacg cttttagtgg tgcttctggg tcaccatctg gagctggcac   1260
aacttcaact attttctcta gtatctcttc aattccaatg ttagatttag cacttgctaa   1320
aacaacatcg tcttggtcta aacctatcat atcttcaatt tcttgtttca cgcgttcagg   1380
ttctgcagca ggtaaatcaa ttttgttaat aacaggcaat aactctaact cattatctaa   1440
tgctaaataa acatttgcta atgtttgtgc ttcgatacct tgagccgcat ctactactaa   1500
aatcgcgccc tcacaagctg ccaaagaacg tgacacttca tatgtaaaat cgacgtgtcc   1560
aggcgtatcg attaaatgga atgtataagt atttccatct ttagcttcgt actttaaacg   1620
tactgcgttt aatttgattg taataccacg ttctctttct aaatccattg aatctagtaa   1680
ctgatcttgc atatctcttg tttcaactga tttggtattt tctaaaattc tatcagccaa   1740
tgtagatttt ccgtggtcaa tatgtgctat aatcgagaaa ttccttatat tctctcttct   1800
ttttaagcgt tgctcattat ccat                                           1824
```

```
<210> SEQ ID NO 118
<211> LENGTH: 1824
<212> TYPE: DNA
<213> ORGANISM: Staphylococcus aureus

<400> SEQUENCE: 118

ttattcgtca tccattttca atacagccaa gaaagcatcc tgtggaattt caatattacc     60
aactgctttc atcttagctt tacctgcttt ttgtttttca agtaatttac gtttacggct    120
tatgtcaccg ccataacatt tagctaaaac gtttttaccc attgatttaa tatttgtacg    180
cgctacaatt ttttgtccta ttgcagcctg tacaggtact tcaaattgct gtcttggaat    240
taacgtttta agtttttcaa ctaatgcttt accacgttca tatgcaaaat ctctatgaac    300
tatgaagctt agcgcatcca ctttatcacc gtttaataaa atatccatct taactaaatt    360
actttcttta ttttcgatga attcataatc aaatgatgca tatcctttag tattagattt    420
aagttgatcg aagaaatcaa atacaacttc agctaaaggt aattcataaa caatatttac    480
acgaatatca tctaaatagt ccatatttat aaattgtcca cgtttacgtt gacataattc    540
cattactgca cctacatagt catttggaac catcatagtt gcacgaacat atggctcaaa    600
tattttatca attttatcac gatctggcat ttgtgctggg ttatcaaccg tcacttctga    660
accgtccctt aaaatacatt gataaattac agatggtgct gttgcaatta attcaatgcc    720
```

```
aaattctctt tcaattcttt cttgaattat ttccatgtgt aacataccta agaaaccagt    780
tctataacca aaacctaatg cttgtgacga ttcaggctca aattctaatg atgcatcatt    840
caattgtaat ttttctaatg cttctcttaa atcattataa tttttgttat ctattgggaa    900
cagtccgcaa tataccattg gattcatttt cttataacct tgcaatggtt ctgatgcagg    960
tctactagct aatgtgatgg tgtcaccaac cctagaatca tcaacatttt taatacttgc   1020
aataatataa ccaacatcac caactgttaa ttcatcaact ggaagctgct taggtgtatt   1080
aattccaact tctgttactt cgaactcttt accagtcgcc atcattcgaa ttttatctcc   1140
ggctttaaca acaccgtcta caattcttat cgatgaaatt acccctctat atggatcata   1200
ctcagaatca aatattaacg cttttagtgg tgcttctggg tcgccatctg gagctggcac   1260
aacttcaact attttctcta gtatctcttc aattccaatg ttagatttag cacttgctaa   1320
aacaacatcg tcttggtcta aacctatcat atcttcaatt tcttgtttca cgcgttcagg   1380
ttctgcagca ggtaaatcaa ttttgttaat aacaggcaat aactctaact cattatctaa   1440
tgctaaataa acatttgcta atgtttgtgc ttcgatacct tgagccgcat ctactactaa   1500
aatcgcgccc tcacaagctg ccaaagaacg tgacacttca tatgtaaaat cgacgtgtcc   1560
aggcgtatcg attaaatgga atgtataagt atttccatct ttagcttcgt actttaaacg   1620
aactgcgttt aatttgattg taataccacg ttctctttct aaatccattg aatctagtaa   1680
ctgatcttgc atatctcttg tttcaactga tttggtattt tctaaaattc tatcagccaa   1740
tgtagatttt ccgtggtcaa tatgtgctat aatcgagaaa ttccttatat tctctcttct   1800
ttttaagcgt tgctcattat ccat                                          1824
```

<210> SEQ ID NO 119
<211> LENGTH: 1824
<212> TYPE: DNA
<213> ORGANISM: Staphylococcus aureus

<400> SEQUENCE: 119

```
ttattcgtca tccattttca atacagccaa gaaagcatcc tgtggaattt caacattacc     60
aactgctttc atcttagctt tacctgcttt ttgtttttca agtaatttac gtttacggct    120
tatgtcaccg ccataacatt tagctaaaac gtttttaccc attgatttaa tatttgtacg    180
cgctacaatt ttttgtccta ttgcagcctg tacaggtact tcaaattgct gtcttggaat    240
taacgtttta agtttttcaa ctaatgcttt accacgttca tatgcaaaat ctctatgaac    300
tatgaagctc agcgcatcca ctttatcacc gtttaataaa atatccatct taactaaatt    360
actttcttta ttttcgatga attcataatc aaatgatgca tatcctttag tattagattt    420
aagttgatcg aagaaatcaa atacaacttc agctaaaggt aattcataaa caatatttac    480
acgaatatca tctaaatagt ccatatttat aaattgtcca cgtttacgtt gacataattc    540
cattactgca cctacatagt catttggaac catcatagtt gcacgaacat atggctcaaa    600
tattttatca attttatcac gatctggcat ttgtgctggg ttatcaaccg tcacttctga    660
accgtccctt aaaatacatt gataaattac agatggtgct gttgcaatta attcaatgcc    720
aaattctctt tcaattcttt cttgaattat ttccatgtgt aacataccta agaaaccagt    780
tctataacca aaacctaatg cttgtgacga ttcaggctca aattctaatg atgcatcatt    840
caattgtaat ttttctaatg cttctcttaa atcattataa tttttgttat ctattgggaa    900
cagtccgcaa tataccattg gattcatttt cttataacct tgcaatggtt ctgatgcagg    960
```

-continued

```
tctactagct aatgtgatgg tgtcaccaac cctagaatca tcaacatttt taatacttgc   1020

aataatataa ccaacatcac caactgttaa ttcatcaact ggaagctgct taggtgtatt   1080

aattccaact tctgttactt cgaactcttt accagtggcc atcattcgaa ttttatctcc   1140

agctttaaca acaccgtcta caattcttat cgatgaaatt acccctctat atggatcata   1200

ctcagaatca aatattaatg cttttagtgg tgcttctggg tcaccatctg gagctggcac   1260

aacttcaact attttctcta gtatctcttc aattccaatg ttagatttag cacttgctaa   1320

aacaacatcg tcttggtcta aacctatcat atcttcaatt tcttgtttca cgcgttcagg   1380

ttctgcagca ggtaaatcaa ttttgttaat aacaggcaat aactctaact cattatctaa   1440

tgccaaataa acatttgcta atgtttgtgc ttcgatacct tgagccgcat ctactactaa   1500

aatcgcaccc tcacaagctg ccaaagaacg tgacacttca tatgtaaaat cgacgtgtcc   1560

aggcgtatcg attaaatgga atgtataagt atttccatct ttagcttcgt actttaaacg   1620

aactgcgttt aatttgattg taataccacg ttctctttct aaatccattg aatctagtaa   1680

ctgatcttgc atatctcttg tttcaactga tttggtattt tctaaaattc tatcagccaa   1740

tgtagatttt ccgtggtcaa tatgtgctat aatcgagaaa ttccttatat tctctcttct   1800

ttttaagcgt tgctcattat ccat                                          1824
```

```
<210> SEQ ID NO 120
<211> LENGTH: 1824
<212> TYPE: DNA
<213> ORGANISM: Staphylococcus aureus

<400> SEQUENCE: 120

ttattcgtca tccattttta atacagccaa gaaagcatcc tgtggaattt caacattacc     60

aactgctttc atcttagctt tacctgcttt ttgtttttca agtaatttac gtttacggct    120

tatgtcaccg ccataacatt tagctaaaac gtttttaccc attgatttaa tatttgtacg    180

tgctacaatt ttttgtccta ttgcagcctg tacaggtact tcaaattgct gtcttggaat    240

taaggtttta agtttttcaa ctaatgcttt accacgttca tatgcaaaat ctctatgaac    300

tatgaagctt agagcatcca ctttatcgcc gtttaataaa atatccatct tcactaaatt    360

actttcttta ttttcgatga actcataatc aaatgatgca tatcctttgg tattagattt    420

aagttgatcg aagaaatcaa atacaacttc agctaaaggt aattcataaa caatatttac    480

acgaatatca tctaaatagt ccatatttat aaattgtccg cgtttacgtt gacataattc    540

cattacagca cctacatagt catttggaac catcatagtt gcacgaacat atggctcaaa    600

tattttatca attttatcac gatctggcat ttgtgctggg ttatcaaccg tcacttctga    660

accatccctt aaaatacatt gataaattac agatggtgcg gttgcaatta attcaatgcc    720

aaattctctt tcaattcttt cttgaattat ttccatgtgt aacataccta agaaaccagt    780

tctataacca aaacctaatg cttgtgatga ttcaggctcg aattctaacg atgcatcatt    840

caattgtaat ttttctaatg cttctcttaa atcattataa tttttgttat ctatcgggaa    900

cagtccgcaa tataccattg gattcatttt cttataacct tgcaatggtt ctgatgcagg    960

tctactagct aatgtgattg tgtcaccaac cctagaatca tcaacatttt taatacttgc   1020

aataatataa ccaacatcac caactgttaa ttcatcaact ggaagctgct taggtgtatt   1080

aattccaact tctgttactt cgaactcttt accagtggcc atcattcgaa ttttatctcc   1140

ggctttaaca acaccgtcta caattcttat cgatgaaatt acccctctat atggatcata   1200

ctcagaatca aatattaatg cttttaatgg tgcttctggg tcaccatctg gagctggcac   1260
```

```
aacttcaact attttctcta gtatctcttc aattccaatg ttagatttag cacttgctaa   1320

aacaacatcg tcttggtcta aacctatcat atcttcaatt tcttgtttca cgcgttcagg   1380

ttcagcagca ggtaaatcaa ttttgttaat aacaggcaat aactctaact cattatctaa   1440

tgctaaataa acatttgcta atgtttgtgc ttcgatacct tgagccgcat ctactactaa   1500

aatcgcgccc tcacaagctg ccaaagaacg tgacacttca tatgtaaaat cgacgtgtcc   1560

aggcgtatcg attaaatgga atgtataagt atttccatct ttagcttcgt actttaaacg   1620

tactgcgttt aatttgattg taataccacg ttctctttct aaatccattg aatctagtaa   1680

ctgatcttgc atatctcttg tttcaactga tttggtattt tctaaaattc tatcagccaa   1740

tgtagatttt ccgtggtcaa tatgtgctat aatcgagaaa ttccttatat tctctcttct   1800

ttttaagcgt tgctcattat ccat                                          1824


<210> SEQ ID NO 121
<211> LENGTH: 1824
<212> TYPE: DNA
<213> ORGANISM: Staphylococcus aureus

<400> SEQUENCE: 121

ttattcgtca tccatttca atacagccaa gaaagcatcc tgtggaattt caacattacc      60

aactgctttc atcttagctt tacctgcttt ttgtttttca agtaatttac gtttacggct    120

tatgtcaccg ccataacatt tagctaaaac gtttttaccc attgatttaa tatttgtacg    180

cgctacaatt ttttgtccta ttgcagcctg tacaggtact tcaaattgct gtcttggaat    240

taacgtttta agtttttcaa ctaatgcttt accacgttca tatgcaaaat ctctatgaac    300

tatgaagctt agcgcatcca ctttatcacc gtttaataaa atatccatct taactaaatt    360

actttcttta ttttcgatga attcataatc aaatgatgca tatcctttag tattagattt    420

aagttgatcg aagaaatcaa atacaacttc agctaaaggt aattcataaa caatatttac    480

acgaatatca tctaaatagt ccatatttat aaattgtcca cgtttacgtt gacataattc    540

cattactgca cctacatagt catttggaac catcatagtt gcacgaacat atggctcaaa    600

tattttatca attttatcac gatctggcat ttgtgctggg ttatcaaccg tcacttctga    660

accgtccctt aaaatacatt gataaattac agatggtgct gttgcaatta attcaatgcc    720

aaattctctt tcaattcttt cttgaattat ttccatgtgt aacataccta agaaaccagt    780

tctataacca aaacctaatg cttgtgacga ttcaggctca aattctaatg atgcatcatt    840

caattgtaat ttttctaatg cttctcttaa atcattataa tttttgttat ctattgggaa    900

cagtccgcaa tataccattg gattcatttt cttataacct tgcaatggtt ctgatgcagg    960

tctactagct aatgtgatgg tgtcaccaac cctagaatca tcaacatttt taatacttgc   1020

aataatataa ccaacatcac caactgttaa ttcatcaact ggaagctgct taggtgtatt   1080

aattccaact tctgttactt cgaactcttt accagtggcc atcattcgaa ttttatctcc   1140

agctttaaca acaccgtcta caattcttat cgatgaaatt acccctctat atggatcata   1200

ctcagaatca aatattaatg cttttagtgg tgcttctggg tcaccatctg gagctggcac   1260

aacttcaact attttctcta gtatctcttc aattccaatg ttagatttag cacttgctaa   1320

aacaacatcg tcttggtcta aacctatcat atcttcaatt tcttgtttca cgcgttcagg   1380

ttctgcagca ggtaaatcaa ttttgttaat aacaggcaat aactctaact cattatctaa   1440

tgccaaataa acatttgcta atgtttgtgc ttcgatacct tgagccgcat ctactactaa   1500
```

-continued

```
aatcgcaccc tcacaagctg ccaaagaacg tgacacttca tatgtaaaat cgacgtgtcc   1560

aggcgtatcg attaaatgga atgtataagt atttccatct ttagcttcgt actttaaacg   1620

aactgcgttt aatttgattg taataccacg ttctctttct aaatccattg aatctagtaa   1680

ctgatcttgc atatctcttg tttcaactga tttggtattt tctaaaattc tatcagccaa   1740

tgtagatttt ccgtggtcaa tatgtgctat aatcgagaaa ttccttatat tctctcttct   1800

ttttaagcgt tgctcattat ccat                                          1824
```

<210> SEQ ID NO 122
<211> LENGTH: 1824
<212> TYPE: DNA
<213> ORGANISM: Staphylococcus aureus

<400> SEQUENCE: 122

```
ttattcgtca tccattttca atacagccaa gaaagcatcc tgtggaattt caacattacc     60

aactgctttc atcttagctt tacctgcttt ttgtttttca agtaatttac gtttacggct    120

tatgtcaccg ccataacatt tagctaaaac gtttttaccc attgatttaa tatttgtacg    180

cgctacaatt ttttgtccta ttgcagcctg tacaggtact tcaaattgct gtcttggaat    240

taacgtttta agtttttcaa ctaatgcttt accacgttca tatgcaaaat ctctatgaac    300

tatgaagctt agcgcatcca ctttatcacc gtttaataaa atatccatct taactaaatt    360

actttcttta ttttcgatga attcataatc aaatgatgca tatcctttag tattagattt    420

aagttgatcg aagaaatcaa atacaacttc agctaaaggt aattcataaa caatatttac    480

acgaatatca tctaaatagt ccatatttat aaattgtcca cgtttacgtt gacataattc    540

cattactgca cctacatagt catttggaac catcatagtt gcacgaacat atggctcaaa    600

tattttatca attttatcac gatctggcat ttgtgctggg ttatcaaccg tcacttctga    660

accgtccctt aaaatacatt gataaattac agatggtgct gttgcaatta attcaatgcc    720

aaattctctt tcaattcttt cttgaattat ttccatgtgt aacataccta agaaaccagt    780

tctataacca aaacctaatg cttgtgacga ttcaggctca aattctaatg atgcatcatt    840

caattgtaat ttttctaatg cttctcttaa atcattataa tttttgttat ctattgggaa    900

cagtccgcaa tataccattg gattcatttt cttataacct tgcaatggtt ctgatgcagg    960

tctactagct aatgtgatgg tgtcaccaac cctagaatca tcaacatttt taatacttgc   1020

aataatataa ccaacatcac caactgttaa ttcatcaact ggaagctgct taggtgtatt   1080

aattccaact tctgttactt cgaactcttt accagtggcc atcattcgaa ttttatctcc   1140

agctttaaca acaccgtcta caattcttat cgatgaaatt acccctctat atggatcata   1200

ctcagaatca aatattaatg cttttagtgg tgcttctggg tcaccatctg gagctggcac   1260

aacttcaact attttctcta gtatctcttc aattccaatg ttagatttag cacttgctaa   1320

aacaacatcg tcttggtcta aacctatcat atcttcaatt tcttgtttca cgcgttcagg   1380

ttctgcagca ggtaaatcaa ttttgttaat aacaggcaat aactctaact cattatctaa   1440

tgccaaataa acatttgcta atgtttgtgc ttcgatacct tgagccgcat ctactactaa   1500

aatcgcaccc tcacaagctg ccaaagaacg tgacacttca tatgtaaaat cgacgtgtcc   1560

aggcgtatcg attaaatgga atgtataagt atttccatct ttagcttcgt actttaaacg   1620

aactgcgttt aatttgattg taataccacg ttctctttct aaatccattg aatctagtaa   1680

ctgatcttgc atatctcttg tttcaactga tttggtattt tctaaaattc tatcagccaa   1740

tgtagatttt ccgtggtcaa tatgtgctat aatcgagaaa ttccttatat tctctcttct   1800
```

ttttaagcgt tgctcattat ccat 1824

<210> SEQ ID NO 123
<211> LENGTH: 1824
<212> TYPE: DNA
<213> ORGANISM: Staphylococcus aureus

<400> SEQUENCE: 123
ttattcatca tccattttca atacagccaa gaaagcatct tgtggaattt caacattacc 60
aactgctttc atcttagctt tacctgcttt ttgtttttca agtaatttac gtttacggct 120
tatgtcaccg ccataacatt tagctaaaac gtttttaccc attgatttaa tatttgtacg 180
cgctacaatt ttttgtccta ttgcagcctg tacaggtact tcaaattgct gtcttggaat 240
taacgtttta agtttttcaa ctaatgcttt accacgttca tatgcaaaat ctctatgaac 300
tatgaagctt agcgcatcca ctttatcacc atttaataaa atatccatct tgactaaatt 360
actttcttta ttttcgatga attcataatc aaatgatgca tatcctttag tattagattt 420
aagttgatcg aagaaatcaa atacaacttc agctaaaggt aattcataaa caatatttac 480
acgaatatca tctaaatagt ccatatttat aaattgtcca cgtttacgtt gacataattc 540
cattactgca ccgacatagt catttggaac catcatagtt gcacgaacat atggctcaaa 600
tattttatca attttatcac gatctggcat ttgtgctggg ttatcaaccg tcacttctga 660
cccgtccctt aaaacacatt gataaattac agatggtgca gttgcaatta attcaatacc 720
aaattctctt tcaattcttt cttgaattat ttccatgtgt aacataccta agaaaccagt 780
tctataacca aaacctaatg cttgtgacga ttcaggctca aattctaatg atgcatcatt 840
caattgtaat ttttctaatg cttctcttaa atcattataa tttttgttat ctattgggaa 900
cagtccgcaa tataccattg gattcatttt cttataacct tgcaatggtt ctgatgcagg 960
tctactagct aatgtgatgg tgtcaccaac cctagaatca tcaacatttt taatacttgc 1020
aataatataa ccaacatcac caactgttaa ttcatcaact ggaagctgct taggtgtatt 1080
aattccaact tctgttactt cgaactcttt accagtggcc atcattcgaa ttttatctcc 1140
ggctttaaca acaccgtcca caattcttat cgatgaaatt acccctctat atggatcata 1200
ctcagaatca aatattaacg cttttagtgg tgcttctggg tcaccatctg gagctggcac 1260
aacttcaact attttctcta gtatctcttc aattccaatg ttagatttag cacttgctaa 1320
aacaacatcg tcttggtcta aacctatcat atcttcaatt tcttgtttca cgcgttcagg 1380
ttctgcagca ggtaaatcaa ttttgttaat aacaggcaat aactctaact cattatctaa 1440
tgctaaataa acatttgcta atgtttgtgc ttcgatacct tgagccgcat ctactactaa 1500
aatcgcgccc tcacaagctg ccaaagaacg tgacacttca tatgtaaaat cgacgtgtcc 1560
aggcgtatcg attaaatgga atgtataagt atttccatct ttagcttcgt actttaaacg 1620
tactgcgttt aatttgattg taataccacg ttctctttct aaatccattg aatctagtaa 1680
ctgatcttgc atatctcttg tttcaactga tttggtattt tctaaaattc tatcagccaa 1740
tgtagatttt ccgtggtcaa tatgtgctat aatcgagaaa ttccttatat tctctcttct 1800
ttttaagcgt tgctcattat ccat 1824

<210> SEQ ID NO 124
<211> LENGTH: 1824
<212> TYPE: DNA
<213> ORGANISM: Staphylococcus aureus

<400> SEQUENCE: 124
ttattcgtca tccattttca atacagccaa gaaagcatcc tgtggaattt caacattacc 60
aactgctttc atcttagctt tacctgcttt ttgtttttca agtaatttac gtttacggct 120
tatgtcaccg ccataacatt tagctaaaac gtttttaccc attgatttaa tatttgtacg 180
cgctacaatt ttttgtccta ttgcagcctg tacaggtact tcaaattgct gtcttggaat 240
taacgtttta agtttttcaa ctaatgcttt accacgttca tatgcaaaat ctctatgaac 300
tatgaagctt agcgcatcca ctttatcacc gtttaataaa atatccatct taactaaatt 360
actttcttta ttttcgatga attcataatc aaatgatgca tatcctttag tattagattt 420
aagttgatcg aagaaatcaa atacaacttc agctaaaggt aattcataaa caatatttac 480
acgaatatca tctaaatagt ccatatttat aaattgtcca cgtttacgtt gacataattc 540
cattactgca cctacatagt catttggaac catcatagtt gcacgaacat atggctcaaa 600
tattttatca attttatcac gatctggcat ttgtgctggg ttatcaaccg tcacttctga 660
accgtccctt aaaatacatt gataaattac agatggtgct gttgcaatta attcaatgcc 720
aaattctctt tcaattcttt cttgaattat ttccatgtgt aacataccta agaaaccagt 780
tctataacca aaacctaatg cttgtgacga ttcaggctca aattctaatg atgcatcatt 840
caattgtaat ttttctaatg cttctcttaa atcattataa tttttgttat ctattgggaa 900
cagtccgcaa tataccattg gattcatttt cttataacct tgcaatggtt ctgatgcagg 960
tctactagct aatgtgatgg tgtcaccaac cctagaatca tcaacatttt taatacttgc 1020
aataatataa ccaacatcac caactgttaa ttcatcaact ggaagctgct taggtgtatt 1080
aattccaact tctgttactt cgaactcttt accagtcgcc atcattcgaa ttttatctcc 1140
ggctttaaca acaccgtcta caattcttat cgatgaaatt acccctctat atggatcata 1200
ctcagaatca aatattaacg cttttagtgg tgcttctggg tcgccatctg gagctggcac 1260
aacttcaact attttctcta gtatctcttc aattccaatg ttagatttag cacttgctaa 1320
aacaacatcg tcttggtcta aacctatcat atcttcaatt tcttgtttca cgcgttcagg 1380
ttctgcagca ggtaaatcaa ttttgttaat aacaggcaat aactctaact cattatctaa 1440
tgctaaataa acatttgcta atgtttgtgc ttcgatacct tgagccgcat ctactactaa 1500
aatcgcgccc tcacaagctg ccaaagaacg tgacacttca tatgtaaaat cgacgtgtcc 1560
aggcgtatcg attaaatgga atgtataagt atttccatct ttagcttcgt actttaaacg 1620
aactgcgttt aatttgattg taataccacg ttctctttct aaatccattg aatctagtaa 1680
ctgatcttgc atatctcttg tttcaactga tttggtattt tctaaaattc tatcagccaa 1740
tgtagatttt ccgtggtcaa tatgtgctat aatcgagaaa ttccttatat tctctcttct 1800
ttttaagcgt tgctcattat ccat 1824

<210> SEQ ID NO 125
<211> LENGTH: 1824
<212> TYPE: DNA
<213> ORGANISM: Staphylococcus aureus

<400> SEQUENCE: 125
ttattcatca tccattttca atacagccaa gaaagcatct tgtggaattt caacattacc 60
aactgctttc atcttagctt tacctgcttt ttgtttttca agtaatttac gtttacggct 120
tatgtcaccg ccataacatt tagctaaaac gtttttaccc attgatttaa tatttgtacg 180
cgctacaatt ttttgtccta ttgcagcctg tacaggtact tcaaattgct gtcttggaat 240
taacgtttta agtttttcaa ctaatgcttt accacgttca tatgcaaaat ctctatgaac 300
tatgaagctt agcgcatcca ctttatcacc atttaataaa atatccatct tgactaaatt 360
actttcttta ttttcgatga attcataatc aaatgatgca tatcctttag tattagattt 420
aagttgatcg aagaaatcaa atacaacttc agctaaaggt aattcataaa caatatttac 480
acgaatatca tctaaatagt ccatatttat aaattgtcca cgtttacgtt gacataattc 540
cattactgca ccgacatagt catttggaac catcatagtt gcacgaacat atggctcaaa 600
tattttatca attttatcac gatctggcat ttgtgctggg ttatcaaccg tcacttctga 660
accgtccctt aaaacacatt gataaattac agatggtgca gttgcaatta attcaatacc 720
aaattctctt tcaattcttt cttgaattat ttccatgtgt aacataccta agaaaccagt 780
tctataacca aaacctaatg cttgtgacga ttcaggctca aattctaatg atgcatcatt 840
caattgtaat ttttctaatg cttctcttaa atcattataa tttttgttat ctattgggaa 900
cagtccgcaa tataccattg gattcatttt cttataacct tgcaatggtt ctgatgcagg 960
tctactagct aatgtgatgg tgtcaccaac cctagaatca tcaacatttt taatacttgc 1020
aataatataa ccaacatcac caactgttaa ttcatcaact ggaagctgct taggtgtatt 1080
aattccaact tctgttactt cgaactcttt accagtggcc atcattcgaa ttttatctcc 1140
ggctttaaca acaccgtcca caattcttat cgatgaaatt acccctctat atggatcata 1200
ctcagaatca aatattaacg cttttagtgg tgcttctggg tcaccatctg gagctggcac 1260
aacttcaact attttctcta gtatctcttc aattccaatg ttagatttag cacttgctaa 1320
aacaacatcg tcttggtcta aacctatcat atcttcaatt tcttgtttca cgcgttcagg 1380
ttctgcagca ggtaaatcaa ttttgttaat aacaggcaat aactctaact cattatctaa 1440
tgctaaataa acatttgcta atgtttgtgc ttcgatacct tgagccgcat ctactactaa 1500
aatcgcgccc tcacaagctg ccaaagaacg tgacacttca tatgtaaaat cgacgtgtcc 1560
aggcgtatcg attaaatgga atgtataagt atttccatct ttagcttcgt actttaaacg 1620
tactgcgttt aatttgattg taataccacg ttctctttct aaatccattg aatctagtaa 1680
ctgatcttgc atatctcttg tttcaactga tttggtattt tctaaaattc tatcagccaa 1740
tgtagatttt ccgtggtcaa tatgtgctat aatcgagaaa ttccttatat tctctcttct 1800
ttttaagcgt tgctcattat ccat 1824

<210> SEQ ID NO 126
<211> LENGTH: 1824
<212> TYPE: DNA
<213> ORGANISM: Staphylococcus epidermidis

<400> SEQUENCE: 126
ttattcatcg tccattttta atactgctaa aaatgcatct tgcggaattt ctacattgcc 60
tactgctttc attttagctt tacctgcttt ttgtttttct aaaagtttc gtttacgact 120 gatatctcca ccataacatt tagataaaac atttttaccc atagatttaa tgtttgttcg 180
tgcaacaatt ttttgaccaa tagccgcctg aactggcact tcaaattgtt gtcgtggaat 240
taatgttttt aatttttcga caagcgcttt ccctctttca tatgcaaaat ctctatggac 300
aataaaactt agagcatcaa ctttatctcc attcagtaat atgtccattt taacaagatt 360
actttcttta ttctcaataa attcataatc aaaagaagca taccttttg tgttagattt 420 aagttgatca aagaaatcga aaactacttc tgataatgga atttcataaa caatattaac 480

```
tcttatatca tcaagataat ccatgtttat aaattgacct cttttacgtt gacataattc    540
catcactgca cctacataat cattcggcac catcatcgta gctttgacaa atggttcata    600
aatatgttct attttatctc tttcgggcat ttgtgctgga ttatcaactg aaacttcaga    660
accatctttt aagatacatt gatagataac agaaggcgct gttgcaatga gttcaatacc    720
aaattctctt tcaattcttt cttgaataat ctccatatgt aacattccta aaaatccagt    780
tctgtatcca aaaccaagtg cttgtgaaga ctctggttca aactctaagg atgcgtcatt    840
aagttgtaat ttttctaaag cttctcttag gtcattatag tctttattgt caatagggaa    900
tagaccacaa aataccattg gattcatctt tttatatcct tgtaacggtt tgtcagcagg    960
tctttcagct aaagtaattg tgtcacctac tctagaatca tcaacatttt tgatacttgc   1020
gataatataa cccacatcac caactgttaa ttcttctacc ggtagttgct taggtgtatt   1080
gattccgact tctgtaactt caaattcttt accggtagcc atcattttaa tcctatctcc   1140
agctttaaca acaccatcaa taattcgaat tgaagatatt actcctctgt atggatcata   1200
ttctgaatca aagataagtg ctttaagtgg ggcttctgga tcaccgtccg gtgctggtac   1260
aacatcaact attttctcta aaatttcttc aatacctata tttgacttag cacttgcaag   1320
tactacatct tcttgatcta tacctataac atcttctaat tcttgcttaa ctctatcggg   1380
ctcagctgca ggcaagtcta ttttattaac aactggcaaa agttccaaat cgttatctaa   1440
tgctaaataa acgtttgcta aggtttgtgc ttctatacct tgggcagcat caactacaag   1500
aattgcacct tcacatgcag ctaatgagcg agaaacctca tatgtaaagt cgacatgtcc   1560
tggtgtatct atcaaatgaa atgtgtaagt ttctccatct ttagcttcgt attttaatcg   1620
aacagcattt agtttaatag tgatgcctcg ttctctttcc aaatccatag agtcaagtaa   1680
ttgatcttgc atttctcgag tttcaactga ttttgtattc tctaaaattc gatcagctaa   1740
tgtcgattta ccatggtcta tatgagcaat aatggagaaa tttctaatat tttctcttct   1800
attgtatcgt tcttgcttat ccat                                          1824
```

<210> SEQ ID NO 127
<211> LENGTH: 1824
<212> TYPE: DNA
<213> ORGANISM: Staphylococcus epidermidis

<400> SEQUENCE: 127

```
ttattcatcg tccattttta atactgctaa aaatgcatct tgcggaattt ctacattgcc     60
tactgctttc attttagctt tacctgcttt ttgtttttct aaaagttttc gtttacgact    120
gatatctcca ccataacatt tagataaaac atttttaccc atagatttaa tgtttgttcg    180
tgcaacaatt ttttgaccaa tagccgcctg aactggcact tcaaattgtt gtcgtggaat    240
taatgttttt aatttttcga caagcgcttt ccctctttca tacgcaaaat ctctatggac    300
aataaaactt agagcatcaa ctttatctcc attcagtaat atgtccattt taacaagatt    360
actttcttta ttctcaataa attcataatc aaaagaagca taccttttg tgttagattt    420
aagttgatca aagaaatcga aaactacttc tgataatgga atttcataaa caatattaac    480
tcttatatca tcaagataat ccatgtttat aaattgacct cttttacgtt gacataattc    540
catcactgca cctacataat cattcggcac catcatcgta gctttgacaa atggttcata    600
aatatgttct attttatctc tttcgggcat ttgtgctgga ttatcaactg aaacttcaga    660
accatctttt aagatacatt gataaataac agaaggcgct gttgcaatga gttcaatacc    720
aaattctctt tcaattcttt cttgaataat ctccatatgt aacattccta aaaatccagt    780
```

tctgtatcca aaaccaagtg cttgtgaaga ctctggttca aactctaagg atgcgtcatt 840
aagttgtaat ttttctaaag cttctcttag gtcattatag tctttattgt caatagggaa 900
tagaccacaa aataccattg gattcatctt tttatatcct tgtaacggtt tgtcagcagg 960
tctttcagct aaagtaattg tgtcacctac tctagaatca tcaacatttt tgatacttgc 1020
gataatataa cccacatcac caactgttaa ttcttctacc ggtagttgct taggtgtatt 1080
gattccgact tctgtaactt caaattcttt accggtagcc atcattttaa tcctatctcc 1140
agctttaaca acaccatcaa taattcgaat tgaagatatt actcctctgt atggatcata 1200
ttctgaatca aagataagtg ctttaagtgg ggcttctgga tcaccgtccg gtgctggtac 1260
aacatcaact attttctcta aaatttcttc aatacctata tttgacttag cacttgcaag 1320
tactacatct tcttgatcta tacctataac atcttctaat tcttgcttaa ctctatcagg 1380
ctcagctgca ggcaagtcta ttttattaac aactggcaaa agttccaaat cgttatctaa 1440
tgctaaataa acgtttgcta aggtttgtgc ttctatacct tgggcagcat caactacaag 1500
aattgcacct tcacatgcag ctaatgagcg agaaacctca tatgtaaagt cgacatgtcc 1560
tggtgtatct atcaaatgaa atgtgtaagt ttctccatct ttagcttcgt attttaatcg 1620
aacagcattt agtttaatag tgatgcctcg ttctctttcc aaatccatag agtcaagtaa 1680
ttgatcttgc atttctcgag tttcaactga ttttgtattc tctaaaattc gatcagctaa 1740
tgtcgattta ccatggtcta tatgagcaat aatggagaaa tttctaatat tttctcttct 1800
attgtatcgt tcttgcttat ccat 1824

<210> SEQ ID NO 128
<211> LENGTH: 1824
<212> TYPE: DNA
<213> ORGANISM: Staphylococcus haemolyticus

<400> SEQUENCE: 128
ctattcatca tccattttta gtacagctag gaaagcatct tgaggaattt caacactacc 60
aacggctttc attttagcct tacctgcttt ttgtttttca agtaacttac gtttacggct 120
aatatcccca ccataacatt tagataatac atttttaccc attgatttga tgtttgttct 180
tgcaacaatt ttttggccaa tagctgcttg tacaggtact tcaaattgtt gacgtggtat 240
aagcgttttt aatttttcaa ctaatgcttt tccacgttcg tatgcaaagt ctttatggac 300
aataaagctt aaagcatcaa ctttatcccc attaagtagg atgtccattt tcactaagtt 360
actttcttta ttttcaataa attcataatc aaatgaagcg taacctttag tgttggattt 420
aagttgatca aagaaatcaa aaacaacttc agaaagtggt atctcgtata cgatattaac 480
tctaatatca tctaaataat ccatattaat aaattgtcca cgtttacgtt ggcataactc 540
cataactgct ccaacgtaat catttggaac catcattgta gctttcacat atggttcata 600
aattgagtca atcttatctc tttctggcat ttgagccgga ttatctactg taacctctga 660
tccatccttc ataatacatt gataaattac tgatggcgcg gtagcaatca attcaatacc 720
aaattctctt tcaattcttt cttgaatgat ttccatgtga agcattccta agaaacctgt 780
tctaaaacca aaaccaagag cctgagaaga ttctggctca aattctaatg aagcgtcatt 840
taattgtaat ttttcaagcg cttctcttaa atcattatag tctttatttt caattgggaa 900
caaaccacaa tataccattg ggttcatttt tttataacct tttaatggtg cttcagctgg 960
tctattagca tgagtaattg tatcacccac acgtgagtca tcaacatttt tgatgcttgc 1020
aataatatac cctacatcac ctacagttag ttcttctata ggtagttgtt taggagtatt 1080
aatgcctact tcactaactt caaattcttt acctgtagcc atcattttaa ttttatcacc 1140
agctttaaca acgccttcca tcacacgtat tgatgaaata acacctctat aagggtcgta 1200
ttctgaatca aaaattaatg ctttcaatgg ttcactaggg tcaccttcag gtggtgggac 1260
aacttctaca attttctcta aaatatcttc aataccaata tttgactttg cacttgccag 1320
tactacatcg tcttgattta aaccaattac atcttctaat tcttgtttta ctctttcagg 1380
ttcagctgca ggtaaatcaa ttttatttac aacaggtaat aattctagat cattatcaag 1440
tgctaagtat acgtttgcta atgtttgtgc ttcaatacct tgtgctgcat ccaccactaa 1500
tattgcaccc tcacatgctg ctaaagatcg tgaaacctcg tatgaaaagt ctacatgccc 1560
tggtgtatca attaaatgaa atgtatatgt ttgaccatca tttgcttcat attttaatcg 1620
cacggcattt aatttaattg tgatgccacg ttctctttca agatccattg aatctaataa 1680
ttgatcttgc atttctcttg tttctacaga tttagtattt tctaaaattc tatctgctaa 1740
tgttgattta ccatgatcaa tatgagcaat aatagaaaaa tttcgtatat tttctcttct 1800
gttatagcgt tcttgcatat ccat 1824

<210> SEQ ID NO 129
<211> LENGTH: 1824
<212> TYPE: DNA
<213> ORGANISM: Staphylococcus saprophyticus

<400> SEQUENCE: 129
ttaatcttca tccattttga gtactgcaag gaaagcatct tgtggaattt ctacatttcc 60
cactgctttc attttggctt tacccgcttt ttgtttttct aataattttc tcttacgtgt 120
aatgtctccg ccataacatt tagacaatac atttttcccc atagatttaa tgtttgttct 180
cgcgacaatt ttttgtccta cagcagcttg tactggtact tcaaattgtt gtcttggtat 240
taatgttttc aacttatcga caagagtttt accacgttcg tatgcaaatt ctttatgcac 300
gataaagcta agagcatcga ctttttcacc atttaataaa atatccatct taaccaggtc 360
actttcttta ttatcaataa attcataatc aaaagaagca tagcctttag tattagattt 420
taattgatcg aagaaatcaa atactacttc tgataatgga atttcataaa taatattcac 480
tcgaatatca tccatgtatt ccatattaat aaattgacca cgtttacgtt gacacaattc 540
cattacagca ccgacataat catttggtac catcatagtc gcacgtacaa acggctcata 600
aatggtttct attttatcgc gatctggcat attcgctgga ttatctacag atacttcctc 660
accagatttt aatatacatt ggtaaattac cgatggcgca gttgcgatta attcaatgcc 720
gaattcacgt tcaattcttt cttgaataat ttccatgtgt aacataccta aaaaaccagt 780
acggtagcca aaacctaatg cttgagaaga ttctggttca aattctaatg aggcatcgtt 840
taattgcagc ttctctaaag cttctcttaa atcgttatag tctttgttat caatagggaa 900
taatccacag aataccattg gattcatttt tttataacct tgtagtggcg cttcagcagg 960
tctctctgca tgcgtgattg tatcacctac acgggaatca tcaacatttt taatactagc 1020
aatgatataa cctacatcac ccactgttaa ttcatctact gataattgtt ttggggtgtt 1080
aatacctact tcagttactt caaattcttt tccagtagcc atcattttga tacgatctcc 1140
agctttaaca acgccttcca taacacgtat ggatgaaatg acacctctat atggatcata 1200
ctcagaatca aatattaaag cttttaaagg tgcttctgga tcaccttcag gtggtggtac 1260
tacctcaact atttttcca atatatcttc aatacctatg tttgattttg cacttgcaag 1320
tacgacatcc tctttatcaa taccaataac gtcttcaagt tcttgtttaa cgcgttctgg 1380
ctcagctgca ggcaaatcaa ttttattgat aacaggtaga agctctaaat cattatccag 1440
tgctaaatag acattagcta gtgtttgtgc ctcaatacct tgtgctgcgt ccactactaa 1500
aatagcaccc tcacacgctg caagtgatct agatacttca tatgtaaaat ctacgtgtcc 1560
tggtgtatca atcaaatgga acgtgtatgt ttctccatcc ttcgcttcgt atttcaatcg 1620
tactgcgttt agttttatag taataccgcg ttctctctct aaatccatag aatctagcaa 1680
ctgtgattgc atgtctcttg tttcaactga tttagtattt tctaaaattc tatcagctaa 1740
agtagattta ccatggtcta tatgtgcgat aatagaaaag tttcttatat ttttgcgtcg 1800
attataacga tcttgtttat ccat 1824

<210> SEQ ID NO 130
<211> LENGTH: 1839
<212> TYPE: DNA
<213> ORGANISM: Lactobacillus sakei

<400> SEQUENCE: 130
ttatttacct ttggtatctt catcattcat cttaagaatg gacatgaagg cttcctgcgg 60
cacttccact gagcccacgg atttcatccg tttcttccca gccttttgct tttctaacaa 120
tttccgtttc cgggtgatgt caccaccgta acacttggca agcacgtttt tccggaaagc 180
tttaacggtt gaacgggcaa taatcttatt cccgatagcg gcttggattg gcacttcgaa 240
ttgttgacgc ggaatcgttt ctttcaactt accaacaatc acacggctcc gttcaaaggc 300
aaagtcccga tgcacgatga aactcaaggc atcaaccgct tcaccattca agagaatatc 360
aatcttaacc aggtcactgg cacgatagcc tgtcacttcg taatcaaacg atgcgtaacc 420
cttggtgttt gatttcaaat catcgaagaa atcaaaaatg atttcagaaa gtggcatgtt 480
gtagatcaca ttaacacggt acgtatctaa ataatccatc gtcacgaatt cgccccgttt 540
acgttgggct aattccatca cagccccaac ataatcgtta gggaccatga ttgacgcttt 600
gacgtatggt tctttaactt ctgaaatatt tgatgtttct ggcatttctg atgggttatc 660
aatcacttct tcagtcccat cagtcaaggc aacgtggtaa tcaaccgatg gtgctgtcat 720
gatcaagtct aaattaaatt cacgttccaa tcgttcttga acaacatcca tgtgtaacag 780
acccaagaaa ccacaccgga acccaaagcc taaagcttgc gatgattctg gttcgaactc 840
taaagccgca tcgtttaatt gtaatttctc aagcgcttca cgtaaatcat taaacttcgc 900
attatcaacg ggatacatcc ctgaataaac cattggttgg atatgacgat aaccatcaag 960
tggtgcatca gctggattat cagctaaagt gaccgtatcc ccaacgcgtg tatcttgaat 1020
tgttttgatg ctagctgtga tataaccaac atcaccgacc attaagaaat cacgtttaac 1080
cgctttgggt gacatcacac caacttctgt gacttcaaat tctttaccgc tgttcattaa 1140
acgaatcttg tcgccgactt taaccgttcc atcgaccact cgaatattta aaacaacccc 1200
gcggtaacta tcataatttg aatcaaaaat taaggctttt aatggcgctt ctaaatcacc 1260
agttggggct ggtacatccg tcactagttt ttcaagaatt tcttcaatcc caatcccact 1320
tttggcactg gcaagaacgg cttctgacgc atctaaccca atcatttctt caatttcagc 1380
cttaacaaca tcaggttgcg ctgatgggag gtcaatttta ttaataaccg gtacgatttc 1440
aagatcatcg tcgactgcta aataaacgtt ggccaatgtt tgggcttcaa cgccttgcgc 1500
tgcatcaaca actaataagg ccccttcgca ggccgccaaa cttcgtgaca cttcatatga 1560

-continued aaaatcgaca tgccctggcg tatcgattaa atggaaaata taagtttcgc catctttagc 1620
atggtagtgc aattccaccg cgttcaactt aatggtaatc ccacgttcac gttctaattc 1680
catgtcatct aagacttgcg cttgcatatc gcgcttggca atagtatccg tcatctcaag 1740
aattcgatca gctaatgttg atttaccatg atcaatatgc gcgatgatcg aaaagttacg 1800
aatgtgtttt tgccggtcta acatttctgc gtaatccat 1839

<210> SEQ ID NO 131
<211> LENGTH: 1839
<212> TYPE: DNA
<213> ORGANISM: Lactobacillus delbrueckii

<400> SEQUENCE: 131
ttacttgccg ttgatgtcat cgtcattcat ccgtaatact gccataaagg cgtcctgcgg 60
gacttccacc cggccaactg acttcatccg cttcttgccc cgcttctgct tctccagaag 120
cttggcccgc cggtccgggt caccggtgtg gatcttccag gtaacgtctt ttcggtaagg 180
cttgatcgta gcccgggaaa tgatcttgga cccgattgct ccttggatgt cgacttggaa 240
gttttgccgc gggatcagct tcttcaacag gctgcacatc tggacggccc ggtcccgggc 300
ttcttcgcgg tgggcgatga agctcaaggc atcgattggt tccttgttca agagaatgtc 360
gatcttgacc aggttggtgg ccttgtagcc gatgatttca tagtccaaag aagcatagcc 420
cttggttgaa gacttaagct ggtcaaagaa atcgtaaata atttctgcca ggggcatttc 480
gtagatcacg ttgacccggt acttgtccag gtagtccatg gtctggaact cgccccgctt 540
gccttcacac agctgcatta cagcaccgac gaagtcgttt ggcaccatga tttccgcctt 600
gacgtaaggc tcttgcaatt ccttgtattc accggcatcc ggcaggtcag ccgggttgtc 660
gatcagcttg acctcaccag tcggcatgat agcgtggtag tcaactgacg gcgcggtcat 720
gatgaggtcc aggtcaaatt cctgctccaa gcgctcttgc acgacgtcca tgtgcaaaag 780
gcccaaaaag ccgcagcgga aaccaaagcc cagggcttgg gaagtttccg gctcaaattc 840
cagagacgca tcgttaagct gtaatttctg cagggcttcc ttcaagtcgt catagtcccg 900
gttgtcggtt ggatacatac cagagtagac cattggcgga atctgccggt agcctggcaa 960
agcttctgcc gtcgggtttt cagcgctggt gatggtatcc ccgacccggg tttcccggac 1020
agacttgatg ttggcagtaa tatagccaac gtccccggca atcaagatgt cttctttaac 1080
cgggtggggg ctggaaacgc cgacttcggt tacttcatac tttttgccgg tgttcatgat 1140
catgatttcg tcgcctggct taaccgtgcc ttcttcaatt ctgactgaca tgaccacccc 1200
ccggtagtca tcatacttgg agtcaaagat caaggccttg aggggcttgg tcaagtcccc 1260
agtcggcgct gagatgtcgg tcacgattct ttccaaaagt tccggaatcc ctgccccggt 1320
cttgccggaa acttccacgg cgtcgctggc gtctaagccc agcatgtcgc cgatttcgct 1380
cttggccatg tccgggtcgg cgcttggcag gtcgatcttg tttaaaacag gcaggatttc 1440
caggtcgttt tccaaagcca ggtaagtgtt ggacagggtc tgggcctgga caccctggga 1500
ggcgtcaacg accaggacag ccccttcaca ggcagccagg gaccgggaaa cttcatagga 1560
gaagtcgacg tggccggggg tgtcgatcaa gtggaaaatg tagtcttccc cgtcattggc 1620
gtgatacttg acctgcaccg agttcatctt gatggtgatc ccccgctgcc gttcaagggg 1680
catgtcatcc agcatttgat ttttcagctg ccgcttggaa accgtgtccg tcagttccag 1740
aatccggtcg gcaatcgttg atttgccgtg gtcaacgtgg gccacgattg aaaaattgcg 1800
gatgtgcttt tggtagtctt ttaatttttc taagtccat 1839

<210> SEQ ID NO 132
<211> LENGTH: 1839
<212> TYPE: DNA
<213> ORGANISM: Lactobacillus acidophilus

<400> SEQUENCE: 132
ttatttacct tttatatcat catcattcat cttaagaaca gccataaatg catcttgagg 60
tacttctaca cgtccaacag ccttcattct cttcttaccg cgcttctgct tttcaagcaa 120
tttggcacga cgatcaggat caccagtatg gattttccaa gtaacatcct tacgatatgg 180
cttaatcgta gcacgtgaaa taatcttagc accgattgca ccttgaatat ctacctcaaa 240
gttttgtcta ggaatcaact tcttaagcat tgaggtcatt tgacgagcac gatcttgcgc 300
ttcacttctg tgtgcaataa agctaagagc atcaatcggt tccttattaa gcaaaatatc 360
aatcttgact aagtcagttg cacgataacc agtaatctca tagtcaagtg aggcatagcc 420
cttagttgat gattttaaat catcgaaaaa gtcaaaaata atctcagcta aaggcatgtt 480
gtaaataaca ttaacacgat atttatctaa ataatccatt gtaacaaatt cgccgcgttt 540
acgttggcaa agttccatta caggaccaac ataatcatta ggaaccataa tttctgcctt 600
aacgtaaggt tcttgcactt ctttatattc accagcatct ggtaaatcag atggattatc 660
aatcacctta gtcgtaccat cattcattat tgcatgatag tcaacacttg gtgcggtcat 720
gattaaatca aggtcaaact cttgctccaa tctttcttga actacgtcca tatgaagtaa 780
gccaaggaaa ccacaacgga aaccaaatcc taaagcagta gaagtttctg gttcaaattc 840
caaagcagca tcatttaatt gcaacttttg taaagcttct tttaaatcat cgtaatcacg 900
attatctact ggatacatac cagagtatac cattggtgga atttgacggt aacctggaag 960
tggttcagca gttgggtgcc cagcatcagt gattgtatca cctacacgag tttcacgaac 1020
tgatttaatg ttggcagtaa tatatcctac atcaccagcg attaaaatat ctttctttac 1080
tggatgagga cttgaaacac caacttcagt aacttcatat tccttgccag tattcataat 1140
ttgaatctta tcaccgggct taactgtacc atcttcaatt ctaactgata aaacaacccc 1200
acgataatca tcatattttg aatcgaaaat aagtgcttta agtggcgctt caatatcacc 1260
tgatggtgca ggaatgtcag ttactatctt ttccaataat tcaggtattc cttgacctgt 1320
tttcccagat acttcaacag cgtctgaagc gtcaagacct aacatttcct cgatttcttc 1380
tttagcattt tctggatcag cagaaggtaa atcaatttta ttgattactg gtacaatttc 1440
caaatcgtca tcaatggcta agtaagtatt agctaaagtt tgtgcttgaa caccttgtga 1500
agcatcaacc accaataatg caccttcaca tgcagctaag gagcgtgata cttcatatga 1560
aaagtctacg tgtcctggtg tatcaattaa gtggaaaata taatcttcgc catttttggc 1620
atgatactta acttcaaccg agttcatctt gatggtaata ccacgttgtc tttcaagtgg 1680
catatcatca agcatttgat tttttaattg tctttcagat actgtatctg ttaactctaa 1740
gattcggtca gcaattgttg acttaccatg gtcaatatgg gcaacaattg aaaagttacg 1800
aatgtgattt tgataatctt ttaatttttt tatatccat 1839

<210> SEQ ID NO 133
<211> LENGTH: 1803
<212> TYPE: DNA
<213> ORGANISM: Rickettsia prowazekii

<400> SEQUENCE: 133

-continued

```
ttattcacct ccaatttgca atgctgcaat aaatgcagat tgtgggattt ctatattacc     60

gtactgtctc attttctttt tacccgcttt ttgcttctca agtagtttac gtttacggct    120

tatatcaccg ccataacatt ttgataaaac atctttacgt aaggctttaa tagtttcacg    180

agcaataata cgactaccaa cacttgcttg aattgctata tcgatctgtt gtcttggtat    240

taaatccttt aatcttatgc ataaagccct accacgctgt tccgcacgtg atcgatgtac    300

tatagttgat aacgcatcaa caacctcccc attaactaaa atcctaagat taacaagatc    360

agaaagttca taaacatcca tttgccattc aaaacttgca taacctttag aacagctttt    420

caaacgatca taaaaatcat aaactatctc atttagcggt aatttataaa ctattttagc    480

tctatttgat atataactat gatcaagttg tatacctctt ttttctgtac aaagcgataa    540

tacagtccct ataaactcat ccggaactat tatagttgcc ttaatccatg gctcttccat    600

cgatgcgatt ttttgcaaat caggtaaatc ggctgggtta tgaatctcta agttctgacc    660

atccaacata ttgattttat agatcacact tggagcagta gtgattaaat ctaaatcgaa    720

ttccctactt aaacgttctt gtatgatctc taaatgtaat agccctaaaa aaccacacct    780

aaaacctact ccaagagctg aggagctttc catttcatac tcaaaactgg catcattaag    840

acgtaattta gctaaagaat ccttgagatg ttcgaattct gcactatctg tcggataaaa    900

accacaaaat actacgggta tattcggctt aaagccaggt agtgcttgtt cacaagattt    960

tttctcatca gtaatagtat caccaacttt acaatctgat acccgtttta tagaagctgt   1020

aaaaaaacct atttcccctg catataaaac atccgaaata tgttttttg gagtaaaaaa    1080

accaacatgc tcgacggtat aaacagaatt tgtcctcatc attttaacac gcatattttt   1140

acgtaaagca ccatcaataa tacgtaccaa aataactaca ccaagatacg gatcgtacca   1200

actatcaaca agtaacgctt ttaagatatc tgtgctactt tcttttgggg caggtaattt   1260

attgattatt gcttctagaa ctgaatcaat gcctataccg tttttagcag atattaaaac   1320

agcttcactt gcatcaatgc caattatatc ctctatttgc gtcttaacat aatcaggttc   1380

tgaagctgct aaatcaatct tgttaagcac tggtacaatc aaatgatcat tcgcaattgc   1440

ttgataaaca tttgcaagag tttgagcctc tactccttga gtactatcca ctactaataa   1500

cgaaccttca catgcagcca aggacctact aacctcataa gcaaaatcaa catgacccgg   1560

agtatccatg agattcaaat agtaagtatt accgttttta gctttatata caagccgtac   1620

agtttgggct ttaatagtaa tacctcgttc tctctctata tccatcgaat ctaatacttg   1680

ctgactcatt tccctagcat tcaaacctcc acaatactcg attagcctat cagctaacgt   1740

agatttacca tgatctatat gagcgattat tgagaaattc cttatatatt tttgattatt   1800

cat                                                                 1803
```

<210> SEQ ID NO 134
<211> LENGTH: 1794
<212> TYPE: DNA
<213> ORGANISM: Bordetella pertussis

<400> SEQUENCE: 134

```
ctatttgtct tcgacttgca ggatggcgag gaacgcctct tgcgggattt ccacgctgcc     60

gacctgcttc atgcgcttct tgccggcctt ctgcttttcc agcaacttct tcttgcgcga    120

gatatcgccg ccatagcact tggccagcac gttcttgcgc agcgccttga cgttctcgcg    180

cgcgatgacc tccgcgccga ttgccgcctg gatggccacg tcgaacatct ggcgcgggat    240

caggccgcgc atgcgcgaaa ccacctcgcg cgcccggtag cgcgcattgt tgcggtgcgc    300
```

gatcatggcc agcgcatcga cgcggtcgcc gttgatcagc agatccacct tgaccacgtc 360
ggccgagcgg tattccacga actcgtagtc catcgacgca tagccgcgcg acaccgattt 420
cagtttgtcg aagaaatcga gcacgatctc ggccagcgga atctcgtagg tcaggtgcac 480
ctggcgcccg tggtagctca tgttgagctg gacgccgcgc ttgttgttgc acagtgtcat 540
caccggcccc acgtattcct ggggcatgaa cagcgtcacc ttgacgatgg gttcgcggat 600
atcggcgatc ttggcgattt ccggcatgcg cgacgggctt tcgatggtca cgaccgtgcc 660
gtcgcgctgt tcgacctcat agaccaccga tggcgcggtg gtgatgatgt ccatgtcgaa 720
ctcgcgctcc aggcgctcct gcacgatttc catgtgcagc agccccagga agccgcagcg 780
aaagccgaag cccagcgcct gcgacacttc gggctcgaac atcagcgcgg cgtcgttgag 840
cttcagcttt tccagcgaat cgcgcagctg gtcgtattcg gagctttcca ccggatacag 900
gccggcgaac acctgcggct tgacttcctt gaagcccggc agcggctcgg ccgccggctt 960
gcccgccagg gtgatggtgt cgcccacctt ggcgtgttcc agttccttga tgccggcgat 1020
gacaaagccc acttcgccgg ccgacaactc cggccgcggc tgcgatttgg gcgtgaacac 1080
gccgatctgc tcgcacagat gcgtggcgtg ggacgccatc agcaggatct tgtccttggg 1140
cttgagcacg ccgttgacga tgcgcaccag catgaccacg cccacgtagt tgtcgaacca 1200
cgaatcgatg atcagcgcct gcagcggcgc ggacggatcg cccttgggcg gcggcacccg 1260
cgccacgatg gattcgagga tctcgtcgat gcccatgccg gtcttggcgc tggccagcac 1320
cgcctcggac gcgtcgatgc cgatcacgtc ttcgacctcc tggcgcgcgg cttccgggtc 1380
ggcctgcggc aggtccatct tgttgagcac cggcagcact tccatgccca gttcgatggc 1440
cgtgtagcag ttggccacgg tctgggcctc gacgccctgc gaagcgtcga ccaccagcaa 1500
ggcgccttcg caggccgaca gcgaacgact gacttcgtac gagaaatcga cgtgtccggg 1560
ggtatcgatc aggttgaggt tgtagaccgt gccgtcctgc gacttgtact gcagggacgc 1620
ggtctgcgcc ttgatcgtga taccccgttc gcgctcgata tccatggaat caagcacttg 1680
cgcggacatt tcgcgctcgg ccagcccccc gcaacggtgg atcaggcgat cggcgagcgt 1740
cgatttaccg tgatcaatgt gggcaatgat ggaaaagttg cggatatgct gcat 1794

<210> SEQ ID NO 135
<211> LENGTH: 1794
<212> TYPE: DNA
<213> ORGANISM: Bordetella pertussis

<400> SEQUENCE: 135
ctatttgtct tcgacttgca ggatggcgag gaacgcctct tgcgggattt ccacgctgcc 60
gacctgcttc atgcgcttct tgccggcctt ctgcttttcc agcaacttct tcttgcgcga 120
gatatcgccg ccatagcact tggccagcac gttcttgcgc agcgccttga cgttctcgcg 180
cgcgatgacc tccgcgccga ttgccgcctg gatggccacg tcgaacatct ggcgcgggat 240
caggccgcgc atgcgcgaaa ccacctcgcg cgcccggtag cgcgcattgt tgcggtgcgc 300
gatcatggcc agcgcatcga cgcggtcgcc gttgatcagc agatccacct tgaccacgtc 360
ggccgagcgg tattccacga actcgtagtc catcgacgca tagccgcgcg acaccgattt 420
cagtttgtcg aagaaatcga gcacgatctc ggccagcgga atctcgtagg tcaggtgcac 480
ctggcgcccg tggtagctca tgttgagctg gacgccgcgc ttgttgttgc acagtgtcat 540
caccggcccc acgtattcct ggggcatgaa cagcgtcacc ttgacgatgg gttcgcggat 600

```
atcggcgatc ttggcgattt ccggcatgcg cgacgggctt tcgatggtca cgaccgtgcc    660
gtcgcgctgt tcgacctcat agaccaccga tggcgcggtg gtgatgatgt ccatgtcgaa    720
ctcgcgctcc aggcgctcct gcacgatttc catgtgcagc agccccagga agccgcagcg    780
aaagccgaag cccagcgcct gcgacacttc gggctcgaac atcagcgcgg cgtcgttgag    840
cttcagcttt tccagcgaat cgcgcagctg gtcgtattcg gagctttcca ccggatacag    900
gccggcgaac acctgcggct tgacttcctt gaagcccggc agcggctcgg ccgccggctt    960
gcccgccagg gtgatggtgt cgcccacctt ggcgtgttcc agttccttga tgccggcgat   1020
gacaaagccc acttcgccgg ccgacaactc cggccgcggc tgcgatttgg gcgtgaacac   1080
gccgatctgc tcgcacagat gcgtggcgtg ggacgccatc agcaggatct tgtccttggg   1140
cttgagcacg ccgttgacga tgcgcaccag catgaccacg cccacgtagt tgtcgaacca   1200
cgaatcgatg atcagcgcct gcagcggcgc ggacggatcg cccttgggcg gcggcacccg   1260
cgccacgatg gattcgagga tctcgtcgat gcccatgccg gtcttggcgc tggccagcac   1320
cgcctcggac gcgtcgatgc cgatcacgtc ttcgacctcc tggcgcgcgg cttccgggtc   1380
ggcctgcggc aggtccatct tgttgagcac cggcagcact tccatgccca gttcgatggc   1440
cgtgtagcag ttggccacgg tctgggcatc gacgccctgc gaagcgtcga ccaccagcaa   1500
ggcgccttcg caggccgaca gcgaacgact gacttcgtac gagaaatcga cgtgtccggg   1560
ggtatcgatc aggttgaggt tgtagaccgt gccgtcctgc gacttgtact gcagggacgc   1620
ggtctgcgcc ttgatcgtga taccccgttc gcgctcgata tccatggaat caagcacttg   1680
cgcggacatt tcgcgctcgg ccagcccccc gcaacggtgg atcaggcgat cggcgagcgt   1740
cgatttaccg tgatcaatgt gggcaatgat ggaaaagttg cggatatgct gcat         1794
```

<210> SEQ ID NO 136
<211> LENGTH: 1794
<212> TYPE: DNA
<213> ORGANISM: Bordetella pertussis

<400> SEQUENCE: 136

```
ctatttgtct tcgacttgca ggatggcgag gaacgcctct tgcgggattt ccacgctgcc     60
gacctgcttc atgcgcttct tgccggcctt ctgcttttcc agcaacttct tcttgcgcga    120
gatatcgccg ccatagcact tggccagcac gttcttgcgc agcgccttga cgttctcgcg    180
cgcgatgacc tccgcgccga ttgccgcctg gatggccacg tcgaacatct ggcgcgggat    240
caggccgcgc atgcgcgaaa ccacctcgcg cgcccggtag cgcgcattgt tgcggtgcgc    300
gatcatggcc agcgcatcga cgcggtcgcc gttgatcagc agatccacct tgaccacgtc    360
ggccgagcgg tattccacga actcgtagtc catcgacgca tagccgcgcg acaccgattt    420
cagtttgtcg aagaaatcga gcacgatctc ggccagcgga atctcgtagg tcaggtgcac    480
ctggcgcccg tggtagctca tgttgagctg gacgccgcgc ttgttgttgc acagtgtcat    540
caccggcccc acgtattcct ggggcatgaa cagcgtcacc ttgacgatgg gttcgcggat    600
atcggcgatc ttggcgattt ccggcatgcg cgacgggctt tcgatggtca cgaccgtgcc    660
gtcgcgctgt tcgacctcat agaccaccga tggcgcggtg gtgatgatgt ccatgtcgaa    720
ctcgcgctcc aggcgctcct gcacgatttc catgtgcagc agccccagga agccgcagcg    780
aaagccgaag cccagcgcct gcgacacttc gggctcgaac atcagcgcgg cgtcgttgag    840
cttcagcttt tccagcgaat cgcgcagctg gtcgtattcg gagctttcca ccggatacag    900
gccggcgaac acctgcggct tgacttcctt gaagcccggc agcggctcgg ccgccggctt    960
```

gcccgccagg gtgatggtgt cgcccacctt ggcgtgttcc agttccttga tgccggcgat 1020
gacaaagccc acttcgccgg ccgacaactc cggccgcggc tgcgatttgg gcgtgaacac 1080
gccgatctgc tcgcacagat gcgtggcgtg ggacgccatc agcaggatct tgtccttggg 1140
cttgagcacg ccgttgacga tgcgcaccag catgaccacg cccacgtagt tgtcgaacca 1200
cgaatcgatg atcagcgcct gcagcggcgc ggacggatcg cccttgggcg gcggcacccg 1260
cgccacgatg gattcgagga tctcgtcgat gcccatgccg gtcttggcgc tggccagcac 1320
cgcctcggac gcgtcgatgc cgatcacgtc ttcgacctcc tggcgcgcgg cttccgggtc 1380
ggcctgcggc aggtccatct tgttgagcac cggcagcact tccatgccca gttcgatggc 1440
cgtgtagcag ttggccacgg tctgggcctc gacgccctgc gaagcgtcga ccaccagcaa 1500
ggcgccttcg caggccgaca gcgaacgact gacttcgtac gagaaatcga cgtgtccggg 1560
ggtatcgatc aggttgaggt tgtagaccgt gccgtcctgc gacttgtact gcagggacgc 1620
ggtctgcgcc ttgatcgtga taccccgttc gcgctcgata tccatggaat caagcacttg 1680
cgcggacatt tcgcgctcgg ccagccccccc gcaacggtgg atcaggcgat cggcgagcgt 1740
cgatttaccg tgatcaatgt gggcaatgat ggaaaagttg cggatatgct gcat 1794

<210> SEQ ID NO 137
<211> LENGTH: 1794
<212> TYPE: DNA
<213> ORGANISM: Bordetella bronchiseptica

<400> SEQUENCE: 137
ttacttgtct tcgacttgca ggatggcgag gaacgcctct tgcgggattt ccacgctgcc 60
gacctgcttc atgcgcttct tgccggcctt ctgcttttcc agcaacttct tcttgcgcga 120
gatatcgccg ccatagcact tggccagcac gttcttgcgc agcgccttga cgttctcgcg 180
cgcgatgacc tccgcgccga ttgccgcctg gatggccacg tcgaacatct ggcgcgggat 240
caggccgcgc atgcgcgaaa ccacctcgcg cgcccggtag cgcgcattgt tgcggtgcgc 300
gatcatggcc agcgcatcga cgcggtcgcc gttgatcagc agatccacct tgaccacgtc 360
ggccgagcgg tattccacga actcgtagtc catcgacgca tagccgcgcg acaccgattt 420
cagtttgtcg aagaaatcga gcacgatctc ggccagcgga atctcgtagg tcaggtgcac 480
ctgacgcccg tgatagctca tgttgagctg gacgccgcgc ttgttgttgc acagcgtcat 540
caccggcccc acgtattcct ggggcatgaa cagcgtcacc ttgacgatgg gttcgcggat 600
atcggcgatc ttggcgattt ccggcatgcg cgacgggctt tcgatggtca cgaccgtgcc 660
gtcgcgctgt tcgacctcat agaccaccga tggcgcggtg gtgatgatgt ccatgtcgaa 720
ctcgcgctcc aggcgctcct gcacgatttc catgtgcagc agccccagga agccgcagcg 780
aaagccgaag cccagcgcct gcgacacttc gggttcgaac atcagcgcgg cgtcgttgag 840
cttcagcttt tccagcgaat cgcgcagctg gtcgtattcg gagctttcca ccggatacag 900
gccggcgaac acctgcggct tgacttcctt gaagcccggc agcggctcgg ccgccggctt 960
gcccgccagg gtgatggtgt cgcccacctt ggcgtgttcc agttccttga tgccggcgat 1020
gacaaagccc acttcgccgg ccgacaactc cggccgcggc tgcgatttgg gcgtgaacac 1080
gccgatctgc tcgcacagat gcgtggcgtg ggacgccatc agcaggatct tgtccttggg 1140
cttgagcacg ccgttgacga tgcgcaccag catgaccacg cccacgtagt tgtcgaacca 1200
cgaatcgatg atcagcgcct gcagcggcgc ggacggatcg cccttgggcg gcggcacgcg 1260

-continued

```
cgccacgatg gattcgagga tttcgtcgat gcccatgccg gtcttggcgc tggccagcac   1320
cgcctcggac gcgtcgatgc cgatcacgtc ttcgacctcc tggcgcgcgg cttccggatc   1380
ggcctgcggc aggtccatct tgttgagcac cggcagcact tccacgccca gctcgatggc   1440
cgtgtagcag ttggccacgg tctgggcctc gacgccctgc gaggcgtcga ccaccagcaa   1500
ggcgccttcg caggccgaca gcgaacgact gacttcgtac gagaaatcga cgtgtccggg   1560
ggtatcgatc aggttgaggt tgtagaccgt gccgtcctgc gacttgtact gcagggacgc   1620
ggtctgcgcc ttgatcgtga taccccgttc gcgctcgata tccatggaat caagcacttg   1680
cgcggacatt tcgcgctcgg ccagcccccc gcaacggtgg atcaggcgat cggcgagcgt   1740
cgatttaccg tgatcgatgt gggcaatgat ggaaaagttg cggatatgct gcat         1794
```

<210> SEQ ID NO 138
<211> LENGTH: 1794
<212> TYPE: DNA
<213> ORGANISM: Bordetella bronchiseptica

<400> SEQUENCE: 138

```
ttacttgtct tcgacttgca ggatggcgag gaacgcctct tgcgggattt ccacgctgcc     60
gacctgcttc atgcgcttct tgccggcctt ctgcttttcc agcaacttct tcttgcgcga    120
gatatcgccg ccatagcact tggccagcac gttcttgcgc agcgccttga cgttctcgcg    180
cgcgatgacc tccgcgccga ttgccgcctg gatggccacg tcgaacatct ggcgcgggat    240
caggccgcgc atgcgcgaaa ccacctcgcg cgcccggtag cgcgcattgt tgcggtgcgc    300
gatcatggcc agcgcatcga cgcggtcgcc gttgatcagc agatccacct tgaccacgtc    360
ggccgagcgg tattccacga actcgtagtc catcgacgca tagccgcgcg acaccgattt    420
cagtttgtcg aagaaatcga gcacgatctc ggccagcgga atctcgtagg tcaggtgcac    480
ctgacgcccg tgatagctca tgttgagctg gacgccgcgc ttgttgttgc acagcgtcat    540
caccggcccc acgtattcct ggggcatgaa cagcgtcacc ttgacgatgg gttcgcggat    600
atcggcgatc ttggcgattt ccggcatgcg cgacgggctt tcgatggtca cgaccgtgcc    660
gtcgcgctgt tcgacctcat agaccaccga tggcgcggtg gtgatgatgt ccatgtcgaa    720
ctcgcgctcc aggcgctcct gcacgatttc catgtgcagc agccccagga agccgcagcg    780
aaagccgaag cccagcgcct gcgacacttc gggttcgaac atcagcgcgg cgtcgttgag    840
cttcagcttt tccagcgaat cgcgcagctg gtcgtattcg gagctttcca ccggatacag    900
gccggcgaac acctgcggct tgacttcctt gaagcccggc agcggctcgg ccgccggctt    960
gcccgccagg gtgatggtgt cgcccacctt ggcgtgttcc agttccttga tgccggcgat   1020
gacaaagccc acttcgccgg ccgacaactc cggccgcggc tgcgatttgg gcgtgaacac   1080
gccgatctgc tcgcacagat gcgtggcgtg ggacgccatc agcaggatct tgtccttggg   1140
cttgagcacg ccgttgacga tgcgcaccag catgaccacg cccacgtagt tgtcgaacca   1200
cgaatcgatg atcagcgcct gcagcggcgc ggacggatcg cccttgggcg gcggcacgcg   1260
cgccacgatg gattcgagga tttcgtcgat gcccatgccg gtcttggcgc tggccagcac   1320
cgcctcggac gcgtcgatgc cgatcacgtc ttcgacctcc tggcgcgcgg cttccggatc   1380
ggcctgcggc aggtccatct tgttgagcac cggcagcact tccacgccca gctcgatggc   1440
cgtgtagcag ttggccacgg tctgggcctc gacgccctgc gaggcgtcga ccaccagcaa   1500
ggcgccttcg caggccgaca gcgaacgact gacttcgtac gagaaatcga cgtgtccggg   1560
ggtatcgatc aggttgaggt tgtagaccgt gccgtcctgc gacttgtact gcagggacgc   1620
```

ggtctgcgcc ttgatcgtga taccccgttc gcgctcgata tccatggaat caagcacttg 1680
cgcggacatt tcgcgctcgg ccagcccccc gcaacggtgg atcaggcgat cggcgagcgt 1740
cgatttaccg tgatcgatgt gggcaatgat ggaaaagttg cggatatgct gcat 1794

<210> SEQ ID NO 139
<211> LENGTH: 1794
<212> TYPE: DNA
<213> ORGANISM: Bordetella parapertussis

<400> SEQUENCE: 139
ttacttgtct tcgacttgca ggatggcgag gaacgcctct tgcgggattt ccacgctgcc 60
gacctgcttc atgcgcttct tgccggcctt ctgcttttcc agcaacttct tcttgcgcga 120
gatatcgccg ccatagcact tggccagcac gttcttgcgc agcgccttga cgttctcgcg 180
cgcgatgacc tccgcgccga ttgccgcctg gatggccacg tcgaacatct ggcgcgggat 240
caggccgcgc atgcgcgaaa ccacctcgcg cgcccggtag cgcgcattgt tgcggtgcgc 300
gatcatggcc agcgcatcga cgcggtcgcc gttgatcagc agatccacct tgaccacgtc 360
ggccgagcgg tattccacga actcgtagtc catcgacgca tagccgcgcg acaccgattt 420
cagtttgtcg aagaaatcga gcacgatctc ggccagcgga atctcgtagg tcaggtgcac 480
ctgacgcccg tgatagctca tgttgagctg gacgccgcgc ttgttgttgc acagcgtcat 540
caccggcccc acgtattcct ggggcatgaa cagcgtcacc ttgacgatgg gttcgcggat 600
atcggcgatc ttggcgattt ccggcatgcg cgacgggctt tcgatggtca cgaccgtgcc 660
gtcgcgctgt tcgacctcat agaccaccga tggcgcggtg gtgatgatgt ccatgtcgaa 720
ctcgcgctcc aggcgctcct gcacgatttc catgtgcagc agccccagga agccgcagcg 780
aaagccgaag cccagcgcct gcgacacttc gggttcgaac atcagcgcgg cgtcgttgag 840
cttcagcttt tccagcgaat cgcgcagctg gtcgtattcg gagctttcca ccggatacag 900
gccggcgaac acctgcggct tgacttcctt gaagcccggc agcggctcgg ccgccggctt 960
gcccgccagg gtgatggtgt cgcccacctt ggcgtgttcc agttccttga tgccggcgat 1020
gacaaagccc acttcgccgg ccgacaactc cggccgcggc tgcgatttgg gcgtgaacac 1080
gccgatctgc tcgcacagat gcgtggcgtg ggacgccatc agcaggatct tgtccttggg 1140
cttgagcacg ccgttgacga tgcgcaccag catgaccacg cccacgtagt tgtcgaacca 1200
cgaatcgatg atcagcgcct gcagcggcgc ggacggatcg cccttgggcg gcggcacgcg 1260
cgccacgatg gattcgagga tttcgtcgat gcccatgccg gtcttggcgc tggccagcac 1320
cgcctcggac gcgtcgatgc cgatcacgtc ttcgacctcc tggcgcgcgg cttccggatc 1380
ggcctgcggc aggtccatct tgttgagcac cggcagcact tccacgccca gctcgatggc 1440
cgtgtagcag ttggccacgg tctgggcctc gacgccctgc gaggcgtcga ccaccagcaa 1500
ggcgccttcg caggccgaca gcgaacgact gacttcgtac gagaaatcga cgtgtccggg 1560
ggtatcgatc aggttgaggt tgtagaccgt gccgtcctgc gacttgtact gcagggacgc 1620
ggtctgcgcc ttgatcgtga taccccgttc gcgctcgata tccatggaat caagcacttg 1680
cgcggacatt tcgcgctcgg ccagcccccc gcaacggtgg atcaggcgat cggcgagcgt 1740
cgatttaccg tgatcgatgt gggcaatgat ggaaaagttg cggatatgct gcat 1794

<210> SEQ ID NO 140
<211> LENGTH: 1794
<212> TYPE: DNA

<213> ORGANISM: Bordetella petrii

<400> SEQUENCE: 140
ctacttgtct tcgacttgca ggatggccag gaacgcttcc tgggggatct cgacgctgcc 60
cacctgcttc atgcgtttct tgccggcttt ctgcttttcg agaagttttt tcttgcgggt 120
gatgtcgccg ccgtagcact tggccagcac gttcttgcgt agcgccttga cgttctcgcg 180
cgcgatgacc tcggcgccga tagccgcctg aatggccacg tcgaacatct ggcgcgggat 240
cagcccgcgc atgcgcgtga ccacgtcgcg cgcgcgatag cgggcattgg cccggtgcac 300
gatcatggcc aacgcgtcga cgcggtcgcc gttgatgagc aggtcgaccc gcaccacgtc 360
ggccgaacgg tattccagga attcgtaatc catcgaggca tagccgcgcg acaccgactt 420
gagcttgtcg aagaagtcga gcacgatctc ggccagcgga atctcgtagg tcaggtgcac 480
ctggcggccg tggtagctca tgttgatctg cacgccgcgc ttgttgttgc acaacgtcat 540
gaccggaccc acgtattcct ggggcatgaa cagcgtgacc ttgacgatgg gctcgcggat 600
gtcggcgatc ttgcccactt cgggcatgcg cgccgggcta tcgacgattt cgatgctgcc 660
gtcgcgttgt tcgacttcgt acaccaccga cggcgcggta gtgatgatgt ccatgtcgaa 720
ctcgcgctcg aggcgctctt gcacgatttc catgtgcagc aggcccagga agccgcagcg 780
gaaaccgaag cccagcgcct gcgagacctc gggttcgaac atcagcgcgg catcgttgag 840
cttgagcttt tcgagcgaat cgcgtagttg gtcgtattcg gagctttcta ccggatacag 900
gccggcgaac acctgcggct tgacttcctt gaagcccggc agcggcgcgt tggccggctt 960
gcccgccagg gtgacggtat cgcccacctt ggcatgcgcc agctctttga tgccggcaat 1020
gatgaacccg acctcgcccg cggacagctc ggtgcgcggc tgcgacttgg gcgtgaacac 1080
gccgacctgc tcgcacaggt gggtggcgcc cgaggccatc agcaggatct tgtctttggg 1140
acgcagcacg ccgttgatga tgcgcaccag catcaccacg cccacgtagt tgtcgaacca 1200
ggagtcgatg atcagggcct gcagtgcgcc gtcggggttg ccctgaggcg ccggcacgcg 1260
ggccacgatg gtctcgagga tctcgtcgat gcccatgccc gtcttggcgc tggccagcac 1320
cgcgttcgag gcgtcgatgc cgatgacgtc ttcgacctct tggcgcgcgg cgtcgggatc 1380
ggcctgcggc aggtccatct tgttgagcac gggcagcact tcgacgccca gttcgatggc 1440
ggtgtagcag ttcgccaccg tctgggcctc gacgccctgc gaggcatcga ccaccagcag 1500
cgccccttcg caagccgaca gcgaacggct gacttcgtac gagaagtcga cgtgccccgg 1560
ggtgtcgatg aggttcaggt tgtaggtctt gccgtcctgg gcctggtatt gcagcgcggc 1620
ggtctgggcc ttgatggtga tgccccgctc gcgctcgatt tccatggagt ccagcacctg 1680
cgcggacatt tcgcgcgccg ccaacccgcc gcaacgctgg atcaggcggt cggccaaggt 1740
cgatttgccg tgatcgatgt gggcgatgat ggagaaattg cggatatgct gcat 1794

<210> SEQ ID NO 141
<211> LENGTH: 1794
<212> TYPE: DNA
<213> ORGANISM: Bordetella petrii

<400> SEQUENCE: 141
ctacttgtct tcgacttgca ggatggccag gaacgcttcc tgggggatct cgacgctgcc 60
cacctgcttc atgcgtttct tgccggcttt ctgcttttcg agaagttttt tcttgcgggt 120
gatgtcgccg ccgtagcact tggccagcac gttcttgcgt agcgccttga cgttctcgcg 180
cgcgatgacc tcggcgccga tagccgcctg aatggccacg tcgaacatct ggcgcgggat 240
cagcccgcgc atgcgcgtga ccacgtcgcg cgcgcgatag cgggcattgg cccggtgcac 300
gatcatggcc aacgcgtcga cgcggtcgcc gttgatgagc aggtcgaccc gcaccacgtc 360
ggccgaacgg tattccagga attcgtaatc catcgaggca tagccgcgcg acaccgactt 420
gagcttgtcg aagaagtcga gcacgatctc ggccagcgga atctcgtagg tcaggtgcac 480
ctggcggccg tggtagctca tgttgatctg cacgccgcgc ttgttgttgc acaacgtcat 540
gaccggaccc acgtattcct ggggcatgaa cagcgtgacc ttgacgatgg gctcgcggat 600
gtcggcgatc ttgcccactt cgggcatgcg cgccgggcta tcgacgattt cgatgctgcc 660
gtcgcgttgt tcgacttcgt acaccaccga cggcgcggta gtgatgatgt ccatgtcgaa 720
ctcgcgctcg aggcgctctt gcacgatttc catgtgcagc aggcccagga agccgcagcg 780
gaaaccgaag cccagcgcct gcgagacctc gggttcgaac atcagcgcgg catcgttgag 840
cttgagcttt tcgagcgaat cgcgtagttg gtcgtattcg gagctttcta ccggatacag 900
gccggcgaac acctgcggct tgacttcctt gaagcccggc agcggcgcgt tggccggctt 960
gcccgccagg gtgacggtat cgcccacctt ggcatgcgcc agctctttga tgccggcaat 1020
gatgaacccg acctcgcccg cggacagctc ggtgcgcggc tgcgacttgg gcgtgaacac 1080
gccgacctgc tcgcacaggt gggtggcgcc cgaggccatc agcaggatct tgtctttggg 1140
acgcagcacg ccgttgatga tgcgcaccag catcaccacg cccacgtagt tgtcgaacca 1200
ggagtcgatg atcagggcct gcagtgcgcc gtcggggttg ccctgaggcg ccggcacgcg 1260
ggccacgatg gtctcgagga tctcgtcgat gcccatgccc gtcttggcgc tggccagcac 1320
cgcgttcgag gcgtcgatgc cgatgacgtc ttcgacctct tggcgcgcgg cgtcgggatc 1380
ggcctgcggc aggtccatct tgttgagcac gggcagcact tcgacgccca gttcgatggc 1440
ggtgtagcag ttcgccaccg tctgggcctc gacgccctgc gaggcatcga ccaccagcag 1500
cgccccttcg caagccgaca gcgaacggct gacttcgtac gagaagtcga cgtgccccgg 1560
ggtgtcgatg aggttcaggt tgtaggtctt gccgtcctgg gcctggtatt gcagcgcggc 1620
ggtctgggcc ttgatggtga tgccccgctc gcgctcgatt tccatggagt ccagcacctg 1680
cgcggacatt tcgcgcgccg ccaacccgcc gcaacgctgg atcaggcggt cggccaaggt 1740
cgatttgccg tgatcgatgt gggcgatgat ggagaaattg cggatatgct gcat 1794

<210> SEQ ID NO 142
<211> LENGTH: 1461
<212> TYPE: DNA
<213> ORGANISM: Bordetella pertussis

<400> SEQUENCE: 142
gcgcgcgatg acctccgcgc cgattgccgc ctggatggcc acgtcgaaca tctggcgcgg 60
gatcaggccg cgcatgcgcg aaaccacctc gcgcgcccgg tagcgcgcat tgttgcggtg 120
cgcgatcatg gccagcgcat cgacgcggtc gccgttgatc agcagatcca ccttgaccac 180
gtcggccgag cggtattcca cgaactcgta gtccatcgac gcatagccgc gcgacaccga 240
tttcagtttg tcgaagaaat cgagcacgat ctcggccagc ggaatctcgt aggtcaggtg 300
cacctggcgc ccgtggtagc tcatgttgag ctggacgccg cgcttgttgt tgcacagtgt 360
catcaccggc cccacgtatt cctggggcat gaacagcgtc accttgacga tgggttcgcg 420
gatatcggcg atcttggcga tttccggcat gcgcgacggg ctttcgatgg tcacgaccgt 480
gccgtcgcgc tgttcgacct catagaccac cgatggcgcg gtggtgatga tgtccatgtc 540
gaactcgcgc tccaggcgct cctgcacgat ttccatgtgc agcagcccca ggaagccgca 600
gcgaaagccg aagcccagcg cctgcgacac ttcgggctcg aacatcagcg cggcgtcgtt 660
gagcttcagc ttttccagcg aatcgcgcag ctggtcgtat tcggagcttt ccaccggata 720
caggccggcg aacacctgcg gcttgacttc cttgaagccc ggcagcggct cggccgccgg 780
cttgcccgcc agggtgatgg tgtcgcccac cttggcgtgt tccagttcct tgatgccggc 840
gatgacaaag cccacttcgc cggccgacaa ctccggccgc ggctgcgatt tgggcgtgaa 900
cacgccgatc tgctcgcaca gatgcgtggc gtgggacgcc atcagcagga tcttgtcctt 960
gggcttgagc acgccgttga cgatgcgcac cagcatgacc acgcccacgt agttgtcgaa 1020
ccacgaatcg atgatcagcg cctgcagcgg cgcggacgga tcgcccttgg gcggcggcac 1080
ccgcgccacg atggattcga ggatctcgtc gatgcccatg ccggtcttgg cgctggccag 1140
caccgcctcg gacgcgtcga tgccgatcac gtcttcgacc tcctggcgcg cggcttccgg 1200
gtcggcctgc ggcaggtcca tcttgttgag caccggcagc acttccatgc ccagttcgat 1260
ggccgtgtag cagttggcca cggtctgggc ctcgacgccc tgcgaagcgt cgaccaccag 1320
caaggcgcct tcgcaggccg acagcgaacg actgacttcg tacgagaaat cgacgtgtcc 1380
gggggtatcg atcaggttga ggttgtagac cgtgccgtcc tgcgacttgt actgcaggga 1440
cgcggtctgc gccttgatsg t 1461

<210> SEQ ID NO 143
<211> LENGTH: 904
<212> TYPE: DNA
<213> ORGANISM: Bordetella pertussis

<400> SEQUENCE: 143
gcgcgcgatg acctccgcgc cgattgccgc ctggatggcc acgtcgaaca tctggcgcgg 60
gatcaagccg cgcatgcgcg aaaccacctc gcgcgcccgg tagcgcgcat tgttgcggtg 120
cgcgatcatg gccagcgcat cgacgcggtc gccgttgatc agcagatcca ccttgaccac 180
gtcggccgag cggtattcca cgaactcgta gtccatcgac gcatagccgc gcgacaccga 240
tttcagtttg tcgaagaaat cgagcacgat ctcggccagc ggaatctcgt aggtcaggtg 300
cacctggcgc ccgtggtagc tcatgttgag ctggacgccg cgcttgttgt tgcacagtgt 360
catcaccggc cccacgtatt cctggggcat gaacagcgtc accttgacga tgggttcgcg 420
gatatcggcg atcttggcga tttccggcat gcgcgacggg ctttcgatgg tcacgaccgt 480
gccgtcgcgc tgttcgacct catagaccac cgatggcgcg gtggtgatga tgtccatgtc 540
gaactcgcgc tccaggcgct cctgcacgat ttccatgtgc agcagcccca ggaagccgca 600
gcgaaagccg aagcccagcg cctgcgacac ttcgggctcg aacatcagcg cggcgtcgtt 660
gagcttcagc ttttccagcg aatcgcgcag ctggtcgtat tcggagcttt ccaccggata 720
caggccggcg aacacctgcg gcttgacttc cttgaagccc ggcagcggct cggccgccgg 780
cttgcccgcc agggtgatgg tgtcgcccac cttggcgtgt tccagttcct tgatgccggc 840
gatgacaaag cccacttcgc cggccgacaa ctccggccgc ggctgcgatt tgggcgtgaa 900
cacg 904

<210> SEQ ID NO 144
<211> LENGTH: 904
<212> TYPE: DNA
<213> ORGANISM: Bordetella pertussis

<400> SEQUENCE: 144

-continued

```
gcgcgcgatg acctccgcgc cgattgccgc ctggatggcc acgtcgaaca tctggcgcgg     60

gatcaggccg cgcatgcgcg aaaccacctc gcgcgcccgg tagcgcgcat tgttgcggtg    120

cgcgatcatg gccagcgcat cgacgcggtc gccgttgatc agcagatcca ccttgaccac    180

gtcggccgag cggtattcca cgaactcgta gtccatcgac gcatagccgc gcgacaccga    240

tttcagtttg tcgaagaaat cgagcacgat ctcggccagc ggaatctcgt aggtcaggtg    300

cacctggcgc ccgtggtagc tcatgttgag ctggacgccg cgcttgttgt tgcacagtgt    360

catcaccggc cccacgtatt cctggggcat gaacagcgtc accttgacga tgggttcgcg    420

gatatcggcg atcttggcga tttccggcat gcgcgacggg ctttcgatgg tcacgaccgt    480

gccgtcgcgc tgttcgacct catagaccac cgatggcgcg gtggtgatga tgtccatgtc    540

gaactcgcgc tccaggcgct cctgcacgat ttccatgtgc agcagcccca ggaagccgca    600

gcgaaagccg aagcccagcg cctgcgacac ttcgggctcg aacatcagcg cggcgtcgtt    660

gagcttcagc ttttccagcg aatcgcgcag ctggtcgtat tcggagcttt ccaccggata    720

caggccggcg aacacctgcg gcttgacttc cttgaagccc ggcagcggct cggccgccgg    780

cttgcccgcc agggtgatgg tgtcgcccac cttggcgtgt tccagttcct tgatgccggc    840

gatgacaaag cccacttcgc cggccgacaa ctccggccgc ggctgcgatt tgggcgtgaa    900

cacg                                                                 904
```

<210> SEQ ID NO 145
<211> LENGTH: 904
<212> TYPE: DNA
<213> ORGANISM: Bordetella bronchiseptica

<400> SEQUENCE: 145

```
gcgcgcgatg acctccgcgc cgattgccgc ctggatggcc acgtcgaaca tctggcgcgg     60

gatcaggccg cgcatgcgcg aaaccacctc gcgcgcccgg tagcgcgcat tgttgcggtg    120

cgcgatcatg gccagcgcat cgacgcggtc gccgttgatc agcagatcca ccttgaccac    180

gtcggccgag cggtattcca cgaactcgta gtccatcgac gcatagccgc gcgacaccga    240

tttcagtttg tcgaagaaat cgagcacgat ctcggccagc ggaatctcgt aggtcaggtg    300

cacctgacgc ccgtgatagc tcatgttgag ctggacgccg cgcttgttgt tgcacagcgt    360

catcaccggc cccacgtatt cctggggcat gaacagcgtc accttgacga tgggttcgcg    420

gatatcggcg atcttggcga tttccggcat gcgcgacggg ctttcgatgg tcacgaccgt    480

gccgtcgcgc tgttcgacct catagaccac cgatggcgcg gtggtgatga tgtccatgtc    540

gaactcgcgc tccaggcgct cctgcacgat ttccatgtgc agcagcccca ggaagccgca    600

gcgaaagccg aagcccagcg cctgcgacac ttcgggttcg aacatcagcg cggcgtcgtt    660

gagcttcagc ttttccagcg aatcgcgcag ctggtcgtat tcggagcttt ccaccggata    720

caggccggcg aacacctgcg gcttgacttc cttgaagccc ggcagcggct cggccgccgg    780

cttgcccgcc agggtgatgg tgtcgcccac cttggcgtgt tccagttcct tgatgccggc    840

gatgacaaag cccacttcgc cggccgacaa ctccggccgc ggctgcgatt tgggcgtgaa    900

cacg                                                                 904
```

<210> SEQ ID NO 146
<211> LENGTH: 904
<212> TYPE: DNA
<213> ORGANISM: Bordetella bronchiseptica

<400> SEQUENCE: 146
gcgcgcgatg acctccgcgc cgattgccgc ctggatggcc acgtcgaaca tctggcgcgg 60
gatcaggccg cgcatgcgcg aaaccacctc gcgcgcccgg tagcgcgcat tgttgcggtg 120
cgcgatcatg gccagcgcat cgacgcggtc gccgttgatc agcagatcca ccttgaccac 180
gtcggccgag cggtattcca cgaactcgta gtccatcgac gcatagccgc gcgacaccga 240
tttcagtttg tcgaagaaat cgagcacgat ctcggccagc ggaatctcgt aggtcaggtg 300
cacctgacgc ccgtgatagc tcatgttgag ctggacgccg cgcttgttgt tgcacagcgt 360
catcaccggc cccacgtatt cctggggcat gaacagcgtc accttgacga tgggttcgcg 420
gatatcggcg atcttggcga tttccggcat gcgcgacggg ctttcgatgg tcacgaccgt 480
gccgtcgcgc tgttcgacct catagaccac cgatggcgcg gtggtgatga tgtccatgtc 540
gaactcgcgc tccaggcgct cctgcacgat ttccatgtgc agcagcccca ggaagccgca 600
gcgaaagccg aagcccagcg cctgcgacac ttcgggttcg aacatcagcg cggcgtcgtt 660
gagcttcagc ttttccagcg aatcgcgcag ctggtcgtat tcggagcttt ccaccggata 720
caggccggcg aacacctgcg gcttgacttc cttgaagccc ggcagcggct cggccgccgg 780
cttgcccgcc agggtgatgg tgtcgcccac cttggcgtgt tccagttcct tgatgccggc 840
gatgacaaag cccacttcgc cggccgacaa ctccggccgc ggctgcgatt tgggcgtgaa 900
cacg 904

<210> SEQ ID NO 147
<211> LENGTH: 1451
<212> TYPE: DNA
<213> ORGANISM: Bordetella bronchiseptica

<400> SEQUENCE: 147
acctccgcgc cgattgccgc ctggatggcc acgtcgaaca tctggcgcgg gatcaggccg 60
cgcatgcgcg aaaccacctc gcgcgcccgg tagcgcgcat tgttgcggtg cgcgatcatg 120
gccagcgcat cgacgcggtc gccgttgatc agcagatcca ccttgaccac gtcggccgag 180
cggtattcca cgaactcgta gtccatcgac gcatagccgc gcgacaccga tttcagtttg 240
tcgaagaaat cgagcacgat ctcggccagc ggaatctcgt aggtcaggtg cacctgacgc 300
ccgtgatagc tcatgttgag ctggacgccg cgcttgttgt tgcacagcgt catcaccggc 360
cccacgtatt cctggggcat gaacagcgtc accttgacga tgggttcgcg gatatcggcg 420
atcttggcga tttccggcat gcgcgacggg ctttcgatgg tcacgaccgt gccgtcgcgc 480
tgttcgacct catagaccac cgatggcgcg gtggtgatga tgtccatgtc gaactcgcgc 540
tccaggcgct cctgcacgat ttccatgtgc agcagcccca ggaagccgca gcgaaagccg 600
aagcccagcg cctgcgacac ttcgggttcg aacatcagcg cggcgtcgtt gagcttcagc 660
ttttccagcg aatcgcgcag ctggtcgtat tcggagcttt ccaccggata caggccggcg 720
aacacctgcg gcttgacttc cttgaagccc ggcagcggct cggccgccgg cttgcccgcc 780
agggtgatgg tgtcgcccac cttggcgtgt tccagttcct tgatgccggc gatgacaaag 840
cccacttcgc cggccgacaa ctccggccgc ggctgcgatt tgggcgtgaa cacgccgatc 900
tgctcgcaca gatgcgtggc gtgggacgcc atcagcagga tcttgtcctt gggcttgagc 960
acgccgttga cgatgcgcac cagcatgacc acgcccacgt agttgtcgaa ccacgaatcg 1020
atgatcagcg cctgcagcgg cgcggacgga tcgcccttgg gcggcggcac gcgcgccacg 1080
atggattcga ggatttcgtc gatgcccatg ccggtcttgg cgctggccag caccgcctcg 1140
gacgcgtcga tgccgatcac gtcttcgacc tcctggcgcg cggcttccgg atcggcctgc 1200
ggcaggtcca tcttgttgag caccggcagc acttccacgc ccagctcgat ggccgtgtag 1260
cagttggcca cggtctgggc ctcgacgccc tgcgaggcgt cgaccaccag caaggcgcct 1320
tcgcaggccg acagcgaacg actgacttcg tacgagaaat cgacgtgtcc gggggtatcg 1380
atcaggttga ggttgtagac cgtgccgtcc tgcgacttgt actgcaggga cgcggtctgc 1440
gccttgatsg t 1451

<210> SEQ ID NO 148
<211> LENGTH: 904
<212> TYPE: DNA
<213> ORGANISM: Bordetella parapertussis

<400> SEQUENCE: 148
gcgcgcgatg acctccgcgc cgattgccgc ctggatggcc acgtcgaaca tctggcgcgg 60
gatcaggccg cgcatgcgcg aaaccacctc gcgcgcccgg tagcgcgcat tgttgcggtg 120
cgcgatcatg gccagcgcat cgacgcggtc gccgttgatc agcagatcca ccttgaccac 180
gtcggccgag cggtattcca cgaactcgta gtccatcgac gcatagccgc gcgacaccga 240
tttcagtttg tcgaagaaat cgagcacgat ctcggccagc ggaatctcgt aggtcaggtg 300
cacctgacgc ccgtgatagc tcatgttgag ctggacgccg cgcttgttgt tgcacagcgt 360
catcaccggc cccacgtatt cctggggcat gaacagcgtc accttgacga tgggttcgcg 420
gatatcggcg atcttggcga tttccggcat gcgcgacggg ctttcgatgg tcacgaccgt 480
gccgtcgcgc tgttcgacct catagaccac cgatggcgcg gtggtgatga tgtccatgtc 540
gaactcgcgc tccaggcgct cctgcacgat ttccatgtgc agcagcccca ggaagccgca 600
gcgaaagccg aagcccagcg cctgcgacac ttcgggttcg aacatcagcg cggcgtcgtt 660
gagcttcagc ttttccagcg aatcgcgcag ctggtcgtat tcggagcttt ccaccggata 720
caggccggcg aacacctgcg gcttgacttc cttgaagccc ggcagcggct cggccgccgg 780
cttgcccgcc agggtgatgg tgtcgcccac cttggcgtgt tccagttcct tgatgccggc 840
gatgacaaag cccacttcgc cggccgacaa ctccggccgc ggctgcgatt tgggcgtgaa 900
cacg 904

<210> SEQ ID NO 149
<211> LENGTH: 904
<212> TYPE: DNA
<213> ORGANISM: Bordetella parapertussis

<400> SEQUENCE: 149
gcgcgcgatg acctccgcgc cgattgccgc ctggatggcc acgtcgaaca tctggcgcgg 60
gatcaggccg cgcatgcgcg aaaccacctc gcgcgcccgg tagcgcgcat tgttgcggtg 120
cgcgatcatg gccagcgcat cgacgcggtc gccgttgatc agcagatcca ccttgaccac 180
gtcggccgag cggtattcca cgaactcgta gtccatcgac gcatagccgc gcgacaccga 240
tttcagtttg tcgaagaaat cgagcacgat ctcggccagc ggaatctcgt aggtcaggtg 300
cacctgacgc ccgtgatagc tcatgttgag ctggacgccg cgcttgttgt tgcacagcgt 360
catcaccggc cccacgtatt cctggggcat gaacagcgtc accttgacga tgggttcgcg 420
gatatcggcg atcttggcga tttccggcat gcgcgacggg ctttcgatgg tcacgaccgt 480
gccgtcgcgc tgttcgacct catagaccac cgatggcgcg gtggtgatga tgtccatgtc 540

-continued

```
gaactcgcgc tccaggcgct cctgcacgat ttccatgtgc agcagcccca ggaagccgca    600

gcgaaagccg aagcccagcg cctgcgacac ttcgggttcg aacatcagcg cggcgtcgtt    660

gagcttcagc ttttccagcg aatcgcgcag ctggtcgtat tcggagcttt ccaccggata    720

caggccggcg aacacctgcg gcttgacttc cttgaagccc ggcagcggct cggccgccgg    780

cttgcccgcc agggtgatgg tgtcgcccac cttggcgtgt tccagttcct tgatgccggc    840

gatgacaaag cccacttcgc cggccgacaa ctccggccgc ggctgcgatt tgggcgtgaa    900

cacg                                                                 904
```

<210> SEQ ID NO 150
<211> LENGTH: 904
<212> TYPE: DNA
<213> ORGANISM: Bordetella parapertussis

<400> SEQUENCE: 150

```
gcgcgcgatg acctccgcgc cgattgccgc ctggatggcc acgtcgaaca tctggcgcgg     60

gatcaggccg cgcatgcgcg aaaccacctc gcgcgcccgg tagcgcgcat tgttgcggtg    120

cgcgatcatg gccagcgcat cgacgcggtc gccgttgatc agcagatcca ccttgaccac    180

gtcggccgag cggtattcca cgaactcgta gtccatcgac gcatagccgc gcgacaccga    240

tttcagtttg tcgaagaaat cgagcacgat ctcggccagc ggaatctcgt aggtcaggtg    300

cacctgacgc ccgtgatagc tcatgttgag ctggacgccg cgcttgttgt tgcacagcgt    360

catcaccggc cccacgtatt cctggggcat gaacagcgtc accttgacga tgggttcgcg    420

gatatcggcg atcttggcga tttccggcat gcgcgacggg ctttcgatgg tcacgaccgt    480

gccgtcgcgc tgttcgacct catagaccac cgatggcgcg gtggtgatga tgtccatgtc    540

gaactcgcgc tccaggcgct cctgcacgat ttccatgtgc agcagcccca ggaagccgca    600

gcgaaagccg aagcccagcg cctgcgacac ttcgggttcg aacatcagcg cggcgtcgtt    660

gagcttcagc ttttccagcg aatcgcgcag ctggtcgtat tcggagcttt ccaccggata    720

caggccggcg aacacctgcg gcttgacttc cttgaagccc ggcagcggct cggccgccgg    780

cttgcccgcc agggtgatgg tgtcgcccac cttggcgtgt tccagttcct tgatgccggc    840

gatgacaaag cccacttcgc cggccgacaa ctccggccgc ggctgcgatt tgggcgtgaa    900

cacg                                                                 904
```

<210> SEQ ID NO 151
<211> LENGTH: 1794
<212> TYPE: DNA
<213> ORGANISM: Bordetella petrii

<400> SEQUENCE: 151

```
ctacttgtct tcgacttgca ggatggccag gaacgcttcc tgggggatct cgacgctgcc     60

cacctgcttc atgcgtttct tgccggcttt ctgcttttcg agaagttttt tcttgcgggt    120

gatgtcgccg ccgtagcact tggccagcac gttcttgcgt agcgccttga cgttctcgcg    180

cgcgatgacc tcggcgccga tagccgcctg aatggccacg tcgaacatct ggcgcgggat    240

cagcccgcgc atgcgcgtga ccacgtcgcg cgcgcgatag cgggcattgg cccggtgcac    300

gatcatggcc aacgcgtcga cgcggtcgcc gttgatgagc aggtcgaccc gcaccacgtc    360

ggccgaacgg tattccagga attcgtaatc catcgaggca tagccgcgcg acaccgactt    420

gagcttgtcg aagaagtcga gcacgatctc ggccagcgga atctcgtagg tcaggtgcac    480

ctggcggccg tggtagctca tgttgatctg cacgccgcgc ttgttgttgc acaacgtcat    540
```

gaccggaccc acgtattcct ggggcatgaa cagcgtgacc ttgacgatgg gctcgcggat 600
gtcggcgatc ttgcccactt cgggcatgcg cgccgggcta tcgacgattt cgatgctgcc 660
gtcgcgttgt tcgacttcgt acaccaccga cggcgcggta gtgatgatgt ccatgtcgaa 720
ctcgcgctcg aggcgctctt gcacgatttc catgtgcagc aggcccagga agccgcagcg 780
gaaaccgaag cccagcgcct gcgagacctc gggttcgaac atcagcgcgg catcgttgag 840
cttgagcttt tcgagcgaat cgcgtagttg gtcgtattcg gagctttcta ccggatacag 900
gccggcgaac acctgcggct tgacttcctt gaagcccggc agcggcgcgt tggccggctt 960
gcccgccagg gtgacggtat cgcccacctt ggcatgcgcc agctctttga tgccggcaat 1020
gatgaacccg acctcgcccg cggacagctc ggtgcgcggc tgcgacttgg gcgtgaacac 1080
gccgacctgc tcgcacaggt gggtggcgcc cgaggccatc agcaggatct tgtctttggg 1140
acgcagcacg ccgttgatga tgcgcaccag catcaccacg cccacgtagt tgtcgaacca 1200
ggagtcgatg atcagggcct gcagtgcgcc gtcggggttg ccctgaggcg ccggcacgcg 1260
ggccacgatg gtctcgagga tctcgtcgat gcccatgccc gtcttggcgc tggccagcac 1320
cgcgttcgag gcgtcgatgc cgatgacgtc ttcgacctct tggcgcgcgg cgtcgggatc 1380
ggcctgcggc aggtccatct tgttgagcac gggcagcact tcgacgccca gttcgatggc 1440
ggtgtagcag ttcgccaccg tctgggcctc gacgccctgc gaggcatcga ccaccagcag 1500
cgccccttcg caagccgaca gcgaacggct gacttcgtac gagaagtcga cgtgccccgg 1560
ggtgtcgatg aggttcaggt tgtaggtctt gccgtcctgg gcctggtatt gcagcgcggc 1620
ggtctgggcc ttgatggtga tgccccgctc gcgctcgatt tccatggagt ccagcacctg 1680
cgcggacatt tcgcgcgccg ccaacccgcc gcaacgctgg atcaggcggt cggccaaggt 1740
cgatttgccg tgatcgatgt gggcgatgat ggagaaattg cggatatgct gcat 1794

<210> SEQ ID NO 152
<211> LENGTH: 1461
<212> TYPE: DNA
<213> ORGANISM: Bordetella avium

<400> SEQUENCE: 152
acgcgcaatg acttcagcgc cgatcgctgc ctgaatggca acgtcataca tctggcgcgg 60
aatcagggca cgcatgcgcg acaccacatc acgggcacgg tagcgggcat tcgagcggtg 120
cacaatcatg gcaagcgcat cgacccggtc gccattgatc agcagatcga ccttaaccac 180
gtctgccggg cggtactcga ggaactcgta gtccatcgag gcataaccgc gcgacacgga 240
cttcagacga tcgaagaagt ccagcacgat ttcagccagc gggatctcat aggtgagatg 300
cacctgccga ccatggtagg tcatgttgat ctggttgccg cgcttgttat tacacagcgt 360
catcaccgga ccgacatact cctgcggcat gaaaagcgtg accttgacga taggctcgcg 420
gatttcggca atcttgccga cttccggcat gcgcgagggg ctttcgatgg tcaacaccgt 480
accgtcgcgc tcaacgacct cgtacaccac cgacggcgcg gtggtgatga tgtccatatc 540
gaactcgcgc tccagacgct cctgcacgat ttccatgtgc aagagcccaa gaaaaccgca 600
acgaaaaccg aaacccaggg cctgcgacac ttcaggctcg aacatgagcg cagcgtcgtt 660
aagcttgagt ttttcgagcg agtcgcgcaa ctgatcgtat tcggaactct cgaccgggta 720
gaggccggcg aaaacctgcg gctggacctc tttgaagccc ggcaaaggcg cggcggcggg 780
cttgccagcc aaggtgatgg tgtcacccac tttggcatgc sccaactctt tgatgcccgc 840

```
aatgatgaag cccacctcgc ctgccgacaa ctgcgcacgc ggctgcgact tgggcgtgaa    900

cacgccggtc tgctcgcaca gatgcgtggc accggaagcc atcagcaaaa tcttgtcttt    960

cgggcgcaat acaccgttga cgatgcgcac cagcatcacg acaccgacat agttatcgaa   1020

ccaggagtcg ataatcagcg cctgcagcgc agcttccggg tcaccctcag gggacggcac   1080

acgggccacg atggcctcaa gaatctcgtc aatgcccatc ccggtcttgg cgctggccag   1140

tacggcgtcg gaggcgtcga tgccgatgac atcttcgacc tcctggcgcg cgccctcggg   1200

atcggcctgg ggcaagtcca ttttattcag gacagccagc acctccacgc ccagatcgat   1260

agccgtatag cagttggcca cggtttgcgc ttcgacgccc tgggacgcgt ccaccaccag   1320

caatgcgccc tcgcaagccg acaaggaacg gctcacttca taagaaaagt ctacgtgacc   1380

cggggtgtcg atcagattga ggttgtaaac cttgccgtcc tgggccttgt actccagcgc   1440

cgccgtctgg gccttgatsg t                                              1461
```

```
<210> SEQ ID NO 153
<211> LENGTH: 1461
<212> TYPE: DNA
<213> ORGANISM: Bordetella avium

<400> SEQUENCE: 153

acgcgcaatg acttcagcgc cgatcgctgc ctgaatggca acgtcataca tctggcgcgg     60

aatcagggca cgcatgcgcg acaccacatc acgggcacgg tagcgggcat tcgatcggtg    120

cacaatcatg gcaagcgcat cgacccggtc gccattgatc agcagatcga ccttaaccac    180

gtctgccggg cggtactcga ggaactcgta gtccatcgag gcataaccgc gcgacacgga    240

cttcagacga tcgaagaagt ccagcacgat ttcagccagc gggatctcat aggtgagatg    300

cacctgccga ccatggtagg tcatgttgat ctggttgccg cgcttgttat tacacagcgt    360

catcaccgga ccgacatact cctgcggcat gaaaagcgtg accttgacga taggctcgcg    420

gatttcggca atcttgccga cttccggcat gcgcgagggg ctttcgatgg tcaacaccgt    480

accgtcgcgc tcaacgacct cgtacaccac cgacggcgcg gtggtgatga tgtccatatc    540

gaactcgcgc tccagacgct cctgcacgat ttccatgtgc aagagcccaa gaaaaccgca    600

acgaaaaccg aaacccaggg cctgcgacac ttcaggctcg aacatgagcg cagcgtcgtt    660

aagcttgagt ttttcgagcg agtcgcgcaa ctgatcgtat tcggaactct cgaccgggta    720

gaggccggcg aaaacctgcg gctggacctc tttgaagccc ggcaaaggcg cggcggcggg    780

cttgccagcc aaggtgatgg tgtcacccac tttggcatgc gccaactctt tgatgcccgc    840

tatgatgaag cccacctcgc ctgccgacag ctgcgcacgc ggctgcgact tgggcgtgaa    900

cacgccggtc tgctcgcaca gatgcgtggc accggaagcc atcagcaaaa tcttgtcttt    960

cgggcgcaat acaccgttga cgatgcgcac cagcatcacg acaccgacat agttatcgaa   1020

ccaggagtcg ataatcagcg cctgcagcgc agcttccggg tcaccctcag gggacggcac   1080

acgggccacg atggcctcaa gaatctcgtc aatgcccatc ccggtcttgg cgctggccag   1140

tacggcgtcg gaggcgtcga tgccgatgac atcttcgacc tcctggcgcg cgccctcggg   1200

atcggcctgg ggcaagtcca ttttattcag gacagccagc acctccacgc ccagatcgat   1260

agccgtatag cagttggcca cggtttgcgc ttcgacgccc tgggacgcgt ccaccaccag   1320

caatgcgccc tcgcaagccg acaaggaacg gctcacttca taagaaaagt ctacgtgacc   1380

cggggtgtcg atcagattga ggttgtaaac cttgccgtcc tgggccttgt actccagcgc   1440

cgccgtctgg gccttgatsg t                                              1461
```

<210> SEQ ID NO 154
<211> LENGTH: 1457
<212> TYPE: DNA
<213> ORGANISM: Bordetella holmesii

<400> SEQUENCE: 154
gcgatcactt ccgcaccgat agcggcttga atggccacgt catacatttg acgggggatg 60
agctcacgca tgcgcgagac aacctcgcgc gcacgatagc gcgcattgga gcggtgaacg 120
atcatcgcca gggcgtcgac ccggtcgctg ttgatcagca agtccacttt gaccacgtcc 180
gcggatcggt actccaggaa ttcatagtcc atggaggcat agccgcgcga gaccgacttc 240
aagcggtcga agaagtccaa cacgatctcg gccagcggaa tctcataggt caaatgcacc 300
tggcgtccgt ggtaggtcat gttgatctgc gtgccgcgct tgttgttgca cagcgtcatg 360
accggcccca catactcctg gggcatgaac aaggtgacct tgacgatggg ttctcgaata 420
tcggcaatct tgcccacgtc aggcatgcgc gacgggcttt cgatggtcag caccgtgcca 480
tcgcgctcct gaacctcata gaccaccgac ggcgcggtgg tgatgatgtc catgtcaaac 540
tcgcgctcga gccgctcctg cacgatttcc atgtgcagca ggcccagaaa gccgcagcga 600
aagccaaacc ccaaggcttg caagacttcc ggctcgaaca tcagcgccgc gtcgttgagc 660
ttgagtttct ccagcgaatc acgcaactga tcgtattcgg agctctcgac cggatacaga 720
ccggcgaaca cctgcggctg gacctctttg aagccaggca acggttcggt tgccggcttg 780
ccggccaggg taatcgtatc gcccaccttg gcattggcca gctctttgat gcccgcgatg 840
acaaaaccca cttcgcccgc ggacagatgg gggcgttgct gcgatttggg cgtaaacacc 900
cctgtctgct cgcacagatg cgtcgcgccc gaagccatca gcagaatctt gtccttgggc 960
cgcagcacgc cgttgacgat acgcaccaac atcaccacgc cgacgtagtt gtcgaaccat 1020
gagtcaatga tgagggcctg caatggcgcc gctgggtcgc ccttgggcgg cggcacacgc 1080
gcgacgacca tttccaggat ctcgtcgatc cccatccctg tcttggcact ggccagcacg 1140
gcatccgtgg catcgatgcc aatcacatcc tcgacttcct ggcgcgcacc atctggatcg 1200
gcctggggca ggtccatctt gttcaggacc gccagcacct caacgccaag atcgatggcg 1260
gtataacagt tggccacggt ctgcgcctct acgccctgcg aggcatcgac caccagcagc 1320
gccccctcac atgctgacag cgagcggctg acctcgtagg agaagtccac atgccccggt 1380
gtgtcgatca ggttgaggtt gtagatcttg ccgtcctgag ccttgtactg cagcgccgca 1440
gtctgcgcct tgatsgt 1457

<210> SEQ ID NO 155
<211> LENGTH: 900
<212> TYPE: DNA
<213> ORGANISM: Bordetella holmesii

<400> SEQUENCE: 155
gcgatcactt ccgcaccgat agcggcttga atggccacgt catacatttg acgggggatg 60
agctcacgca tgcgcgagac aacctcgcgc gcacgatagc gcgcattgga gcggtgaacg 120
atcatcgcca gggcgtcgac ccggtcgctg ttgatcagca agtccacttt gaccacgtcc 180
gcggatcggt actccaggaa ttcatagtcc atggaggcat agccgcgcga gaccgacttc 240
aagcggtcga agaagtccaa cacgatctcg gccagcggaa tctcataggt caaatgcacc 300
tggcgtccgt ggtaggtcat gttgatctgc gtgccgcgct tgttgttgca cagcgtcatg 360

-continued

```
accggcccca catactcctg gggcatgaac aaggtgacct tgacgatggg ttctcgaata    420

tcggcaatct tgcccacgtc aggcatgcgc gacgggcttt cgatggtcag caccgtgcca    480

tcgcgctcct gaacctcata gaccaccgac ggcgcggtgg tgatgatgtc catgtcaaac    540

tcgcgctcga gccgctcctg cacgatttcc atgtgcagca ggcccagaaa gccgcagcga    600

aagccaaacc ccaaggcttg caagacttcc ggctcgaaca tcagcgccgc gtcgttgagc    660

ttgagtttct ccagcgaatc acgcaactga tcgtattcgg agctctcgac cggatacaga    720

ccggcgaaca cctgcggctg gacctctttg aagccaggca acggttcggt tgccggcttg    780

ccggccaggg taatcgtatc gcccaccttg gcattggcca gctctttgat gcccgcgatg    840

acaaaaccca cttcgcccgc ggacagatgg gggcgttgct gcgatttggg cgtgaacacg    900
```

<210> SEQ ID NO 156
<211> LENGTH: 896
<212> TYPE: DNA
<213> ORGANISM: Bordetella hinzii

<400> SEQUENCE: 156

```
acstgcggcg cgcgatagcc gcctggatgg ccacgtcata catctggcgc gggatgagtt     60

cacgcatgcg cgaaaccact tcgcgggcgc gatagcgcgc attggagcgg tgcacgatca    120

tggccagggc atcgacccgg tcgccgttga tcagcaggtc caccttgacc acgtcggccg    180

agcggtactc caggaattca taatccatgg aggcgtagcc gcgcgaaacc gatttcaggc    240

ggtcaaagaa gtccagcacg atctcggcca gcgggatctc ataggtgaga tgcacctgcc    300

ggccgtggta ggtcatgttg atctgcgtgc cgcgcttgtt attgcacaac gtcatgacgg    360

gcccgacata ctcctgcggc atgaacaggg tgaccttgac gatgggctcg cggatatcgg    420

cgatcttgcc gacttccggc atgcgcgaag ggctttcgat ggtcaacacc gtgccatcgc    480

gctcctggac ctcatagacc accgaaggcg cggtggtgat gatgtccatg tcgaactcgc    540

gctccaggcg ctcttgcacg atttccatgt gcaacagccc caggaagccg caacggaagc    600

cgaagcccag cgcctgggag acttcaggct cgaacatcag cgccgcgtca ttgagcttga    660

gcttctcgag cgagtcccgc agttgatcgt actcggagct ttcgaccgga tacagcccgg    720

caaacacctg cggcttgact tccttgaagc ccggcagcgg ttcgtcggcg ggcttgccgg    780

ccagggtgat ggtgtcgccc accttggcat gcgccagctc cttgatgccg gcgatgacga    840

agcccacctc gccggccgag agctgcgggc gggattgcga yttgggcgtg aacacg        896
```

<210> SEQ ID NO 157
<211> LENGTH: 888
<212> TYPE: DNA
<213> ORGANISM: Bordetella hinzii

<400> SEQUENCE: 157

```
gcgccgatag ccgcctggat ggccacgtca tacatctggc gcgggatgag ttcacgcatg     60

cgcgaaacca cttcgcgggc gcgatagcgc gcattggagc ggtgcacgat catggccagg    120

gcatcgaccc ggtcgccgtt gatcagcagg tccaccttga ccacgtcggc cgagcggtac    180

tccaggaatt cataatccat ggaggcgtag ccgcgcgaaa ccgatttcag gcggtcaaag    240

aagtccagca cgatctcggc cagcgggatc tcataggtga gatgcacctg ccggccgtgg    300

taggtcatgt tgatctgcgt gccgcgcttg ttattgcaca acgtcatgac gggcccgaca    360

tactcctgcg gcatgaacag ggtgaccttg acgatgggct cgcggatatc ggcgatcttg    420

ccgacttccg gcatgcgcga agggctttcg atggtcaaca ccgtgccatc gcgctcctgg    480
```

acctcataga ccaccgaagg cgcggtggtg atgatgtcca tgtcgaactc gcgctccagg 540
cgctcttgca cgatctccat gtgcaacagc cccaggaagc cgcaacggaa gccgaagccc 600
agcgcctggg agacttcagg ctcgaacatc agcgccgcgt cattgagctt gagcttctcg 660
agcgagtccc gcagttgatc gtactcggag ctttcgaccg gatacagccc ggcaaacacc 720
tgcggcttga cttccttgaa gcccggcagc ggttcgtcgg cgggcttgcc ggccagggtg 780
atggtgtcgc ccaccttggc atgcgccagc tccttgatgc cggcgatgac gaagcccacc 840
tcgccggccg agagctgcgg gcgggattgc gayttgggcg tgaacacg 888

<210> SEQ ID NO 158
<211> LENGTH: 489
<212> TYPE: DNA
<213> ORGANISM: Bordetella trematum

<400> SEQUENCE: 158
tcgcgaatgt cgttgatctt gcccacttcg ggcatgcgcg aagggctttc gaccgtcagg 60
accgtgccat cgcgttgttc gacctcatag accaccgacg gcgcggtggt gatgatgtcc 120
atgtcgaatt cgcgttccag gcgctcctgc acgatttcca tgtgcagcag accgagaaag 180
ccgcaacgaa agccgaagcc cagcgcctgc gacacctcgg gctcgaacat cagcgcggcg 240
tcgttgagct tgagcttctc cagcgaatcg cgcagttgat cgtactccga gctctcgacc 300
ggatacaggc cggcgaacac ctgcggctgc acctccttga aaccaggcag cggcttgctg 360
gcgggcttgc cggccagcgt gatggtatcg cccaccttgg cgtgttcgag ctccttgatg 420
ccggtgatca caaacccgac ttcgccggcc gacaactggg tacgggcctg cgayttgggc 480
gtgaacacg 489

<210> SEQ ID NO 159
<211> LENGTH: 596
<212> TYPE: DNA
<213> ORGANISM: Mycobacterium africanum

<400> SEQUENCE: 159
gtaaacggag tcgaaaatca ttgcgcgggt aggtgcctcg gcgtcgccct gagggggcgg 60
cacctgtcgg accacctcgt cgagcaggtc ggacacgcct tcgccggttt tgccggacac 120
ccgcaacacc tcggccggct cgcagccgat gatgtgtgcc atctcggcgg cgtaacggtc 180
cgggtcggcc gcgggcaggt cgatcttgtt gagcaccggg atgatgtgca ggtcgcggtc 240
caacgccagg tagaggttcg ccagcgtctg cgcctcgatg ccttgcgcgg catcgaccaa 300
cagcaccgca ccctcgcaag cctccagcgc acgcgagact tcgtaggtga agtcgacatg 360
gcccggggtg tcgatcagat gcagcacgta gtcggtcttg tcgacccgcc agggtagccg 420
cacattctgg gccttgatgg tgatgccgcg ttcccgctcg atgtccatcc gatccaagta 480
ctgggcccgc atagagcgtt cgtcgaccac tccggtgagc tgcagcatcc ggtcggccaa 540
cgttgacttg ccgtggtcga tgtgggcgat gatgcaaaag ttcctaatct gcgccg 596

<210> SEQ ID NO 160
<211> LENGTH: 596
<212> TYPE: DNA
<213> ORGANISM: Mycobacterium africanum

<400> SEQUENCE: 160
gtaaacggag tcgaaaatca ttgcgcgggt aggtgcctcg gcgtcgccct gagggggcgg 60

-continued

```
cacctgtcgg accacctcgt cgagcaggtc ggacacgcct tcgccggttt tgccggacac    120

ccgcaacacc tcggccggct cgcagccgat gatgtgtgcc atctcggcgg cgtaacggtc    180

cgggtcggcc gcgggcaggt cgatcttgtt gagcaccggg atgatgtgca ggtcgcggtc    240

caacgccagg tagaggttcg ccagcgtctg cgcctcgatg ccttgcgcgg catcgaccaa    300

cagcaccgca ccctcgcaag cctccagcgc acgcgagact tcgtaggtga agtcgacatg    360

gcccggggtg tcgatcagat gcagcacgta gtcggtcttg tcgacccgcc agggtagccg    420

cacattctgg gccttgatgg tgatgccgcg ttcccgctcg atgtccatcc gatccaagta    480

ctgggcccgc atagagcgtt cgtcgaccac tccggtgagc tgcagcatcc ggtcggccaa    540

cgttgacttg ccgtggtcga tgtgggcgat gatgcaaaag ttcctaatct gcgccg        596
```

<210> SEQ ID NO 161
<211> LENGTH: 596
<212> TYPE: DNA
<213> ORGANISM: Mycobacterium africanum

<400> SEQUENCE: 161

```
gtaaacggag tcgaaaatca ttgcgcgggt aggtgcctcg gcgtcgccct gagggggcgg     60

cacctgtcgg accacctcgt cgagcaggtc ggacacgcct tcgccggttt tgccggacac    120

ccgcaacacc tcggccggct cgcagccgat gatgtgtgcc atctcggcgg cgtaacggtc    180

cgggtcggcc gcgggcaggt cgatcttgtt gagcaccggg atgatgtgca ggtcgcggtc    240

caacgccagg tagaggttcg ccagcgtctg cgcctcgatg ccttgcgcgg catcgaccaa    300

cagcaccgca ccctcgcaag cctccagcgc acgcgagact tcgtaggtga agtcgacatg    360

gcccggggtg tcgatcagat gcagcacgta gtcggtcttg tcgacccgcc agggtagccg    420

cacattctgg gccttgatgg tgatgccgcg ttcccgctcg atgtccatcc gatccaagta    480

ctgggcccgc atagagcgtt cgtcgaccac gccggtgagc tgcagcatcc ggtcggccaa    540

cgttgacttg ccgtggtcga tgtgggcgat gatgcaaaag ttcctaatct gcgccg        596
```

<210> SEQ ID NO 162
<211> LENGTH: 596
<212> TYPE: DNA
<213> ORGANISM: Mycobacterium africanum

<400> SEQUENCE: 162

```
gtaaacggag tcgaaaatca ttgcgcgggt aggtgcctcg gcgtcgccct gagggggcgg     60

cacctgtcgg accacctcgt cgagcaggtc ggacacgcct tcgcaggttt tgccggacac    120

ccgcaacacc tcggccggct cgcagccgat gatgtgtgcc atctcggcgg cgtaacggtc    180

cgggtcggcc gcgggcaggt cgatcttgtt gagcaccggg atgatgtgca ggtcgcggtc    240

caacgccagg tagaggttcg ccagcgtctg cgcctcgatg ccttgcgcgg catcgaccaa    300

cagcaccgca ccctcgcaag cctccagcgc acgcgagact tcgtaggtga agtcgacatg    360

gcccggggtg tcgatcagat gcagcacgta gtcggtcttg tcgacccgcc agggtagccg    420

cacattctgg gccttgatgg tgatgccgcg ttcccgctcg atgtccatcc gatccaagta    480

ctgggcccgc atagagcgtt cgtcgaccac gccggtgagc tgcagcatcc ggtcggccaa    540

cgttgacttg ccgtggtcga tgtgggcgat gatgcaaaag ttcctaatct gcgccg        596
```

<210> SEQ ID NO 163
<211> LENGTH: 596
<212> TYPE: DNA
<213> ORGANISM: Mycobacterium bovis

<400> SEQUENCE: 163
gtaaacggag tcgaaaatca ttgcgcgggt aggtgcctcg gcgtcgccct gagggggcgg 60
cacctgtcgg accacctcgt cgagcaggtc ggacacgcct tcgccggttt tgccggacac 120
ccgcaacacc tcggccggct cgcagccgat gatgtgtgcc atctcggcgg cgtaacggtc 180
cgggtcggcc gcgggcaggt cgatcttgtt gagcaccggg atgatgtgca ggtcgcggtc 240
caacgccagg tagaggttcg ccagcgtctg cgcctcgatg ccttgcgcgg catcgaccaa 300
cagcaccgca ccctcgcaag cctccagcgc acgcgagact tcgtaggtga agtcgacatg 360
gcccggggtg tcgatcagat gcagcacgta gtcggtcttg tcgacccgcc agggtagccg 420
cacattctgg gccttgatgg tgatgccgcg ttcccgctcg atgtccatcc gatccaagta 480
ctgggcccgc atagagcgtt cgtcgaccac tccggtgagc tgcagcatcc ggtcggccaa 540
cgttgacttg ccgtggtcga tgtgggcgat gatgcaaaag ttcctaatct gcgccg 596

<210> SEQ ID NO 164
<211> LENGTH: 596
<212> TYPE: DNA
<213> ORGANISM: Mycobacterium bovis

<400> SEQUENCE: 164
gtaaacggag tcgaaaatca ttgcgcgggt aggtgcctcg gcgtcgccct gagggggcgg 60
cacctgtcgg accacctcgt cgagcaggtc ggacacgcct tcgccggttt tgccggacac 120
ccgcaacacc tcggccggct cgcagccgat gatgtgtgcc atctcggcgg cgtaacggtc 180
cgggtcggcc gcgggcaggt cgatcttgtt gagcaccggg atgatgtgca ggtcgcggtc 240
caacgccagg tagaggttcg ccagcgtctg cgcctcgatg ccttgcgcgg catcgaccaa 300
cagcaccgca ccctcgcaag cctccagcgc acgcgagact tcgtaggtga agtcgacatg 360
gcccggggtg tcgatcagat gcagcacgta gtcggtcttg tcgacccgcc agggtagccg 420
cacattctgg gccttgatgg tgatgccgcg ttcccgctcg atgtccatcc gatccaagta 480
ctgggcccgc atagagcgtt cgtcgaccac tccggtgagc tgcagcatcc ggtcggccaa 540
cgttgacttg ccgtggtcga tgtgggcgat gatgcaaaag ttcctaatct gcgccg 596

<210> SEQ ID NO 165
<211> LENGTH: 596
<212> TYPE: DNA
<213> ORGANISM: Mycobacterium canetti

<400> SEQUENCE: 165
gtaaacggag tcgaaaatca ttgcgcgggt aggtgcctcg gcgtcgccct gcgggggcgg 60
cacctgtcgg accacctcgt cgagcaggtc ggacacgcct tcgccggttt tgccggacac 120
ccgcaacacc tcggccggct cgcagccgat gatgtgtgcc atctcggcgg cgtaacggtc 180
cgggtcggcc gcgggcaggt cgatcttgtt gagcaccggg atgatgtgca ggtcgcggtc 240
caacgccagg tagaggttcg ccagcgtctg cgcctcgatg ccttgcgcgg catcgaccaa 300
cagcaccgca ccctcgcaag cctccagcgc acgcgagact tcgtaggtga agtcgacatg 360
gcccggggtg tcgatcagat gcagcacgta gtcggtcttg tcgacccgcc agggtagccg 420
cacattctgg gccttgatgg tgatgccgcg ttcccgctcg atgtccatcc gatccaagta 480
ctgggcccgc atagagcgtt cgtcgaccac gccggtgagc tgcagcatcc ggtcggccaa 540
cgttgacttg ccgtggtcga tgtgggcgat gatgcaaaag ttcctaatct gcgccg 596

<210> SEQ ID NO 166
<211> LENGTH: 596
<212> TYPE: DNA
<213> ORGANISM: Mycobacterium canetti

<400> SEQUENCE: 166
gtaaacggag tcgaaaatca ttgcgcgggt aggtgcctcg gcgtcgccct gcgggggcgg 60
cacctgtcgg accacctcgt cgagcaggtc ggacacgcct tcgccggttt tgccggacac 120
ccgcaacacc tcggccggct cgcagccgat gatgtgtgcc atctcggcgg cgtaacggtc 180
cgggtcggcc gcgggcaggt cgatcttgtt gagcaccggg atgatgtgca ggtcgcggtc 240
caacgccagg tagaggttcg ccagcgtctg cgcctcgatg ccttgcgcgg catcgaccaa 300
cagcaccgca ccctcgcaag cctccagcgc acgcgagact tcgtaggtga agtcgacatg 360
gcccggggtg tcgatcagat gcagcacgta gtcggtcttg tcgacccgcc agggtagccg 420
cacattctgg gccttgatgg tgatgccgcg ttcccgctcg atgtccatcc gatccaagta 480
ctgggcccgc atagagcgtt cgtcgaccac gccggtgagc tgcagcatcc ggtcggccaa 540
cgttgacttg ccgtggtcga tgtgggcgat gatgcaaaag ttcctaatct gcgccg 596

<210> SEQ ID NO 167
<211> LENGTH: 596
<212> TYPE: DNA
<213> ORGANISM: Mycobacterium caprae

<400> SEQUENCE: 167
gtaaacggag tcgaaaatca ttgcgcgggt aggtgcctcg gcgtcgccct gagggggcgg 60
cacctgtcgg accacctcgt cgagcaggtc ggacacgcct tcgccggttt tgccggacac 120
ccgcaacacc tcggccggct cgcagccgat gatgtgtgcc atctcggcgg cgtaacggtc 180
cgggtcggcc gcgggcaggt cgatcttgtt gagcaccggg atgatgtgca ggtcgcggtc 240
caacgccagg tagaggttcg ccagcgtctg cgcctcgatg ccttgcgcgg catcgaccaa 300
cagcaccgca ccctcgcaag cctccagcgc acgcgagact tcgtaggtga agtcgacatg 360
gcccggggtg tcgatcagat gcagcacgta gtcggtcttg tcgacccgcc agggtagccg 420
cacattctgg gccttgatgg tgatgccgcg ttcccgctcg atgtccatcc gatccaagta 480
ctgggcccgc atagagcgtt cgtcgaccac tccggtgagc tgcagcatcc ggtcggccaa 540
cgttgacttg ccgtggtcga tgtgggcgat gatgcaaaag ttcctaatct gcgccg 596

<210> SEQ ID NO 168
<211> LENGTH: 596
<212> TYPE: DNA
<213> ORGANISM: Mycobacterium caprae

<400> SEQUENCE: 168
gtaaacggag tcgaaaatca ttgcgcgggt aggtgcctcg gcgtcgccct gagggggcgg 60
cacctgtcgg accacctcgt cgagcaggtc ggacacgcct tcgccggttt tgccggacac 120
ccgcaacacc tcggccggct cgcagccgat gatgtgtgcc atctcggcgg cgtaacggtc 180
cgggtcggcc gcgggcaggt cgatcttgtt gagcaccggg atgatgtgca ggtcgcggtc 240
caacgccagg tagaggttcg ccagcgtctg cgcctcgatg ccttgcgcgg catcgaccaa 300
cagcaccgca ccctcgcaag cctccagcgc acgcgagact tcgtaggtga agtcgacatg 360
gcccggggtg tcgatcagat gcagcacgta gtcggtcttg tcgacccgcc agggtagccg 420
cacattctgg gccttgatgg tgatgccgcg ttcccgctcg atgtccatcc gatccaagta 480
ctgggcccgc atagagcgtt cgtcgaccac tccggtgagc tgcagcatcc ggtcggccaa 540
cgttgacttg ccgtggtcga tgtgggcgat gatgcaaaac ttcctaatct gcgccg 596

<210> SEQ ID NO 169
<211> LENGTH: 596
<212> TYPE: DNA
<213> ORGANISM: Mycobacterium microtti

<400> SEQUENCE: 169
gtaaacggag tcgaaaatca ttgcgcgggt aggtgcctcg gcgtcgccct gagggggcgg 60
cacctgtcgg accacctcgt cgagcaggtc ggacacgcct tcgccggttt tgccggacac 120
ccgcaacacc tcggccggct cgcagccgat gatgtgtgcc atctcggcgg cgtaacggtc 180
cgggtcggcc gcgggcaggt cgatcttgtt gagcaccggg atgatgtgca ggtcgcggtc 240
caacgccagg tagaggttcg ccagcgtctg cgcctcgatg ccttgcgcgg catcgaccaa 300
cagcaccgca ccctcgcaag cctccagcgc acgcgagact tcgtaggtga agtcgacatg 360
gcccggggtg tcgatcagat gcagcacgta gtcggtcttg tcgacccgcc agggtagccg 420
cacattctgg gccttgatgg tgatgccgcg ttcccgctcg atgtccatcc gatccaagta 480
ctgggcccgc atagagcgtt cgtcgaccac tccggtgagc tgcagcatcc ggtcggccaa 540
cgttgacttg ccgtggtcga tgtgggcgat gatgcaaaag ttcctaatct gcgccg 596

<210> SEQ ID NO 170
<211> LENGTH: 596
<212> TYPE: DNA
<213> ORGANISM: Mycobacterium pinipedii

<400> SEQUENCE: 170
gtaaacggag tcgaaaatca ttgcgcgggt aggtgcctcg gcgtcgccct gagggggcgg 60
cacctgtcgg accacctcgt cgagcaggtc ggacacgcct tcgccggttt tgccggacac 120
ccgcaacacc tcggccggct cgcagccgat gatgtgtgcc atctcggcgg cgtaacggtc 180
cgggtcggcc gcgggcaggt cgatcttgtt gagcaccggg atgatgtgca ggtcgcggtc 240
caacgccagg tagaggttcg ccagcgtctg cgcctcgatg ccttgcgcgg catcgaccaa 300
cagcaccgca ccctcgcaag cctccagcgc acgcgagact tcgtaggtga agtcgacatg 360
gcccggggtg tcgatcagat gcagcacgta gtcggtcttg tcgacccgcc agggtagccg 420
cacattctgg gccttgatgg tgatgccgcg ttcccgctcg atgtccatcc gatccaagta 480
ctgggcccgc atagagcgtt cgtcgaccac tccggtgagc tgcagcatcc ggtcggccaa 540
cgttgacttg ccgtggtcga tgtgggcgat gatgcaaaac ttcctaatct gcgccg 596

<210> SEQ ID NO 171
<211> LENGTH: 596
<212> TYPE: DNA
<213> ORGANISM: Mycobacterium tuberculosis

<400> SEQUENCE: 171
gtaaacggag tcgaaaatca ttgcgcgggt aggtgcctcg gcgtcgccct gagggggcgg 60
cacctgtcgg accacctcgt cgagcaggtc ggacacgcct tcgccggttt tgccggacac 120
ccgcaacacc tcggccggct cgcagccgat gatgtgtgcc atctcggcgg cgtaacggtc 180
cgggtcggcc gcgggcaggt cgatcttgtt gagcaccggg atgatgtgca ggtcgcggtc 240
caacgccagg tagaggttcg ccagcgtctg cgcctcgatg ccttgcgcgg catcgaccaa 300
cagcaccgca ccctcgcaag cctccagcgc acgcgagact tcgtaggtga agtcgacatg 360
gcccggggtg tcgatcagat gcagcacgta gtcggtcttg tcgacccgcc agggtagccg 420
cacattctgg gccttgatgg tgatgccgcg ttcccgctcg atgtccatcc gatccaagta 480
ctgggcccgc atagagcgtt cgtcgaccac gccggtgagc tgcagcatcc ggtcggccaa 540
cgttgacttg ccgtggtcga tgtgggcgat gatgcaaaag ttcctaatct gcgccg 596

<210> SEQ ID NO 172
<211> LENGTH: 617
<212> TYPE: DNA
<213> ORGANISM: Mycobacterium smegmatis

<400> SEQUENCE: 172
gtacacggag tcgaagatca tcgcgcgcgt cggggcgtcg gggtcaccga ccggcggcgg 60
caccttacgc accacctcgt cgagcagctc ggccacgcct tcgccggtct tgcccgagac 120
acgcagcacg tccgacggct cacacccgat gatgtgggcg agctcgtcgg catagcggtc 180
cgggtcagcg gcgggcaggt cgatcttgtt gagcaccggg atgatcgcca ggtcgcggtc 240
cagcgccagg tacaggttgg ccagcgtctg cgcctcgatg ccctgcgccg cgtcgaccag 300
cagcaccgcg ccctcgcagg cctccagcgc gcgcgacacc tcgtaggtga agtcgacgtg 360
gcccggggtg tcgatcaggt gcagcacgta atcacccgcg tccgcgccgt cttggccgtc 420
cttcagcgtc cacggaagcc ggacgttctg agccttgatg gtgatcccgc gctcacgttc 480
gatgtccatg cggtcgaggt actgggcccg catcgaccgc tcatcgacaa caccggtgag 540
ctgcagcatc cggtcggcca gcgtcgactt gccgtggtcg atgtgggcga tgatgcagaa 600
gttcctaatc tgcgccg 617

<210> SEQ ID NO 173
<211> LENGTH: 572
<212> TYPE: DNA
<213> ORGANISM: Mycobacterium celatum

<400> SEQUENCE: 173
ccgggtgggg gcttcggcgt cgccgactgg cggtggaacc tgcttgacga cggcgtcgag 60
cagttcgggc accccctcgc cggtcttgcc ggagacccgc agcacgtcgt cgggttcgca 120
gccgatgatg tgggcgatct cgccggcgta gcggtccggg tcggcggccg gcaggtcgat 180
cttgttgagc accgggatga tcgccaggtc gcggtccagc gccaggtaca ggttggccag 240
cgtctgcgcc tcgatgccct gcgcggcgtc caccagcagc accgcccctt cgcaggcggc 300
cagcgcgcgg gacacctcgt aggtgaagtc gacgtggccc ggggtgtcga tcaggtgcag 360
gacgtggtcg gtgtccccga ctcgccaggg caggcgcaca ttttgcgcct tgatcgtgat 420
cccccgttcg cgctcgatgt ccatccggtc caggtactgc gcccgcatgg accgctcgtc 480
gacgactccg gtcagctgca gcatccggtc ggccagcgtg gacttgccgt ggtcgatgtg 540
ggcgatgatg cagaagttcc taatctgcgc cg 572

<210> SEQ ID NO 174
<211> LENGTH: 596
<212> TYPE: DNA
<213> ORGANISM: Mycobacterium fortuitum

<400> SEQUENCE: 174
gtacacggag tcgaagatca tcgcgcgcgt gggcgcgtcg ggatcaccca ccggcggcgg 60
cacctggcgc accacctcgt cgagcagttc ggccacgccc tcaccggtct tgccggagac 120

```
gcgcagcacg tcggaaggct cacagccgat gatgtgggcg agctcgccgg cgtagcggtc    180

cgggtccgcg gcgggcaggt cgatcttgtt gagcaccggg atgatcgcca ggtcgcggtc    240

cagtgccagg tacaggttgg ccagcgtctg cgcctcgatg ccctgtgcgg cgtcgaccag    300

cagcaccgca ccctcgcagg cctcgagcgc acgggacacc tcgtaggtga agtcgacgtg    360

gcccggggtg tcgatcaggt gcaggacgtg atcctgcccg tcgacgcgcc agggcagccg    420

aacgttctgc gccttgatcg tgatcccgcg ctcacgctcg atgtccatgc ggtcgaggta    480

ctgggcacgc atcgaccgct cgtcgacgac gccggtgagc tgcagcatcc ggtcggccag    540

cgtcgacttg ccatggtcga tgtgagcgat gatgcagaag ttcctaatct gcgccg        596
```

```
<210> SEQ ID NO 175
<211> LENGTH: 564
<212> TYPE: DNA
<213> ORGANISM: Mycobacterium intracellulare

<400> SEQUENCE: 175

gcgcgtcggc cttgccctgc gggggcggca cctggcccac cacctcgtcg agcagctcgg     60

ccactccctc gccggttttg ccggacaccc gcagcacgtc gtcgggctcg cagccgatga    120

tgtgggcgag ctctcctgcg tagcggtccg ggtcggccgc cggcaggtcg atcttgttga    180

gcaccgggat gatggtcagg tcacggtcca gcgccaggta gaggttggcc agggtctgcg    240

cctcgatgcc ctgggcggcg tcgaccaaca gcaccgcgcc ctcgcaggcc tccagcgcgc    300

gcgacacctc gtaggtgaag tcgacgtggc ccggggtgtc gatcaggtgc aggacatggt    360

cttcgtcgtc gactttccac gggagccgga cgttctgcgc cttgatggtg atgccgcgct    420

cgcgctcgat gtccatccgg tccaggtact gggcgcgcat cgagcgctca tcgacgacgc    480

cggtgagctg cagcatccgg tcggccagcg tcgacttgcc gtgatcgatg tgggcgatga    540

tgcagaagtt cctaatctgc gccg                                           564
```

```
<210> SEQ ID NO 176
<211> LENGTH: 591
<212> TYPE: DNA
<213> ORGANISM: Mycobacterium malmoense

<400> SEQUENCE: 176

cagagtcgaa gatcatcgcg cgggtgggcg cgtcggcgtc gccctgcggc ggcggcacct     60

gacggaccac ctcgtcgaga aggtgcgcga cgccctcgcc ggtcttgccg gacacccgca    120

gcacgtcggt cggctcgcag cccatgatgt gggcgatctc ggccgcgtag cggtccggat    180

cggcggccgg cagatcgatc ttgttgagca ccgggatgat ggtcaggtca cggtccagcg    240

ccaggtagag gttggccagg gtctgggcct cgatgccctg ggccgcgtcg accagcagca    300

ccgcgccctc acaggcctcc agcgcgcggg agacctcgta ggtgaagtcg acgtgaccag    360

gggtgtcgat caggtgcagg acgtactggg ttccatcgac ttgccagggc agccggacgt    420

tctgggcctt gatggtgatc ccgcgctccc gctcgatgtc catccggtcc aggtattggg    480

cgcgcatcga tcgctcgtcg acgacgccgg tgagctggag catccggtcc gcgagcgtcg    540

acttgccatg gtcgatgtga gcgatgatgc agaagttcct aatctgcgcc g             591
```

```
<210> SEQ ID NO 177
<211> LENGTH: 606
<212> TYPE: DNA
<213> ORGANISM: Mycobacterium paratuberculosis
```

-continued

<400> SEQUENCE: 177

```
cagagtcgaa gatcatcgcg cgcagcggcg catcggcctg cccctgcggc ggcggcacct     60

ggcgcaccac ctcgtcgagc agccgcgcca cgccctcccc ggttttgccg gacacccaca    120

gcacgtcgtc gggttcgcac ccgatgatgt gggcgagctc gccggcgtag cgatccgggt    180

cggcggccgg caggtcgatc ttgttgagga ccgggatgat ggtcagatcg cggtccagcg    240

ccaggtagag gttggccagc gtctgggcct cgatgccctg cgcggcgtcg accagcagca    300

cggcaccttc gcaggcctcc agtgcgcgcg acacctcgta ggtgaagtcg acgtggcccg    360

gggtgtcgat caggtgcagg acaaattctt tgccggcgtc ctcgccgccg gagacctgcc    420

agggcagccg cacgttctgc gccttgatgg tgatgccgcg ctcccgctcg atgtccatcc    480

ggtccaggta ctgggcgcgc atcgaccgct cgtcgacgac gccggtgagc tgcagcatcc    540

ggtcggccag cgtcgacttg ccgtgatcga tgtgggcgat gatgcagaag ttcctaatct    600

gcgccg                                                               606
```

<210> SEQ ID NO 178
<211> LENGTH: 596
<212> TYPE: DNA
<213> ORGANISM: Mycobacterium scrofulaceum

<400> SEQUENCE: 178

```
gtaaacggag tcgaaaatca ttgcgcgggt aggtgcctcg gcgtcgccct gagggggcgg     60

cacctgtcgg accacctcgt cgagcaggtc ggacacgcct tcgccggttt tgccggacac    120

ccgcaacacc tcggccggct cgcagccgat gatgtgtgcc atctcggcgg cgtaacggtc    180

cgggtcggcc gcgggcaggt cgatcttgtt gagcaccggg atgatgtgca ggtcgcggtc    240

caacgccagg tagaggttcg ccagcgtctg cgcctcgatg ccttgcgcgg catcgaccaa    300

cagcaccgca ccctcgcaag cctccagcgc acgcgagact tcgtaggtga agtcgacatg    360

gcccggggtg tcgatcagat gcagcacgta gtcggtcttg tcgacccgcc agggtagccg    420

cacattctgg gccttgatgg tgatgccgcg ttcccgctcg atgtccatcc gatccaagta    480

ctgggcccgc atagagcgtt cgtcgaccac tccggtgagc tgcagcatcc ggtcggccaa    540

cgttgacttg ccgtggtcga tgtgggcgat gatgcaaaag ttcctaatct gcgccg        596
```

*LEPA*/GUF1 GENE SEQUENCES AS A DIAGNOSTIC TARGET FOR THE IDENTIFICATION OF BACTERIAL SPECIES

CROSS-REFERENCE TO RELATED APPLICATIONS

This application claims the benefit under 35 U.S.C. §371 of PCT International Application No. PCT/EP2009/057389, filed Jun. 15, 2009, which in turn claims priority to Irish Application No. 2008/0494, filed Jun. 16, 2008, the contents of each which are hereby incorporated by reference in their entirety.

FIELD OF THE INVENTION

The present invention relates to nucleic acid primers and probes to detect one or more bacterial and yeast and fungal species. More specifically the invention relates to the LepA and Guf1 gene sequences, their corresponding RNAs, specific probes, primers and oligonucleotides related thereto and their use in diagnostic assays to detect and/or discriminate bacterial, yeast and fungal species, i.e. microorganisms.

BACKGROUND TO THE INVENTION

Microbial infections represent a major cause of morbidity and mortality worldwide, and the spectrum of microorganisms causing disease continues to increase. Microorganisms (bacteria, fungi and yeast) responsible for causing infectious diseases are traditionally detected in hospital laboratories with the aid of microbiological culture methods with poor sensitivity (25-82%), which are very time-consuming, generally taking from two to five days to complete, and up to eight days for the diagnosis of fungal infections. Definitive diagnosis is usually based on either, the recovery and identification of a specific microorganism from clinical specimens or microscopic demonstration of fungi with distinct morphological features. However, there are numerous cases where these methods fail to provide conclusive proof as to the infecting agent or microrganism. In these instances, the detection of specific host antibody responses can be used, although again this can be affected by the immune status of the patient.

Time is critical in the detection and identification of infectious microorganisms. Effective treatment depends on finding the source of infection and making appropriate decisions about antibiotics quickly and efficiently. Only after pathogens are correctly identified, can targeted therapy using a specific antibiotic begin. Many physicians would like to see the development of better in vitro amplification and direct detection diagnostic techniques for the early diagnosis of microbial infection. Recently, Roche™ launched a real time PCR based assay (Septifast™), for the detection of microbial DNA in clinical samples. Therefore, there is a clear need for the development of novel rapid diagnostic tests for clinically significant bacterial and fungal pathogens for bioanalysis applications in the clinical sector. This has led the current inventors to identify novel nucleic acid targets for application in Nucleic Acid Diagnostic (NAD) tests.

It is clear though, that development of faster, more accurate diagnostic methods are required, particularly in light of the selection pressure caused by modern anti-microbial treatments which give rise to increased populations of resistant virulent strains with mutated genome sequences. Methods that enable early diagnosis of microbial causes of infection enable the selection of a specific narrow spectrum antibiotic or antifungal to treat the infection (Datamonitor report:

Stakeholder opinion—Invasive fungal infections, options outweigh replacements 2004; Datamonitor report: Stakeholder Opinion-Sepsis, under reaction to an overreaction, 2006).

LepA (leader peptidase A) has recently been assigned the function of ribosomal elongation factor (Qin et al., 2006, Cell). LepA is highly conserved and is present in all bacteria and mitochondria. There are 2444 LepA gene sequences (~1.8 kb in length) available in GenBank including 2229 bacterial sequences. Using Clustal W sequence alignments, the LepA gene of *Bacillus, Listeria*, Enterobacteriaceae, *Mycobacteria*, Staphylococci and Streptococci were compared in silico to other molecular targets including tufA and the ssrA genes. In general, LepA seemed to have sufficient sequence heterogeneity to enable its application for microorganism species identification in nucleic acid based tests (Table 1).

TABLE 1

Percentage range of homology between *Bacillus* species, *Listeria* species, Enterobacteriaceae, *Mycobacterium* species, *Streptococcus* species and *Staphylococcus* species in the LepA gene compared to the tufA (equivalent commercialised mRNA) and ssrA genes (RiboSEQ technology).

| | LepA (range of % homology between species) | tufA (range of % homology between species) | ssrA (range of % homology between species) |
|---|---|---|---|
| *Bacillus* species | 72-97 | 81-99 | 62-100 |
| *Listeria* species | 89-90 | 99 | 97-99 |
| Enterobacteriaceae (including *E. coli*) | 59-99 | 83-99 | 92-99 |
| *Mycobacterium* species | 78-99 | 87-100 | 84-100 |
| *Streptococcus* species | 70-91 | 76-97 | 62-100 |
| *Staphylococcus* species | 80-83 | 91-95 | 81-99 |

GUF1, which is similar to the *E. coli* elongation factor-type GTP-binding protein LepA, is a gene encoding a novel evolutionarily conserved GTPase coding protein (GTPase of Unknown Function 1, Kiser G L and Weinert T A (1995) GUF1, a gene encoding a novel evolutionarily conserved GTPase in budding yeast. Yeast 11(13): 1311-6), which, was predicted to be the GTPase of the elongation factor-type class. There are 94 Guf1 sequences available in NCBI GeneBank including 3 *Candida* and 6 *Aspergillus*.

DEFINITIONS

"Synthetic oligonucleotide" refers to molecules of nucleic acid polymers of 2 or more nucleotide bases that are not derived directly from genomic DNA or live organisms. The term synthetic oligonucleotide is intended to encompass DNA, RNA, and DNA/RNA hybrid molecules that have been manufactured chemically, or synthesized enzymatically in vitro.

An "oligonucleotide" is a nucleotide polymer having two or more nucleotide subunits covalently joined together. Oligonucleotides are generally about 10 to about 100 nucleotides. The sugar groups of the nucleotide subunits may be ribose, deoxyribose, or modified derivatives thereof such as OMe. The nucleotide subunits may be joined by linkages such as phosphodiester linkages, modified linkages or by non-nucleotide moieties that do not prevent hybridization of the oligonucleotide to its complementary target nucleotide sequence. Modified linkages include those in which a standard phosphodiester linkage is replaced with a different linkage, such as a phosphorothioate linkage, a methylphosphonate linkage, or a neutral peptide linkage. Nitrogenous base analogs also may be components of oligonucleotides in accordance with the invention.

A "target nucleic acid" is a nucleic acid comprising a target nucleic acid sequence. A "target nucleic acid sequence," "target nucleotide sequence" or "target sequence" is a specific deoxyribonucleotide or ribonucleotide sequence that can be hybridized to a complementary oligonucleotide.

An "oligonucleotide probe" is an oligonucleotide having a nucleotide sequence sufficiently complementary to its target nucleic acid sequence to be able to form a detectable hybrid probe:target duplex under high stringency hybridization conditions. An oligonucleotide probe is an isolated chemical species and may include additional nucleotides outside of the targeted region as long as such nucleotides do not prevent hybridization under high stringency hybridization conditions. Non-complementary sequences, such as promoter sequences, restriction endonuclease recognition sites, or sequences that confer a desired secondary or tertiary structure such as a catalytic active site can be used to facilitate detection using the invented probes. An oligonucleotide probe optionally may be labelled with a detectable moiety such as a radioisotope, a fluorescent moiety, a chemiluminescent, a nanoparticle moiety, an enzyme or a ligand, which can be used to detect or confirm probe hybridization to its target sequence. Oligonucleotide probes are preferred to be in the size range of from about 10 to about 100 nucleotides in length, although it is possible for probes to be as much as and above about 500 nucleotides in length, or below 10 nucleotides in length.

A "hybrid" or a "duplex" is a complex formed between two single-stranded nucleic acid sequences by Watson-Crick base pairings or non-canonical base pairings between the complementary bases. "Hybridization" is the process by which two complementary strands of nucleic acid combine to form a double-stranded structure ("hybrid" or "duplex").

"Complementarity" is a property conferred by the base sequence of a single strand of DNA or RNA which may form a hybrid or double-stranded DNA:DNA, RNA:RNA or DNA:RNA through hydrogen bonding between Watson-Crick base pairs on the respective strands. Adenine (A) ordinarily complements thymine (T) or uracil (U), while guanine (G) ordinarily complements cytosine (C).

The term "stringency" is used to describe the temperature, ionic strength and solvent composition existing during hybridization and the subsequent processing steps. Those skilled in the art will recognize that "stringency" conditions may be altered by varying those parameters either individually or together. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. Stringency conditions are chosen to maximize the difference in stability between the hybrid formed with the target and the non-target nucleic acid.

'High stringency' conditions are those equivalent to binding or hybridization at 42° C. in a solution consisting of 5×SSPE (43.8 g/l NaCl, 6.9 g/l $NaH_2PO_4H_2O$ and 1.85 g/l EDTA, ph adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42° C. when a probe of about 500 nucleotides in length is used.

"Medium stringency' conditions are those equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 1.0×SSPE, 1.0% SDS at 42° C., when a probe of about 500 nucleotides in length is used.

'Low stringency' conditions are those equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 μg/ml denatured salmon sperm DNA followed by washing in a solution comprising 5×SSPE, 0.1% SDS at 42° C., when a probe of about 500 nucleotides in length is used.

In the context of nucleic acid in-vitro amplification based technologies, "stringency" is achieved by applying temperature conditions and ionic buffer conditions that are particular to that in-vitro amplification technology. For example, in the context of PCR and real-time PCR, "stringency" is achieved by applying specific temperatures and ionic buffer strength for hybridisation of the oligonucleotide primers and, with regards to real-time PCR hybridisation of the probe/s, to the target nucleic acid for in-vitro amplification of the target nucleic acid.

One skilled in the art will understand that substantially corresponding probes of the invention can vary from the referred-to sequence and still hybridize to the same target nucleic acid sequence. This variation from the nucleic acid may be stated in terms of a percentage of identical bases within the sequence or the percentage of perfectly complementary bases between the probe and its target sequence. Probes of the present invention substantially correspond to a nucleic acid sequence if these percentages are from about 100% to about 80% or from 0 base mismatches in about 10 nucleotide target sequence to about 2 bases mismatched in an about 10 nucleotide target sequence. In preferred embodiments, the percentage is from about 100% to about 85%. In more preferred embodiments, this percentage is from about 90% to about 100%; in other preferred embodiments, this percentage is from about 95% to about 100%

By "sufficiently complementary" or "substantially complementary" is meant nucleic acids having a sufficient amount of contiguous complementary nucleotides to form, under high stringency hybridization conditions, a hybrid that is stable for detection.

By "nucleic acid hybrid" or "probe:target duplex" is meant a structure that is a double-stranded, hydrogen-bonded structure, preferably about 10 to about 100 nucleotides in length, more preferably 14 to 50 nucleotides in length, although this will depend to an extent on the overall length of the oligonucleotide probe. The structure is sufficiently stable to be detected by means such as chemiluminescent or fluorescent light detection, autoradiography, electrochemical analysis or gel electrophoresis. Such hybrids include RNA:RNA, RNA:DNA, or DNA:DNA duplex molecules.

"RNA and DNA equivalents" refer to RNA and DNA molecules having the same complementary base pair hybridization properties. RNA and DNA equivalents have different sugar groups (i.e., ribose versus deoxyribose), and may differ by the presence of uracil in RNA and thymine in DNA. The difference between RNA and DNA equivalents do not contribute to differences in substantially corresponding nucleic acid sequences because the equivalents have the same degree of complementarity to a particular sequence.

By "preferentially hybridize" is meant that under high stringency hybridization conditions oligonucleotide probes can hybridize their target nucleic acids to form stable probe:target hybrids (thereby indicating the presence of the target nucleic acids) without forming stable probe:non-target hybrids (that would indicate the presence of non-target nucleic acids from other organisms). Thus, the probe hybridizes to target nucleic acid to a sufficiently greater extent than to non-target nucleic acid to enable one skilled in the art to accurately detect the presence of (for example *Candida*) and distinguish these species from other organisms. Preferential hybridization can be measured using techniques known in the art and described herein.

By "theranostics" is meant the use of diagnostic testing to diagnose the disease, choose the correct treatment regime and monitor the patient response to therapy. The theranostics of the invention may be based on the use of an NAD assay of this invention on samples, swabs or specimens collected from the patient.

OBJECT OF THE INVENTION

It is an object of the current invention to provide sequences and/or diagnostic assays to detect and identify one or more microorganism species (bacteria, yeast, fungi). The current inventors have made use of the LepA and Guf1 gene sequences to design primers and probes for use in the detection and identification of bacterial and yeast and fungal species.

SUMMARY OF THE INVENTION

The present invention provides a diagnostic kit for detection and identification of bacterial and yeast and fungal species i.e. microorganisms, comprising at least one oligonucleotide probe capable of binding to at least a portion of the LepA gene or Guf1 gene or its corresponding mRNA. The oligonucleotide probe may have a sequence substantially homologous to or substantially complementary to a portion of the LepA or Guf1 gene or its corresponding mRNA. It will thus be capable of binding or hybridizing with a complementary DNA or RNA molecule. The nucleic acid molecule may be synthetic.

The kit may comprise more than one such probe. In particular the kit may comprise a plurality of such probes. In addition the kit may comprise additional probes for other organisms, such as, for example, bacterial species or viruses.

The portion of the LepA gene may, for example, be equivalent to a portion of the region of the gene between base pair (bp) position 57 to bp 228 or by position 522 to by position 659 in *Staphylococcus aureus*. Particularly preferred are portions equivalent to a portion of the region of the gene between base pair positions 66 to 215, 66 to 81, 200 to 215 and 167 to 189 of the Group B streptoccal LepA gene, and positions 57 to 228, 57 to 74, 209 to 228 and 112 to 134 of the *S. aureus* LepA gene. The portion of the LepA gene may, for example, be equivalent to a portion of the region of the gene between by position 66 to by 215 in Group B *Streptococcus*. For *Mycobacteria*, the portion of LepA may be equivalent to a portion of the region of the gene between by 618 to 772 and by 1203 to by 1817 in *M. tuberculosis* or the equivalent regions in other *Mycobacterium tuberculosis* complex (MTC) species and non-MTC mycobacteria. In *Bordetella*, the portion of the LepA may be equivalent to 3 regions by 160 to by 612, by 552 to by 1081 and by 1006 to by 1638.

The portion of the Guf1 gene may be equivalent to a portion of the region of the gene from base pair position 190 to base pair position 2204 of the gene. Particularly preferred are portions equivalent to a portion of the region of the gene from base pair positions 190 to 1064, 270 to 300, 190 to 212, 466 to 491, 507 to 537, 466 to 489, 740 to 762, 828 to 858, 740 to 762 and 1043 to 1064 of the *C. albicans* Guf1 gene, or from base pair position 613 to 2204, 613 to 635, 820 to 839, 1339 to 1358, 1573 to 1592, 1951 to 1973 and 2183 to 2204 of the *A. fumagatus* Guf1 gene.

The oligonucleotide probe may have a sequence selected from the group comprising SEQ ID NO 11 or SEQ ID NO 12, SEQ ID NO 15, SEQ ID NO 20, SEQ ID NO 21, SEQ ID NO 26, SEQ ID NO 27, SEQ ID NO 30, SEQ ID NO 35, SEQ ID NO 36, SEQ ID NO 37, SEQ ID NO 40, SEQ ID NO 43, SEQ ID NO 46, SEQ ID NO 49, SEQ ID NO 52 or a sequence substantially homologous to or substantially complementary to those sequences, which can also act as a probe for the LepA and or Guf1 genes.

The kit may comprise more than one such probe. In particular the kit may comprise a plurality of such probes. In addition the kit may comprise additional probes for other organisms, such as, for example, bacterial species or viruses.

The identified sequences are suitable not only for in vitro DNA/RNA amplification based detection systems but also for signal amplification based detection systems. Furthermore, the sequences of the invention identified as suitable targets provide the advantages of having significant intragenic sequence heterogeneity in some regions, which is advantageous and enables aspects of the invention to be directed towards group or species-specific targets, and also having significant sequence homogeneity in some regions, which enables aspects of the invention to be directed towards genus-specific microorganism primers and probes for use in direct nucleic acid detection technologies, signal amplification nucleic acid detection technologies, and nucleic acid in vitro amplification technologies for microorganism diagnostics. The LepA and Guf1 sequences allow for multi-test capability and automation in diagnostic assays.

One of the advantages of the sequences of the present invention is that the intragenic LepA and Guf1 nucleotide sequence diversity between closely related microorganism species enables specific primers and probes for use in diagnostics assays for the detection of bacteria to be designed. The LepA and Guf1 nucleotide sequences, both DNA and RNA can be used with direct detection, signal amplification detection and in vitro amplification technologies in diagnostics assays. The LepA and Guf1 sequences allow for multi-test capability and automation in diagnostic assays.

The kit may further comprise at least one primer for amplification of at least a portion of the LepA or Guf1 genes. Suitably the kit comprises a forward and a reverse primer for a portion of the LepA or Guf1 gene. The kit may also comprise additional primers or probes.

The primer may have a sequence selected from the group comprising SEQ ID NO 1, 2, 3, 4, 5, 6, 7, 8, 9, 10, 13, 14, 16, 17, 18, 19, 22, 23, 24, 25, 28, 29, 31, 32, 33, 34, 38, 39, 41, 42, 44, 45, 47, 48, 50, 51, 53, 54 or a sequence substantially homologous to or substantially complementary to those sequences, which can also act as a primers for the LepA or Guf1 genes.

The kit may comprise at least one forward in vitro amplification primer and/or at least one reverse in vitro amplification primer, the forward amplification primer having a sequence selected from the group consisting of SEQ ID NO 1, 3 5, 7, 9, 13, 16, 18, 22, 24, 28, 31, 33, 38, 41, 44, 47, 50, 53, or a sequence being substantially homologous or complementary thereto which can also act as a forward amplification primer for the LepA or Guf1 gene, and the reverse amplification primer having a sequence selected from the group consisting of SEQ ID NO 2, 4, 6, 8, 10, 14, 17, 19, 23, 25, 29, 32, 34, 39, 42, 45, 48, 51, 54, or a sequence being substantially homologous or complementary thereto which can also act as a reverse amplification primer for the LepA or Guf1 gene.

The diagnostic kit may be based on direct nucleic acid detection technologies, signal amplification nucleic acid detection technologies, and nucleic acid in vitro amplification technologies is selected from one or more of Polymerase Chain Reaction (PCR), Ligase Chain Reaction (LCR), Nucleic Acids Sequence Based Amplification (NASBA), Strand Displacement Amplification (SDA), Transcription Mediated Amplification (TMA), Branched DNA technology (bDNA) and Rolling Circle Amplification Technology (RCAT)), or other in vitro enzymatic amplification technologies.

The invention also provides a nucleic acid molecule selected from the group consisting of SEQ ID NO.1 to SEQ ID NO. 178 and sequences substantially homologous thereto, or substantially complementary to a portion thereof and having a function in diagnostics based on the LepA and/or Guf1 genes. The nucleic acid molecule may comprise an oligonucleotide having a sequence substantially homologous to or substantially complementary to a portion of a nucleic acid molecule of SEQ ID NO.1 to SEQ ID NO. 178. The invention also provides a method of detecting a target organism in a test sample comprising the steps of:

(i) mixing the test sample with at least one oligonucleotide probe as defined above under appropriate conditions; and
(ii) hybridizing under high stringency conditions any nucleic acid that may be present in the test sample with the oligonucleotide to form a probe:target duplex; and
(iii) determining whether a probe:target duplex is present; the presence of the duplex positively identifying the presence of the target organism in the test sample.

The nucleic acid molecule and kits of the present invention may be used in a diagnostic assay to detect the presence of one or more bacterial species, to measure microorganism titres in a patient or in a method of assessing the efficacy of a treatment regime designed to reduce microorganism titre in a patient or to measure microorganism contamination in an environment. The environment may be a hospital, or it may be a food sample, an environmental sample e.g. water, an industrial sample such as an in-process sample or an end product requiring bioburden or quality assessment.

The kits and the nucleic acid molecule of the invention may be used in the identification and/or characterization of one or more disruptive agents that can be used to disrupt the LepA or Guf1 gene function. The disruptive agent may be selected from the group consisting of antisense RNA, PNA, and siRNA.

In some embodiments of the invention, a nucleic acid molecule comprising a species-specific probe can be used to discriminate between species of the same genus.

The oligonucleotides of the invention may be provided in a composition for detecting the nucleic acids of microorganism target organisms. Such a composition may also comprise buffers, enzymes, detergents, salts and so on, as appropriate to the intended use of the compositions. It is also envisioned that the compositions, kits and methods of the invention, while described herein as comprising at least one synthetic oligonucleotide, may also comprise natural oligonucleotides with substantially the same sequences as the synthetic nucleotide fragments in place of, or alongside synthetic oligonucleotides.

The invention also provides for an in vitro amplification diagnostic kit for a target microorganism comprising at least one forward in vitro amplification primer and at least one reverse in vitro amplification primer, the forward amplification primer being selected from the group consisting of one or more of a sequence being substantially homologous or complementary thereto which can also act as a forward amplification primer, and the reverse amplification primer being selected from the group consisting of one or more of or a sequence being substantially homologous or complementary thereto which can also act as a reverse amplification primer.

The invention also provides for a diagnostic kit for detecting the presence of candidate microorganism species, comprising one or more DNA probes comprising a sequence substantially complementary to, or substantially homologous to the sequence of the LepA or Guf1 gene of the candidate microorganism species. The present invention also provides for one or more synthetic oligonucleotides having a nucleotide sequence substantially homologous to or substantially complementary to one or more of the group consisting of the LepA or Guf1 gene or mRNA transcript thereof, the microorganism LepA gene or mRNA transcript thereof, one or more of SEQ ID NO 1-SEQ ID NO 178.

The nucleotide may comprise DNA. The nucleotide may comprise RNA. The nucleotide may comprise a mixture of DNA, RNA and PNA. The nucleotide may comprise synthetic nucleotides. The sequences of the invention (and the sequences relating to the methods, kits compositions and assays of the invention) may be selected to be substantially homologous to a portion of the coding region of the LepA or Guf1 gene. The gene may be a gene from a target microorganism. The sequences of the invention are preferably sufficient so as to be able form a probe:target duplex to the portion of the sequence.

The invention also provides for a diagnostic kit for a target microorganism comprising an oligonucleotide probe substantially homologous to or substantially complementary to an oligonucleotide of the invention (which may be synthetic). It will be appreciated that sequences suitable for use as in vitro amplification primers may also be suitable for use as oligonucleotide probes: while it is preferable that amplification primers may have a complementary portion of between about 15 nucleotides and about 30 nucleotides (more preferably about 15-about 23, most preferably about 20 to about 23), oligonucleotide probes of the invention may be any suitable length. The skilled person will appreciate that different hybridization and or annealing conditions will be required depending on the length, nature & structure (eg. Hybridization probe pairs for LightCycler, Taqman 5' exonuclease probes, hairpin loop structures etc. and sequence of the oligonucleotide probe selected.

Kits and assays of the invention may also be provided wherein the oligonucleotide probe is immobilized on a surface. Such a surface may be a bead, a membrane, a column, dipstick, a nanoparticle, the interior surface of a reaction chamber such as the well of a diagnostic plate or inside of a reaction tube, capillary or vessel or the like.

The target microorganism may be selected from the group consisting of *Streptococcus, Enterococcus, Mycobacterium, Bacillus, Listeria*, Enterobacteriaceae, *Neisseria, Chlamydia, Mycoplasma, Haemophilus, Clostridia, Bordetella* and Staphylococci, *Gardnerella, Candida, Aspergillus*

Under these circumstances, the amplification primers and oligonucleotide probes of the invention may be designed to a gene specific or genus specific region so as to be able to identify one or more, or most, or substantially all of the desired organisms of the target organism grouping.

The test sample may comprise cells of the target microorganism. The method may also comprise a step for releasing nucleic acid from any cells of the target organism that may be present in said test sample. Ideally, the test sample is a biological sample obtained from a patient (such as a swab, or blood, urine, saliva, a bronchial lavage dental specimen, skin specimen, scalp specimen, transplant organ biopsy, stool, mucus, or discharge sample). The test samples may be a food sample, a water sample an environmental sample, an end product, end product or in-process industrial sample.

The invention also provides for the use of any one of SEQ ID NO.1 to SEQ ID NO. 178 in a diagnostic assay for the presence of one or more microorganism species. The species may be selected from the group consisting of *Streptococcus, Enterococcus, Mycobacterium, Bacillus, Listeria*, Enterobacteriaceae, *Neisseria, Chlamydia, Mycoplasma, Haemophilus, Clostridia, Bordetella* and Staphylococci, *Gardnerella, Candida, Aspergillus*

The invention also provides for kits for use in clinical diagnostics, theranostics, food safety diagnostics, industrial microbiology diagnostics, environmental monitoring, veterinary diagnostics, bio-terrorism diagnostics comprising one or more of the synthetic oligonucleotides of the invention. The kits may also comprise one or more articles selected from the group consisting of appropriate sample collecting instruments, reagent containers, buffers, labelling moieties, solutions, detergents and supplementary solutions. The invention also provides for use of the sequences, compositions, nucleotide fragments, assays, and kits of the invention in theranostics, Food safety diagnostics, Industrial microbiology diagnostics, Environmental monitoring, Veterinary diagnostics, Bio-terrorism diagnostics.

The nucleic acid molecules, composition, kits or methods may be used in a diagnostic nucleic acid based assay for the detection of microorganism species.

The nucleic acid molecules, composition, kits or methods may be used in a diagnostic assay to measure microorganism titres in a patient. The titres may be measured in vitro.

The nucleic acid molecules, composition, kits or methods may be used in a method of assessing the efficacy of a treatment regime designed to reduce microorganism titre in a patient comprising assessing the microorganism titre in the patient (by in vivo methods or in vitro methods) at one or more key stages of the treatment regime. Suitable key stages may include before treatment, during treatment and after treatment. The treatment regime may comprise an anti-microbial or anti-fungal agent, such as a pharmaceutical drug.

The nucleic acid molecules, composition, kits or methods may be used in a diagnostic assay to measure potential micro-organism contamination, for example, in a hospital.

The nucleic acid molecules, composition, kits or methods may be used in the identification and/or characterization of one or more disruptive agents that can be used to disrupt the LepA and Guf 1 gene functions. Suitable disruptive agents may be selected from the group consisting of antisense RNA, PNA, siRNA.

DETAILED DESCRIPTION OF THE INVENTION

Materials and Methods

Figure 1:
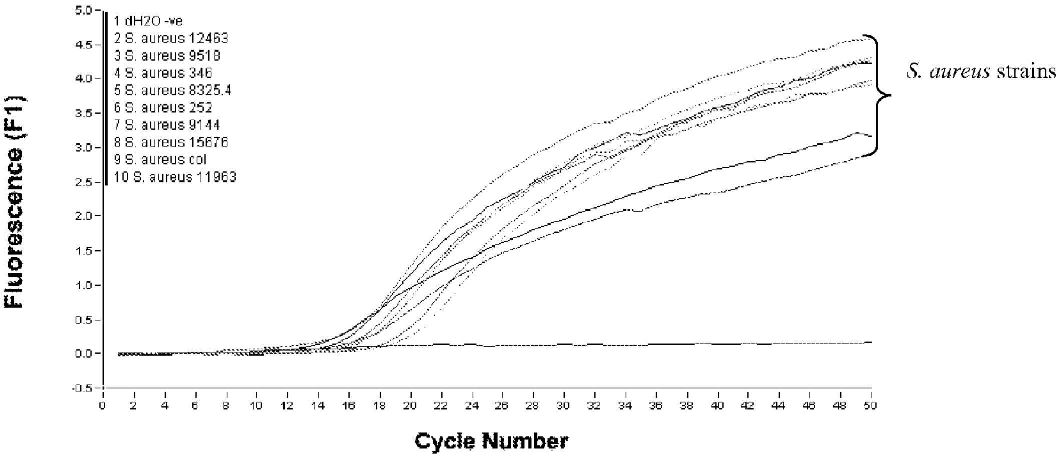
FIG. 1: Real-time PCR amplification assay based on LepA for *S. aureus* demonstrating the inclusivity of the *S. aureus* LepA real-time PCR assay.

Bacterial Strains:

DNA stocks for *Mycobacteria* spp. used in this study were obtained from an independent laboratory. Other bacterial species were grown in either Tryptone Soya broth, Luria broth, nutrient broth or nutrient agar overnight at 37° C.

DNA Extraction

DNA was isolated from bacterial cells using the MagNA Pure System (Roche Molecular Systems) in combination with the MagNA pure Yeast and Bacterial isolation kit III or using the Edge Biosystems PurElute™ Bacterial Genomic Kit.

LepA Gene Sequence Analysis for Diagnostics Assay Design

The publicly available sequences of the LepA genes for *Mycobacteria* and *Bordetella* spp. were acquired from the Genbank database and aligned using Clustal W. PCR primers (Table 2) were designed to amplify regions of the LepA gene in a range of Mycobacterial and *Bordetella* species. For *Bordetella*, PCR primers BRIF/BRIR amplify a region equivalent to 160 bp to 612 bp of the *B. pertussis* Tohama-a gene. PCR primers BR2F/BR2R amplify a region equivalent to 552 bp to 1081 bp of the *B. pertussis* Tohama-a gene. Primer set BR3F/BR3R amplify from by position 1006 to by position 1638 bp of *B. pertussis* Tohama-a gene. Primer set MycobSF3/MycobSR2 amplify a region equivalent to by 1203 to 1817 bp in the *Mycobacterium tuberculosis* LepA gene. Conventional PCR amplification of these sequence regions in *Bordetella* and *Mycobacteria* species was performed using Sigma SuperPak™ reagents on the MWG Biotech Primus using the thermocycling conditions outlined in table 3. PCR products were purified for DNA sequencing using either the High Pure PCR Product Purification Kit from Roche or the ExoSAP-IT purification kit according to manufacturers instructions. Purified PCR products were sent to the external sequence service provider for sequencing. DNA sequence information for LepA was generated for regions 1-3 for *B. pertussis, B. avium, B. petrii* and *B. holmessii* for regions 1-2 for *B. parapertussis* and *B. bronchiseptica, B. hinzii* and region 2 of *B. trematum*. DNA sequence information was generated for Mycobacterial species Lep A region equivalent to 1203 bp to 1817 bp in *M. africanum, M. bovis, M. bovis* BCG, *M. canettii, M. caprae, M. microtti, M. pinipedii, M. tuberculosis, M. smegmatis, M. celatum, M. fortuitum, M. intracellulare, M. malmonense, M. paratuberculosis* and *M. scrofulaceum*.

TABLE 2

| Sequencing primers for *Bordetella* and *Mycobacterial* spp. | |
|---|---|
| Oligonucleotide Name | 5'-3' sequence |
| BR1F | AGCGCCTTGACGTTCTC |
| BR1R | AAGATYGCCGAHATCCGC |
| BR2F | RTAYTCCTGSGGCATGAA |
| BR2R | CGTGTTCACGCCCAART |
| BR3F | TTGATGCCSGCRATGA |
| BR3R | ACSATCAAGGCSCAGAC |
| MycobSF3 | CACTCCGCGGTAGATGTC |
| MycobSR2 | AAGTTCCTAATCTGCGCCG |

TABLE 3

Thermocycling conditions used for amplification of LepA gene regions in *Bordetella* and *Mycobacteria* spp.

| Step | | Temperature | Time | Cycles |
|---|---|---|---|---|
| 1 | Denaturation | 95° C. | 3-4 min | 1 |
| 2 | Amplification | | | |
| | a. Denaturation | 95° C. | 30 sec | 30-35 |
| | b. Annealing | 50° C. or 55° C. | 30 sec or 1 min | 30-35 |
| | c. Elongation | 72° C. | 30 sec | 30-35 |
| 3 | Final Elongation | 72° C. | 7 min | 1 |
| 4 | d. Hold | 8° C. | | 1 |

PCR Primer and DNA Probe Design for Lep A and Guf A Targets.

LepA sequences available in GenBank for Staphylococci and closely related species were aligned and PCR primer sets SAF1/R1 and SAF2/R2 and oligonucleotide probes SAP1 and SAP2 were designed. Similarly, PCR primers GBSF1/R1 and oligonucleotide probe GBSP1 were designed based on in silico analysis of published LepA sequences for Streptococci and closely related species. Sequence information generated for LepA regions 1-3 in *Bordetella* spp. was aligned with available LepA sequences for *Bordetella* and closely related species in GenBank and 5 primer sets, 2 for region 1, 2 for region 3 and 1 for region 2 were designed in addition to 2 oligonucleotide probes each for regions 1 and 3 and 1 probe for region 2 for *B. pertussis* specific identification. Sequence information in GenBank and sequence information generated in this study for Mycobacterial species was analysed to design Primer set MTC F/R and oligonucleotide probe MTCP for the detection of the MTC complex species. Additionally oligonucleotide probe MSP was designed for *M. smegmatis* LepA identification (Table 4). In silico analysis of GenBank Guf 1 sequences for *Candida* and *Aspergillus* identified 3 gene regions suitable for oligonucleotide primer and probe design. A selection of primers and probes were designed from these regions for the identification of *C. albicans* and *Aspergillus fumigatus*.

TABLE 4

| Oligonucleotide primers and probes based on LepA for bacterial species identification | |
|---|---|
| Oligonucleotide name | Oligonucleotide sequence 5'-'3 |
| *S. aureus* | |
| SAF1 | TACCAACTGCTTTCATCT |
| SAR1 | CAATTTGAAGTACCTGTACA |
| SAF2 | TTTACGTTGACATAATTCCA |
| SAR2 | CAGAAGTGACGGTTGATA |
| SAP1 | TTTACG GCT TAT GTCACCGCCAT |
| SAP2 | TAGTTGCACGAACATATGGCTC |
| Group B *Streptococci* | |
| GBSF1 | AACCAATTGCTTTCAT |
| GBSR1 | CAGCTATTGGACAAAA |
| GBSP1 | CGTAGTGCTTTTATATCAGAACG |
| *Bordetella pertussis* | |
| BPF1A | ACGAACTCGTAGTCCATCGAC |
| BPR1A | GCGCTTGTTGTTGCACAGT |
| BPF1B | GTCGAAGAAATCGAGCAC |
| BPR1B | GTATTCCTGGGGCATGAA |
| BP1PA | CTGGCGCCCGTGGTAGCTC |
| BP1PB | TTGTTGCACAGTGTCATCACCG |
| BP2F1 | CGCTGTTCGACCTCATAG |
| BP2R1 | CAGCTGGTCGTATTCGGA |
| BP2P | GACACTTCGGGCTCGAACATCA |
| BP3FI | TCCATCTTGTTGAGCAC |
| BP3R1 | AACGACTGACTTCGTAC |
| BP3F2 | TGCCGATCACGTCTT |
| BP3R2 | GGTGGTTCGACGCTTC |
| BP3P1 | ACTTCCATGCCCAGTTCG |
| BP3P2 | CGAACTGGGCATGGAAG |
| *Mycobacteria* | |
| MTCF1 | AGACCGTGCGGATCTTG |
| MTCR1 | CATGGAGATCACCCGTGA |
| MTCP | TCGTCTTTGTGCACCCGATAC |
| MSP | ACGACCTTCTCGGAACCGT |

Demonstration of LepA as a Target for Bacterial Species Identification in Real-Time PCR Assays.

To demonstrate the application of LepA as a target for bacterial spp. identification real-time PCR assays were worked up for *S. aureus*, GBS, *Mycobacterium* complex species (MTC) and *Bordetella pertussis*.

Figure 2:
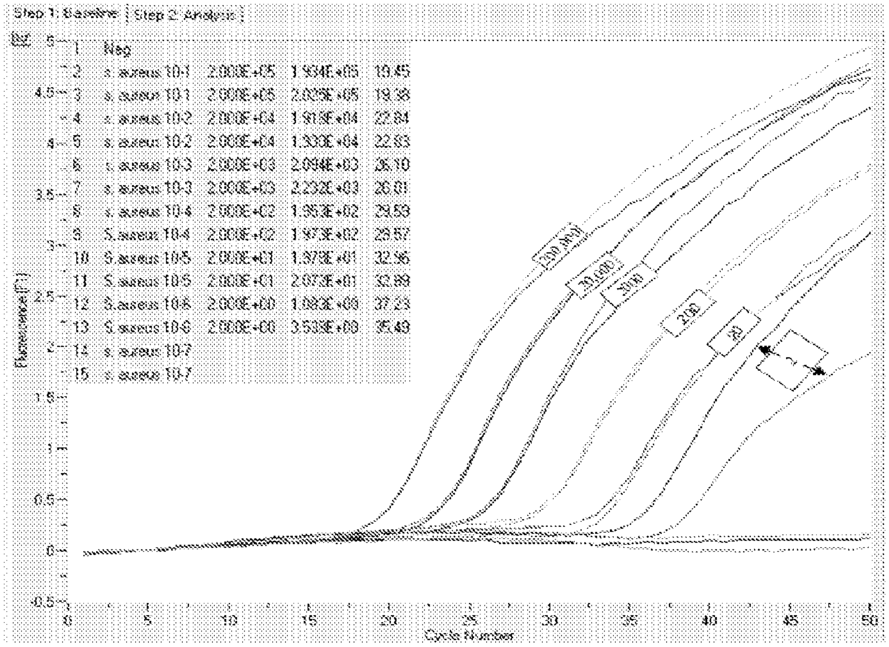
FIG. 2: Real-time PCR amplification assay based on LepA for *S. aureus* demonstrating the sensitivity of the *S. aureus* LepA real-time PCR assay.

*S. aureus* LepA Real-Time PCR Assay:

The *S. aureus* LepA real-time PCR assay was demonstrated using PCR primer set SAF2/R2 (0.5 mM final concentration) and 5' exonuclease probe SAP2 (0.2 mM final concentration) on the LightCycler 1.5 using the LightCycler Fast Start DNA Master HybProbe Kit and thermocycling conditions (Table 5). The panel of *S. aureus* strains listed in table 6 were tested for inclusivity and all were detected in the *S. aureus* LepA (FIG. 1) while the other staphylococci species and related species (Table 6) were not detected in the test. The limit of detection of the *S. aureus* LepA real-time PCR test was established to be 2-20 *S. aureus* cell equivalents (FIG. 2).

GBS LepA Real-Time PCR Assay:

The GBS LepA real-time PCR assay was demonstrated using PCR primer set GBSF1/R1 (0.5 mM final concentration) and 5' exonuclease probe GBSP12 (0.2 mM final concentration) on the LightCycler 1.5 using the LightCycler Fast Start DNA Master HybProbe Kit and thermocycling conditions (Table 5). The panel of GBS strains listed in table 6 were tested for inclusivity and all were detected in the assay while the other streptococci species and related species (Table 7) were not detected in the test.

Figure 3:
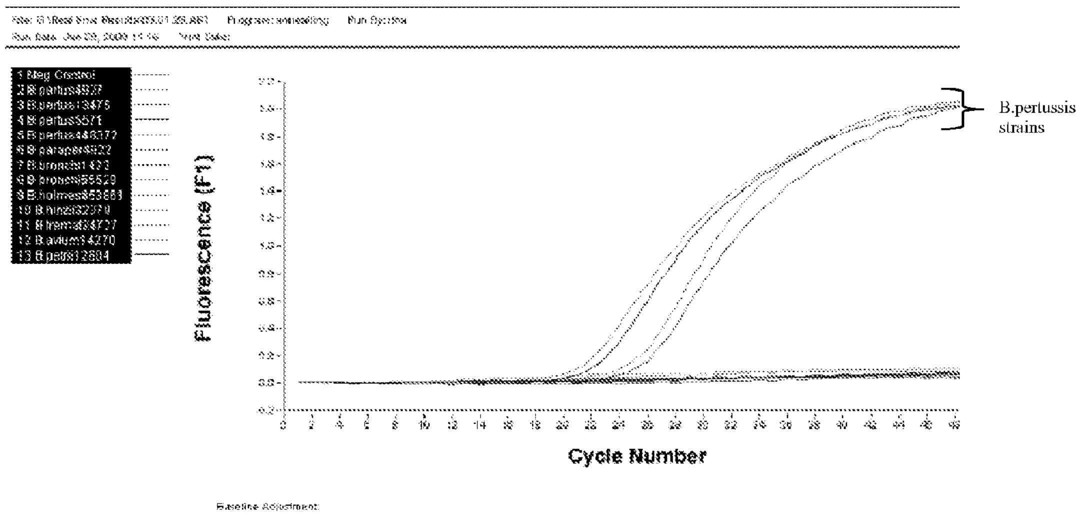
FIG. 3: Real-time PCR amplification assay based on LepA for *B. pertussis* demonstrating the inclusivity of the *B. pertussis* LepA real-time PCR assay.
Figure 4:
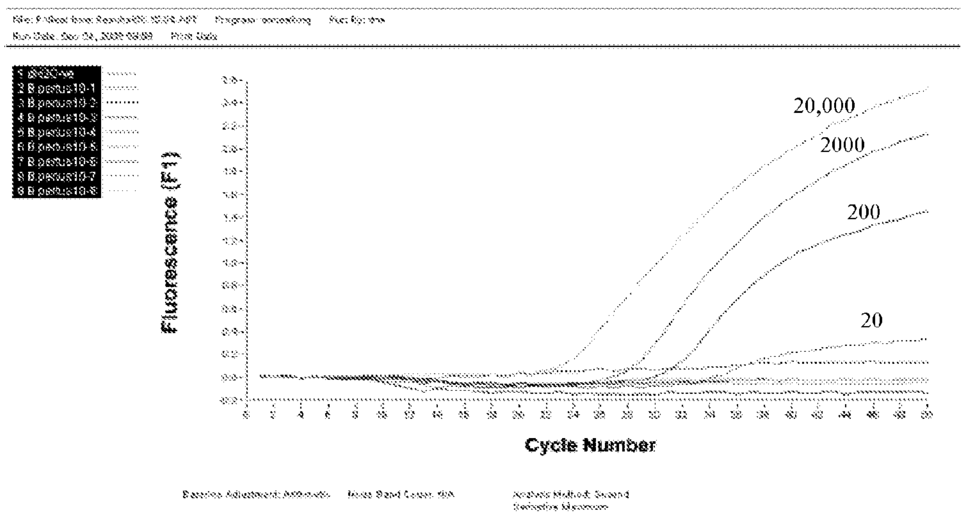
FIG. 4: Real-time PCR amplification assay based on LepA for *B. pertussis* demonstrating the sensitivity of the *B. pertussis* LepA real-time PCR assay.

B. pertussis LepA Real-Time PCR Assay:

The *B. pertussis* LepA real-time PCR assay was demonstrated using PCR primer set BP3F2/R2 (0.5 mM final concentration) and 5' exonuclease probe BP3P2 (0.2 mM final concentration) on the LightCycler 1.5 using the LightCycler Fast Start DNA Master HybProbe Kit and thermocycling conditions (Table 5). Inclusivity testing detected 4 of 4 *B. pertussis* strains tested and did not detect other *Bordetella* spp. strains (FIG. 3). The limit of detection based on amplification of serial dilutions of *B. pertussis* genomic DNA in the *B. pertussis* LepA real-time PCR assay was established as 20 *B. pertussis* cell equivalents (FIG. 4).

Figure 5:
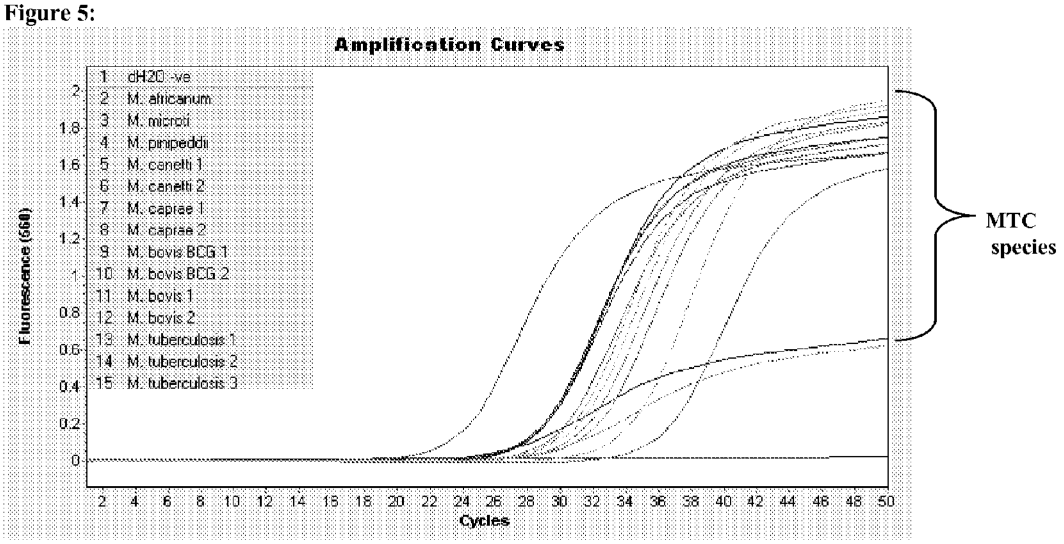
FIG. 5: Real-time PCR amplification assay based on LepA for *Mycobacterium tuberculosis* complex demonstrating the inclusivity of the *Mycobacterium tuberculosis* complex LepA real-time PCR assay.
Figure 6:
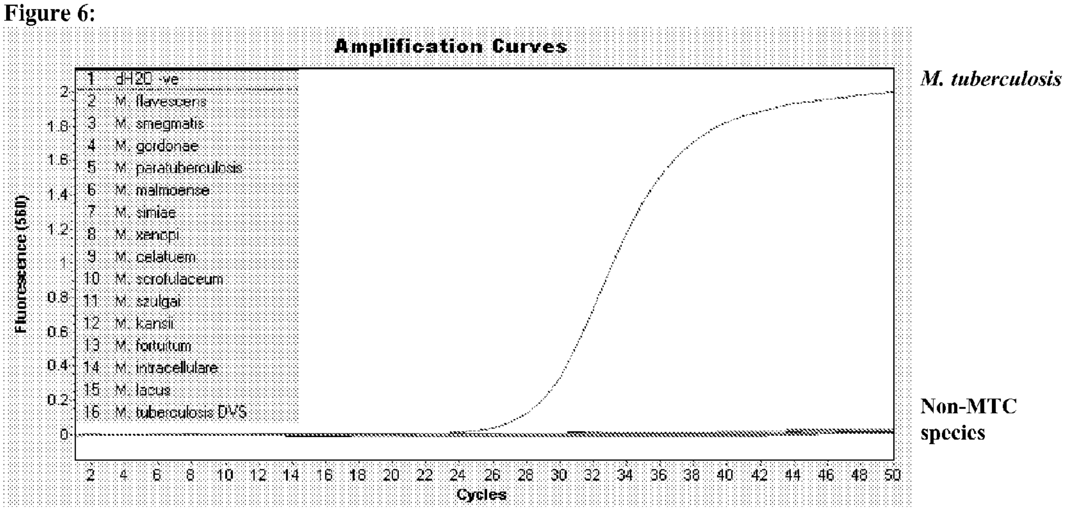
FIG. 6: Real-time PCR amplification assay based on LepA for *Mycobacterium tuberculosis* complex demonstrating the exclusivity of the *Mycobacterium tuberculosis* complex LepA real-time PCR assay.
Figure 7:
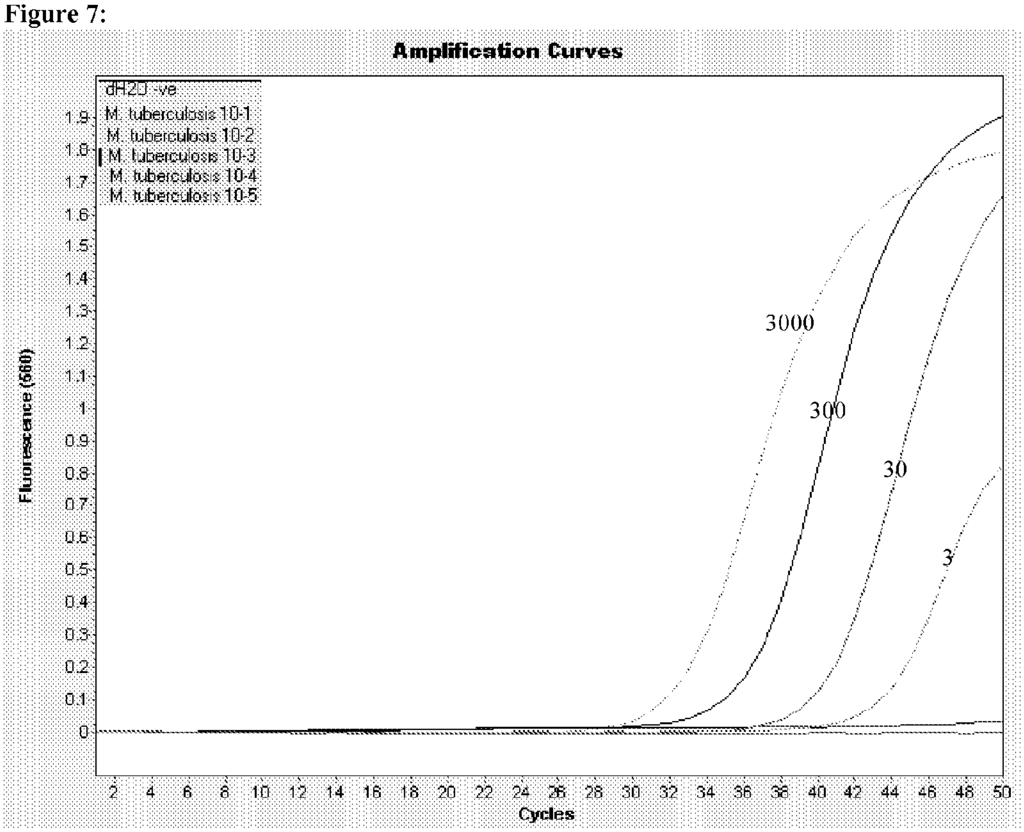
FIG. 7: Real-time PCR amplification assay based on LepA for *Mycobacterium tuberculosis* complex demonstrating the sensitivity of the *Mycobacterium tuberculosis* complex LepA real-time PCR assay.

MTC LepA Real-Time PCR Assay:

A biplex real-time PCR assay for the detection of MTC LepA and *M. smegmatis* LepA has been configured on the LightCycler 2.0 instrument incorporating PCR primers MTCF1/R1 (0.5 mM) for the co-amplification of MTC species and *M. smegmatis* and 5' exonuclease probes MTCP (0.2 mM) labelled with HEX/BHQ1 dye quencher combination and probe MSP (0.2 mM) labelled with CY5/BHQ2 dye quencher moieties. Thermocycling is performed as described in table 5. Inclusivity testing for the MTC assay showed detection of all members of the MTC while non-MTC species were not detected FIGS. 5, 6. The LOD of the MTC assay for M. tb DNA was approximately 3 cell equivalents (FIG. 7).

TABLE 5

Real-time PCR conditions for the *S. aureus* LepA real-time PCR

| Step | | Temperature | Time | Cycles |
|---|---|---|---|---|
| 1 | Denaturation | 95° C. | 10 min | 1 |
| 2 | Amplification | | | |
| | Denaturation | 95° C. | 10 sec | 50 |
| | Annealing/elongation | 60° C. | 30 sec | 50 |
| 3 | Cooling | 40° C. | 30 sec | 1 |

TABLE 6

*S. aureus* strains, *Staphylococci* and other species tested in the *S. aureus* LepA real-time PCR assay.

| Species panel | Source/Strain |
|---|---|
| S. aureus | DSM12463 |
| S. aureus | 9518 |
| S. aureus | DSM346 |
| S. aureus | 8325.4 |

TABLE 6-continued

*S. aureus* strains, *Staphylococci* and other species tested in the *S. aureus* LepA real-time PCR assay.

| Species panel | Source/Strain |
|---|---|
| S. aureus | 252 |
| S. aureus | ATCC 9144 |
| S. aureus | DSM 15676 |
| S. aureus | col |
| S. aureus | NCTC 11963 |
| E. coli | DSM 301 |
| K. aerogens | ATCC 43086 |
| K. oxytoca | NCTC 9528 |
| L. monocytogenes | Serovar 7 |
| L. monocytogenes | Food isolate |
| S. algalactiae | DSM 2134 |
| S. epidermidis | DSM 20044 |
| S. epidermidis | untyped |
| S. haemolyticus | DSM 20263 |
| S. saprophyticus | ATCC 15305 |
| P. mirabilis | DSM 4479 |
| B. cereus | DSM 31 |
| S. chromogenes | DSM 20454 |
| M. caesolyticus | DSM 20597 |

TABLE 7

GBS strains, *Streptococci* species and related species tested in the LepA GBS real-time PCR assay.
Species panel
GBS n = 10

| |
|---|
| *Streptococcus dysagalacticae* |
| *Streptococcus pneumoniae* |
| *Streptococcus parasanguinis* |
| *Streptococcus intermedius* |
| *Streptococcus uberis* |
| *Streptococcus mitis* |
| *Enterococcus faecalis* |
| *Enterococcus faecium* |
| *Streptococcus mutans* |
| *Streptococcus pyogenes* |
| *Streptococcus sanguis* |
| *Streptococcus porcinus* |
| *Streptococcus bovis* |
| *Staphylococcus aureus* |
| *Bacillus cereus* |
| *Enterococcus faecalis* |
| *Enterococcus faecium* |
| *Staphylococcus epidermidis* |
| *Staphylococcus haemolyticus* |
| *Staphylococcus saprophyticus* |

PCR primers and TaqMan probes were designed from LepA sequence information for *S. aureus* and *S. agalactiae* (Table 2). Real-time PCR assays incorporating these primers and probes were demonstrated on the LightCycler. Specificity testing was performed using a selection of the relevant closely species listed in Table 3. The *S. aureus* assay was 100% specific for *S. aureus* and the *S. agalactiae* assays detected all *S. agalactiae* strains and did not cross-react with any closely related Streptococcal species.

SEQ IDs

Sites of probes, oligonucleotides etc. are shown in bold and underlined.

N or x=any nucleotide; w=a/t, m=a/c, r=a/g, k=g/t, s=c/g, y=c/t, h=a/t/c, v=a/g/c, d=a/g/t, b=g/t/c. In some cases, specific degeneracy options are indicated in parenthesis: e.g.: (a/g) is either A or G.

*Bordetella* spp. primers and probes:
SEQ ID NO 1:
BR1F-5'-AGCGCCTTGACGTTCTC-3'

SEQ ID NO 2:
BR1R: 5'-AAGATYGCCGAHATCCGC-3'

SEQ ID NO 3:
BR2F: 5'-RTAYTCCTGSGGCATGAA-3'

SEQ ID NO 4:
BR2R: 5'-CGTGTTCACGCCCAART-3'

SEQ ID NO 5:
BR3F: 5'-TTGATGCCSGCRATGA-3'

SEQ ID NO 6:
BR3R: 5'-ACSATCAAGGCSCAGAC-3'

SEQ ID NO 7:
BPF1A: 5'-ACGAACTCGTAGTCCATCGAC-3'

SEQ ID NO 8:
BPR1A: 5'-GCGCTTGTTGTTGCACAGT-3'

SEQ ID NO 9:
BPF1B: 5'-GTCGAAGAAATCGAGCAC-3'

SEQ ID NO 10:
BPR1B: 5'-GTATTCCTGGGGCATGAA-3'

SEQ ID NO 11:
BP1PA: 5'-CTGGCGCCCGTGGTAGCTC-3'

SEQ ID NO 12:
BP1PB: 5'-TTGTTGCACAGTGTCATCACCG-3'

SEQ ID NO 13:
BP2F1: 5'-CGCTGTTCGACCTCATAG-3'

SEQ ID NO 14:
BP2R1: 5'-CAGCTGGTCGTATTCGGA-3'

SEQ ID NO 15:
BP2P: 5'-GACACTTCGGGCTCGAACATCA-3'

SEQ ID NO 16:
BP3FI: 5'-TCCATCTTGTTGAGCAC-3'

SEQ ID NO 17:
BP3R1: 5'-AACGACTGACTTCGTAC-3'

SEQ ID NO 18:
BP3F2: 5'-TGCCGATCACGTCTT-3'

SEQ ID NO 19:
BP3R2: 5'-GGTGGTTCGACGCTTC-3'

SEQ ID NO 20:
BP3P1: 5'-ACTTCCATGCCCAGTTCG-3'

SEQ ID NO 21:
BP3P2: 5'-CGA ACT GGG CAT GGA AG-3'

*S. aureus* primers and probes:
SEQ ID NO 22:
SAF1: 5'-TACCAACTGCTTTCATCT-3'

SEQ ID NO 23:
SAR1: 5'-CAATTTGAAGTACCTGTACA-3'

SEQ ID NO 24:
SAF2: 5'-TTTACGTTGACATAATTCCA-3'

SEQ ID NO 25:
SAR2: 5'-CAGAAGTGACGGTTGATA-3'

SEQ ID NO 26:
SAP1: 5'-TTTACGGCTTATGTCACCGCCAT-3'

-continued

SEQ ID NO 27:
SAP2: 5'-TAGTTGCACGAACATATGGCTC-3'

GBS primers and probes;
SEQ ID NO 28:
GBSF1: 5'-AACCAATTGCTTTCAT-3'

SEQ ID NO 29:
GBSR1: 5'-CAGCTATTGGACAAAA-3'

SEQ ID NO 30:
GBSP1: 5'-CGTAGTGCTTTTATATCAGAACG-3'

*Mycobacterium* primers and probes:
SEQ ID NO 31:
MycobSF3: 5'-CACTCCGCGGTAGATGTC-3'

SEQ ID NO 32:
MycobSR2: 5'-AAGTTCCTAATCTGCGCCG-3'

SEQ ID NO 33:
MTCF1: 5'-AGACCGTGCGGATCTTG-3'

SEQ ID NO 34:
MTCR1: 5'-CATGGAGATCACCCGTGA-3'

SEQ ID NO 35:
MTCP: 5'-TCGTCTTTGTGCACCCGATAC-3'

SEQ ID NO 36:
MSP: 5'-ACGACCTTCTCGGAACCGT-3'

*Candida albicans* primers and probes:
SEQ ID NO 37: Guf1 Region 1 Probe P1-CalbiGuf1: 5'-CGA GAG GGA AAG AGG AAT TAC AGT GAA AGC C-3' Guf1 gene nucleotide base position from 270 to 300

SEQ ID NO 38: Guf1 Region 1 CanGuf1-1f Forward primer: 5'-ATT GTG GCA CAC GTT GAC CAT GG-3' Guf1 gene nucleotide base position from 190 to 212

SEQ ID NO 39: Guf1 Region 1 CanGuf1-1r Reverse primer: 5'-TGT GCT TGA ACT CCT TGA GAT GCA TC-3' Guf1 gene nucleotide base position from 466 to 491

SEQ ID NO 40: Guf1 Region 2 Probe P2-CalbiGuf1: 5'-CTA CTT GGC ATA CAG CAT GGG ATT GAA ATT G-3' Guf1 gene nucleotide base position from 507 to 537

SEQ ID NO 41: Guf1 Region 1 CanGuf1-2f Forward primer: 5'-GAT GCA TCT CAA GGA GTT CAA GC-3' Guf1 gene nucleotide base position from 466 to 489

SEQ ID NO 42: Guf1 Region 2 CanGuf1-2r Reverse primer: 5'-ATC ATG CCA AGA ATC CAC CAA TA-3' Guf1 gene nucleotide base position from 740 to 762

SEQ ID NO 43: Guf1 Region 3 Probe P3-CalbiGuf1: 5'-CTT GTC AGC GCA CAC AAA TAG GAC ATA CGA C-3' Guf1 gene nucleotide base position from 828 to 858

SEQ ID NO 44: Guf1 Region 3 CanGuf1-3f, Forward primer: 5'-TAT TGG TGG ATT CTT GGC ATG AT-3' Guf1 gene nucleotide base position from 740 to 762

SEQ ID NO 45: Guf1 Region 3 CanGuf1-3r, Reverse primer: 5'-GGG AAT GCC CCA ACA AAT ACC A-3' Guf1 gene nucleotide base position from 1043 to 1064

*Aspergillus fumigatus* primers and probes:
SEQ ID NO 46: Guf1 Region 1 probe P1-AfumiGuf1 5'-CGC AAA CCT GCT CGA TGA TAT ACA ATC AC-3'

SEQ ID NO 47: Guf1 Region 1 AspGuf1-1f, Forward primer: 5'-GCC CAT GTC GAT CAT GGC AAA AG-3' Guf1 gene nucleotide base position from 613 to 635

SEQ ID NO 48: Guf1 Region 1 AspGuf1-1r Revere primer: 5'-ACC TCT GCA CGG AAG TCC AC-3' Guf1 gene nucleotide base position from 820 to 839

SEQ ID NO 49: Guf1 Region 2 probe P2-AfumiGuf1 5'-CAC CAC AGA GCG TGC TCC GTG CCG GC-3'

SEQ ID NO 50: Guf1 Region 2 AspGuf1-2f, Forward primer: 5'-GAG GTT GGC ATC ATG TAT CC-3' Guf1 gene nucleotide base position from 1339 to 1358

SEQ ID NO 51: Guf1 Region 2 AspGuf1-2r Reverse primer: 5'-AGC TGG TTG ATA CTG TCT TC-3' Guf1 gene nucleotide base position from 1573 to 1592

-continued

SEQ ID NO 52: Guf1 Region 3 probe P3-AfumiGuf1
5'-CCACTCAAGTCAAGTGGAAAGGCTCGGAC-3'

SEQ ID NO 53: Guf1 Region 3 AspGuf1-3f Forward primer: 5'-GAG TAT TTC ACA CCA ACG CAG GT-3' Guf1 gene nucleotide base position from 1951 to 1973

SEQ ID NO 54: Guf1 Region 2 AspGuf1-3r Reverse primer: 5'-TTG AAT TTT GTC ACC CAT TGT C-3' Guf1 gene nucleotide base position from 2183 to 2204

SEQ ID 55 to 158
Guf1/LepA Sequences from public databases

SEQ ID NO 55
>Aspergillus_fumigatus Af293 GTP binding protein Guf1, putative (AFUA_3G14350) mRNA, complete cds

ATGAGTATGCGTTGCACCCATCCTCCAGCGCACATCAACATACAGGATGGAGTTTA

TCGAGTATTCAAACTAAGTCTTGTCAACCGGTGTTCTCCGTCCAGATCGATGGAATT

GACTCACGAATTCTGCCACGAGCTTCGCCGAGCCTGTCATAGATGGATGGGATGCT

TTCTCGTTCGTGAGGTCTCTTGGCTGGTCAGAAACGAGGCAGCTTTTGTTTACCTCG

ATAGTCACCTCAGCAATCCGTTGTTCCACCGCCCGGAGCTAAGCACTTTTTCTCCGC

AGCAAGTGATCCGTTGCCGCAGTTTTTCTTTTCTCGGAATCGGCAGTGGAAAACTCG

AATCCTCATCCCAAAAGGCATTTTATTCCCATGCCATTGCAGTACTCCAGATGCGAG

GATGCTTGCAGTTAGCCAGATGGCTGAGCGCTGCACCGAAAGGCACAGCTGCAAGC

CTGACGAGGGCGCCGTTCGTCCTTGCTAACGCTCCCCGGTATTTCACCAGCTCCGCT

TCTCGTGCTGGATCGAGATCGACCGCTACCAAGCCGTTATCCGACCTCGAGAAGAG

AATATCTGCGATTCCAATCGAGCGATACCGGAACTTTTGCATCGTTGCCCATGTCGA

TCATGGCAAAAGCACACTTTCGGACCGCCTGCTCGAACTCACGGGGACGATTGAGC

CCGGCTCGAACAAACAAGTGTTGGACAAGCTCGACGTGGAGCGTGAACGTGGCATC

ACCGTGAAGGCGCAAACCTGCTCGATGATATACAATCACAATGGTGAAGACTATTT

ATTGCACCTGGTTGATACTCCAGGCCATGTGGACTTCCGTGCAGAGGTATCCCGTAG

TTATGCTAGTTGCGGAGGAGCATTGCTCCTGGTCGATGCCAGTCAAGGAATCCAGG

CACAGACCGTTGCGAACTTCTACCTCGCTTTTGCGCAGGGCTTGGAATTGATTCCAG

TCATCAACAAGGTAGATTTGCCCTCGGCTGAACCAGAGCGAGCTCTTGAGCAGATG

AAGAATTCCTTCGAGCTCGACACCGAGAACGCAGTGATGGTTTCAGCTAAGACAGG

CCTCAATGTTGAGAAATTACTTCCGACAGTTATTGAGAAGATCCCAGCGTATGGCC

ATTTCCCCGTCGATTCTCATGAGCTGCTTCCGTTACTGACTCTTAGCAGCCCCATCG

GCGATTGCAAGAAGCCCCTGCGAATGTTACTCGTTGACTCGTGGTACGATTCCTACA

AAGGCGTAATCTGTCTGGTCCGCATCTTCGACGGTGAAATTCGAGCAGGCCAGCAG

GTCGTGTCGTTTGCGACGGGTCTTAAATACTACGTTGGCGAGGTTGGCATCATGTAT

CCAAATGAAACACCACAGAGCGTGCTCCGTGCCGGCCAAGTTGGATACATCTACTT

CAACCCAGGTATGAAACGAAGCAAAGAAGCGAAGATTGGTGACACATTTACAAGG

GTCGGATTTGAGAAAGCCGTTGAACCACTTCCTGGCTTTGAGGAGCCCAAAGCGAT

GGTTTTTGTGGCGGCTTACCCGGTGGATGCAGACCATTTTGAGCACTTGGAAGACA

GTATCAACCAGCTCGTGCTTAACGACAGGAGTATCACCGTGCAGAAGGAGTCCTCA

GAGGCTCTTGGCGCCGGCTTCAGATTGGGATTTCTAGGCACACTGCACTGTTCTGTG

TTTGAGGATCGTTTGCGTCAGGAGCATGGTGCTAGCATCATCATCACACCTCCATCA

GTGCCTGTCAAGATCATTTGGAAGGACGGAAAAGAGGAGATCATTACCAGCCCTGC

CAAATTTCCTGAAGACGAAGAACTGCGCTCCAAGGTGGCTGAGATTCAAGAGCCCT

-continued

ACGTCCTGGCTACACTGACCTTCCCCGAGGAGTACCTTGGCAAGGTCATTGAGCTTT

GCGAGGCAAACAGAGGCGAGCAGAAGAGTTTAGAGTATTTCACACCAACGCAGGT

CATTCTTAAGTATGAACTGCCTCTTGCTCAACTCGTTGATGACTTCTTCGGCAAGCT

CAAGGGGTCTACCAAAGGCTACGCCAGCCTGGACTATGAGGAGTCCGCTTGGCAAA

CAGGGAACATCGTCAAGCTGCAACTTTTGGTAAATAAGGCGCCTGTCGATGCTGTT

GCTCGCATCGTCCACTCAAGTCAAGTGGAAAGGCTCGGACGACAATGGGTGACAAA

ATTCAAGGAGCATGTCGATCGACAACTGTTCGAGGTTGTGATCCAGGCTGCTGTTG

GTAAAAAGATCATCGCCCGAGAGACAGTCAAACCCTACCGAAAAGATGTCTTGGCC

AAGCTCCATGCTAGCGATGTCAGTCGGCGCCGGAAACTGCTGGAGAAGCAGAAAG

AAGGACGAAAGAGACTGAGAGCTGTTGGAAACGTGGTGATTGAGCACAAGGCATT

CCAGGCCTTCCTCGCCAAATAA

SEQ ID NO 56
>Aspergillus_terreus NIH2624 GTP-binding protein GUF1 (ATEG_03492) mRNA, complete cds
ATGCGAGGATGCCTGCAGTTAGCCAGATGGCTGAGCGCAGCGCCAACCCGCCCTGC

TGCTAGCCATTGGCCTGGCCTTTGCGCCGCTCCGCGGTTTTTCTCCCATTCAGCGAT

CCTCCGAGCCTCCGCAAGGACAGCCCGCGCGGCGGCGAGCAAACCTCCCTCCGACC

TTGAATCGCGAATCGCGGCGATCCCAATCGAGCGGTACCGGAATTTCTGCATCGTC

GCGCACGTCGACCATGGCAAAAGCACCCTCTCTGACCGACTGCTGGAACTGACGG

GGACGATTGAGCCGGGGACAAACAAGCAGGTTCTGGACAAACTCGATGTGGAGCG

TGAACGGGGTATCACAGTCAAGGCGCAGACATGTACGATGATCTACAATCACAACG

GCGAGGACTATCTGCTGCATCTGGTCGATACCCCGGGACATGTGGATTTCCGTGCG

GAGGTCTCGCGCAGTTACGCCAGCTGCGGCGGTGCGTTGCTTCTTGTTGATGCGAGC

CAGGGTGTCCAGGCGCAGACCGTGGCGAACTTCTACCTCGCCTTTGCCCAGGGTCT

GGAGCTTATCCCTGTCATTAACAAAGTAGATTTGCCGTCGGCGGAGCCCGAGCGCG

CCCTCGAGCAGATGAAACAGTCTTTCGAACTCGACACGGAAAATGCTGTGATGGTT

TCGGCGAAGTCGGGACTGAATGTGGAGAAACTTCTTCCTACGGTGGTGGATAAGAT

TCCAGCACCGATTGGCGACTGCAAAAAGCCCCTGCGAATGCTCCTTGTCGACTCGT

GGTACGACTCCTACAAAGGCGTGATATGCTTGGTCCGCGTATTCGACGGCGAAATC

CGCGCGGGGGACCAATTGGTGTCGTTCGCCACGGGCATCAAGTACTACGTGGGCGA

GGTCGGCATCATGTATCCCAACGAGACTCCTCAGACGGTCATTCGTGCGGGACAAG

TCGGATACATCTTCTTCAACCCGGGTATGAAGCGCAGTAAGGAAGCCAAGATTGGG

GACACCTACACGAAAGTCGGCTCCGAGAAGGCTGTTGAGCCGCTTCCGGGCTTCGA

AGAACCAAAGGCGATGGTCTTTGTGGCGGCATACCCCGTGGACGCCGACCATTTCG

AGCATCTCGAAGACAGCATCAACCAGCTTATGCTGAACGACCGGAGCATCACGGTG

CAGAAGGAGTCTTCCGAGGCTCTGGGCGCGGGCTTCCGGCTCGGATTTCTGGGAAC

ACTGCATTGCTCCGTATTCGAGGACCGTCTGCGCCAGGAGCACGGCGCCAGCATCA

TTATCACCCCGCCTTCAGTGCCCGTGAAGGTTCTGTGGAAAGACGGGCGGGAGGAG

ATCGTCACCAGCCCTGCAAAGTTCCCAGATGAAGATGAACTGCGGTCTAAGGTCGC

GGAGATCAAGGAACCCTACGTGCTGGCTACCTTGACGTTCCCAGATGAATACCTCG

GAAAAGTCATTGAACTGTGCGAATCCAACCGTGGTGTCCAGCAGAGCCTCGAGTAC

TTCACGTCAACGCAGGTCATCCTCAAATACGAACTGCCAATGGCTCAGCTTGTGGA

-continued

CGATTTCTTCGGAAAGCTGAAGGGATCGACGAAGGGCTACGCGTCTTTAGACTACG

AGGAATCCGCTTGGCAGACGAGCAACATTGTGAAGCTGCAGCTCCTCGTCAATAAA

GCTCCTGTGGATGCTGTGGCGAGAATTGTGCACTATAGTCAAATTGAGAGACTTGG

CAGGAAATGGGTGACCAAGTTCAAGGAACATGTTGATCGGCAGCTCTTCGAGGTCG

TGATCCAAGCCGCTGTCGGACGGAAGGTCATTGCGCGTGAAACGGTCAAACCGTAC

CGCAAAGACGTCCTCGCCAAACTCCATGCCAGCGATGTCAGTCGACGGAGAAAACT

GTTGGAGAAGCAGAAGGAGGGACGGAAGAGACTGAGAGCAGTCGGCAATGTCGTG

ATAGAACATAAGGCGTTCCAGGCTTTCTTGTCCAAGTGA

SEQ ID No 57
>Aspergillus_clavatus NRRL 1 GTP binding protein Guf1, putative (ACLA_041830) mRNA, complete cds
ATGCGAGGATGCCTGCAGTTAGCCAGATGGCTGAGCGCAGCACCGAAAGGCACCG

CTGCAAGCCTGACCAGGGCGCCATTTGGCCTTGCTAACGCAACTCGGTTTTTCACCA

ATTCCGCTGCGCGCGCCGGCTCAAGAGCCACTGCCAGCAAACCGGTAACCGATCTC

GAGAACAGAATATCCGCGATTCCGATCGAGCGCTACCGCAATTTCTGCATCGTCGC

CCACGTTGATCATGGCAAAAGCACCCTTTCCGACCGGCTGCTCGAACTGACGGGCA

CCATCCAGCCCGGTTCGAACAAGCAAGTCCTGGACAAACTCGATGTCGAACGAGAA

CGCGGCATCACTGTGAAGGCACAGACGTGTACTATGATATATAACCACAACGGCGA

AGACTACTTGTTGCATCTGGTTGATACCCCGGGACATGTGGACTTCCGCGCGGAGG

TCTCGCGCAGTTATGCCAGCTGCGGAGGAGCACTGCTCTTGGTCGACGCCAGTCAG

GGAGTCCAGGCACAGACGGTTGCGAACTTTTATCTTGCTTTTGCACAGGGATTAGA

ATTGATCCCCGTCATCAACAAGGTGGATCTACCGTCGGCTGAGCCACAGCGGGCTT

TAGACCAGATGAAGCATACCTTTGAGCTTGATACAGAAAACGCAGTCATGGTTTCG

GCCAAGACAGGACTCAATGTCGAGCAGTTGCTTCCGACAGTTGTTGACAAGATTCC

TGCGCCGATCGGCGATTGCAAGAAACCCCTCCGAATGTTACTCGTTGATTCCTGGTA

TGATTCCTACAAGGGTGTTATCTGTTTGGTTCGTATCTTCGACGGCGAACTGCGG

GCTGGCCAGCAAGTTGTGTCATTTGCCACGGGTCTCAAATACTATGTGGGAGAAGT

AGGAATTATGTATCCGAACGAGACAGCGCAGAGCGTGATCCGTGCTGGTCAAGTCG

GTTATATCTATTTCAACCCCGGCATGAAACGGAGCCAGGAAGCGAAAATTGGCGAC

ACATTTACAAAGGTCGGCTCGGAGAAAGCTGTGCAGCCCCTTCCAGGCTTCGAAGA

GCCGAAGGCAATGGTCTTTGTCGCCGCTTATCCTGTGGATGCGGACCATTTCGAGC

ATCTGGAAGACAGTATCAACCAGCTTGTGCTCAATGATAGAAGTATCACGGTTCAG

AAGGAGTCCTCGGAGGCCCTTGGTGCAGGCTTCAGACTCGGATTCCTTGGGACCTT

GCATTGTTCGGTCTTCGAGGATCGTCTGCGTCAGGAACACGGCGCCAGTATCATCAT

CACTCCCCCTTCAGTGCCTGTGAAGGTCATTTGGACGGACGGCAAAGAGGAAATCA

TCACGAGCCCAGTCCGTTTCCCAGATGATGAGGAAGTGCGTAACAAGATCGCAGA

GATTCAAGAGCCGTATGTCCTGGCCACATTGACATTCCCAGAAGAATATCTTGGCA

AAGTGATCGAACTTTGCGAGGCCAATCGGGGTGAGCAGAAGACTCTCGAGTATTTC

ACAGCAACCCAGGTCATTCTCAAGTATGAGCTGCCTCTTGCGCAATTGGTTGACGA

CTTCTTTGGAAAGCTGAAAGGGTCTACCAAAGGATATGCCAGCTTGGACTATGAAG

AATCCGCGTGGCAACCGGGACATATCGTCAAGCTGCAACTCTTGGTCAACAAGGCA

CCGGTCGATGCTGTTGCGCGCATCATGCATTCGAGCCAAGTCGATAGGCTCGCAAG

-continued

ACAATGGGTAACCAAGTTCAAACAACACGTCGATCGACAGCTGTTCGAAGTCGTGA

TCCAGGCTGCTGTCGGTCGCAAGGTCATCGCACGAGAGACGGTCAAGCCGTACCGG

AAGGATGTCTTGGCGAAGCTACATGCTAGTGATGTGAGTCGGCGCCGGAAACTGCT

CGAGAAGCAGAAAGAAGGACGAAAGAGGCTCCGGGCAGTTGGGAACGTGGTGATT

GAGCACAAGGCATTCCAGGCTTTTCTCGCGAAATAG

SEQ ID No 58
>Aspergillus_niger CBS 513.88 hypothetical protein (An09g04110) mRNA, complete cds
ATGCGAGGATGCCTGCAGTTAGCCAGGTGGCTGCGCGCAGCACCGAAATGTCCTGC

TGCAAGCCTTCTCAAGCCGCCATCCGGCCTTGCTAATCCAGCCCGGTTTTTCACGAC

TTCCACCGCATGCTGGGCATCGCGCTCCAGGGCTCCGGCCAGCCAGCCATCCTCCG

ACCTTGAATCAAGAATCGCAGCTATCCCGATTGATCGATACCGTAACTTCTGCATTG

TCGCCCACGTCGATCATGGCAAAAGTACCCTCTCCGATCGGCTGTTGGAACTCACA

GGAACGATCCAGCCCGGTATGAACAAGCAGGTTTTGGACAAGCTTGACGTCGAGCG

TGAACGGGGTATTACGGTGAAGGCACAGACATGTACAATGATTTACAACCATAATG

GCGAGGACTATCTGTTGCATCTGGTTGATACACCGGGACATGTGGACTTCCGTGCG

GAGGTTTCGCGCAGTTATGCCAGTTGCGGAGGAGCGTTGCTCTTAGTTGACGCCAG

TCAAGGTATCCAGGCTCAGACAGTCGCCAACTTCTATCTCGCATTCTCTCAGGGCCT

GGAGTTGATCCCCGTCATCAACAAGGTGGACCTGCCGTCCGCTGATCCGGAGCGTG

CTCTTGACCAGATGGAACAGTCTTTTGAGCTTGACACGGAAAGTGCAGTGTTGGTA

TCAGCCAAGACGGGACTTAATGTGCAGCAATTGCTTCCTACTGTAGTCGAGAAGAT

TCCGGCACCGGTGGGAGATGTTAACAATCCCCTACGGATGCTTCTCGTCGATTCCTG

GTATGATTCGTACCGAGGTGTCATCTGCTTGGTCCGCGTTTTCGACGGCGAAATCCG

GGCAGGAGACCAGCTTGTGTCGTTCGCGACTGGAATCAAATACTTCGTGGGCGAGG

TCGGAATTATGTATCCCAACGAGACGGCCCAGTCGGTCCTTCGGGCTGGCCAGGTC

GGCTACATCTTCTTCAACCCTGGTATGAAGCGAAGCAAGGAAGCTAAAATCGGTGA

TACCTACACCAAGGTTGGGTTTGAGAAAGTCGTCGAGCCGCTTCCGGGCTTCGAAG

AACCCAAGGCAATGGTTTTCGTGGCCGCCTATCCCGTGGACGCCGATCACTTCGAG

CACTTGGAAGATAGTATCAACCAGCTTTGTCTGAACGACCGGAGTATTACTGTGCA

AAAAGAGTCATCTCATGCTCTTGGAGCAGGTTTCCGGTTGGGCTTTTTGGGAACACT

GCATTGCTCTGTCTTTGAGGATCGTCTGCGCCAGGAGCACGGTGCCAGTATCATCAT

CACTCCTCCTTCCGTTCCCGTGAAACTCATCTGGAAAGACGGCAAGGAAGAGATCA

TCTCCAATCCCGCCAAGTTCCCGGAGGATGAAGAGCTTCGTGGCAAGATCTCCGAG

ATTCAGGAGCCTTATGTTGTCGCTACTTTGACCCTCCCCGATGAGTATCTTGGAAAG

GTCATCGAGCTCTGCGAGTCCAACCGAGGCGTGCAAAAGAGCCTCGAGTATTTCAC

ATCCACTCAGGTTATTCTCAAGTATGAACTGCCCCTTGCGCAGCTGGTTGATGACTT

CTTCGGAAAGCTGAAGGGCTCTACTAAGGGCTACGCCACCCTTGATTACGAGGAAT

CTGCGTGGCAAACAAGCAACATCGTCAAGTTACAACTTCTGGTCAACAAGGCTCCG

GTGGATGCGGTCGCACGGCTCGTTCATTACAGCCAAGTAGAGCGATTGGGCAGACA

ATGGGTGACTAAGTTCAAAGAGCACGTTGACCGGCAACTGTTCGAGATCGTCATCC

AAGCAGCTGTTGGCCGTAAGGTTGTGGCGCGTGAGACCGTTAAGCCGTACCGGAAG

GATGTCCTCGCGAAGCTGCATGCCAGTGATGTCAGTCGGCGCAGGAAGCTCTTGGA

-continued

AAAGCAGAAGGAGGGACGCAAGAAGCTGCGGGCTGTTGGAAACGTGGTGATTGAA

CAAAAGGCATTCCAGGCATTCTTGGCTAAATAA

SEQ ID NO 59
>Candida_albicans SC5314 EF-type GTP-binding protein (CaO19.5483), mRNA
ATGCTACTAAGGCCGAATTCTGGGAATACTTTAAAGTATGGTTGTCTTCTAACGAAA

AGATGGTTAACAACTCTGAAACTACTATACTCTGTGGAAGATATGAAGATCAAGAT

TGGTCAGGAACAATATCGAAAGGCACTTGAAGAAAGGATAGATAAAATACCAATT

GAAAACTACCGGAACTTCAGTATTGTGGCACACGTTGACCATGGCAAGTCCACATT

ATCAGATCGATTATTAGAAATGACAGGGGTGATCAAACCAGGATCCAAGTCTCAGG

TTTTGGATAAATTAGATGTCGAGAGGGAAAGAGGAATTACAGTGAAAGCCCAGACT

GTGTCTATGTTTTATAACGATGGGAAACAAGATTATTTGTTACATTTGGTTGACACA

CCAGGGCATGTGGATTTCAGAGCAGAAGTGTCAAGGTCATATGCATCTTGTGGAGG

AGCATTGTTGTTAGTCGATGCATCTCAAGGAGTTCAAGCACAGACAGTAGCAAATT

TCTACTTGGCATACAGCATGGGATTGAAATTGATTCCCATAATAAACAAAATTGATT

TGGATCTGGCTAACATTCCTGGAGCGAGGGAGCAAATTGAAACGACATTTGAGTTA

GACCCCAATGAATGCATCCCAGTGAGCGCCAAAACCGGTTTAAATGTCGAACAAAT

AATACCGTCTGTAATTAAAAATATCCCATCTCCTGTATGTGATGTGAACAAGCCTTT

GCGAGCTTTATTGGTGGATTCTTGGCATGATCCCTACGTTGGTGTGGTAATGCTTGT

TCATATTGTGGATGGTAGAATGAAAAAAGGTATGAAAATCTTGTCAGCGCACACAA

ATAGGACATACGACGTTAAGGAAGTTGGGATAATGTATCCAGATAGAACACCGACC

AGTTTCATTAAAGCTGGACAAGTCGCCTATATTATACCGGGGATGAAGAACCCTCG

GGAAGCGCTTGTGGGTGACACGTTTTATCAAATGGGCAAACATGAAGGTCTTGAAC

CTTTACCAGGATTTGAAGAACCTAAGCCAATGGTATTTGTTGGGGCATTCCCTGCAG

ATGGGAAAGAGTTTAATGCTATGGATGATCAAATGCAGAATTTAGTTTTGAATGAT

AGGTCGGTAACCTTAGAGCAGGAAACATCAAATGCATTGGGGTTAGGTTGGAGATT

GGGATTCTTAGGCTCATTACATGCGTCAGTGTTTAAAGAAAGATTAGAAAAAGAAT

ATGGGGCGAAAATTATTTTGACAGCCCCCACCGTGCCCTACAAGATTATCTATAAA

AATGGCGAAGAAAAAATTGTTACTAATCCTGATGATTTTCCAGACAACCAGAAACA

TCACGATGTTGAAAGCTATATGGAACCATATGTTGAGGCGATAATGACCGTTCCAA

ATGAATATGTTGGAAATGTTATGACTTTGTGTTTAAATAATCGAGGAGAACAGAAA

GAGATCGAATACTTGACAACAGGACAGGTATTGCTAAAGTATGAGATCCCAACCTC

ACAACTAGTGGAGGATTTTTTTGGGAAACTAAAAGGATGCACCAAAGGATATGCTT

CGCTTGACTATGAAGAAGCAGGATATAGAAAATCAGATATAGTTAAGATGCAGCTT

TGTGTGAATGGTGAGCCACAAGATGCGTTAACTACAGTTATACACAGATCACAAGC

GCAAGCAAGGGGTAAGGAGTACGTTACGAGGTTTAAGAAATTTTTGAGCTACCAGC

TATTTGAAGTTGCCATTCAAGCAAAAATTAATAACAAAGTGGTGGCAAGAGAAACC

ATCAAAGCAAAAAGAAAAGACGTAACACAAAGATTACATGCAGCAGACATATCAA

GATATAAGAAATTGTTGGAAAGACAAAAGGAGGGTAAGAAACAGATGAAATTAAG

CGGCAGAGTGACAATCAAGAACGACGCTTATCAAGCCTTCTTACGTAGAGAAGACT

AA

SEQ ID NO 60
>C._glabrata CBS138 hypothetical protein (CAGL0I00660g) partial mRNA
ATGCTGAAGACCTTAGGTTTAAGAAGTTTGTGCCCTTCACTTGGTGGTCGAGGCTTT -continued

CGAAGGCATCCCAATATTAATAAATACACATTGTCGTTGGTCAGAGTACGATGGAA

TCACCATTTAAGTAATGCTGAGATACAGGCACGAATTGAGAACATACCACAGGAGA

ACTATAGAAACTTTTCGATTGTCGCCCATGTTGATCATGGGAAATCGACTTTGAGTG

ATCGATTGTTAGAGATAACGGGAGTCATAGACAAGAACTCTTCAAACAAACAAGTG

CTTGATAAATTAGAAGTAGAAAGAGAAAGAGGTATTACAATCAAAGCTCAGACTTG

TACAATGTTCTACCATGACAAGCGTAATGGAGAAGATTATTTGCTACATTTAGTCGA

TACGCCAGGTCATGTTGATTTTCGAGGAGAAGTCTCGAGGTCTTATGCTTCTTGTGG

TGGAGCTCTATTGCTTGTTGATGCATCTCAAGGAGTTCAAGCTCAAACAGTTGCTAA

TTTTTATCTTGCTTATAGTATGGGCTTAAAACTTATACCTGTGGTCAACAAAATTGA

TTTAAATGTTGCAGATGTCGAAAGAGCTAAAGCTGAAATCGAGGACAATTTTGAGC

TACCGAGAGATGAAATAATTGGTGTGAGTGCTAAAACAGGTCTTAATGTCAAAGAG

ATGCTTCTGCCTACCATCGTTGATAGAATCCCTCCTCCTACTGGTAATAAGAAGAAA

CCATTCCGCGCACTATTGGTGGATTCTTGGTATGATTCATACTTAGGAGTAATACTT

CTAGTAAATATTGTTGACGGAAAATTAAAAAAGGGTGAAAAGGTACTATGTGCACA

TACTAACAAAAAGTATGAGGTGAAAGAACTTGGCATTATGTATCCTGATAGAGTTC

CAACCGGTTCATTGGTTGTGGGTCAAGTAGGGTATGTCGTTTTGGGAATGAAAGAC

TCTTCAGATGCCCATGTAGGTGATACATTAATGCATGTAGGAAAAGAGAGTGTGAC

AGATATTCTACCTGGATTCGAGGAACAAAAACCAATGGTCTATGTTGGAGCTTTCC

CCTCTACTGGAACTGAATTTAAGGCAATGGACGATGATATTAACCGGTTGGTTCTG

AATGATAGGTCGGTAACACTGGAAAGAGAAACATCTAATGCTTTAGGGCAAGGAT

GGAGATTAGGGTTTTTGGGCTCCTTGCATGCATCTGTATTTAGAGAAAGACTAGAA

AAGGAATACGGCTCAAAGCTAATTATCACACAACCCACGGTCCCATATATGGTAAG

AATGACAGATGGTACAGAGTCTATTATTACAAATCCTGATGACTTTCCAGATAGCG

CTACAAGGCGAATGAAGGTTGAAGAACTTCTGGAACCCTTTGTAGAAGCCACCATA

ACATTGCCTCAAGAATTTCTGGGAAATGTCATTAAACTCTGTGATGCCAATAGAGG

TCAACAGAAGGAAATAACTTATTTGAATACAAGAGGCCAAGTTGTCTTGAAATACC

ATTTGCCATTGGCTCATCTAGTAGATGACTTCTTTGGAAAATTGAAAGCGGCGTCTA

AGGGATATGCCTCTTTAGATTATGAAGATATTGGCTACAGAGAATCTGATGTAGTC

AAACTAGAGCTTTTGGTTAATGGTCAAAGTATTGATGCTTTAGCAAGGGTGCTTCAT

CGAACTGAAGTTGAAAAAGTGGGTAGAGAATGGGTGCAAAAGTTCAAGGAGTATG

TTAAGTCTCAATTATTTGAAGTTGTAATCCAGGCTAGGGCAGGCACCAAGATTGTA

GCTAGACAAACAATAAAGGCTAGAAGAAAGGATGTTCTTGCAAGGTTGCATGCTTC

AGATGTATCCAGAAGAAAGAAGTTGCTTGAAAAGCAAAAGGAAGGTAAAAAACAA

ATGAGATCGGTTGGTAGAGTACAAATAAACCAAGAGGCATATCAAGCCTTTTTGAA

ACGTTGA

LepA sequences from public databases.
SEQ ID NO 61
>Bacillus_anthracis_0581_lepA
ATGAACAAAGAAGAAAGAGCAAAAAGACAGTCCAAAATTCGTAATTTCTCTATCAT

TGCTCATATTGACCACGGAAAGTCAACGTTAGCAGACCGTATTTTAGAGAAAACAA

ACGCGTTAACACAACGTGAAATGAAAGCTCAGTTGCTTGACTCTATGGATTTAGAG

CGTGAGCGTGGTATTACAATTAAATTAAACGCAATACAATTAAACTATAAAGCAAA

-continued

AGACGGCGAAGAATATATTCTTCACTTAATTGATACACCAGGACACGTCGACTTTA

CGTACGAAGTATCTCGTAGTTTAGCGGCTTGTGAAGGTGCGATTCTTGTAGTAGATG

CAGCGCAAGGTATTGAAGCGCAAACGTTAGCAAACGTATACTTAGCGCTTGATAAC

AATTTAGAAATTTTACCGGTTATTAATAAAATCGACTTACCAAGTGCAGACCCAGA

GCGTGTACGCCAAGAAGTAGAAGATGTAATTGGATTAGATGCATCAGAAGCTGTAC

TTGCTTCTGCAAAAGCTGGGATTGGTATTGAAGAGATTTTAGAACAAATCGTTGAA

AAAGTACCAGCACCAACAGGTGATTCAGAAGAACCGTTACAATGTATGATCTTTGA

CTCTTTATATGATCCATACCGCGGTGTAATTGCGTATATCCGTGTTGTAAATGGAAC

GGTAAAAGTTGGCGATAAAGTACGTATGATGGCAACTGGAAAAGAATTTGAAGTA

ACAGAAGTAGGTGTATTTACACCGAAAACTACGCAACGTGACGAGTTAACAGTAGG

TGATGTAGGTTTCTTAGCGGCATCGATTAAAAATGTTGGTGATACACGCGTTGGTGA

TACGATTACACACGCGAAACGTCCGGCAGCTGAGCCGTTAGCAGGTTATCGTAAAT

TAAATCCAATGGTATTCTGTGGTTTATATCCGATTGATTCTGCACGTTATAACGACT

TACGTGATGCGTTAGAAAAATTAGAATTAAACGATTCTGCACTTGAGTTTGAACCA

GAAACATCTCAAGCGCTAGGATTTGGTTTCCGTTGTGGATTCTTAGGACTTCTTCAT

ATGGAAATCCTTCAAGAACGTATTGAACGTGAATTTAAGATTGATTTAATTACAAC

AGCGCCAAGCGTTATTTATAAAGTATTCTTAACAAATGGTGAAGACATGATTGTCG

ATAACCCGTCTAATATGCCGGATCCACAAACAATTGATCGTGTTGAAGAGCCATTT

GTTAAAGCTGCAATTATGGTTCCGAACGACTATGTTGGAGCTGTAATGGAAATTTG

CCAAGGTAAACGCGGAACATTTATTGATATGCAATATTTAGATGAAACGCGTGTTA

CATTGACATATGAAATCCCGTTATCAGAAATCGTATATGACTTCTTCGATCAGTTGA

AATCAAATACGAAAGGATATGCATCATTTGATTATGAGTTAATTGGTTACAAACCA

TCTAAACTTGTAAAAATGGATATTCTTTTAAATTCTGAGCAAGTCGATGCTCTATCA

TTTATCGTACACCGTGATTCAGCGTATGACCGTGGTAAAGTAATCGTAGAAAAATT

AAAAGAATTAATTCCAAGACAGCAGTTCGAAGTGCCAATTCAAGCGACTATCGGAA

ACAAAGTTGTAGCGCGTTCTACAATTAAGGCGATGCGTAAAAACGTACTTGCGAAA

TGTTACGGTGGTGACATTTCTCGTAAGCGTAAACTTCTTGACAAGCAAAAAGAAGG

TAAAAAACGTATGAAGTCTGTTGGTTCTGTAGAAGTACCGCAAGAAGCATTCATGG

CTGTACTGAAAATGGATGACAAC

SEQ ID NO 62
>Bacillus_cereus_10987_lepA
ATGAACAAAGAAGAAAGAGCAAAAAGACAGTCCAAAATTCGTAATTTCTCTATCAT

TGCTCATATTGACCACGGAAAGTCAACGTTAGCAGACCGTATTTTAGAGAAAACAA

ACGCGTTAACACAACGTGAAATGAAAGCTCAGTTGCTTGACTCTATGGATTTAGAG

CGTGAGCGTGGTATTACAATTAAATTAAACGCAGTACAATTAAACTATAAAGCAAA

AGACGGTGAAGAATATATTCTTCACTTAATTGATACACCAGGACACGTCGACTTTA

CGTACGAAGTATCTCGTAGTTTAGCGGCTTGTGAAGGTGCAATTCTTGTAGTAGATG

CAGCGCAAGGTATTGAAGCGCAAACGTTAGCGAACGTATACTTAGCGCTTGATAAC

AATTTAGAAATTTTACCGGTTATTAATAAAATCGACTTACCAAGTGCAGACCCAGA

GCGTGTACGCCAAGAGGTGGAAGATGTAATTGGGTTAGATGCATCAGAAGCTGTAC

TTGCTTCGGCAAAAGCTGGGATTGGTATCGAAGAGATTCTAGAACAAATCGTTGAA

-continued

AAAGTGCCAGCACCAACAGGTGATTCAGAAGAACCGTTACAATGTATGATCTTTGA

CTCTTTATATGATCCATACCGCGGTGTAATTGCGTATATCCGTGTTGTAAATGGAAC

GGTAAAAGTTGGCGATAAAGTACGTATGATGGCAACTGGAAAAGAATTTGAAGTA

ACAGAAGTAGGTGTGTTTACACCGAAAACTACGCAACGTGATGAGTTAACAGTAGG

TGATGTAGGTTTCTTAGCGGCATCGATTAAAAATGTTGGTGACACACGCGTTGGTG

ATACGATTACACATGCGAAACGTCCAGCAGCTGAGCCATTACCTGGTTACCGTAAA

TTAAATCCAATGGTATTCTGTGGTCTGTACCCGATTGACTCTGCACGTTACAACGAC

TTACGTGATGCGCTAGAGAAATTAGAATTAAACGATTCTGCTCTTGAGTTTGAGCCA

GAAACATCTCAAGCGCTAGGATTTGGTTTCCGTTGTGGATTCTTAGGACTTCTTCAT

ATGGAAATCATTCAAGAGCGTATTGAACGTGAATTTAAAATTGATTTAATTACAAC

AGCGCCAAGTGTTATTTATAAAGTATTCTTAACGAATGGTGAAGACATGATTGTCG

ATAACCCGTCTAATATGCCGGATCCACAGACAATTGATCGTGTTGAAGAGCCATTT

GTTAAAGCGGCAATTATGGTTCCGAATGACTATGTTGGAGCTGTAATGGAAATTTG

CCAAGGTAAACGCGGAACGTTTATTGATATGCAATATTTAGATGAAACGCGTGTTA

CATTGACATATGAAATCCCATTATCAGAAATCGTATATGACTTCTTCGATCAGTTGA

AATCAAATACGAAAGGATATGCATCATTTGATTATGAGTTAATTGGTTATAAACCA

TCTAAACTTGTGAAAATGGATATTCTTTTAAATTCTGAGCAAGTCGATGCTCTATCA

TTTATCGTACACCGTGATTCAGCGTATGACCGTGGTAAAGTAATCGTAGAAAAATT

AAAAGAATTAATTCCAAGACAGCAGTTCGAAGTGCCAATTCAAGCGACGATCGGA

AACAAAGTTGTAGCGCGTTCTACAATTAAGGCGATGCGTAAAAACGTACTTGCGAA

ATGTTACGGTGGTGACATTTCTCGTAAGCGTAAACTTCTTGATAAGCAAAAAGAAG

GTAAAAAACGTATGAAGTCTGTTGGTTCTGTAGAAGTACCGCAAGAAGCATTCATG

GCTGTACTGAAAATGGATGACAAC

SEQ ID NO 63
>Bacillus_halodurans_lepA
ATGAACAGAGAGGAACGTCTCGCTCGTCAGTCGCGAATTCGGAATTTCTCGATTAT

CGCCCACATTGACCATGGGAAGTCAACGTTGGCGGACCGAATTCTTGAGAAGACGA

GTGCCCTCACGCAACGAGAAATGAAAGACCAGATGTTGGATGCTATGGATCTTGAG

CGTGAACGGGGCATAACCATTAAGCTGAATGCAGTTCAGCTTGTTTATAAAGCGAA

CGATGGAAATGAGTACATTTTTCATTTAATTGATACACCAGGTCACGTGGATTTCTC

ATATGAAGTTTCCCGGAGTTTAGCTGCCTGTGAAGGGGCACTGCTTATTGTTGATGC

GGCGCAAGGGATTGAGGCGCAAACGTTGGCCAATGTTTATTTAGCCCTCGATAATG

ATCTTGAAATCCTACCGGTTATTAATAAAATTGATTTGCCGAGTGCTGAGCCTGAGC

GTGTTCGCCAAGAAGTGGAGGATGTGATCGGTCTTGATGCGTCGGAAGCTGTCCTT

GCTTCAGCTAAAAATGGAATTGGGATTGAAGAAATTTTAGAACAAATTGTTGAAAA

AGTTCCAGCGCCGAGTGGAGATCCAGAAGGTCCGCTAAAAGCATTGATTTTCGATT

CATTGTACGATTCTTATCGAGGCGTTGTTGCCTATATTCGAATTGTAGAAGGATCTG

TGAAACCTGGACAAAAAATTAAAATGATGGCAACTGGAAAAGAGTTTGAAGTTAC

CGAAGTGGGCGTCTTCACACCAAAGCCTGAGAAGCGGGAAGAGCTTACTGTAGGTG

ATGTTGGCTTTCTAACCGCTTCTATAAAAAATGTCGGTGATACTCGGGTCGGTGATA

CGATCACGAGCGCGAACAACCCGGCGGACGAGCCCCTTCCTGGTTATCGACGAATG

AATCCGATGGTTTACTGCGGCTTATACCCAGTCGATACGAATGATTACAACGACTTG

-continued

CGCGAGGCGTTAGAGCGTCTTGAATTGAACGATGCGTCATTGCAATATGAACCTGA

AACGTCACAAGCTCTCGGTTTTGGTTTTCGCTGCGGCTTCTTAGGACTTCTCCATAT

GGAAATCATTCAAGAGCGGATCGAGCGAGAATTTGGTATTGATTTAATTACGACGG

CACCAAGCGTTGTATATAGCGTTCAACTGACGAACGGGGAAGTACAGCAAATTGAT

AATCCGTCTAACATGCCTGATAGGCAAAAGATTGAGGAAGTAGAAGAGCCGTATGT

CAAAGCGACGATCATGGTTCCAAACGATTTTGTCGGAGCTGTCATGGAGCTTTGTC

AAGGGAAGCGCGGGATTTTCATCGACATGCAATACCTTGATGAAAACAGAGTGCAA

ATCATTTATGAAATTCCCCTATCAGAAATCGTCTATGATTTCTTTGATCAATTAAAA

TCAAACACGAAAGGATACGCCTCCTTTGACTATGAATTGATCGGTTATAAGCCATCT

AACTTAGTGAAAATGGACATTTTGCTGAATGGTGAAGTCGTTGATGCCCTTTCTGTC

ATTGTCCACCGTGACTCTGCATATGAACGAGGAAAACAAATTGTTGAAAAGCTAAA

AGAACTCATCCCACGCCAGCAATTTGAGGTGCCAGTTCAAGCGAGTATTGGCACGA

AAATTATTGCCCGTTCAACGATCAAAGCGATGCGTAAAAACGTATTAGCGAAATGT

TACGGCGGTGACATCTCACGTAAACGGAAGCTTCTAGAAAAGCAAAAAGAAGGAA

AGAAGCGAATGAAAGCTGTGGGGAATGTGGAGGTTCCACAGGAAGCATTTATGGC

CGTATTGCGTATGGATGAACCGAAAAAG

SEQ ID NO 64
>Bacillus_subtilis_lepA
ATGACAGATAAAGAAAAGCGTTTAGAGAGGCAATCGAGAATACGGAATTTCTCTAT

CATTGCCCATATTGACCACGGAAAATCGACCTTAGCGGATCGTATTTTAGAAAAAA

CGTCGGCAATCACTCAACGAGAAATGAAAGAACAATTGCTCGATTCTATGGATCTT

GAACGTGAGCGGGGCATAACCATTAAATTAAACTCTGTTCAGCTTAAATATAAAGC

AAAAGACGGAGAAGAATATATCTTTCATCTAATCGATACGCCGGGACACGTCGACT

TCACGTATGAAGTATCCCGAAGCCTTGCTGCCTGCGAGGGAGCGATTCTTGTCGTG

GATGCAGCCCAGGGGATTGAAGCGCAGACGCTCGCCAATGTCTACTTAGCGCTTGA

CAACGATCTTGAAATCCTTCCGGTCATCAATAAAATCGACCTTCCGAGCGCCGAGC

CCGAACGTGTGCGCCAAGAGGTAGAAGACGTTATCGGCCTTGACGCATCAGAAGCC

GTGCTTGCTTCAGCAAAAGCCGGTATCGGGATTGAGGAGATTTTAGAACAAATCGT

AGAAAAGGTGCCAGCTCCGACCGGAGATCCGGAGGCGCCGCTCAAAGCGCTGATC

TTCGACTCGCTTTATGACGCCTACCGCGGTGTCGTGGCTTATATCAGAGTCGTTGAA

GGAACGGTAAAGCCGGGACAAAAAATCAAAATGATGGCAACCGGCAAAGAATTCG

AAGTAACAGAGGTGGGCGTGTTCACGCCGAAAGCAACTCCGACAAATGAACTGAC

GGTCGGTGATGTAGGCTTCCTGACTGCCTCAATCAAAAATGTTGGTGACACACGTG

TCGGTGATACAATAACGAGCGCTGCCAATCCTGCAGAAGAAGCGCTGCCGGGATAC

CGCAAGCTAAACCCGATGGTGTACTGTGGTTTGTATCCGATTGATACAGCGAAGTA

TAATGATTTAAGGGAAGCTCTTGAAAAGCTTGAGCTGAATGATTCCTCCCCTTCAATA

TGAAGCGGAAACTTCGCAAGCGCTTGGATTCGGGTTCCGCTGCGGATTTTTAGGCA

TGCTTCACATGGAGATCATTCAGGAGCGAATTGAGCGTGAGTTCAACATCGACCTG

ATTACGACAGCGCCAAGCGTTATCTATGACGTGTATATGACAGACGGCGAAAAGGT

CGTTGTCGACAACCCGTCCAACATGCCGGATCCTCAAAAGATCGAAAGGGTTGAGG

AGCCATACGTAAAAGCGACGATGATGGTGCCGAATGACTATGTCGGCGCTGTAATG

-continued
GAGCTTTGCCAAGGAAAACGCGGCAATTTCATTGATATGCAGTATTTAGACGCAAA

CCGTGTCAGCATCATTTATGATATGCCATTAGCGGAAATCGTATATGAGTTTTTTGA

TCAGCTGAAATCAAGCACTAAAGGCTATGCGTCCTTTGATTATGAACTGATCGGCT

ACAAACCGTCCAAGCTTGTGAAAATGGACATTATGCTGAATGGTGAAAAAATCGAT

GCCCTTTCCTTTATCGTGCATCGTGATTACGCATATGAACGGGGAAAAGTGATCGTT

GAAAAACTGAAAGAACTCATTCCGCGCCAGCAGTTTGAAGTTCCGGTACAAGCCGC

AATCGGCCAGAAAATCGTGGCCCGCTCCACCATAAAAGCAATGCGTAAAAACGTAT

TGGCTAAATGTTACGGAGGGGACATCTCGCGTAAACGGAAACTTCTTGAAAAACAA

AAAGAAGGAAAGCGCCGTATGAAGCAGGTCGGCTCAGTTGAAGTGCCGCAAGAAG

CATTTATGGCAGTTCTGAAAATGGACGACAGTCCGAAAAAACAA

SEQ ID NO 65
>Bacillus_licheniformis DSM 13, complete genome
GTGACAGATAAAGAAAAACGATTACAAAGGCAGTCGAGAATCCGAAATTTCTCTAT

TATCGCCCATATCGACCACGGCAAGTCAACGCTTGCGGATCGAATCTTGGAAAAAA

CGGCGGCAATCACTCAAAGGGAAATGAAAGAACAGCCTCGACTCAATGGATTTG

GAACGTGAAAGAGGAATCACCATTAAACTGAACTCCGTACAGCTGAAATATCAGGC

GAAGGACGGAGAGGAATATATTTTTCATCTGATCGATACCCCGGGACACGTCGATT

TTACGTATGAGGTTTCGAGAAGCCTTGCCGCATGCGAAGGCGCGATTCTCGTCGTA

GACGCCGCCCAGGGAATCGAGGCGCAAACGCTGGCAAACGTTTACCTTGCGCTTGA

CAACGACCTTGAAATCCTGCCGGTCATTAATAAAATCGACCTTCCGAGCGCAGAAC

CCGAACGCGTCCGCCAGGAAGTCGAGGATGTTATCGGTCTTGACGCTTCAGAAGCC

GTCCTTGCTTCAGCAAAAGCAGGCATCGGAATTGAGGAAATATTGGAGCAGATCGT

TGAAAAGGTTCCCGCACCAAGCGGAGATCCGGAAGCGCCGCTTCAGGCGCTGATCT

TTGACTCCCTGTATGATGCTTACCGCGGGGTCGTCGCCTATATCAGAGTCGTGCAAG

GTACCGTAAAAGCCGGTCAAAAAATCAAGATGATGGCGACCGGAAAGGAATTTGA

AGTCACTGAAGTCGGCGTTTTCACACCGAAGGCCGTTCCGGCTGACGAACTGACTG

TCGGCGACGTCGGATTCCTGACGGCCGCAATCAAAAACGTCGGAGACACTCGTGTA

GGGGATACGATTACGAGCGCGGAAAACCCTGCACCCGAAGCCCTGCCAGGCTACA

GAAAGCTGAATCCGATGGTTTATTGCGGCCTGTATCCGATTGATACAGCGAAATAC

AACGACTTGCGGGAAGCGCTTGAAAAAACTTGAGCTGAACGATTCAGCCCTGCAGTA

CGAAGCGGAAACGTCCCAAGCTCTCGGATTCGGCTTCCGCTGCGGTTTCTTAGGGA

TGCTCCACATGGAAATCATCCAGGAGCGGATTGAACGCGAATTCAACATCGATTTG

ATTACGACGGCTCCGAGCGTAATCTACGACGTGTACATGACAGACGGTGAAAAAAT

CGTCGTCGATAACCCGTCAAACATGCCTGATCCGCAGAAGATCGACCGGGTGGAAG

AACCGTTCGTCAAAGCGACGATGATGGTGCCGAACGACTTTGTCGGAGCGGTCATG

GAACTGTGCCAGGGCAAGCGCGGCCAGTTTATTGATATGCAGTACCTTGATGCGAA

CCGCGTCAGCATTGTCTACGAAATTCCGCTTGCGGAAATCGTCTACGAGTTTTTCGA

TCAGCTTAAATCAAATACGAAAGGCTATGCGTCATTTGATTACGAACTCATCGGAT

ATAAACCGTCCAAGCTCGTGAAAATGGATATTATGCTGAACGGCGAAAAAATCGAT

GCCCTTTCCTTTATCGTTCACCGCGATTATGCTTATGAACGAGGAAAAGTTATCGTC

GAAAAGCTGAAAGAGCTCATTCCGCGCCAGCAGTTTGAAGTGCCTGTCCAGGCAGC

CATCGGTACAAAAATTGTCGCCCGTTCAACCATCAAAGCAATGCGCAAAAACGTTT

-continued

TGGCGAAGTGCTACGGCGGGGATATTTCCAGAAAGCGCAAACTGCTTGAAAAGCA

AAAGGAAGGAAAGCGAAGAATGAAACAGGTCGGCTCTGTCGAAGTTCCGCAGGAA

GCCTTTATGGCAGTCCTGAAAATGGACGACAGCGGCCCGAAATCATAA

SEQ ID NO 66
>Bacillus_cereus_10987_lepA
ATGAACAAAGAAGAAAGAGCAAAAAGACAGTCCAAAATTCGTAATTTCTCTATCAT

TGCTCATATTGACCACGGAAAGTCAACGTTAGCAGACCGTATTTTAGAGAAAACAA

ACGCGTTAACACAACGTGAAATGAAAGCTCAGTTGCTTGACTCTATGGATTTAGAG

CGTGAGCGTGGTATTACAATTAAATTAAACGCAGTACAATTAAACTATAAAGCAAA

AGACGGTGAAGAATATATTCTTCACTTAATTGATACACCAGGACACGTCGACTTTA

CGTACGAAGTATCTCGTAGTTTAGCGGCTTGTGAAGGTGCAATTCTTGTAGTAGATG

CAGCGCAAGGTATTGAAGCGCAAACGTTAGCGAACGTATACTTAGCGCTTGATAAC

AATTTAGAAATTTTACCGGTTATTAATAAAATCGACTTACCAAGTGCAGACCCAGA

GCGTGTACGCCAAGAGGTGGAAGATGTAATTGGGTTAGATGCATCAGAAGCTGTAC

TTGCTTCGGCAAAAGCTGGGATTGGTATCGAAGAGATTCTAGAACAAATCGTTGAA

AAAGTGCCAGCACCAACAGGTGATTCAGAAGAACCGTTACAATGTATGATCTTTGA

CTCTTTATATGATCCATACCGCGGTGTAATTGCGTATATCCGTGTTGTAAATGGAAC

GGTAAAAGTTGGCGATAAAGTACGTATGATGGCAACTGGAAAAGAATTTGAAGTA

ACAGAAGTAGGTGTGTTTACACCGAAAACTACGCAACGTGATGAGTTAACAGTAGG

TGATGTAGGTTTCTTAGCGGCATCGATTAAAAATGTTGGTGACACACGCGTTGGTG

ATACGATTACACATGCGAAACGTCCAGCAGCTGAGCCATTACCTGGTTACCGTAAA

TTAAATCCAATGGTATTCTGTGGTCTGTACCCGATTGACTCTGCACGTTACAACGAC

TTACGTGATGCGCTAGAGAAATTAGAATTAAACGATTCTGCTCTTGAGTTTGAGCCA

GAAACATCTCAAGCGCTAGGATTTGGTTTCCGTTGTGGATTCTTAGGACTTCTTCAT

ATGGAAATCATTCAAGAGCGTATTGAACGTGAATTTAAAATTGATTTAATTACAAC

AGCGCCAAGTGTTATTTATAAAGTATTCTTAACGAATGGTGAAGACATGATTGTCG

ATAACCCGTCTAATATGCCGGATCCACAGACAATTGATCGTGTTGAAGAGCCATTT

GTTAAAGCGGCAATTATGGTTCCGAATGACTATGTTGGAGCTGTAATGGAAATTTG

CCAAGGTAAACGCGGAACGTTTATTGATATGCAATATTTAGATGAAACGCGTGTTA

CATTGACATATGAAATCCCATTATCAGAAATCGTATATGACTTCTTCGATCAGTTGA

AATCAAATACGAAAGGATATGCATCATTTGATTATGAGTTAATTGGTTATAAACCA

TCTAAACTTGTGAAAATGGATATTCTTTTAAATTCTGAGCAAGTCGATGCTCTATCA

TTTATCGTACACCGTGATTCAGCGTATGACCGTGGTAAAGTAATCGTAGAAAAATT

AAAAGAATTAATTCCAAGACAGCAGTTCGAAGTGCCAATTCAAGCGACGATCGGA

AACAAAGTTGTAGCGCGTTCTACAATTAAGGCGATGCGTAAAAACGTACTTGCGAA

ATGTTACGGTGGTGACATTTCTCGTAAGCGTAAACTTCTTGATAAGCAAAAAGAAG

GTAAAAAACGTATGAAGTCTGTTGGTTCTGTAGAAGTACCGCAAGAAGCATTCATG

GCTGTACTGAAAATGGATGACAAC

SEQ ID NO 67
>Bacillus_cereus_14579_lepA
ATGAATAAAGAAGAAAGAGCAAAAAGACAGTCCAAAATCCGTAATTTCTCTATTAT

TGCTCATATTGACCACGGAAAATCAACGTTAGCAGACCGTATTTTAGAGAAAACAA

-continued

ACGCGTTAACACAACGTGAAATGAAAGCTCAGTTGCTTGACTCTATGGATTTAGAG

CGTGAGCGTGGTATTACAATCAAATTAAACGCAGTACAATTAAACTATAAAGCAAA

AGATGGTGAAGAGTATATTCTTCATTTAATTGATACACCAGGACACGTCGACTTTAC

GTACGAAGTATCTCGTAGTTTAGCGGCTTGTGAAGGCGCGATTCTTGTAGTAGATGC

AGCGCAAGGTATTGAAGCGCAAACGTTAGCAAACGTATACTTAGCGCTTGATAATA

ATTTAGAAATTTTACCAGTTATTAATAAAATCGACTTACCGAGTGCGGATCCAGAA

CGTGTACGTCAAGAGGTAGAAGATGTAATTGGTTTAGATGCATCAGAAGCGGTACT

TGCTTCTGCGAAAGCTGGAATTGGTTTGAAGAAATTTTAGAACAAATTGTTGAAAA

AGTACCAGCTCCGGCGGGTGATTCAGAAGAGCCGTTACAATGTATGATTTTCGACT

CTTTATATGATCCATACCGCGGTGTAATTGCTTATATCCGTGTTGTAAATGGAACAG

TAAAAGTTGGCGATAAAGTACGTATGATGGCAACGGGTAAAGAATTTGAAGTAAC

AGAAGTAGGTGTATTTACACCGAAAACTACGCAACGTGACGAGTTAACGGTAGGTG

ATGTAGGTTTCTTAGCAGCATCGATTAAAAATGTTGGTGACACACGCGTTGGTGAT

ACGATTACACATGCGAAACGTCCAGCTGCAGAGCCGTTAGCAGGTTACCGTAAGTT

AAACCCGATGGTATTCTGTGGTCTGTATCCAATTGACTCTGCTCGTTATAACGATTT

ACGTGATGCATTAGAAAAATTAGAGTTAAACGATTCTGCCCTTGAGTTTGAACCAG

AAACATCTCAAGCGCTAGGATTTGGTTTCCGTTGTGGTTTCTTAGGACTTCTTCACA

TGGAAATCATTCAAGAACGTATTGAACGTGAATTTAAGATTGACTTAATTACAACA

GCGCCAAGCGTTATTTATAAAGTTTATTTAACTAACGGTGAAGATGTTATTGTTGAT

AACCCATCTAATATGCCAGATCCACAGTCTATCGATCGTGTAGAAGAGCCGTTTGT

GAAGGCTTCAATTATGGTTCCGAATGACTATGTTGGAGCTGTAATGGAGATTTGCC

AAGGTAAACGTGGAACGTTTATTGATATGCAATATTTAGATGAAACGCGTGTTACA

TTAACATATGAAATCCCGTTATCAGAAATCGTATATGACTTCTTTGATCAATTGAAA

TCAAATACGAAAGGGTATGCATCATTTGACTACGAGTTAATTGGCTATAAACCATC

TAAACTTGTGAAAATGGATATTCTTTTAAATAATGAACAAGTGGATGCTTTATCATT

TATCGTACACCGTGATTCAGCGTATGACCGTGGTAAAGTAATCGTAGAGAAATTAA

AAGAATTAATTCCGAGACAACAGTTCGAAGTGCCAATTCAGGCGACTATCGGAAAT

AAAGTTGTAGCACGTTCTACAATTAAAGCGATGCGTAAAAACGTACTTGCAAAATG

TTACGGCGGTGACATTTCTCGTAAGCGTAAACTTCTTGATAAGCAAAAAGAAAGTA

AAAAACGTATGAAGTCCGTTGGCTCTGTAGAAGTACCGCAAGAAGCATTCATGGCT

GTACTGAAAATGGATGACAAC

SEQ ID NO 68
>Eschericia_coli_K12_lepA
ATGAAGAATATACGTAACTTTTCGATCATAGCTCACATTGACCACGGTAAATCGAC

GCTGTCTGACCGTATTATCCAGATCTGCGGTGGCCTGTCTGACCGTGAAATGGAGG

CGCAGGTTCTCGATTCCATGGATCTTGAGCGTGAGCGTGGCATTACCATCAAAGCG

CAAAGCGTGACGCTGGACTACAAAGCGTCTGACGGCGAAACCTATCAGCTTAACTT

TATCGACACCCCGGGCCACGTAGACTTCTCCTATGAAGTTTCCCGTTCGCTGGCTGC

CTGTGAAGGTGCATTGCTGGTGGTCGACGCCGGGCAGGGCGTAGAAGCGCAAACCC

TGGCAAACTGCTACACCGCCATGGAAATGGATCTCGAAGTTGTGCCGGTACTGAAC

AAGATTGACCTGCCGGCAGCCGATCCTGAACGCGTGGCGGAAGAAATTGAAGATAT

CGTCGGCATCGACGCCACCGACGCGGTGCGCTGTTCAGCGAAAACCGGCGTTGGTG

-continued

TGCAGGACGTTCTCGAACGTCTGGTGCGCGACATTCCGCCGCCGGAAGGCGATCCG

GAAGGCCCGTTGCAGGCACTAATTATCGACTCATGGTTCGACAACTACCTGGGCGT

TGTTTCACTTATCCGTATTAAAAACGGCACCCTGCGTAAGGGCGACAAAGTGAAAG

TCATGAGTACCGGGCAGACCTATAACGCCGACCGTCTGGGCATCTTCACGCCGAAA

CAGGTTGACCGCACTGAACTGAAATGTGGCGAAGTAGGCTGGCTCGTATGTGCGAT

TAAAGATATCCACGGCGCTCCAGTCGGCGATACCTTAACGCTGGCGCGTAATCCGG

CAGAAAAGGCGCTGCCTGGCTTTAAGAAAGTCAAACCGCAGGTATACGCCGGTCTG

TTCCCGGTAAGTTCCGACGACTATGAAGCCTTCCGTGACGCGCTGGGTAAACTCAG

CCTGAACGATGCCTCACTGTTCTATGAGCCGGAAAGCTCCAGCGCGCTGGGCTTTG

GTTTCCGCTGCGGCTTCCTCGGCCTGCTGCACATGGAGATCATCCAGGAACGTCTGG

AACGTGAATACGATCTGGATCTGATCACCACTGCGCCGACCGTAGTGTATGAAGTT

GAAACCACGTCAAGAGAAGTTATCTACGTCGACAGCCCATCCAAGCTGCCTGCGGT

AAATAACATCTACGAACTGCGCGAGCCGATTGCAGAGTGTCACATGCTGCTGCCGC

AGGCATATCTCGGCAACGTTATTACGTTGTGCGTAGAAAAACGCGGCGTGCAGACC

AATATGGTTTACCACGGTAATCAGGTGGCGCTGACGTACGAGATCCCGATGGCGGA

AGTGGTGCTCGACTTCTTCGATCGCCTGAAATCTACCTCGCGTGGTTATGCGTCTCT

GGATTACAACTTCAAGCGCTTCCAGGCGTCCGACATGGTACGTGTAGACGTATTAA

TCAACGGTGAACGTGTTGATGCGCTGGCGTTGATCACCCACCGTGATAATTCGCAA

AACCGCGGTCGCGAGTTGGTGGAGAAGATGAAAGATCTGATCCCACGCCAGCAGTT

TGATATCGCCATTCAGGCAGCGATTGGTACGCACATCATTGCGCGATCCACCGTGA

AACAGCTGCGTAAAAACGTACTGGCTAAATGTTATGGCGGCGATATCAGCCGTAAG

AAAAAGCTGCTGCAGAAGCAGAAAGAAGGTAAGAAACGCATGAAGCAGATCGGTA

ACGTCGAGCTGCCGCAGGAAGCGTTCCTCGCCATTCTGCACGTCGGCAAAGACAAC

AAA

SEQ ID NO 69
>Eschericia_coli_O157_H7_lepA
ATGAAGAATATACGTAACTTTTCGATCATAGCTCACATTGACCACGGTAAATCGAC

GCTGTCTGACCGTATTATCCAGATCTGCGGTGGCCTGTCTGACCGTGAAATGGAGG

CGCAGGTTCTCGATTCCATGGATCTTGAGCGTGAGCGTGGCATTACCATCAAAGCG

CAAAGCGTGACGCTGGACTACAAAGCGTCTGACGGCGAAACCTATCAGCTTAACTT

TATCGACACCCCGGGCCACGTAGACTTCTCCTATGAAGTTTCCCGTTCGCTGGCTGC

CTGTGAAGGTGCATTGCTGGTGGTCGACGCCGGGCAGGGCGTGGAAGCGCAAACCC

TGGCAAACTGCTACACCGCCATGGAAATGGATCTCGAAGTGGTGCCGGTACTGAAC

AAGATTGACCTGCCGGCAGCCGATCCTGAACGCGTGGCGGAAGAAATTGAAGATAT

CGTCGGCATCGACGCCACTGACGCGGTGCGCTGTTCAGCGAAAACCGGCGTTGGCG

TGCAGGACGTTCTCGAACGTCTGGTGCGCGACATTCCGCCGCCGGAAGGCGATCCG

GAAGGCCCGTTGCAGGCACTAATTATCGACTCATGGTTCGACAACTACCTGGGCGT

TGTTTCACTTATCCGTATTAAAAACGGCACCCTGCGTAAGGGCGACAAAGTGAAAG

TCATGAGTACCGGGCAGACCTATAACGCCGACCGTCTGGGCATCTTCACGCCGAAA

CAGGTTGACCGCACTGAACTGAAATGTGGCGAAGTAGGCTGGCTCGTATGTGCGAT

TAAAGATATCCACGGCGCTCCAGTCGGCGATACCTTAACGCTGGCGCGTAATCCGG

-continued
CAGAAAAGGCGCTGCCTGGCTTTAAGAAAGTCAAACCGCAGGTATACGCCGGTCTG

TTCCCGGTAAGTTCCGACGACTATGAAGCCTTCCGTGACGCGCTGGGTAAACTCAG

CCTGAACGATGCCTCACTGTTCTATGAGCCGGAAAGCTCCAGCGCGCTGGGCTTTG

GTTTCCGCTGCGGCTTCCTTGGCCTGCTGCACATGGAGATCATCCAGGAGCGTCTGG

AACGTGAATACGATCTGGATCTGATCACCACTGCGCCGACCGTAGTGTATGAAGTT

GAAACCACGTCAAGGGAAGTTATCTACGTCGACAGCCCATCCAAGCTGCCTGCGGT

AAATAACATTTACGAACTGCGCGAGCCGATTGCAGAGTGTCACATGCTGCTGCCGC

AGGCATATCTCGGCAACGTTATTACGCTGTGCGTAGAAAAACGCGGCGTGCAGACC

AATATGGTTTACCACGGTAATCAGGTGGCGCTGACGTACGAGATCCCGATGGCGGA

AGTGGTGCTCGACTTCTTCGATCGCCTGAAATCTACCTCGCGTGGTTATGCGTCTCT

GGATTACAACTTCAAACGCTTCCAGGCGTCCGACATGGTACGTGTAGACGTATTAA

TCAACGGTGAACGTGTTGATGCGCTGGCGTTGATCACCCACCGTGATAATTCGCAA

AACCGCGGTCGCGAGTTGGTGGAGAAGATGAAAGATCTGATCCCACGCCAGCAGTT

TGATATCGCCATTCAGGCAGCGATTGGTACGCACATTATTGCGCGATCCACCGTGA

AACAGCTGCGTAAAAACGTACTGGCTAAATGTTATGGCGGCGATATCAGCCGTAAG

AAAAAGCTGCTGCAGAAGCAGAAAGAAGGTAAGAAACGCATGAAGCAGATCGGTA

ACGTCGAGCTGCCGCAGGAAGCGTTCCTCGCCATTCTGCACGTCGGCAAAGACAAC

AAA

SEQ ID NO 70
>Eschericia_coli_O157_H7_EDL933_lepA
ATGAAGAATATACGTAACTTTTCGATCATAGCTCACATTGACCACGGTAAATCGAC

GCTGTCTGACCGTATTATCCAGATCTGCGGTGGCCTGTCTGACCGTGAAATGGAGG

CGCAGGTTCTCGATTCCATGGATCTTGAGCGTGAGCGTGGCATTACCATCAAAGCG

CAAAGCGTGACGCTGGACTACAAAGCGTCTGACGGCGAAACCTATCAGCTTAACTT

TATCGACACCCCGGGCCACGTAGACTTCTCCTATGAAGTTTCCCGTTCGCTGGCTGC

CTGTGAAGGTGCATTGCTGGTGGTCGACGCCGGGCAGGGCGTGGAAGCGCAAACCC

TGGCAAACTGCTACACCGCCATGGAAATGGATCTCGAAGTGGTGCCGGTACTGAAC

AAGATTGACCTGCCGGCAGCCGATCCTGAACGCGTGGCGGAAGAAATTGAAGATAT

CGTCGGCATCGACGCCACTGACGCGGTGCGCTGTTCAGCGAAAACCGGCGTTGGCG

TGCAGGACGTTCTCGAACGTCTGGTGCGCGACATTCCGCCGCCGGAAGGCGATCCG

GAAGGCCCGTTGCAGGCACTAATTATCGACTCATGGTTCGACAACTACCTGGGCGT

TGTTTCACTTATCCGTATTAAAAACGGCACCCTGCGTAAGGGCGACAAAGTGAAAG

TCATGAGTACCGGGCAGACCTATAACGCCGACCGTCTGGGCATCTTCACGCCGAAA

CAGGTTGACCGCACTGAACTGAAATGTGGCGAAGTAGGCTGGCTCGTATGTGCGAT

TAAAGATATCCACGGCGCTCCAGTCGGCGATACCTTAACGCTGGCGCGTAATCCGG

CAGAAAAGGCGCTGCCTGGCTTTAAGAAAGTCAAACCGCAGGTATACGCCGGTCTG

TTCCCGGTAAGTTCCGACGACTATGAAGCCTTCCGTGACGCGCTGGGTAAACTCAG

CCTGAACGATGCCTCACTGTTCTATGAGCCGGAAAGCTCCAGCGCGCTGGGCTTTG

GTTTCCGCTGCGGCTTCCTTGGCCTGCTGCACATGGAGATCATCCAGGAGCGTCTGG

AACGTGAATACGATCTGGATCTGATCACCACTGCGCCGACCGTAGTGTATGAAGTT

GAAACCACGTCAAGGGAAGTTATCTACGTCGACAGCCCATCCAAGCTGCCTGCGGT

AAATAACATTTACGAACTGCGCGAGCCGATTGCAGAGTGTCACATGCTGCTGCCGC

-continued

AGGCATATCTCGGCAACGTTATTACGCTGTGCGTAGAAAAACGCGGCGTGCAGACC

AATATGGTTTACCACGGTAATCAGGTGGCGCTGACGTACGAGATCCCGATGGCGGA

AGTGGTGCTCGACTTCTTCGATCGCCTGAAATCTACCTCGCGTGGTTATGCGTCTCT

GGATTACAACTTCAAACGCTTCCAGGCGTCCGACATGGTACGTGTAGACGTATTAA

TCAACGGTGAACGTGTTGATGCGCTGGCGTTGATCACCCACCGTGATAATTCGCAA

AACCGCGGTCGCGAGTTGGTGGAGAAGATGAAAGATCTGATCCCACGCCAGCAGTT

TGATATCGCCATTCAGGCAGCGATTGGTACGCACATTATTGCGCGATCCACCGTGA

AACAGCTGCGTAAAAACGTACTGGCTAAATGTTATGGCGGCGATATCAGCCGTAAG

AAAAAGCTGCTGCAGAAGCAGAAAGAAGGTAAGAAACGCATGAAGCAGATCGGTA

ACGTCGAGCTGCCGCAGGAAGCGTTCCTCGCCATTCTGCACGTCGGCAAAGACAAC

AAA

SEQ ID NO 71
>Enterobacter_faecalis_V583_lepA
ATGAACAATAAAGAAATGAAAGCAAGACAAGAGAAAATTCGTAATTTCTCGATCA

TTGCCCACATTGACCATGGGAAGTCAACTTTAGCCGACCGGATTTTGGAAAAAACA

AATACAGTTAGCAGTCGAGAAATGCAAGATCAATTACTTGATTCAATGGATTTAGA

GAGAGAACGCGGCATTACTATCAAATTAAACGCAATTGAATTAAACTATACAGCCA

AAGATGGTGAAATCTATACTTTCCATTTGATTGACACACCAGGGCACGTCGATTTCA

CCTACGAAGTTTCTCGTAGCTTGGCAGCTTGTGAAGGGGCTGTTCTAGTTGTTGATG

CGGCGCAAGGAATTGAAGCGCAAACGCTAGCAAATGTCTATTTGGCATTGGATAAT

GACTTAGAAATTTTACCTGTTATTAATAAAATTGATTTACCCGCCGCTGATCCAGAG

CGTGTTCGGACAGAGATTGAAGACGTAATTGGAATTGATGCATCGGAAGCTGTTTT

AGCAAGTGCAAAAGCAGGGATTGGGATTGAAGATATTTTAGAACAAGTGGTGGAG

TATGTACCAGCTCCATCAGGCGATATTGAGGCTCCTTTAAAGGCTTTGATTTTTGAC

TCTATTTACGATAGTTATCGGGGGGTCGTTTTAAACATCCGTGTAATTGACGGTGTC

GTTCGTCCTGGGGATAAAATCCAAATGATGAGTAACGGTAAAACGTTTGATGTAAC

AGAAGTCGGCGTTTTTTCACCGAAACCGATTGCTCGTGATTATTTAATGGTTGGTGA

TGTGGGCTATATCACCGCTAGCATTAAAACGGTTCAAGATACACGGGTCGGGGATA

CAGTGACTTTGGCCGACAATCCAGCAGCAGAAGCACTACCAGGCTACCGCAAAATG

AATCCAATGGTTTATTGTGGTTTATATCCAATTGATACGTCGCGCTACAACGATTTA

CGGGAAGCATTAGAAAAATTACAATTAAATGATGCGGCGTTACAATTTGAACCGGA

AACATCGCAAGCTTTAGGGTTTGGTTTCCGTTGTGGTTTCTTAGGTTTGCTGCACAT

GGATGTTGTTCAGGAACGTTTGGAACGAGAATTTAATTTAGAGTTAATTACAACAG

CACCGTCTGTAATCTATCACGTTAATAAAACTGACGGAACAACCGTTGTTGTTGACA

ACCCAGCTGAATTTCCAGAACCAGTAACGATTGAATCTGTGGAAGAACCTTATGTT

AAAGCGCAAATCATGGTGCCAAACGATTATGTAGGAGCAGTAATGGAATTATCACA

ACGTAAACGTGGCGAATTCATTACAATGGATTACTTAGACGATTATCGTGTAAACG

TAGTTTATGAAATTCCGTTATCTGAAATCGTGTTTGACTTTTTCGATAAATTGAAAT

CAAGTACAAAAGGCTATGCATCCTTAGATTACGAAATGGCTGGCTATCGTACCAGC

CGCCTAGTGAAAATGGATATTCTATTAAATGCTGAAAAAGTGGATGCTTTAAGCTTT

ATTGTTCACCGAGATTTCGCATTTGAGCGTGGTAAAGCGATTGTTGAGAAACTGAA

-continued

AAAACTAATTCCACGTCAACAGTTTGAAGTCCCAGTTCAAGCGGCGATTGGTCAAA

AAATTGTGGCTCGTTCAGATATTAAAGCCTTACGCAAAAACGTACTGGCTAAATGC

TATGGTGGCGATGTTTCTCGTAAACGTAAATTGTTAGAGAAACAAAAAGAAGGGAA

GAAACGGATGAAACAAATTGGATCCGTGGAAGTTCCTCAAGAAGCCTTTATGGCGG

TTCTGAAAATGGACGACCAAGATAACGCGAAA

SEQ ID NO 72
>Erwinia_carotovora_SCRI1043_lepA
ATGAAGCATATACGAAATTTCTCCATTATTGCCCATATCGACCACGGTAAATCGAC

ATTATCTGACCGTATTATCCAGATCTGCGGCGGATTAACCGAACGTGAAATGGCTG

CGCAGGTTCTGGATTCCATGGATCTGGAACGTGAACGCGGAATAACGATTAAAGCG

CAAAGCGTGACGCTGGATTATAAATCGCAGGACGGCCAAACCTACCAGTTAAACTT

CATTGATACGCCTGGGCACGTAGACTTCTCTTATGAGGTTTCCCGCTCGCTTGCCGC

CTGTGAAGGTGCGCTGCTTGTTGTTGATGCCGGGCAGGGTGTTGAAGCTCAAACGT

TGGCTAACTGTTATACCGCGTTGGATATGAATCTGGAAGTGGTGCCTGTCCTAAACA

AGATTGACCTGCCTGCTGCTGACCCGGATCGTGTTGCTCAAGAAATTGAAGATATC

GTTGGTATCGATGCCACTGATGCTGTGCGCTGCTCCGCGAAAACAGGGGTTGGTGT

GCCGGATATTCTGGATCGTTTGGTGCGTGATATTCCGCCGCCGGAAGGCAGCCCTG

ATGCGCCGTTGCAAGCGCTGATTATCGACTCCTGGTTTGATAACTACCTTGGCGTTG

TGTCGCTGGTTCGTATCAAAAACGGCACGATGCGCAAAGGCGACAAAATTAAGGTG

ATGAGTACGGGTCAGGTGTATAACGCCGACCGTCTCGGTATTTTTACACCGAAGCA

GATTGACCGCGATGTATTGAATTGCGGTGAAGTAGGCTGGCTGGTGTGCGCCATCA

AAGATATTTTGGGTGCGCCAGTCGGGGATACCCTGACGCTGGCACGTCAGCCAGCT

GAAAAAGCGCTGCCGGGCTTCAAAAAAGTCAAACCTCAGGTCTATGCCGGTTTGTT

CCCGATCAGTTCCGACGACTATGAAGCATTCCGTGACGCGTTAGGTAAGCTGAGTC

TCAATGATGCCTCTCTGTTCTATGAACCGGAAAGCTCTACCGCGCTGGGCTTTGGTT

TCCGCTGCGGCTTCCTAGGTCTGCTGCACATGGAGATCATTCAGGAACGTCTGGAG

CGTGAATACGATCTGGAACTGATCACCACGGCGCCGACGGTAGTGTATGAAGTAGA

AACGACGGCTAAAGAAACCATTTATGTCGATAGTCCGTCTAAACTGCCGCCGCTGA

ATAATATTCAGGAACTGCGCGAACCGATTGCCGAGTGTCACATGCTGATGCCTCAG

GAATATCTGGGTAACGTGATTACGCTCTGTATTGAGAAGCGCGGTGTGCAGACGAA

TATGGTGTATCACGGTAATCAGGTTGCATTGACCTATGAGATCCCGATGGCCGAGG

TGGTGCTCGATTTCTTTGACCGTCTGAAATCAACCTCTCGGGGTTATGCATCGCTGG

ATTACGGCTTCAAACGTTTCCAGACATCGGACATGGTGCGCGTTGATGTATTAATCA

ACAACGAGCGTGTCGATGCGTTGGCCCTGATTACTCACCGTGATAACTCACAATAT

CGTGGCCGTGAGTTTGTCGAAAAAATGAAAGAACTCATTCCGCGTCAGCAGTTTGA

TATTGCGATTCAGGCTGCGATTGGTAACCACATTATTGCGCGTGCGACGGTTAAGC

AATTGCGTAAAAACGTACTGGCCAAGTGTTATGGTGGTGACGTCAGCCGTAAGAAG

AAACTGTTGCAGAAACAGAAAGACGGTAAGAAGCGTATGAAGCAGGTCGGTAACG

TCGAGCTGCCGCAAGAAGCGTTTCTGGCAATTCTGCACGTCGGCAAAGACAGTAAA

SEQ ID NO 73
>Salmonella_Typhi_Ty2_lepA
ATGAAGAACATACGTAACTTTTCGATCATTGCTCACATTGACCACGGTAAATCGAC

GCTGTCTGACCGTATTATCCAAATCTGCGGTGGCCTGTCTGACCGTGAAATGGAAG

-continued

CTCAGGTACTTGATTCGATGGATCTTGAGCGTGAGCGCGGTATTACTATTAAAGCCC

AGAGTGTGACGCTGGATTTTAAAGCGTCTGATGGTGAAACTTATCAACTGAACTTT

ATCGACACGCCGGGACACGTTGACTTTTCCTATGAAGTTTCCCGTTCGTTAGCCGCC

TGCGAGGGCGCGCTGCTGGTGGTGGATGCCGGCCAGGGCGTAGAAGCGCAAACGT

TGGCGAACTGCTACACCGCGATGGAAATGGATCTTGAAGTGGTGCCGGTGCTTAAC

AAGATTGACCTGCCGGCCGCCGATCCGGAGCGTGTGGCGGAAGAAATCGAAGACA

TTGTCGGCATCGATGCGACGGACGCGGTACGCTGCTCCGCCAAAACGGGTGTCGGC

GTGACGGACGTTCTGGAACGCCTGGTGCGCGATATCCCGCCGCCGCAAGGCGATCC

GGACGGCCCGCTGCAGGCGCTGATTATTGACTCCTGGTTCGATAACTACCTGGGCG

TGGTATCCCTGGTGCGTATTAAAAACGGCACCATGCGTAAAGGCGACAAAATTAAA

GTGATGAGCACCGGGCAGACCTACAACGCTGACCGCCTGGGGATCTTCACGCCGAA

ACAGGTTGATCGTACCGAGCTGAAGTGCGGCGAAGTAGGCTGGCTGGTCTGCGCCA

TTAAAGATATCCTCGGCGCGCCGGTTGGCGATACCTTAACCTCAGCGCGTAACCCA

GCTGAAAAAGCGTTGCCGGGCTTTAAGAAGGTGAAACCGCAGGTCTATGCAGGTCT

GTTCCCGGTCAGCTCCGACGATTATGAAAGTTTCCGCGACGCGCTCGGCAAGCTGA

GCCTGAACGATGCCTCACTGTTTTATGAACCGGAAAGCTCCTCGGCGCTGGGCTTTG

GTTTCCGCTGCGGCTTCCTCGGCCTGTTGCACATGGAGATCATTCAGGAGCGTCTGG

AACGCGAATACGATCTGGATCTGATCACCACTGCGCCGACCGTGGTTTATGAAGTA

GAAACAACGGCGAAAGAGACTATCTATGTTGATAGCCCCTCCAAGCTGCCGCCGTT

GAATAACATTTATGAACTGCGCGAGCCTATCGCCGAATGTCATATGCTGTTACCAC

AAGCCTATTTAGGTAACGTTATTACGCTGTGTATTGAGAAACGCGGCGTACAAACT

AACATGGTGTATCACGGTAACCAGGTTGCGTTGACCTATGAAATCCCGATGGCGGA

AGTGGTGCTCGACTTCTTTGACCGTCTGAAATCAACGTCGCGCGGCTATGCGTCTCT

GGATTATAACTTCAAGCGCTTCCAGGCTTCCGATATGGTGCGTGTTGATGTGTTAAT

CAACAACGAGCGTGTCGATGCGCTGGCGCTGATCACGCACCGTGATAACTCGCAAA

GCCGTGGTCGCGAGCTGGTGGAGAAAATGAAAGATTTGATTCCACGCCAGCAGTTT

GATATCGCGATTCAGGCGGCGATTGGTACGCATATTATTGCCCGTTCGACGGTAAA

ACAGTTACGTAAAAACGTGCTGGCGAAGTGCTACGGCGGCGATATCAGTCGTAAGA

AAAAACTGCTGCAGAAACAGAAAGAAGGTAAGAAACGCATGAAGCAGATCGGTAA

CGTCGAGCTGCCTCAGGAGGCGTTCCTCGCCATTCTGCATGTCGGTAAAGACAATA

AA

SEQ ID NO 74
>Salmonella_typhimurium_LT2_lepA
ATGAAGAACATAAGAAATTTCTCCATCATTGCTCACATTGACCACGGTAAATCGAC

GCTGTCTGACCGTATTATCCAAATCTGCGGTGGCCTGTCTGACCGTGAAATGGAAG

CTCAGGTACTTGATTCGATGGATCTTGAGCGTGAGCGCGGTATTACTATTAAAGCCC

AGAGTGTGACGCTGGATTTTAAAGCGTCTGATGGTGAAACTTATCAACTGAACTTT

ATCGACACGCCGGGACACGTTGACTTTTCCTATGAAGTTTCCCGTTCGTTAGCCGCC

TGCGAGGGCGCGCTGCTGGTGGTGGATGCCGGCCAGGGCGTAGAAGCGCAAACGT

TGGCGAACTGCTACACCGCGATGGAAATGGATCTTGAAGTGGTGCCGGTGCTTAAC

AAGATTGACCTGCCGGCCGCCGATCCGGAGCGTGTGGCGGAAGAAATCGAAGACA

-continued

TTGTCGGTATCGATGCGACGGACGCGGTACGCTGCTCCGCCAAAACGGGTGTCGGC

GTGACGGATGTTCTGGAACGCCTGGTGCGCGATATCCCGCCGCCGCAAGGCGATCC

GGACGGCCCGCTGCAGGCGCTGATTATTGACTCCTGGTTCGATAACTACCTGGGCG

TGGTATCGCTGGTGCGTATTAAAAACGGCACCATGCGTAAAGGCGACAAAATTAAA

GTGATGAGCACCGGGCAGACCTACAACGCTGACCGCCTGGGGATCTTCACGCCAAA

ACAGGTTGATCGTACCGAGCTGAAGTGCGGCGAAGTAGGCTGGCTGGTCTGCGCCA

TTAAAGATATCCTCGGCGCGCCGGTTGGCGATACCTTAACCTCAGCGCGTAACCCA

GCGGAAAAAGCGTTGCCGGGCTTTAAGAAGGTGAAACCGCAGGTCTATGCAGGTCT

GTTCCCGGTCAGCTCCGACGATTATGAAAGTTTCCGCGACGCGCTCGGCAAGCTGA

GCCTGAACGATGCCTCACTGTTTTATGAACCGGAAAGCTCCTCGGCGCTGGGCTTTG

GTTTCCGCTGCGGCTTCCTCGGCCTGTTGCACATGGAGATCATTCAGGAGCGTCTGG

AACGCGAATACGATCTGGATCTGATCACCACTGCGCCGACCGTGGTGTATGAAGTA

GAAACAACGGCGAAAGAGACTATCTATGTTGATAGCCCCTCCAAGCTGCCGCCGTT

GAATAACATTTATGAACTGCGCGAGCCTATCGCCGAATGTCATATGCTGTTACCAC

AAGCCTATTTAGGTAACGTTATTACGCTGTGTATTGAGAAACGCGGCGTACAAACT

AACATGGTGTATCACGGTAACCAGGTCGCGTTGACCTATGAAATCCCGATGGCGGA

AGTGGTGCTCGACTTCTTTGACCGTCTGAAATCAACGTCGCGCGGCTATGCGTCTCT

GGATTATAACTTCAAGCGCTTCCAGGCTTCCGATATGGTGCGTGTTGATGTGTTAAT

CAACAACGAGCGTGTCGATGCGCTGGCGCTGATCACGCACCGTGATAACTCGCAAA

GCCGTGGTCGCGAGCTGGTGGAGAAGATGAAAGATTTGATCCCACGCCAGCAGTTT

GATATCGCGATTCAGGCGGCGATTGGTACGCATATTATTGCCCGTTCGACGGTAAA

ACAGTTACGTAAAAACGTGCTGGCGAAGTGCTACGGCGGCGATATCAGTCGTAAGA

AAAAACTGCTGCAGAAACAGAAAGAAGGTAAGAAACGCATGAAGCAGATCGGTAA

CGTCGAGCTGCCTCAGGAAGCGTTCCTCGCCATTCTGCATGTCGGTAAAGACAATA

AA

SEQ ID NO 75
>Shigella_flexneri
ATGAAGAATATACGTAACTTTTCGATCATAGCTCACATTGACCACGGTAAATCGAC

GCTGTCTGACCGTATTATCCAGATCTGCGGTGGCCTGTCTGACCGTGAAATGGAGG

CGCAGGTTCTCGATTCCATGGATCTTGAGCGTGAGCGTGGCATTACCATCAAAGCG

CAAAGCGTGACGCTGGACTACAAAGCGTCTGACGGCGAAACCTATCAGCTTAACTT

TATCGACACCCCGGGCCACGTAGACTTCTCCTATGAAGTTTCCCGTTCGCTGGCTGC

CTGTGAAGGTGCATTGCTGGTGGTCGACGCCGGGCAGGGCGTAGAAGCGCAAACCC

TGGCAAACTGCTACACCGCCATGGAAATGGATCTCGAAGTGGTGCCGGTACTGAAC

AAGATTGACCTGCCGGCAGCCGATCCTGAACGCGTGGCGGAAGAAATTGAAGATAT

CGTCGGCATCGACGCCACCGATGCAGTGCGCTGTTCAGCGAAAACCGGCGTTGGCG

TGCAGGACGTTCTCGAACGTCTGGTGCGCGACATTCCGCCGCCGGAAGGCGATCCG

GAAGGCCCGTTGCAGGCACTAATTATCGACTCCTGGTTCGACAACTACCTGGGCGT

TGTTTCACTTATCCGTATTAAAAACGGCACCCTGCGTAAGGGCGACAAAGTGAAAG

TCATGAGTACCGGGCAGACCTATAACGCCGACCGTCTGGGCATCTTCACGCCGAAA

CAGGTTGACCGCACTGAACTGAAATGTGGCGAAGTAGGCTGGCTCGTATGTGCGAT

TAAAGATATCCACGGCGCTCCAGTCGGCGATACCTTAACGCTGGCGCGTAATCCGG

-continued

CAGAAAAGGCGCTGCCTGGCTTTAAGAAAGTCAAACCGCAGGTATACGCCGGTCTG

TTCCCGGTAAGTTCCGACGACTATGAAGCCTTCCGTGACGCGCTGGGTAAACTCAG

CCTGAACGATGCCTCACTGTTCTATGAGCCGGAAAGCTCCAGCGCGCTGGGCTTTG

GTTTCCGCTGCGGCTTCCTTGGCCTGCTGCACATGGAGATCATCCAGGAGCGTCTGG

AACGTGAATACGATCTGGATCTGATCACCACTGCGCCGACCGTAGTGTATGAAGTT

GAAACCACGTCAAGGGAAGTTATCTACGTCGACAGCCCATCCAAGCTGCCTGCGGT

AAATAACATTTACGAACTGCGCGAGCCGATTGCAGAGTGTCACATGCTGCTGCCGC

AGGCATATCTCGGCAACGTTATTACGCTGTGCGTAGAAAAACGCGGCGTGCAGACC

AATATGGTTTACCACGGTAATCAGGTGGCGCTGACGTACGAGATCCCGATGGCGGA

AGTGGTGCTCGACTTCTTCGATCGCCTGAAATCTACCTCGCGTGGTTATGCGTCTCT

GGATTACAACTTCAAACGCTTCCAGGCGTCCGACATGGTACGTGTAGACGTATTAA

TCAACGGTGAACGTGTTGATGCGCTGGCGTTGATCACCCACCGTGATAATTCGCAA

AACCGCGGTCGCGAGTTGGTGGAGAAGATGAAAGATCTGATCCCACGCCAGCAGTT

TGATATCGCCATTCAGGCAGCGATTGGTACGCACATTATTGCGCGATCCACCGTGA

AACAGCTGCGTAAAAACGTACTGGCTAAATGTTATGGCGGCGATATCAGCCGTAAG

AAAAAGCTGCTGCAGAAGCAGAAAGAAGGTAAGAAACGCATGAAGCAGATCGGTA

ACGTTGAGCTGCCGCAGGAAGCGTTCCTCGCCATTCTGCACGTCGGCAAAGACAAC

AAATAA

SEQ ID NO 76
>Yersinia_pestis_KIM_lepA
ATGAAGCACATAAGAAACTTTTCTATTATTGCCCATATTGACCACGGTAAGTCGAC

GCTGTCTGATCGGATTATTCAGATCTGTGGCGGTTTATCTGAGCGTGAAATGGCCGC

ACAGGTACTGGATTCCATGGATCTAGAACGTGAGCGTGGTATTACCATCAAGGCAC

AGAGTGTGACGCTTGATTACCATTCGAAGGATGGTCAAACCTATCAACTTAACTTTA

TCGATACCCCCGGCCATGTTGACTTCTCTTATGAAGTTTCACGCTCTTTAGCCGCGT

GTGAAGGGGCTCTATTGGTTGTGGATGCAGGGCAAGGCGTTGAGGCTCAGACGCTA

GCAAACTGCTACACCGCGATGGAGATGGACCTGGAAGTTGTTCCGGTTCTGAACAA

AATTGATTTGCCTGCTGCCGATCCTGAGCGGGTTGCTGAAGAAATCGAAGACATTG

TGGGGATTGATGCCACTGATGCGATTCGTTGCTCGGCAAAAACCGGTGTGGGCGTG

CCTGATGTTCTTGAGCGGTTGGTCCGCGATATTCCAGCCCCTGAGGGGGATCCAAAT

GGGCCATTGCAGGCATTGATTATCGATTCCTGGTTTGATAACTACCTGGGTGTTGTG

TCATTAATACGTATCAAGAATGGTTCGTTGCGTAAAGGCGATAAAGTTAAGGTTAT

GAGTACCGGCCAGAGCTATAACGCGGATCGTTTAGGGATATTTACACCAAAACGTG

TTGATCGTGATGTTCTGAACTGCGGCGAAGTAGGCTGGTTGGTTTGTGCAATAAAA

GACATTCTTGGCGCACCTGTTGGCGATACATTGACATTAACGCGTAACCCGGCAGA

AAAATCATTGCCTGGCTTTAAGAAAGTAAAACCACAAGTTTATGCGGGCCTGTTCC

CGATAAGCTCTGATGATTATGAATCTTTCCGGGATGCGTTAGGTAAGTTAAGTCTTA

ACGATGCCTCTTTGTTCTATGAACCAGAAAGCTCTACAGCATTAGGCTTTGGTTTCC

GATGCGGCTTCCTTGGCTTGTTACATATGGAGATCATCCAGGAGCGTCTGGAGCGT

GAATATGATCTGGAACTGATTACTACGGCACCAACAGTGGTGTACGAGGTGATTAC

GACTAATCAGGAAACGGTCTATGTCGATAGCCCTTCTAAACTGCCTGCGTTGAACA

-continued

ATATTGAAGAACTGCGCGAACCGATCGCTGAATGCCATATGTTGTTGCCACAGGAA

TACCTCGGTAACGTCATTACATTGTGTATCGAAAAACGTGGTACACAGACCAATAT

GGTTTATCACGGTAAGCAAGTCGCGCTGACATATGAAATTCCAATGGCGGAAGTCG

TGCTTGATTTCTTTGATCGTTTGAAATCAACGTCACGGGGTTATGCTTCACTGGATT

ATAATTTCAAACGCTTCCAGACGTCTGACATGGTACGTGTTGATGTATTAATCAATA

ACGAACGTGTGGATGCGCTGGCACTGATCACGCATCGTGATAATGCACAATATCGT

GGCCGTGATTTGGTTGAGAAAATGAAAGAACTGATCCCACGTCAACAATTTGATAT

TGCGATCCAGGCTGCGATTGGTAACCACATCATTGCTCGCTCAACGGTAAAACAGC

TACGTAAAAACGTATTGGCGAAGTGTTATGGTGGGGATGTTAGCCGTAAGAAAAAA

CTTCTGCAGAAACAAAAAGACGGTAAGAAACGTATGAAGCAAGTCGGTAACGTTG

AATTACCACAAGAGGCCTTCCTGGCTATTCTGCATGTTGGAAAAGACAGTAAA

SEQ ID NO 77
>Streptococcus_agalactiae_NEM316
TTATTTTTTGTCATCATCGTCCATTGATAAAACACTTAAGAAAGCTTCCTGAGGAAC

TTCGACGGAACCAATTGCTTTCATGCGCTTTTTACCAGCTTTTTGTTTTTCAAGCAAC

TTACGTTTACGTGAAACGTCACCACCATAACATTTTGCTAAGACATTTTTGCGTAGT

GCTTTTATATCAGAACGAGCCACAATTTTTTGTCCAATAGCTGCTTGGATAGGAACT

TCAAACTGCTGACGAGGAATGATTTTTTTCAACTTATCAACGATCAATTTACCACGT

TCATAAGCAAATTCTTTGTGAACAATAAAGCTTAAAGCATCAACTTTATCACCATTT

AAAAGAATATCCATTTTAACTAACTGTGAGCGACGATATTCGGAAATTTCATAATC

AAAACTAGCATAGCCTCGTGTTGATGATTTAAGCTTATCAAAGAAGTCAAACACAA

TTTCAGCTAAAGGAATTTGGTAAATAACATTAACACGATTATCATCAATATAATCCA

TTGTTACAAAGTCACCACGTTTACGTTGTGCTAACTCCATTACAGCACCGACAAATT

CTTGAGGAACCATAATTTGCGCCTTAACATATGGTTCTTCAATGCTGTCAACACGAG

TAGGATCAGGAAATTCAGATGGATTCGAAACTTCAAGCATTTCACCGTCAGTTGTA

TTAACATGATAAACTACTGATGGTGCAGTCATAATAAGATCAATATTGAACTCTCGT

TCCAAGCGCTCTTGGATAACGTCCATATGTAAAAGTCCTAAGAAACCACAACGGAA

ACCAAACCCTAATGCTTGTGATGTTTCCGGTTCAAACTGTAGACTAGCATCATTCAA

TTGTAATTTTTCAAGGGCTTCACGCAGATCGTTATACTTATTTGATTCAATTGGATA

AAGACCGGCAAAAACCATCGGGTTCATTTGCTTATAGCCATGCAAAGGTTCTATTG

CTGGGTTATTAGCAAGGGTAATGGTATCACCAACACGTGTATCAGCAACCGTTTTA

ATTGAGGCAGCAATATACCCTACATCTCCAGTTGCTAAAAAATCACGTCCAACTGC

TTTGGGAGTGAAAATACCAACCTCAGTAACGTCGAAGGTTTTACCATTAGACATCA

TTTGAATTTTATCTCCTGGCTTAACCATACCATTTACAATCCTTACTTGCAGAATTAC

CCCACGATAAGCATCGTAAACAGAATCAAAAATTAAAGCTTGCAGAGGAGCATCTA

CTTCCCCAGTCGGAGCAGGAACTTTTTCAACGATCTGCTCTAAAATTTCTTCAATAC

CAATCCCTGCCTTAGCTGAGGCAAGCACAGCTTCTGAAGCATCTAGACCAATAACA

TCCTCTACTTCTGCACGTACACGTTCTGGATCTGCTGCTGGTAAATCAATTTTATTAA

TAACTGGTAGTATCTCTAAATCATTGTCTAGAGCCAAATAAACATTTGCCAGAGTTT

GAGCTTCAATTCCTTGAGCTGCGTCAACAACCAGTATAGCACCCTCACAAGCTGCT

AATGAACGTGATACTTCATATGTGAAGTCAACATGCCCTGGCGTGTCAATCAAGTG

-continued

AAAAATGTAAGTTTCACCATCTTTAGCAGTATAATTAAGCTCAATAGCATTTAACTT

TATAGTAATCCCACGCTCACGTTCTAGATCCATAGAGTCCAACAGCTGCGCCTGCAT

TTCACGACTAGAAACCGTTTCTGTTTTCTCTAAAATACGGTCTGCTAAGGTTGATTT

TCCATGGTCAATATGAGCGATAATCGAAAAGTTTCTAATCTTTTCTTGACGTTTCTT

CAAATCTTCAATATTCAT

SEQ ID NO 78
>Streptococcus_agalactiae_18RS21
TTATTTTTTGTCATCATCGTCCATTGATAAAACACTTAAGAAAGCTTCCTGAGGAAC

TTCGACGGAACCAATTGCTTTCATGCGCTTTTTACCAGCTTTTTGTTTTTCAAGCAAC

TTACGTTTACGTGAAACGTCACCACCATAACATTTTGCTAAGACATTTTTACGTAGT

GCTTTTATATCAGAACGGGCCACAATTTTTTGTCCAATAGCTGCTTGGATAGGAACT

TCAAACTGCTGACGAGGAATGATTTTTTTCAACTTATCAACGATCAATTTACCACGT

TCATAGGCAAATTCTTTGTGAACAATAAAGCTTAAAGCATCCACTTTATCACCATTT

AAAAGAATATCCATTTTAACTAATTGTGAGCGACGATATTCGGAAATTTCATAATC

AAAACTAGCATAGCCACGTGTTGATGATTTAAGCTTATCAAAGAAGTCAAACACAA

TTTCAGCTAAAGGAATTTGGTAAATAACATTAACACGATTATCATCAATATAATCCA

TTGTTACAAAGTCACCACGTTTACGTTGTGCTAACTCCATTACAGCACCGACAAATT

CTTGAGGAACCATAATTTGCGCCTTAACATATGGTTCTTCAATGCTGTCAACACGAG

TAGGATCAGGAAATTCAGATGGATTCGAAACTTCAAGCATTTCACCGTCAGTTGTA

TTAACATGATAAACTACTGATGGTGCAGTCATAATAAGATCAATATTGAACTCTCGT

TCCAAGCGCTCTTGGATAACGTCCATATGTAAAAGTCCTAAGAAACCACAACGGAA

ACCAAACCCTAATGCTTGTGATGTTTCCGGTTCAAACTGTAGACTAGCATCATTCAA

TTGTAATTTTTCAAGGGCTTCACGCAGATCGTTATACTTATTTGATTCAATTGGATA

AAGACCGGCAAAAACCATTGGGTTCATTTGCTTATAGCCATGCAAGGGTTCTATTG

CTGGGTTATTAGCAAGGGTAATGGTATCACCAACACGTGTATCAGCAACCGTTTTA

ATTGAGGCAGCAATATACCCTACATCTCCAGTTGCTAAAAAATCACGTCCAACTGC

TTTGGGAGTGAAAATACCAACCTCAGTAACGTCGAAGGTTTTACCATTAGACATCA

TTTGAATCTTATCTCCTGGCTTAACCATACCATTTACAATCCTTACTTGAAGAATTA

CTCCACGATAAGCATCATAAACAGAATCAAAAATTAGAGCTTGAAGAGGAGCATCT

ACTTCCCCAGTCGGTGCAGGAACTTTTTCAACGATCTGCTCTAAAATTTCTTCAATA

CCAATCCCTGCCTTAGCTGAGGCAAGCACAGCTTCTGAAGCATCTAGACCAATAAC

ATCCTCTACTTCTGCACGTACACGTTCTGGATCTGCTGCTGGTAAATCAATTTTATTA

ATAACTGGTAGTATCTCTAAATCATTGTCTAGAGCCAAATAAACATTTGCCAGAGTT

TGAGCTTCAATTCCTTGGGCTGCATCAACAACCAGTATAGCACCCTCACAAGCTGCC

AATGAACGTGATACTTCATATGTGAAGTCAACATGCCCTGGCGTGTCAATCAAGTG

AAAAATGTAAGTTTCACCATCTTTAGCAGTATAATTAAGCTCAATAGCATTTAACTT

TATAGTAATTCCACGCTCACGTTCTAGATCCATAGAGTCCAACAGTTGCGCCTGCAT

TTCACGACTAGAAACCGTTTCTGTTTTCTCTAAAATACGGTCTGCTAAGGTTGATTT

TCCATGGTCAATATGAGCGATAATCGAAAAGTTTCTAATCTTTTCTTGACGTTTCTT

CAAATCTTCAATATTCAT

-continued

SEQ ID NO 79
>Streptococcus_agalactiae_H36B
TTATTTTTTGTCATCATCGTCCATTGATAAAACACTTAAGAAAGCTTCCTGAGGAAC

TTCGACGGAACCAATTGCTTTCATGCGCTTTTTACCAGCTTTTTGTTTTTCAAGCAAC

TTACGTTTACGTGAAACGTCACCACCATAACATTTTGCTAAGACATTTTTACGTAGT

GCTTTTATATCAGAACGGGCCACAATTTTTTGTCCAATAGCTGCTTGGATAGGAACT

TCAAACTGCTGACGAGGAATGATTTTTTTCAACTTATCAACGATCAATTTACCACGT

TCATAGGCAAATTCTTTGTGAACAATAAAGCTTAAAGCATCCACTTTATCACCATTT

AAAAGAATATCCATTTTAACTAATTGTGAGCGACGATATTCGGAAATTTCATAATC

AAAACTAGCATAGCCACGTGTTGATGATTTAAGCTTATCAAAGAAGTCAAACACAA

TTTCAGCTAAAGGAATTTGGTAAATAACATTAACACGATTATCATCAATATAATCCA

TTGTTACAAAGTCACCACGTTTACGTTGTGCTAACTCCATTACAGCACCGACAAATT

CTTGAGGAACCATAATTTGCGCCTTAACATATGGTTCTTCAATGCTGTCAACACGAG

TAGGATCAGGAAATTCAGATGGATTCGAAACTTCAAGCATTTCACCGTCAGTTGTA

TTAACATGATAAACTACTGATGGTGCAGTCATAATAAGATCAATATTGAACTCTCGT

TCCAAGCGCTCTTGGATAACGTCCATATGTAAAAGTCCTAAGAAACCACAACGGAA

ACCAAACCCTAATGCTTGTGATGTTTCCGGTTCAAACTGTAGACTAGCATCATTCAA

TTGTAATTTTTCAAGGGCTTCACGCAGATCGTTATACTTATTTGATTCAATTGGATA

AAGACCGGCAAAAACCATTGGGTTCATTTGCTTATAGCCATGCAAGGGTTCTATTG

CTGGGTTATTAGCAAGGGTAATGGTATCACCAACACGTGTATCAGCAACCGTTTTA

ATTGAGGCAGCAATATACCCTACATCTCCAGTTGCTAAAAAATCACGTCCAACTGC

TTTGGGAGTGAAAATACCAACCTCAGTAACGTCGAAGGTTTTACCATTAGACATCA

TTTGAATCTTATCTCCTGGCTTAACCATACCATTTACAATCCTTACTTGAAGAATTA

CTCCACGATAAGCATCATAAACAGAATCAAAAATTAGAGCTTGAAGAGGAGCATCT

ACTTCCCCAGTCGGTGCAGGAACTTTTTCAACGATCTGCTCTAAAATTTCTTCAATA

CCAATCCCTGCCTTAGCTGAGGCAAGCACAGCTTCTGAAGCATCTAGACCAATAAC

ATCCTCTACTTCTGCACGTACACGTTCTGGATCTGCTGCTGGTAAATCAATTTTATTA

ATAACTGGTAGTATCTCTAAATCATTGTCTAGAGCCAAATAAACATTTGCCAGAGTT

TGAGCTTCAATTCCTTGGGCTGCATCAACAACCAGTATAGCACCCTCACAAGCTGCC

AATGAACGTGATACTTCATATGTGAAGTCAACATGCCCTGGCGTGTCAATCAAGTG

AAAAATGTAAGTTTCACCATCTTTAGCAGTATAATTAAGCTCAATAGCATTTAACTT

TATAGTAATTCCACGCTCACGTTCTAGATCCATAGAGTCCAACAGTTGCGCCTGCAT

TTCACGACTAGAAACCGTTTCTGTTTTCTCTAAAATACGGTCTGCTAAGGTTGATTT

TCCATGGTCAATATGAGCGATAATCGAAAAGTTTCTAATCTTTTCTTGACGTTTCTT

CAAATCTTCAATATTCAT

SEQ ID NO 80
>Streptococcus_agalactiae_COH1
TTATTTTTTGTCATCATCGTCCATTGATAAAACACTTAAGAAAGCTTCCTGAGGAAC

TTCGACGGAACCAATTGCTTTCATACGCTTTTTACCAGCTTTTTGTTTTTCAAGCAAC

TTACGTTTACGTGAAACGTCACCACCATAACATTTTGCTAAGACATTTTTGCGTAGT

GCTTTTATATCAGAACGAGCCACAATTTTTTGTCCAATAGCTGCTTGGATAGGAACT

TCAAACTGCTGACGAGGAATGATTTTTTTCAACTTATCAACGATCAATTTACCACGT

-continued

```
TCATAGGCAAATTCTTTGTGAACAATAAAGCTTAAAGCATCCACTTTATCACCATTT

AAAAGAATATCCATTTTAACTAACTGTGAGCGACGATATTCGGAAATTTCATAATC

AAAACTAGCATAGCCACGTGTTGATGATTTAAGCTTATCAAAGAAGTCAAACACAA

TTTCAGCTAAAGGAATTTGGTAAATAACATTAACACGATTATCATCAATATAATCCA

TTGTTACAAAGTCACCACGTTTACGTTGTGCTAACTCCATTACAGCACCGACAAATT

CTTGAGGAACCATAATTTGCGCCTTAACATATGGTTCTTCAATGCTGTCAACACGAG

TAGGATCAGGAAATTCAGATGGATTCGAAACTTCAAGCATTTCACCATCAGTTGTA

TTAACATGATAAACTACTGATGGTGCAGTCATAATAAGATCAATATTGAACTCTCGT

TCCAAGCGCTCTTGGATAACGTCCATATGTAAAAGTCCTAAGAAACCACAACGGAA

ACCAAACCCTAATGCTTGTGATGTTTCCGGTTCAAACTGTAGACTAGCATCATTCAA

TTGTAATTTTTCAAGGGCTTCACGCAGATCGTTATACTTATTTGATTCAATTGGATA

AAGACCGGCAAAAACCATTGGGTTCATTTGCTTATAGCCATGCAAGGGGTCTATAG

CTGGGTTATTAGCAAGGGTAATGGTATCACCAACACGTGTATCAGCAACTGTTTTA

ATTGAGGCAGCAATATACCCTACATCTCCAGTTGCTAAAAAATCACGTCCAACTGC

TTTGGGAGTGAAAATACCAACCTCAGTAACGTCGAAGGTTTTACCATTAGACATCA

TTTGAATCTTATCTCCTGGCTTAACCATACCATTTACAATCCTTACTTGCAGAATTA

CTCCACGATAAGCATCGTAAACAGAATCAAAAATTAGAGCTTGAAGAGGAGCATCT

ACTTCCCCAGTCGGAGCAGGAACTTTTTCAACGATCTGCTCTAAAATTTCTTCAATA

CCAATCCCTGCCTTAGCTGAGGCAAGTACAGCTTCTGAAGCATCTAGACCAATAAC

ATCCTCTACTTCTGCACGTACACGTTCTGGATCTGCTGCTGGTAAATCAATTTTATTA

ATAACTGGTAGTATCTCTAAATCATTGTCTAGAGCCAAATAAACATTTGCCAGAGTT

TGAGCTTCAATTCCTTGGGCTGCATCAACAACCAGTATAGCACCCTCACAAGCTGCC

AATGAACGTGATACTTCATATGTAAAGTCAACATGCCCTGGCGTGTCAATCAAGTG

AAAAATGTAAGTTTCACCATCTTTAGCAGTATAATTAAGCTCAATAGCATTTAACTT

TATAGTAATCCCACGCTCACGTTCTAGGTCCATAGAGTCCAACAGTTGCGCCTGCAT

TTCACGACTAGAAACCGTTTCTGTTTTCTCTAAAATACGGTCTGCTAAGGTTGATTT

TCCATGGTCAATATGAGCGATAATCGAAAAGTTTCTAATCTTTTCTTGACGTTTCTT

CAAATCTTCAATATTCAT
```

SEQ ID NO 81
>Streptococcus_agalactiae_CJB111

```
TTATTTTTTGTCATCATCGTCCATTGATAAAACACTTAAGAAAGCTTCCTGAGGAAC

TTCGACGGAACCAATTGCTTTCATGCGCTTTTTACCAGCTTTTTGTTTTTCAAGCAAC

TTACGTTTACGTGAAACGTCACCACCATAACATTTTGCTAAGACATTTTTACGTAGT

GCTTTTATATCAGAACGGGCCACAATTTTTTGTCCAATAGCTGCTTGGATAGGAACT

TCAAACTGCTGACGAGGAATGATTTTTTTCAACTTATCAACGATCAATTTACCACGT

TCATAGGCAAATTCTTTGTGAACAATAAAGCTTAAAGCATCCACTTTATCACCATTT

AAAAGAATATCCATTTTAACTAATTGTGAGCGACGATATTCGGAAATTTCATAATC

AAAACTAGCATAGCCACGTGTTGATGATTTAAGCTTATCAAAGAAGTCAAACACAA

TTTCAGCTAAAGGAATTTGGTAAATAACATTAACACGATTATCATCAATATAATCCA

TTGTTACAAAGTCACCACGTTTACGTTGTGCTAACTCCATTACAGCACCGACAAATT

CTTGAGGAACCATAATTTGCGCCTTAACATATGGTTCTTCAATGCTGTCAACACGAG

TAGGATCAGGAAATTCAGATGGATTCGAAACTTCAAGCATTTCACCGTCAGTTGTA
```

-continued

```
TTAACATGATAAACTACTGATGGTGCAGTCATAATAAGATCAATATTGAACTCTCGT
TCCAAGCGCTCTTGGATAACGTCCATATGTAAAAGTCCTAAGAAACCACAACGGAA
ACCAAACCCTAATGCTTGTGATGTTTCCGGTTCAAACTGTAGACTAGCATCATTCAA
TTGTAATTTTTCAAGGGCTTCACGCAGATCGTTATACTTATTTGATTCAATTGGATA
AAGACCGGCAAAAACCATTGGGTTCATTTGCTTATAGCCATGCAAGGGTTCTATTG
CTGGGTTATTAGCAAGGGTAATGGTATCACCAACACGTGTATCAGCAACCGTTTTA
ATTGAGGCAGCAATATACCCTACATCTCCAGTTGCTAAAAAATCACGTCCAACTGC
TTTGGGAGTGAAAATACCAACCTCAGTAACGTCGAAGGTTTTACCATTAGACATCA
TTTGAATCTTATCTCCTGGCTTAACCATACCATTTACAATCCTTACTTGAAGAATTA
CTCCACGATAAGCATCATAAACAGAATCAAAAATTAGAGCTTGAAGAGGAGCATCT
ACTTCCCCAGTCGGTGCAGGAACTTTTTCAACGATCTGCTCTAAAATTTCTTCAATA
CCAATCCCTGCCTTAGCTGAGGCAAGCACAGCTTCTGAAGCATCTAGACCAATAAC
ATCCTCTACTTCTGCACGTACACGTTCTGGATCTGCTGCTGGTAAATCAATTTTATTA
ATAACTGGTAGTATCTCTAAATCATTGTCTAGAGCCAAATAAACATTTGCCAGAGTT
TGAGCTTCAATTCCTTGGGCTGCATCAACAACCAGTATAGCACCCTCACAAGCTGCC
AATGAACGTGATACTTCATATGTGAAGTCAACATGCCCTGGCGTGTCAATCAAGTG
AAAAATGTAAGTTTCACCATCTTTAGCAGTATAATTAAGCTCAATAGCATTTAACTT
TATAGTAATTCCACGCTCACGTTCTAGATCCATAGAGTCCAACAGTTGCGCCTGCAT
TTCACGACTAGAAACCGTTTCTGTTTTCTCTAAAATACGGTCTGCTAAGGTTGATTT
TCCATGGTCAATATGAGCGATAATCGAAAAGTTTCTAATCTTTTCTTGACGTTTCTT
CAAATCTTCAATATTCAT
```

SEQ ID NO 82
>Streptococcus_agalactiae_2603V/R
```
TTATTTTTTGTCATCATCGTCCATTGATAAAACACTTAAGAAAGCTTCCTGAGGAAC
TTCGACGGAACCAATTGCTTTCATGCGCTTTTTACCAGCTTTTTGTTTTTCAAGCAAC
TTACGTTTACGTGAAACGTCACCACCATAACATTTTGCTAAGACATTTTTACGTAGT
GCTTTTATATCAGAACGGGCCACAATTTTTTGTCCAATAGCTGCTTGGATAGGAACT
TCAAACTGCTGACGAGGAATGATTTTTTTCAACTTATCAACGATCAATTTACCACGT
TCATAGGCAAATTCTTTGTGAACAATAAAGCTTAAAGCATCCACTTTATCACCATTT
AAAAGAATATCCATTTTAACTAATTGTGAGCGACGATATTCGGAAATTTCATAATC
AAAACTAGCATAGCCACGTGTTGATGATTTAAGCTTATCAAAGAAGTCAAACACAA
TTTCAGCTAAAGGAATTTGGTAAATAACATTAACACGATTATCATCAATATAATCCA
TTGTTACAAAGTCACCACGTTTACGTTGTGCTAACTCCATTACAGCACCGACAAATT
CTTGAGGAACCATAATTTGCGCCTTAACATATGGTTCTTCAATGCTGTCAACACGAG
TAGGATCAGGAAATTCAGATGGATTCGAAACTTCAAGCATTTCACCGTCAGTTGTA
TTAACATGATAAACTACTGATGGTGCAGTCATAATAAGATCAATATTGAACTCTCGT
TCCAAGCGCTCTTGGATAACGTCCATATGTAAAAGTCCTAAGAAACCACAACGGAA
ACCAAACCCTAATGCTTGTGATGTTTCCGGTTCAAACTGTAGACTAGCATCATTCAA
TTGTAATTTTTCAAGGGCTTCACGCAGATCGTTATACTTATTTGATTCAATTGGATA
AAGACCGGCAAAAACCATTGGGTTCATTTGCTTATAGCCATGCAAGGGTTCTATTG
CTGGGTTATTAGCAAGGGTAATGGTATCACCAACACGTGTATCAGCAACCGTTTTA
```

```
ATTGAGGCAGCAATATACCCTACATCTCCAGTTGCTAAAAAATCACGTCCAACTGC

TTTGGGAGTGAAAATACCAACCTCAGTAACGTCGAAGGTTTTACCATTAGACATCA

TTTGAATCTTATCTCCTGGCTTAACCATACCATTTACAATCCTTACTTGAAGAATTAC

TCCACGATAAGCATCATAAACAGAATCAAAAATTAGAGCTTGAAGAGGAGCATCTA

CTTCCCCAGTCGGTGCAGGAACTTTTTCAACGATCTGCTCTAAAATTTCTTCAATAC

CAATCCCTGCCTTAGCTGAGGCAAGCACAGCTTCTGAAGCATCTAGACCAATAACA

TCCTCTACTTCTGCACGTACACGTTCTGGATCTGCTGCTGGTAAATCAATTTTATTAA

TAACTGGTAGTATCTCTAAATCATTGTCTAGAGCCAAATAAACATTTGCCAGAGTTT

GAGCTTCAATTCCTTGGGCTGCATCAACAACCAGTATAGCACCCTCACAAGCTGCC

AATGAACGTGATACTTCATATGTGAAGTCAACATGCCCTGGCGTGTCAATCAAGTG

AAAAATGTAAGTTTCACCATCTTTAGCAGTATAATTAAGCTCAATAGCATTTAACTT

TATAGTAATTCCACGCTCACGTTCTAGATCCATAGAGTCCAACAGTTGCGCCTGCAT

TTCACGACTAGAAACCGTTTCTGTTTTCTCTAAAATACGGTCTGCTAAGGTTGATTT

TCCATGGTCAATATGAGCGATAATCGAAAAGTTTCTAATCTTTTCTTGACGTTTCTT

CAAATCTTCAATATTCAT

SEQ ID NO 83
>Streptococcus_agalactiae_A909
TTATTTTTTGTCATCATCGTCCATTGATAAAACACTTAAGAAAGCTTCCTGAGGAAC

TTCGACGGAACCAATTGCTTTCATGCGCTTTTTACCAGCTTTTTGTTTTTCAAGCAAC

TTACGTTTACGTGAAACGTCACCACCATAACATTTTGCTAAGACATTTTTACGTAGT

GCTTTTATATCAGAACGGGCCACAATTTTTTGTCCAATAGCTGCTTGGATAGGAACT

TCAAACTGCTGACGAGGAATGATTTTTTTCAACTTATCAACGATCAATTTACCACGT

TCATAGGCAAATTCTTTGTGAACAATAAAGCTTAAAGCATCCACTTTATCACCATTT

AAAAGAATATCCATTTTAACTAATTGTGAGCGACGATATTCGGAAATTTCATAATC

AAAACTAGCATAGCCACGTGTTGATGATTTAAGCTTATCAAAGAAGTCAAACACAA

TTTCAGCTAAAGGAATTTGGTAAATAACATTAACACGATTATCATCAATATAATCCA

TTGTTACAAAGTCACCACGTTTACGTTGTGCTAACTCCATTACAGCACCGACAAATT

CTTGAGGAACCATAATTTGCGCCTTAACATATGGTTCTTCAATGCTGTCAACACGAG

TAGGATCAGGAAATTCAGATGGATTCGAAACTTCAAGCATTTCACCGTCAGTTGTA

TTAACATGATAAACTACTGATGGTGCAGTCATAATAAGATCAATATTGAACTCTCGT

TCCAAGCGCTCTTGGATAACGTCCATATGTAAAAGTCCTAAGAAACCACAACGGAA

ACCAAACCCTAATGCTTGTGATGTTTCCGGTTCAAACTGTAGACTAGCATCATTCAA

TTGTAATTTTTCAAGGGCTTCACGCAGATCGTTATACTTATTTGATTCAATTGGATA

AAGACCGGCAAAAACCATTGGGTTCATTTGCTTATAGCCATGCAAGGGTTCTATTG

CTGGGTTATTAGCAAGGGTAATGGTATCACCAACACGTGTATCAGCAACCGTTTTA

ATTGAGGCAGCAATATACCCTACATCTCCAGTTGCTAAAAAATCACGTCCAACTGC

TTTGGGAGTGAAAATACCAACCTCAGTAACGTCGAAGGTTTTACCATTAGACATCA

TTTGAATCTTATCTCCTGGCTTAACCATACCATTTACAATCCTTACTTGAAGAATTAC

TCCACGATAAGCATCATAAACAGAATCAAAAATTAGAGCTTGAAGAGGAGCATCTA

CTTCCCCAGTCGGTGCAGGAACTTTTTCAACGATCTGCTCTAAAATTTCTTCAATAC

CAATCCCTGCCTTAGCTGAGGCAAGCACAGCTTCTGAAGCATCTAGACCAATAACA

TCCTCTACTTCTGCACGTACACGTTCTGGATCTGCTGCTGGTAAATCAATTTTATTAA
```

-continued

TAACTGGTAGTATCTCTAAATCATTGTCTAGAGCCAAATAAACATTTGCCAGAGTTT

GAGCTTCAATTCCTTGGGCTGCATCAACAACCAGTATAGCACCCTCACAAGCTGCC

AATGAACGTGATACTTCATATGTGAAGTCAACATGCCCTGGCGTGTCAATCAAGTG

AAAAATGTAAGTTTCACCATCTTTAGCAGTATAATTAAGCTCAATAGCATTTAACTT

TATAGTAATTCCACGCTCACGTTCTAGATCCATAGAGTCCAACAGTTGCGCCTGCAT

TTCACGACTAGAAACCGTTTCTGTTTTCTCTAAAATACGGTCTGCTAAGGTTGATTT

TCCATGGTCAATATGAGCGATAATCGAAAAGTTTCTAATCTTTTCTTGACGTTTCTT

CAAATCTTCAATATTCAT

SEQ ID NO 84
>Streptococcus_agalactiae_515
TTATTTTTTGTCATCATCGTCCATTGATAAAACACTTAAGAAAGCTTCCTGAGGAAC

TTCGACGGAACCAATTGCTTTCATGCGCTTTTTACCAGCTTTTTGTTTTTCAAGCAAC

TTACGTTTACGTGAAACGTCACCACCATAACATTTTGCTAAGACATTTTTGCGTAGT

GCTTTTATATCAGAACGAGCCACAATTTTTTGTCCAATAGCTGCTTGGATAGGAACT

TCAAACTGCTGACGAGGAATGATTTTTTTCAACTTATCAACGATCAATTTACCACGT

TCATAAGCAAATTCTTTGTGAACAATAAAGCTTAAAGCATCAACTTTATCACCATTT

AAAAGAATATCCATTTTAACTAACTGTGAGCGACGATATTCGGAAATTTCATAATC

AAAACTAGCATAGCCTCGTGTTGATGATTTAAGCTTATCAAAGAAGTCAAACACAA

TTTCAGCTAAAGGAATTTGGTAAATAACATTAACACGATTATCATCAATATAATCCA

TTGTTACAAAGTCACCACGTTTACGTTGTGCTAACTCCATTACAGCACCGACAAATT

CTTGAGGAACCATAATTTGCGCCTTAACATATGGTTCTTCAATGCTGTCAACACGAG

TAGGATCAGGAAATTCAGATGGATTCGAAACTTCAAGCATTTCACCGTCAGTTGTA

TTAACATGATAAACTACTGATGGTGCAGTCATAATAAGATCAATATTGAACTCTCGT

TCCAAGCGCTCTTGGATAACGTCCATATGTAAAAGTCCTAAGAAACCACAACGGAA

ACCAAACCCTAATGCTTGTGATGTTTCCGGTTCAAACTGTAGACTAGCATCATTCAA

TTGTAATTTTTCAAGGGCTTCACGCAGATCGTTATACTTATTTGATTCAATTGGATA

AAGACCGGCAAAAACCATCGGGTTCATTTGCTTATAGCCATGCAAAGGTTCTATTG

CTGGGTTATTAGCAAGGGTAATGGTATCACCAACACGTGTATCAGCAACCGTTTTA

ATTGAGGCAGCAATATACCCTACATCTCCAGTTGCTAAAAAATCACGTCCAACTGC

TTTGGGAGTGAAAATACCAACCTCAGTAACGTCGAAGGTTTTACCATTAGACATCA

TTTGAATTTTATCTCCTGGCTTAACCATACCATTTACAATCCTTACTTGCAGAATTAC

CCCACGATAAGCATCGTAAACAGAATCAAAAATTAAAGCTTGCAGAGGAGCATCTA

CTTCCCCAGTCGGAGCAGGAACTTTTTCAACGATCTGCTCTAAAATTTCTTCAATAC

CAATCCCTGCCTTAGCTGAGGCAAGCACAGCTTCTGAAGCATCTAGACCAATAACA

TCCTCTACTTCTGCACGTACACGTTCTGGATCTGCTGCTGGTAAATCAATTTTATTAA

TAACTGGTAGTATCTCTAAATCATTGTCTAGAGCCAAATAAACATTTGCCAGAGTTT

GAGCTTCAATTCCTTGAGCTGCGTCAACAACCAGTATAGCACCCTCACAAGCTGCT

AATGAACGTGATACTTCATATGTGAAGTCAACATGCCCTGGCGTGTCAATCAAGTG

AAAAATGTAAGTTTCACCATCTTTAGCAGTATAATTAAGCTCAATAGCATTTAACTT

TATAGTAATCCCACGCTCACGTTCTAGATCCATAGAGTCCAACAGCTGCGCCTGCAT

TTCACGACTAGAAACCGTTTCTGTTTTCTCTAAAATACGGTCTGCTAAGGTTGATTT

-continued

TCCATGGTCAATATGAGCGATAATCGAAAAGTTTCTAATCTTTTCTTGACGTTTCTT

CAAATCTTCAATATTCAT

SEQ ID NO 85
>Streptococcus_pyogenes_MGAS10270
TTATTTCTTGGCATCGTCATCCATTGAAAGAACACTCAAGAAGGCTTCTTGAGGGAC

TTCGACAGAACCAATAGCCTTCATCCGTTTTTTACCAGCCTTTTGTTTTTCGAGCAAT

TTACGTTTACGAGACACGTCACCACCATAACACTTCGCCAAAACGTTTTTACGAAG

GGCCTTGATGTCTGAACGCGCAACAATTTTTTGACCAATAGCGGCTTGGATCGGCA

CTTCAAACTGTTGACGTGGAATGATTTTTTTCAATTTCTCAACAATAATTTTCCCACG

TTCATAAGCAAATTCTTTATGAACAATAAAGCTGAGCGCATCGACCTTATCACCGTT

CAAAAGAATGTCCATTTTCACCAATTGTGACCTGCGGTATTCTGACATGTCATAATC

AAAACTCGCATAGCCTCGCGTTGAGGATTTCAATTTATCAAAGAAATCAAAGACAA

TTTCAGCCAGCGGGATTTGGTAAATCACATTGACACGGTTATCATCAATGTAATCCA

TGGTCACAAAATCACCACGCTTGCGCTGCGATAATTCCATAACAGCCCCTACGAAC

TCTTGTGGCACCATGATTTGCGCTTTAACATAAGGCTCTTCAATAAAAGCCACCCGT

GTTGGGTCTGGAAATTCTGAAGGGTTAGACACTTCAATCATGTCCTCATCTGTTGTG

TGAACATGGTAGACTACAGATGGTGCTGTCATGATCAAATCAATGTTAAATTCACG

TTCCAAACGTTCTTGAATCACATCCATGTGAAGCAAGCCTAAAAAACCGCATCGAA

AACCAAAGCCAAGCGCTTGTGACGTTTCGGGTTCAAACTGTAAACTGGCATCGTTA

AGCTGTAATTTTTCAAGCGCTTCACGCAAGTCATTGTATTTATTTGATTCAATCGGA

TAAATCCCTGCAAAGACCATCGGGTTCATCTGCTTGTAGCCATGCAAGGCTTCCTTA

GCAGGGTTATTAGCTAAAGTCACCGTATCCCCCACACGGGTATCTGCTACCGTTTTG

ATAGAGGCCGCAACATAACCAACATCTCCCGTCGCAAGGAAATCTCGTCCAACTGC

CTTAGGAGTGAAAATGCCAACTTCTGTAACATCAAAAGTTTTTCCATTCGACATCAT

CTGGATTTTATCGCCAGACTTGACAATACCGTTCACAATCCGAACTTGCAGGATAAC

GCCTCGATAAGCATCGTAAACAGAGTCAAAAATCAAGGCCTGTAAAGGCGCATCCA

CATCACCCGTAGGAGCAGGAACCTTCTCAACAATTTGCTCAAGAATCTCTTCGATCC

CAATACCAGCCTTGGCTGACGCCAGAACAGCCTCAGAAGCATCAAGTCCAATGACA

TCTTCTACTTCATGGCGGACCCTCTCAGGGTCTGCAGCTGGCAAATCAATTTTATTG

ATAACCGGTAAAATTTCCAAATCATTATCGAGGGCTAGGTAAACATTGGCCAGGGT

CTGTGCTTCAATGCCCTGCGCTGCATCCACAACTAGAATCGCTCCCTCACAGGCTGC

CAACGAACGCGATACTTCATAAGTAAAGTCCACATGCCCTGGGGTATCAATAAGGT

GGAAAATGTAGGTTTCCCCATCTTTAGCCGTGTAATTAAGCTCAATGGCGTTTAACT

TGATGGTAATCCCACGCTCACGCTCCAAATCCATGGAGTCCAATAACTGAGCCTGC

ATTTCACGAGACGAAACCGTCTCTGTCTTTTCCAAAATGCGGTCAGCGAGAGTAGA

TTTTCCATGGTCAATATGTGCAATAATGGAGAAATTACGAATCTTCTCCTGACGTTT

TTTTAAATCTTGACTGTTCAT

SEQ ID NO 86
>Streptococcus_pyogenes_MGAS10750
CATCCATTGAAAGAACACTCAAGAAGGCTTCTTGAGGGACTTCGACAGAACCAATA

GCCTTCATTCCGTTTTTTACCAGCCTTTTGTTTTTCGAGCAATTTACGTTTACGAGAC

ACGTCACCGCCATAACACTTCGCTAAAACGTTTTTACGAAGGGCCTTGATGTCTGAA

CGCGCAACAATTTTTTGACCAATAGCGGCTTGGATCGGCACTTCAAACTGTTGACGT

-continued

GGAATGATTTTTTTCAATTTCTCAACAATAATTTTCCCGCGTTCATAAGCAAATTCTT

TATGAACAATAAAGCTGAGCGCATCGACCTTATCACCGTTCAAAAGAATGTCCATT

TTCACCAATTGTGACCTGCGGTATTCTGACATGTCATAATCAAAACTCGCATAGCCT

CGCGTTGAGGATTTCAATTTATCAAAGAAATCAAAGACAATTTCAGCCAGCGGGAT

TTGGTAAATCACATTGACACGGTTATCATCAATGTAATCCATGGTCACAAAATCACC

ACGCTTGCGCTGCGATAATTCCATAACAGCCCCTACGAACTCTTGTGGCACCATGAT

TTGCGCTTTAACATAAGGCTCTTCAATAAAAGCCACACGGGTTGGGTCTGGAAATT

CTGAAGGGTTAGACACTTCAATCATATCCTCATCTGTTGTGTGAACGTGATACACCA

CGGACGGTGCTGTCATGATCAAATCAATGTTAAATTCACGCTCTAAACGTTCTTGAA

TCACGTCCATGTGAAGCAAACCTAAAAAGCCGCATCGAAAACCAAAGCCAAGCGC

TTGTGACGTTTCGGGTTCAAACTGTAAACTGGCATCGTTCAGTTGTAATTTTTCAAG

CGCTTCACGCAAGTCATTGTATTTATTTGATTCAATCGGATAAATCCCTGCAAAGAC

CATCGGGTTCATCTGCTTGTAGCCATGCAAGGCTTCCTTAGCAGGGTTATTAGCTAA

AGTCACCGTATCCCCCACACGGGTATCTGCTACCGTTTTGATAGAAGCCGCAACAT

AACCAACATCTCCCGTCGCAAGGAAATCTCGTCCAACTGCCTTAGGAGTGAAAATC

CCAACTTCTGTAACATCAAAGGTTTTTCCATTCGACATCATCTGGATTTTATCGCCA

GGCTTGACAATACCGTTCACAATCCGAACCTGCAAAATTACCCCTCGGTAAGCATC

ATACACAGAGTCAAAAATCAAGGCCTGTAAAGGCGCATCCACATCACCCGTAGGA

GCAGGAACCTTCTCAACAATTTGCTCAAGAATCTCTTCGATCCCAATACCAGCCTTG

GCTGACGCCAGAACAGCCTCAGAAGCATCAAGTCCAATGACATCTTCTACTTCATG

GCGGACTCTCTCAGGGTCAGCAGCAGGCAAATCAATTTTATTGATAACCGGTAAAA

TTTCCAAATCATTATCAAGAGCTAGGTAAACATTGGCAAGGGTCTGCGCTTCAATG

CCCTGCGCTGCATCCACAACTAAAATCGCTCCCTCACAGGCTGCCAACGAACGCGA

TACTTCATAAGTAAAGTCCACATGCCCTGGGGTATCAATAAGGTGGAAAATGTAGG

TTTCCCCATCTTTAGCCGTGTAATTAAGCTCAATGGCGTTTAACTTAATGGTAATCC

CACGCTCACGCTCCAAATCCATGGAGTCCAATAACTGAGCCTGCATTTCACGAGAC

GAAACCGTCTCTGTCTTTTCCAAAATGCGGTCAGCGAGAGTAGATTTGCCATGGTCA

ATATGTGCAATAATGGAGAAATTACGAATCTTCTCCTGACGTTTTTTTAAATCTTGA

CTGTTCAT

SEQ ID NO 87
>Streptococcus_pneumoniae_TIGR4
TTATTCTTCATCCATACTCAAGACGCTGAGGAAGGCTTCTTGCGGAACTTCAACTGA

TCCGATGGATTTCATGCGTTTCTTACCAGCTTTTTGTTTTTCAAGGAGTTTACGCTTA

CGAGAAACGTCACCACCATAACATTTAGCAAGTACGTTCTTACGAAGGGCCTTGAT

ATCAGTACGAGCGACAATCTTGTGTCCAATAGCCGCTTGGATTGGAACTTCAAATT

GTTGGCGAGGGATGATTTTCTTGAGTTTATCAACGATGAGTTTCCCACGTTCGTAGG

CAAAGTCCTTGTGAACGATAAAGCTGAGGGCATCCACCTTATCTCCATTGAGAAGA

ATATCCATTTTCACCAGCTTAGATGGGCGATATTCTGACAATTCGTAGTCAAAGCTT

GCATAACCACGTGTCGAAGACTTAAGTTTATCAAAGAAGTCAAAGACAATTTCAGC

AAGAGGAATTTGATAGATAACATTGACACGGTTATCATCAATATAGTCCATAGTCA

CAAAGTCCCCACGCTTACGCTGAGCTAGCTCCATTACTGCTCCGACGAACTCCTGTG

-continued

GTACCATGATTTGCGCCTTGACATAAGGCTCTTCAATGGTCGCAATCTTAGTTGGGT

CTGGAAACTCAGATGGGTTAGACACATCCATAGACTCACCGTCGGTCAAATTAACT

TTGTAAATAACAGACGGAGCTGTCATGATGAGGTCAATATTGAACTCACGCTCTAA

ACGTTCCTGGATAACATCCATATGGAGAAGTCCAAGAAATCCACAACGGAAACCAA

ATCCAAGTGCCTGAGATGTTTCTGGTTCAAACTGAAGACTAGCATCATTCAGTTGCA

ATTTTTCAAGCGCTTCACGCAGGTCATTGTACTTGTTTGATTCGATTGGGTAGAGAC

CCGCAAAGACCATAGGATTCATCTGCTTATAACCATGTAATGGTTCTGCCGCAGGA

TTGGTTGCCAAGGTAACGGTATCACCCACACGAGTATCCTGAACCGTCTTGATAGA

CGCCGCAATGTAACCAACATCACCAGTCGCAAGGAAATCACGACCAACCGCTTTTG

GTGTAAAAATACCGACTTCGGCCACATCAAAGGTCTTACTATTGCTCATGAGCTGA

ATCTTATCACCAGGTTTGACCACTCCGTCCATGACACGCACTTGGAGGATAACCCCA

CGGTAAGCATCGTAAACAGAGTCGAAAATCAAGGCCTTAAGTGGCGCCGTCACATC

ACCCGTTGGTGCTGGTACTTTTTCTACAATTTGCTCGAGGATTTCTTCAATCCCAATA

CCAGCCTTGGCAGAAGCCAAAACTGCTTCACTGGCATCCAAACCAATCACATCTTC

AATCTCTGTACGCACGCGCTCCGGATCTGCAGCCGGCAGGTCAATTTTATTAATGAT

AGGCATGATTTCCAAATCATTATCCAAAGCCAGATAAACGTTGGCAAGAGTTTGAG

CCTCAATTCCTTGAGCCGCATCGACCACCAAAATAGCACCCTCACAGGCAGCTAGC

GAACGTGAAACTTCATAGGTAAAGTCAACGTGCCCTGGTGTGTCAATCAAGTGGAA

AATATAAGTTTCCCCATCTTTTGCAGTGTAATTCAACTCGATGGCATTCAACTTAAT

AGTAATTCCACGTTCCCGCTCTAGCTCCATGCTATCCAAAAGCTGGGCCTGCATTTC

ACGACTTGAAACCGTCTCTGTTTTTTCCAAAATGCGGTCTGCTAGAGTTGATTTTCC

GTGGTCAATATGGGCGATAATAGAGAAGTTACGGATCTTCTCCTGTCGTTTTTTCAA

TTCTTCTAAGTTCAT

SEQ ID NO 88
>Streptococcus_mutans_UA159
CTATTTTTTCTTATCGTCATCATCCATGGACAGAACGCTGAGAAAGGCTTCCTGAGG

GACCTCAACTGAACCAATTGATTTCATCCGCTTTTTACCAGCCTTTTGTTTTTCCAAA

AGTTTACGCTTTCTGGAAACATCTCCGCCATAACATTTAGCAAGAACATTTTTCCGC

AAGGCCTTAATATCAGAACGCGCCACAATTTTTTGACCGATCGCTGCTTGAATGGG

AACTTCGAATTGTTGCCGCGGAATGATCTTCTTCAACTTTTCAACAATTAATTTCCC

CCTTTCATAGGCAAACTCTTTATGGACAATGAAGCTAAGCGCATCAACTTTATCACC

ATTGAGCAAAATATCCATTTTTACCAGCTTAGACTTGCGATACTCAGAAATATCATA

ATCAAAACTAGCATAACCACGGGTAGAGGATTTTAGTTTATCAAAAAAATCAAAAA

CAATTTCAGCCAAAGGGATCTGGTAAATAACATTGACTCGGTTATTATCAATGTAAT

CCATAGTCACAAAGTCGCCGCGCTTACGTTGTGATAATTCCATGACAGCTCCCACAT

ACTCTTGCGGCACCATAATCTGGGCTTTAACGTAAGGTTCCTCAATACTATCAACCT

TAGTTGGATCAGGAAATTCAGATGGATTAGAAACCTCAAGCCTCTCCCCATCTGTG

GTATAAACATGGTAAACTACAGATGGCGCTGTCATAATGAGATCAATATTAAACTC

ACGCTCCAATCGCTCTTGAATGACATCCATATGCAAAAGACCTAAGAAGCCACAAC

GAAAACCAAAGCCAAGGGCTTGAGAAGTCTCAGGTTCAAAGTGAAGACTGGCATC

ATTAAGCTGTAATTTCTCTAGGGCTTCACGCATGTCATTATATTTGCTGGAATCAAT

AGGATAAATTCCTGCAAAAACCATGGGATTCAACTGCTTATAACCATGCAAAGGTG

-continued

CTTCGGCAGGGCAGTCCGCCAGAGTCACTGTATCACCAACACGAGTGTCTGCCACT

GTCTTGATTGAAGCAGCTAAATAACCTACATCACCCGTTGCCAAAAAGTCACGATT

AACAGCCTTAGGAGTGAAAATTCCTACTTCTGTCACGTCAAAAGTCTTGCCATTGCT

CATGAGTTCAATTTTATCTCCGGGTTTGACCATACCATCCATGACCCGAATTTGCAG

AATAACGCCGCGATAAGCATCATAGACAGAATCAAAAATAAGAGCTTTGAGTGGG

GCTTCAACATCCCCCTTTGGAGCTGGTACTTTTTCCACAATTTGCTCCAAAATCTCTT

CAATCCCGATGCCTGCTTTGGCGGAAGCCAAAACAGCTTCACTAGCATCCAGTCCA

ATGACATCTTCAATCTCAGTGCGCACACGTTCAGGATCAGCTGCTGGCAAGTCAATT

TTATTGATAACAGGTAAAATTTCCAGATCATTATCTAAAGCCAAATAAACATTGGC

TAAGGTCTGCGCTTCAATACCTTGTGCAGCATCTACCACCAAAATGGCACCTTCACA

GGCTGCCAAAGAACGTGACACTTCATAAGTAAAGTCAACATGTCCTGGCGTGTCAA

TCAAGTGAAAAATATAAGTTTCACCATTTTTAGCCTTATAATTAAGCTCAATCGCAT

TTAATTTAATGGTAATACCACGCTCACGTTCTAAGTCCATGCTGTCCAAAAGCTGAG

CTTGCATTTCTCTGCTAGAAACAGTTTCTGTCTGTTCCAAAATACGATCTGCCAGCG

TTGACTTCCCATGGTCTATATGGGCAATAATAGAGAAATTACGAATTTTCTCCTGAC

GATTTTTAAGTTGTTCTATAGTCAT

SEQ ID NO 89
>Streptococcus_thermophilus_LMG18311
TTATTTCTCATCTTCGTCCATTGAAAGCACAGACAAGAAGGCTTCTTGTGGTACCTC

CACCGAACCGATGGCTTTCATACGTTTCTTACCGGCTTTTTGTTTTTCGAGGAGTTTA

CGTTTACGTGAAACGTCACCACCGTAACATTTAGCCAAGACGTTTTTACGAAGAGC

TTTGATATCTGTACGGGCAACAATTTTTTGACCAATAGCCGCTTGGATAGGAACTTC

AAATTGTTGACGTGGAATAATTTTCTTAAGTTTATCAACGATAAGTTTTCCACGTTC

GTAGGCAAATTCTCTATGGACAATAAAGCTAAGGGCATCGACCTTATCACCATTAA

GGAGAATATCCATTTTCACCAATTGTGAACGACGGTACTCTGACAATTCATAGTCA

AAACTTGCATAACCACGAGTTGATGACTTCAATTTATCAAAGAAGTCAAAGACGAT

TTCAGCAAGTGGAATTTGATAGATAACGTTAACACGATTATCATCAATATATTCCAT

GGTTTCAAAATCACCACGTTTACGTTGCGCCAACTCCATAACAGCACCAACATACTC

TTGAGGAACCATAATTTGAGCTTTGACATAAGGCTCTTCAATGGTATCAATACGTGT

AGGATCTGGAAATTCAGATGGGTTGGACACTTCAAGCATTTCACCGTCAGTAGTGT

TAACATGGTAAACTACTGATGGTGCAGTCATGATGAGATCGATGTTAAACTCACGT

TCCAAACGCTCTTGGATAACATCCATGTGAAGAAGGCCCAAGAAACCACAACGGA

AACCAAAACCAAGAGCTTGAGACGTTTCAGGCTCAAATTGAAGACTGGCATCATTC

AATTGGAGCTTTTCAAGAGCCTCACGCAAGTCGTTATATTTATTTGACTCAATTGGA

TAAAGACCAGCAAAGACCATTGGGTTCATTTGCTTATAACCATGAAGTGGTTCTGC

GGCTGGATTATCCGCAAGTGTCACTGTATCACCGACACGAGTATCCGCAACTGTCTT

AATTGAAGCTGCTACATAACCAACATCTCCAGTCGCAAGGTAGTCACGGCCAACAG

CTTTAGGAGTGAAAATACCAACCTCAGTAACGTCAAAGGTCTTGCCATTAGACATC

ATTTGAATCTTATCACCCGTTTTAACCATTCCGTTAACCACACGCACTTGGAGTATG

ACGCCACGATACGCATCATAAACAGAGTCAAAGATAAGGGCTTGGAGAGGTGCTTC

CACATCACCTTGGGGCGCAGGAACTTTCTCAACAATTTGTTCGAGAATCTCTTCGAT

-continued

ACCAATGCCAGCCTTAGCTGATGCAAGCACAGCTTCCGAGGCATCTAATCCGATAA

CATCTTCAATCTCTGTACGTACACGCTCAGGATCTGCCGCTGGAAGGTCGATTTTAT

TGATAACTGGTAAGATTTCCAAGTCATTATCAAGTGCCAAGTAAACATTGGCAAGT

GTTTGTGCTTCAATCCCTTGAGCTGCATCTACCACCAAGATAGCACCCTCACAGGCG

GCAAGGGAACGTGACACCTCATAAGTAAAGTCCACATGTCCCGGTGTGTCGATAAG

GTGGAAAATATAAGTCTCGCCGTCTTTAGCTTTGTAGTTAAGCTCAATGGCATTCAG

TTTGATAGTGATACCACGTTCGCGCTCAAGATCCATACTATCAAGGAGTTGTGCCTG

CATCTCACGACTTGATACAGTCTCAGTCTTTTCCAAGATACGGTCAGCAAGCGTTGA

TTTACCATGGTCAATATGAGCAATAATCGAGAAGTTGCGAATCTTCTCCTGTCTTTG

TTTTAATTCTTCAATATTTGGCAT

SEQ ID NO 90
>Enterococcus_faecalis_V583
CTATTTCGCGTTATCTTGGTCGTCCATTTTCAGAACCGCCATAAAGGCTTCTTGAGG

AACTTCCACGGATCCAATTTGTTTCATCCGTTTCTTCCCTTCTTTTTGTTTCTCTAACA

ATTTACGTTTACGAGAAACATCGCCACCATAGCATTTAGCCAGTACGTTTTTGCGTA

AGGCTTTAATATCTGAACGAGCCACAATTTTTTGACCAATCGCCGCTTGAACTGGGA

CTTCAAACTGTTGACGTGGAATTAGTTTTTCAGTTTCTCAACAATCGCTTTACCAC

GCTCAAATGCGAAATCTCGGTGAACAATAAAGCTTAAAGCATCCACTTTTTCAGCA

TTTAATAGAATATCCATTTTCACTAGGCGGCTGGTACGATAGCCAGCCATTTCGTAA

TCTAAGGATGCATAGCCTTTTGTACTTGATTTCAATTTATCGAAAAAGTCAAACACG

ATTTCAGATAACGGAATTTCATAAACTACGTTTACACGATAATCGTCTAAGTAATCC

ATTGTAATGAATTCGCCACGTTTACGTTGTGATAATTCCATTACTGCTCCTACATAA

TCGTTTGGCACCATGATTTGCGCTTTAACATAAGGTTCTTCCACAGATTCAATCGTT

ACTGGTTCTGGAAATTCAGCTGGGTTGTCAACAACAACGGTTGTTCCGTCAGTTTTA

TTAACGTGATAGATTACAGACGGTGCTGTTGTAATTAACTCTAAATTAAATTCTCGT

TCCAAACGTTCCTGAACAACATCCATGTGCAGCAAACCTAAGAAACCACAACGGAA

ACCAAACCCTAAAGCTTGCGATGTTTCCGGTTCAAATTGTAACGCCGCATCATTTAA

TTGTAATTTTTCTAATGCTTCCCGTAAATCGTTGTAGCGCGACGTATCAATTGGATA

TAAACCACAATAAACCATTGGATTCATTTTGCGGTAGCCTGGTAGTGCTTCTGCTGC

TGGATTGTCGGCCAAAGTCACTGTATCCCCGACCCGTGTATCTTGAACCGTTTTAAT

GCTAGCGGTGATATAGCCCACATCACCAACCATTAAATAATCACGAGCAATCGGTT

TCGGTGAAAAAACGCCGACTTCTGTTACATCAAACGTTTTACCGTTACTCATCATTT

GGATTTTATCCCCAGGACGAACGACACCGTCAATTACACGGATGTTTAAAACGACC

CCCCGATAACTATCGTAAATAGAGTCAAAAATCAAAGCCTTTAAAGGAGCCTCAAT

ATCGCCTGATGGAGCTGGTACATACTCCACCACTTGTTCTAAAATATCTTCAATCCC

AATCCCTGCTTTTGCACTTGCTAAAACAGCTTCCGATGCATCAATTCCAATTACGTC

TTCAATCTCTGTCCGAACACGCTCTGGATCAGCGGCGGGTAAATCAATTTTATTAAT

AACAGGTAAAATTTCTAAGTCATTATCCAATGCCAAATAGACATTTGCTAGCGTTTG

CGCTTCAATTCCTTGCGCCGCATCAACAACTAGAACAGCCCCTTCACAAGCTGCCA

AGCTACGAGAAACTTCGTAGGTGAAATCGACGTGCCCTGGTGTGTCAATCAAATGG

AAAGTATAGATTTCACCATCTTTGGCTGTATAGTTTAATTCAATTGCGTTTAATTTG

ATAGTAATGCCGCGTTCTCTCTCTAAATCCATTGAATCAAGTAATTGATCTTGCATT

-continued

TCTCGACTGCTAACTGTATTTGTTTTTTCCAAAATCCGGTCGGCTAAAGTTGACTTCC

CATGGTCAATGTGGGCAATGATCGAGAAATTACGAATTTTCTCTTGTCTTGCTTTCA

TTTCTTTATTGTTCAT

SEQ ID NO 91
>Enterococcus_faecium_DOctg621
CTATTTCTTCGGTTCGTCCTCGTCCATTTTCAGAACGGCCATGAAGGCTTCTTGCGG

AACTTCGACGGAGCCGATTTGTTTCATCCGCTTCTTCCCTTCTTTTTGTTTCTCTAAG

AGTTTACGTTTACGAGAAACATCTCCACCATAACATTTAGCCAAGACGTTTTTACGC

AAGGCTTTGATGTCTGAACGGGCAACGATTTTTTGTCCAATAGCTGCTTGGATTGGC

ACCTCAAATTGTTGGCGTGGGATTAGTTTTTTCAGTTTTTCAACGATTGCTTTTCCAC

GTTCATAGGCAAAGTCTCGGTGAACGATAAAGCTTAATGCATCGACTTTTTCTCCAT

TCAGCAAGATGTCCATCTTCACTAACTTGCTTTTTTGATAACCAGACATTTCATAAT

CCAATGAGGCATAGCCTTTCGTGCTTGATTTCAATTTGTCGAAAAAGTCAAAGACA

ATTTCAGAAAGCGGAATATTATAGACGACATTTACTCGGTAATCATCTAAATAATC

CATCGTAATGAATTCTCCCCGTTTTCGTTGAGAAAGTTCCATTACTGCACCGACAAA

ATCATTTGGGACCATGATCTGTGCTTTGACGAATGGTTCTTCTACATCCTGAATCGT

TACAGGTTCAGGAAAATCTGCCGGGTTATCTACTGTAGCAGTCGTACCATCCGTTTT

ATTAACATGGTAAATAACGGATGGTGCAGTCGTGATCAATTCTAGATTGAATTCCC

GTTCCAAGCGTTCTTGGACGACATCCATATGAAGAAGTCCGAGGAATCCACAGCGG

AACCCAAAACCTAATGCTTGAGAGGTTTCTGGTTCGAATTGTAAAGCAGCATCATT

CAATTGCAGTTTTTCTAAAGCTTCCCGCAAATCGTTGTAACGAGAAGTATCAATTGG

ATAAAGACCACAATAAACCATCGGATTCATTTTTCGGTAACCTGGTAAAGCTTCAG

CGGCAGGATTGTCTGCTAACGTTACTGTATCCCCTACTCGTGTATCTTGGACAGTTT

TGATACTTGCTGTGATATAACCGACATCACCGACCATCAAAAAGTCTCTAGCAACT

GCTTTTGGCGAGAAGACCCCGACCTCTGTAACATCAAATGTTTTGCCATTACTCATC

AGTTTGATTTTGTCTCCGGGTTTGACCATACCGTCCGTGATCCGGACATTTAGAACA

ACACCGCGGTAACTATCATAAATAGAGTCAAAGATCAAAGCTTTTAGCGGTGCATC

TAAGTCTCCACTTGGTGCAGGAACATATTCCACGATCTGCTCGAGAATATCTTCAAT

CCCAATCCCTGATTTGGCACTGGCTAATACAGCTTCACTAGCATCGATTCCGATTAC

GTCTTCGATTTCTTGACGGACACGTTCGGGATCTGCTGCGGGTAGGTCGATTTTATT

GATGACTGGCAGGATCTCCAAATCATTGTCTAACGCTAAATAAACATTGGCCAATG

TTTGTGCTTCGATTCCTTGTGCTGCATCGACCACTAAAACGGCACCCTCACAGGCAG

CAAGGCTTCGAGAGACTTCATAGGTGAAGTCGACGTGCCCTGGGGTGTCAATCAAG

TGAAAGATATATGTTTCTCCATTTTTCGCTGTGTAATTGAGTTCTACAGCATTTAATT

TAATCGTGATTCCACGTTCACGTTCCAAATCCATCGAGTCTAACAGCTGATCTTGCA

TTTCGCGAGACGTCACAGTGTGCGTCATTTCTAAAATACGATCGGCCAATGTAGATT

TCCCATGGTCGATATGAGCGATGATCGAAAAATTACGAATCTGCTCTTGGCGTTCTT

TCATTTTCTTTATATCCAT

SEQ ID NO 92
>Streptococcus_sanguinis
TTATTCCTCATCCATACTCAGGACGCTGAGGAAGGCTTCTTGTGGAACTTCGACAGA

TCCGATAGCTTTCATCCGTTTTTTACCGGCTTTTTGTTTTTCTAGGAGTTTGCGCTTC

-continued

CGAGAAACGTCACCACCATAACACTTGGCCAAGACATTCTTACGCAGAGCCTTGAT

GTCTGTCCGAGCCACGATTTTCTGACCAATAGCAGCCTGAATGGGTACTTCAAATTG

CTGACGAGGAATGATTTTCTTGAGCTTGTCTACAATCAGCTTACCACGCTCATAGGC

AAATTCCTTGTGAACGATAAAGCTGAGAGCATCGACCTTGTCGCCATTAAGGAGAA

TATCCATCTTCACCAGCTTGGACGAGCGATACTCGGAGATTTCGTAGTCAAAGCTCG

CATAGCCACGAGTAGAGGACTTGAGCTTGTCAAAGAAGTCAAAGACGATTTCAGCA

AGTGGGATTTGATAGATGACATTGACCCGATTATCATCGATATAGTCCATGGTCAC

AAAGTCACCGCGCTTGCGTTGAGCCAACTCCATCACCGCTCCGACAAATTCCTGGG

GAACCATAATCTGCGCCTTGACATAGGGCTCCTCGATGGAATCAATCTTGGTCGGG

TCCGGAAACTCGCTCGGATTGGACACATCAAGAGAAGTCCCATCCGTCATATTGAC

CTTATAGATAACAGACGGAGCCGTCATAATCAGATCAATATTAAACTCGCGCTCCA

AACGCTCCTGAATGACGTCCATGTGCAGTAAGCCCAGGAATCCACAACGGAACCCA

AATCCTAATGCCTGTGATGTTTCTGGCTCAAACTGCAGACTGGCATCGTTTAGCTGG

AGCTTTTCAAGGGCCTCACGCAGGTCGTTGTATTTATTGGACTCGATAGGATAGAG

ACCAGCGAAGACCATAGGATTCATCTGCTTGTAGCCAGCTAATGGCTCAGCAGCTG

GATTGTCCGCCAAGGTCACTGTATCTCCGACCCGAGTGTCCTGTACCGTCTTGATAG

AGGCTGCGATATAGCCAACATCCCCAGTAGCCAAGAAATCACGACCAATGGCTTTG

GGAGTAAAGATGCCGACCTCAGTCACGTCAAAGGTCTTACCATTGCTCATGAGCTG

AATGATATCTCCTGGCTTGACCACACCGTCCATCACCCGCACTTGCAGGATTACCCC

ACGATAGGCGTCATAGACCGAGTCAAAGATTAAGGCCTTGAGCGGTGCTTCAACAT

TTCCAGTCGGAGCTGGAACTTTCTCCACAATCTGCTCTAAAATTTCCTCAATTCCGA

TACCAGCCTTGGCAGAAGCCAATACGGCTTCGCTAGCATCCAGTCCAATCACGTCTT

CAATTTCTGCCCGCACCCGCTCTGGATCCGCAGCTGGCAGGTCAATTTTATTGATGA

CTGGCAGGATTTCCAAGTCATTATCCAGCGCTAGATAAACATTAGCCAAGGTCTGA

GCCTCAATCCCCTGAGCCGCATCCACAACCAAAATAGCCCCTTCGCAGGCCGCTAA

CGACCGCGATACCTCATAGGTAAAGTCCACGTGTCCCGGCGTGTCAATCAAGTGGA

AGATATAGGTTTCACCGTCCTTGGCGGTATAATTGAGCTCGATAGCATTGAGCTTAA

TGGTGATGCCGCGCTCCCGCTCCAAGTCCATGCTGTCCAAGAGTTGGGCCTGCATTT

CCCGACTGGAAACCGTCTCAGTCGCCTCCAAAATCCGGTCAGCCAAGGTTGATTTC

CCGTGGTCAATGTGAGCAATGATGGAGAAATTGCGGATCTTCTCCTGACGTTTTTC

AAATCTTCTAAATTCATTTTTCTCAT

SEQ ID NO 93
>Streptococcus_gordonii_str_Challis
TTATTCCTCATCCATACTCAAGACACTGAGGAAAGCTTCTTGTGGAACTTCGACTGA

GCCGATAGCTTTCATCCGTTTTTTACCAGCTTTTTGTTTTTCAAGGAGTTTGCGCTTC

CGAGAAACGTCACCACCATAACACTTGGCCAAGACATTCTTACGCAAGGCTTTGAT

GTCTGTCCGAGCCACAATTTTCTGACCGATAGCAGCCTGAATGGGTACTTCAAACTG

CTGACGAGGAATGATTTTCTTGAGCTTGTCTACAATCAGCTTACCACGCTCATAAGC

AAATTCCTTGTGAACGATAAAGCTAAGGGCATCAACCTTGTCGCCATTGAGGAGAA

TATCCATCTTCACCAGCTTGGACGAGCGGTACTCAGAAATCTCATAGTCAAAGCTC

GCATAGCCACGAGTAGAGGACTTGAGCTTGTCAAAAAAGTCAAAGACAATTTCAGC

AAGCGGAATTTGATAGATGACATTGACCCGATTATCGTCGATATAGTCCATAGTCA

-continued

CAAAGTCACCGCGCTTGCGTTGAGCCAACTCCATCACTGCTCCGACAAATTCCTGTG

GCACCATAATCTGCGCCTTAACATAAGGCTCCTCGATAGAATCAATCTTGGTCGGAT

CCGGAAACTCACTCGGATTAGAGACATCAATGGCTTCACCATCTGTCAGATTAACC

TTATAGATAACGGACGGAGCCGTCATAATCAGATCAATATTAAACTCACGCTCCAA

GCGCTCCTGAATAACATCCATGTGTAGCAAGCCCAAGAAGCCACAACGGAATCCAA

ATCCTAGCGCTTGTGATGTTTCTGGCTCAAACTGCAAGCTGGCATCGTTTAGCTGGA

GCTTTTCAAGAGCCTCACGTAAGTCATTGTATTTATTGGACTCGATAGGATAGAGAC

CAGCAAAAACCATCGGGTTCATCTGCTTGTAGCCATGCAGAGGTTCTGTAGCTGGA

TTATCAGCCAAGGTTACAGTATCTCCGACTCGGGTATCCTGTACCGTCTTGATAGAG

GCTGCAATATAGCCAACATCCCCTGTCGCTAAGAAATCACGCCCAATAGCCTTAGG

TGTAAAGATGCCAACCTCAGTTACGTCAAAGGTCTTGCCATTGCTCATGAGCTGAAT

GGTATCTCCTGGCTTGACCACACCATCCATCACCCTCACTTGTAGAATTACCCCACG

ATAGGCGTCATAGACTGAGTCAAAAATCAAGGCCTTGAGTGGCGCTTCAACATTTC

CAGTCGGAGCTGGAACTTTCTCCACAATCTGCTCTAGAATATCTTCAATCCCGATAC

CAGCCTTGGCAGAAGCTAATACGGCTTCGCTAGCATCTAGTCCAATCACATCTTCAA

TCTCAGCTCGCACCCGTTCTGGATCCGCAGCTGGCAGGTCAATCTTATTGATAACCG

GCAGAATTTCCAAATCATTGTCCAGCGCTAGATAGACATTTGCCAAGGTCTGAGCTT

CAATCCCCTGAGCTGCATCAACGACCAAAATAGCTCCTTCACAGGCTGCTAACGAC

CGCGATACTTCATAGGTAAAGTCCACGTGTCCAGGCGTGTCAATGAGGTGGAAGAT

ATAGGTTTCACCATCTTTAGCTGTGTAATTAAGCTCGATAGCATTTAGTTTGATGGT

GATACCGCGCTCCCGCTCCAAGTCCATGCTGTCCAAGAGTTGGGCCTGCATTTCCCG

GCTGGAAACCGTCTCAGTCGCCTCCAAAATCCGGTCAGCCAAGGTTGATTTCCCGT

GGTCGATATGGGCAATGATGGAGAAATTACGGATCTTCTCCTGACGTTTTTTCAAAT

CTTCTAAATTCAT

SEQ ID NO 94
>Streptococcus_suis_98HAH33
TTATTTCTTATCGTCTTCATCCATGCTGAGAACACTGAGGAAGGCTTCTTGTGGAAC

TTCGACAGAGCCGATGGCTTTCATCCGTTTTTTACCAGCTTTTTGCTTTTCTAGGAGT

TTGCGTTTACGGGAAACGTCACCACCATAACACTTGGCCAAAACGTTCTTCCGAAG

AGCCTTGATGTCGCTACGGGCAACAATTTTCTGACCGATAGCTGCTTGTATTGGTAC

TTCAAACTGTTGACGGGGAATGATTTTCTTGAGTTTGTCCACGATAATTTTCCCACG

TTCGTAGGCAAATTCCTTGTGGACGATAAAGCTGAGGGCATCGACCTTGTCACCATT

GAGGAGAATATCCATTTTCACCAACTTGGATGAACGGTATTCAGAAATCTCATAGT

CGAAGCTGGCATAACCACGAGTGGACGACTTAAGCTTATCAAAGAAGTCAAAAAC

AATCTCCGCAAGTGGAATTTGGTAGATGACATTGACACGATTATCATCGATGTAAT

CCATAGTCACAAAGTCACCGCGTTTGCGTTGGGCCAATTCCATGACTGCACCGACG

TATTCCTGTGGTACCATGATTTGTGCCTTAACGTAAGGCTCTTCGATAGTGGCAATC

TTTGTTGGGTCTGGGAATTCGGATGGGTTGGCTACATCAATCATTTCACCGTCCGTC

ATGTTGACATGGTAAACCACCGACGGTGCTGTCATGATGAGGTCAATGTTAAACTC

ACGCTCAATCCGTTCTTGGATAACATCCATGTGCAAGAGGCCCAAGAATCCACAAC

GGAAACCAAATCCGAGTGCCTGCGATGTTTCTGGCTCAAACTGCAAGCTGGCATCG

```
TTGAGTTGGAGTTTTTCCAAGGCTTCACGGAGGTCATTGTACTTGTTGGAATCGATT

GGATAGATACCTGCAAAGACCATTGGATTCATCTGCTTGTAGCCCGCTAGTGGCTC

GCTGGCAGGATTTTCTGCCAAGGTTACCGTATCACCGACACGGGTATCTGCAACGG

TCTTGATAGAGGCTGCAATGTAACCAACATCACCAGTCGCCAAATAATCACGACCG

ATTGCTTTGGGTGTGAAAATCCCCACTTCCGTCACATCGAAAGTCTTACCATTGCTC

ATCATCTGAATGGTGTCACCAGGTTTTACCACACCATTGACGATACGAACTTGGAG

GATAACGCCTCGATACGGATCGTAAACCGAGTCAAAAATCAAGGCTTGCAATGGAG

CTTCGACATCACCAGTCGGTGCTGGAACCTTCTCGACAATCTGCTCCAAGATTTCCT

CGATACCAATACCTGCCTTGGCTGATGTTGGCACTGCTTCAGAAGCATCCAAACCA

ATCACATCTTCGATTTCCTGACGAACACGTTCTGGGTCTGCTGCTGGCAGGTCAATC

TTGTTAATGATTGGCAAGATTTCCAAATCATTGTCCAAGGCTAGATAAACGTTGGCC

AAGGTCTGTGCTTCAATCCCTTGAGCAGCATCCACCACTAAAATCGCTCCTTCACAG

GCAGCCAACGAACGCGATACCTCATAGGTAAAATCCACGTGTCCTGGTGTGTCAAT

CAAGTGGAAAATGTATGTCTCTCCATCTTTAGCTGTATAGTTGAGTTCGATTGCGTT

GAGTTTAATTGTGATACCACGCTCGCGTTCCAAGTCCATACTATCCAGCAACTGGGC

TTGCATTTCACGGCTGGAAACTGTTTCCGTCTTCTCAAGAATACGGTCAGCCAAGGT

TGATTTACCATGGTCGATGTGGGCAATAATGGAGAAATTACGAATTTTCTCCTGTCG

TTTTTTCAAATCTTCTAAATTCAT

SEQ ID NO 95
>Listeria_monocytogenes_4b_F2365_lepA
ATGAACAAAGAAGAAATGAATGCAAGACAAAAGAAAATTAGAAACTTTTCGATTA

TCGCGCACATAGATCATGGTAAATCTACACTCGCTGATCGGATTTTAGAACAAACG

GGTGCTTTGACGCATCGTGAAATGAAAAATCAGCTACTAGATTCGATGGATTTAGA

ACGTGAACGCGGGATAACCATAAAATTAAATGCTGTACAATTAAAATATAAAGCAA

AAGATGGAGAAACATATATCTTCCATCTGATTGATACGCCTGGGCATGTCGATTTCA

CCTATGAAGTATCAAGAAGTTTAGCTGCATGTGAGGGAGCAATCCTTGTTGTAGAT

GCTGCGCAAGGAATTGAAGCACAAACCCTTGCTAATGTTTATTTAGCACTAGACAA

CGATTTAGAAATTTTACCAGTCATTAACAAAATCGATTTACCAGCGGCCGATCCGG

AAAGAGTCCGCGAAGAAATTGAAGATGTAATTGGTTTAGATGCTTCTGACGCTGTA

CTTGCTTCTGCGAAATCTGGTATTGGTATTGAAGACATTCTAGAACAAATTGTCGAA

AAAGTTCCTGAGCCATCTGGTGATGTAAATAAACCACTAAAAGCGCTCATTTTTGA

CTCTGTTTTTGATGCATATCGTGGTGTTATTGCTAATATCCGTATCATGGATGGTGTT

GTAAAAGCAGGCGACCGAATTAAAATGATGTCCAATGGCAAAGAATTCGAAGTAA

CGGAGGTTGGTGTATTCTCACCAAAGGCAACACCACGTGACGAATTACTTGTTGGT

GACGTTGGTTACTTAACAGCAGCTATAAAAAATGTTGGAGATACGCGCGTAGGTGA

TACAATCACACTTGCGAATAATCCAGCTGAAGAAGCGCTGGATGGTTACCGTAAAT

TAAATCCAATGGTTTATTGTGGTCTATATCCAATCGACTCCTCTAAATATAATGATC

TTCGTGATGCTTTAGAAAAACTAGAATTAAATGACTCTGCTTTGCAATTTGAAGCGG

AAACTTCTCAAGCATTAGGTTTTGGTTTCCGTTGTGGTTTCTTAGGATTACTACATAT

GGAAATTATTCAAGAGCGAATCGAACGTGAATTTAACATTGATTTAATTACCACTG

CTCCAAGTGTTATCTATCATGTCAACTTGACAGATGGTTCTAACATTGTGGTTGATA

ATCCTGCTGAAATGCCAGAACCTGGTGTTATTGAAAGCGTGGAAGAGCCATATGTA
```

-continued

AAAGCAACTGTGATGGTTCCAAATGATTATGTTGGTGCAGTGATGGAACTGGCACA

AAACAAACGTGGAAACTTCATTACGATGGAGTACTTAGATGATATTCGCGTAAGTA

TTGTGTACGAAATTCCATTATCCGAAATCGTATATGACTTTTTTGACCAATTAAAAT

CATCTACAAAAGGTTATGCGTCCTTTGATTATGAATTAATTGGCTATAAAGCTTCTA

AACTTGTGAAAATGGATATTCTTTTAAATGCAGAAAAAGTTGATGCACTTAGCTTTA

TCGTTCACCGTGATTTTGCTTATGAGCGTGGAAAAATCATCGTGGAGAAATTAAAA

GAACTTATTCCAAGACAACAATTTGAAGTACCTATTCAAGCAGCAATTGCCACAAA

AATTGTTTCTCGTTCTACTATTAAAGCGTTGCGAAAAAACGTACTTGCTAAATGTTA

CGGTGGGGACGTATCTCGTAAACGAAAACTTTTAGAGAAACAAAAAGAAGGTAAA

AAACGAATGAAACAAATCGGTTCAGTTGAAGTCCCGCAAGAAGCATTTATGGCAAT

CTTGAAAATGGACGAATCCAAA

SEQ ID NO 96
>Listeria_welshimeri
ATGAACAAAGAAGAAATGAATGCAAGACAAAAGAAAATTAGAAACTTTTCGATTA

TCGCGCACATAGATCATGGTAAATCTACACTCGCTGATCGGATTTTAGAACAAACT

GGTGCTTTAACGCATCGTGAAATGAAAAATCAGCTACTAGATTCGATGGATTTAGA

ACGTGAACGCGGGATAACCATAAAATTAAATGCTGTACAATTAAAATATAAAGCAA

AAGACGGGGAAACTTATATCTTTCATTTAATTGATACGCCTGGGCATGTCGATTTTA

CCTATGAAGTATCAAGAAGTTTAGCTGCATGTGAGGGAGCAATCCTTGTTGTAGAT

GCTGCGCAAGGAATTGAAGCACAAACCCTTGCCAATGTTTATTTAGCACTAGACAA

TGATTTAGAAATCTTACCAGTAATAAATAAAATTGATTTGCCAGCAGCTGACCCAG

AACGCGTTCGTGCAGAAATTGAAGATGTCATTGGTTTAGATGCTTCTGACGCTGTAC

TTGCTTCTGCAAAATCTGGTATTGGTATTGAAGACATTCTAGAACAAATTGTTGAAA

AAGTTCCTGAGCCATCTGGTGATGTAAATAAACCACTAAAAGCGCTCATTTTCGACT

CTGTTTTTGATGCGTATCGCGGTGTTATTGCCAATATTCGTATCATGGACGGCGTTG

TAAAGGCTGGCGACAGAATAAAAATGATGTCGAATGGCAAAGAATTTGAAGTGAC

CGAAGTAGGTGTTTTTTCACCAAAGGCAACACCGCGAGATGAGCTACTTGTTGGTG

ATGTAGGGTATTTAACAGCAGCCATCAAAAATGTTGGAGATACTCGAGTTGGTGAT

ACTATCACACTTGCGAATAATCCAGCGGAAGAAGCACTAGATGGTTATCGTAAATT

AAATCCAATGGTATATTGTGGTCTTTATCCAATTGATTCTTCTAAGTATAATGATTT

GCGTGATGCACTTGAAAAGCTTGAACTAAATGATTCGGCTTTACAATTTGAAGCAG

AAACTTCTCAAGCATTAGGTTTTGGATTCCGTTGTGGGTTCTTAGGGTTGTTACACA

TGGAAATTATTCAAGAAAGAATCGAGCGCGAATTTAATATAGACTTAATTACTACT

GCACCAAGCGTAATCTATCATGTGAATTTGACAGATGGATCTAATATTGTGGTTGAT

AATCCAGCAGACATGCCTGAACCTGGTGTCATTGAAAGTGTAGAAGAGCCTTATGT

AAAAGCAACTGTTATGGTGCCAAATGATTATGTTGGTGCGGTAATGGAACTTGCAC

AAAACAAACGGGGTAACTTCATTACGATGGAGTACCTGGATGATATTCGAGTAAGT

ATTGTGTACGAAATTCCACTATCTGAAATAGTATACGACTTCTTCGACCAATTAAAA

TCATCTACAAAAGGCTATGCTTCTTTTGATTATGAATTAATTGGCTATAAAGCTTCT

AAACTTGTGAAAATGGATATTCTATTGAACGCAGAAAAAGTCGATGCTTTAAGCTT

TATTGTTCATCGTGATTTTGCTTACGAGCGTGGAAAAATTATCGTAGAAAAACTAAA

-continued

AGAACTTATTCCTAGACAACAATTTGAAGTCCCAATTCAAGCAGCAATTGCAACAA

AAATTGTTTCTCGTTCCACTATTAAAGCACTTCGTAAAAACGTACTTGCAAAATGCT

ATGGTGGGGATGTATCGCGTAAAAGAAAACTTTTAGAGAAACAAAAAGAAGGTAA

AAAACGAATGAAACAAATTGGGTCAGTTGAAGTTCCTCAAGAAGCCTTCATGGCAA

TCTTAAAAAATGGATGAATCAAAATAA

SEQ ID NO 97
>Listeria_innocua
ATGAACAAAGAAGAAATGAATGCAAGACAAAAGAAAATTAGAAACTTTTCGATTA

TCGCGCACATAGATCATGGTAAATCTACACTCGCTGATCGGATTTTAGAACAAACA

GGTGCTTTGACGCATCGTGAAATGAAAAATCAGCTACTAGATTCGATGGATTTAGA

ACGTGAACGCGGGATAACCATAAAATTAAATGCTGTACAATTAAAATATAAAGCAA

AAGACGGAGAAACGTATATCTTTCATTTAATCGATACACCGGGACACGTCGATTTC

ACTTATGAAGTATCTAGAAGTTTAGCCGCATGTGAAGGTGCTATTTTAGTAGTAGAC

GCTGCACAAGGTATCGAAGCGCAAACACTGGCAAACGTTTATTTAGCTCTAGATAA

TGATTTAGAAATTTTACCTGTAATTAATAAGATTGATTTGCCAGCAGCAGATCCAGA

AAGAGTTCGTGCTGAAATTGAAGATGTTATTGGCTTGGATGCATCAGATACTGTCCT

TGCTTCTGCAAAATCAGGCATCGGGATTGAAGACATCCTTGAACAAATAGTTGAAA

AAGTACCAGAACCATCTGGTGACGTTGATAAACCACTTAAAGCACTTATTTTTGATT

CTGTTTTTGATGCGTATCGTGGCGTAATAGCTAATATCCGTATTATGGATGGTGTTG

TAAAAGCTGGCGACAGAATTAAGATGATGTCAAACGGCAAAGAGTTTGAAGTTAC

AGAAGTTGGTGTTTTCTCTCCAAAAGCAACACCACGTGATGAGCTTCTTGTTGGTGA

CGTTGGTTACTTAACAGCTGCAATCAAAAATGTTGGAGATACTCGAGTGGGTGATA

CAATCACACTTGCGAACAATCCTGCTGAAGAAGCTCTTGACGGATACCGCAAATTA

AATCCAATGGTTTATTGCGGACTTTATCCAATTGACTCTTCCAAATATAACGATTTA

CGTGATGCACTTGAAAAATTAGAACTCAATGATTCAGCTTTACAATTTGAAGCAGA

GACTTCTCAAGCATTAGGTTTTGGATTCCGTTGTGGATTTTTAGGTCTACTACACAT

GGAAATTATTCAAGAAAGAATTGAGCGCGAATTTAATATCGATTTAATTACTACGG

CCCCAAGTGTTATTTACCACGTGAATTTAACAGATGGATCTAATATTGTGGTCGATA

ACCCAGCTGATATGCCTGAACCTGGCGTAATTGAAAGCGTGGAAGAACCATACGTT

AAAGCAACTGTCATGGTTCCAAATGATTATGTTGGTGCGGTAATGGAACTTGCACA

AAACAAACGGGGGAACTTCATTACAATGGAGTACTTGGATGATATTCGCGTTAGTA

TTGTGTACGAAATTCCACTATCTGAAATAGTTTACGACTTCTTCGACCAATTAAAAT

CTTCTACAAAAGGCTATGCGTCCTTTGATTATGAATTAATTGGCTATAAAGCTTCTA

AACTTGTGAAAATGGATATTCTTTTAAATGCAGAAAAAGTGGATGCACTTAGCTTT

ATCGTTCACCGTGATTTTGCCTACGAGCGTGGAAAAATCATTGTCGAGAAATTAAA

AGAACTTATTCCAAGACAACAATTTGAAGTACCTATTCAAGCAGCAATTGCAACAA

AAATTGTTTCTCGTTCCACTATTAAAGCTCTACGTAAAAACGTACTTGCTAAATGTT

ATGGTGGGGACGTATCGCGTAAACGAAAACTCTTAGAGAAACAAAAAGAAGGTAA

AAAACGAATGAAACAAATCGGTTCTGTGGAAGTGCCGCAAGAAGCTTTCATGGCAA

TCTTGAAAATGGACGAATCGAAATAA

-continued

SEQ ID NO 98
>Mycobacterium_bovis_AF2122/97
TCACTTCTTGCCTTTGTCCCCGGCGGCATCGGTGGACAATGCCGCGACGAAAGCCTC

CTGTGGCACCTCGACGCGCCCGATGGTCTTCATCCGCTTCTTGCCTTCCTTCTGCTTC

TCCAGCAGCTTGCGTTTGCGCGTGATGTCGCCGCCGTAGCACTTGGACAACACGTCC

TTGCGGATCGCGCGGATGTTTTCGCGGGCAATGATTTTCGATCCGATGGCGGCCTGC

ACCGGCACCTCGAACTGCTGGCGCGGGATCAGCTCCTTGAGTTTGGTGGTCATCTTG

TTGCCGTAGGCATACGCCGTGTCCTTGTGCACGATCGCGCTGAACGCATCCACCGCC

TCGCCCTGCAGCAGGATGTCGACCTTGACCAGCGCGGCCTCCTGTTCGCCGGCCTCC

TCGTAGTCGAGGCTGGCATAGCCGCGGGTGCGCGATTTCAGTGCGTCGAAGAAGTC

GAAGATGATCTCGCCGAGCGGCATGGTGTAGCGCAGTTCCACCCGCTCGGGGGAGA

GATAGTCCATGCCGCCCAACTCGCCGCGGCGCGACTGGCACAGCTCCATGATGGTG

CCGATGAACTCGCTGGGCGCGATGATGGTGGTCTTGACGACGGGCTCGTAGACCGT

GCGGATCTTGCCCTCCGGCCAGTCCGACGGATTGGTCACCCGGATTTCGGTGCCGTC

GTCTTTGTGCACCCGATACACCACATTGGGTGAGGTCGAGATCAGGTCCAGGCCGA

ACTCGCGCTCAAGGCGCTCACGGGTGATCTCCATGTGCAGCAGGCCCAAGAAACCG

CACCGGAACCCAAAACCCAGCGCCACCGAGGTTTCCGGCTCATAGGTCAAGGCCGC

GTCGTTGAGCTGCAGCTTGTCCAGGGCGTCGCGCAGGTTCGGGTAGTCCGAACCGT

CGACCGGATACAACCCCGAGTAGACCATCGGTTTGGGCTCACGGTAGCCGGTCAAC

GCTTCGGCGGCAGCCCCGCGGGCCCGGGAGAGGCTGGTCACGGTGTCGCCCACCTT

GGACTGGCGGACGTCCTTGACGCCGGTGATCAGGTAACCCACCTCGCCGACACCGA

GGCCCTCACACGGTTTCGGCTCGGGTGAGACGATGCCGACCTCAAGCAGCTCGTGG

GTGGCGCCGGTGGACATCATCATGATGCGCTCACGGGGGCTGATCTTGCCGTCGAC

GACGCGGACGTAGGTCACCACTCCGCGGTAGATGTCGTAAACGGAGTCGAAAATCA

TTGCGCGGGTAGGTGCCTCGGCGTCGCCCTGAGGGGGCGGCACCTGTCGGACCACC

TCGTCGAGCAGGTCGGACACGCCTTCGCCGGTTTTGCCGGACACCCGCAACACCTC

GGCCGGCTCGCAGCCGATGATGTGTGCCATCTCGGCGGCGTAACGGTCCGGGTCGG

CCGCGGGCAGGTCGATCTTGTTGAGCACCGGGATGATGTGCAGGTCGCGGTCCAAC

GCCAGGTAGAGGTTCGCCAGCGTCTGCGCCTCGATGCCTTGCGCGGCATCGACCAA

CAGCACCGCACCCTCGCAAGCCTCCAGCGCACGCGAGACTTCGTAGGTGAAGTCGA

CATGGCCCGGGGTGTCGATCAGATGCAGCACGTAGTCGGTCTTGTCGACCCGCCAG

GGTAGCCGCACATTCTGGGCCTTGATGGTGATGCCGCGTTCCCGCTCGATGTCCATC

CGATCCAAGTACTGGGCCCGCATAGAGCGTTCGTCGACCACTCCGGTGAGCTGCAG

CATCCGGTCGGCCAACGTTGACTTGCCGTGGTCGATGTGGGCGATGATGCAAAAGT

TCCTAATCTGCGCCGGCGCAGTGAAGGTTTTGTCGGCGAAACTGCTGATGGGAATC

TCCTGGAGCGGGGGTTGACGGGTATCCAGGGT

ATCCGCGTCGGGCAGCTGCGACCCAATCGCGCTCGGTCGATCGCGTCTATGCTGCG

AGCATGGCGTCCGC

AC

-continued

SEQ ID NO 99
>Mycobacterium_bovis_BCG_Pasteur_1173P2
TCACTTCTTGCCTTTGTCCCCGGCGGCATCGGTGGACAATGCCGCGACGAAAGCCTC

CTGTGGCACCTCGACGCGCCCGATGGTCTTCATCCGCTTCTTGCCTTCCTTCTGCTTC

TCCAGCAGCTTGCGTTTGCGCGTGATGTCGCCGCCGTAGCACTTGGACAACACGTCC

TTGCGGATCGCGCGGATGTTTTCGCGGGCAATGATTTTCGATCCGATGGCGGCCTGC

ACCGGCACCTCGAACTGCTGGCGCGGGATCAGCTCCTTGAGTTTGGTGGTCATCTTG

TTGCCGTAGGCATACGCCGTGTCCTTGTGCACGATCGCGCTGAACGCATCCACCGCC

TCGCCCTGCAGCAGGATGTCGACCTTGACCAGCGCGGCCTCCTGTTCGCCGGCCTCC

TCGTAGTCGAGGCTGGCATAGCCGCGGGTGCGCGATTTCAGTGCGTCGAAGAAGTC

GAAGATGATCTCGCCGAGCGGCATGGTGTAGCGCAGTTCCACCCGCTCGGGGGAGA

GATAGTCCATGCCGCCCAACTCGCCGCGGCGCGACTGGCACAGCTCCATGATGGTG

CCGATGAACTCGCTGGGCGCGATGATGGTGGTCTTGACGACGGGCTCGTAGACCGT

GCGGATCTTGCCCTCCGGCCAGTCCGACGGATTGGTCACCCGGATTTCGGTGCCGTC

GTCTTTGTGCACCCGATACACCACATTGGGTGAGGTCGAGATCAGGTCCAGGCCGA

ACTCGCGCTCAAGGCGCTCACGGGTGATCTCCATGTGCAGCAGGCCCAAGAAACCG

CACCGGAACCCAAAACCCAGCGCCACCGAGGTTTCCGGCTCATAGGTCAAGGCCGC

GTCGTTGAGCTGCAGCTTGTCCAGGGCGTCGCGCAGGTTCGGGTAGTCCGAACCGT

CGACCGGATACAACCCCGAGTAGACCATCGGTTTGGGCTCACGGTAGCCGGTCAAC

GCTTCGGCGGCAGCCCCGCGGGCCCGGGAGAGGCTGGTCACGGTGTCGCCCACCTT

GGACTGGCGGACGTCCTTGACGCCGGTGATCAGGTAACCCACCTCGCCGACACCGA

GGCCCTCACACGGTTTCGGCTCGGGTGAGACGATGCCGACCTCAAGCAGCTCGTGG

GTGGCGCCGGTGGACATCATCATGATGCGCTCACGGGGGCTGATCTTGCCGTCGAC

GACGCGGACGTAGGTCACCACTCCGCGGTAGATGTCGTAAACGGAGTCGAAAATCA

TTGCGCGGGTAGGTGCCTCGGCGTCGCCCTGAGGGGGCGGCACCTGTCGGACCACC

TCGTCGAGCAGGTCGGACACGCCTTCGCCGGTTTTGCCGGACACCCGCAACACCTC

GGCCGGCTCGCAGCCGATGATGTGTGCCATCTCGGCGGCGTAACGGTCCGGGTCGG

CCGCGGGCAGGTCGATCTTGTTGAGCACCGGGATGATGTGCAGGTCGCGGTCCAAC

GCCAGGTAGAGGTTCGCCAGCGTCTGCGCCTCGATGCCTTGCGCGGCATCGACCAA

CAGCACCGCACCCTCGCAAGCCTCCAGCGCACGCGAGACTTCGTAGGTGAAGTCGA

CATGGCCCGGGGTGTCGATCAGATGCAGCACGTAGTCGGTCTTGTCGACCCGCCAG

GGTAGCCGCACATTCTGGGCCTTGATGGTGATGCCGCGTTCCCGCTCGATGTCCATC

CGATCCAAGTACTGGGCCCGCATAGAGCGTTCGTCGACCACTCCGGTGAGCTGCAG

CATCCGGTCGGCCAACGTTGACTTGCCGTGGTCGATGTGGGCGATGATGCAAAAGT

TCCTAATCTGCGCCGGCGCAGTGAAGGTTTTGTCGGCGAAACTGCTGATGGGAATC

TCCTGGAGCGGGGGTTGACGGGTATCCAGGGTATCCGCGTCGGGCAGCTGCGACCC

AATCGCGCTCGGTCGATCGCGTCTATGCTGCGAGCATGGCGTCCGCAC

SEQ ID NO 100
>Mycobacterium_tuberculosis_str_Haarlem
TCACTTCTTGCCTTTGTCCCCGGCGGCATCGGTGGACAATGCCGCGACGAAAGCCTC

CTGTGGCACCTCGACGCGCCCGATGGTCTTCATCCGCTTCTTGCCTTCCTTCTGCTTC

TCCAGCAGCTTGCGTTTGCGCGTGATGTCGCCGCCGTAGCACTTGGACAACACGTCC

-continued

TTGCGGATCGCGCGGATGTTTTCGCGGGCAATGATTTTCGATCCGATGGCGGCCTGC

ACCGGCACCTCGAACTGCTGGCGCGGGATCAGCTCCTTGAGTTTGGTGGTCATCTTG

TTGCCGTAGGCATACGCCGTGTCCTTGTGCACGATCGCGCTGAACGCATCCACCGCC

TCGCCCTGCAGCAGGATGTCGACCTTGACCAGCGCGGCCTCCTGTTCGCCGGCCTCC

TCGTAGTCGAGGCTGGCATAGCCGCGGGTGCGCGATTTCAGTGCGTCGAAGAAGTC

GAAGATGATCTCGCCGAGCGGCATGGTGTAGCGCAGTTCCACCCGCTCGGGGGAGA

GATAGTCCATGCCGCCCAACTCGCCGCGGCGCGACTGGCACAGCTCCA

TGATGGTGCCGATGAACTCGCTGGGCGCGATGATGGTGGTCTTGACGACGGGCTCG

TAGACCGTGCGGATCTTGCCCTCCGGCCAGTCCGACGGATTGGTCACCCGGATTTCG

GTGCCGTCGTCTTTGTGCACCCGATACACCACATTGGGTGAGGTCGAGATCAGGTC

CAGGCCGAACTCGCGCTCAAGGCGCTCACGGGTGATCTCCATGTGCAGCAGGCCCA

AGAAACCGCACCGGAACCCAAAACCCAGCGCCACCGAGGTTTCCGGCTCATAGGT

CAAGGCCGCGTCGTTGAGCTGCAGCTTGTCCAGGGCGTCGCGCAGGTTCGGGTAGT

CCGAACCGTCGACCGGATACAACCCCGAGTAGACCATCGGTTTGGGCTCACGGTAG

CCGGTCAACGCTTCGGCGGCAGCCCCGCGGGCCCGGGAGAGGCTGGTCACGGTGTC

GCCCACCTTGGACTGGCGGACGTCCTTGACGCCGGTGATCAGGTAACCCACCTCGC

CGACACCGAGGCCCTCACACGGTTTCGGCTCGGGTGAGACGATGCCGACCTCAAGC

AGCTCGTGGGTGGCGCCGGTGGACATCATCATGATGCGCTCACGGGGGCTGATCTT

GCCGTCGACGACGCGGACGTAGGTCACCACTCCGCGGTAGATGTCGTAAACGGAGT

CGAAAATCATTGCGCGGGTAGGTGCCTCGGCGTCGCCCTGAGGGGGCGGCACCTGT

CGGACCACCTCGTCGAGCAGGTCGGACACGCCTTCGCCGGTTTTGCCGGACACCCG

CAACACCTCGGCCGGCTCGCAGCCGATGATGTGTGCCATCTCGGCGGCGTAACGGT

CCGGGTCGGCCGCGGGCAGGTCGATCTTGTTGAGCACCGGGATGATGTGCAGGTCG

CGGTCCAACGCCAGGTAGAGGTTCGCCAGCGTCTGCGCCTCGATGCCTTGCGCGGC

ATCGACCAACAGCACCGCACCCTCGCAAGCCTCCAGCGCACGCGAGACTTCGTAGG

TGAAGTCGACATGGCCCGGGGTGTCGATCAGATGCAGCACGTAGTCGGTCTTGTCG

ACCCGCCAGGGTAGCCGCACATTCTGGGCCTTGATGGTGATGCCGCGTTCCCGCTC

GATGTCCATCCGATCCAAGTACTGGGCCCGCATAGAGCGTTCGTCGACCACGCCGG

TGAGCTGCAGCATCCGGTCGGCCAACGTTGACTTGCCGTGGTCGATGTGGGCGATG

ATGCAAAAGTTCCTAATCTGCGCCGGCGCAGTGAAGGTTTTGTCGGCGAAACTGCT

GATGGGAATCTCCTGGAGCGGGGGTTGACGGGTATCCAGGGTATCCGCGTCGGGCA

GCTGCGACCCAATCGCGCTCGGTCGATCGCGTCTATGCTGCGAGCATGGCGTCCGC

AC

SEQ ID NO 101
>Mycobacterium_tuberculosis_C
TCACTTCTTGCCTTTGTCCCCGGCGGCATCGGTGGACAATGCCGCGACGAAAGCCTC

CTGTGGCACCTCGACGCGCCCGATGGTCTTCATCCGCTTCTTGCCTTCCTTCTGCTTC

TCCAGCAGCTTGCGTTTGCGCGTGATGTCGCCGCCGTAGCACTTGGACAACACGTCC

TTGCGGATCGCGCGGATGTTTTCGCGGGCAATGATTTTCGATCCGATGGCGGCCTGC

ACCGGCACCTCGAACTGCTGGCGCGGGATCAGCTCCTTGAGTTTGGTGGTCATCTTG

TTGCCGTAGGCATACGCCGTGTCCTTGTGCACGATCGCGCTGAACGCATCCACCGCC

TCGCCCTGCAGCAGGATGTCGACCTTGACCAGCGCGGCCTCCTGTTCGCCGGCCTCC

-continued

TCGTAGTCGAGGCTGGCATAGCCGCGGGTGCGCGATTTCAGTGCGTCGAAGAAGTC

GAAGATGATCTCGCCGAGCGGCATGGTGTAGCGCAGTTCCACCCGCTCGGGGGAGA

GATAGTCCATGCCGCCCAACTCGCCGCGGCGCGACTGGCACAGCTCCATGATGGTG

CCGATGAACTCGCTGGGCGCGATGATGGTGGTCTTGACGACGGGCTCGTAGACCGT

GCGGATCTTGCCCTCCGGCCAGTCCGACGGATTGGTCACCCGGATTTCGGTGCCGTC

GTCTTTGTGCACCCGATACACCACATTGGGTGAGGTCGAGATCAGGTCCAGGCCGA

ACTCGCGCTCAAGGCGCTCACGGGTGATCTCCATGTGCAGCAGGCCCAAGAAACCG

CACCGGAACCCAAAACCCAGCGCCACCGAGGTTTCCGGCTCATAGGTCAAGGCCGC

GTCGTTGAGCTGCAGCTTGTCCAGGGCGTCGCGCAGGTTCGGGTAGTCCGAACCGT

CGACCGGATACAACCCCGAGTAGACCATCGGTTTGGGCTCACGGTAGCCGGTCAAC

GCTTCGGCGGCAGCCCCGCGGGCCCGGGAGAGGCTGGTCACGGTGTCGCCCACCTT

GGACTGGCGGACGTCCTTGACGCCGGTGATCAGGTAACCCACCTCGCCGACACCGA

GGCCCTCACACGGTTTCGGCTCGGGTGAGACGATGCCGACCTCAAGCAGCTCGTGG

GTGGCGCCGGTGGACATCATCATGATGCGCTCACGGGGGCTGATCTTGCCGTCGAC

GACGCGGACGTAGGTCACCACTCCGCGGTAGATGTCGTAAACGGAGTCGAAAATCA

TTGCGCGGGTAGGTGCCTCGGCGTCGCCCTGAGGGGGCGGCACCTGTCGGACCACC

TCGTCGAGCAGGTCGGACACGCCTTCGCCGGTTTTGCCGGACACCCGCAACACCTC

GGCCGGCTCGCAGCCGATGATGTGTGCCATCTCGGCGGCGTAACGGTCCGGGTCGG

CCGCGGGCAGGTCGATCTTGTTGAGCACCGGGATGATGTGCAGGTCGCGGTCCAAC

GCCAGGTAGAGGTTCGCCAGCGTCTGCGCCTCGATGCCTTGCGCGGCATCGACCAA

CAGCACCGCACCCTCGCAAGCCTCCAGCGCACGCGAGACTTCGTAGGTGAAGTCGA

CATGGCCCGGGGTGTCGATCAGATGCAGCACGTAGTCGGTCTTGTCGACCCGCCAG

GGTAGCCGCACATTCTGGGCCTTGATGGTGATGCCGCGTTCCCGCTCGATGTCCATC

CGATCCAAGTACTGGGCCCGCATAGAGCGTTCGTCGACCACGCCGGTGAGCTGCAG

CATCCGGTCGGCCAACGTTGACTTGCCGTGGTCGATGTGGGCGATGATGCAAAAGT

TCCTAATCTGCGCCGGCGCAGTGAAGGTTTTGTCGGCGAAACTGCTGATGGGAATC

TCCTGGAGCGGGGGTTGACGGGTATCCAGGGTATCCGCGTCGGGCAGCTGCGACCC

AATCGCGCTCGGTCGATCGCGTCTATGCTGCGAGCATGGCGTCCGCACGGAAGTCAC

SEQ ID NO 102
>Mycobacterium_tuberculosis_F11
TCACTTCTTGCCTTTGTCCCCGGCGGCATCGGTGGACAATGCCGCGACGAAAGCCTC

CTGTGGCACCTCGACGCGCCCGATGGTCTTCATCCGCTTCTTGCCTTCCTTCTGCTTC

TCCAGCAGCTTGCGTTTGCGCGTGATGTCGCCGCCGTAGCACTTGGACAACACGTCC

TTGCGGATCGCGCGGATGTTTTCGCGGGCAATGATTTTCGATCCGATGGCGGCCTGC

ACCGGCACCTCGAACTGCTGGCGCGGGATCAGCTCCTTGAGTTTGGTGGTCATCTTG

TTGCCGTAGGCATACGCCGTGTCCTTGTGCACGATCGCGCTGAACGCATCCACCGCC

TCGCCCTGCAGCAGGATGTCGACCTTGACCAGCGCGGCCTCCTGTTCGCCGGCCTCC

TCGTAGTCGAGGCTGGCATAGCCGCGGGTGCGCGATTTCAGTGCGTCGAAGAAGTC

GAAGATGATCTCGCCGAGCGGCATGGTGTAGCGCAGTTCCACCCGCTCGGGGGAGA

GATAGTCCATGCCGCCCAACTCGCCGCGGCGCGACTGGCACAGCTCCATGATGGTG

CCGATGAACTCGCTGGGCGCGATGATGGTGGTCTTGACGACGGGCTCGTAGACCGT

-continued

GCGGATCTTGCCCTCCGGCCAGTCCGACGGATTGGTCACCCGGATTTCGGTGCCGTC

GTCTTTGTGCACCCGATACACCACATTGGGTGAGGTCGAGATCAGGTCCAGGCCGA

ACTCGCGCTCAAGGCGCTCACGGGTGATCTCCATGTGCAGCAGGCCCAAGAAACCG

CACCGGAACCCAAAACCCAGCGCCACCGAGGTTTCCGGCTCATAGGTCAAGGCCGC

GTCGTTGAGCTGCAGCTTGTCCAGGGCGTCGCGCAGGTTCGGGTAGTCCGAACCGT

CGACCGGATACAACCCCGAGTAGACCATCGGTTTGGGCTCACGGTAGCCGGTCAAC

GCTTCGGCGGCAGCCCCGCGGGCCCGGGAGAGGCTGGTCACGGTGTCGCCCACCTT

GGACTGGCGGACGTCCTTGACGCCGGTGATCAGGTAACCCACCTCGCCGACACCGA

GGCCCTCACACGGTTTCGGCTCGGGTGAGACGATGCCGACCTCAAGCAGCTCGTGG

GTGGCGCCGGTGGACATCATCATGATGCGCTCACGGGGGCTGATCTTGCCGTCGAC

GACGCGGACGTAGGTCACCACTCCGCGGTAGATGTCGTAAACGGAGTCGAAAATCA

TTGCGCGGGTAGGTGCCTCGGCGTCGCCCTGAGGGGGCGGCACCTGTCGGACCACC

TCGTCGAGCAGGTCGGACACGCCTTCGCCGGTTTTGCCGGACACCCGCAACACCTC

GGCCGGCTCGCAGCCGATGATGTGTGCCATCTCGGCGGCGTAACGGTCCGGGTCGG

CCGCGGGCAGGTCGATCTTGTTGAGCACCGGGATGATGTGCAGGTCGCGGTCCAAC

GCCAGGTAGAGGTTCGCCAGCGTCTGCGCCTCGATGCCTTGCGCGGCATCGACCAA

CAGCACCGCACCCTCGCAAGCCTCCAGCGCACGCGAGACTTCGTAGGTGAAGTCGA

CATGGCCCGGGGTGTCGATCAGATGCAGCACGTAGTCGGTCTTGTCGACCCGCCAG

GGTAGCCGCACATTCTGGGCCTTGATGGTGATGCCGCGTTCCCGCTCGATGTCCATC

CGATCCAAGTACTGGGCCCGCATAGAGCGTTCGTCGACCACGCCGGTGAGCTGCAG

CATCCGGTCGGCCAACGTTGACTTGCCGTGGTCGATGTGGGCGATGATGCAAAAGT

TCCTAATCTGCGCCGGCGCAGTGAAGGTTTTGTCGGCGAAACTGCTGATGGGAATC

TCCTGGAGCGGGGGTTGACGGGTATCCAGGGTATCCGCGTCGGGCAGCTGCGACCC

AATCGCGCTCGGTCGATCGCGTCTATGCTGCGAGCATGGCGTCCGCAC

SEQ ID NO 103
>Mycobacterium_tuberculosis_H37Rv
TCACTTCTTGCCTTTGTCCCCGGCGGCATCGGTGGACAATGCCGCGACGAAAGCCTC

CTGTGGCACCTCGACGCGCCCGATGGTCTTCATCCGCTTCTTGCCTTCCTTCTGCTTC

TCCAGCAGCTTGCGTTTGCGCGTGATGTCGCCGCCGTAGCACTTGGACAACACGTCC

TTGCGGATCGCGCGGATGTTTTCGCGGGCAATGATTTTCGATCCGATGGCGGCCTGC

ACCGGCACCTCGAACTGCTGGCGCGGGATCAGCTCCTTGAGTTTGGTGGTCATCTTG

TTGCCGTAGGCATACGCCGTGTCCTTGTGCACGATCGCGCTGAACGCATCCACCGCC

TCGCCCTGCAGCAGGATGTCGACCTTGACCAGCGCGGCCTCCTGTTCGCCGGCCTCC

TCGTAGTCGAGGCTGGCATAGCCGCGGGTGCGCGATTTCAGTGCGTCGAAGAAGTC

GAAGATGATCTCGCCGAGCGGCATGGTGTAGCGCAGTTCCACCCGCTCGGGGGAGA

GATAGTCCATGCCGCCCAACTCGCCGCGGCGCGACTGGCACAGCTCCATGATGGTG

CCGATGAACTCGCTGGGCGCGATGATGGTGGTCTTGACGACGGGCTCGTAGACCGT

GCGGATCTTGCCCTCCGGCCAGTCCGACGGATTGGTCACCCGGATTTCGGTGCCGTC

GTCTTTGTGCACCCGATACACCACATTGGGTGAGGTCGAGATCAGGTCCAGGCCGA

ACTCGCGCTCAAGGCGCTCACGGGTGATCTCCATGTGCAGCAGGCCCAAGAAACCG

CACCGGAACCCAAAACCCAGCGCCACCGAGGTTTCCGGCTCATAGGTCAAGGCCGC

GTCGTTGAGCTGCAGCTTGTCCAGGGCGTCGCGCAGGTTCGGGTAGTCCGAACCGT

-continued

CGACCGGATACAACCCCGAGTAGACCATCGGTTTGGGCTCACGGTAGCCGGTCAAC

GCTTCGGCGGCAGCCCCGCGGGCCCGGGAGAGGCTGGTCACGGTGTCGCCCACCTT

GGACTGGCGGACGTCCTTGACGCCGGTGATCAGGTAACCCACCTCGCCGACACCGA

GGCCCTCACACGGTTTCGGCTCGGGTGAGACGATGCCGACCTCAAGCAGCTCGTGG

GTGGCGCCGGTGGACATCATCATGATGCGCTCACGGGGGCTGATCTTGCCGTCGAC

GACGCGGACGTAGGTCACCACTCCGCGGTAGATGTCGTAAACGGAGTCGAAAATCA

TTGCGCGGGTAGGTGCCTCGGCGTCGCCCTGAGGGGGCGGCACCTGTCGGACCACC

TCGTCGAGCAGGTCGGACACGCCTTCGCCGGTTTTGCCGGACACCCGCAACACCTC

GGCCGGCTCGCAGCCGATGATGTGTGCCATCTCGGCGGCGTAACGGTCCGGGTCGG

CCGCGGGCAGGTCGATCTTGTTGAGCACCGGGATGATGTGCAGGTCGCGGTCCAAC

GCCAGGTAGAGGTTCGCCAGCGTCTGCGCCTCGATGCCTTGCGCGGCATCGACCAA

CAGCACCGCACCCTCGCAAGCCTCCAGCGCACGCGAGACTTCGTAGGTGAAGTCGA

CATGGCCCGGGGTGTCGATCAGATGCAGCACGTAGTCGGTCTTGTCGACCCGCCAG

GGTAGCCGCACATTCTGGGCCTTGATGGTGATGCCGCGTTCCCGCTCGATGTCCATC

CGATCCAAGTACTGGGCCCGCATAGAGCGTTCGTCGACCACGCCGGTGAGCTGCAG

CATCCGGTCGGCCAACGTTGACTTGCCGTGGTCGATGTGGGCGATGATGCAAAAGT

TCCTAATCTGCGCCGGCGCAGTGAAGGTTTTGTCGGCGAAACTGCTGATGGGAATC

TCCTGGAGCGGGGGTTGACGGGTATCCAGGGTATCCGCGTCGGGCAGCTGCGACCC

AATCGCGCTCGGTCGATCGCGTCTATGCTGCGAGCATGGCGTCCGCAC

SEQ ID NO 104
>M_tuberculosis_H37Ra
TCACTTCTTGCCTTTGTCCCCGGCGGCATCGGTGGACAATGCCGCGACGAAAGCCTC

CTGTGGCACCTCGACGCGCCCGATGGTCTTCATCCGCTTCTTGCCTTCCTTCTGCTTC

TCCAGCAGCTTGCGTTTGCGCGTGATGTCGCCGCCGTAGCACTTGGACAACACGTCC

TTGCGGATCGCGCGGATGTTTTCGCGGGCAATGATTTTCGATCCGATGGCGGCCTGC

ACCGGCACCTCGAACTGCTGGCGCGGGATCAGCTCCTTGAGTTTGGTGGTCATCTTG

TTGCCGTAGGCATACGCCGTGTCCTTGTGCACGATCGCGCTGAACGCATCCACCGCC

TCGCCCTGCAGCAGGATGTCGACCTTGACCAGCGCGGCCTCCTGTTCGCCGGCCTCC

TCGTAGTCGAGGCTGGCATAGCCGCGGGTGCGCGATTTCAGTGCGTCGAAGAAGTC

GAAGATGATCTCGCCGAGCGGCATGGTGTAGCGCAGTTCCACCCGCTCGGGGGAGA

GATAGTCCATGCCGCCCAACTCGCCGCGGCGCGACTGGCACAGCTCCATGATGGTG

CCGATGAACTCGCTGGGCGCGATGATGGTGGTCTTGACGACGGGCTCGTAGACCGT

GCGGATCTTGCCCTCCGGCCAGTCCGACGGATTGGTCACCCGGATTTCGGTGCCGTC

GTCTTTGTGCACCCGATACACCACATTGGGTGAGGTCGAGATCAGGTCCAGGCCGA

ACTCGCGCTCAAGGCGCTCACGGGTGATCTCCATGTGCAGCAGGCCCAAGAAACCG

CACCGGAACCCAAAACCCAGCGCCACCGAGGTTTCCGGCTCATAGGTCAAGGCCGC

GTCGTTGAGCTGCAGCTTGTCCAGGGCGTCGCGCAGGTTCGGGTAGTCCGAACCGT

CGACCGGATACAACCCCGAGTAGACCATCGGTTTGGGCTCACGGTAGCCGGTCAAC

GCTTCGGCGGCAGCCCCGCGGGCCCGGGAGAGGCTGGTCACGGTGTCGCCCACCTT

GGACTGGCGGACGTCCTTGACGCCGGTGATCAGGTAACCCACCTCGCCGACACCGA

GGCCCTCACACGGTTTCGGCTCGGGTGAGACGATGCCGACCTCAAGCAGCTCGTGG

-continued

GTGGCGCCGGTGGACATCATCATGATGCGCTCACGGGGGCTGATCTTGCCGTCGAC

GACGCGGACGTAGGTCACCACTCCGCGGTAGATGTCGTAAACGGAGTCGAAAATCA

TTGCGCGGGTAGGTGCCTCGGCGTCGCCCTGAGGGGGCGGCACCTGTCGGACCACC

TCGTCGAGCAGGTCGGACACGCCTTCGCCGGTTTTGCCGGACACCCGCAACACCTC

GGCCGGCTCGCAGCCGATGATGTGTGCCATCTCGGCGGCGTAACGGTCCGGGTCGG

CCGCGGGCAGGTCGATCTTGTTGAGCACCGGGATGATGTGCAGGTCGCGGTCCAAC

GCCAGGTAGAGGTTCGCCAGCGTCTGCGCCTCGATGCCTTGCGCGGCATCGACCAA

CAGCACCGCACCCTCGCAAGCCTCCAGCGCACGCGAGACTTCGTAGGTGAAGTCGA

CATGGCCCGGGGTGTCGATCAGATGCAGCACGTAGTCGGTCTTGTCGACCCGCCAG

GGTAGCCGCACATTCTGGGCCTTGATGGTGATGCCGCGTTCCCGCTCGATGTCCATC

CGATCCAAGTACTGGGCCCGCATAGAGCGTTCGTCGACCACGCCGGTGAGCTGCAG

CATCCGGTCGGCCAACGTTGACTTGCCGTGGTCGATGTGGGCGATGATGCAAAAGT

TCCTAATCTGCGCCGGCGCAGTGAAGGTTTTGTCGGCGAAACTGCTGATGGGAATC

TCCTGGAGCGGGGGTTGACGGGTATCCAGGGTATCCGCGTCGGGCAGCTGCGACCC

AATCGCGCTCGGTCGATCGCGTCTATGCTGCGAGCATGGCGTCCGCAC

SEQ ID NO 105
>Mycobacterium_tuberculosis_CDC1551
TCACTTCTTGCCTTTGTCCCCGGCGGCATCGGTGGACAATGCCGCGACGAAAGCCTC

CTGTGGCACCTCGACGCGCCCGATGGTCTTCATCCGCTTCTTGCCTTCCTTCTGCTTC

TCCAGCAGCTTGCGTTTGCGCGTGATGTCGCCGCCGTAGCACTTGGACAACACGTCC

TTGCGGATCGCGCGGATGTTTTCGCGGGCAATGATTTTCGATCCGATGGCGGCCTGC

ACCGGCACCTCGAACTGCTGGCGCGGGATCAGCTCCTTGAGTTTGGTGGTCATCTTG

TTGCCGTAGGCATACGCCGTGTCCTTGTGCACGATCGCGCTGAACGCATCCACCGCC

TCGCCCTGCAGCAGGATGTCGACCTTGACCAGCGCGGCCTCCTGTTCGCCGGCCTCC

TCGTAGTCGAGGCTGGCATAGCCGCGGGTGCGCGATTTCAGTGCGTCGAAGAAGTC

GAAGATGATCTCGCCGAGCGGCATGGTGTAGCGCAGTTCCACCCGCTCGGGGGAGA

GATAGTCCATGCCGCCCAACTCGCCGCGGCGCGACTGGCACAGCTCCATGATGGTG

CCGATGAACTCGCTGGGCGCGATGATGGTGGTCTTGACGACGGGCTCGTAGACCGT

GCGGATCTTGCCCTCCGGCCAGTCCGACGGATTGGTCACCCGGATTTCGGTGCCGTC

GTCTTTGTGCACCCGATACACCACATTGGGTGAGGTCGAGATCAGGTCCAGGCCGA

ACTCGCGCTCAAGGCGCTCACGGGTGATCTCCATGTGCAGCAGGCCCAAGAAACCG

CACCGGAACCCAAAACCCAGCGCCACCGAGGTTTCCGGCTCATAGGTCAAGGCCGC

GTCGTTGAGCTGCAGCTTGTCCAGGGCGTCGCGCAGGTTCGGGTAGTCCGAACCGT

CGACCGGATACAACCCCGAGTAGACCATCGGTTTGGGCTCACGGTAGCCGGTCAAC

GCTTCGGCGGCAGCCCCGCGGGCCCGGGAGAGGCTGGTCACGGTGTCGCCCACCTT

GGACTGGCGGACGTCCTTGACGCCGGTGATCAGGTAACCCACCTCGCCGACACCGA

GGCCCTCACACGGTTTCGGCTCGGGTGAGACGATGCCGACCTCAAGCAGCTCGTGG

GTGGCGCCGGTGGACATCATCATGATGCGCTCACGGGGGCTGATCTTGCCGTCGAC

GACGCGGACGTAGGTCACCACTCCGCGGTAGATGTCGTAAACGGAGTCGAAAATCA

TTGCGCGGGTAGGTGCCTCGGCGTCGCCCTGAGGGGGCGGCACCTGTCGGACCACC

TCGTCGAGCAGGTCGGACACGCCTTCGCCGGTTTTGCCGGACACCCGCAACACCTC

GGCCGGCTCGCAGCCGATGATGTGTGCCATCTCGGCGGCGTAACGGTCCGGGTCGG

-continued

CCGCGGGCAGGTCGATCTTGTTGAGCACCGGGATGATGTGCAGGTCGCGGTCCAAC

GCCAGGTAGAGGTTCGCCAGCGTCTGCGCCTCGATGCCTTGCGCGGCATCGACCAA

CAGCACCGCACCCTCGCAAGCCTCCAGCGCACGCGAGACTTCGTAGGTGAAGTCGA

CATGGCCCGGGGTGTCGATCAGATGCAGCACGTAGTCGGTCTTGTCGACCCGCCAG

GGTAGCCGCACATTCTGGGCCTTGATGGTGATGCCGCGTTCCCGCTCGATGTCCATC

CGATCCAAGTACTGGGCCCGCATAGAGCGTTCGTCGACCACGCCGGTGAGCTGCAG

CATCCGGTCGGCCAACGTTGACTTGCCGTGGTCGATGTGGGCGATGATGCAAAAGT

TCCTAATCTGCGCCGGCGCAGTGAAGGTTTTGTCGGCGAAACTGCTGATGGGAATC

TCCTGGAGCGGGGGTTGACGGGTATCCAGGGTATCCGCGTCGGGCAGCTGCGACCC

AATCGCGCTCGGTCGATCGCGTCTATGCTGCGAGCATGGCGTCCGCAC

SEQ ID NO 106
>Mycobacterium_avium_subsp_Paratuberculosis_str_k10
TTACTTCTTGGATTTGTCGCCCGCGGCGTCGGCGGACAGCGCGGCGACGAACGCCT

CCTGCGGCACGTCGACCCGGCCGATGGTCTTCATCCGCTTCTTGCCCTCCTTCTGCTT

TTCCAGAAGTTTGCGCTTGCGGGTGATGTCACCGCCGTAACACTTGGACAGCACGT

CCTTGCGGATGGCCCGAATGTTCTCGCGGGCAATGATTTTCGAGCCGATCGCGGCCT

GGACGGGCACCTCGAACTGCTGGCGCGGGATCAGCTCCTTGAGCTTGGTGGTCATC

TTGTTGCCGTACGCGAACGCCGCATCCTTGTGCACGATCGCGCTGAACGCGTCGAC

GGCCTCCCCCTGCAACAGGATGTCCACCTTGACCAGCTGGGCCTCCTGCTCGCCGGC

CTCCTCGTAGTCCAGGCTGGCGTAGCCGCGGGTCCGCGACTTCAGCGAGTCGAAGA

AGTCGAAGATGATCTCGCCCAACGGCATGGTGTAGCGCAGCTCAACCCGTTCCGGC

GACAGGTAATCCATGCCGCCCAGCTCGCCGCGGCGGGACTGGCACAGCTCCATGAT

GGTGCCGATGAATTCGCTGGGCGCGATGATGGTGGTCTTGACCACCGGCTCGTACA

CCGTGCGCACCTTGCCCTCGGGCCAGTCCGACGGGTTGGTCACCACGATCTCGGTG

CCGTCCTCTTTGATCACCCGGTACACCACGTTGGGCGACGTCGAGATCAGGTCGAG

GTCGAACTCGCGCTCCAGGCGCTCGCGGGTGATCTCCATGTGCAGCAAACCCAAAA

AGCCACAACGGAATCCGCAGCCCAGCGCCACCGATGTCTCCGGTTCGTAGGTGAGC

GCGGCGTCGTTGAGCCGCAGCCGGTCCAGCGCGTCGCGCAGATCCGGATAGTCCGA

GCCGTCCACCGGATACAGACCCGAATAGACCATCGGCTTGGGTTCGCGGTATCCGG

TCAGCGCCTCTTGCGCGCCGTGGCGCGCGCTGGTGACGGTGTCGCCCACTTTGGACT

GGCGGACGTCCTTCACCCCGGTGATCAGGTAGCCCACCTCGCCGACGCCAAGGCCG

TCGCTGGCCTTCGGCTCGGGTGAGACGATGCCGACCTCGAGCAGTTCGTGGGTGGC

GCCGGTGGACATCATCGCGATGCGTTCGCGCGGGGTGATCTTGCCGTCGACCACCC

GCACGTAGGTCACCACGCCGCGGTAGATGTCGTAGACCGAGTCGAAGATCATCGCG

CGCAGCGGCGCATCGGCCTGCCCCTGCGGCGGCGGCACCTGGCGCACCACCTCGTC

GAGCAGCCGCGCCACGCCCTCCCCGGTTTTGCCGGACACCCACAGCACGTCGTCGG

GTTCGCACCCGATGATGTGGGCGAGCTCGCCGGCGTAGCGATCCGGGTCGGCGGCC

GGCAGGTCGATCTTGTTGAGGACCGGGATGATGGTCAGATCGCGGTCCAGCGCCAG

GTAGAGGTTGGCCAGCGTCTGGGCCTCGATGCCCTGCGCGGCGTCGACCAGCAGCA

CGGCACCTTCGCAGGCCTCCAGTGCGCGCGACACCTCGTAGGTGAAGTCGACGTGG

CCCGGGGTGTCGATCAGGTGCAGGACAAATTCTTTGCCGGCGTCCTCGCCGCCGGA

-continued

GACCTGCCAGGGCAGCCGCACGTTCTGCGCCTTGATGGTGATGCCGCGCTCCCGCT

CGATGTCCATCCGGTCCAGGTACTGGGCGCGCATCGACCGCTCGTCGACGACGCCG

GTGAGCTGCAGCATCCGGTCGGCCAGCGTCGACTTGCCGTGATCGATGTGGGCGAT

GATGCAGAAGTTGCGAATCTGCGCCGGCGCGGTGAAGGTCTTGTCGGCGAAACTGC

TGATGGGTATCTCCTGGTCCGGGCCTGCTAGACGGCGGTTCGCAAGTGTGTCCAGC

GTATCGGCGCGGCCGGACTGCGGCACAATCGGCGCGTCTATGCTGCGAATATGGCG

TCCGGCCGGAAGTCGCAG

SEQ ID NO 107
>Mycobacterium_leprae_cosmid_B1937
TTATTTCTTGTCCTTGTCTCCTGCGGCATCGGCGGACAACGCGGCGACAAACGCTTC

CTGCGGCACCTCGACCCGCCCAATGGTCTTCATCCGTTTCTTGCCTTCCTTCTGCTTT

TCCAGAAGCTTACGTTTGCGGGTGATATCGCCGCCATAACATTTCGACAGCACATCC

TTGCGTATCGCCCTAATATTTTCGCGCGCAATGACTTTCGATCCAATAGCCGCCTGT

ACTGGCACCTCAAACTGCTGACGTGGGATCAGTTCTTTGAGCTTGTTGGTCATCTTG

TTGCCATAGGCAGAGGCTGAATCCTTGTGCACAATCGCGCTGAATGCGTCGACGGC

CTCGCCTTGCAGCAGGATGTCAACCTTGACCAGTTGGGCCTCCTGCTCGCCAGCCTC

CTCATAGTCGAGGCTAGCGTAGCCCCGGGTGCGTGACTTCAGCGAATCGAAGAAAT

CGAAGATGATTTCCCCGAGCGGCATAATGTAGCGTAACTCGACTCGCTCAGGTGAA

AGATAGTCCATGCCACCTAATTCGCCACGGCGCGACTGGCACAGCTCCATGATCGT

TCCGATGAACTCGCTGGGCGCAATGATGGTGATCTTCACCACTGGCTCGTACACCGT

TCGGATCTTGCCCTCCGGCCAGTCTGACGGGTTGGTCACCACAATCTCGGTGTTATC

TTCTGTCACCACACGGTATACGACGTTGGGCGACGTGGAGATCAGGTCCAGGTCGA

ACTCGCGCTCTAAGCGTTCGCGGGTTATATCTATGTGCAGCAAACCGAGGAAGCCG

CACCGGTACCCAACGCCCAGCGCCACCGATGTTTCCGGCTCGTAGGTCAGCGCCGC

GTCGTTGAGCTGTAACTTACCTAGAGCGTCACGCAAACTCGGGTAGTCCGAACTGT

CGACGGGATACAGCCCGGAGTACACCATGGGCTTGGGTTCTCGGTAGCCAGTTAAC

GGTTCAGTGGCACCATAACGAACCGTCGTTACAGTGTCGCCGACTTTGGATTGGCG

GACGTCTTTAACCCCAGTAATCAGGTAGCCCACCTCCCCCACGCCCAGGCCCGCGC

TGGCCTTCGGTTCAGGCGACACGATGCCGACCTCGAGCAGTTCGTACGTCGCACCG

GTGGACATCATCGCGATGCGCTCACGCGGGCTGATCTTGCCGTCGACCACACGGAC

GTAGGTGACCACGCCTCGGTAGATGTCGTAGACGGAGTCGAAGATCATCGCGCGGG

TAGGCGCATCAGGGTCACCTTGCGGATGCGGCACCCGACGGACCACCTCGTCAAGA

AGGTCAGAAACCCCCTCGCCGGTTTTGCCGGACACCCGAAGCACATCGCCTGACTC

ATAACCAATGATGTGGGCGATCTCAGCGGCGTAACGGTCCGGATCGGCAGCCGGCA

GGTCGATTTTGTTTAGCACCGGAATAATCGTCAAGTCACGCTCCAGAGCGAGATAG

AGATTGGCCAAGGTCTGAGCTTCGATGCCCTGGACGGCGTCTACCAGCAGCACCGC

ACCCTCACAGGCTTCCAATGCTCGCGATACCTCGTAGGTGAAGTCCACATGGCCGG

GGGTGTCGATCAAGTGCAACACATAATTCTCAGTCGTCCCACCAGCTGTGACACTC

CAAGACAGCCGCACGTTCTGCGCTTTAATCGTGATTCCGCGCTCACGTTCGATGTCC

ATCCGGTCCAGGTACTGGGCACGCATCGACCGCTCATCGACGACACCAGTCAGCTG

AAGCATCCGGTCCGCCAGCGTGGATTTGCCGTGATCAATATGAGCGATTATGCAGA

AGTTCCTAATCTGCGCCGGCGCGGTAAAGGTCTTGTCAGCGAAACTGCTGATGGGA

-continued

ATCTCCTGGGCTCCAGTTACTAGAGAATGTTTGAACGGCGATTCGCCGGTGTCCGGC

TTATCCACGCGAAGTGACCAAGACAC

SEQ ID NO 108
>Mycobacterium_smegmatis_str._MC2_155
CTACTTCTTGGGCTTGTCGCCCGCCGCGTCGGTGGACAGCGCCGCGACGAATGCCTC

CTGCGGCACGTCGACCCGGCCGATCGTCTTCATGCGCTTCTTGCCCTCTTTCTGCTTC

TCGAGCAGCTTGCGCTTACGGGTGATGTCACCGCCGTAGCACTTCGAGAGCACGTC

CTTGCGGATGGCCCGGATGTTTTCGCGCGCAATGATTCTCGAGCCGATCGCGGCCTG

CACCGGGACCTCGAACTGCTGTCGCGGGATCAGTTCTTTGAGCTTGGAGGTCATCTT

GTTGCCGTAGGCCGACGCACCGTCCTTGTGGACGATAGCCGAGAACGCGTCGACGG

CCTCGCCCTGCAGCAGGATGTCGACCTTGACCAGATCGGCCTCCTGCTCACCGGCCT

CCTCGTAGTCGAGGCTCGCGTAGCCGCGGGTGCGGGACTTCAGCGAGTCGAAGAAG

TCGAAGATGATCTCGCCCAACGGCATGATGTAGCGCAGTTCGACACGCTCGGGCGA

CAGGTAGTCCATGCCCTGCAGTTCGCCGCGACGGGACTGGCACAGCTCCATGATGG

TGCCGATGAACTCGCTGGGCGCGATGATCGTGGTCTTCACGACGGGCTCGAACACC

GTGCGGATCTTGCCTTCCGGCCAGTCCGACGGGTTCGTCACGACCTTCTCGGAACCG

TCGTCCTGCACGACGCGGTACACCACGTTGGGTGAGGTGGAGATCAGGTCCAGGCC

GAACTCGCGCTCCAGGCGTTCACGGGTGATCTCCATGTGCAGCAGTCCGAGGAAGC

CGCAGCGGAACCCGAAGCCCAGGGCCACCGAGGTCTCCGGCTCATACGTCAGTGCG

GCGTCGTTGAGTTGCAGCTTGTCCAGCGCGTCACGCAGATCCGGGTAGTCCGAACC

GTCGACGGGATACAGGCCCGAGTACACCATCGGCTTGGGCTCGCGATAACCCGTGA

GCGCCTCGGTCGCGCCCTTGCGCGCCGTGGTCACCGTGTCACCGACCTTCGACTGGC

GGACGTCCTTCACACCCGTGATCAGGTAACCGACCTCACCGACGCCCAGGCCCGCA

CTGGCCTTCGGTTCCGGTGAGACGATGCCGACCTCGAGCAGTTCATGGGTGGCGCC

GGTGGACATCATCGCGATGCGTTCGCGCGGCACGATCTTGCCGTCGACCACACGGA

CGTAGGTCACCACGCCGCGGTAGATGTCGTACACGGAGTCGAAGATCATCGCGCGC

GTCGGGGCGTCGGGGTCACCGACCGGCGGCGGCACCTTACGCACCACCTCGTCGAG

CAGCTCGGCCACGCCTTCGCCGGTCTTGCCCGAGACACGCAGCACGTCCGACGGCT

CACACCCGATGATGTGGGCGAGCTCGTCGGCATAGCGGTCCGGGTCAGCGGCGGGC

AGGTCGATCTTGTTGAGCACCGGGATGATCGCCAGGTCGCGGTCCAGCGCCAGGTA

CAGGTTGGCCAGCGTCTGCGCCTCGATGCCCTGCGCCGCGTCGACCAGCAGCACCG

CGCCCTCGCAGGCCTCCAGCGCGCGCGACACCTCGTAGGTGAAGTCGACGTGGCCC

GGGGTGTCGATCAGGTGCAGCACGTAATCACCCGCGTCCGCGCCGTCTTGGCCGTC

CTTCAGCGTCCACGGAAGCCGGACGTTCTGAGCCTTGATGGTGATCCCGCGCTCAC

GTTCGATGTCCATGCGGTCGAGGTACTGGGCCCGCATCGACCGCTCATCGACAACA

CCGGTGAGCTGCAGCATCCGGTCGGCCAGCGTCGACTTGCCGTGGTCGATGTGGGC

GATGATGCAGAAGTTCCGAATCTGCGCCGGCGCAGTGAACGTCTTGTCGGCGAAGC

TGCTGATGGGAATCTCCTGGTGAGCGTGGGTCAAGCGCAC

SEQ ID NO 109
>Mycobacterium_ulcerans_Agy99
CTACTTCTTGCCCTTATCCCCCGCGGCGTCGGTGGACAGTGCCGCGACAAACGCCTC

CTGCGGCACCTCGACCCGGCCGATGGACTTCATCCGCTTCTTGCCCTCTTTCTGCTTT

-continued

TCCAGCAGCTTGCGTTTGCGGGTGATGTCACCGCCGTAGCACTTCGACAACACATCC

TTGAGGATCGCGCGGATGTTCTCGCGCGCGATGATCTTGGAACCGATGGCCGCCTG

CACCGGCACCTCGAACTGCTGACGCGGAATCAGCTCCTTGAGCTTGGTGGTCATCTT

GTTGCCGTAGGCGAACGCCGAATCCTTGTGGACGATAGCGCTGAACGCATCGACGG

CCTCGCCTTGCAGCAGGATGTCGACCTTGACCAGTTGGGCTTCCTGCTCGCCGGACT

CCTCGTAATCGAGACTGGCGTAGCCACGGGTCCGCGATATGAGCGAGTCGAAGAAG

TCAAAGATGATCTCCCCCAACGGCATTGTGTATCGCAGTTCCACCCGTTCGGGCGAC

AAATAGTCCATGCCCCCCAGCTCGCCGCGCCGCGACTGGCACAGCTCCATGATGGT

GCCGATGAATTCGCTGGGCGCGATGATGGTGGTCTTCACCACCGGCTCGTAGACGG

TGCGGATCTTGCCCTCGGGCCAGTCCGACGGGTTGGTCACCTGCATTTCGGTGCCGT

CGTCCTTGATGACGCGGTACACGACGTTGGGCGAGGTCGAGATCAGGTCGAGGTCG

AACTCGCGCTCCAGACGTTCCCGACTGATCTCCATGTGCAGCAGGCCCAGGAAGCC

GCACCGGAATCCGAAACCCAGCGCCACCGACGTTTCGGGCTCATAGGTCAGGGCCG

CGTCGTTGAGCTGCAGCTTGTCCAGGGCGTCCCGCAGGTTCGGATAGTCCGATCCGT

CAACGGGATACAGTCCCGAATACACCATCGGCTTGGGTTCGCGGTAGCCGGTCAGT

GCCTCGGTGGCACCTTTTCGGGCGGTCGTGACGGTGTCGCCGACCTTGGACTGCCAC

ACGTCCTTGACCCCGGTGATAAGATAACCCACCTCGCCGACACCAAGGCCGTCGCT

GGCCTTGGGTTCGGGTGAGACGATGCCGACCTCGAGCAGTTCGTGGGTGGCGCCGG

TGGACATCATGGCGATGCGCTCGCGGGGGGTGATCTTGCCGTCGACGACGCGGACG

TAGGTGACCACACCGCGGTAGATGTCATAGACGGAGTCGAAGATCATTGCGCGAGT

GGGTGCGTCGGCATCGCCCTGCGGTGGCGGCACCTCGCGCACCACGTGGTCGAGCA

GGTCTGCGACGCCTTCCCCGGTTTTGCCGGAAACCCGCAGCACGTCGCCGGGCTCG

CAGCCGATGATGTGAGCAATCTCGCCCGCGTAGCGGTCCGGGTCGGCGGCCGGCAG

GTCGATCTTGTTCAGCACCGGAATGATGTGCAGGTCGCGGTCCAGTGCCAGGTAGA

GGTTGGCCAGCGTCTGGGCCTCGATGCCCTGGGCGGCGTCAACCAGCAGCACCGCG

CCCTCGCAGGCCTCCAGCGCACGTGACACCTCGTAGGTGAAGTCGACGTGTCCTGG

CGTGTCGATGAGATGCAGGACGTACTCGGTTCCATCGAGCTGCCAGGGCAGCCGCA

CATTCTGCGCCTTGATGGTGATCCCGCGTTCGCGTTCGATATCCATCCGGTCCAGGT

ACTGGGCCCGCATCGAGCGCTCGTCAACGACCCCGGTCAACTGCAGCAT

SEQ ID NO 110
>Mycobacterium_avium_104
TTACTTCTTGGATTTGTCGCCCGCGGCGTCGGCGGACAGCGCCGCGACGAACGCCT

CCTGCGGCACGTCGACCCGGCCGATGGTCTTCATCCGCTTCTTGCCCTCCTTCTGCTT

TTCCAGAAGTTTGCGCTTACGGGTGATGTCACCGCCGTAACACTTGGACAGCACGT

CCTTGCGGATGGCCCGAATGTTCTCGCGGGCAATGATTTTCGAGCCGATCGCGGCCT

GGACGGGCACCTCGAACTGCTGACGGGGGATCAGCTCCTTGAGCTTGGTGGTCATC

TTGTTGCCGTAGGCGAACGCCGCATCCTTGTGCACGATCGCGCTGAACGCGTCGAC

GGCCTCCCCCTGCAACAGGATGTCCACCTTGACCAGCTGGGCCTCCTGCTCGCCGGC

CTCCTCGTAGTCCAGGCTGGCGTAGCCGCGGGTCCGCGACTTCAGCGAGTCGAAGA

AGTCGAAGATGATCTCGCCCAACGGCATGGTGTAGCGCAGCTCGACCCGTTCCGGC

GACAGGTAATCCATGCCGCCCAGCTCGCCGCGGCGGGACTGGCACAGCTCCATGAT

GGTGCCGATGAATTCGCTGGGCGCGATGATGGTGGTCTTGACCACCGGCTCGTACA

-continued

CCGTGCGCACCTTGCCCTCGGGCCAGTCCGACGGGTTGGTCACCACGATCTCGGTG

CCGTCCTCTTTGATCACCCGGTACACCACGTTGGGCGACGTCGAGATCAGGTCGAG

GTCGAACTCGCGCTCCAGGCGCTCGCGGGTGATCTCCATGTGCAGCAAACCCAAAA

AGCCGCAACGGAATCCGAAGCCCAGCGCCACCGACGTCTCCGGTTCGTAGGTGAGC

GCGGCGTCGTTGAGCCGCAGCCGGTCCAGCGCGTCGCGCAGATCCGGATAGTCCGA

GCCGTCCACCGGATACAGACCCGAATAGACCATCGGCTTGGGTTCGCGATATCCGG

TCAGCGCCTCTTGCGCGCCGTGGCGCGCGCTGGTCACGGTGTCGCCCACTTTGGACT

GGCGGACGTCCTTCACCCCGGTGATCAGGTAGCCCACCTCGCCGACGCCCAGGCCG

TCGCTGGCCTTCGGCTCGGGTGAGACGATGCCGACTTCGAGCAGTTCGTGGGTGGC

GCCGGTGGACATCATCGCGATGCGTTCGCGCGGGGTGATCTTGCCGTCGACCACCC

GCACGTAGGTCACCACGCCGCGGTAGATGTCGTAGACCGAGTCGAAGATCATCGCG

CGCAGCGGCGCATCGGCCTGCCCCTGCGGCGGCGGCACCTGGCGCACCACCTCGTC

GAGCAGCCGCGCCACGCCCTCCCCGGTTTTGCCGGACACCCGCAGCACGTCGTCGG

GTTCGCACCCGATGATGTGGGCGAGCTCGCCGGCGTACCGGTCCGGGTCGGCGGCC

GGCAGGTCGATCTTGTTGAGGACCGGGATGATGGTCAGATCGCGGTCCAGCGCCAG

GTAGAGGTTGGCCAGCGTCTGGGCCTCGATGCCCTGCGCGGCGTCGACCAGCAGCA

CGGCACCTTCGCAGGCCTCCAGTGCGCGCGACACCTCGTAGGTGAAGTCGACGTGG

CCCGGGGTGTCGATCAGGTGCAGGACAAATTCTTTGCCGGCGTCCTCGCCGCCGGA

GACCTGCCAGGGCAGCCGCACGTTCTGCGCCTTGATGGTGATGCCGCGCTCCCGCT

CGATGTCCATCCGGTCCAGGTACTGGGCGCGCATCGACCGCTCGTCGACGACGCCG

GTGAGCTGCAGCATCCGGTCGGCCAGCGTCGACTTGCCGTGATCGATGTGGGCGAT

GATGCAGAAGTTGCGAATCTGCGCCGGCGCGGTGAAGGTCTTGTCGGCGAAACTGC

TGATGGGTATCTCCTGGTCCGGGCCTGCTAGACGGCGGTTCGCAAGTGTGTCCAGC

GTATCGGCGCGGCCGGACTGCGGCAC

SEQ ID NO 111
>Mycobacterium_vanbaalenii_PYR-1
TCATTTCTTCGGCTTGTCCGCGGTGGATTCGGTGGACAGCGCGGCGACGAAGGCCT

CCTGCGGGACGTCGACCCGGCCGATGGTCTTCATCCGCTTCTTGCCTTCCTTCTGCTT

TTCCAGCAGCTTGCGCTTACGGGTGATGTCACCGCCGTAGCACTTGGACAGCACAT

CCTTGCGGATCGCCCGAATGTTCTCGCGGGCAATGATTCTCGAGCCGACGGCGGCC

TGCACGGGCACCTCGAACTGCTGGCGCGGGATGAGCTCCTTGAGCTTGGTGGTCAT

CTTGTTGCCGTAGGCCGAGGCCCCGTCCTTGTGCACGATCGCCGAGAACGCGTCGA

CGGCCTCGCCCTGCAGCAGGATGTCGACCTTGACCAGGTCGGCCTCCTGCTCGCCTG

CCTCCTCGTAGTCCAGGCTGGCGTAGCCGCGGGTGCGCGATTTCAGCGAGTCGAAG

AAGTCGAAGATGATCTCGCCCAGCGGCATGGTGTAGCGCAGCTCGACGCGCTCGGG

CGACAGGTAGTCCATTCCGCCGAGTTCACCGCGCCGCGACTGGCACAGCTCCATGA

TCGTGCCGATGAACTCGCTGGGCGCGATCACCGTCGTCTTGACCACCGGCTCGAAC

ACCGATCGCACCTTGCCCTCGGGCCAGTCCGAGGGGTTGGTGACGATGATCTCGGA

CCCGTCGTCCTTGACGACGCGGTAGACCACGTTGGGCGCGGTCGAGATCAGGTCCA

GGTTGAACTCGCGCTCCAGGCGTTCCCGGGTGATCTCCATGTGCAGCAGCCCGAGG

AACCCGCAGCGGAACCCGAACCCGAGCGCCACCGACGTCTCGGGTTCGTACGTCAG

-continued

CGCCGCGTCGTTGAGTTGCAGCTTGTCCAGCGCCTCGCGCAGCACCGGGTAGTCCG

AGCCGTCGACCGGATACAGGCCCGAGTAGACCATCGGCCTGGGCTCCCGGTAGCCG

GTCAACGCTTCCTTGGCACCGTTACGCGCCGTCGTCACCGTGTCGCCGACCTTGGAC

TGGCGCACGTCCTTCACACCGGTGATGAGGTAGCCGACCTCGCCGACGCCGAGGCC

GTCGGAGGGCTTGGGCTCGGGTGAGACGATTCCCACCTCGAGCAGTTCGTGGGTGG

CGCCGGTCGACATCATCGCGATGCGCTCGCGCGGGGTGATCTTCCCGTCCACCACC

CGCACGTAGGTCACCACGCCGCGGTAGATGTCGTAGACCGAGTCGAAGATCATCGC

GCGGGCAGGCGCGTCCGGGTCGCCCTGCGGCGCCGGGATCTCCCGCACCACGTGGT

CGAGCAGCTCGGCCACACCCTCACCCGTCTTGCCCGACACCCGCAACACGTCCTCG

GGCTCGCAGCCGATGATGTGGGCGATCTCGGCGGCGTACCGGTCCGGGTCTGCGGC

GGGCAGATCGATCTTGTTCAGCACCGGGATGATCGTCAGGTCGCGGTCCAGCGCCA

GATACAGGTTCGCCAGCGTCTGCGCTTCGATGCCCTGGGCGGCGTCGACCAGCAGC

ACCGCGCCCTCGCACGCCTCCAGCGCGCGGGACACCTCATAGGTGAAATCAACATG

GCCGGGCGTGTCAATCAAATGCAGCACGAACTCCTCACCGTTGACCACCCACGGCA

GCCGCACGTTCTGCGCCTTGATCGTGATCCCGCGCTCACGCTCGATGTCCATCCGGT

CCAGGTACTGCGCCCGCATCGAGCGCTCGTCGACCACACCGGTGAGCTGCAGCATC

CGGTCGGCCAGGGTGGACTTTCCGTGGTCGATGTGGGCGATGATGCAGAAGTTCCG

AATCTGCGCCGGCGCAGTGAACGTCTTGTCGGCGAAGCTGCTGATGGGAATCTCCT

GGTGAGCGGGTCGTGGCGGCCTGAACAGGCCTGTCCAGAGTATCGAGCGCACACCC

CCGCGACACAATCGAGCCGTGATCGAGGCGGCTTCGGGGCACCGGGGCAC

SEQ ID NO 112
>Mycobacterium_gilvum_PYR-GCK
CTACTTCTTCGGCTTGTCCGCGGCGGACTCGGTCGACAGTGCCGCGACGAAGGCCT

CCTGCGGCACCTCGACCCGGCCGATCGTCTTCATCCGCTTCTTGCCTTCCTTCTGCTT

CTCCAGCAGCTTGCGCTTACGAGTGATGTCACCGCCGTAGCACTTCGACAGCACGT

CCTTGCGGATCGCCCGGATGTTCTCTCGCGCAATGATTCTCGAGCCGATCGCGGCCT

GCACGGGCACCTCGAACTGCTGGCGTGGGATCAGTTCCTTCAGCTTGGTCGTCATCT

TGTTGCCGTACGCCGCGGCACCGTCCTTGTGGACGATGGCGCTGAACGCGTCGACG

GCTTCGCCCTGCAGCAGGATGTCGACCTTGACCAGGTCGGCCTCCTGCTCGCCCGCC

TCCTCGTAGTCGAGGCTCGCGTAGCCGCGGGTGCGGGACTTCAGCGAGTCGAAGAA

GTCGAAGATGATCTCGCCCAGCGGCATCGTGTAGCGCAGCTCGACCCGCTCGGGTG

ACAGGTAGTCCATGCCGCCGAGCTCGCCACGGCGCGACTGGCACAGCTCCATGATC

GTTCCGATGAACTCACTCGGCGCGATCACCGTCGTCTTGACGACCGGCTCGAACAC

CGAACGGACCTTGCCCTCGGGCCAGTCCGACGGGTTGGTGACCGTGAGCTCGCTGT

TGTCCTCTTTGATGACGCGGTAGACGACGTTGGGCGCGGTCGAGATCAGGTCGAGG

TTGAACTCGCGTTCGAGCCGCTCGCGCGTGATCTCCATGTGCAGCAAGCCCAGGAA

GCCGCAGCGGAAGCCGAACCCGAGCGCGACCGACGTCTCCGGCTCGTAAGTCAGTG

CCGCGTCGTTCAGCTGCAGTTTGTCGAGCGCCTCGCGCAACACCGGGTAGTCGGAA

CCGTCCACGGGATACAGGCCCGAGTAGACCATCGGCTTGGGCTCGCGGTAGCCGGT

CAGCGCTTCGGTGGCACCCTTGCGTGCCGTCGTCACCGTGTCGCCGACCTTGGACTG

ACGCACGTCCTTCACGCCGGTGATCAGGTAGCCGACCTCGCCGACACCGAGACCGA

CCGAAGGCTTGGGGTCCGGCGAGACGATGCCCACTTCGAGGAGTTCGTGCGTCGCG

-continued

CCGGTCGACATCATCGCGATGCGCTCACGCGGGGTGATCCTGCCGTCGACGACGCG

CACATAGGTGACGACGCCGCGGTAGATGTCGTACACCGAGTCGAAGATCATCGCGC

GCGCCGGAGCGTCCGGGTCGCCCTGCGGCGGCGGGATCTCCCGGACGACGTGGTCG

AGCAGGTCGCCGACGCCGGCGCCGGTCTTGCCCGACACCCGCAGCACATCCTCCGG

TTCGCAGCCGATGATGTGCGCGATCTCACCGGCGTAGCGGTCGGGGTCGGCGGCGG

GCAGGTCGATCTTGTTGAGCACCGGGATGATTGTCAGGTCGCGATCCAGCGCCAGG

TACAGGTTCGCCAGGGTCTGCGCCTCGATGCCCTGGGCGGCGTCGACCAGCAGCAC

CGCACCCTCGCAGGCCTCCAGCGCGCGCGACACCTCGTAGGTGAAATCGACGTGGC

CAGGGGTGTCGATCAGATGCAGGACGAACTCTTCGCCGTTGACGACCCACGGCAGG

CGCACGTTCTGCGCCTTGATCGTGATGCCGCGTTCCCGCTCGATGTCCATCCGGTCC

AGGTACTGCGCCCGCATGTCCCTGTCCGCGACCACACCGGTGAGCTGCAGCATCCG

ATCGGCCAGGGTGGACTTGCCGTGGTCGATGTGGGCGATGATGCAGAAGTTCCTGA

TCTGCGCCGGCGCAGTGAACGTCTTGTCGGCGAAGCTGGCGATGGGAATCTCCTGG

TGAGCGGGGTCTGTCGGCCTGAGCAGGCCAGTCCAGAGTATCGAGCGCAT

SEQ ID NO 113
>Staphylococcus_aureus_Mu50
TTATTCGTCATCCATTTTCAATACAGCCAAGAAAGCATCCTGTGGAATTTCAACATT

ACCAACTGCTTTCATCTTAGCTTTACCTGCTTTTTGTTTTTCAAGTAATTTACGTTTA

CGGCTTATGTCACCGCCATAACATTTAGCTAAAACGTTTTTACCCATTGATTTAATA

TTTGTACGCGCTACAATTTTTTGTCCTATTGCAGCCTGTACAGGTACTTCAAATTGCT

GTCTTGGAATTAACGTTTTAAGTTTTTCAACTAATGCTTTACCACGTTCATATGCAA

AATCTCTATGAACTATGAAGCTCAGCGCATCCACTTTATCACCGTTTAATAAAATAT

CCATCTTAACTAAATTACTTTCTTTATTTTCGATGAATTCATAATCAAATGATGCATA

TCCTTTAGTATTAGATTTAAGTTGATCGAAGAAATCAAATACAACTTCAGCTAAAG

GTAATTCATAAACAATATTTACACGAATATCATCTAAATAGTCCATATTTATAAATT

GTCCACGTTTACGTTGACATAATTCCATTACTGCACCTACATAGTCATTTGGAACCA

TCATAGTTGCACGAACATATGGCTCAAATATTTTATCAATTTTATCACGATCTGGCA

TTTGTGCTGGGTTATCAACCGTCACTTCTGAACCGTCCCTTAAAATACATTGATAAA

TTACAGATGGTGCTGTTGCAATTAATTCAATGCCAAATTCTCTTTCAATTCTTTCTTG

AATTATTTCCATGTGTAACATACCTAAGAAACCAGTTCTATAACCAAAACCTAATGC

TTGTGACGATTCAGGCTCAAATTCTAATGATGCATCATTCAATTGTAATTTTTCTAA

TGCTTCTCTTAAATCATTATAATTTTTGTTATCTATTGGGAACAGTCCGCAATATACC

ATTGGATTCATTTTCTTATAACCTTGCAATGGTTCTGATGCAGGTCTACTAGCTAAT

GTGATGGTGTCACCAACCCTAGAATCATCAACATTTTTAATACTTGCAATAATATAA

CCAACATCACCAACTGTTAATTCATCAACTGGAAGCTGCTTAGGTGTATTAATTCCA

ACTTCTGTTACTTCGAACTCTTTACCAGTGGCCATCATTCGAATTTTATCTCCAGCTT

TAACAACACCGTCTACAATTCTTATCGATGAAATTACCCCTCTATATGGATCATACT

CAGAATCAAATATTAATGCTTTTAGTGGTGCTTCTGGGTCACCATCTGGAGCTGGCA

CAACTTCAACTATTTTCTCTAGTATCTCTTCAATTCCAATGTTAGATTTAGCACTTGC

TAAAACAACATCGTCTTGGTCTAAACCTATCATATCTTCAATTTCTTGTTTCACGCGT

TCAGGTTCTGCAGCAGGTAAATCAATTTTGTTAATAACAGGCAATAACTCTAACTCA

-continued

TTATCTAATGCCAAATAAACATTTGCTAATGTTTGTGCTTCGATACCTTGAGCCGCA

TCTACTACTAAAATCGCACCCTCACAAGCTGCCAAAGAACGTGACACTTCATATGT

AAAATCGACGTGTCCAGGCGTATCGATTAAATGGAATGTATAAGTATTTCCATCTTT

AGCTTCGTACTTTAAACGAACTGCGTTTAATTTGATTGTAATACCACGTTCTCTTTCT

AAATCCATTGAATCTAGTAACTGATCTTGCATATCTCTTGTTTCAACTGATTTGGTAT

TTTCTAAAATTCTATCAGCCAATGTAGATTTTCCGTGGTCAATATGTGCTATAATCG

AGAAATTCCTTATATTCTCTCTTCTTTTTAAGCGTTGCTCATTATCCAT

SEQ ID NO 114
>Staphylococcus_aureus_USA300_FPR3757
TTATTCATCATCCATTTTCAATACAGCCAAGAAAGCATCTTGTGGAATTTCAACATT

ACCAACTGCTTTCATCTTAGCTTTACCTGCTTTTTGTTTTTCAAGTAATTTACGTTTA

CGGCTTATGTCACCGCCATAACATTTAGCTAAAACGTTTTTACCCATTGATTTAATA

TTTGTACGCGCTACAATTTTTTGTCCTATTGCAGCCTGTACAGGTACTTCAAATTGCT

GTCTTGGAATTAACGTTTTAAGTTTTTCAACTAATGCTTTACCACGTTCATATGCAA

AATCTCTATGAACTATGAAGCTTAGCGCATCCACTTTATCACCATTTAATAAAATAT

CCATCTTGACTAAATTACTTTCTTTATTTTCGATGAATTCATAATCAAATGATGCATA

TCCTTTAGTATTAGATTTAAGTTGATCGAAGAAATCAAATACAACTTCAGCTAAAG

GTAATTCATAAACAATATTTACACGAATATCATCTAAATAGTCCATATTTATAAATT

GTCCACGTTTACGTTGACATAATTCCATTACTGCACCGACATAGTCATTTGGAACCA

TCATAGTTGCACGAACATATGGCTCAAATATTTTATCAATTTTATCACGATCTGGCA

TTTGTGCTGGGTTATCAACCGTCACTTCTGAACCGTCCCTTAAAACACATTGATAAA

TTACAGATGGTGCAGTTGCAATTAATTCAATACCAAATTCTCTTTCAATTCTTTCTTG

AATTATTTCCATGTGTAACATACCTAAGAAACCAGTTCTATAACCAAAACCTAATGC

TTGTGACGATTCAGGCTCAAATTCTAATGATGCATCATTCAATTGTAATTTTTCTAA

TGCTTCTCTTAAATCATTATAATTTTTGTTATCTATTGGGAACAGTCCGCAATATACC

ATTGGATTCATTTTCTTATAACCTTGCAATGGTTCTGATGCAGGTCTACTAGCTAAT

GTGATGGTGTCACCAACCCTAGAATCATCAACATTTTTAATACTTGCAATAATATAA

CCAACATCACCAACTGTTAATTCATCAACTGGAAGCTGCTTAGGTGTATTAATTCCA

ACTTCTGTTACTTCGAACTCTTTACCAGTGGCCATCATTCGAATTTTATCTCCGGCTT

TAACAACACCGTCCACAATTCTTATCGATGAAATTACCCCTCTATATGGATCATACT

CAGAATCAAATATTAACGCTTTTAGTGGTGCTTCTGGGTCACCATCTGGAGCTGGCA

CAACTTCAACTATTTTCTCTAGTATCTCTTCAATTCCAATGTTAGATTTAGCACTTGC

TAAAACAACATCGTCTTGGTCTAAACCTATCATATCTTCAATTTCTTGTTTCACGCGT

TCAGGTTCTGCAGCAGGTAAATCAATTTTGTTAATAACAGGCAATAACTCTAACTCA

TTATCTAATGCTAAATAAACATTTGCTAATGTTTGTGCTTCGATACCTTGAGCCGCA

TCTACTACTAAAATCGCGCCCTCACAAGCTGCCAAAGAACGTGACACTTCATATGT

AAAATCGACGTGTCCAGGCGTATCGATTAAATGGAATGTATAAGTATTTCCATCTTT

AGCTTCGTACTTTAAACGTACTGCGTTTAATTTGATTGTAATACCACGTTCTCTTTCT

AAATCCATTGAATCTAGTAACTGATCTTGCATATCTCTTGTTTCAACTGATTTGGTAT

TTTCTAAAATTCTATCAGCCAATGTAGATTTTCCGTGGTCAATATGTGCTATAATCG

AGAAATTCCTTATATTCTCTCTTCTTTTTAAGCGTTGCTCATTATCCAT

-continued

SEQ ID NO 115
>Staphylococcus_aureus_N315
TTATTCGTCATCCATTTTCAATACAGCCAAGAAAGCATCCTGTGGAATTTCAACATT

ACCAACTGCTTTCATCTTAGCTTTACCTGCTTTTTGTTTTTCAAGTAATTTACGTTTA

CGGCTTATGTCACCGCCATAACATTTAGCTAAAACGTTTTTACCCATTGATTTAATA

TTTGTACGCGCTACAATTTTTTGTCCTATTGCAGCCTGTACAGGTACTTCAAATTGCT

GTCTTGGAATTAACGTTTTAAGTTTTTCAACTAATGCTTTACCACGTTCATATGCAA

AATCTCTATGAACTATGAAGCTCAGCGCATCCACTTTATCACCGTTTAATAAAATAT

CCATCTTAACTAAATTACTTTCTTTATTTTCGATGAATTCATAATCAAATGATGCATA

TCCTTTAGTATTAGATTTAAGTTGATCGAAGAAATCAAATACAACTTCAGCTAAAG

GTAATTCATAAACAATATTTACACGAATATCATCTAAATAGTCCATATTTATAAATT

GTCCACGTTTACGTTGACATAATTCCATTACTGCACCTACATAGTCATTTGGAACCA

TCATAGTTGCACGAACATATGGCTCAAATATTTTATCAATTTTATCACGATCTGGCA

TTTGTGCTGGGTTATCAACCGTCACTTCTGAACCGTCCCTTAAAATACATTGATAAA

TTACAGATGGTGCTGTTGCAATTAATTCAATGCCAAATTCTCTTTCAATTCTTTCTTG

AATTATTTCCATGTGTAACATACCTAAGAAACCAGTTCTATAACCAAAACCTAATGC

TTGTGACGATTCAGGCTCAAATTCTAATGATGCATCATTCAATTGTAATTTTTCTAA

TGCTTCTCTTAAATCATTATAATTTTTGTTATCTATTGGGAACAGTCCGCAATATACC

ATTGGATTCATTTTCTTATAACCTTGCAATGGTTCTGATGCAGGTCTACTAGCTAAT

GTGATGGTGTCACCAACCCTAGAATCATCAACATTTTTAATACTTGCAATAATATAA

CCAACATCACCAACTGTTAATTCATCAACTGGAAGCTGCTTAGGTGTATTAATTCCA

ACTTCTGTTACTTCGAACTCTTTACCAGTGGCCATCATTCGAATTTTATCTCCAGCTT

TAACAACACCGTCTACAATTCTTATCGATGAAATTACCCCTCTATATGGATCATACT

CAGAATCAAATATTAATGCTTTTAGTGGTGCTTCTGGGTCACCATCTGGAGCTGGCA

CAACTTCAACTATTTTCTCTAGTATCTCTTCAATTCCAATGTTAGATTTAGCACTTGC

TAAAACAACATCGTCTTGGTCTAAACCTATCATATCTTCAATTTCTTGTTTCACGCGT

TCAGGTTCTGCAGCAGGTAAATCAATTTTGTTAATAACAGGCAATAACTCTAACTCA

TTATCTAATGCCAAATAAACATTTGCTAATGTTTGTGCTTCGATACCTTGAGCCGCA

TCTACTACTAAAATCGCACCCTCACAAGCTGCCAAAGAACGTGACACTTCATATGT

AAAATCGACGTGTCCAGGCGTATCGATTAAATGGAATGTATAAGTATTTCCATCTTT

AGCTTCGTACTTTAAACGAACTGCGTTTAATTTGATTGTAATACCACGTTCTCTTTCT

AAATCCATTGAATCTAGTAACTGATCTTGCATATCTCTTGTTTCAACTGATTTGGTAT

TTTCTAAAATTCTATCAGCCAATGTAGATTTTCCGTGGTCAATATGTGCTATAATCG

AGAAATTCCTTATATTCTCTCTTCTTTTTAAGCGTTGCTCATTATCCAT

SEQ ID NO 116
>Staphylococcus_aureus_MRSA252
TTATTCGTCATCCATTTTCAATACAGCCAAAAAAGCATCCTGTGGAATTTCAACATT

ACCAACTGCTTTCATCTTAGCTTTACCTGCTTTTTGTTTTTCAAGTAATTTACGTTTA

CGGCTTATGTCACCGCCATAACATTTAGCTAAAACGTTTTTACCCATTGATTTAATA

TTTGTACGTGCTACAATTTTTTGTCCTATTGCAGCTTGTACAGGTACTTCAAATTGCT

GTCTTGGAATTAACGTTTTAAGTTTTTCAACTAATGCTTTACCACGTTCATATGCAA

AATCTCTATGGACTATGAAGCTTAGAGCATCCACTTTATCACCGTTTAATAAAATAT

-continued

CCATCTTCACTAAATTACTTTCTTTATTTTCGATGAACTCATAATCAAATGATGCATA

TCCTTTAGTATTAGATTTAAGTTGATCGAAGAAATCAAATACAACTTCAGCTAAAG

GTAATTCATAAACAATATTTACACGAATATCATCTAAATAGTCCATATTTATAAATT

GTCCACGTTTACGTTGACATAATTCCATTACTGCACCTACATAGTCATTTGGAACCA

TCATAGTTGCACGAACATATGGCTCGAATATTTTATCAATTTTATCACGGTCTGGCA

TTTGTGCTGGATTATCAACCGTCACTTCTGAACCGTCCCTTAAAATACATTGATAAA

TTACAGATGGTGCGGTTGCAATTAATTCAATGCCAAATTCTCTTTCAATTCTTTCTTG

AATTATTTCCATGTGTAACATACCTAAGAAACCAGTTCTATAACCAAAACCTAATGC

TTGTGATGATTCAGGCTCAAATTCTAATGATGCATCATTCAATTGTAATTTTTCTAAT

GCTTCTCTTAAATCATTATAATTTTTGTTATCTATTGGGAACAGTCCGCAATATACC

ATTGGATTCATTTTCTTATAACCTTGCAATGGTTCTGATGCAGGTCTACTAGCTAAT

GTGATTGTGTCACCAACCCTAGAATCATCAACATTTTTAATACTTGCAATAATGTAA

CCAACATCACCAACTGTTAATTCATCAACTGGAAGTTGCTTAGGTGTATTAATTCCA

ACTTCTGTTACTTCGAACTCTTTACCAGTGGCCATCATTCGAATTTTATCTCCGGCTT

TAACAACACCGTCTACAATTCTTATCGATGAAATTACCCCTCTATATGGATCATACT

CAGAATCAAATATTAACGCTTTTAGTGGTGCTTCTGGGTCACCATCTGGAGCTGGCA

CAACTTCAACTATTTTCTCAAGTATCTCTTCAATTCCAATGTTAGATTTAGCACTTGC

TAAAACAACATCGTCTTGGTCTAAACCTATCATATCTTCAATTTCTTGTTTCACGCGT

TCAGGTTCTGCAGCAGGTAAATCAATTTTGTTAATAACAGGCAATAACTCTAACTCA

TTATCTAATGCCAAATAAACATTTGCTAATGTTTGTGCTTCGATACCTTGAGCCGCA

TCTACTACTAAAATCGCGCCCTCACAAGCTGCCAAAGAACGTGACACTTCATATGT

AAAATCGACGTGTCCAGGCGTATCGATTAAATGGAATGTATAAGTATTTCCATCTTT

AGCTTCGTACTTTAAACGTACTGCGTTTAATTTGATTGTAATACCACGTTCTCTTTCT

AAATCCATTGAATCTAGTAACTGATCTTGCATATCTCTTGTTTCAACTGATTTGGTAT

TTTCTAAAATTCTATCAGCCAATGTAGATTTTCCGTGGTCAATATGTGCTATAATCG

AGAAATTCCTTATATTCTCTCTTCTTTTTAAGCGTTGCTCATTATCCAT

SEQ ID NO 117
>Staphylococcus_aureus_COL
TTATTCATCATCCATTTTCAATACAGCCAAGAAAGCATCTTGTGGAATTTCAACATT

ACCAACTGCTTTCATCTTAGCTTTACCTGCTTTTTGTTTTTCAAGTAATTTACGTTTA

CGGCTTATGTCACCGCCATAACATTTAGCTAAAACGTTTTTACCCATTGATTTAATA

TTTGTACGCGCTACAATTTTTTGTCCTATTGCAGCCTGTACAGGTACTTCAAATTGCT

GTCTTGGAATTAACGTTTTAAGTTTTTCAACTAATGCTTTACCACGTTCATATGCAA

AATCTCTATGAACTATGAAGCTTAGCGCATCCACTTTATCACCATTTAATAAAATAT

CCATCTTGACTAAATTACTTTCTTTATTTTCGATGAATTCATAATCAAATGATGCATA

TCCTTTAGTATTAGATTTAAGTTGATCGAAGAAATCAAATACAACTTCAGCTAAAG

GTAATTCATAAACAATATTTACACGAATATCATCTAAATAGTCCATATTTATAAATT

GTCCACGTTTACGTTGACATAATTCCATTACTGCACCGACATAGTCATTTGGAACCA

TCATAGTTGCACGAACATATGGCTCAAATATTTTATCAATTTTATCACGATCTGGCA

TTTGTGCTGGGTTATCAACCGTCACTTCTGAACCGTCCCTTAAAACACATTGATAAA

TTACAGATGGTGCAGTTGCAATTAATTCAATACCAAATTCTCTTTCAATTCTTTCTTG

AATTATTTCCATGTGTAACATACCTAAGAAACCAGTTCTATAACCAAAACCTAATGC

-continued

TTGTGACGATTCAGGCTCAAATTCTAATGATGCATCATTCAATTGTAATTTTTCTAA

TGCTTCTCTTAAATCATTATAATTTTTGTTATCTATTGGGAACAGTCCGCAATATACC

ATTGGATTCATTTTCTTATAACCTTGCAATGGTTCTGATGCAGGTCTACTAGCTAAT

GTGATGGTGTCACCAACCCTAGAATCATCAACATTTTTAATACTTGCAATAATATAA

CCAACATCACCAACTGTTAATTCATCAACTGGAAGCTGCTTAGGTGTATTAATTCCA

ACTTCTGTTACTTCGAACTCTTTACCAGTGGCCATCATTCGAATTTTATCTCCGGCTT

TAACAACACCGTCCACAATTCTTATCGATGAAATTACCCCTCTATATGGATCATACT

CAGAATCAAATATTAACGCTTTTAGTGGTGCTTCTGGGTCACCATCTGGAGCTGGCA

CAACTTCAACTATTTTCTCTAGTATCTCTTCAATTCCAATGTTAGATTTAGCACTTGC

TAAAACAACATCGTCTTGGTCTAAACCTATCATATCTTCAATTTCTTGTTTCACGCGT

TCAGGTTCTGCAGCAGGTAAATCAATTTTGTTAATAACAGGCAATAACTCTAACTCA

TTATCTAATGCTAAATAAACATTTGCTAATGTTTGTGCTTCGATACCTTGAGCCGCA

TCTACTACTAAAATCGCGCCCTCACAAGCTGCCAAAGAACGTGACACTTCATATGT

AAAATCGACGTGTCCAGGCGTATCGATTAAATGGAATGTATAAGTATTTCCATCTTT

AGCTTCGTACTTTAAACGTACTGCGTTTAATTTGATTGTAATACCACGTTCTCTTTCT

AAATCCATTGAATCTAGTAACTGATCTTGCATATCTCTTGTTTCAACTGATTTGGTAT

TTTCTAAAATTCTATCAGCCAATGTAGATTTTCCGTGGTCAATATGTGCTATAATCG

AGAAATTCCTTATATTCTCTCTTCTTTTTAAGCGTTGCTCATTATCCAT

SEQ ID NO 118
>Staphylococcus_aureus_MW2
TTATTCGTCATCCATTTTCAATACAGCCAAGAAAGCATCCTGTGGAATTTCAATATT

ACCAACTGCTTTCATCTTAGCTTTACCTGCTTTTTGTTTTTCAAGTAATTTACGTTTA

CGGCTTATGTCACCGCCATAACATTTAGCTAAAACGTTTTTACCCATTGATTTAATA

TTTGTACGCGCTACAATTTTTTGTCCTATTGCAGCCTGTACAGGTACTTCAAATTGCT

GTCTTGGAATTAACGTTTTAAGTTTTTCAACTAATGCTTTACCACGTTCATATGCAA

AATCTCTATGAACTATGAAGCTTAGCGCATCCACTTTATCACCGTTTAATAAAATAT

CCATCTTAACTAAATTACTTTCTTTATTTTCGATGAATTCATAATCAAATGATGCATA

TCCTTTAGTATTAGATTTAAGTTGATCGAAGAAATCAAATACAACTTCAGCTAAAG

GTAATTCATAAACAATATTTACACGAATATCATCTAAATAGTCCATATTTATAAATT

GTCCACGTTTACGTTGACATAATTCCATTACTGCACCTACATAGTCATTTGGAACCA

TCATAGTTGCACGAACATATGGCTCAAATATTTTATCAATTTTATCACGATCTGGCA

TTTGTGCTGGGTTATCAACCGTCACTTCTGAACCGTCCCTTAAAATACATTGATAAA

TTACAGATGGTGCTGTTGCAATTAATTCAATGCCAAATTCTCTTTCAATTCTTTCTTG

AATTATTTCCATGTGTAACATACCTAAGAAACCAGTTCTATAACCAAAACCTAATGC

TTGTGACGATTCAGGCTCAAATTCTAATGATGCATCATTCAATTGTAATTTTTCTAA

TGCTTCTCTTAAATCATTATAATTTTTGTTATCTATTGGGAACAGTCCGCAATATACC

ATTGGATTCATTTTCTTATAACCTTGCAATGGTTCTGATGCAGGTCTACTAGCTAAT

GTGATGGTGTCACCAACCCTAGAATCATCAACATTTTTAATACTTGCAATAATATAA

CCAACATCACCAACTGTTAATTCATCAACTGGAAGCTGCTTAGGTGTATTAATTCCA

ACTTCTGTTACTTCGAACTCTTTACCAGTCGCCATCATTCGAATTTTATCTCCGGCTT

TAACAACACCGTCTACAATTCTTATCGATGAAATTACCCCTCTATATGGATCATACT

-continued

CAGAATCAAATATTAACGCTTTTAGTGGTGCTTCTGGGTCGCCATCTGGAGCTGGCA

CAACTTCAACTATTTTCTCTAGTATCTCTTCAATTCCAATGTTAGATTTAGCACTTGC

TAAAACAACATCGTCTTGGTCTAAACCTATCATATCTTCAATTTCTTGTTTCACGCGT

TCAGGTTCTGCAGCAGGTAAATCAATTTTGTTAATAACAGGCAATAACTCTAACTCA

TTATCTAATGCTAAATAAACATTTGCTAATGTTTGTGCTTCGATACCTTGAGCCGCA

TCTACTACTAAAATCGCGCCCTCACAAGCTGCCAAAGAACGTGACACTTCATATGT

AAAATCGACGTGTCCAGGCGTATCGATTAAATGGAATGTATAAGTATTTCCATCTTT

AGCTTCGTACTTTAAACGAACTGCGTTTAATTTGATTGTAATACCACGTTCTCTTTCT

AAATCCATTGAATCTAGTAACTGATCTTGCATATCTCTTGTTTCAACTGATTTGGTAT

TTTCTAAAATTCTATCAGCCAATGTAGATTTTCCGTGGTCAATATGTGCTATAATCG

AGAAATTCCTTATATTCTCTCTTCTTTTTAAGCGTTGCTCATTATCCAT

SEQ ID NO 119
>Staphylococcus_aureus_Mu3
TTATTCGTCATCCATTTTCAATACAGCCAAGAAAGCATCCTGTGGAATTTCAACATT

ACCAACTGCTTTCATCTTAGCTTTACCTGCTTTTTGTTTTTCAAGTAATTTACGTTTA

CGGCTTATGTCACCGCCATAACATTTAGCTAAAACGTTTTTACCCATTGATTTAATA

TTTGTACGCGCTACAATTTTTTGTCCTATTGCAGCCTGTACAGGTACTTCAAATTGCT

GTCTTGGAATTAACGTTTTAAGTTTTTCAACTAATGCTTTACCACGTTCATATGCAA

AATCTCTATGAACTATGAAGCTCAGCGCATCCACTTTATCACCGTTTAATAAAATAT

CCATCTTAACTAAATTACTTTCTTTATTTTCGATGAATTCATAATCAAATGATGCATA

TCCTTTAGTATTAGATTTAAGTTGATCGAAGAAATCAAATACAACTTCAGCTAAAG

GTAATTCATAAACAATATTTACACGAATATCATCTAAATAGTCCATATTTATAAATT

GTCCACGTTTACGTTGACATAATTCCATTACTGCACCTACATAGTCATTTGGAACCA

TCATAGTTGCACGAACATATGGCTCAAATATTTTATCAATTTTATCACGATCTGGCA

TTTGTGCTGGGTTATCAACCGTCACTTCTGAACCGTCCCTTAAAATACATTGATAAA

TTACAGATGGTGCTGTTGCAATTAATTCAATGCCAAATTCTCTTTCAATTCTTTCTTG

AATTATTTCCATGTGTAACATACCTAAGAAACCAGTTCTATAACCAAAACCTAATGC

TTGTGACGATTCAGGCTCAAATTCTAATGATGCATCATTCAATTGTAATTTTTCTAA

TGCTTCTCTTAAATCATTATAATTTTTGTTATCTATTGGGAACAGTCCGCAATATACC

ATTGGATTCATTTTCTTATAACCTTGCAATGGTTCTGATGCAGGTCTACTAGCTAAT

GTGATGGTGTCACCAACCCTAGAATCATCAACATTTTTAATACTTGCAATAATATAA

CCAACATCACCAACTGTTAATTCATCAACTGGAAGCTGCTTAGGTGTATTAATTCCA

ACTTCTGTTACTTCGAACTCTTTACCAGTGGCCATCATTCGAATTTTATCTCCAGCTT

TAACAACACCGTCTACAATTCTTATCGATGAAATTACCCCTCTATATGGATCATACT

CAGAATCAAATATTAATGCTTTTAGTGGTGCTTCTGGGTCACCATCTGGAGCTGGCA

CAACTTCAACTATTTTCTCTAGTATCTCTTCAATTCCAATGTTAGATTTAGCACTTGC

TAAAACAACATCGTCTTGGTCTAAACCTATCATATCTTCAATTTCTTGTTTCACGCGT

TCAGGTTCTGCAGCAGGTAAATCAATTTTGTTAATAACAGGCAATAACTCTAACTCA

TTATCTAATGCCAAATAAACATTTGCTAATGTTTGTGCTTCGATACCTTGAGCCGCA

TCTACTACTAAAATCGCACCCTCACAAGCTGCCAAAGAACGTGACACTTCATATGT

AAAATCGACGTGTCCAGGCGTATCGATTAAATGGAATGTATAAGTATTTCCATCTTT

AGCTTCGTACTTTAAACGAACTGCGTTTAATTTGATTGTAATACCACGTTCTCTTTCT

-continued

AAATCCATTGAATCTAGTAACTGATCTTGCATATCTCTTGTTTCAACTGATTTGGTAT

TTTCTAAAATTCTATCAGCCAATGTAGATTTTCCGTGGTCAATATGTGCTATAATCG

AGAAATTCCTTATATTCTCTCTTCTTTTTAAGCGTTGCTCATTATCCAT

SEQ ID NO 120
>Staphylococcus_aureus_RF122
TTATTCGTCATCCATTTTTAATACAGCCAAGAAAGCATCCTGTGGAATTTCAACATT

ACCAACTGCTTTCATCTTAGCTTTACCTGCTTTTTGTTTTTCAAGTAATTTACGTTTA

CGGCTTATGTCACCGCCATAACATTTAGCTAAAACGTTTTTACCCATTGATTTAATA

TTTGTACGTGCTACAATTTTTTGTCCTATTGCAGCCTGTACAGGTACTTCAAATTGCT

GTCTTGGAATTAAGGTTTTAAGTTTTTCAACTAATGCTTTACCACGTTCATATGCAA

AATCTCTATGAACTATGAAGCTTAGAGCATCCACTTTATCGCCGTTTAATAAAATAT

CCATCTTCACTAAATTACTTTCTTTATTTTCGATGAACTCATAATCAAATGATGCATA

TCCTTTGGTATTAGATTTAAGTTGATCGAAGAAATCAAATACAACTTCAGCTAAAG

GTAATTCATAAACAATATTTACACGAATATCATCTAAATAGTCCATATTTATAAATT

GTCCGCGTTTACGTTGACATAATTCCATTACAGCACCTACATAGTCATTTGGAACCA

TCATAGTTGCACGAACATATGGCTCAAATATTTTATCAATTTTATCACGATCTGGCA

TTTGTGCTGGGTTATCAACCGTCACTTCTGAACCATCCCTTAAAATACATTGATAAA

TTACAGATGGTGCGGTTGCAATTAATTCAATGCCAAATTCTCTTTCAATTCTTTCTTG

AATTATTTCCATGTGTAACATACCTAAGAAACCAGTTCTATAACCAAAACCTAATGC

TTGTGATGATTCAGGCTCGAATTCTAACGATGCATCATTCAATTGTAATTTTTCTAA

TGCTTCTCTTAAATCATTATAATTTTTGTTATCTATCGGGAACAGTCCGCAATATACC

ATTGGATTCATTTTCTTATAACCTTGCAATGGTTCTGATGCAGGTCTACTAGCTAAT

GTGATTGTGTCACCAACCCTAGAATCATCAACATTTTTAATACTTGCAATAATATAA

CCAACATCACCAACTGTTAATTCATCAACTGGAAGCTGCTTAGGTGTATTAATTCCA

ACTTCTGTTACTTCGAACTCTTTACCAGTGGCCATCATTCGAATTTTATCTCCGGCTT

TAACAACACCGTCTACAATTCTTATCGATGAAATTACCCCTCTATATGGATCATACT

CAGAATCAAATATTAATGCTTTTAATGGTGCTTCTGGGTCACCATCTGGAGCTGGCA

CAACTTCAACTATTTTCTCTAGTATCTCTTCAATTCCAATGTTAGATTTAGCACTTGC

TAAAACAACATCGTCTTGGTCTAAACCTATCATATCTTCAATTTCTTGTTTCACGCGT

TCAGGTTCAGCAGCAGGTAAATCAATTTTGTTAATAACAGGCAATAACTCTAACTC

ATTATCTAATGCTAAATAAACATTTGCTAATGTTTGTGCTTCGATACCTTGAGCCGC

ATCTACTACTAAAATCGCGCCCTCACAAGCTGCCAAAGAACGTGACACTTCATATG

TAAAATCGACGTGTCCAGGCGTATCGATTAAATGGAATGTATAAGTATTTCCATCTT

TAGCTTCGTACTTTAAACGTACTGCGTTTAATTTGATTGTAATACCACGTTCTCTTTC

TAAATCCATTGAATCTAGTAACTGATCTTGCATATCTCTTGTTTCAACTGATTTGGTA

TTTTCTAAAATTCTATCAGCCAATGTAGATTTTCCGTGGTCAATATGTGCTATAATC

GAGAAATTCCTTATATTCTCTCTTCTTTTTAAGCGTTGCTCATTATCCAT

SEQ ID NO 121
>Staphylococcus_aureus_JH9
TTATTCGTCATCCATTTTCAATACAGCCAAGAAAGCATCCTGTGGAATTTCAACATT

ACCAACTGCTTTCATCTTAGCTTTACCTGCTTTTTGTTTTTCAAGTAATTTACGTTTA

CGGCTTATGTCACCGCCATAACATTTAGCTAAAACGTTTTTACCCATTGATTTAATA

-continued

TTTGTACGCGCTACAATTTTTTGTCCTATTGCAGCCTGTACAGGTACTTCAAATTGCT

GTCTTGGAATTAACGTTTTAAGTTTTTCAACTAATGCTTTACCACGTTCATATGCAA

AATCTCTATGAACTATGAAGCTTAGCGCATCCACTTTATCACCGTTTAATAAAATAT

CCATCTTAACTAAATTACTTTCTTTATTTTCGATGAATTCATAATCAAATGATGCATA

TCCTTTAGTATTAGATTTAAGTTGATCGAAGAAATCAAATACAACTTCAGCTAAAG

GTAATTCATAAACAATATTTACACGAATATCATCTAAATAGTCCATATTTATAAATT

GTCCACGTTTACGTTGACATAATTCCATTACTGCACCTACATAGTCATTTGGAACCA

TCATAGTTGCACGAACATATGGCTCAAATATTTTATCAATTTTATCACGATCTGGCA

TTTGTGCTGGGTTATCAACCGTCACTTCTGAACCGTCCCTTAAAATACATTGATAAA

TTACAGATGGTGCTGTTGCAATTAATTCAATGCCAAATTCTCTTTCAATTCTTTCTTG

AATTATTTCCATGTGTAACATACCTAAGAAACCAGTTCTATAACCAAAACCTAATGC

TTGTGACGATTCAGGCTCAAATTCTAATGATGCATCATTCAATTGTAATTTTTCTAA

TGCTTCTCTTAAATCATTATAATTTTTGTTATCTATTGGGAACAGTCCGCAATATACC

ATTGGATTCATTTTCTTATAACCTTGCAATGGTTCTGATGCAGGTCTACTAGCTAAT

GTGATGGTGTCACCAACCCTAGAATCATCAACATTTTTAATACTTGCAATAATATAA

CCAACATCACCAACTGTTAATTCATCAACTGGAAGCTGCTTAGGTGTATTAATTCCA

ACTTCTGTTACTTCGAACTCTTTACCAGTGGCCATCATTCGAATTTTATCTCCAGCTT

TAACAACACCGTCTACAATTCTTATCGATGAAATTACCCCTCTATATGGATCATACT

CAGAATCAAATATTAATGCTTTTAGTGGTGCTTCTGGGTCACCATCTGGAGCTGGCA

CAACTTCAACTATTTTCTCTAGTATCTCTTCAATTCCAATGTTAGATTTAGCACTTGC

TAAAACAACATCGTCTTGGTCTAAACCTATCATATCTTCAATTTCTTGTTTCACGCGT

TCAGGTTCTGCAGCAGGTAAATCAATTTTGTTAATAACAGGCAATAACTCTAACTCA

TTATCTAATGCCAAATAAACATTTGCTAATGTTTGTGCTTCGATACCTTGAGCCGCA

TCTACTACTAAAATCGCACCCTCACAAGCTGCCAAAGAACGTGACACTTCATATGT

AAAATCGACGTGTCCAGGCGTATCGATTAAATGGAATGTATAAGTATTTCCATCTTT

AGCTTCGTACTTTAAACGAACTGCGTTTAATTTGATTGTAATACCACGTTCTCTTTCT

AAATCCATTGAATCTAGTAACTGATCTTGCATATCTCTTGTTTCAACTGATTTGGTAT

TTTCTAAAATTCTATCAGCCAATGTAGATTTTCCGTGGTCAATATGTGCTATAATCG

AGAAATTCCTTATATTCTCTCTTCTTTTTAAGCGTTGCTCATTATCCAT

SEQ ID NO 122
>Staphylococcus_aureus_JH1
TTATTCGTCATCCATTTTCAATACAGCCAAGAAAGCATCCTGTGGAATTTCAACATT

ACCAACTGCTTTCATCTTAGCTTTACCTGCTTTTTGTTTTTCAAGTAATTTACGTTTA

CGGCTTATGTCACCGCCATAACATTTAGCTAAAACGTTTTTACCCATTGATTTAATA

TTTGTACGCGCTACAATTTTTTGTCCTATTGCAGCCTGTACAGGTACTTCAAATTGCT

GTCTTGGAATTAACGTTTTAAGTTTTTCAACTAATGCTTTACCACGTTCATATGCAA

AATCTCTATGAACTATGAAGCTTAGCGCATCCACTTTATCACCGTTTAATAAAATAT

CCATCTTAACTAAATTACTTTCTTTATTTTCGATGAATTCATAATCAAATGATGCATA

TCCTTTAGTATTAGATTTAAGTTGATCGAAGAAATCAAATACAACTTCAGCTAAAG

GTAATTCATAAACAATATTTACACGAATATCATCTAAATAGTCCATATTTATAAATT

GTCCACGTTTACGTTGACATAATTCCATTACTGCACCTACATAGTCATTTGGAACCA

TCATAGTTGCACGAACATATGGCTCAAATATTTTATCAATTTTATCACGATCTGGCA

-continued

TTTGTGCTGGGTTATCAACCGTCACTTCTGAACCGTCCCTTAAAATACATTGATAAA

TTACAGATGGTGCTGTTGCAATTAATTCAATGCCAAATTCTCTTTCAATTCTTTCTTG

AATTATTTCCATGTGTAACATACCTAAGAAACCAGTTCTATAACCAAAACCTAATGC

TTGTGACGATTCAGGCTCAAATTCTAATGATGCATCATTCAATTGTAATTTTTCTAA

TGCTTCTCTTAAATCATTATAATTTTTGTTATCTATTGGGAACAGTCCGCAATATACC

ATTGGATTCATTTTCTTATAACCTTGCAATGGTTCTGATGCAGGTCTACTAGCTAAT

GTGATGGTGTCACCAACCCTAGAATCATCAACATTTTTAATACTTGCAATAATATAA

CCAACATCACCAACTGTTAATTCATCAACTGGAAGCTGCTTAGGTGTATTAATTCCA

ACTTCTGTTACTTCGAACTCTTTACCAGTGGCCATCATTCGAATTTTATCTCCAGCTT

TAACAACACCGTCTACAATTCTTATCGATGAAATTACCCCTCTATATGGATCATACT

CAGAATCAAATATTAATGCTTTTAGTGGTGCTTCTGGGTCACCATCTGGAGCTGGCA

CAACTTCAACTATTTTCTCTAGTATCTCTTCAATTCCAATGTTAGATTTAGCACTTGC

TAAAACAACATCGTCTTGGTCTAAACCTATCATATCTTCAATTTCTTGTTTCACGCGT

TCAGGTTCTGCAGCAGGTAAATCAATTTTGTTAATAACAGGCAATAACTCTAACTCA

TTATCTAATGCCAAATAAACATTTGCTAATGTTTGTGCTTCGATACCTTGAGCCGCA

TCTACTACTAAAATCGCACCCTCACAAGCTGCCAAAGAACGTGACACTTCATATGT

AAAATCGACGTGTCCAGGCGTATCGATTAAATGGAATGTATAAGTATTTCCATCTTT

AGCTTCGTACTTTAAACGAACTGCGTTTAATTTGATTGTAATACCACGTTCTCTTTCT

AAATCCATTGAATCTAGTAACTGATCTTGCATATCTCTTGTTTCAACTGATTTGGTAT

TTTCTAAAATTCTATCAGCCAATGTAGATTTTCCGTGGTCAATATGTGCTATAATCG

AGAAATTCCTTATATTCTCTCTTCTTTTTAAGCGTTGCTCATTATCCAT

SEQ ID NO 123
>Staphylococcus_aureus_Newman
TTATTCATCATCCATTTTCAATACAGCCAAGAAAGCATCTTGTGGAATTTCAACATT

ACCAACTGCTTTCATCTTAGCTTTACCTGCTTTTTGTTTTTCAAGTAATTTACGTTTA

CGGCTTATGTCACCGCCATAACATTTAGCTAAAACGTTTTTACCCATTGATTTAATA

TTTGTACGCGCTACAATTTTTTGTCCTATTGCAGCCTGTACAGGTACTTCAAATTGCT

GTCTTGGAATTAACGTTTTAAGTTTTTCAACTAATGCTTTACCACGTTCATATGCAA

AATCTCTATGAACTATGAAGCTTAGCGCATCCACTTTATCACCATTTAATAAAATAT

CCATCTTGACTAAATTACTTTCTTTATTTTCGATGAATTCATAATCAAATGATGCATA

TCCTTTAGTATTAGATTTAAGTTGATCGAAGAAATCAAATACAACTTCAGCTAAAG

GTAATTCATAAACAATATTTACACGAATATCATCTAAATAGTCCATATTTATAAATT

GTCCACGTTTACGTTGACATAATTCCATTACTGCACCGACATAGTCATTTGGAACCA

TCATAGTTGCACGAACATATGGCTCAAATATTTTATCAATTTTATCACGATCTGGCA

TTTGTGCTGGGTTATCAACCGTCACTTCTGACCCGTCCCTTAAAACACATTGATAAA

TTACAGATGGTGCAGTTGCAATTAATTCAATACCAAATTCTCTTTCAATTCTTTCTTG

AATTATTTCCATGTGTAACATACCTAAGAAACCAGTTCTATAACCAAAACCTAATGC

TTGTGACGATTCAGGCTCAAATTCTAATGATGCATCATTCAATTGTAATTTTTCTAA

TGCTTCTCTTAAATCATTATAATTTTTGTTATCTATTGGGAACAGTCCGCAATATACC

ATTGGATTCATTTTCTTATAACCTTGCAATGGTTCTGATGCAGGTCTACTAGCTAAT

GTGATGGTGTCACCAACCCTAGAATCATCAACATTTTTAATACTTGCAATAATATAA

-continued

CCAACATCACCAACTGTTAATTCATCAACTGGAAGCTGCTTAGGTGTATTAATTCCA

ACTTCTGTTACTTCGAACTCTTTACCAGTGGCCATCATTCGAATTTTATCTCCGGCTT

TAACAACACCGTCCACAATTCTTATCGATGAAATTACCCCTCTATATGGATCATACT

CAGAATCAAATATTAACGCTTTTAGTGGTGCTTCTGGGTCACCATCTGGAGCTGGCA

CAACTTCAACTATTTTCTCTAGTATCTCTTCAATTCCAATGTTAGATTTAGCACTTGC

TAAAACAACATCGTCTTGGTCTAAACCTATCATATCTTCAATTTCTTGTTTCACGCGT

TCAGGTTCTGCAGCAGGTAAATCAATTTTGTTAATAACAGGCAATAACTCTAACTCA

TTATCTAATGCTAAATAAACATTTGCTAATGTTTGTGCTTCGATACCTTGAGCCGCA

TCTACTACTAAAATCGCGCCCTCACAAGCTGCCAAAGAACGTGACACTTCATATGT

AAAATCGACGTGTCCAGGCGTATCGATTAAATGGAATGTATAAGTATTTCCATCTTT

AGCTTCGTACTTTAAACGTACTGCGTTTAATTTGATTGTAATACCACGTTCTCTTTCT

AAATCCATTGAATCTAGTAACTGATCTTGCATATCTCTTGTTTCAACTGATTTGGTAT

TTTCTAAAATTCTATCAGCCAATGTAGATTTTCCGTGGTCAATATGTGCTATAATCG

AGAAATTCCTTATATTCTCTCTTCTTTTTAAGCGTTGCTCATTATCCAT

SEQ ID NO 124
>Staphylococcus_aureus_MSSA476
TTATTCGTCATCCATTTTCAATACAGCCAAGAAAGCATCCTGTGGAATTTCAACATT

ACCAACTGCTTTCATCTTAGCTTTACCTGCTTTTTGTTTTTCAAGTAATTTACGTTTA

CGGCTTATGTCACCGCCATAACATTTAGCTAAAACGTTTTTACCCATTGATTTAATA

TTTGTACGCGCTACAATTTTTTGTCCTATTGCAGCCTGTACAGGTACTTCAAATTGCT

GTCTTGGAATTAACGTTTTAAGTTTTTCAACTAATGCTTTACCACGTTCATATGCAA

AATCTCTATGAACTATGAAGCTTAGCGCATCCACTTTATCACCGTTTAATAAAATAT

CCATCTTAACTAAATTACTTTCTTTATTTTCGATGAATTCATAATCAAATGATGCATA

TCCTTTAGTATTAGATTTAAGTTGATCGAAGAAATCAAATACAACTTCAGCTAAAG

GTAATTCATAAACAATATTTACACGAATATCATCTAAATAGTCCATATTTATAAATT

GTCCACGTTTACGTTGACATAATTCCATTACTGCACCTACATAGTCATTTGGAACCA

TCATAGTTGCACGAACATATGGCTCAAATATTTTATCAATTTTATCACGATCTGGCA

TTTGTGCTGGGTTATCAACCGTCACTTCTGAACCGTCCCTTAAAATACATTGATAAA

TTACAGATGGTGCTGTTGCAATTAATTCAATGCCAAATTCTCTTTCAATTCTTTCTTG

AATTATTTCCATGTGTAACATACCTAAGAAACCAGTTCTATAACCAAAACCTAATGC

TTGTGACGATTCAGGCTCAAATTCTAATGATGCATCATTCAATTGTAATTTTTCTAA

TGCTTCTCTTAAATCATTATAATTTTTGTTATCTATTGGGAACAGTCCGCAATATACC

ATTGGATTCATTTTCTTATAACCTTGCAATGGTTCTGATGCAGGTCTACTAGCTAAT

GTGATGGTGTCACCAACCCTAGAATCATCAACATTTTTAATACTTGCAATAATATAA

CCAACATCACCAACTGTTAATTCATCAACTGGAAGCTGCTTAGGTGTATTAATTCCA

ACTTCTGTTACTTCGAACTCTTTACCAGTCGCCATCATTCGAATTTTATCTCCGGCTT

TAACAACACCGTCTACAATTCTTATCGATGAAATTACCCCTCTATATGGATCATACT

CAGAATCAAATATTAACGCTTTTAGTGGTGCTTCTGGGTCGCCATCTGGAGCTGGCA

CAACTTCAACTATTTTCTCTAGTATCTCTTCAATTCCAATGTTAGATTTAGCACTTGC

TAAAACAACATCGTCTTGGTCTAAACCTATCATATCTTCAATTTCTTGTTTCACGCGT

TCAGGTTCTGCAGCAGGTAAATCAATTTTGTTAATAACAGGCAATAACTCTAACTCA

TTATCTAATGCTAAATAAACATTTGCTAATGTTTGTGCTTCGATACCTTGAGCCGCA

-continued

TCTACTACTAAAATCGCGCCCTCACAAGCTGCCAAAGAACGTGACACTTCATATGT

AAAATCGACGTGTCCAGGCGTATCGATTAAATGGAATGTATAAGTATTTCCATCTTT

AGCTTCGTACTTTAAACGAACTGCGTTTAATTTGATTGTAATACCACGTTCTCTTTCT

AAATCCATTGAATCTAGTAACTGATCTTGCATATCTCTTGTTTCAACTGATTTGGTAT

TTTCTAAAATTCTATCAGCCAATGTAGATTTTCCGTGGTCAATATGTGCTATAATCG

AGAAATTCCTTATATTCTCTCTTCTTTTTAAGCGTTGCTCATTATCCAT

SEQ ID NO 125
>Staphylococcus_aureus_NCTC 8325
TTATTCATCATCCATTTTCAATACAGCCAAGAAAGCATCTTGTGGAATTTCAACATT

ACCAACTGCTTTCATCTTAGCTTTACCTGCTTTTTGTTTTTCAAGTAATTTACGTTTA

CGGCTTATGTCACCGCCATAACATTTAGCTAAAACGTTTTTACCCATTGATTTAATA

TTTGTACGCGCTACAATTTTTTGTCCTATTGCAGCCTGTACAGGTACTTCAAATTGCT

GTCTTGGAATTAACGTTTTAAGTTTTTCAACTAATGCTTTACCACGTTCATATGCAA

AATCTCTATGAACTATGAAGCTTAGCGCATCCACTTTATCACCATTTAATAAAATAT

CCATCTTGACTAAATTACTTTCTTTATTTTCGATGAATTCATAATCAAATGATGCATA

TCCTTTAGTATTAGATTTAAGTTGATCGAAGAAATCAAATACAACTTCAGCTAAAG

GTAATTCATAAACAATATTTACACGAATATCATCTAAATAGTCCATATTTATAAATT

GTCCACGTTTACGTTGACATAATTCCATTACTGCACCGACATAGTCATTTGGAACCA

TCATAGTTGCACGAACATATGGCTCAAATATTTTATCAATTTTATCACGATCTGGCA

TTTGTGCTGGGTTATCAACCGTCACTTCTGAACCGTCCCTTAAAACACATTGATAAA

TTACAGATGGTGCAGTTGCAATTAATTCAATACCAAATTCTCTTTCAATTCTTTCTTG

AATTATTTCCATGTGTAACATACCTAAGAAACCAGTTCTATAACCAAAACCTAATGC

TTGTGACGATTCAGGCTCAAATTCTAATGATGCATCATTCAATTGTAATTTTTCTAA

TGCTTCTCTTAAATCATTATAATTTTTGTTATCTATTGGGAACAGTCCGCAATATACC

ATTGGATTCATTTTCTTATAACCTTGCAATGGTTCTGATGCAGGTCTACTAGCTAAT

GTGATGGTGTCACCAACCCTAGAATCATCAACATTTTTAATACTTGCAATAATATAA

CCAACATCACCAACTGTTAATTCATCAACTGGAAGCTGCTTAGGTGTATTAATTCCA

ACTTCTGTTACTTCGAACTCTTTACCAGTGGCCATCATTCGAATTTTATCTCCGGCTT

TAACAACACCGTCCACAATTCTTATCGATGAAATTACCCCTCTATATGGATCATACT

CAGAATCAAATATTAACGCTTTTAGTGGTGCTTCTGGGTCACCATCTGGAGCTGGCA

CAACTTCAACTATTTTCTCTAGTATCTCTTCAATTCCAATGTTAGATTTAGCACTTGC

TAAAACAACATCGTCTTGGTCTAAACCTATCATATCTTCAATTTCTTGTTTCACGCGT

TCAGGTTCTGCAGCAGGTAAATCAATTTTGTTAATAACAGGCAATAACTCTAACTCA

TTATCTAATGCTAAATAAACATTTGCTAATGTTTGTGCTTCGATACCTTGAGCCGCA

TCTACTACTAAAATCGCGCCCTCACAAGCTGCCAAAGAACGTGACACTTCATATGT

AAAATCGACGTGTCCAGGCGTATCGATTAAATGGAATGTATAAGTATTTCCATCTTT

AGCTTCGTACTTTAAACGTACTGCGTTTAATTTGATTGTAATACCACGTTCTCTTTCT

AAATCCATTGAATCTAGTAACTGATCTTGCATATCTCTTGTTTCAACTGATTTGGTAT

TTTCTAAAATTCTATCAGCCAATGTAGATTTTCCGTGGTCAATATGTGCTATAATCG

AGAAATTCCTTATATTCTCTCTTCTTTTTAAGCGTTGCTCATTATCCAT

-continued

SEQ ID NO 126
>Staphylococcus_epidermidis_RP62A
TTATTCATCGTCCATTTTTAATACTGCTAAAAATGCATCTTGCGGAATTTCTACATTG

CCTACTGCTTTCATTTTAGCTTTACCTGCTTTTTGTTTTTCTAAAAGTTTTCGTTTACG

ACTGATATCTCCACCATAACATTTAGATAAAACATTTTTACCCATAGATTTAATGTT

TGTTCGTGCAACAATTTTTTGACCAATAGCCGCCTGAACTGGCACTTCAAATTGTTG

TCGTGGAATTAATGTTTTTAATTTTTCGACAAGCGCTTTCCCTCTTTCATATGCAAAA

TCTCTATGGACAATAAAACTTAGAGCATCAACTTTATCTCCATTCAGTAATATGTCC

ATTTTAACAAGATTACTTTCTTTATTCTCAATAAATTCATAATCAAAAGAAGCATAC

CCTTTTGTGTTAGATTTAAGTTGATCAAAGAAATCGAAAACTACTTCTGATAATGGA

ATTTCATAAACAATATTAACTCTTATATCATCAAGATAATCCATGTTTATAAATTGA

CCTCTTTTACGTTGACATAATTCCATCACTGCACCTACATAATCATTCGGCACCATC

ATCGTAGCTTTGACAAATGGTTCATAAATATGTTCTATTTTATCTCTTTCGGGCATTT

GTGCTGGATTATCAACTGAAACTTCAGAACCATCTTTTAAGATACATTGATAGATAA

CAGAAGGCGCTGTTGCAATGAGTTCAATACCAAATTCTCTTTCAATTCTTTCTTGAA

TAATCTCCATATGTAACATTCCTAAAAATCCAGTTCTGTATCCAAAACCAAGTGCTT

GTGAAGACTCTGGTTCAAACTCTAAGGATGCGTCATTAAGTTGTAATTTTTCTAAAG

CTTCTCTTAGGTCATTATAGTCTTTATTGTCAATAGGGAATAGACCACAAAATACCA

TTGGATTCATCTTTTTATATCCTTGTAACGGTTTGTCAGCAGGTCTTTCAGCTAAAGT

AATTGTGTCACCTACTCTAGAATCATCAACATTTTTGATACTTGCGATAATATAACC

CACATCACCAACTGTTAATTCTTCTACCGGTAGTTGCTTAGGTGTATTGATTCCGAC

TTCTGTAACTTCAAATTCTTTACCGGTAGCCATCATTTTAATCCTATCTCCAGCTTTA

ACAACACCATCAATAATTCGAATTGAAGATATTACTCCTCTGTATGGATCATATTCT

GAATCAAAGATAAGTGCTTTAAGTGGGGCTTCTGGATCACCGTCCGGTGCTGGTAC

AACATCAACTATTTTCTCTAAAATTTCTTCAATACCTATATTTGACTTAGCACTTGCA

AGTACTACATCTTCTTGATCTATACCTATAACATCTTCTAATTCTTGCTTAACTCTAT

CGGGCTCAGCTGCAGGCAAGTCTATTTTATTAACAACTGGCAAAAGTTCCAAATCG

TTATCTAATGCTAAATAAACGTTTGCTAAGGTTTGTGCTTCTATACCTTGGGCAGCA

TCAACTACAAGAATTGCACCTTCACATGCAGCTAATGAGCGAGAAACCTCATATGT

AAAGTCGACATGTCCTGGTGTATCTATCAAATGAAATGTGTAAGTTTCTCCATCTTT

AGCTTCGTATTTTAATCGAACAGCATTTAGTTTAATAGTGATGCCTCGTTCTCTTTCC

AAATCCATAGAGTCAAGTAATTGATCTTGCATTTCTCGAGTTTCAACTGATTTTGTA

TTCTCTAAAATTCGATCAGCTAATGTCGATTTACCATGGTCTATATGAGCAATAATG

GAGAAATTTCTAATATTTTCTCTTCTATTGTATCGTTCTTGCTTATCCAT

SEQ ID NO 127
>Staphylococcus_epidermidis_ATCC_12228
TTATTCATCGTCCATTTTTAATACTGCTAAAAATGCATCTTGCGGAATTTCTACATTG

CCTACTGCTTTCATTTTAGCTTTACCTGCTTTTTGTTTTTCTAAAAGTTTTCGTTTACG

ACTGATATCTCCACCATAACATTTAGATAAAACATTTTTACCCATAGATTTAATGTT

TGTTCGTGCAACAATTTTTTGACCAATAGCCGCCTGAACTGGCACTTCAAATTGTTG

TCGTGGAATTAATGTTTTTAATTTTTCGACAAGCGCTTTCCCTCTTTCATACGCAAAA

TCTCTATGGACAATAAAACTTAGAGCATCAACTTTATCTCCATTCAGTAATATGTCC

-continued

ATTTTAACAAGATTACTTTCTTTATTCTCAATAAATTCATAATCAAAAGAAGCATAC

CCTTTTGTGTTAGATTTAAGTTGATCAAAGAAATCGAAAACTACTTCTGATAATGGA

ATTTCATAAACAATATTAACTCTTATATCATCAAGATAATCCATGTTTATAAATTGA

CCTCTTTTACGTTGACATAATTCCATCACTGCACCTACATAATCATTCGGCACCATC

ATCGTAGCTTTGACAAATGGTTCATAAATATGTTCTATTTTATCTCTTTCGGGCATTT

GTGCTGGATTATCAACTGAAACTTCAGAACCATCTTTTAAGATACATTGATAAATAA

CAGAAGGCGCTGTTGCAATGAGTTCAATACCAAATTCTCTTTCAATTCTTTCTTGAA

TAATCTCCATATGTAACATTCCTAAAAATCCAGTTCTGTATCCAAAACCAAGTGCTT

GTGAAGACTCTGGTTCAAACTCTAAGGATGCGTCATTAAGTTGTAATTTTTCTAAAG

CTTCTCTTAGGTCATTATAGTCTTTATTGTCAATAGGGAATAGACCACAAAATACCA

TTGGATTCATCTTTTTATATCCTTGTAACGGTTTGTCAGCAGGTCTTTCAGCTAAAGT

AATTGTGTCACCTACTCTAGAATCATCAACATTTTTGATACTTGCGATAATATAACC

CACATCACCAACTGTTAATTCTTCTACCGGTAGTTGCTTAGGTGTATTGATTCCGAC

TTCTGTAACTTCAAATTCTTTACCGGTAGCCATCATTTTAATCCTATCTCCAGCTTTA

ACAACACCATCAATAATTCGAATTGAAGATATTACTCCTCTGTATGGATCATATTCT

GAATCAAAGATAAGTGCTTTAAGTGGGGCTTCTGGATCACCGTCCGGTGCTGGTAC

AACATCAACTATTTTCTCTAAAATTTCTTCAATACCTATATTTGACTTAGCACTTGCA

AGTACTACATCTTCTTGATCTATACCTATAACATCTTCTAATTCTTGCTTAACTCTAT

CAGGCTCAGCTGCAGGCAAGTCTATTTTATTAACAACTGGCAAAAGTTCCAAATCG

TTATCTAATGCTAAATAAACGTTTGCTAAGGTTTGTGCTTCTATACCTTGGGCAGCA

TCAACTACAAGAATTGCACCTTCACATGCAGCTAATGAGCGAGAAACCTCATATGT

AAAGTCGACATGTCCTGGTGTATCTATCAAATGAAATGTGTAAGTTTCTCCATCTTT

AGCTTCGTATTTTAATCGAACAGCATTTAGTTTAATAGTGATGCCTCGTTCTCTTTCC

AAATCCATAGAGTCAAGTAATTGATCTTGCATTTCTCGAGTTTCAACTGATTTTGTA

TTCTCTAAAATTCGATCAGCTAATGTCGATTTACCATGGTCTATATGAGCAATAATG

GAGAAATTTCTAATATTTTCTCTTCTATTGTATCGTTCTTGCTTATCCAT

SEQ ID NO 128
>Staphylococcus_haemolyticus_JCSC1435
CTATTCATCATCCATTTTTAGTACAGCTAGGAAAGCATCTTGAGGAATTTCAACACT

ACCAACGGCTTTCATTTTAGCCTTACCTGCTTTTTGTTTTTCAAGTAACTTACGTTTA

CGGCTAATATCCCCACCATAACATTTAGATAATACATTTTTACCCATTGATTTGATG

TTTGTTCTTGCAACAATTTTTTGGCCAATAGCTGCTTGTACAGGTACTTCAAATTGTT

GACGTGGTATAAGCGTTTTTAATTTTTCAACTAATGCTTTTCCACGTTCGTATGCAA

AGTCTTTATGGACAATAAAGCTTAAAGCATCAACTTTATCCCCATTAAGTAGGATGT

CCATTTTCACTAAGTTACTTTCTTTATTTTCAATAAATTCATAATCAAATGAAGCGTA

ACCTTTAGTGTTGGATTTAAGTTGATCAAAGAAATCAAAAACAACTTCAGAAAGTG

GTATCTCGTATACGATATTAACTCTAATATCATCTAAATAATCCATATTAATAAATT

GTCCACGTTTACGTTGGCATAACTCCATAACTGCTCCAACGTAATCATTTGGAACCA

TCATTGTAGCTTTCACATATGGTTCATAAATTGAGTCAATCTTATCTCTTTCTGGCAT

TTGAGCCGGATTATCTACTGTAACCTCTGATCCATCCTTCATAATACATTGATAAAT

TACTGATGGCGCGGTAGCAATCAATTCAATACCAAATTCTCTTTCAATTCTTTCTTG

AATGATTTCCATGTGAAGCATTCCTAAGAAACCTGTTCTAAAACCAAAACCAAGAG

-continued

CCTGAGAAGATTCTGGCTCAAATTCTAATGAAGCGTCATTTAATTGTAATTTTTCAA

GCGCTTCTCTTAAATCATTATAGTCTTTATTTTCAATTGGGAACAAACCACAATATA

CCATTGGGTTCATTTTTTTATAACCTTTTAATGGTGCTTCAGCTGGTCTATTAGCATG

AGTAATTGTATCACCCACACGTGAGTCATCAACATTTTTGATGCTTGCAATAATATA

CCCTACATCACCTACAGTTAGTTCTTCTATAGGTAGTTGTTTAGGAGTATTAATGCC

TACTTCACTAACTTCAAATTCTTTACCTGTAGCCATCATTTTAATTTTATCACCAGCT

TTAACAACGCCTTCCATCACACGTATTGATGAAATAACACCTCTATAAGGGTCGTAT

TCTGAATCAAAAATTAATGCTTTCAATGGTTCACTAGGGTCACCTTCAGGTGGTGGG

ACAACTTCTACAATTTTCTCTAAAATATCTTCAATACCAATATTTGACTTTGCACTTG

CCAGTACTACATCGTCTTGATTTAAACCAATTACATCTTCTAATTCTTGTTTTACTCT

TTCAGGTTCAGCTGCAGGTAAATCAATTTTATTTACAACAGGTAATAATTCTAGATC

ATTATCAAGTGCTAAGTATACGTTTGCTAATGTTTGTGCTTCAATACCTTGTGCTGC

ATCCACCACTAATATTGCACCCTCACATGCTGCTAAAGATCGTGAAACCTCGTATGA

AAAGTCTACATGCCCTGGTGTATCAATTAAATGAAATGTATATGTTTGACCATCATT

TGCTTCATATTTTAATCGCACGGCATTTAATTTAATTGTGATGCCACGTTCTCTTTCA

AGATCCATTGAATCTAATAATTGATCTTGCATTTCTCTTGTTTCTACAGATTTAGTAT

TTTCTAAAATTCTATCTGCTAATGTTGATTTACCATGATCAATATGAGCAATAATAG

AAAAATTTCGTATATTTTCTCTTCTGTTATAGCGTTCTTGCATATCCAT

SEQ ID NO 129
>Staphylococcus_saprophyticus_ATCC_15305
TTAATCTTCATCCATTTTGAGTACTGCAAGGAAAGCATCTTGTGGAATTTCTACATT

TCCCACTGCTTTCATTTTGGCTTTACCCGCTTTTTGTTTTTCTAATAATTTTCTCTTAC

GTGTAATGTCTCCGCCATAACATTTAGACAATACATTTTTCCCCATAGATTTAATGT

TTGTTCTCGCGACAATTTTTTGTCCTACAGCAGCTTGTACTGGTACTTCAAATTGTTG

TCTTGGTATTAATGTTTTCAACTTATCGACAAGAGTTTTACCACGTTCGTATGCAAA

TTCTTTATGCACGATAAAGCTAAGAGCATCGACTTTTTCACCATTTAATAAAATATC

CATCTTAACCAGGTCACTTTCTTTATTATCAATAAATTCATAATCAAAAGAAGCATA

GCCTTTAGTATTAGATTTTAATTGATCGAAGAAATCAAATACTACTTCTGATAATGG

AATTTCATAAATAATATTCACTCGAATATCATCCATGTATTCCATATTAATAAATTG

ACCACGTTTACGTTGACACAATTCCATTACAGCACCGACATAATCATTTGGTACCAT

CATAGTCGCACGTACAAACGGCTCATAAATGGTTTCTATTTTATCGCGATCTGGCAT

ATTCGCTGGATTATCTACAGATACTTCCTCACCAGATTTTAATATACATTGGTAAAT

TACCGATGGCGCAGTTGCGATTAATTCAATGCCGAATTCACGTTCAATTCTTTCTTG

AATAATTTCCATGTGTAACATACCTAAAAAACCAGTACGGTAGCCAAAACCTAATG

CTTGAGAAGATTCTGGTTCAAATTCTAATGAGGCATCGTTTAATTGCAGCTTCTCTA

AAGCTTCTCTTAAATCGTTATAGTCTTTGTTATCAATAGGGAATAATCCACAGAATA

CCATTGGATTCATTTTTTTATAACCTTGTAGTGGCGCTTCAGCAGGTCTCTCTGCATG

CGTGATTGTATCACCTACACGGGAATCATCAACATTTTTAATACTAGCAATGATATA

ACCTACATCACCCACTGTTAATTCATCTACTGATAATTGTTTTGGGGTGTTAATACC

TACTTCAGTTACTTCAAATTCTTTTCCAGTAGCCATCATTTTGATACGATCTCCAGCT

TTAACAACGCCTTCCATAACACGTATGGATGAAATGACACCTCTATATGGATCATA

-continued

CTCAGAATCAAATATTAAAGCTTTTAAAGGTGCTTCTGGATCACCTTCAGGTGGTGG

TACTACCTCAACTATTTTTTCCAATATATCTTCAATACCTATGTTTGATTTTGCACTT

GCAAGTACGACATCCTCTTTATCAATACCAATAACGTCTTCAAGTTCTTGTTTAACG

CGTTCTGGCTCAGCTGCAGGCAAATCAATTTTATTGATAACAGGTAGAAGCTCTAA

ATCATTATCCAGTGCTAAATAGACATTAGCTAGTGTTTGTGCCTCAATACCTTGTGC

TGCGTCCACTACTAAAATAGCACCCTCACACGCTGCAAGTGATCTAGATACTTCATA

TGTAAAATCTACGTGTCCTGGTGTATCAATCAAATGGAACGTGTATGTTTCTCCATC

CTTCGCTTCGTATTTCAATCGTACTGCGTTTAGTTTTATAGTAATACCGCGTTCTCTC

TCTAAATCCATAGAATCTAGCAACTGTGATTGCATGTCTCTTGTTTCAACTGATTTA

GTATTTTCTAAAATTCTATCAGCTAAAGTAGATTTACCATGGTCTATATGTGCGATA

ATAGAAAAGTTTCTTATATTTTTGCGTCGATTATAACGATCTTGTTTATCCAT

SEQ ID NO 130
>Lactobacillus_sakei_subsp_sakei
TTATTTACCTTTGGTATCTTCATCATTCATCTTAAGAATGGACATGAAGGCTTCCTGC

GGCACTTCCACTGAGCCCACGGATTTCATCCGTTTCTTCCCAGCCTTTTGCTTTTCTA

ACAATTTCCGTTTCCGGGTGATGTCACCACCGTAACACTTGGCAAGCACGTTTTTCC

GGAAAGCTTTAACGGTTGAACGGGCAATAATCTTATTCCCGATAGCGGCTTGGATT

GGCACTTCGAATTGTTGACGCGGAATCGTTTCTTTCAACTTACCAACAATCACACGG

CTCCGTTCAAAGGCAAAGTCCCGATGCACGATGAAACTCAAGGCATCAACCGCTTC

ACCATTCAAGAGAATATCAATCTTAACCAGGTCACTGGCACGATAGCCTGTCACTT

CGTAATCAAACGATGCGTAACCCTTGGTGTTTGATTTCAAATCATCGAAGAAATCA

AAAATGATTTCAGAAAGTGGCATGTTGTAGATCACATTAACACGGTACGTATCTAA

ATAATCCATCGTCACGAATTCGCCCCGTTTACGTTGGGCTAATTCCATCACAGCCCC

AACATAATCGTTAGGGACCATGATTGACGCTTTGACGTATGGTTCTTTAACTTCTGA

AATATTTGATGTTTCTGGCATTTCTGATGGGTTATCAATCACTTCTTCAGTCCCATCA

GTCAAGGCAACGTGGTAATCAACCGATGGTGCTGTCATGATCAAGTCTAAATTAAA

TTCACGTTCCAATCGTTCTTGAACAACATCCATGTGTAACAGACCCAAGAAACCAC

ACCGGAACCCAAAGCCTAAAGCTTGCGATGATTCTGGTTCGAACTCTAAAGCCGCA

TCGTTTAATTGTAATTTCTCAAGCGCTTCACGTAAATCATTAAACTTCGCATTATCA

ACGGGATACATCCCTGAATAAACCATTGGTTGGATATGACGATAACCATCAAGTGG

TGCATCAGCTGGATTATCAGCTAAAGTGACCGTATCCCCAACGCGTGTATCTTGAAT

TGTTTTGATGCTAGCTGTGATATAACCAACATCACCGACCATTAAGAAATCACGTTT

AACCGCTTTGGGTGACATCACACCAACTTCTGTGACTTCAAATTCTTTACCGCTGTT

CATTAAACGAATCTTGTCGCCGACTTTAACCGTTCCATCGACCACTCGAATATTTAA

AACAACCCCGCGGTAACTATCATAATTTGAATCAAAAATTAAGGCTTTTAATGGCG

CTTCTAAATCACCAGTTGGGGCTGGTACATCCGTCACTAGTTTTTCAAGAATTTCTT

CAATCCCAATCCCACTTTTGGCACTGGCAAGAACGGCTTCTGACGCATCTAACCCA

ATCATTTCTTCAATTTCAGCCTTAACAACATCAGGTTGCGCTGATGGGAGGTCAATT

TTATTAATAACCGGTACGATTTCAAGATCATCGTCGACTGCTAAATAAACGTTGGCC

AATGTTTGGGCTTCAACGCCTTGCGCTGCATCAACAACTAATAAGGCCCCTTCGCAG

GCCGCCAAACTTCGTGACACTTCATATGAAAAATCGACATGCCCTGGCGTATCGAT

TAAATGGAAAATATAAGTTTCGCCATCTTTAGCATGGTAGTGCAATTCCACCGCGTT

-continued

CAACTTAATGGTAATCCCACGTTCACGTTCTAATTCCATGTCATCTAAGACTTGCGC

TTGCATATCGCGCTTGGCAATAGTATCCGTCATCTCAAGAATTCGATCAGCTAATGT

TGATTTACCATGATCAATATGCGCGATGATCGAAAAGTTACGAATGTGTTTTTGCCG

GTCTAACATTTCTGCGTAATCCAT

SEQ ID NO 131
>Lactobacillus_delbrueckii_subsp. Bulgaricus_ATCC11842
TTACTTGCCGTTGATGTCATCGTCATTCATCCGTAATACTGCCATAAAGGCGTCCTG

CGGGACTTCCACCCGGCCAACTGACTTCATCCGCTTCTTGCCCCGCTTCTGCTTCTCC

AGAAGCTTGGCCCGCCGGTCCGGGTCACCGGTGTGGATCTTCCAGGTAACGTCTTTT

CGGTAAGGCTTGATCGTAGCCCGGGAAATGATCTTGGACCCGATTGCTCCTTGGAT

GTCGACTTGGAAGTTTTGCCGCGGGATCAGCTTCTTCAACAGGCTGCACATCTGGAC

GGCCCGGTCCCGGGCTTCTTCGCGGTGGGCGATGAAGCTCAAGGCATCGATTGGTT

CCTTGTTCAAGAGAATGTCGATCTTGACCAGGTTGGTGGCCTTGTAGCCGATGATTT

CATAGTCCAAAGAAGCATAGCCCTTGGTTGAAGACTTAAGCTGGTCAAAGAAATCG

TAAATAATTTCTGCCAGGGGCATTTCGTAGATCACGTTGACCCGGTACTTGTCCAGG

TAGTCCATGGTCTGGAACTCGCCCCGCTTGCCTTCACACAGCTGCATTACAGCACCG

ACGAAGTCGTTTGGCACCATGATTTCCGCCTTGACGTAAGGCTCTTGCAATTCCTTG

TATTCACCGGCATCCGGCAGGTCAGCCGGGTTGTCGATCAGCTTGACCTCACCAGTC

GGCATGATAGCGTGGTAGTCAACTGACGGCGCGGTCATGATGAGGTCCAGGTCAAA

TTCCTGCTCCAAGCGCTCTTGCACGACGTCCATGTGCAAAAGGCCCAAAAAGCCGC

AGCGGAAACCAAAGCCCAGGGCTTGGGAAGTTTCCGGCTCAAATTCCAGAGACGC

ATCGTTAAGCTGTAATTTCTGCAGGGCTTCCTTCAAGTCGTCATAGTCCCGGTTGTC

GGTTGGATACATACCAGAGTAGACCATTGGCGGAATCTGCCGGTAGCCTGGCAAAG

CTTCTGCCGTCGGGTTTTCAGCGCTGGTGATGGTATCCCCGACCCGGGTTTCCCGGA

CAGACTTGATGTTGGCAGTAATATAGCCAACGTCCCCGGCAATCAAGATGTCTTCTT

TAACCGGGTGGGGGCTGGAAACGCCGACTTCGGTTACTTCATACTTTTTGCCGGTGT

TCATGATCATGATTTCGTCGCCTGGCTTAACCGTGCCTTCTTCAATTCTGACTGACAT

GACCACCCCCCGGTAGTCATCATACTTGGAGTCAAAGATCAAGGCCTTGAGGGGCT

TGGTCAAGTCCCCAGTCGGCGCTGAGATGTCGGTCACGATTCTTTCCAAAAGTTCCG

GAATCCCTGCCCCGGTCTTGCCGGAAACTTCCACGGCGTCGCTGGCGTCTAAGCCC

AGCATGTCGCCGATTTCGCTCTTGGCCATGTCCGGGTCGGCGCTTGGCAGGTCGATC

TTGTTTAAAACAGGCAGGATTTCCAGGTCGTTTTCCAAAGCCAGGTAAGTGTTGGA

CAGGGTCTGGGCCTGGACACCCTGGGAGGCGTCAACGACCAGGACAGCCCCTTCAC

AGGCAGCCAGGGACCGGGAAACTTCATAGGAGAAGTCGACGTGGCCGGGGGTGTC

GATCAAGTGGAAAATGTAGTCTTCCCCGTCATTGGCGTGATACTTGACCTGCACCG

AGTTCATCTTGATGGTGATCCCCCGCTGCCGTTCAAGGGGCATGTCATCCAGCATTT

GATTTTTCAGCTGCCGCTTGGAAACCGTGTCCGTCAGTTCCAGAATCCGGTCGGCAA

TCGTTGATTTGCCGTGGTCAACGTGGGCCACGATTGAAAAATTGCGGATGTGCTTTT

GGTAGTCTTTTAATTTTTCTAAGTCCAT

-continued

SEQ ID NO 132
>Lactobacillus_acidophilus
TTATTTACCTTTTATATCATCATCATTCATCTTAAGAACAGCCATAAATGCATCTTGA

GGTACTTCTACACGTCCAACAGCCTTCATTCTCTTCTTACCGCGCTTCTGCTTTTCAA

GCAATTTGGCACGACGATCAGGATCACCAGTATGGATTTTCCAAGTAACATCCTTA

CGATATGGCTTAATCGTAGCACGTGAAATAATCTTAGCACCGATTGCACCTTGAAT

ATCTACCTCAAAGTTTTGTCTAGGAATCAACTTCTTAAGCATTGAGGTCATTTGACG

AGCACGATCTTGCGCTTCACTTCTGTGTGCAATAAAGCTAAGAGCATCAATCGGTTC

CTTATTAAGCAAAATATCAATCTTGACTAAGTCAGTTGCACGATAACCAGTAATCTC

ATAGTCAAGTGAGGCATAGCCCTTAGTTGATGATTTTAAATCATCGAAAAAGTCAA

AAATAATCTCAGCTAAAGGCATGTTGTAAATAACATTAACACGATATTTATCTAAA

TAATCCATTGTAACAAATTCGCCGCGTTTACGTTGGCAAAGTTCCATTACAGGACCA

ACATAATCATTAGGAACCATAATTTCTGCCTTAACGTAAGGTTCTTGCACTTCTTTA

TATTCACCAGCATCTGGTAAATCAGATGGATTATCAATCACCTTAGTCGTACCATCA

TTCATTATTGCATGATAGTCAACACTTGGTGCGGTCATGATTAAATCAAGGTCAAAC

TCTTGCTCCAATCTTTCTTGAACTACGTCCATATGAAGTAAGCCAAGGAAACCACAA

CGGAAACCAAATCCTAAAGCAGTAGAAGTTTCTGGTTCAAATTCCAAAGCAGCATC

ATTTAATTGCAACTTTTGTAAAGCTTCTTTTAAATCATCGTAATCACGATTATCTACT

GGATACATACCAGAGTATACCATTGGTGGAATTTGACGGTAACCTGGAAGTGGTTC

AGCAGTTGGGTGCCCAGCATCAGTGATTGTATCACCTACACGAGTTTCACGAACTG

ATTTAATGTTGGCAGTAATATATCCTACATCACCAGCGATTAAAATATCTTTCTTTA

CTGGATGAGGACTTGAAACACCAACTTCAGTAACTTCATATTCCTTGCCAGTATTCA

TAATTTGAATCTTATCACCGGGCTTAACTGTACCATCTTCAATTCTAACTGATAAAA

CAACCCCACGATAATCATCATATTTTGAATCGAAAATAAGTGCTTTAAGTGGCGCTT

CAATATCACCTGATGGTGCAGGAATGTCAGTTACTATCTTTTCCAATAATTCAGGTA

TTCCTTGACCTGTTTTCCCAGATACTTCAACAGCGTCTGAAGCGTCAAGACCTAACA

TTTCCTCGATTTCTTCTTTAGCATTTTCTGGATCAGCAGAAGGTAAATCAATTTTATT

GATTACTGGTACAATTTCCAAATCGTCATCAATGGCTAAGTAAGTATTAGCTAAAGT

TTGTGCTTGAACACCTTGTGAAGCATCAACCACCAATAATGCACCTTCACATGCAGC

TAAGGAGCGTGATACTTCATATGAAAAGTCTACGTGTCCTGGTGTATCAATTAAGT

GGAAAATATAATCTTCGCCATTTTTGGCATGATACTTAACTTCAACCGAGTTCATCT

TGATGGTAATACCACGTTGTCTTTCAAGTGGCATATCATCAAGCATTTGATTTTTTA

ATTGTCTTTCAGATACTGTATCTGTTAACTCTAAGATTCGGTCAGCAATTGTTGACTT

ACCATGGTCAATATGGGCAACAATTGAAAAGTTACGAATGTGATTTTGATAATCTT

TTAATTTTTTTATATCCAT

SEQ ID NO 133
>Rickettsia_prowazekii_Madrid E
TTATTCACCTCCAATTTGCAATGCTGCAATAAATGCAGATTGTGGGATTTCTATATT

ACCGTACTGTCTCATTTTCTTTTTACCCGCTTTTTGCTTCTCAAGTAGTTTACGTTTAC

GGCTTATATCACCGCCATAACATTTTGATAAAACATCTTTACGTAAGGCTTTAATAG

TTTCACGAGCAATAATACGACTACCAACACTTGCTTGAATTGCTATATCGATCTGTT

GTCTTGGTATTAAATCCTTTAATCTTATGCATAAAGCCCTACCACGCTGTTCCGCAC

-continued

GTGATCGATGTACTATAGTTGATAACGCATCAACAACCTCCCCATTAACTAAAATCC

TAAGATTAACAAGATCAGAAAGTTCATAAACATCCATTTGCCATTCAAAACTTGCA

TAACCTTTAGAACAGCTTTTCAAACGATCATAAAAATCATAAACTATCTCATTTAGC

GGTAATTTATAAACTATTTTAGCTCTATTTGATATATAACTATGATCAAGTTGTATA

CCTCTTTTTTCTGTACAAAGCGATAATACAGTCCCTATAAACTCATCCGGAACTATT

ATAGTTGCCTTAATCCATGGCTCTTCCATCGATGCGATTTTTTGCAAATCAGGTAAA

TCGGCTGGGTTATGAATCTCTAAGTTCTGACCATCCAACATATTGATTTTATAGATC

ACACTTGGAGCAGTAGTGATTAAATCTAAATCGAATTCCCTACTTAAACGTTCTTGT

ATGATCTCTAAATGTAATAGCCCTAAAAAACCACACCTAAAACCTACTCCAAGAGC

TGAGGAGCTTTCCATTTCATACTCAAAACTGGCATCATTAAGACGTAATTTAGCTAA

AGAATCCTTGAGATGTTCGAATTCTGCACTATCTGTCGGATAAAAACCACAAAATA

CTACGGGTATATTCGGCTTAAAGCCAGGTAGTGCTTGTTCACAAGATTTTTTCTCAT

CAGTAATAGTATCACCAACTTTACAATCTGATACCCGTTTTATAGAAGCTGTAAAAA

AACCTATTTCCCCTGCATATAAAACATCCGAAATATGTTTTTTTGGAGTAAAAAAAC

CAACATGCTCGACGGTATAAACAGAATTTGTCCTCATCATTTTAACACGCATATTTT

TACGTAAAGCACCATCAATAATACGTACCAAAATAACTACACCAAGATACGGATCG

TACCAACTATCAACAAGTAACGCTTTTAAGATATCTGTGCTACTTTCTTTTGGGGCA

GGTAATTTATTGATTATTGCTTCTAGAACTGAATCAATGCCTATACCGTTTTTAGCA

GATATTAAAACAGCTTCACTTGCATCAATGCCAATTATATCCTCTATTTGCGTCTTA

ACATAATCAGGTTCTGAAGCTGCTAAATCAATCTTGTTAAGCACTGGTACAATCAA

ATGATCATTCGCAATTGCTTGATAAACATTTGCAAGAGTTTGAGCCTCTACTCCTTG

AGTACTATCCACTACTAATAACGAACCTTCACATGCAGCCAAGGACCTACTAACCT

CATAAGCAAAATCAACATGACCCGGAGTATCCATGAGATTCAAATAGTAAGTATTA

CCGTTTTTAGCTTTATATACAAGCCGTACAGTTTGGGCTTTAATAGTAATACCTCGT

TCTCTCTCTATATCCATCGAATCTAATACTTGCTGACTCATTTCCCTAGCATTCAAAC

CTCCACAATACTCGATTAGCCTATCAGCTAACGTAGATTTACCATGATCTATATGAG

CGATTATTGAGAAATTCCTTATATATTTTTGATTATTCAT

SEQ ID NO 134
>gi|33591275: 2575127-2576920 *Bordetella pertussis* Tohama I, complete genome
CTATTTGTCTTCGACTTGCAGGATGGCGAGGAACGCCTCTTGCGGGATTTCCACGCT

GCCGACCTGCTTCATGCGCTTCTTGCCGGCCTTCTGCTTTTCCAGCAACTTCTTCTTG

CGCGAGATATCGCCGCCATAGCACTTGGCCAGCACGTTCTTGCGCAGCGCCTTGAC

GTTCTCGCGCGCGATGACCTCCGCGCCGATTGCCGCCTGGATGGCCACGTCGAACA

TCTGGCGCGGGATCAGGCCGCGCATGCGCGAAACCACCTCGCGCGCCCGGTAGCGC

GCATTGTTGCGGTGCGCGATCATGGCCAGCGCATCGACGCGGTCGCCGTTGATCAG

CAGATCCACCTTGACCACGTCGGCCGAGCGGTATTCCACGAACTCGTAGTCCATCG

ACGCATAGCCGCGCGACACCGATTTCAGTTTGTCGAAGAAATCGAGCACGATCTCG

GCCAGCGGAATCTCGTAGGTCAGGTGCACCTGGCGCCCGTGGTAGCTCATGTTGAG

CTGGACGCCGCGCTTGTTGTTGCACAGTGTCATCACCGGCCCCACGTATTCCTGGGG

CATGAACAGCGTCACCTTGACGATGGGTTCGCGGATATCGGCGATCTTGGCGATTT

CCGGCATGCGCGACGGGCTTTCGATGGTCACGACCGTGCCGTCGCGCTGTTCGACC

TCATAGACCACCGATGGCGCGGTGGTGATGATGTCCATGTCGAACTCGCGCTCCAG

-continued

GCGCTCCTGCACGATTTCCATGTGCAGCAGCCCCAGGAAGCCGCAGCGAAAGCCGA

AGCCCAGCGCCTGCGACACTTCGGGCTCGAACATCAGCGCGGCGTCGTTGAGCTTC

AGCTTTTCCAGCGAATCGCGCAGCTGGTCGTATTCGGAGCTTTCCACCGGATACAG

GCCGGCGAACACCTGCGGCTTGACTTCCTTGAAGCCCGGCAGCGGCTCGGCCGCCG

GCTTGCCCGCCAGGGTGATGGTGTCGCCCACCTTGGCGTGTTCCAGTTCCTTGATGC

CGGCGATGACAAAGCCCACTTCGCCGGCCGACAACTCCGGCCGCGGCTGCGATTTG

GGCGTGAACACGCCGATCTGCTCGCACAGATGCGTGGCGTGGGACGCCATCAGCAG

GATCTTGTCCTTGGGCTTGAGCACGCCGTTGACGATGCGCACCAGCATGACCACGC

CCACGTAGTTGTCGAACCACGAATCGATGATCAGCGCCTGCAGCGGCGCGGACGGA

TCGCCCTTGGGCGGCGGCACCCGCGCCACGATGGATTCGAGGATCTCGTCGATGCC

CATGCCGGTCTTGGCGCTGGCCAGCACCGCCTCGGACGCGTCGATGCCGATCACGT

CTTCGACCTCCTGGCGCGCGGCTTCCGGGTCGGCCTGCGGCAGGTCCATCTTGTTGA

GCACCGGCAGCACTTCCATGCCCAGTTCGATGGCCGTGTAGCAGTTGGCCACGGTC

TGGGCCTCGACGCCCTGCGAAGCGTCGACCACCAGCAAGGCGCCTTCGCAGGCCGA

CAGCGAACGACTGACTTCGTACGAGAAATCGACGTGTCCGGGGGTATCGATCAGGT

TGAGGTTGTAGACCGTGCCGTCCTGCGACTTGTACTGCAGGGACGCGGTCTGCGCC

TTGATCGTGATACCCCGTTCGCGCTCGATATCCATGGAATCAAGCACTTGCGCGGAC

ATTTCGCGCTCGGCCAGCCCCCCGCAACGGTGGATCAGGCGATCGGCGAGCGTCGA

TTTACCGTGATCAATGTGGGCAATGATGGAAAAGTTGCGGATATGCTGCAT

SEQ ID NO 135
>gi|5932441: 340-2133 *Bordetella pertussis* lep operon, (also Tomaha I) complete sequence
CTATTTGTCTTCGACTTGCAGGATGGCGAGGAACGCCTCTTGCGGGATTTCCACGCT

GCCGACCTGCTTCATGCGCTTCTTGCCGGCCTTCTGCTTTTCCAGCAACTTCTTCTTG

CGCGAGATATCGCCGCCATAGCACTTGGCCAGCACGTTCTTGCGCAGCGCCTTGAC

GTTCTCGCGCGCGATGACCTCCGCGCCGATTGCCGCCTGGATGGCCACGTCGAACA

TCTGGCGCGGGATCAGGCCGCGCATGCGCGAAACCACCTCGCGCGCCCGGTAGCGC

GCATTGTTGCGGTGCGCGATCATGGCCAGCGCATCGACGCGGTCGCCGTTGATCAG

CAGATCCACCTTGACCACGTCGGCCGAGCGGTATTCCACGAACTCGTAGTCCATCG

ACGCATAGCCGCGCGACACCGATTTCAGTTTGTCGAAGAAATCGAGCACGATCTCG

GCCAGCGGAATCTCGTAGGTCAGGTGCACCTGGCGCCCGTGGTAGCTCATGTTGAG

CTGGACGCCGCGCTTGTTGTTGCACAGTGTCATCACCGGCCCCACGTATTCCTGGGG

CATGAACAGCGTCACCTTGACGATGGGTTCGCGGATATCGGCGATCTTGGCGATTT

CCGGCATGCGCGACGGGCTTTCGATGGTCACGACCGTGCCGTCGCGCTGTTCGACC

TCATAGACCACCGATGGCGCGGTGGTGATGATGTCCATGTCGAACTCGCGCTCCAG

GCGCTCCTGCACGATTTCCATGTGCAGCAGCCCCAGGAAGCCGCAGCGAAAGCCGA

AGCCCAGCGCCTGCGACACTTCGGGCTCGAACATCAGCGCGGCGTCGTTGAGCTTC

AGCTTTTCCAGCGAATCGCGCAGCTGGTCGTATTCGGAGCTTTCCACCGGATACAG

GCCGGCGAACACCTGCGGCTTGACTTCCTTGAAGCCCGGCAGCGGCTCGGCCGCCG

GCTTGCCCGCCAGGGTGATGGTGTCGCCCACCTTGGCGTGTTCCAGTTCCTTGATGC

CGGCGATGACAAAGCCCACTTCGCCGGCCGACAACTCCGGCCGCGGCTGCGATTTG

GGCGTGAACACGCCGATCTGCTCGCACAGATGCGTGGCGTGGGACGCCATCAGCAG

-continued

GATCTTGTCCTTGGGCTTGAGCACGCCGTTGACGATGCGCACCAGCATGACCACGC

CCACGTAGTTGTCGAACCACGAATCGATGATCAGCGCCTGCAGCGGCGCGGACGGA

TCGCCCTTGGGCGGCGGCACCCGCGCCACGATGGATTCGAGGATCTCGTCGATGCC

CATGCCGGTCTTGGCGCTGGCCAGCACCGCCTCGGACGCGTCGATGCCGATCACGT

CTTCGACCTCCTGGCGCGCGGCTTCCGGGTCGGCCTGCGGCAGGTCCATCTTGTTGA

GCACCGGCAGCACTTCCATGCCCAGTTCGATGGCCGTGTAGCAGTTGGCCACGGTC

TGGGCATCGACGCCCTGCGAAGCGTCGACCACCAGCAAGGCGCCTTCGCAGGCCGA

CAGCGAACGACTGACTTCGTACGAGAAATCGACGTGTCCGGGGGTATCGATCAGGT

TGAGGTTGTAGACCGTGCCGTCCTGCGACTTGTACTGCAGGGACGCGGTCTGCGCC

TTGATCGTGATACCCCGTTCGCGCTCGATATCCATGGAATCAAGCACTTGCGCGGAC

ATTTCGCGCTCGGCCAGCCCCCCGCAACGGTGGATCAGGCGATCGGCGAGCGTCGA

TTTACCGTGATCAATGTGGGCAATGATGGAAAAGTTGCGGATATGCTGCAT

SEQ ID NO 136
>gi|33572656: 143317-145110 *Bordetella pertussis* strain Tohama I
CTATTTGTCTTCGACTTGCAGGATGGCGAGGAACGCCTCTTGCGGGATTTCCACGCT

GCCGACCTGCTTCATGCGCTTCTTGCCGGCCTTCTGCTTTTCCAGCAACTTCTTCTTG

CGCGAGATATCGCCGCCATAGCACTTGGCCAGCACGTTCTTGCGCAGCGCCTTGAC

GTTCTCGCGCGCGATGACCTCCGCGCCGATTGCCGCCTGGATGGCCACGTCGAACA

TCTGGCGCGGGATCAGGCCGCGCATGCGCGAAACCACCTCGCGCGCCCGGTAGCGC

GCATTGTTGCGGTGCGCGATCATGGCCAGCGCATCGACGCGGTCGCCGTTGATCAG

CAGATCCACCTTGACCACGTCGGCCGAGCGGTATTCCACGAACTCGTAGTCCATCG

ACGCATAGCCGCGCGACACCGATTTCAGTTTGTCGAAGAAATCGAGCACGATCTCG

GCCAGCGGAATCTCGTAGGTCAGGTGCACCTGGCGCCCGTGGTAGCTCATGTTGAG

CTGGACGCCGCGCTTGTTGTTGCACAGTGTCATCACCGGCCCCACGTATTCCTGGGG

CATGAACAGCGTCACCTTGACGATGGGTTCGCGGATATCGGCGATCTTGGCGATTT

CCGGCATGCGCGACGGGCTTTCGATGGTCACGACCGTGCCGTCGCGCTGTTCGACC

TCATAGACCACCGATGGCGCGGTGGTGATGATGTCCATGTCGAACTCGCGCTCCAG

GCGCTCCTGCACGATTTCCATGTGCAGCAGCCCCAGGAAGCCGCAGCGAAAGCCGA

AGCCCAGCGCCTGCGACACTTCGGGCTCGAACATCAGCGCGGCGTCGTTGAGCTTC

AGCTTTTCCAGCGAATCGCGCAGCTGGTCGTATTCGGAGCTTTCCACCGGATACAG

GCCGGCGAACACCTGCGGCTTGACTTCCTTGAAGCCCGGCAGCGGCTCGGCCGCCG

GCTTGCCCGCCAGGGTGATGGTGTCGCCCACCTTGGCGTGTTCCAGTTCCTTGATGC

CGGCGATGACAAAGCCCACTTCGCCGGCCGACAACTCCGGCCGCGGCTGCGATTTG

GGCGTGAACACGCCGATCTGCTCGCACAGATGCGTGGCGTGGGACGCCATCAGCAG

GATCTTGTCCTTGGGCTTGAGCACGCCGTTGACGATGCGCACCAGCATGACCACGC

CCACGTAGTTGTCGAACCACGAATCGATGATCAGCGCCTGCAGCGGCGCGGACGGA

TCGCCCTTGGGCGGCGGCACCCGCGCCACGATGGATTCGAGGATCTCGTCGATGCC

CATGCCGGTCTTGGCGCTGGCCAGCACCGCCTCGGACGCGTCGATGCCGATCACGT

CTTCGACCTCCTGGCGCGCGGCTTCCGGGTCGGCCTGCGGCAGGTCCATCTTGTTGA

GCACCGGCAGCACTTCCATGCCCAGTTCGATGGCCGTGTAGCAGTTGGCCACGGTC

TGGGCCTCGACGCCCTGCGAAGCGTCGACCACCAGCAAGGCGCCTTCGCAGGCCGA

CAGCGAACGACTGACTTCGTACGAGAAATCGACGTGTCCGGGGGTATCGATCAGGT

-continued

TGAGGTTGTAGACCGTGCCGTCCTGCGACTTGTACTGCAGGGACGCGGTCTGCGCC

TTGATCGTGATACCCCGTTCGCGCTCGATATCCATGGAATCAAGCACTTGCGCGGAC

ATTTCGCGCTCGGCCAGCCCCCCGCAACGGTGGATCAGGCGATCGGCGAGCGTCGA

TTTACCGTGATCAATGTGGGCAATGATGGAAAAGTTGCGGATATGCTGCAT

SEQ ID NO 137
>gi|33598993: 3971204-3972997 *Bordetella bronchiseptica* RB50, complete genome
TTACTTGTCTTCGACTTGCAGGATGGCGAGGAACGCCTCTTGCGGGATTTCCACGCT

GCCGACCTGCTTCATGCGCTTCTTGCCGGCCTTCTGCTTTTCCAGCAACTTCTTCTTG

CGCGAGATATCGCCGCCATAGCACTTGGCCAGCACGTTCTTGCGCAGCGCCTTGAC

GTTCTCGCGCGCGATGACCTCCGCGCCGATTGCCGCCTGGATGGCCACGTCGAACA

TCTGGCGCGGGATCAGGCCGCGCATGCGCGAAACCACCTCGCGCGCCCGGTAGCGC

GCATTGTTGCGGTGCGCGATCATGGCCAGCGCATCGACGCGGTCGCCGTTGATCAG

CAGATCCACCTTGACCACGTCGGCCGAGCGGTATTCCACGAACTCGTAGTCCATCG

ACGCATAGCCGCGCGACACCGATTTCAGTTTGTCGAAGAAATCGAGCACGATCTCG

GCCAGCGGAATCTCGTAGGTCAGGTGCACCTGACGCCCGTGATAGCTCATGTTGAG

CTGGACGCCGCGCTTGTTGTTGCACAGCGTCATCACCGGCCCCACGTATTCCTGGGG

CATGAACAGCGTCACCTTGACGATGGGTTCGCGGATATCGGCGATCTTGGCGATTT

CCGGCATGCGCGACGGGCTTTCGATGGTCACGACCGTGCCGTCGCGCTGTTCGACC

TCATAGACCACCGATGGCGCGGTGGTGATGATGTCCATGTCGAACTCGCGCTCCAG

GCGCTCCTGCACGATTTCCATGTGCAGCAGCCCCAGGAAGCCGCAGCGAAAGCCGA

AGCCCAGCGCCTGCGACACTTCGGGTTCGAACATCAGCGCGGCGTCGTTGAGCTTC

AGCTTTTCCAGCGAATCGCGCAGCTGGTCGTATTCGGAGCTTTCCACCGGATACAG

GCCGGCGAACACCTGCGGCTTGACTTCCTTGAAGCCCGGCAGCGGCTCGGCCGCCG

GCTTGCCCGCCAGGGTGATGGTGTCGCCCACCTTGGCGTGTTCCAGTTCCTTGATGC

CGGCGATGACAAAGCCCACTTCGCCGGCCGACAACTCCGGCCGCGGCTGCGATTTG

GGCGTGAACACGCCGATCTGCTCGCACAGATGCGTGGCGTGGGACGCCATCAGCAG

GATCTTGTCCTTGGGCTTGAGCACGCCGTTGACGATGCGCACCAGCATGACCACGC

CCACGTAGTTGTCGAACCACGAATCGATGATCAGCGCCTGCAGCGGCGCGGACGGA

TCGCCCTTGGGCGGCGGCACGCGCGCCACGATGGATTCGAGGATTTCGTCGATGCC

CATGCCGGTCTTGGCGCTGGCCAGCACCGCCTCGGACGCGTCGATGCCGATCACGT

CTTCGACCTCCTGGCGCGCGGCTTCCGGATCGGCCTGCGGCAGGTCCATCTTGTTGA

GCACCGGCAGCACTTCCACGCCCAGCTCGATGGCCGTGTAGCAGTTGGCCACGGTC

TGGGCCTCGACGCCCTGCGAGGCGTCGACCACCAGCAAGGCGCCTTCGCAGGCCGA

CAGCGAACGACTGACTTCGTACGAGAAATCGACGTGTCCGGGGGTATCGATCAGGT

TGAGGTTGTAGACCGTGCCGTCCTGCGACTTGTACTGCAGGGACGCGGTCTGCGCC

TTGATCGTGATACCCCGTTCGCGCTCGATATCCATGGAATCAAGCACTTGCGCGGAC

ATTTCGCGCTCGGCCAGCCCCCCGCAACGGTGGATCAGGCGATCGGCGAGCGTCGA

TTTACCGTGATCGATGTGGGCAATGATGGAAAAGTTGCGGATATGCTGCAT

SEQ ID NO 138
>gi|33577019: 140181-141974 *Bordetella bronchiseptica* strain RB50, complete genome;
segment 12/16
TTACTTGTCTTCGACTTGCAGGATGGCGAGGAACGCCTCTTGCGGGATTTCCACGCT

GCCGACCTGCTTCATGCGCTTCTTGCCGGCCTTCTGCTTTTCCAGCAACTTCTTCTTG

-continued

CGCGAGATATCGCCGCCATAGCACTTGGCCAGCACGTTCTTGCGCAGCGCCTTGAC

GTTCTCGCGCGCGATGACCTCCGCGCCGATTGCCGCCTGGATGGCCACGTCGAACA

TCTGGCGCGGGATCAGGCCGCGCATGCGCGAAACCACCTCGCGCGCCCGGTAGCGC

GCATTGTTGCGGTGCGCGATCATGGCCAGCGCATCGACGCGGTCGCCGTTGATCAG

CAGATCCACCTTGACCACGTCGGCCGAGCGGTATTCCACGAACTCGTAGTCCATCG

ACGCATAGCCGCGCGACACCGATTTCAGTTTGTCGAAGAAATCGAGCACGATCTCG

GCCAGCGGAATCTCGTAGGTCAGGTGCACCTGACGCCCGTGATAGCTCATGTTGAG

CTGGACGCCGCGCTTGTTGTTGCACAGCGTCATCACCGGCCCCACGTATTCCTGGGG

CATGAACAGCGTCACCTTGACGATGGGTTCGCGGATATCGGCGATCTTGGCGATTT

CCGGCATGCGCGACGGGCTTTCGATGGTCACGACCGTGCCGTCGCGCTGTTCGACC

TCATAGACCACCGATGGCGCGGTGGTGATGATGTCCATGTCGAACTCGCGCTCCAG

GCGCTCCTGCACGATTTCCATGTGCAGCAGCCCCAGGAAGCCGCAGCGAAAGCCGA

AGCCCAGCGCCTGCGACACTTCGGGTTCGAACATCAGCGCGGCGTCGTTGAGCTTC

AGCTTTTCCAGCGAATCGCGCAGCTGGTCGTATTCGGAGCTTTCCACCGGATACAG

GCCGGCGAACACCTGCGGCTTGACTTCCTTGAAGCCCGGCAGCGGCTCGGCCGCCG

GCTTGCCCGCCAGGGTGATGGTGTCGCCCACCTTGGCGTGTTCCAGTTCCTTGATGC

CGGCGATGACAAAGCCCACTTCGCCGGCCGACAACTCCGGCCGCGGCTGCGATTTG

GGCGTGAACACGCCGATCTGCTCGCACAGATGCGTGGCGTGGGACGCCATCAGCAG

GATCTTGTCCTTGGGCTTGAGCACGCCGTTGACGATGCGCACCAGCATGACCACGC

CCACGTAGTTGTCGAACCACGAATCGATGATCAGCGCCTGCAGCGGCGCGGACGGA

TCGCCCTTGGGCGGCGGCACGCGCGCCACGATGGATTCGAGGATTTCGTCGATGCC

CATGCCGGTCTTGGCGCTGGCCAGCACCGCCTCGGACGCGTCGATGCCGATCACGT

CTTCGACCTCCTGGCGCGCGGCTTCCGGATCGGCCTGCGGCAGGTCCATCTTGTTGA

GCACCGGCAGCACTTCCACGCCCAGCTCGATGGCCGTGTAGCAGTTGGCCACGGTC

TGGGCCTCGACGCCCTGCGAGGCGTCGACCACCAGCAAGGCGCCTTCGCAGGCCGA

CAGCGAACGACTGACTTCGTACGAGAAATCGACGTGTCCGGGGGTATCGATCAGGT

TGAGGTTGTAGACCGTGCCGTCCTGCGACTTGTACTGCAGGGACGCGGTCTGCGCC

TTGATCGTGATACCCCGTTCGCGCTCGATATCCATGGAATCAAGCACTTGCGCGGAC

ATTTCGCGCTCGGCCAGCCCCCCGCAACGGTGGATCAGGCGATCGGCGAGCGTCGA

TTTACCGTGATCGATGTGGGCAATGATGGAAAAGTTGCGGATATGCTGCAT

SEQ ID NO 139
>gi|33574176: 76674-78467 *Bordetella parapertussis* strain 12822, complete genome; segment 11/14
TTACTTGTCTTCGACTTGCAGGATGGCGAGGAACGCCTCTTGCGGGATTTCCACGCT

GCCGACCTGCTTCATGCGCTTCTTGCCGGCCTTCTGCTTTTCCAGCAACTTCTTCTTG

CGCGAGATATCGCCGCCATAGCACTTGGCCAGCACGTTCTTGCGCAGCGCCTTGAC

GTTCTCGCGCGCGATGACCTCCGCGCCGATTGCCGCCTGGATGGCCACGTCGAACA

TCTGGCGCGGGATCAGGCCGCGCATGCGCGAAACCACCTCGCGCGCCCGGTAGCGC

GCATTGTTGCGGTGCGCGATCATGGCCAGCGCATCGACGCGGTCGCCGTTGATCAG

CAGATCCACCTTGACCACGTCGGCCGAGCGGTATTCCACGAACTCGTAGTCCATCG

ACGCATAGCCGCGCGACACCGATTTCAGTTTGTCGAAGAAATCGAGCACGATCTCG

GCCAGCGGAATCTCGTAGGTCAGGTGCACCTGACGCCCGTGATAGCTCATGTTGAG

-continued

CTGGACGCCGCGCTTGTTGTTGCACAGCGTCATCACCGGCCCCACGTATTCCTGGGG

CATGAACAGCGTCACCTTGACGATGGGTTCGCGGATATCGGCGATCTTGGCGATTT

CCGGCATGCGCGACGGGCTTTCGATGGTCACGACCGTGCCGTCGCGCTGTTCGACC

TCATAGACCACCGATGGCGCGGTGGTGATGATGTCCATGTCGAACTCGCGCTCCAG

GCGCTCCTGCACGATTTCCATGTGCAGCAGCCCCAGGAAGCCGCAGCGAAAGCCGA

AGCCCAGCGCCTGCGACACTTCGGGTTCGAACATCAGCGCGGCGTCGTTGAGCTTC

AGCTTTTCCAGCGAATCGCGCAGCTGGTCGTATTCGGAGCTTTCCACCGGATACAG

GCCGGCGAACACCTGCGGCTTGACTTCCTTGAAGCCCGGCAGCGGCTCGGCCGCCG

GCTTGCCCGCCAGGGTGATGGTGTCGCCCACCTTGGCGTGTTCCAGTTCCTTGATGC

CGGCGATGACAAAGCCCACTTCGCCGGCCGACAACTCCGGCCGCGGCTGCGATTTG

GGCGTGAACACGCCGATCTGCTCGCACAGATGCGTGGCGTGGGACGCCATCAGCAG

GATCTTGTCCTTGGGCTTGAGCACGCCGTTGACGATGCGCACCAGCATGACCACGC

CCACGTAGTTGTCGAACCACGAATCGATGATCAGCGCCTGCAGCGGCGCGGACGGA

TCGCCCTTGGGCGGCGGCACGCGCGCCACGATGGATTCGAGGATTTCGTCGATGCC

CATGCCGGTCTTGGCGCTGGCCAGCACCGCCTCGGACGCGTCGATGCCGATCACGT

CTTCGACCTCCTGGCGCGCGGCTTCCGGATCGGCCTGCGGCAGGTCCATCTTGTTGA

GCACCGGCAGCACTTCCACGCCCAGCTCGATGGCCGTGTAGCAGTTGGCCACGGTC

TGGGCCTCGACGCCCTGCGAGGCGTCGACCACCAGCAAGGCGCCTTCGCAGGCCGA

CAGCGAACGACTGACTTCGTACGAGAAATCGACGTGTCCGGGGGTATCGATCAGGT

TGAGGTTGTAGACCGTGCCGTCCTGCGACTTGTACTGCAGGGACGCGGTCTGCGCC

TTGATCGTGATACCCCGTTCGCGCTCGATATCCATGGAATCAAGCACTTGCGCGGAC

ATTTCGCGCTCGGCCAGCCCCCCGCAACGGTGGATCAGGCGATCGGCGAGCGTCGA

TTTACCGTGATCGATGTGGGCAATGATGGAAAAGTTGCGGATATGCTGCAT

SEQ ID NO 140
>gi|163258032: 1817720-1819513 *Bordetella petrii* strain DSM 12804, complete genome
CTACTTGTCTTCGACTTGCAGGATGGCCAGGAACGCTTCCTGGGGGATCTCGACGCT

GCCCACCTGCTTCATGCGTTTCTTGCCGGCTTTCTGCTTTTCGAGAAGTTTTTTCTTG

CGGGTGATGTCGCCGCCGTAGCACTTGGCCAGCACGTTCTTGCGTAGCGCCTTGAC

GTTCTCGCGCGCGATGACCTCGGCGCCGATAGCCGCCTGAATGGCCACGTCGAACA

TCTGGCGCGGGATCAGCCCGCGCATGCGCGTGACCACGTCGCGCGCGCGATAGCGG

GCATTGGCCCGGTGCACGATCATGGCCAACGCGTCGACGCGGTCGCCGTTGATGAG

CAGGTCGACCCGCACCACGTCGGCCGAACGGTATTCCAGGAATTCGTAATCCATCG

AGGCATAGCCGCGCGACACCGACTTGAGCTTGTCGAAGAAGTCGAGCACGATCTCG

GCCAGCGGAATCTCGTAGGTCAGGTGCACCTGGCGGCCGTGGTAGCTCATGTTGAT

CTGCACGCCGCGCTTGTTGTTGCACAACGTCATGACCGGACCCACGTATTCCTGGGG

CATGAACAGCGTGACCTTGACGATGGGCTCGCGGATGTCGGCGATCTTGCCCACTT

CGGGCATGCGCGCCGGGCTATCGACGATTTCGATGCTGCCGTCGCGTTGTTCGACTT

CGTACACCACCGACGGCGCGGTAGTGATGATGTCCATGTCGAACTCGCGCTCGAGG

CGCTCTTGCACGATTTCCATGTGCAGCAGGCCCAGGAAGCCGCAGCGGAAACCGAA

GCCCAGCGCCTGCGAGACCTCGGGTTCGAACATCAGCGCGGCATCGTTGAGCTTGA

GCTTTTCGAGCGAATCGCGTAGTTGGTCGTATTCGGAGCTTTCTACCGGATACAGGC

-continued

CGGCGAACACCTGCGGCTTGACTTCCTTGAAGCCCGGCAGCGGCGCGTTGGCCGGC

TTGCCCGCCAGGGTGACGGTATCGCCCACCTTGGCATGCGCCAGCTCTTTGATGCCG

GCAATGATGAACCCGACCTCGCCCGCGGACAGCTCGGTGCGCGGCTGCGACTTGGG

CGTGAACACGCCGACCTGCTCGCACAGGTGGGTGGCGCCCGAGGCCATCAGCAGG

ATCTTGTCTTTGGGACGCAGCACGCCGTTGATGATGCGCACCAGCATCACCACGCC

CACGTAGTTGTCGAACCAGGAGTCGATGATCAGGGCCTGCAGTGCGCCGTCGGGGT

TGCCCTGAGGCGCCGGCACGCGGGCCACGATGGTCTCGAGGATCTCGTCGATGCCC

ATGCCCGTCTTGGCGCTGGCCAGCACCGCGTTCGAGGCGTCGATGCCGATGACGTC

TTCGACCTCTTGGCGCGCGGCGTCGGGATCGGCCTGCGGCAGGTCCATCTTGTTGAG

CACGGGCAGCACTTCGACGCCCAGTTCGATGGCGGTGTAGCAGTTCGCCACCGTCT

GGGCCTCGACGCCCTGCGAGGCATCGACCACCAGCAGCGCCCCTTCGCAAGCCGAC

AGCGAACGGCTGACTTCGTACGAGAAGTCGACGTGCCCCGGGGTGTCGATGAGGTT

CAGGTTGTAGGTCTTGCCGTCCTGGGCCTGGTATTGCAGCGCGGCGGTCTGGGCCTT

GATGGTGATGCCCCGCTCGCGCTCGATTTCCATGGAGTCCAGCACCTGCGCGGACA

TTTCGCGCGCCGCCAACCCGCCGCAACGCTGGATCAGGCGGTCGGCCAAGGTCGAT

TTGCCGTGATCGATGTGGGCGATGATGGAGAAATTGCGGATATGCTGCAT

SEQ ID NO 141
>gi|163854304: 1817720-1819513 *Bordetella petrii* DSM 12804, complete genome
CTACTTGTCTTCGACTTGCAGGATGGCCAGGAACGCTTCCTGGGGGATCTCGACGCT

GCCCACCTGCTTCATGCGTTTCTTGCCGGCTTTCTGCTTTTCGAGAAGTTTTTTCTTG

CGGGTGATGTCGCCGCCGTAGCACTTGGCCAGCACGTTCTTGCGTAGCGCCTTGAC

GTTCTCGCGCGCGATGACCTCGGCGCCGATAGCCGCCTGAATGGCCACGTCGAACA

TCTGGCGCGGGATCAGCCCGCGCATGCGCGTGACCACGTCGCGCGCGCGATAGCGG

GCATTGGCCCGGTGCACGATCATGGCCAACGCGTCGACGCGGTCGCCGTTGATGAG

CAGGTCGACCCGCACCACGTCGGCCGAACGGTATTCCAGGAATTCGTAATCCATCG

AGGCATAGCCGCGCGACACCGACTTGAGCTTGTCGAAGAAGTCGAGCACGATCTCG

GCCAGCGGAATCTCGTAGGTCAGGTGCACCTGGCGGCCGTGGTAGCTCATGTTGAT

CTGCACGCCGCGCTTGTTGTTGCACAACGTCATGACCGGACCCACGTATTCCTGGGG

CATGAACAGCGTGACCTTGACGATGGGCTCGCGGATGTCGGCGATCTTGCCCACTT

CGGGCATGCGCGCCGGGCTATCGACGATTTCGATGCTGCCGTCGCGTTGTTCGACTT

CGTACACCACCGACGGCGCGGTAGTGATGATGTCCATGTCGAACTCGCGCTCGAGG

CGCTCTTGCACGATTTCCATGTGCAGCAGGCCCAGGAAGCCGCAGCGGAAACCGAA

GCCCAGCGCCTGCGAGACCTCGGGTTCGAACATCAGCGCGGCATCGTTGAGCTTGA

GCTTTTCGAGCGAATCGCGTAGTTGGTCGTATTCGGAGCTTTCTACCGGATACAGGC

CGGCGAACACCTGCGGCTTGACTTCCTTGAAGCCCGGCAGCGGCGCGTTGGCCGGC

TTGCCCGCCAGGGTGACGGTATCGCCCACCTTGGCATGCGCCAGCTCTTTGATGCCG

GCAATGATGAACCCGACCTCGCCCGCGGACAGCTCGGTGCGCGGCTGCGACTTGGG

CGTGAACACGCCGACCTGCTCGCACAGGTGGGTGGCGCCCGAGGCCATCAGCAGG

ATCTTGTCTTTGGGACGCAGCACGCCGTTGATGATGCGCACCAGCATCACCACGCC

CACGTAGTTGTCGAACCAGGAGTCGATGATCAGGGCCTGCAGTGCGCCGTCGGGGT

TGCCCTGAGGCGCCGGCACGCGGGCCACGATGGTCTCGAGGATCTCGTCGATGCCC

ATGCCCGTCTTGGCGCTGGCCAGCACCGCGTTCGAGGCGTCGATGCCGATGACGTC

-continued

TTCGACCTCTTGGCGCGCGGCGTCGGGATCGGCCTGCGGCAGGTCCATCTTGTTGAG

CACGGGCAGCACTTCGACGCCCAGTTCGATGGCGGTGTAGCAGTTCGCCACCGTCT

GGGCCTCGACGCCCTGCGAGGCATCGACCACCAGCAGCGCCCCTTCGCAAGCCGAC

AGCGAACGGCTGACTTCGTACGAGAAGTCGACGTGCCCCGGGGTGTCGATGAGGTT

CAGGTTGTAGGTCTTGCCGTCCTGGGCCTGGTATTGCAGCGCGGCGGTCTGGGCCTT

GATGGTGATGCCCCGCTCGCGCTCGATTTCCATGGAGTCCAGCACCTGCGCGGACA

TTTCGCGCGCCGCCAACCCGCCGCAACGCTGGATCAGGCGGTCGGCCAAGGTCGAT

TTGCCGTGATCGATGTGGGCGATGATGGAGAAATTGCGGATATGCTGCAT

SEQ ID NO 142
>DSM4927-*B. pertussis*
GCGCGCGATGACCTCCGCGCCGATTGCCGCCTGGATGGCCACGTCGAACATCTGGC

GCGGGATCAGGCCGCGCATGCGCGAAACCACCTCGCGCGCCCGGTAGCGCGCATTG

TTGCGGTGCGCGATCATGGCCAGCGCATCGACGCGGTCGCCGTTGATCAGCAGATC

CACCTTGACCACGTCGGCCGAGCGGTATTCCACGAACTCGTAGTCCATCGACGCAT

AGCCGCGCGACACCGATTTCAGTTTGTCGAAGAAATCGAGCACGATCTCGGCCAGC

GGAATCTCGTAGGTCAGGTGCACCTGGCGCCCGTGGTAGCTCATGTTGAGCTGGAC

GCCGCGCTTGTTGTTGCACAGTGTCATCACCGGCCCCACGTATTCCTGGGGCATGAA

CAGCGTCACCTTGACGATGGGTTCGCGGATATCGGCGATCTTGGCGATTTCCGGCAT

GCGCGACGGGCTTTCGATGGTCACGACCGTGCCGTCGCGCTGTTCGACCTCATAGA

CCACCGATGGCGCGGTGGTGATGATGTCCATGTCGAACTCGCGCTCCAGGCGCTCC

TGCACGATTTCCATGTGCAGCAGCCCCAGGAAGCCGCAGCGAAAGCCGAAGCCCA

GCGCCTGCGACACTTCGGGCTCGAACATCAGCGCGGCGTCGTTGAGCTTCAGCTTTT

CCAGCGAATCGCGCAGCTGGTCGTATTCGGAGCTTTCCACCGGATACAGGCCGGCG

AACACCTGCGGCTTGACTTCCTTGAAGCCCGGCAGCGGCTCGGCCGCCGGCTTGCC

CGCCAGGGTGATGGTGTCGCCCACCTTGGCGTGTTCCAGTTCCTTGATGCCGGCGAT

GACAAAGCCCACTTCGCCGGCCGACAACTCCGGCCGCGGCTGCGATTTGGGCGTGA

ACACGCCGATCTGCTCGCACAGATGCGTGGCGTGGGACGCCATCAGCAGGATCTTG

TCCTTGGGCTTGAGCACGCCGTTGACGATGCGCACCAGCATGACCACGCCCACGTA

GTTGTCGAACCACGAATCGATGATCAGCGCCTGCAGCGGCGCGGACGGATCGCCCT

TGGGCGGCGGCACCCGCGCCACGATGGATTCGAGGATCTCGTCGATGCCCATGCCG

GTCTTGGCGCTGGCCAGCACCGCCTCGGACGCGTCGATGCCGATCACGTCTTCGAC

CTCCTGGCGCGCGGCTTCCGGGTCGGCCTGCGGCAGGTCCATCTTGTTGAGCACCG

GCAGCACTTCCATGCCCAGTTCGATGGCCGTGTAGCAGTTGGCCACGGTCTGGGCC

TCGACGCCCTGCGAAGCGTCGACCACCAGCAAGGCGCCTTCGCAGGCCGACAGCGA

ACGACTGACTTCGTACGAGAAATCGACGTGTCCGGGGGTATCGATCAGGTTGAGGT

TGTAGACCGTGCCGTCCTGCGACTTGTACTGCAGGGACGCGGTCTGCGCCTTGATSGT

SEQ ID NO 143
>DSM5571-*B. pertussis*
GCGCGCGATGACCTCCGCGCCGATTGCCGCCTGGATGGCCACGTCGAACATCTGGC

GCGGGATCAAGCCGCGCATGCGCGAAACCACCTCGCGCGCCCGGTAGCGCGCATTG

TTGCGGTGCGCGATCATGGCCAGCGCATCGACGCGGTCGCCGTTGATCAGCAGATC

CACCTTGACCACGTCGGCCGAGCGGTATTCCACGAACTCGTAGTCCATCGACGCAT

-continued

AGCCGCGCGACACCGATTTCAGTTTGTCGAAGAAATCGAGCACGATCTCGGCCAGC

GGAATCTCGTAGGTCAGGTGCACCTGGCGCCCGTGGTAGCTCATGTTGAGCTGGAC

GCCGCGCTTGTTGTTGCACAGTGTCATCACCGGCCCCACGTATTCCTGGGGCATGAA

CAGCGTCACCTTGACGATGGGTTCGCGGATATCGGCGATCTTGGCGATTTCCGGCAT

GCGCGACGGGCTTTCGATGGTCACGACCGTGCCGTCGCGCTGTTCGACCTCATAGA

CCACCGATGGCGCGGTGGTGATGATGTCCATGTCGAACTCGCGCTCCAGGCGCTCC

TGCACGATTTCCATGTGCAGCAGCCCCAGGAAGCCGCAGCGAAAGCCGAAGCCCA

GCGCCTGCGACACTTCGGGCTCGAACATCAGCGCGGCGTCGTTGAGCTTCAGCTTTT

CCAGCGAATCGCGCAGCTGGTCGTATTCGGAGCTTTCCACCGGATACAGGCCGGCG

AACACCTGCGGCTTGACTTCCTTGAAGCCCGGCAGCGGCTCGGCCGCCGGCTTGCC

CGCCAGGGTGATGGTGTCGCCCACCTTGGCGTGTTCCAGTTCCTTGATGCCGGCGAT

GACAAAGCCCACTTCGCCGGCCGACAACTCCGGCCGCGGCTGCGATTTGGGCGTGA

ACACG

SEQ ID NO 144
>CCUG48372-*B. pertussis*
GCGCGCGATGACCTCCGCGCCGATTGCCGCCTGGATGGCCACGTCGAACATCTGGC

GCGGGATCAGGCCGCGCATGCGCGAAACCACCTCGCGCGCCCGGTAGCGCGCATTG

TTGCGGTGCGCGATCATGGCCAGCGCATCGACGCGGTCGCCGTTGATCAGCAGATC

CACCTTGACCACGTCGGCCGAGCGGTATTCCACGAACTCGTAGTCCATCGACGCAT

AGCCGCGCGACACCGATTTCAGTTTGTCGAAGAAATCGAGCACGATCTCGGCCAGC

GGAATCTCGTAGGTCAGGTGCACCTGGCGCCCGTGGTAGCTCATGTTGAGCTGGAC

GCCGCGCTTGTTGTTGCACAGTGTCATCACCGGCCCCACGTATTCCTGGGGCATGAA

CAGCGTCACCTTGACGATGGGTTCGCGGATATCGGCGATCTTGGCGATTTCCGGCAT

GCGCGACGGGCTTTCGATGGTCACGACCGTGCCGTCGCGCTGTTCGACCTCATAGA

CCACCGATGGCGCGGTGGTGATGATGTCCATGTCGAACTCGCGCTCCAGGCGCTCC

TGCACGATTTCCATGTGCAGCAGCCCCAGGAAGCCGCAGCGAAAGCCGAAGCCCA

GCGCCTGCGACACTTCGGGCTCGAACATCAGCGCGGCGTCGTTGAGCTTCAGCTTTT

CCAGCGAATCGCGCAGCTGGTCGTATTCGGAGCTTTCCACCGGATACAGGCCGGCG

AACACCTGCGGCTTGACTTCCTTGAAGCCCGGCAGCGGCTCGGCCGCCGGCTTGCC

CGCCAGGGTGATGGTGTCGCCCACCTTGGCGTGTTCCAGTTCCTTGATGCCGGCGAT

GACAAAGCCCACTTCGCCGGCCGACAACTCCGGCCGCGGCTGCGATTTGGGCGTGA

ACACG

SEQ ID NO 145
>DSM13414-*B. bronchiseptica*
GCGCGCGATGACCTCCGCGCCGATTGCCGCCTGGATGGCCACGTCGAACATCTGGC

GCGGGATCAGGCCGCGCATGCGCGAAACCACCTCGCGCGCCCGGTAGCGCGCATTG

TTGCGGTGCGCGATCATGGCCAGCGCATCGACGCGGTCGCCGTTGATCAGCAGATC

CACCTTGACCACGTCGGCCGAGCGGTATTCCACGAACTCGTAGTCCATCGACGCAT

AGCCGCGCGACACCGATTTCAGTTTGTCGAAGAAATCGAGCACGATCTCGGCCAGC

GGAATCTCGTAGGTCAGGTGCACCTGACGCCCGTGATAGCTCATGTTGAGCTGGAC

GCCGCGCTTGTTGTTGCACAGCGTCATCACCGGCCCCACGTATTCCTGGGGCATGAA

CAGCGTCACCTTGACGATGGGTTCGCGGATATCGGCGATCTTGGCGATTTCCGGCAT

GCGCGACGGGCTTTCGATGGTCACGACCGTGCCGTCGCGCTGTTCGACCTCATAGA

-continued

CCACCGATGGCGCGGTGGTGATGATGTCCATGTCGAACTCGCGCTCCAGGCGCTCC

TGCACGATTTCCATGTGCAGCAGCCCCAGGAAGCCGCAGCGAAAGCCGAAGCCCA

GCGCCTGCGACACTTCGGGTTCGAACATCAGCGCGGCGTCGTTGAGCTTCAGCTTTT

CCAGCGAATCGCGCAGCTGGTCGTATTCGGAGCTTTCCACCGGATACAGGCCGGCG

AACACCTGCGGCTTGACTTCCTTGAAGCCCGGCAGCGGCTCGGCCGCCGGCTTGCC

CGCCAGGGTGATGGTGTCGCCCACCTTGGCGTGTTCCAGTTCCTTGATGCCGGCGAT

GACAAAGCCCACTTCGCCGGCCGACAACTCCGGCCGCGGCTGCGATTTGGGCGTGA

ACACG

SEQ ID NO 146
>CCUG55529-*B. bronchiseptica*
GCGCGCGATGACCTCCGCGCCGATTGCCGCCTGGATGGCCACGTCGAACATCTGGC

GCGGGATCAGGCCGCGCATGCGCGAAACCACCTCGCGCGCCCGGTAGCGCGCATTG

TTGCGGTGCGCGATCATGGCCAGCGCATCGACGCGGTCGCCGTTGATCAGCAGATC

CACCTTGACCACGTCGGCCGAGCGGTATTCCACGAACTCGTAGTCCATCGACGCAT

AGCCGCGCGACACCGATTTCAGTTTGTCGAAGAAATCGAGCACGATCTCGGCCAGC

GGAATCTCGTAGGTCAGGTGCACCTGACGCCCGTGATAGCTCATGTTGAGCTGGAC

GCCGCGCTTGTTGTTGCACAGCGTCATCACCGGCCCCACGTATTCCTGGGGCATGAA

CAGCGTCACCTTGACGATGGGTTCGCGGATATCGGCGATCTTGGCGATTTCCGGCAT

GCGCGACGGGCTTTCGATGGTCACGACCGTGCCGTCGCGCTGTTCGACCTCATAGA

CCACCGATGGCGCGGTGGTGATGATGTCCATGTCGAACTCGCGCTCCAGGCGCTCC

TGCACGATTTCCATGTGCAGCAGCCCCAGGAAGCCGCAGCGAAAGCCGAAGCCCA

GCGCCTGCGACACTTCGGGTTCGAACATCAGCGCGGCGTCGTTGAGCTTCAGCTTTT

CCAGCGAATCGCGCAGCTGGTCGTATTCGGAGCTTTCCACCGGATACAGGCCGGCG

AACACCTGCGGCTTGACTTCCTTGAAGCCCGGCAGCGGCTCGGCCGCCGGCTTGCC

CGCCAGGGTGATGGTGTCGCCCACCTTGGCGTGTTCCAGTTCCTTGATGCCGGCGAT

GACAAAGCCCACTTCGCCGGCCGACAACTCCGGCCGCGGCTGCGATTTGGGCGTGA

ACACG

SEQ ID NO 147
>DSM-10303-*B. bronchiseptica*
ACCTCCGCGCCGATTGCCGCCTGGATGGCCACGTCGAACATCTGGCGCGGGATCAG

GCCGCGCATGCGCGAAACCACCTCGCGCGCCCGGTAGCGCGCATTGTTGCGGTGCG

CGATCATGGCCAGCGCATCGACGCGGTCGCCGTTGATCAGCAGATCCACCTTGACC

ACGTCGGCCGAGCGGTATTCCACGAACTCGTAGTCCATCGACGCATAGCCGCGCGA

CACCGATTTCAGTTTGTCGAAGAAATCGAGCACGATCTCGGCCAGCGGAATCTCGT

AGGTCAGGTGCACCTGACGCCCGTGATAGCTCATGTTGAGCTGGACGCCGCGCTTG

TTGTTGCACAGCGTCATCACCGGCCCCACGTATTCCTGGGGCATGAACAGCGTCAC

CTTGACGATGGGTTCGCGGATATCGGCGATCTTGGCGATTTCCGGCATGCGCGACG

GGCTTTCGATGGTCACGACCGTGCCGTCGCGCTGTTCGACCTCATAGACCACCGATG

GCGCGGTGGTGATGATGTCCATGTCGAACTCGCGCTCCAGGCGCTCCTGCACGATTT

CCATGTGCAGCAGCCCCAGGAAGCCGCAGCGAAAGCCGAAGCCCAGCGCCTGCGA

CACTTCGGGTTCGAACATCAGCGCGGCGTCGTTGAGCTTCAGCTTTTCCAGCGAATC

GCGCAGCTGGTCGTATTCGGAGCTTTCCACCGGATACAGGCCGGCGAACACCTGCG

-continued

GCTTGACTTCCTTGAAGCCCGGCAGCGGCTCGGCCGCCGGCTTGCCCGCCAGGGTG

ATGGTGTCGCCCACCTTGGCGTGTTCCAGTTCCTTGATGCCGGCGATGACAAAGCCC

ACTTCGCCGGCCGACAACTCCGGCCGCGGCTGCGATTTGGGCGTGAACACGCCGAT

CTGCTCGCACAGATGCGTGGCGTGGGACGCCATCAGCAGGATCTTGTCCTTGGGCT

TGAGCACGCCGTTGACGATGCGCACCAGCATGACCACGCCCACGTAGTTGTCGAAC

CACGAATCGATGATCAGCGCCTGCAGCGGCGCGGACGGATCGCCCTTGGGCGGCGG

CACGCGCGCCACGATGGATTCGAGGATTTCGTCGATGCCCATGCCGGTCTTGGCGC

TGGCCAGCACCGCCTCGGACGCGTCGATGCCGATCACGTCTTCGACCTCCTGGCGC

GCGGCTTCCGGATCGGCCTGCGGCAGGTCCATCTTGTTGAGCACCGGCAGCACTTC

CACGCCCAGCTCGATGGCCGTGTAGCAGTTGGCCACGGTCTGGGCCTCGACGCCCT

GCGAGGCGTCGACCACCAGCAAGGCGCCTTCGCAGGCCGACAGCGAACGACTGAC

TTCGTACGAGAAATCGACGTGTCCGGGGGTATCGATCAGGTTGAGGTTGTAGACCG

TGCCGTCCTGCGACTTGTACTGCAGGGACGCGGTCTGCGCCTTGATSGT

SEQ ID NO 148
>DSM4922-*B. parapertussis*
GCGCGCGATGACCTCCGCGCCGATTGCCGCCTGGATGGCCACGTCGAACATCTGGC

GCGGGATCAGGCCGCGCATGCGCGAAACCACCTCGCGCGCCCGGTAGCGCGCATTG

TTGCGGTGCGCGATCATGGCCAGCGCATCGACGCGGTCGCCGTTGATCAGCAGATC

CACCTTGACCACGTCGGCCGAGCGGTATTCCACGAACTCGTAGTCCATCGACGCAT

AGCCGCGCGACACCGATTTCAGTTTGTCGAAGAAATCGAGCACGATCTCGGCCAGC

GGAATCTCGTAGGTCAGGTGCACCTGACGCCCGTGATAGCTCATGTTGAGCTGGAC

GCCGCGCTTGTTGTTGCACAGCGTCATCACCGGCCCCACGTATTCCTGGGGCATGAA

CAGCGTCACCTTGACGATGGGTTCGCGGATATCGGCGATCTTGGCGATTTCCGGCAT

GCGCGACGGGCTTTCGATGGTCACGACCGTGCCGTCGCGCTGTTCGACCTCATAGA

CCACCGATGGCGCGGTGGTGATGATGTCCATGTCGAACTCGCGCTCCAGGCGCTCC

TGCACGATTTCCATGTGCAGCAGCCCCAGGAAGCCGCAGCGAAAGCCGAAGCCCA

GCGCCTGCGACACTTCGGGTTCGAACATCAGCGCGGCGTCGTTGAGCTTCAGCTTTT

CCAGCGAATCGCGCAGCTGGTCGTATTCGGAGCTTTCCACCGGATACAGGCCGGCG

AACACCTGCGGCTTGACTTCCTTGAAGCCCGGCAGCGGCTCGGCCGCCGGCTTGCC

CGCCAGGGTGATGGTGTCGCCCACCTTGGCGTGTTCCAGTTCCTTGATGCCGGCGAT

GACAAAGCCCACTTCGCCGGCCGACAACTCCGGCCGCGGCTGCGATTTGGGCGTGA

ACACG

SEQ ID NO 149
>CCUG33551-*B. parapertussis*
GCGCGCGATGACCTCCGCGCCGATTGCCGCCTGGATGGCCACGTCGAACATCTGGC

GCGGGATCAGGCCGCGCATGCGCGAAACCACCTCGCGCGCCCGGTAGCGCGCATTG

TTGCGGTGCGCGATCATGGCCAGCGCATCGACGCGGTCGCCGTTGATCAGCAGATC

CACCTTGACCACGTCGGCCGAGCGGTATTCCACGAACTCGTAGTCCATCGACGCAT

AGCCGCGCGACACCGATTTCAGTTTGTCGAAGAAATCGAGCACGATCTCGGCCAGC

GGAATCTCGTAGGTCAGGTGCACCTGACGCCCGTGATAGCTCATGTTGAGCTGGAC

GCCGCGCTTGTTGTTGCACAGCGTCATCACCGGCCCCACGTATTCCTGGGGCATGAA

CAGCGTCACCTTGACGATGGGTTCGCGGATATCGGCGATCTTGGCGATTTCCGGCAT

GCGCGACGGGCTTTCGATGGTCACGACCGTGCCGTCGCGCTGTTCGACCTCATAGA

-continued

CCACCGATGGCGCGGTGGTGATGATGTCCATGTCGAACTCGCGCTCCAGGCGCTCC

TGCACGATTTCCATGTGCAGCAGCCCCAGGAAGCCGCAGCGAAAGCCGAAGCCCA

GCGCCTGCGACACTTCGGGTTCGAACATCAGCGCGGCGTCGTTGAGCTTCAGCTTTT

CCAGCGAATCGCGCAGCTGGTCGTATTCGGAGCTTTCCACCGGATACAGGCCGGCG

AACACCTGCGGCTTGACTTCCTTGAAGCCCGGCAGCGGCTCGGCCGCCGGCTTGCC

CGCCAGGGTGATGGTGTCGCCCACCTTGGCGTGTTCCAGTTCCTTGATGCCGGCGAT

GACAAAGCCCACTTCGCCGGCCGACAACTCCGGCCGCGGCTGCGATTTGGGCGTGA

ACACG

SEQ ID NO 150
>CCUG413-*B. parapertussis*
GCGCGCGATGACCTCCGCGCCGATTGCCGCCTGGATGGCCACGTCGAACATCTGGC

GCGGGATCAGGCCGCGCATGCGCGAAACCACCTCGCGCGCCCGGTAGCGCGCATTG

TTGCGGTGCGCGATCATGGCCAGCGCATCGACGCGGTCGCCGTTGATCAGCAGATC

CACCTTGACCACGTCGGCCGAGCGGTATTCCACGAACTCGTAGTCCATCGACGCAT

AGCCGCGCGACACCGATTTCAGTTTGTCGAAGAAATCGAGCACGATCTCGGCCAGC

GGAATCTCGTAGGTCAGGTGCACCTGACGCCCGTGATAGCTCATGTTGAGCTGGAC

GCCGCGCTTGTTGTTGCACAGCGTCATCACCGGCCCCACGTATTCCTGGGGCATGAA

CAGCGTCACCTTGACGATGGGTTCGCGGATATCGGCGATCTTGGCGATTTCCGGCAT

GCGCGACGGGCTTTCGATGGTCACGACCGTGCCGTCGCGCTGTTCGACCTCATAGA

CCACCGATGGCGCGGTGGTGATGATGTCCATGTCGAACTCGCGCTCCAGGCGCTCC

TGCACGATTTCCATGTGCAGCAGCCCCAGGAAGCCGCAGCGAAAGCCGAAGCCCA

GCGCCTGCGACACTTCGGGTTCGAACATCAGCGCGGCGTCGTTGAGCTTCAGCTTTT

CCAGCGAATCGCGCAGCTGGTCGTATTCGGAGCTTTCCACCGGATACAGGCCGGCG

AACACCTGCGGCTTGACTTCCTTGAAGCCCGGCAGCGGCTCGGCCGCCGGCTTGCC

CGCCAGGGTGATGGTGTCGCCCACCTTGGCGTGTTCCAGTTCCTTGATGCCGGCGAT

GACAAAGCCCACTTCGCCGGCCGACAACTCCGGCCGCGGCTGCGATTTGGGCGTGA

ACACG

SEQ ID NO 151
>B. petrii_str. DSM_12804
CTACTTGTCTTCGACTTGCAGGATGGCCAGGAACGCTTCCTGGGGGATCTCGACGCT

GCCCACCTGCTTCATGCGTTTCTTGCCGGCTTTCTGCTTTTCGAGAAGTTTTTTCTTG

CGGGTGATGTCGCCGCCGTAGCACTTGGCCAGCACGTTCTTGCGTAGCGCCTTGAC

GTTCTCGCGCGCGATGACCTCGGCGCCGATAGCCGCCTGAATGGCCACGTCGAACA

TCTGGCGCGGGATCAGCCCGCGCATGCGCGTGACCACGTCGCGCGCGCGATAGCGG

GCATTGGCCCGGTGCACGATCATGGCCAACGCGTCGACGCGGTCGCCGTTGATGAG

CAGGTCGACCCGCACCACGTCGGCCGAACGGTATTCCAGGAATTCGTAATCCATCG

AGGCATAGCCGCGCGACACCGACTTGAGCTTGTCGAAGAAGTCGAGCACGATCTCG

GCCAGCGGAATCTCGTAGGTCAGGTGCACCTGGCGGCCGTGGTAGCTCATGTTGAT

CTGCACGCCGCGCTTGTTGTTGCACAACGTCATGACCGGACCCACGTATTCCTGGGG

CATGAACAGCGTGACCTTGACGATGGGCTCGCGGATGTCGGCGATCTTGCCCACTT

CGGGCATGCGCGCCGGGCTATCGACGATTTCGATGCTGCCGTCGCGTTGTTCGACTT

CGTACACCACCGACGGCGCGGTAGTGATGATGTCCATGTCGAACTCGCGCTCGAGG

-continued

CGCTCTTGCACGATTTCCATGTGCAGCAGGCCCAGGAAGCCGCAGCGGAAACCGAA

GCCCAGCGCCTGCGAGACCTCGGGTTCGAACATCAGCGCGGCATCGTTGAGCTTGA

GCTTTTCGAGCGAATCGCGTAGTTGGTCGTATTCGGAGCTTTCTACCGGATACAGGC

CGGCGAACACCTGCGGCTTGACTTCCTTGAAGCCCGGCAGCGGCGCGTTGGCCGGC

TTGCCCGCCAGGGTGACGGTATCGCCCACCTTGGCATGCGCCAGCTCTTTGATGCCG

GCAATGATGAACCCGACCTCGCCCGCGGACAGCTCGGTGCGCGGCTGCGACTTGGG

CGTGAACACGCCGACCTGCTCGCACAGGTGGGTGGCGCCCGAGGCCATCAGCAGG

ATCTTGTCTTTGGGACGCAGCACGCCGTTGATGATGCGCACCAGCATCACCACGCC

CACGTAGTTGTCGAACCAGGAGTCGATGATCAGGGCCTGCAGTGCGCCGTCGGGGT

TGCCCTGAGGCGCCGGCACGCGGGCCACGATGGTCTCGAGGATCTCGTCGATGCCC

ATGCCCGTCTTGGCGCTGGCCAGCACCGCGTTCGAGGCGTCGATGCCGATGACGTC

TTCGACCTCTTGGCGCGCGGCGTCGGGATCGGCCTGCGGCAGGTCCATCTTGTTGAG

CACGGGCAGCACTTCGACGCCCAGTTCGATGGCGGTGTAGCAGTTCGCCACCGTCT

GGGCCTCGACGCCCTGCGAGGCATCGACCACCAGCAGCGCCCCTTCGCAAGCCGAC

AGCGAACGGCTGACTTCGTACGAGAAGTCGACGTGCCCCGGGGTGTCGATGAGGTT

CAGGTTGTAGGTCTTGCCGTCCTGGGCCTGGTATTGCAGCGCGGCGGTCTGGGCCTT

GATGGTGATGCCCCGCTCGCGCTCGATTTCCATGGAGTCCAGCACCTGCGCGGACA

TTTCGCGCGCCGCCAACCCGCCGCAACGCTGGATCAGGCGGTCGGCCAAGGTCGAT

TTGCCGTGATCGATGTGGGCGATGATGGAGAAATTGCGGATATGCTGCAT

SEQ ID NO 152
>DSM11332-*B. avium*
ACGCGCAATGACTTCAGCGCCGATCGCTGCCTGAATGGCAACGTCATACATCTGGC

GCGGAATCAGGGCACGCATGCGCGACACCACATCACGGGCACGGTAGCGGGCATT

CGAGCGGTGCACAATCATGGCAAGCGCATCGACCCGGTCGCCATTGATCAGCAGAT

CGACCTTAACCACGTCTGCCGGGCGGTACTCGAGGAACTCGTAGTCCATCGAGGCA

TAACCGCGCGACACGGACTTCAGACGATCGAAGAAGTCCAGCACGATTTCAGCCAG

CGGGATCTCATAGGTGAGATGCACCTGCCGACCATGGTAGGTCATGTTGATCTGGT

TGCCGCGCTTGTTATTACACAGCGTCATCACCGGACCGACATACTCCTGCGGCATGA

AAAGCGTGACCTTGACGATAGGCTCGCGGATTTCGGCAATCTTGCCGACTTCCGGC

ATGCGCGAGGGGCTTTCGATGGTCAACACCGTACCGTCGCGCTCAACGACCTCGTA

CACCACCGACGGCGCGGTGGTGATGATGTCCATATCGAACTCGCGCTCCAGACGCT

CCTGCACGATTTCCATGTGCAAGAGCCCAAGAAAACCGCAACGAAAACCGAAACC

CAGGGCCTGCGACACTTCAGGCTCGAACATGAGCGCAGCGTCGTTAAGCTTGAGTT

TTTCGAGCGAGTCGCGCAACTGATCGTATTCGGAACTCTCGACCGGGTAGAGGCCG

GCGAAAACCTGCGGCTGGACCTCTTTGAAGCCCGGCAAAGGCGCGGCGGCGGGCTT

GCCAGCCAAGGTGATGGTGTCACCCACTTTGGCATGCSCCAACTCTTTGATGCCCGC

AATGATGAAGCCCACCTCGCCTGCCGACAACTGCGCACGCGGCTGCGACTTGGGCG

TGAACACGCCGGTCTGCTCGCACAGATGCGTGGCACCGGAAGCCATCAGCAAAATC

TTGTCTTTCGGGCGCAATACACCGTTGACGATGCGCACCAGCATCACGACACCGAC

ATAGTTATCGAACCAGGAGTCGATAATCAGCGCCTGCAGCGCAGCTTCCGGGTCAC

CCTCAGGGGACGGCACACGGGCCACGATGGCCTCAAGAATCTCGTCAATGCCCATC

CCGGTCTTGGCGCTGGCCAGTACGGCGTCGGAGGCGTCGATGCCGATGACATCTTC

-continued

GACCTCCTGGCGCGCGCCCTCGGGATCGGCCTGGGGCAAGTCCATTTTATTCAGGA

CAGCCAGCACCTCCACGCCCAGATCGATAGCCGTATAGCAGTTGGCCACGGTTTGC

GCTTCGACGCCCTGGGACGCGTCCACCACCAGCAATGCGCCCTCGCAAGCCGACAA

GGAACGGCTCACTTCATAAGAAAAGTCTACGTGACCCGGGGTGTCGATCAGATTGA

GGTTGTAAACCTTGCCGTCCTGGGCCTTGTACTCCAGCGCCGCCGTCTGGGCCTTGA

TSGT

SEQ ID NO 153
>CCUG14270-*B. avium*
ACGCGCAATGACTTCAGCGCCGATCGCTGCCTGAATGGCAACGTCATACATCTGGC

GCGGAATCAGGGCACGCATGCGCGACACCACATCACGGGCACGGTAGCGGGCATT

CGATCGGTGCACAATCATGGCAAGCGCATCGACCCGGTCGCCATTGATCAGCAGAT

CGACCTTAACCACGTCTGCCGGGCGGTACTCGAGGAACTCGTAGTCCATCGAGGCA

TAACCGCGCGACACGGACTTCAGACGATCGAAGAAGTCCAGCACGATTTCAGCCAG

CGGGATCTCATAGGTGAGATGCACCTGCCGACCATGGTAGGTCATGTTGATCTGGT

TGCCGCGCTTGTTATTACACAGCGTCATCACCGGACCGACATACTCCTGCGGCATGA

AAAGCGTGACCTTGACGATAGGCTCGCGGATTTCGGCAATCTTGCCGACTTCCGGC

ATGCGCGAGGGGCTTTCGATGGTCAACACCGTACCGTCGCGCTCAACGACCTCGTA

CACCACCGACGGCGCGGTGGTGATGATGTCCATATCGAACTCGCGCTCCAGACGCT

CCTGCACGATTTCCATGTGCAAGAGCCCAAGAAAACCGCAACGAAAACCGAAACC

CAGGGCCTGCGACACTTCAGGCTCGAACATGAGCGCAGCGTCGTTAAGCTTGAGTT

TTTCGAGCGAGTCGCGCAACTGATCGTATTCGGAACTCTCGACCGGGTAGAGGCCG

GCGAAAACCTGCGGCTGGACCTCTTTGAAGCCCGGCAAAGGCGCGGCGGCGGGCTT

GCCAGCCAAGGTGATGGTGTCACCCACTTTGGCATGCGCCAACTCTTTGATGCCCGC

TATGATGAAGCCCACCTCGCCTGCCGACAGCTGCGCACGCGGCTGCGACTTGGGCG

TGAACACGCCGGTCTGCTCGCACAGATGCGTGGCACCGGAAGCCATCAGCAAAATC

TTGTCTTTCGGGCGCAATACACCGTTGACGATGCGCACCAGCATCACGACACCGAC

ATAGTTATCGAACCAGGAGTCGATAATCAGCGCCTGCAGCGCAGCTTCCGGGTCAC

CCTCAGGGGACGGCACACGGGCCACGATGGCCTCAAGAATCTCGTCAATGCCCATC

CCGGTCTTGGCGCTGGCCAGTACGGCGTCGGAGGCGTCGATGCCGATGACATCTTC

GACCTCCTGGCGCGCGCCCTCGGGATCGGCCTGGGGCAAGTCCATTTTATTCAGGA

CAGCCAGCACCTCCACGCCCAGATCGATAGCCGTATAGCAGTTGGCCACGGTTTGC

GCTTCGACGCCCTGGGACGCGTCCACCACCAGCAATGCGCCCTCGCAAGCCGACAA

GGAACGGCTCACTTCATAAGAAAAGTCTACGTGACCCGGGGTGTCGATCAGATTGA

GGTTGTAAACCTTGCCGTCCTGGGCCTTGTACTCCAGCGCCGCCGTCTGGGCCTTGA

TSGT

SEQ ID NO 154
>B. holmesiiDSM-13416-
GCGATCACTTCCGCACCGATAGCGGCTTGAATGGCCACGTCATACATTTGACGGGG

GATGAGCTCACGCATGCGCGAGACAACCTCGCGCGCACGATAGCGCGCATTGGAGC

GGTGAACGATCATCGCCAGGGCGTCGACCCGGTCGCTGTTGATCAGCAAGTCCACT

TTGACCACGTCCGCGGATCGGTACTCCAGGAATTCATAGTCCATGGAGGCATAGCC

GCGCGAGACCGACTTCAAGCGGTCGAAGAAGTCCAACACGATCTCGGCCAGCGGA

-continued

ATCTCATAGGTCAAATGCACCTGGCGTCCGTGGTAGGTCATGTTGATCTGCGTGCCG

CGCTTGTTGTTGCACAGCGTCATGACCGGCCCCACATACTCCTGGGGCATGAACAA

GGTGACCTTGACGATGGGTTCTCGAATATCGGCAATCTTGCCCACGTCAGGCATGC

GCGACGGGCTTTCGATGGTCAGCACCGTGCCATCGCGCTCCTGAACCTCATAGACC

ACCGACGGCGCGGTGGTGATGATGTCCATGTCAAACTCGCGCTCGAGCCGCTCCTG

CACGATTTCCATGTGCAGCAGGCCCAGAAAGCCGCAGCGAAAGCCAAACCCCAAG

GCTTGCAAGACTTCCGGCTCGAACATCAGCGCCGCGTCGTTGAGCTTGAGTTTCTCC

AGCGAATCACGCAACTGATCGTATTCGGAGCTCTCGACCGGATACAGACCGGCGAA

CACCTGCGGCTGGACCTCTTTGAAGCCAGGCAACGGTTCGGTTGCCGGCTTGCCGG

CCAGGGTAATCGTATCGCCCACCTTGGCATTGGCCAGCTCTTTGATGCCCGCGATGA

CAAAACCCACTTCGCCCGCGGACAGATGGGGGCGTTGCTGCGATTTGGGCGTAAAC

ACCCCTGTCTGCTCGCACAGATGCGTCGCGCCCGAAGCCATCAGCAGAATCTTGTC

CTTGGGCCGCAGCACGCCGTTGACGATACGCACCAACATCACCACGCCGACGTAGT

TGTCGAACCATGAGTCAATGATGAGGGCCTGCAATGGCGCCGCTGGGTCGCCCTTG

GGCGGCGGCACACGCGCGACGACCATTTCCAGGATCTCGTCGATCCCCATCCCTGT

CTTGGCACTGGCCAGCACGGCATCCGTGGCATCGATGCCAATCACATCCTCGACTTC

CTGGCGCGCACCATCTGGATCGGCCTGGGGCAGGTCCATCTTGTTCAGGACCGCCA

GCACCTCAACGCCAAGATCGATGGCGGTATAACAGTTGGCCACGGTCTGCGCCTCT

ACGCCCTGCGAGGCATCGACCACCAGCAGCGCCCCCTCACATGCTGACAGCGAGCG

GCTGACCTCGTAGGAGAAGTCCACATGCCCCGGTGTGTCGATCAGGTTGAGGTTGT

AGATCTTGCCGTCCTGAGCCTTGTACTGCAGCGCCGCAGTCTGCGCCTTGATSGT

SEQ ID NO 155
>B. holmesiiCCUG-53681
GCGATCACTTCCGCACCGATAGCGGCTTGAATGGCCACGTCATACATTTGACGGGG

GATGAGCTCACGCATGCGCGAGACAACCTCGCGCGCACGATAGCGCGCATTGGAGC

GGTGAACGATCATCGCCAGGGCGTCGACCCGGTCGCTGTTGATCAGCAAGTCCACT

TTGACCACGTCCGCGGATCGGTACTCCAGGAATTCATAGTCCATGGAGGCATAGCC

GCGCGAGACCGACTTCAAGCGGTCGAAGAAGTCCAACACGATCTCGGCCAGCGGA

ATCTCATAGGTCAAATGCACCTGGCGTCCGTGGTAGGTCATGTTGATCTGCGTGCCG

CGCTTGTTGTTGCACAGCGTCATGACCGGCCCCACATACTCCTGGGGCATGAACAA

GGTGACCTTGACGATGGGTTCTCGAATATCGGCAATCTTGCCCACGTCAGGCATGC

GCGACGGGCTTTCGATGGTCAGCACCGTGCCATCGCGCTCCTGAACCTCATAGACC

ACCGACGGCGCGGTGGTGATGATGTCCATGTCAAACTCGCGCTCGAGCCGCTCCTG

CACGATTTCCATGTGCAGCAGGCCCAGAAAGCCGCAGCGAAAGCCAAACCCCAAG

GCTTGCAAGACTTCCGGCTCGAACATCAGCGCCGCGTCGTTGAGCTTGAGTTTCTCC

AGCGAATCACGCAACTGATCGTATTCGGAGCTCTCGACCGGATACAGACCGGCGAA

CACCTGCGGCTGGACCTCTTTGAAGCCAGGCAACGGTTCGGTTGCCGGCTTGCCGG

CCAGGGTAATCGTATCGCCCACCTTGGCATTGGCCAGCTCTTTGATGCCCGCGATGA

CAAAACCCACTTCGCCCGCGGACAGATGGGGGCGTTGCTGCGATTTGGGCGTGAAC

ACG

-continued

SEQ ID NO 156
>B. hinziiCCUG-32379-
ACSTGCGGCGCGCGATAGCCGCCTGGATGGCCACGTCATACATCTGGCGCGGGATG

AGTTCACGCATGCGCGAAACCACTTCGCGGGCGCGATAGCGCGCATTGGAGCGGTG

CACGATCATGGCCAGGGCATCGACCCGGTCGCCGTTGATCAGCAGGTCCACCTTGA

CCACGTCGGCCGAGCGGTACTCCAGGAATTCATAATCCATGGAGGCGTAGCCGCGC

GAAACCGATTTCAGGCGGTCAAAGAAGTCCAGCACGATCTCGGCCAGCGGGATCTC

ATAGGTGAGATGCACCTGCCGGCCGTGGTAGGTCATGTTGATCTGCGTGCCGCGCT

TGTTATTGCACAACGTCATGACGGGCCCGACATACTCCTGCGGCATGAACAGGGTG

ACCTTGACGATGGGCTCGCGGATATCGGCGATCTTGCCGACTTCCGGCATGCGCGA

AGGGCTTTCGATGGTCAACACCGTGCCATCGCGCTCCTGGACCTCATAGACCACCG

AAGGCGCGGTGGTGATGATGTCCATGTCGAACTCGCGCTCCAGGCGCTCTTGCACG

ATTTCCATGTGCAACAGCCCCAGGAAGCCGCAACGGAAGCCGAAGCCCAGCGCCTG

GGAGACTTCAGGCTCGAACATCAGCGCCGCGTCATTGAGCTTGAGCTTCTCGAGCG

AGTCCCGCAGTTGATCGTACTCGGAGCTTTCGACCGGATACAGCCCGGCAAACACC

TGCGGCTTGACTTCCTTGAAGCCCGGCAGCGGTTCGTCGGCGGGCTTGCCGGCCAG

GGTGATGGTGTCGCCCACCTTGGCATGCGCCAGCTCCTTGATGCCGGCGATGACGA

AGCCCACCTCGCCGGCCGAGAGCTGCGGGCGGGATTGCGAYTTGGGCGTGAACACG

SEQ ID NO 157
>B. hinziiDSM-11333-
GCGCCGATAGCCGCCTGGATGGCCACGTCATACATCTGGCGCGGGATGAGTTCACG

CATGCGCGAAACCACTTCGCGGGCGCGATAGCGCGCATTGGAGCGGTGCACGATCA

TGGCCAGGGCATCGACCCGGTCGCCGTTGATCAGCAGGTCCACCTTGACCACGTCG

GCCGAGCGGTACTCCAGGAATTCATAATCCATGGAGGCGTAGCCGCGCGAAACCGA

TTTCAGGCGGTCAAAGAAGTCCAGCACGATCTCGGCCAGCGGGATCTCATAGGTGA

GATGCACCTGCCGGCCGTGGTAGGTCATGTTGATCTGCGTGCCGCGCTTGTTATTGC

ACAACGTCATGACGGGCCCGACATACTCCTGCGGCATGAACAGGGTGACCTTGACG

ATGGGCTCGCGGATATCGGCGATCTTGCCGACTTCCGGCATGCGCGAAGGGCTTTC

GATGGTCAACACCGTGCCATCGCGCTCCTGGACCTCATAGACCACCGAAGGCGCGG

TGGTGATGATGTCCATGTCGAACTCGCGCTCCAGGCGCTCTTGCACGATCTCCATGT

GCAACAGCCCCAGGAAGCCGCAACGGAAGCCGAAGCCCAGCGCCTGGGAGACTTC

AGGCTCGAACATCAGCGCCGCGTCATTGAGCTTGAGCTTCTCGAGCGAGTCCCGCA

GTTGATCGTACTCGGAGCTTTCGACCGGATACAGCCCGGCAAACACCTGCGGCTTG

ACTTCCTTGAAGCCCGGCAGCGGTTCGTCGGCGGGCTTGCCGGCCAGGGTGATGGT

GTCGCCCACCTTGGCATGCGCCAGCTCCTTGATGCCGGCGATGACGAAGCCCACCT

CGCCGGCCGAGAGCTGCGGGCGGGATTGCGAYTTGGGCGTGAACACG

SEQ ID NO 158
>B. trematumCCUG-24272
TCGCGAATGTCGTTGATCTTGCCCACTTCGGGCATGCGCGAAGGGCTTTCGACCGTC

AGGACCGTGCCATCGCGTTGTTCGACCTCATAGACCACCGACGGCGCGGTGGTGAT

GATGTCCATGTCGAATTCGCGTTCCAGGCGCTCCTGCACGATTTCCATGTGCAGCAG

ACCGAGAAAGCCGCAACGAAAGCCGAAGCCCAGCGCCTGCGACACCTCGGGCTCG

AACATCAGCGCGGCGTCGTTGAGCTTGAGCTTCTCCAGCGAATCGCGCAGTTGATC

-continued

GTACTCCGAGCTCTCGACCGGATACAGGCCGGCGAACACCTGCGGCTGCACCTCCT

TGAAACCAGGCAGCGGCTTGCTGGCGGGCTTGCCGGCCAGCGTGATGGTATCGCCC

ACCTTGGCGTGTTCGAGCTCCTTGATGCCGGTGATCACAAACCCGACTTCGCCGGCC

GACAACTGGGTACGGGCCTGCGAYTTGGGCGTGAACACG

SEQ ID NO 159
>M. africanumtype1
GTAAACGGAGTCGAAAATCATTGCGCGGGTAGGTGCCTCGGCGTCGCCCTGAGGGG

GCGGCACCTGTCGGACCACCTCGTCGAGCAGGTCGGACACGCCTTCGCCGGTTTTG

CCGGACACCCGCAACACCTCGGCCGGCTCGCAGCCGATGATGTGTGCCATCTCGGC

GGCGTAACGGTCCGGGTCGGCCGCGGGCAGGTCGATCTTGTTGAGCACCGGGATGA

TGTGCAGGTCGCGGTCCAACGCCAGGTAGAGGTTCGCCAGCGTCTGCGCCTCGATG

CCTTGCGCGGCATCGACCAACAGCACCGCACCCTCGCAAGCCTCCAGCGCACGCGA

GACTTCGTAGGTGAAGTCGACATGGCCCGGGGTGTCGATCAGATGCAGCACGTAGT

CGGTCTTGTCGACCCGCCAGGGTAGCCGCACATTCTGGGCCTTGATGGTGATGCCG

CGTTCCCGCTCGATGTCCATCCGATCCAAGTACTGGGCCCGCATAGAGCGTTCGTCG

ACCACTCCGGTGAGCTGCAGCATCCGGTCGGCCAACGTTGACTTGCCGTGGTCGAT

GTGGGCGATGATGCAAAAGTTCCTAATCTGCGCCG

SEQ ID NO 160
>M. africanum2
GTAAACGGAGTCGAAAATCATTGCGCGGGTAGGTGCCTCGGCGTCGCCCTGAGGGG

GCGGCACCTGTCGGACCACCTCGTCGAGCAGGTCGGACACGCCTTCGCCGGTTTTG

CCGGACACCCGCAACACCTCGGCCGGCTCGCAGCCGATGATGTGTGCCATCTCGGC

GGCGTAACGGTCCGGGTCGGCCGCGGGCAGGTCGATCTTGTTGAGCACCGGGATGA

TGTGCAGGTCGCGGTCCAACGCCAGGTAGAGGTTCGCCAGCGTCTGCGCCTCGATG

CCTTGCGCGGCATCGACCAACAGCACCGCACCCTCGCAAGCCTCCAGCGCACGCGA

GACTTCGTAGGTGAAGTCGACATGGCCCGGGGTGTCGATCAGATGCAGCACGTAGT

CGGTCTTGTCGACCCGCCAGGGTAGCCGCACATTCTGGGCCTTGATGGTGATGCCG

CGTTCCCGCTCGATGTCCATCCGATCCAAGTACTGGGCCCGCATAGAGCGTTCGTCG

ACCACTCCGGTGAGCTGCAGCATCCGGTCGGCCAACGTTGACTTGCCGTGGTCGAT

GTGGGCGATGATGCAAAAGTTCCTAATCTGCGCCG

SEQ ID NO 161
>M. africanum3
GTAAACGGAGTCGAAAATCATTGCGCGGGTAGGTGCCTCGGCGTCGCCCTGAGGGG

GCGGCACCTGTCGGACCACCTCGTCGAGCAGGTCGGACACGCCTTCGCCGGTTTTG

CCGGACACCCGCAACACCTCGGCCGGCTCGCAGCCGATGATGTGTGCCATCTCGGC

GGCGTAACGGTCCGGGTCGGCCGCGGGCAGGTCGATCTTGTTGAGCACCGGGATGA

TGTGCAGGTCGCGGTCCAACGCCAGGTAGAGGTTCGCCAGCGTCTGCGCCTCGATG

CCTTGCGCGGCATCGACCAACAGCACCGCACCCTCGCAAGCCTCCAGCGCACGCGA

GACTTCGTAGGTGAAGTCGACATGGCCCGGGGTGTCGATCAGATGCAGCACGTAGT

CGGTCTTGTCGACCCGCCAGGGTAGCCGCACATTCTGGGCCTTGATGGTGATGCCG

CGTTCCCGCTCGATGTCCATCCGATCCAAGTACTGGGCCCGCATAGAGCGTTCGTCG

ACCACGCCGGTGAGCTGCAGCATCCGGTCGGCCAACGTTGACTTGCCGTGGTCGAT

GTGGGCGATGATGCAAAAGTTCCTAATCTGCGCCG

-continued

SEQ ID NO 162
>M. africanumH
GTAAACGGAGTCGAAAATCATTGCGCGGGTAGGTGCCTCGGCGTCGCCCTGAGGGG

GCGGCACCTGTCGGACCACCTCGTCGAGCAGGTCGGACACGCCTTCGCAGGTTTTG

CCGGACACCCGCAACACCTCGGCCGGCTCGCAGCCGATGATGTGTGCCATCTCGGC

GGCGTAACGGTCCGGGTCGGCCGCGGGCAGGTCGATCTTGTTGAGCACCGGGATGA

TGTGCAGGTCGCGGTCCAACGCCAGGTAGAGGTTCGCCAGCGTCTGCGCCTCGATG

CCTTGCGCGGCATCGACCAACAGCACCGCACCCTCGCAAGCCTCCAGCGCACGCGA

GACTTCGTAGGTGAAGTCGACATGGCCCGGGGTGTCGATCAGATGCAGCACGTAGT

CGGTCTTGTCGACCCGCCAGGGTAGCCGCACATTCTGGGCCTTGATGGTGATGCCG

CGTTCCCGCTCGATGTCCATCCGATCCAAGTACTGGGCCCGCATAGAGCGTTCGTCG

ACCACGCCGGTGAGCTGCAGCATCCGGTCGGCCAACGTTGACTTGCCGTGGTCGAT

GTGGGCGATGATGCAAAAGTTCCTAATCTGCGCCG

SEQ ID NO 163
>*M. bovis*
GTAAACGGAGTCGAAAATCATTGCGCGGGTAGGTGCCTCGGCGTCGCCCTGAGGGG

GCGGCACCTGTCGGACCACCTCGTCGAGCAGGTCGGACACGCCTTCGCCGGTTTTG

CCGGACACCCGCAACACCTCGGCCGGCTCGCAGCCGATGATGTGTGCCATCTCGGC

GGCGTAACGGTCCGGGTCGGCCGCGGGCAGGTCGATCTTGTTGAGCACCGGGATGA

TGTGCAGGTCGCGGTCCAACGCCAGGTAGAGGTTCGCCAGCGTCTGCGCCTCGATG

CCTTGCGCGGCATCGACCAACAGCACCGCACCCTCGCAAGCCTCCAGCGCACGCGA

GACTTCGTAGGTGAAGTCGACATGGCCCGGGGTGTCGATCAGATGCAGCACGTAGT

CGGTCTTGTCGACCCGCCAGGGTAGCCGCACATTCTGGGCCTTGATGGTGATGCCG

CGTTCCCGCTCGATGTCCATCCGATCCAAGTACTGGGCCCGCATAGAGCGTTCGTCG

ACCACTCCGGTGAGCTGCAGCATCCGGTCGGCCAACGTTGACTTGCCGTGGTCGAT

GTGGGCGATGATGCAAAAGTTCCTAATCTGCGCCG

SEQ ID NO 164
>M. bovisBCG
GTAAACGGAGTCGAAAATCATTGCGCGGGTAGGTGCCTCGGCGTCGCCCTGAGGGG

GCGGCACCTGTCGGACCACCTCGTCGAGCAGGTCGGACACGCCTTCGCCGGTTTTG

CCGGACACCCGCAACACCTCGGCCGGCTCGCAGCCGATGATGTGTGCCATCTCGGC

GGCGTAACGGTCCGGGTCGGCCGCGGGCAGGTCGATCTTGTTGAGCACCGGGATGA

TGTGCAGGTCGCGGTCCAACGCCAGGTAGAGGTTCGCCAGCGTCTGCGCCTCGATG

CCTTGCGCGGCATCGACCAACAGCACCGCACCCTCGCAAGCCTCCAGCGCACGCGA

GACTTCGTAGGTGAAGTCGACATGGCCCGGGGTGTCGATCAGATGCAGCACGTAGT

CGGTCTTGTCGACCCGCCAGGGTAGCCGCACATTCTGGGCCTTGATGGTGATGCCG

CGTTCCCGCTCGATGTCCATCCGATCCAAGTACTGGGCCCGCATAGAGCGTTCGTCG

ACCACTCCGGTGAGCTGCAGCATCCGGTCGGCCAACGTTGACTTGCCGTGGTCGAT

GTGGGCGATGATGCAAAAGTTCCTAATCTGCGCCG

SEQ ID NO 165
>*M. canetti*
GTAAACGGAGTCGAAAATCATTGCGCGGGTAGGTGCCTCGGCGTCGCCCTGCGGGG

GCGGCACCTGTCGGACCACCTCGTCGAGCAGGTCGGACACGCCTTCGCCGGTTTTG

CCGGACACCCGCAACACCTCGGCCGGCTCGCAGCCGATGATGTGTGCCATCTCGGC

-continued

GGCGTAACGGTCCGGGTCGGCCGCGGGCAGGTCGATCTTGTTGAGCACCGGGATGA

TGTGCAGGTCGCGGTCCAACGCCAGGTAGAGGTTCGCCAGCGTCTGCGCCTCGATG

CCTTGCGCGGCATCGACCAACAGCACCGCACCCTCGCAAGCCTCCAGCGCACGCGA

GACTTCGTAGGTGAAGTCGACATGGCCCGGGGTGTCGATCAGATGCAGCACGTAGT

CGGTCTTGTCGACCCGCCAGGGTAGCCGCACATTCTGGGCCTTGATGGTGATGCCG

CGTTCCCGCTCGATGTCCATCCGATCCAAGTACTGGGCCCGCATAGAGCGTTCGTCG

ACCACGCCGGTGAGCTGCAGCATCCGGTCGGCCAACGTTGACTTGCCGTGGTCGAT

GTGGGCGATGATGCAAAAGTTCCTAATCTGCGCCG

SEQ ID NO 166
>*M. canetti*
GTAAACGGAGTCGAAAATCATTGCGCGGGTAGGTGCCTCGGCGTCGCCCTGCGGGG

GCGGCACCTGTCGGACCACCTCGTCGAGCAGGTCGGACACGCCTTCGCCGGTTTTG

CCGGACACCCGCAACACCTCGGCCGGCTCGCAGCCGATGATGTGTGCCATCTCGGC

GGCGTAACGGTCCGGGTCGGCCGCGGGCAGGTCGATCTTGTTGAGCACCGGGATGA

TGTGCAGGTCGCGGTCCAACGCCAGGTAGAGGTTCGCCAGCGTCTGCGCCTCGATG

CCTTGCGCGGCATCGACCAACAGCACCGCACCCTCGCAAGCCTCCAGCGCACGCGA

GACTTCGTAGGTGAAGTCGACATGGCCCGGGGTGTCGATCAGATGCAGCACGTAGT

CGGTCTTGTCGACCCGCCAGGGTAGCCGCACATTCTGGGCCTTGATGGTGATGCCG

CGTTCCCGCTCGATGTCCATCCGATCCAAGTACTGGGCCCGCATAGAGCGTTCGTCG

ACCACGCCGGTGAGCTGCAGCATCCGGTCGGCCAACGTTGACTTGCCGTGGTCGAT

GTGGGCGATGATGCAAAAGTTCCTAATCTGCGCCG

SEQ ID NO 167
>*M. caprae*
GTAAACGGAGTCGAAAATCATTGCGCGGGTAGGTGCCTCGGCGTCGCCCTGAGGGG

GCGGCACCTGTCGGACCACCTCGTCGAGCAGGTCGGACACGCCTTCGCCGGTTTTG

CCGGACACCCGCAACACCTCGGCCGGCTCGCAGCCGATGATGTGTGCCATCTCGGC

GGCGTAACGGTCCGGGTCGGCCGCGGGCAGGTCGATCTTGTTGAGCACCGGGATGA

TGTGCAGGTCGCGGTCCAACGCCAGGTAGAGGTTCGCCAGCGTCTGCGCCTCGATG

CCTTGCGCGGCATCGACCAACAGCACCGCACCCTCGCAAGCCTCCAGCGCACGCGA

GACTTCGTAGGTGAAGTCGACATGGCCCGGGGTGTCGATCAGATGCAGCACGTAGT

CGGTCTTGTCGACCCGCCAGGGTAGCCGCACATTCTGGGCCTTGATGGTGATGCCG

CGTTCCCGCTCGATGTCCATCCGATCCAAGTACTGGGCCCGCATAGAGCGTTCGTCG

ACCACTCCGGTGAGCTGCAGCATCCGGTCGGCCAACGTTGACTTGCCGTGGTCGAT

GTGGGCGATGATGCAAAAGTTCCTAATCTGCGCCG

SEQ ID NO 168
>M. caprae2
GTAAACGGAGTCGAAAATCATTGCGCGGGTAGGTGCCTCGGCGTCGCCCTGAGGGG

GCGGCACCTGTCGGACCACCTCGTCGAGCAGGTCGGACACGCCTTCGCCGGTTTTG

CCGGACACCCGCAACACCTCGGCCGGCTCGCAGCCGATGATGTGTGCCATCTCGGC

GGCGTAACGGTCCGGGTCGGCCGCGGGCAGGTCGATCTTGTTGAGCACCGGGATGA

TGTGCAGGTCGCGGTCCAACGCCAGGTAGAGGTTCGCCAGCGTCTGCGCCTCGATG

CCTTGCGCGGCATCGACCAACAGCACCGCACCCTCGCAAGCCTCCAGCGCACGCGA

GACTTCGTAGGTGAAGTCGACATGGCCCGGGGTGTCGATCAGATGCAGCACGTAGT

CGGTCTTGTCGACCCGCCAGGGTAGCCGCACATTCTGGGCCTTGATGGTGATGCCG

-continued

CGTTCCCGCTCGATGTCCATCCGATCCAAGTACTGGGCCCGCATAGAGCGTTCGTCG

ACCACTCCGGTGAGCTGCAGCATCCGGTCGGCCAACGTTGACTTGCCGTGGTCGAT

GTGGGCGATGATGCAAAACTTCCTAATCTGCGCCG

SEQ ID NO 169
>*M. microtti*
GTAAACGGAGTCGAAAATCATTGCGCGGGTAGGTGCCTCGGCGTCGCCCTGAGGGG

GCGGCACCTGTCGGACCACCTCGTCGAGCAGGTCGGACACGCCTTCGCCGGTTTTG

CCGGACACCCGCAACACCTCGGCCGGCTCGCAGCCGATGATGTGTGCCATCTCGGC

GGCGTAACGGTCCGGGTCGGCCGCGGGCAGGTCGATCTTGTTGAGCACCGGGATGA

TGTGCAGGTCGCGGTCCAACGCCAGGTAGAGGTTCGCCAGCGTCTGCGCCTCGATG

CCTTGCGCGGCATCGACCAACAGCACCGCACCCTCGCAAGCCTCCAGCGCACGCGA

GACTTCGTAGGTGAAGTCGACATGGCCCGGGGTGTCGATCAGATGCAGCACGTAGT

CGGTCTTGTCGACCCGCCAGGGTAGCCGCACATTCTGGGCCTTGATGGTGATGCCG

CGTTCCCGCTCGATGTCCATCCGATCCAAGTACTGGGCCCGCATAGAGCGTTCGTCG

ACCACTCCGGTGAGCTGCAGCATCCGGTCGGCCAACGTTGACTTGCCGTGGTCGAT

GTGGGCGATGATGCAAAAGTTCCTAATCTGCGCCG

SEQ ID NO 170
>*M. pinipedii*
GTAAACGGAGTCGAAAATCATTGCGCGGGTAGGTGCCTCGGCGTCGCCCTGAGGGG

GCGGCACCTGTCGGACCACCTCGTCGAGCAGGTCGGACACGCCTTCGCCGGTTTTG

CCGGACACCCGCAACACCTCGGCCGGCTCGCAGCCGATGATGTGTGCCATCTCGGC

GGCGTAACGGTCCGGGTCGGCCGCGGGCAGGTCGATCTTGTTGAGCACCGGGATGA

TGTGCAGGTCGCGGTCCAACGCCAGGTAGAGGTTCGCCAGCGTCTGCGCCTCGATG

CCTTGCGCGGCATCGACCAACAGCACCGCACCCTCGCAAGCCTCCAGCGCACGCGA

GACTTCGTAGGTGAAGTCGACATGGCCCGGGGTGTCGATCAGATGCAGCACGTAGT

CGGTCTTGTCGACCCGCCAGGGTAGCCGCACATTCTGGGCCTTGATGGTGATGCCG

CGTTCCCGCTCGATGTCCATCCGATCCAAGTACTGGGCCCGCATAGAGCGTTCGTCG

ACCACTCCGGTGAGCTGCAGCATCCGGTCGGCCAACGTTGACTTGCCGTGGTCGAT

GTGGGCGATGATGCAAAACTTCCTAATCTGCGCCG

SEQ ID NO 171
>*M. tuberculosis*
GTAAACGGAGTCGAAAATCATTGCGCGGGTAGGTGCCTCGGCGTCGCCCTGAGGGG

GCGGCACCTGTCGGACCACCTCGTCGAGCAGGTCGGACACGCCTTCGCCGGTTTTG

CCGGACACCCGCAACACCTCGGCCGGCTCGCAGCCGATGATGTGTGCCATCTCGGC

GGCGTAACGGTCCGGGTCGGCCGCGGGCAGGTCGATCTTGTTGAGCACCGGGATGA

TGTGCAGGTCGCGGTCCAACGCCAGGTAGAGGTTCGCCAGCGTCTGCGCCTCGATG

CCTTGCGCGGCATCGACCAACAGCACCGCACCCTCGCAAGCCTCCAGCGCACGCGA

GACTTCGTAGGTGAAGTCGACATGGCCCGGGGTGTCGATCAGATGCAGCACGTAGT

CGGTCTTGTCGACCCGCCAGGGTAGCCGCACATTCTGGGCCTTGATGGTGATGCCG

CGTTCCCGCTCGATGTCCATCCGATCCAAGTACTGGGCCCGCATAGAGCGTTCGTCG

ACCACGCCGGTGAGCTGCAGCATCCGGTCGGCCAACGTTGACTTGCCGTGGTCGAT

GTGGGCGATGATGCAAAAGTTCCTAATCTGCGCCG

-continued

SEQ ID NO 172
>*M. smegmatis*
GTACACGGAGTCGAAGATCATCGCGCGCGTCGGGGCGTCGGGGTCACCGACCGGC

GGCGGCACCTTACGCACCACCTCGTCGAGCAGCTCGGCCACGCCTTCGCCGGTCTT

GCCCGAGACACGCAGCACGTCCGACGGCTCACACCCGATGATGTGGGCGAGCTCGT

CGGCATAGCGGTCCGGGTCAGCGGCGGGCAGGTCGATCTTGTTGAGCACCGGGATG

ATCGCCAGGTCGCGGTCCAGCGCCAGGTACAGGTTGGCCAGCGTCTGCGCCTCGAT

GCCCTGCGCCGCGTCGACCAGCAGCACCGCGCCCTCGCAGGCCTCCAGCGCGCGCG

ACACCTCGTAGGTGAAGTCGACGTGGCCCGGGGTGTCGATCAGGTGCAGCACGTAA

TCACCCGCGTCCGCGCCGTCTTGGCCGTCCTTCAGCGTCCACGGAAGCCGGACGTTC

TGAGCCTTGATGGTGATCCCGCGCTCACGTTCGATGTCCATGCGGTCGAGGTACTGG

GCCCGCATCGACCGCTCATCGACAACACCGGTGAGCTGCAGCATCCGGTCGGCCAG

CGTCGACTTGCCGTGGTCGATGTGGGCGATGATGCAGAAGTTCCTAATCTGCGCCG

SEQ ID NO 173
>*M. celatum*
CCGGGTGGGGGCTTCGGCGTCGCCGACTGGCGGTGGAACCTGCTTGACGACGGCGT

CGAGCAGTTCGGGCACCCCCTCGCCGGTCTTGCCGGAGACCCGCAGCACGTCGTCG

GGTTCGCAGCCGATGATGTGGGCGATCTCGCCGGCGTAGCGGTCCGGGTCGGCGGC

CGGCAGGTCGATCTTGTTGAGCACCGGGATGATCGCCAGGTCGCGGTCCAGCGCCA

GGTACAGGTTGGCCAGCGTCTGCGCCTCGATGCCCTGCGCGGCGTCCACCAGCAGC

ACCGCCCCTTCGCAGGCGGCCAGCGCGCGGGACACCTCGTAGGTGAAGTCGACGTG

GCCCGGGGTGTCGATCAGGTGCAGGACGTGGTCGGTGTCCCCGACTCGCCAGGGCA

GGCGCACATTTTGCGCCTTGATCGTGATCCCCCGTTCGCGCTCGATGTCCATCCGGT

CCAGGTACTGCGCCCGCATGGACCGCTCGTCGACGACTCCGGTCAGCTGCAGCATC

CGGTCGGCCAGCGTGGACTTGCCGTGGTCGATGTGGGCGATGATGCAGAAGTTCCT

AATCTGCGCCG

SEQ ID NO 174
>*M. fortuitum*
GTACACGGAGTCGAAGATCATCGCGCGCGTGGGCGCGTCGGGATCACCCACCGGCG

GCGGCACCTGGCGCACCACCTCGTCGAGCAGTTCGGCCACGCCCTCACCGGTCTTG

CCGGAGACGCGCAGCACGTCGGAAGGCTCACAGCCGATGATGTGGGCGAGCTCGC

CGGCGTAGCGGTCCGGGTCCGCGGCGGGCAGGTCGATCTTGTTGAGCACCGGGATG

ATCGCCAGGTCGCGGTCCAGTGCCAGGTACAGGTTGGCCAGCGTCTGCGCCTCGAT

GCCCTGTGCGGCGTCGACCAGCAGCACCGCACCCTCGCAGGCCTCGAGCGCACGGG

ACACCTCGTAGGTGAAGTCGACGTGGCCCGGGGTGTCGATCAGGTGCAGGACGTGA

TCCTGCCCGTCGACGCGCCAGGGCAGCCGAACGTTCTGCGCCTTGATCGTGATCCC

GCGCTCACGCTCGATGTCCATGCGGTCGAGGTACTGGGCACGCATCGACCGCTCGT

CGACGACGCCGGTGAGCTGCAGCATCCGGTCGGCCAGCGTCGACTTGCCATGGTCG

ATGTGAGCGATGATGCAGAAGTTCCTAATCTGCGCCG

SEQ ID NO 175
>*M. intracellulare*
GCGCGTCGGCCTTGCCCTGCGGGGGCGGCACCTGGCCCACCACCTCGTCGAGCAGC

TCGGCCACTCCCTCGCCGGTTTTGCCGGACACCCGCAGCACGTCGTCGGGCTCGCA

GCCGATGATGTGGGCGAGCTCTCCTGCGTAGCGGTCCGGGTCGGCCGCCGGCAGGT

-continued

CGATCTTGTTGAGCACCGGGATGATGGTCAGGTCACGGTCCAGCGCCAGGTAGAGG

TTGGCCAGGGTCTGCGCCTCGATGCCCTGGGCGGCGTCGACCAACAGCACCGCGCC

CTCGCAGGCCTCCAGCGCGCGCGACACCTCGTAGGTGAAGTCGACGTGGCCCGGGG

TGTCGATCAGGTGCAGGACATGGTCTTCGTCGTCGACTTTCCACGGGAGCCGGACG

TTCTGCGCCTTGATGGTGATGCCGCGCTCGCGCTCGATGTCCATCCGGTCCAGGTAC

TGGGCGCGCATCGAGCGCTCATCGACGACGCCGGTGAGCTGCAGCATCCGGTCGGC

CAGCGTCGACTTGCCGTGATCGATGTGGGCGATGATGCAGAAGTTCCTAATCTGCG

CCG

SEQ ID NO 176
>*M. malmoense*
CAGAGTCGAAGATCATCGCGCGGGTGGGCGCGTCGGCGTCGCCCTGCGGCGGCGGC

ACCTGACGGACCACCTCGTCGAGAAGGTGCGCGACGCCCTCGCCGGTCTTGCCGGA

CACCCGCAGCACGTCGGTCGGCTCGCAGCCCATGATGTGGGCGATCTCGGCCGCGT

AGCGGTCCGGATCGGCGGCCGGCAGATCGATCTTGTTGAGCACCGGGATGATGGTC

AGGTCACGGTCCAGCGCCAGGTAGAGGTTGGCCAGGGTCTGGGCCTCGATGCCCTG

GGCCGCGTCGACCAGCAGCACCGCGCCCTCACAGGCCTCCAGCGCGCGGGAGACCT

CGTAGGTGAAGTCGACGTGACCAGGGGTGTCGATCAGGTGCAGGACGTACTGGGTT

CCATCGACTTGCCAGGGCAGCCGGACGTTCTGGGCCTTGATGGTGATCCCGCGCTC

CCGCTCGATGTCCATCCGGTCCAGGTATTGGGCGCGCATCGATCGCTCGTCGACGA

CGCCGGTGAGCTGGAGCATCCGGTCCGCGAGCGTCGACTTGCCATGGTCGATGTGA

GCGATGATGCAGAAGTTCCTAATCTGCGCCG

SEQ ID NO 177
>*M. paratuberculosis*
CAGAGTCGAAGATCATCGCGCGCAGCGGCGCATCGGCCTGCCCCTGCGGCGGCGGC

ACCTGGCGCACCACCTCGTCGAGCAGCCGCGCCACGCCCTCCCCGGTTTTGCCGGA

CACCCACAGCACGTCGTCGGGTTCGCACCCGATGATGTGGGCGAGCTCGCCGGCGT

AGCGATCCGGGTCGGCGGCCGGCAGGTCGATCTTGTTGAGGACCGGGATGATGGTC

AGATCGCGGTCCAGCGCCAGGTAGAGGTTGGCCAGCGTCTGGGCCTCGATGCCCTG

CGCGGCGTCGACCAGCAGCACGGCACCTTCGCAGGCCTCCAGTGCGCGCGACACCT

CGTAGGTGAAGTCGACGTGGCCCGGGGTGTCGATCAGGTGCAGGACAAATTCTTTG

CCGGCGTCCTCGCCGCCGGAGACCTGCCAGGGCAGCCGCACGTTCTGCGCCTTGAT

GGTGATGCCGCGCTCCCGCTCGATGTCCATCCGGTCCAGGTACTGGGCGCGCATCG

ACCGCTCGTCGACGACGCCGGTGAGCTGCAGCATCCGGTCGGCCAGCGTCGACTTG

CCGTGATCGATGTGGGCGATGATGCAGAAGTTCCTAATCTGCGCCG

SEQ ID NO 178
>*M. scrofulaceum*
GTAAACGGAGTCGAAAATCATTGCGCGGGTAGGTGCCTCGGCGTCGCCCTGAGGGG

GCGGCACCTGTCGGACCACCTCGTCGAGCAGGTCGGACACGCCTTCGCCGGTTTTG

CCGGACACCCGCAACACCTCGGCCGGCTCGCAGCCGATGATGTGTGCCATCTCGGC

GGCGTAACGGTCCGGGTCGGCCGCGGGCAGGTCGATCTTGTTGAGCACCGGGATGA

TGTGCAGGTCGCGGTCCAACGCCAGGTAGAGGTTCGCCAGCGTCTGCGCCTCGATG

CCTTGCGCGGCATCGACCAACAGCACCGCACCCTCGCAAGCCTCCAGCGCACGCGA

GACTTCGTAGGTGAAGTCGACATGGCCCGGGGTGTCGATCAGATGCAGCACGTAGT

CGGTCTTGTCGACCCGCCAGGGTAGCCGCACATTCTGGGCCTTGATGGTGATGCCG

-continued

```
CGTTCCCGCTCGATGTCCATCCGATCCAAGTACTGGGCCCGCATAGAGCGTTCGTCG

ACCACTCCGGTGAGCTGCAGCATCCGGTCGGCCAACGTTGACTTGCCGTGGTCGAT

GTGGGCGATGATGCAAAAGTTCCTAATCTGCGCCG
```

The words "comprises/comprising" and the words "having/including" when used herein with reference to the present invention are used to specify the presence of stated features, integers, steps or components but does not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. A method of specifically detecting a target organism in a test sample comprising the steps of:

(i) mixing the test sample with at least one oligonucleotide probe capable of binding to at least a portion of the LepA or Guf1 gene or its corresponding mRNA under appropriate conditions, wherein the probe is selected from the group consisting of SEQ ID NO 11, SEQ ID NO 12, SEQ ID NO 15, SEQ ID NO 20, SEQ ID NO 21, SEQ ID NO 26, SEQ ID NO 27, SEQ ID NO 30 SEQ ID NO 35, SEQ ID NO 36, SEQ ID NO 37, SEQ ID NO 40, SEQ ID NO 43, SEQ ID NO 46, SEQ ID NO 49, SEQ ID NO 52 and sequences substantially homologous or substantially complementary thereto and also capable of acting as a probe for the LepA or Guf1 gene;

(ii) hybridizing under high stringency conditions any nucleic acid that may be present in the test sample with the oligonucleotide to form a probe:target complex; and (iii) determining whether a probe:target complex is present, the presence of the duplex positively and specifically identifying the presence of the target organism in the test sample.

2. The method of claim 1, wherein the test sample comprises a sample isolated from a patient.

* * * * *